US011542233B2

(12) United States Patent
Burnett et al.

(10) Patent No.: US 11,542,233 B2
(45) Date of Patent: Jan. 3, 2023

(54) COMPOUNDS, COMPOSITIONS AND METHODS OF USE

(71) Applicant: Aquinnah Pharmaceuticals, Inc., Cambridge, MA (US)

(72) Inventors: Duane A. Burnett, Wayland, MA (US); Joseph P. Vacca, Telford, PA (US)

(73) Assignee: Aquinnah Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/472,501

(22) PCT Filed: Dec. 22, 2017

(86) PCT No.: PCT/US2017/068186

§ 371 (c)(1),
(2) Date: Jun. 21, 2019

(87) PCT Pub. No.: WO2018/119395

PCT Pub. Date: Jun. 28, 2018

(65) Prior Publication Data

US 2020/0270211 A1 Aug. 27, 2020

Related U.S. Application Data

(60) Provisional application No. 62/438,836, filed on Dec. 23, 2016, provisional application No. 62/560,493, filed on Sep. 19, 2017.

(51) Int. Cl.

| | |
|---|---|
| ***C07D 209/42*** | (2006.01) |
| ***C07D 235/24*** | (2006.01) |
| ***C07D 405/12*** | (2006.01) |
| ***C07D 413/12*** | (2006.01) |
| ***C07D 471/04*** | (2006.01) |

(52) U.S. Cl.

CPC ......... *C07D 209/42* (2013.01); *C07D 235/24* (2013.01); *C07D 405/12* (2013.01); *C07D 413/12* (2013.01); *C07D 471/04* (2013.01)

(58) Field of Classification Search

CPC .................................................... C07D 209/42

See application file for complete search history.

(56) References Cited

U.S. PATENT DOCUMENTS

| | | | | |
|---|---|---|---|---|
| 5,455,262 | A * | 10/1995 | Schwartz | C07C 323/60 514/399 |
| 2003/0100576 | A1 | 5/2003 | Bonjouklian et al. | |
| 2020/0270211 | A1 | 8/2020 | Burnett et al. | |

FOREIGN PATENT DOCUMENTS

| | | | | |
|---|---|---|---|---|
| EP | 3557998 | A4 | 12/2020 | |
| JP | 2003-508512 | A | 3/2003 | |
| JP | 2004-502761 | A | 1/2004 | |
| JP | 2005-213194 | A | 8/2005 | |
| JP | 2010-138199 | A | 6/2010 | |
| JP | 2010-536869 | A | 12/2010 | |
| JP | 2011-524893 | A | 9/2011 | |
| JP | 2012-505855 | A | 3/2012 | |
| JP | 2012-530713 | A | 12/2012 | |
| JP | 2016-513621 | A | 5/2016 | |
| JP | 2016-533379 | A | 10/2016 | |
| KR | 10-2012-0092768 | A | 8/2012 | |
| WO | WO-2002/100833 | A1 | 12/2002 | |
| WO | WO-2006/040646 | A1 * | 4/2006 | C07D 401/12 |
| WO | WO-2006040646 | A1 | 4/2006 | |
| WO | 2010148197 | A1 | 12/2010 | |
| WO | WO-2010148197 | A1 | 12/2010 | |
| WO | WO-2012/162249 | A1 | 11/2012 | |
| WO | WO-2015/154039 | A2 | 10/2015 | |
| WO | WO-2016/020526 | A1 | 2/2016 | |
| WO | WO-2016/037953 | A1 | 3/2016 | |
| WO | WO-2016/040780 | A1 | 3/2016 | |
| WO | WO-2016/058544 | A1 | 4/2016 | |
| WO | WO-2016/105528 | A2 | 6/2016 | |
| WO | WO-2018/119395 | A1 | 6/2018 | |

OTHER PUBLICATIONS

Chemical Abstracts Registry No. 52217-80-8, indexed in the Registry file Nov. 16, 1984. (Year: 1984).*
Wang et al., Bioorganic & Medicinal Chemistry Letters (2009), 19(17), pp. 5140-5145. (Year: 2009).*
Li et al., ACS Medicinal Chemistry Letters (2014), 5(6), pp. 690-695. (Year: 2014).*
Goulet et al., Bioorganic & Medicinal Chemistry Letters (2010), 20(1), pp. 196-200. (Year: 2010).*
Chemical Abstracts Registry No. 1424266-81-8, indexed in the Registry file on STN CAS Online Mar. 15, 2013. (Year: 2013).*
Buchs et al. "Reversible aminal formation: Controlling the evaporation of bioactive volatiles by dynameic combinatorial/covalent chemistry," Eur. J. Org. Chem., 2011, 681-695.
Pubmed compound summary for CID 11742590, U.S. National Library of Medicine, Oct. 26, 2006, 1-13.
Pubmed compound summary for CID 22713737, U.S. National Library of Medicine, Dec. 5, 2007, 1-12.
Pubmed compound summary for CID 77385382, U.S. National Library of Medicine, Sep. 14, 2014, 1-9.
Pubmed compound summary for CID 90667051, U.S. National Library of Medicine, Mar. 11, 2015, 1-10.
Pubmed compound summary for CID 97232202, U.S. National Library of Medicine, Dec. 11, 2015, 1-10.
Agrawal et al. "Ligand-based pharmacophore detection, screening of potential pharmacophore and docking studies, to get effective glycogen synthase kinase inhibitors" Medicinal Chemistry Research, (2013) 22:5504-5535.
Buchs et al. "Reversible Aminal Formation: Controlling the Evaporation of Bioactive Volatiles by Dynamic Combinatorial/Covalent Chemistry" Eur. J. Org. Chem. 2011, 681-695.

(Continued)

*Primary Examiner* — Laura L Stockton
(74) *Attorney, Agent, or Firm* — Goodwin Procter LLP

(57) ABSTRACT

Herein, compounds, compositions and methods for modulating inclusion formation and stress granules in cells related to the onset of neurodegenerative diseases, musculoskeletal diseases, cancer, ophthalmological diseases, and viral infections are described.

27 Claims, 30 Drawing Sheets

(56) References Cited

OTHER PUBLICATIONS

Burke et al. Study of 2-Naphthol-Hexamethylenetetramine Condensation Products, Journal of the Chemical Society, 1956, 805-808.
Catto et al. "Design, synthesis and biological evaluation of coumarin alkylamines as potent and selective dual binding site inhibitors of acetylcholinesterase" Bioorganic & Medicinal Chemistry, 2013, 21(1), 146-152.
Coughlin et al. "Opportunities to address lung cancer disparities among African Americans" Cancer Medicinevol. 3, Issue 6 p. 1467-1476, Sep. 14, 2014.
Desper et al. "Strategies for Nonmacrocyclic Polythioether Ligands: New Pentacoordinating Architectures" Angew. Chem., Int. Ed. Engl., 1994, 33(3), 319-21).
Goulet et al. "Discovery of benzimidazole-diamide finger loop (Thumb Pocket I) allosteric inhibitors of HCV NS5B polymerase: Implementing parallel synthesis for rapid linker optimization" Bioorganic & Medicinal Chemistry Letters, Pergamon, Amsterdam, NL, vol. 20, No. 1, Jan. 1, 2010 (Jan. 1, 2010), pp. 196-200.
CAS RN 1424266-81-8, STN Entry Date Mar. 15, 2013.
Li et al. "Diamine Derivatives as Novel Small-Molecule, Potent, and Subtype-Selective Somatostatin SST3 Receptor Agonists", ACS Medicinal Chemistry Letters, vol. 5, No. 6, Apr. 25, 2014 (Apr. 25, 2014), pp. 690-695.
Liu et al. "Novel benzothiazole derivatives with a broad antifungal spectrum: design, synthesis and structure-activity relationships" MedChemComm, 2013, 4(12), 1551-1561.
Pizot et al. "Physical activity, hormone replacement therapy and breast cancer risk: A meta-analysis of prospective studies" Dec. 11, 2015, vol. 52, 138-154.
Pubchem, (1R,3S)-N-[2-(Cyclopentanecarbonylamino)-1,3-Benzoxazol-6-Yl]-3-(Naphthalen-2-Remarks: [Online], Mar. 11, 2015, pp. 1-8, https://pubchem.ncbi.nlm.nih.gov/compound/90667051, Ylmethylamino)Cyclohexane-1-Carboxamide.
Pubchem, N-(1-Benzofuran-2-Ylmethyl)-N'-(6-Methoxy-4-Methylquinolin-2-Yl)Cyclohexane-1,3-Diamine, [Online], Oct. 26, 2006, pp. 1-8, https://pubchem.ncbi.nlm.nih.gov/compound/11742590.
Database Pubmed U.S. National Library of Medicine; Dec. 5, 2007 (Dec. 5, 2007), "Ijngyzviixwdie-Uhfffaoysa-N", Database accession No. 22713737.
Registry(STN)[online], Oct. 17, 2002 [retrieval date: Sep. 23, 2021]CAS Registration No. 462073-68-3.
Registry(STN)[online], Aug. 17, 2004 [retrieval date: Sep. 23, 2021]CAS Registration No. 727656-58-8.
Registry(STN)[online], Jun. 8, 2008 [retrieval date: Sep. 23, 2021]CAS Registration No. 1026383-10-7.
Registry(STN)[online], Dec. 4, 2011 [retrieval date: Sep. 23, 2021] CAS Registration No. 1348377-35-4.
Registry(STN)[online], Mar. 15, 2013 [retrieval date: Oct. 11, 2021]CAS Registration No. 1424266-81-8.
Wang et al. "Inhibitors of HIV-1 attachment. Part 4: A study of the effect of piperazine substitution patterns on antiviral potency in the context of indole-based derivatives", Bioorganic & Medicinal Chemistry Letters, vol. 19, No. 17, Sep. 1, 2009 (Sep. 1, 2009), pp. 5140-5145.
Yamazaki et al. "Synthesis of potent and selective inhibitors of *Candida albicans*N-myristoyltransferase based on the benzothiazole structure", Bioorganic & Medicinal Chemistry 13 (2005) 2509-2522.
Zhang et al. "Selective Monoacylation of Symmetrical Diamines via Prior Complexation with Boron" Bristol-Myers Squibb Pharmaceutical Research Institute; Org. Lett., vol. 5, No. 19, 2003, 3399-3402.
Zhou et al. "Discovery and structure-activity relationship of 1,3-cyclohexyl amide derivatives as novel mGluR5 negative allosteric modulators" Bioorganic & Medicinal Chemistry Letters 23 (2013) 1398-1406.
Pubchem, (1S,3R)-N-Cyclopropyl-3-(2,3-Dihydro-1H-Inden-2-Ylamino)Cyclohexane-1-Carboxamide,[Online], Dec. 11, 2015, pp. 1-8,https://pubchem.ncbi.nlm.nih.gov/compound/97232202.
Pubchem, N-[3-(Benzamidomethyl)Cyclohexyl]-3-(2-Chloro-6-Fluorophe Nyl)-5-Pyrrolidin-1-Yl-Remarks: Pubchem, Dec. 5, 2007, pp. 1-8, https://pubchem.ncbi.nlm.nih.gov/compound/22713737, 1,2-Oxazole-4-Carboxamide.
Pubchem, N-[3-[[2-(5-Chloro-1H-Pyrrolo[2,3-B]Pyridin-3-Yl)-5-Fluor Opyrimidin-4-Yl]Amino] Remarks: [Online], Sep. 14, 2014, pp. 1-8, https://pubchem.ncbi.nlm.nih.gov/compound/77385382,Cyclohex Yl]Oxane-4-Carboxamide.

* cited by examiner

| Compound No. | Structure |
|---|---|
| 100 |  |
| 101 |  (+/-) |
| 102 |  |
| 103 |  |
| 104 |  |
| 105 |  |
| 106 |  |
| 107 |  |

| Compound No. | Structure |
|---|---|
| 108 |  |
| 109 |  |
| 110 |  |
| 111 |  |
| 112 |  |
| 113 |  |
| 114 |  |
| 115 |  |
| 116 |  |

| Compound No. | Structure |
| --- | --- |
| 117 |  |
| 118 |  |
| 119 |  |
| 120 |  |
| 121 |  |
| 122 |  |
| 123 |  |

| Compound No. | Structure |
|---|---|
| 124 |  |
| 125 |  |
| 126 |  |
| 127 |  |
| 128 |  |
| 129 |  |
| 130 |  |

| Compound No. | Structure |
| --- | --- |
| 131 |  |
| 132 |  |
| 133 |  |
| 134 |  |
| 135 |  |
| 136 |  |
| 137 |  |
| 150 |  |

| Compound No. | Structure |
|---|---|
| 151 |  |
| 152 |  |
| 170 |  |
| 171 |  |
| 172 |  |
| 173 |  |
| 174 |  |

| Compound No. | Structure |
| --- | --- |
| 175 |  |
| 176 |  |
| 177 |  |
| 178 |  |
| 179 |  |
| 180 |  |
| 181 |  |

| Compound No. | Structure |
|---|---|
| 182 |  |
| 183 |  |
| 200 |  |
| 300 |  |
| 301 |  |
| 302 |  |
| 303 |  |

| Compound No. | Structure |
|---|---|
| 312 |  |
| 313 |  |
| 314 |  |
| 316 |  |
| 317 |  |
| 318 |  |
| 400 |  |
| 401 |  |

| Compound No. | Structure |
|---|---|
| 402 |  |
| 403 |  |
| 404 |  |
| 405 |  |
| 406 |  |
| 407 |  |
| 408 |  |
| 409 |  |
| 410 |  |

| Compound No. | Structure |
|---|---|
| 411 |  |
| 412 |  |
| 413 |  |
| 414 |  |
| 415 |  |
| 416 |  |
| 417 |  |
| 418 |  |

| Compound No. | Structure |
|---|---|
| 419 |  |
| 420 |  |
| 421 |  |
| 422 |  |
| 423 |  |
| 424 |  |
| 425 |  |
| 426 |  |
| 427 |  |

| Compound No. | Structure |
|---|---|
| 428 |  |
| 429 |  |
| 430 |  |
| 431 |  |
| 432 |  |
| 433 |  |
| 434 |  |
| 435 |  |
| 436 |  |

| Compound No. | Structure |
|---|---|
| 437 |  |
| 438 |  |
| 439 |  |
| 440 |  |
| 441 |  |
| 442 |  |
| 443 |  |
| 444 |  |

| Compound No. | Structure |
|---|---|
| 445 |  |
| 446 |  |
| 447 |  |
| 448 |  |
| 449 |  |
| 450 |  |
| 451 |  |
| 452 |  |
| 453 |  |

| Compound No. | Structure |
|---|---|
| 454 |  |
| 455 |  |
| 456 |  |
| 457 |  |
| 458 |  |
| 459 |  |
| 460 |  |
| 461 |  |

| Compound No. | Structure |
|---|---|
| 462 |  |
| 463 |  |
| 464 |  |
| 465 |  |
| 466 |  |
| 467 |  |
| 468 |  |
| 469 |  |

| Compound No. | Structure |
|---|---|
| 470 |  |
| 471 |  |
| 472 |  |
| 473 |  |
| 474 |  |
| 475 |  |
| 476 |  |
| 477 |  |

| Compound No. | Structure |
|---|---|
| 478 |  |
| 479 |  |
| 480 |  |
| 481 |  |
| 482 |  |
| 483 |  |
| 484 |  |
| 485 |  |

| Compound No. | Structure |
|---|---|
| 486 |  |
| 487 |  |
| 488 |  |
| 489 |  |
| 490 |  |
| 491 |  |
| 492 |  |
| 493 |  |

| Compound No. | Structure |
|---|---|
| 494 |  |
| 495 |  |
| 496 |  |
| 497 |  |
| 498 |  |
| 499 |  |
| 500 |  |
| 501 |  |

| Compound No. | Structure |
|---|---|
| 502 |  |
| 503 |  |
| 504 |  |
| 505 |  |
| 506 |  |
| 507 |  |
| 508 |  |

| Compound No. | Structure |
| --- | --- |
| 509 |  |
| 510 |  |
| 511 |  |
| 512 |  |
| 513 |  |
| 514 |  |
| 515 |  |
| 516 |  |

| Compound No. | Structure |
|---|---|
| 517 |  |
| 518 |  |
| 519 |  |
| 520 |  |
| 521 |  |
| 522 |  |
| 523 |  |
| 524 |  |

| Compound No. | Structure |
|---|---|
| 525 |  |
| 526 |  |
| 527 |  |
| 528 |  |
| 529 |  |
| 530 |  |
| 531 |  |
| 532 |  |

| Compound No. | Structure |
|---|---|
| 533 |  |
| 534 |  |
| 535 |  |
| 536 |  |
| 537 |  |
| 538 |  |
| 539 |  |
| 540 |  |

| Compound No. | Structure |
|---|---|
| 541 |  |
| 542 |  |
| 543 |  |
| 544 |  |
| 545 |  |
| 546 |  |
| 547 |  |

| Compound No. | Structure |
|---|---|
| 548 |  |
| 549 |  |
| 550 |  |
| 551 |  |
| 552 |  |
| 553 |  |
| 554 |  |

| Compound No. | Structure |
| --- | --- |
| 555 |  |
| 556 |  |
| 557 |  |
| 558 |  |
| 559 |  |
| 560 |  |
| 561 |  |
| 562 |  |

| Compound No. | Structure |
|---|---|
| 563 |  |
| 564 |  |
| 565 |  |
| 566 |  |
| 567 |  |
| 568 |  |
| 569 |  |

COMPOUNDS, COMPOSITIONS AND METHODS OF USE

CROSS REFERENCE TO RELATED APPLICATIONS

The present application is a national stage application under 35 U.S.C. 371 of International Application No. PCT/US2017/068186 filed Dec. 22, 2017, which claims priority to U.S. Provisional Application No. 62/438,836, filed on Dec. 23, 2016; and U.S. Provisional Application No. 62/560,493, filed on Sep. 19, 2017. The entire disclosures of each of the foregoing applications are incorporated herein by reference.

FIELD OF THE INVENTION

The invention relates to compounds, compositions and methods for modulating inclusion formation and stress granules in cells, and for treatment of neurodegenerative diseases, musculoskeletal diseases, cancer, ophthalmological diseases, and viral infections.

BACKGROUND OF THE INVENTION

One of the hallmarks of many neurodegenerative diseases is the accumulation of protein inclusions in the brain and central nervous system. These inclusions are insoluble aggregates of proteins and other cellular components that cause damage to cells and result in impaired function. Proteins such as tau, α-synuclein, huntingtin and β-amyloid have all been found to form inclusions in the brain and are linked to the development of a number of neurodegenerative diseases, including Alzheimer's disease and Huntington's disease. Recently, the TDP-43 protein was identified as one of the major components of protein inclusions that typify the neurogenerative diseases Amyotrophic Lateral Sclerosis (ALS) and Frontotemporal Lobar Dementia with ubiquitin inclusions (FTLD-U) (Ash, P. E., et al. (2010) *Hum Mol Genet* 19(16):3206-3218; Hanson, K. A., et al. (2010) *J Biol Chem* 285:11068-11072; Li, Y., et al. (2010) *Proc Natl Acad Sci U.S.A.* 107(7):3169-3174; Neumann, M., et al. (2006) *Science* 314:130-133; Tsai, K. J., et al. (2010) *J Exp Med* 207:1661-1673; Wils, H., et al. (2010) *Proc Natl Acad Sci U.S.A.* 170:3858-3863). Abnormalities in TDP-43 biology appear to be sufficient to cause neurodegenerative disease, as studies have indicated that mutations in TDP-43 occur in familial ALS (Barmada, S. J., et al. (2010) *J Neurosci* 30:639-649; Gitcho, M. A., et al. (2008) *Ann Neurol* 63(4):535-538; Johnson, B. S., et al. (2009) *J Biol Chem* 284:20329-20339; Ling, S. C., et al. (2010) *Proc Natl Acad Sci U.S.A.* 107:13318-13323; Sreedharan, J., et al. (2008) *Science* 319:1668-1672). In addition, TDP-43 has been found to play a role in the stress granule machinery (Colombrita, C., et al. (2009) *J Neurochem* 111(4):1051-1061; Liu-Yesucevitz, L., et al. (2010) *PLoS One* 5(10):e13250). Analysis of the biology of the major proteins that accumulate in other neurodegenerative diseases has lead to major advances in our understanding of the pathophysiology of TDP-43 inclusions as well as the development of new drug discovery platforms.

Currently, it is believed that aggregates that accumulate in neurodegenerative diseases like ALS, FTLD-U, Parkinson's disease and Huntington's disease accumulate slowly and are very difficult to disaggregate or perhaps can't be disaggregated. Thus, there is a need in the art for compositions and methods that can rapidly disaggregate these accumulating proteins, more specifically, TDP-43 and/or inhibit the formation of aggregates altogether.

SUMMARY OF THE INVENTION

In one aspect, the invention provides a compound of Formula (I).

(I)

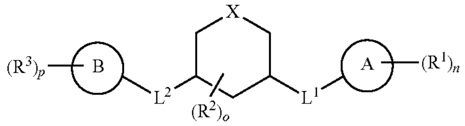

or a pharmaceutically acceptable salt thereof, wherein each of the variables and subvariables thereof are described herein, for example, in the Detailed Description below. In embodiments, a compound of Formula (I) is formulated as a composition (e.g., a pharmaceutical composition).

In another aspect, the invention provides methods for treatment of a neurodegenerative disease or disorder, a musculoskeletal disease or disorder, a cancer, an ophthalmological disease or disorder (e.g., a retinal disease or disorder), and/or a viral infection in a subject, the method comprising administering a compound of Formula (I) to a subject in need thereof.

In another aspect, the invention provides methods of diagnosing a neurodegenerative disease or disorder, a musculoskeletal disease or disorder, a cancer, an ophthalmological disease or disorder (e.g., a retinal disease or disorder), and/or a viral infection in a subject, the method comprising administering a compound of Formula (I) to a subject. For use in diagnosis, the compound of Formula (I) can be modified with a label.

In another aspect, the invention provides methods of modulating stress granules comprising administering a compound of Formula (I) to a cell or a subject in need thereof. In embodiments, the subject has a neurodegenerative disease or disorder, a musculoskeletal disease or disorder, a cancer, an ophthalmological disease or disorder (e.g., a retinal disease or disorder), and/or a viral infection.

In another aspect, the invention provides methods of modulating TDP-43 inclusion formation comprising administering a compound of Formula (I) to a cell or a subject in need thereof. In embodiments, the subject has a neurodegenerative disease or disorder, a musculoskeletal disease or disorder, a cancer, an ophthalmological disease or disorder (e.g., a retinal disease or disorder), and/or a viral infection.

In another aspect, the invention provides a method of screening for modulators of TDP-43 aggregation comprising contacting a compound of Formula (I) with the cell that expresses TDP-43 and develops spontaneous inclusions.

Still other objects and advantages of the invention will become apparent to those of skill in the art from the disclosure herein, which is simply illustrative and not restrictive. Thus, other embodiments will be recognized by the skilled artisan without departing from the spirit and scope of the invention.

DETAILED DESCRIPTION OF THE INVENTION

Figure 1A:
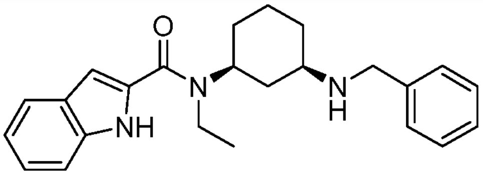
FIG. 1A-FIG. 1DD are a table of exemplary compounds of the invention.

Amyotrophic lateral sclerosis (ALS), also known as Lou Gehrig's disease or Charcot disease, is a fatal neurodegenerative disease that occurs with an incidence of approximately 1/100,000 (Mitchell, J. D. and Borasio, G. D., (2007) *Lancet* 369:2031-41). There is currently no therapy for ALS, and the average survival time of patients from the onset of the disease is roughly four years. ALS presents with motor weakness in the distal limbs that rapidly progresses proximally (Mitchell, J. D. and Borasio, G. D., (2007) *Lancet* 369:2031-41; Lambrechts, D. E., et al. (2004) *Trends Mol Med* 10:275-282). Studies over the past decade have indicated that TDP-43 is the major protein that accumulates in affected motor neurons in sporadic ALS (Neumann, M., et al. (2006) *Science* 314:130-133). The causes of sporadic ALS are not known, but identification of the major pathological species accumulating in the spinal cord of ALS patients represents a seminal advance for ALS research. To date, TDP-43 is the only protein that has been both genetically and pathologically linked with sporadic ALS, which represents the predominant form of the disease. Multiple papers have identified mutations in TDP-43 associated with sporadic and familial ALS (Sreedharan, J., et al. (2008) *Science* 319:1668-1672; Gitcho, M. A., et al. (2008) *Ann Neurol* 63(4):535-538; Neumann, M., et al. (2006) *Science* 314:130-133). Inhibitors of cell death and inclusions linked to TDP-43 represent a novel therapeutic approach to ALS, and may also elucidate the biochemical pathway linked to the formation of TDP-43 inclusions (Boyd, J. B., et al. (2014) *J Biomol Screen* 19(1):44-56). As such, TDP-43 represents one of the most promising targets for pharmacotherapy of ALS.

TDP-43 is a nuclear RNA binding protein that translocates to the cytoplasm in times of cellular stress, where it forms cytoplasmic inclusions. These inclusions then colocalize with reversible protein-mRNA aggregates termed "stress granules" (SGs) (Anderson P. and Kedersha, N. (2008) *Trends Biochem Sci* 33:141-150; Kedersha, N. and Anderson, P. (2002) *Biochem Soc Trans* 30:963-969; Lagier-Tourenne, C., et al. (2010) *Hum Mol Genet* 19:R46-R64). Under many stress-inducing conditions (e.g., arsenite treatment, nutrient deprivation), TDP-43 can co-localize with SGs. The reversible nature of SG-based aggregation offers a biological pathway that might be applied to reverse the pathology and toxicity associated with TDP-43 inclusion formation. Studies show that agents that inhibit SG formation also inhibit formation of TDP-43 inclusions (Liu-Yesucevitz, L., et al. (2010) *PLoS One* 5(10):e13250). The relationship between TDP-43 and stress granules is important because it provides a novel approach for dispersing TDP-43 inclusions using physiological pathways that normally regulate this reversible SG process. Investigating the particular elements of the SG pathway that regulate TDP-43 inclusion formation can identify selective approaches for therapeutic intervention to delay or halt the progression of disease. Stress granule biology also regulates autophagy and apoptosis, both of which are linked to neurodegeneration. Hence, compounds inhibiting TDP-43 aggregation may play a role in inhibiting neurodegeneration.

Compounds

Accordingly, in one aspect, the invention provides a compound of Formula (I):

Formula (I)

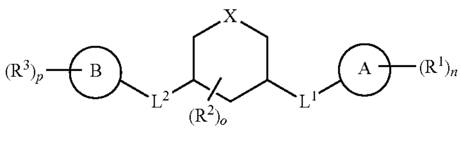

or a pharmaceutically acceptable salt thereof, wherein each of Ring A and Ring B is independently cycloalkyl, heterocyclyl, aryl, or heteroaryl; X is C(R')(R"), O, or $S(O)_x$; each of $L^1$ and $L^2$ is independently —$C_1$-$C_6$ heteroalkyl-, —C(O)$NR^A$—, —$NR^A$—, —$NR^A$C(O)—, —C(O)$NR^A$—$C_1$-$C_6$ alkyl-, —$C_1$-$C_6$ alkyl-C(O)$NR^A$—, —$NR^A$C(O)—$C_1$-$C_6$ alkyl-, —$C_1$-$C_6$ alkyl-$NR^A$C(O)—, —C(O)$NR^A$—$C_1$-$C_6$ heteroalkyl-, —$C_1$-$C_6$ heteroalkyl-C(O)$NR^A$—, —$NR^A$C(O)—$C_1$-$C_6$ heteroalkyl-, —$C_1$-$C_6$ heteroalkyl-$NR^A$C(O)—, —$C_1$-$C_6$ heteroalkyl-C(O)—, or —C(O)—$C_1$-$C_6$ heteroalkyl-, each of which is optionally substituted with 1-5 $R^4$; each of $R^1$ and $R^3$ is independently $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, halo, cyano, nitro, azido, cycloalkyl, heterocyclyl, aryl, heteroaryl, —$OR^B$, —C(O)$R^D$, —C(O)$OR^B$, —$NR^AR^C$, —$NR^A$C(O)$R^D$, —$S(O)_xR^E$, —$OS(O)_xR^E$, —C(O)$NR^A$ $S(O)_xR^E$, —$NR^AS(O)_xR^E$, or —$S(O)_xNR^A$, each of which is optionally substituted with 1-5 $R^5$; or each $R^2$ is independently $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, halo, cyano, or nitro; each of R' and R" is independently H, $C_1$-$C_6$ alkyl, or $C_1$-$C_6$ heteroalkyl; each $R^4$ is independently deuterium, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, halo, cyano, cycloalkyl, heterocyclyl, —$OR^B$, —C(O)$R^D$, —C(O)$OR^B$, —C(O)$NR^AR^C$, or —$SR^E$, each of which is optionally substituted with 1-5 $R^6$; or one $R^4$, taken together with the atoms to which it is attached, forms a ring (e.g., a 5-7 membered ring) with Ring A, optionally substituted with 1-5 $R^5$; or two $R^4$, taken together with the atoms to which they are attached, form a ring (e.g., a 3-7 membered ring), optionally substituted with 1-5 $R^6$; each $R^5$ is independently $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, halo, cyano, or oxo; or two $R^5$, taken together with the atoms to which they are attached, form a ring (e.g., a 3-7 membered ring), optionally substituted with 1-5 $R^6$; each $R^A$, $R^B$, $R^C$, $R^D$, or $R^E$ is independently H, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, or heteroaryl, each of which is optionally substituted with 1-4 $R^6$; or $R^A$ and $R^C$, together with the atoms to which each is attached, form a heterocyclyl ring; each $R^6$ is independently $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_1$-$C_6$ haloalkyl, cycloalkyl, heterocyclyl, aryl, heteroaryl, halo, cyano, or nitro; each of n, o, and p is independently 0, 1, 2, 3, 4, 5, or 6; and x is 0, 1, or 2.

In some embodiments, Ring A is aryl or heteroaryl. In some embodiments, Ring A is aryl. In some embodiments, Ring A is phenyl. In some embodiments, Ring A is

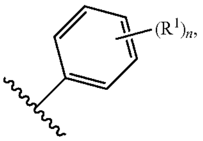 e.g., 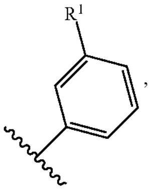,

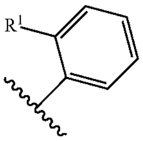, 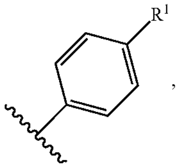,

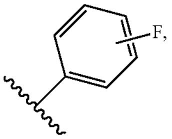 or, 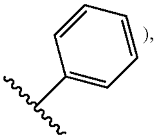),

In some embodiments, Ring A is heteroaryl. In some embodiments, Ring A is a 6-membered heteroaryl. In some embodiments, Ring A is a nitrogen-containing heteroaryl (e.g., a 6-membered nitrogen-containing heteroaryl). In some embodiments, Ring A is pyridyl or pyrimidinyl. In some embodiments, Ring A is

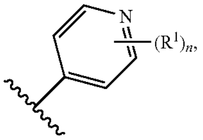 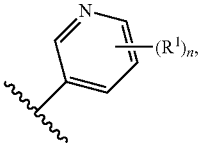

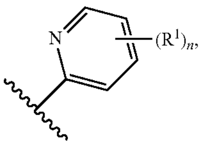 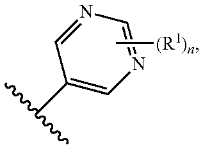

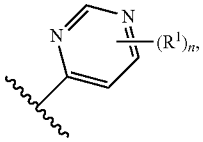 or 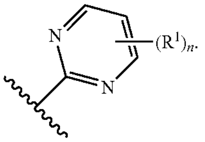

In some embodiments, Ring A is a benzofuran or an azabenzofuran. In some embodiments, Ring A is

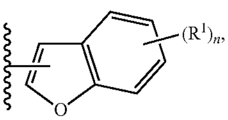 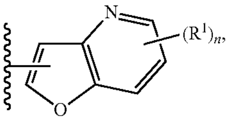

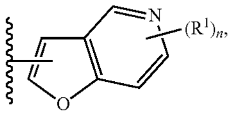 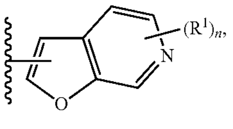 or

-continued

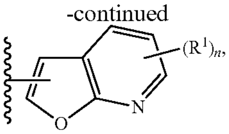

wherein each $R^1$ group can be on either the 5- or 6-membered ring).

In some embodiments, ring A is a benzoxazole (e.g.,

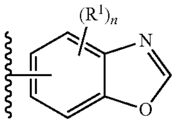, wherein each $R^1$ group can be on either the 5- or 6-membered ring).

In some embodiments, ring A is an isoxazole (e.g., 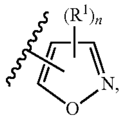, or 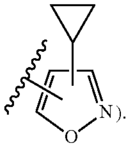).

In some embodiments, Ring A is cycloalkyl. In some embodiments, Ring A is a 3-membered cycloalkyl. In some embodiments, Ring A is cyclopropyl (e.g., 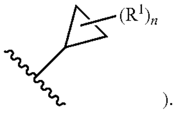).

In some embodiments, Ring A is indanyl (e.g., 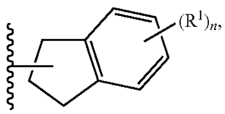, wherein each $R^1$ group can be on either the 5- or 6-membered ring).

In some embodiments, Ring A is heterocyclyl. In some embodiments, Ring A is 6-membered heterocyclyl. In some embodiments, Ring A is an oxygen-containing heterocyclyl. In some embodiments, Ring A is tetrahydropyranyl (e.g., 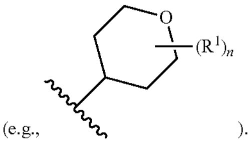).

In some embodiments, Ring A is selected from the group consisting of:

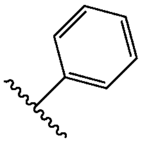, 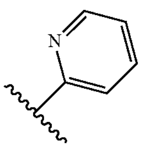, 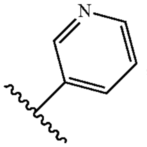, 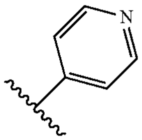, 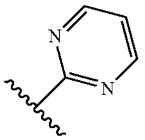, 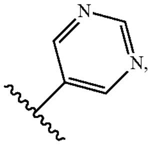 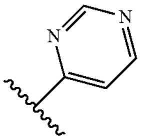, 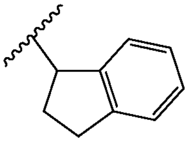, 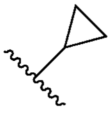, 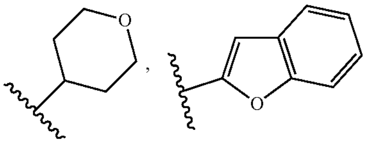, 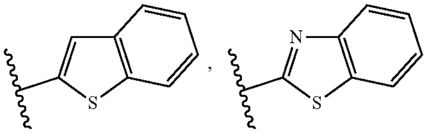, 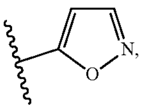 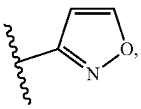 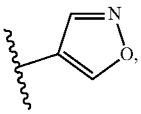 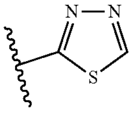, 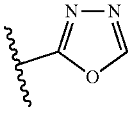, 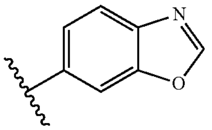, 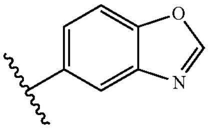, 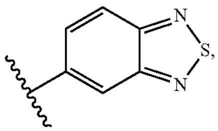, 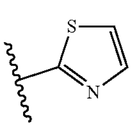, 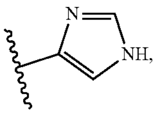 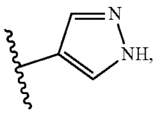 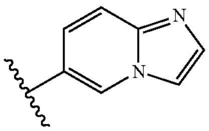, 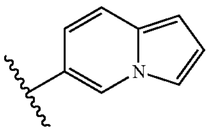, 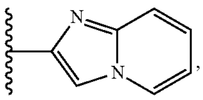, and 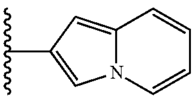, wherein n is 0, 1, or 2.

In some embodiments, o is 0.

In some embodiments, n is 0. In some embodiments, n is 1.

In some embodiments, $R^1$ is $C_1$-$C_6$ alkyl (e.g., Me), halo (e.g., fluoro or chloro), azido, cyclopropyl, 2-propynyloxy, cyano, —C(O)$R^D$ (e.g., —C(O)-(4-ethynyl)phenyl), or —$OR^B$ (e.g., —$OCH_3$ or —$OCF_3$). In some embodiments, $R^1$ is halo (e.g., fluoro or chloro).

In some embodiments, Ring B is aryl. In some embodiments, Ring B is phenyl. In some embodiments, Ring B is

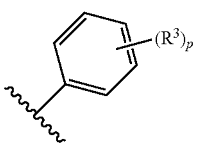 (e.g., 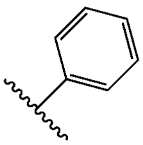).

In some embodiments, Ring B is heteroaryl. In some embodiments, Ring B is a bicyclic heteroaryl (e.g., a bicyclic nitrogen-containing heteroaryl). In some embodiments, Ring B is indolyl or pyrrolypyridinyl

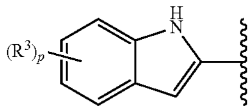 or 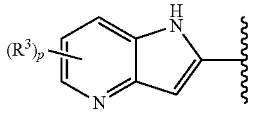 e.g., 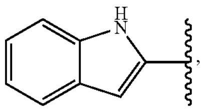, 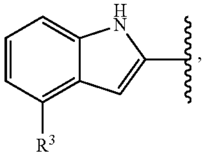, or 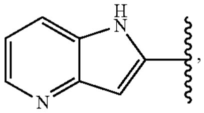, wherein each $R^3$ group if not specified can be on either the 5- or 6-membered ring). In some embodiments, Ring B is indolyl

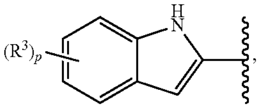, (e.g., 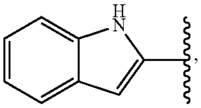, 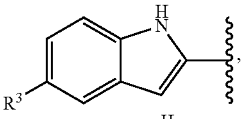, 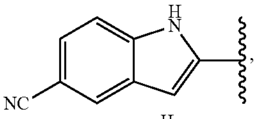, 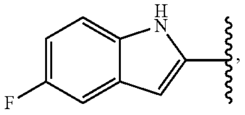, or 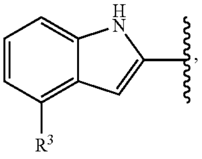, wherein each $R^3$ group if not specified can be on either the 5- or 6-membered ring).

In some embodiments, Ring B is benzimidazolyl

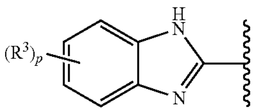 (e.g.,

-continued

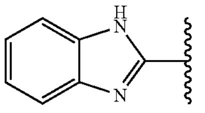 or 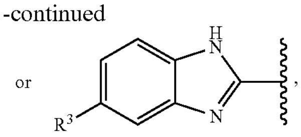, wherein each $R^3$ group if not specified can be on either the 5- or 6-membered ring).

In some embodiments, p is 0. In some embodiments, p is 1.

In some embodiments, $R^3$ is —$OR^B$ (e.g., —$OCH_3$ or $OCF_3$), $C_1$-$C_6$ haloalkyl (e.g., —$CF_3$), halo (e.g., F or Cl), amino, azido, nitro, cyano, cycloalkyl (e.g., cyclopropyl), or $S(O)_xR^E$ (e.g., —$SO_2Me$). In some embodiments, $R^3$ is —$OR^B$ (e.g., —$OCH_3$ or $OCF_3$).

In some embodiments, X is C(R')(R"). In some embodiments, each of R' and R" is independently H.

In some embodiments, X is $S(O)_x$. In some embodiments, x is 1. In some embodiments, x is 2. In some embodiments, X is $SO_2$.

In some embodiments, X is O.

In some embodiments, each of $L^1$ and $L^2$ is independently —$C_1$-$C_6$ heteroalkyl-, —C(O)$NR^A$—, —$NR^A$C(O)—, —C(O)$NR^A$—$C_1$-$C_6$ alkyl-, —$C_1$-$C_6$ alkyl-C(O)$NR^A$—, —$NR^A$C(O)—$C_1$-$C_6$ alkyl-, —$C_1$-$C_6$ alkyl-$NR^A$C(O)—, —C(O)$NR^A$—$C_1$-$C_6$ heteroalkyl-, —$C_1$-$C_6$ heteroalkyl-C(O)$NR^A$—, —$NR^A$C(O)—$C_1$-$C_6$ heteroalkyl-, —$C_1$-$C_6$ heteroalkyl-$NR^A$C(O)—, —$C_1$-$C_6$ heteroalkyl-C(O)—, or —C(O)—$C_1$-$C_6$ heteroalkyl-, each of which is optionally substituted with 1-5 $R^4$.

In some embodiments, each of $L^1$ and $L^2$ is independently —$C_1$-$C_6$ heteroalkyl-, —C(O)$NR^A$—, —$NR^A$C(O)—, —C(O)$NR^A$—$C_1$-$C_6$ alkyl-, —$C_1$-$C_6$ alkyl-C(O)$NR^A$—, —$NR^A$C(O)—$C_1$-$C_6$ alkyl-, or —$C_1$-$C_6$ alkyl-$NR^A$C(O)—, each of which is optionally substituted with 1-5 $R^4$. In some embodiments, each of $L^1$ and $L^2$ is independently $C_1$-$C_6$ heteroalkyl-, —C(O)$NR^A$—, or —$NR^A$C(O)—, each of which is optionally substituted with 1-5 $R^4$.

In some embodiments, $L^1$ is —$C_1$-$C_6$ heteroalkyl- (e.g., —$NHCH_2$—, —$NHCH_2CH_2$—, —$N(CH_3)CH_2$)—, —$N(R^4)CH_2$—, or —$NHC(R^4)_2$—) or —$NR^A$C(O)— (e.g., —NHC(O)—). In some embodiments, $L^1$ is —$C_1$-$C_6$ heteroalkyl- (e.g., —$NHCH_2$—, —$NHCH_2CH_2$—, —$N(CH_3)CH_2$)—, —$N(R^4)CH_2$—, or —$NHC(R^4)_2$—). In some embodiments, $L^1$ is —$NHCH_2$—. In some embodiments, $L^1$ is —$NR^A$C(O)— (e.g., —NHC(O)—). -. In some embodiments, $L^1$ is —$C_1$-$C_6$ heteroalkyl-substituted with at least one deuterium on one or more carbon atoms (e.g., —NHCHD-, —$NHCD_2$-, —$NHCD_2CH_2$—, —$NHCH_2CD_2$-, —$NHCD_2CD_2$-, —$N(CH_3)CD_2$-, —$N(R^4)CD_2$-). In some embodiments, $L^1$ is —$NR^A$C(O)— (e.g., —NHC(O)—).

In some embodiments, $R^4$, taken together with the atoms to which it is attached, forms a ring with Ring A (e.g., a 5-7 membered ring, e.g., a cyclopentyl ring fused to Ring A or a piperidinyl ring fused to Ring A). In some embodiments, one $R^4$ is taken together with the atoms to which it is attached to form a cyclopentyl ring fused to Ring A. In some embodiments, one $R^4$ is taken together with the atoms to which it is attached to form piperidinyl ring fused to Ring A.

In some embodiments, two $R^4$ are taken together with the atoms to which they are attached to form a heterocyclyl ring (e.g., a 4-membered heterocyclyl, e.g., oxetanyl).

In some embodiments, $L^2$ is C(O)$NR^A$—. In some embodiments, $R^A$ is $C_1$-$C_6$ alkyl (e.g., —$CH_2CH_3$) or $C_1$-$C_6$ haloalkyl (e.g., —$CH_2CF_3$). In some embodiments, $R^A$ is $C_1$-$C_6$ alkyl (e.g., —$CH_2CH_3$). In some embodiments, $R^A$ is $C_1$-$C_6$ haloalkyl (e.g., —$CH_2CF_3$).

In some embodiments, the compound of Formula (I) is a compound of Formula (I-a), (I-b), (I-c), or (I-d):

Foormula (I-a)

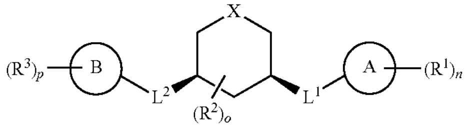

Formula (I-b)

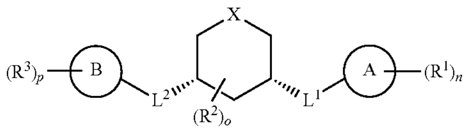

Formula (I-c)

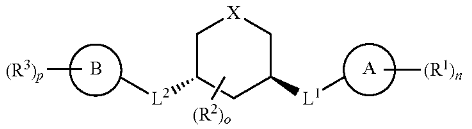

Formula (I-d)

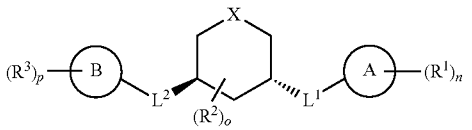

or a pharmaceutically acceptable salt thereof, wherein Ring A, Ring B, X, $L^1$, $L^2$, $R^1$, $R^2$, $R^3$, n, o, p, and subvariables thereof are as described in any of the preceding claims.

In some embodiments, Ring A is aryl or heteroaryl. In some embodiments, Ring A is aryl. In some embodiments, Ring A is phenyl. In some embodiments, Ring A is

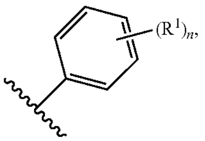 e.g., 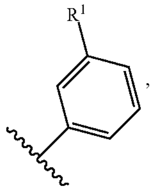,

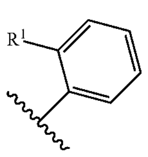, 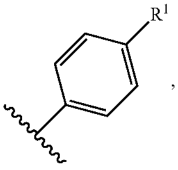,

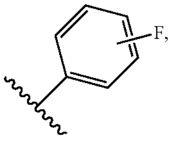 or, 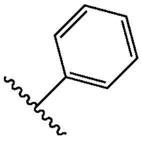),

In some embodiments, Ring A is heteroaryl. In some embodiments, Ring A is a 6-membered heteroaryl. In some embodiments, Ring A is a nitrogen-containing heteroaryl (e.g., a 6-membered nitrogen-containing heteroaryl). In some embodiments, Ring A is pyridyl or pyrimidinyl. In some embodiments, Ring A is

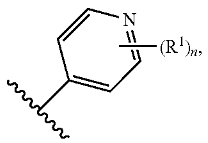
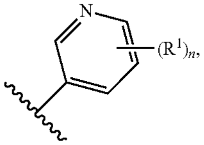
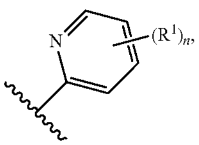
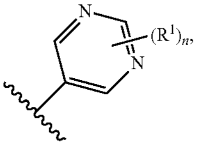
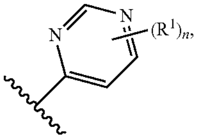
or
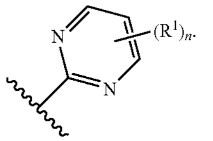

In some embodiments, Ring A is benzofuran or azabenzofuran. In some embodiments, Ring A is

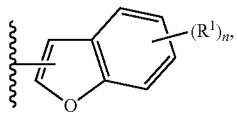
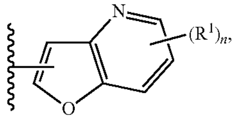
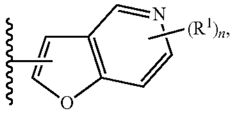
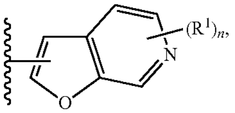
or
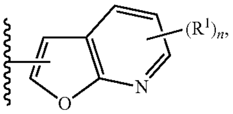

wherein each $R^1$ group can be on either the 5- or 6-membered ring.

In some embodiments, ring A is a benzoxazole (e.g.,

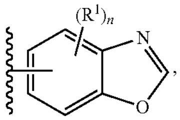

wherein each $R^1$ group can be on either the 5- or 6-membered ring).

In some embodiments, ring A is an isoxazole (e.g., 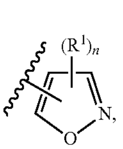 or 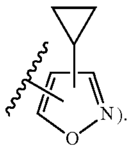

In some embodiments, Ring A is cycloalkyl. In some embodiments, Ring A is a 3-membered cycloalkyl. In some embodiments, Ring A is cyclopropyl

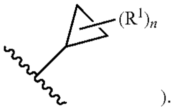

(e.g., ).

In some embodiments, Ring A is indanyl

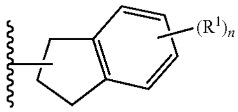

(e.g., , wherein each $R^1$ group can be on either the 5- or 6-membered ring).

In some embodiments, Ring A is heterocyclyl. In some embodiments, Ring A is 6-membered heterocyclyl. In some embodiments, Ring A is an oxygen-containing heterocyclyl. In some embodiments, Ring A is tetrahydropyranyl

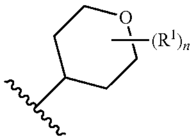

(e.g., ).

In some embodiments, Ring A is selected from the group consisting of:

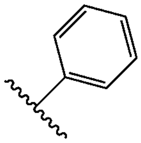, 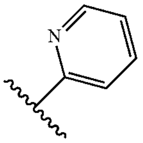, 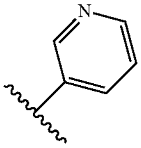,
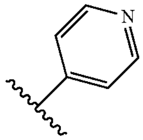, 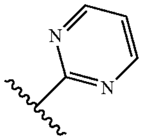, 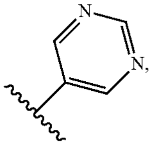
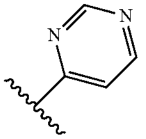, 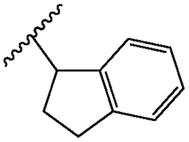, 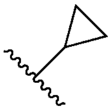,
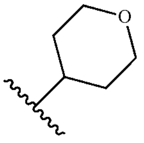, 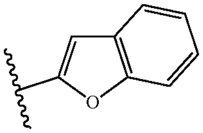,
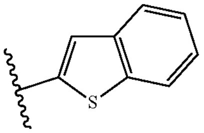, 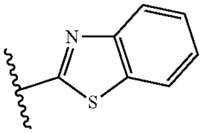,
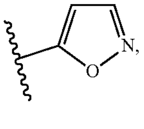 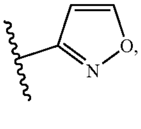 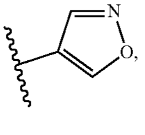

-continued

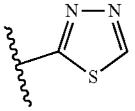, 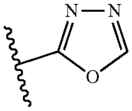, 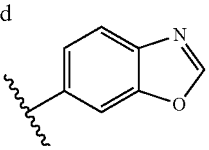,

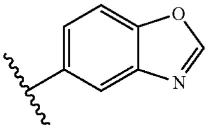, 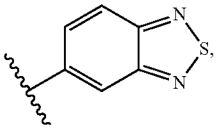

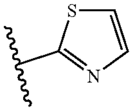, 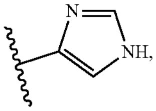 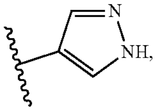

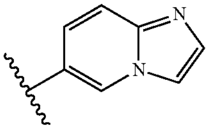, 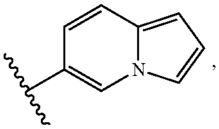,

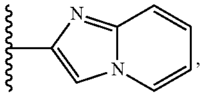, and 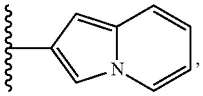, wherein n is 0, 1, or 2.

In some embodiments, o is 0.

In some embodiments, n is 0. In some embodiments, n is 1.

In some embodiments, $R^1$ is halo (e.g., fluoro or chloro), $C_1$-$C_6$ alkyl (e.g., Me), azido, cyclopropyl, 2-propynyloxy, cyano, —C(O)$R^D$ (e.g., —C(O)-(4-ethynyl)phenyl), or —$OR^B$ (e.g., —$OCH_3$ or —$OCF_3$). In some embodiments, $R^1$ is halo (e.g., fluoro or chloro).

In some embodiments, Ring B is aryl. In some embodiments, Ring B is phenyl. In some embodiments, Ring B is

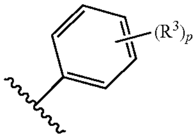 (e.g., 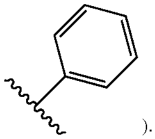 ).

In some embodiments, Ring B is heteroaryl. In some embodiments, Ring B is a bicyclic heteroaryl (e.g., a bicyclic nitrogen-containing heteroaryl). In some embodiments, Ring B is indolyl or pyrrolypyridinyl (e.g., 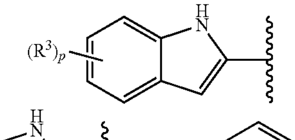 or

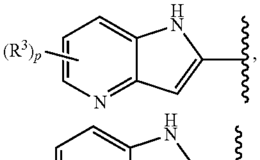, e.g., 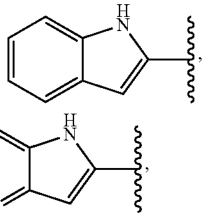,

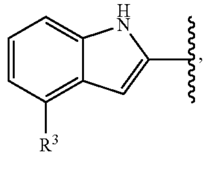, or 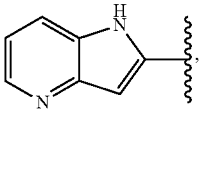, wherein each $R^3$ group if not specified can be on either the 5- or 6-membered ring).). In some embodiments, Ring B is indolyl

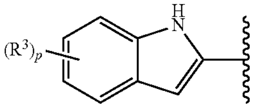, (e.g., 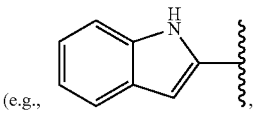,

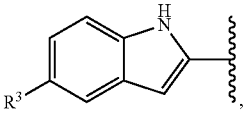, 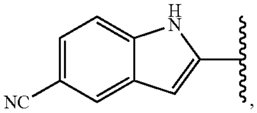,

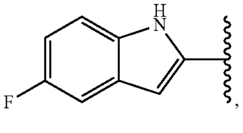, or 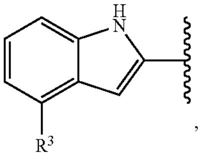, wherein each $R^3$ group if not specified can be on either the 5- or 6-membered ring).). In some embodiments, Ring B is benzimidazolyl

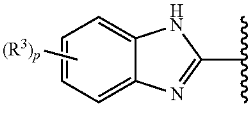 (e.g., 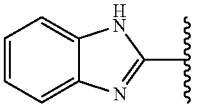 or

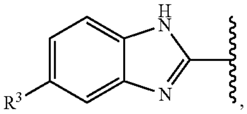, wherein each $R^3$ group if not specified can be on either the 5- or 6-membered ring).).

In some embodiments, p is 0. In some embodiments, p is 1.

In some embodiments, $R^3$ is —$OR^B$ (e.g., —$OCH_3$ or —$OCF_3$), $C_1$-$C_6$ haloalkyl (e.g., —$CF_3$), halo (e.g., F or Cl), amino, azido, nitro, cyano, cycloalkyl (e.g., cyclopropyl), or $S(O)_xR^E$ (e.g., —$SO_2$Me). In some embodiments, $R^3$ is —$OR^B$ (e.g., —$OCH_3$ or $OCF_3$).

In some embodiments, X is C(R')(R"). In some embodiments, each of R' and R" is independently H.

In some embodiments, X is $S(O)_x$. In some embodiments, x is 1. In some embodiments, x is 2. In some embodiments, X is $SO_2$.

In some embodiments, X is O.

In some embodiments, each of $L^1$ and $L^2$ is independently —$C_1$-$C_6$ heteroalkyl-, —C(O)$NR^A$—, —$NR^A$C(O)—, —C(O)$NR^A$—$C_1$-$C_6$ alkyl-, —$C_1$-$C_6$ alkyl-C(O)$NR^A$—, —$NR^A$C(O)—$C_1$-$C_6$ alkyl-, or —$C_1$-$C_6$ alkyl-$NR^A$C(O)—, each of which is optionally substituted with 1-5 $R^4$. In some embodiments, each of $L^1$ and $L^2$ is independently $C_1$-$C_6$ heteroalkyl-, —C(O)$NR^A$—, or —$NR^A$C(O)—, each of which is optionally substituted with 1-5 $R^4$.

In some embodiments, $L^1$ is —$C_1$-$C_6$ heteroalkyl- (e.g., —$NHCH_2$—, —$NHCH_2CH_2$—, —$N(CH_3)CH_2$)—, —$N(R^4)CH_2$—, or —$NHC(R^4)_2$—) or —$NR^A$C(O)— (e.g., —NHC(O)—). In some embodiments, $L^1$ is —$C_1$-$C_6$ heteroalkyl- (e.g., —$NHCH_2$—, —$NHCH_2CH_2$—, —$N(CH_3)$ $CH_2$)—, —$N(R^4)CH_2$—, or —$NHC(R^4)_2$—). In some embodiments, $L^1$ is —$NHCH_2$—. In some embodiments, $L^1$ is —$NR^A$C(O)— (e.g., —NHC(O)—). -. In some embodiments, $L^1$ is —$C_1$-$C_6$ heteroalkyl-substituted with at least one deuterium on one or more carbon atoms (e.g., —NHCHD-, —$NHCD_2$-, —$NHCD_2CH_2$—, —$NHCH_2CD_2$-, —$NHCD_2CD_2$-, —$N(CH_3)CD_2$-, —$N(R^4)$ $CD_2$-).

In some embodiments, $R^4$, taken together with the atoms to which it is attached, forms a ring with Ring A (e.g., a 5-7 membered ring, e.g., a cyclopentyl ring fused to Ring A or a piperidinyl ring fused to Ring A). In some embodiments, one $R^4$ is taken together with the atoms to which it is attached to form a cyclopentyl ring fused to Ring A. In some embodiments, one $R^4$ is taken together with the atoms to which it is attached to form piperidinyl ring fused to Ring A.

In some embodiments, two $R^4$ are taken together with the atoms to which they are attached to form a heterocyclyl ring (e.g., a 4-membered heterocyclyl, e.g., oxetanyl).

In some embodiments, $L^2$ is C(O)$NR^A$—. In some embodiments, $R^A$ is $C_1$-$C_6$ alkyl (e.g., —$CH_2CH_3$) or $C_1$-$C_6$ haloalkyl (e.g., —$CH_2CF_3$). In some embodiments, $R^A$ is $C_1$-$C_6$ alkyl (e.g., —$CH_2CH_3$). In some embodiments, $R^A$ is $C_1$-$C_6$ haloalkyl (e.g., —$CH_2CF_3$).

In some embodiments, the compound of Formula (I) is a compound of Formula (I-e):

Formula (I-e)

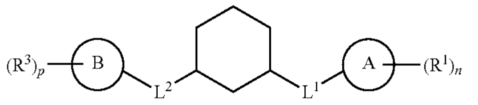

or a pharmaceutically acceptable salt thereof, wherein Ring A, Ring B, $L^1$, $L^2$, $R^1$, $R^2$, $R^3$, n, o, p, and subvariables thereof are as described in any of the preceding claims.

In some embodiments, Ring A is aryl or heteroaryl. In some embodiments, Ring A is aryl. In some embodiments, Ring A is phenyl. In some embodiments, Ring A is

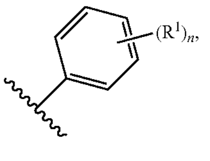 e.g., 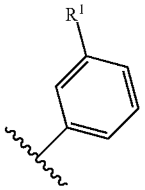, 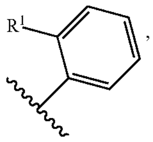, 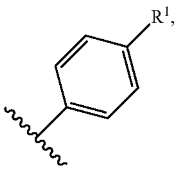, 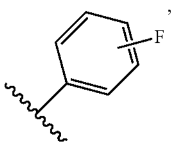, or, 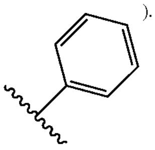).

In some embodiments, Ring A is heteroaryl. In some embodiments, Ring A is a 6-membered heteroaryl. In some embodiments, Ring A is a nitrogen-containing heteroaryl (e.g., a 6-membered nitrogen-containing heteroaryl). In some embodiments, Ring A is pyridyl or pyrimidinyl. In some embodiments, Ring A is

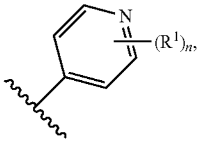 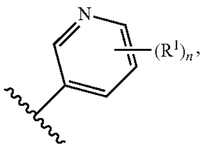

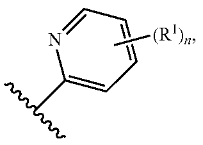 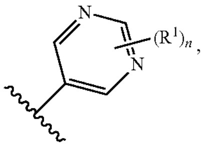

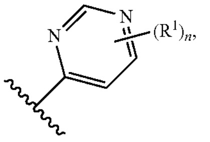 or 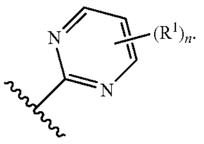

A is a benzofuran or an azabenzofuran (e.g., 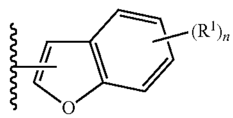, 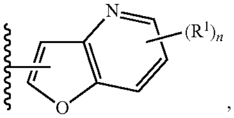,

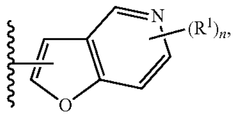 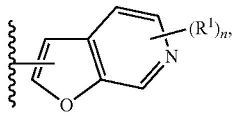

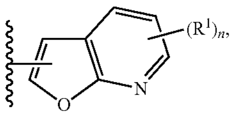

wherein each $R^1$ group can be on either the 5- or 6-membered ring).

In some embodiments, ring A is a benzoxazol (e.g., 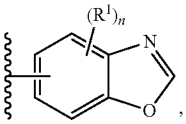, wherein each $R^1$ group can be on either the 5- or 6-membered ring).

In some embodiments, ring A is an isoxazole (e.g., 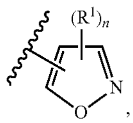, or 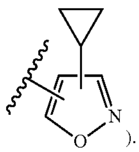).

In some embodiments, Ring A is cycloalkyl. In some embodiments, Ring A is a 3-membered cycloalkyl. In some embodiments, Ring A is cyclopropyl (e.g., 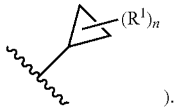 ).

In some embodiments, Ring A is indanyl (e.g., 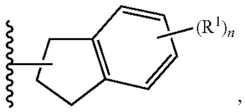, wherein each $R^1$ group can be on either the 5- or 6-membered ring).

In some embodiments, Ring A is heterocyclyl. In some embodiments, Ring A is 6-membered heterocyclyl. In some embodiments, Ring A is an oxygen-containing heterocyclyl. In some embodiments, Ring A is tetrahydropyranyl (e.g., 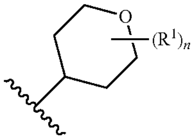 ).

In some embodiments, Ring A is selected from the group consisting of:

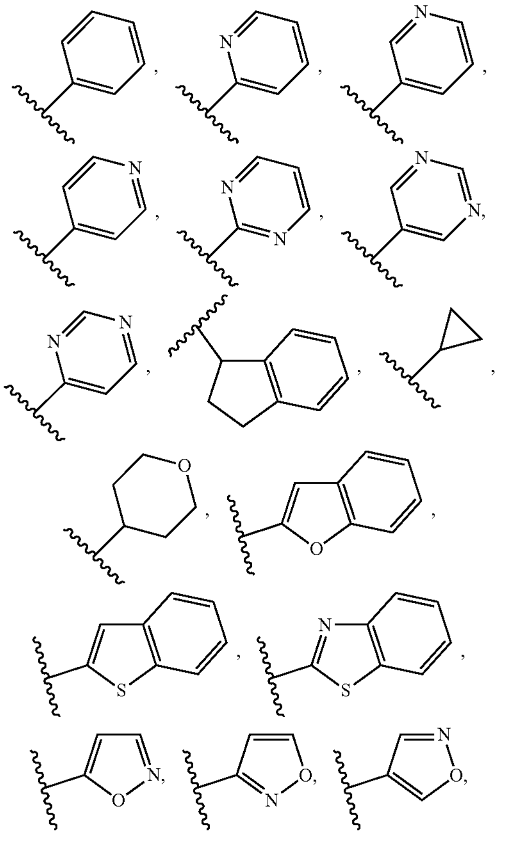

-continued

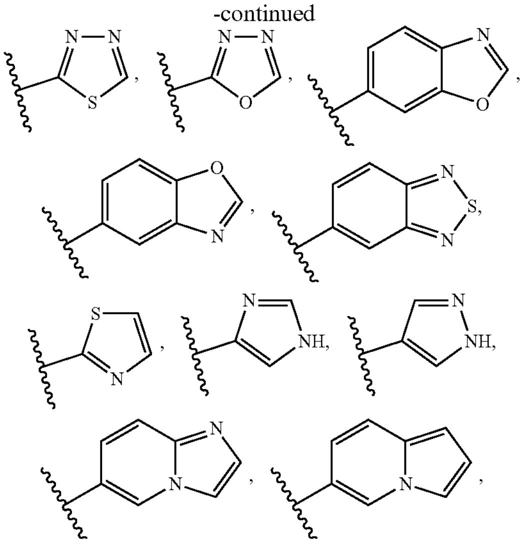

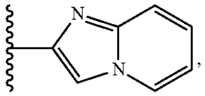, and 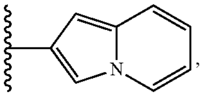, wherein n is 0, 1, or 2.

In some embodiments, o is 0.

In some embodiments, n is 0. In some embodiments, n is 1.

In some embodiments, $R^1$ is halo (e.g., fluoro or chloro), $C_1$-$C_6$ alkyl (e.g., Me), azido, cyclopropyl, 2-propynyloxy, cyano, —C(O)$R^D$ (e.g., —C(O)-(4-ethynyl)phenyl), or —$OR^B$ (e.g., —$OCH_3$ or —$OCF_3$). In some embodiments, $R^1$ is halo (e.g., fluoro or chloro).

In some embodiments, Ring B is aryl. In some embodiments, Ring B is phenyl. In some embodiments, Ring B is

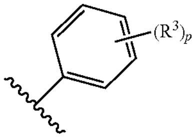 (e.g., 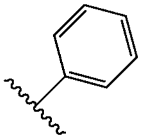 ).

In some embodiments, Ring B is heteroaryl. In some embodiments, Ring B is a bicyclic heteroaryl (e.g., a bicyclic nitrogen-containing heteroaryl). In some embodiments, Ring B is indolyl or pyrrolypyridinyl (e.g., 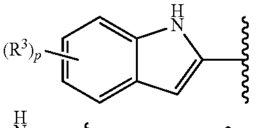 or

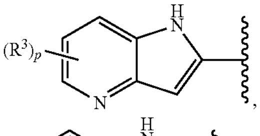, e.g., 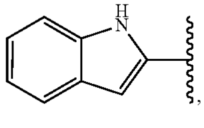,

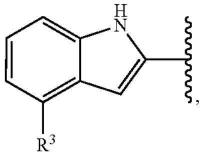, or 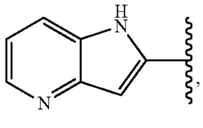, wherein each $R^3$ group if not specified can be on either the 5- or 6-membered ring). In some embodiments, Ring B is indolyl

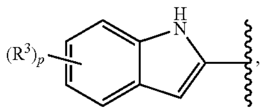
(e.g.,
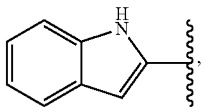
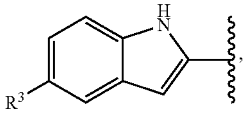
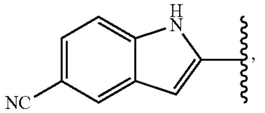
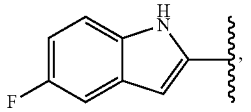
or
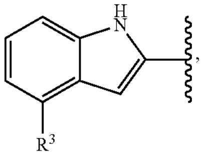

wherein each $R^3$ group if not specified can be on either the 5- or 6-membered ring). In some embodiments, Ring B is benzimidazolyl

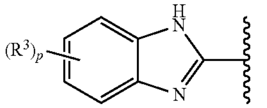
(e.g.,
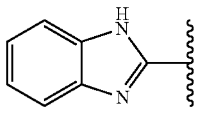
or
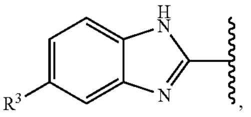

wherein each $R^3$ group if not specified can be on either the 5- or 6-membered ring).

In some embodiments, p is 0. In some embodiments, p is 1.

In some embodiments, $R^3$ is —$OR^B$ (e.g., —$OCH_3$ or —$OCF_3$), $C_1$-$C_6$ haloalkyl (e.g., —$CF_3$), halo (e.g., F or Cl), amino, azido, nitro, cyano, cycloalkyl (e.g., cyclopropyl), or $S(O)_xR^E$ (e.g., —$SO_2Me$). In some embodiments, $R^3$ is —$OR^B$ (e.g., —$OCH_3$ or $OCF_3$).

In some embodiments, each of $L^1$ and $L^2$ is independently —$C_1$-$C_6$ heteroalkyl-, —C(O)$NR^A$—, —$NR^A$C(O)—, —C(O)$NR^A$—$C_1$-$C_6$ alkyl-, —$C_1$-$C_6$ alkyl-C(O)$NR^A$—, —$NR^A$C(O)—$C_1$-$C_6$ alkyl-, or —$C_1$-$C_6$ alkyl-$NR^A$C(O)—, each of which is optionally substituted with 1-5 $R^4$. In some embodiments, each of $L^1$ and $L^2$ is independently $C_1$-$C_6$ heteroalkyl-, —C(O)$NR^A$—, or —$NR^A$C(O)—, each of which is optionally substituted with 1-5 $R^4$.

In some embodiments, $L^1$ is —$C_1$-$C_6$ heteroalkyl- (e.g., —$NHCH_2$—, —$NHCH_2CH_2$—, —$N(CH_3)CH_2$)—, —$N(R^4)CH_2$—, or —$NHC(R^4)_2$—) or —$NR^A$C(O)— (e.g., —NHC(O)—). In some embodiments, $L^1$ is —$C_1$-$C_6$ heteroalkyl- (e.g., —$NHCH_2$—, —$NHCH_2CH_2$—, —$N(CH_3)CH_2$)—, —$N(R^4)CH_2$—, or —$NHC(R^4)_2$—). In some embodiments, $L^1$ is —$NHCH_2$—. In some embodiments, $L^1$ is —$NR^A$C(O)— (e.g., —NHC(O)—). -. In some embodiments, $L^1$ is —$C_1$-$C_6$ heteroalkyl-substituted with at least one deuterium on one or more carbon atoms (e.g., —NHCHD-, —$NHCD_2$-, —$NHCD_2CH_2$—, —$NHCH_2CD_2$-, —$NHCD_2CD_2$-, —$N(CH_3)CD_2$-, —$N(R^4)CD_2$.

In some embodiments, $R^4$, taken together with the atoms to which it is attached, forms a ring with Ring A (e.g., a 5-7 membered ring, e.g., a cyclopentyl ring fused to Ring A or a piperidinyl ring fused to Ring A). In some embodiments, one $R^4$ is taken together with the atoms to which it is attached to form a cyclopentyl ring fused to Ring A. In some embodiments, one $R^4$ is taken together with the atoms to which it is attached to form piperidinyl ring fused to Ring A.

In some embodiments, two $R^4$ are taken together with the atoms to which they are attached to form a heterocyclyl ring (e.g., a 4-membered heterocyclyl, e.g., oxetanyl).

In some embodiments, $L^2$ is C(O)$NR^A$—. In some embodiments, $R^A$ is $C_1$-$C_6$ alkyl (e.g., —$CH_2CH_3$) or $C_1$-$C_6$ haloalkyl (e.g., —$CH_2CF_3$). In some embodiments, $R^A$ is $C_1$-$C_6$ alkyl (e.g., —$CH_2CH_3$). In some embodiments, $R^A$ is $C_1$-$C_6$ haloalkyl (e.g., —$CH_2CF_3$).

In some embodiments, the compound of Formula (I) is a compound of Formula (I-f), Formula (I-g), or Formula (I-h):

Formula (I-f)

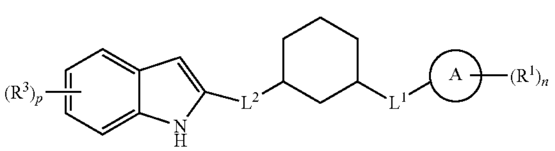

Formula (I-g)

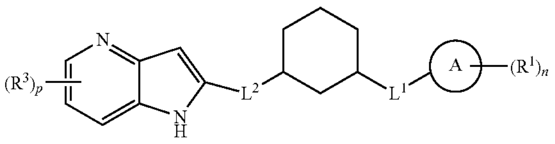

Formula (I-h)

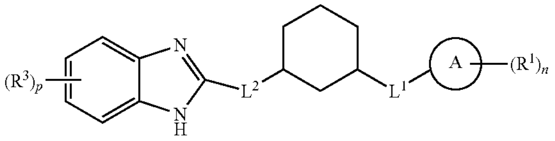

or a pharmaceutically acceptable salt thereof, wherein Ring A, $L^1$, $L^2$, $R^1$, $R^2$, $R^3$, n, p, and subvariables thereof are as described in any of the preceding claims.

In some embodiments, Ring A is aryl or heteroaryl. In some embodiments, Ring A is aryl. In some embodiments, Ring A is phenyl. In some embodiments, Ring A is

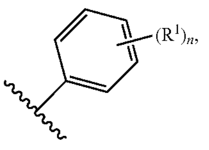
e.g.,
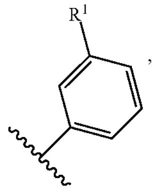
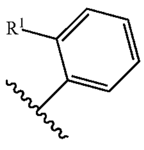
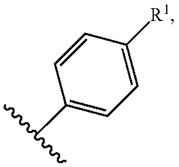
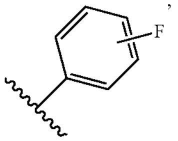
or,
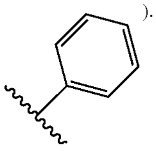
).

In some embodiments, Ring A is heteroaryl. In some embodiments, Ring A is a 6-membered heteroaryl. In some embodiments, Ring A is a nitrogen-containing heteroaryl (e.g., a 6-membered nitrogen-containing heteroaryl). In some embodiments, Ring A is pyridyl or pyrimidinyl. In some embodiments, Ring A is

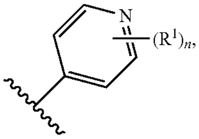
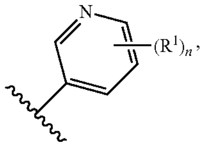
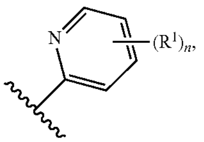
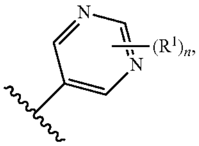
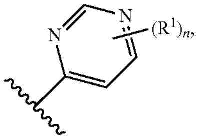 or 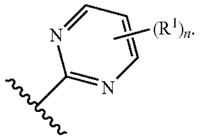

A is a benzofuran or an azabenzofuran (e.g., 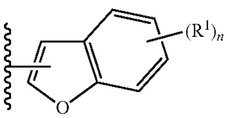, 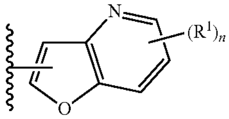, 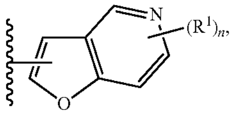 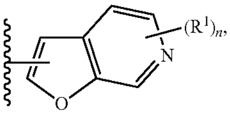 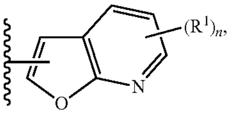

wherein each $R^1$ group can be on either the 5- or 6-membered ring).

In some embodiments, Ring A is a benzoxazole (e.g., 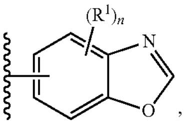, wherein each $R^1$ group can be on either the 5- or 6-membered ring).

In some embodiments, Ring A is an isoxazole (e.g., 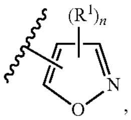, or 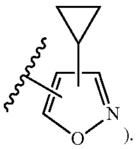).

In some embodiments, Ring A is cycloalkyl. In some embodiments, Ring A is a 3-membered cycloalkyl. In some embodiments, Ring A is cyclopropyl (e.g., 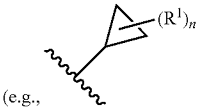).

In some embodiments, Ring A is indanyl (e.g., 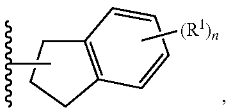, wherein each $R^1$ group can be on either the 5- or 6-membered ring).

In some embodiments, Ring A is heterocyclyl. In some embodiments, Ring A is 6-membered heterocyclyl. In some embodiments, Ring A is an oxygen-containing heterocyclyl. In some embodiments, Ring A is tetrahydropyranyl (e.g., 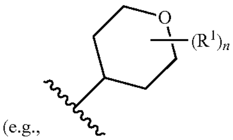).

In some embodiments, Ring A is selected from the group consisting of:

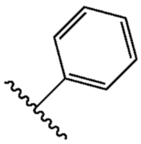, 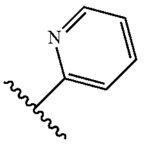, 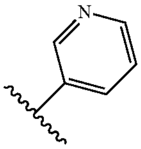,
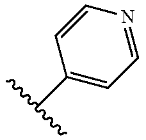, 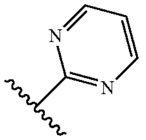, 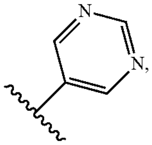,
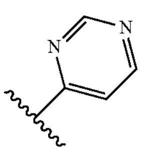, 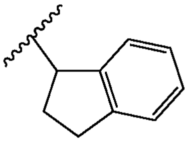, 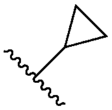,
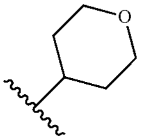, 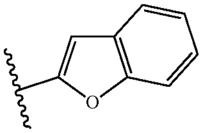,
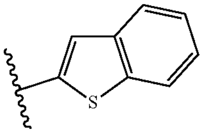, 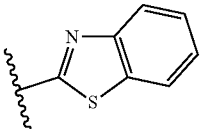,
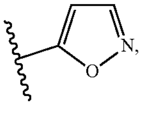, 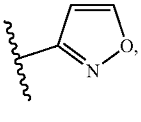, 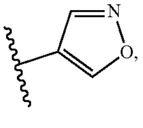, -continued

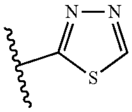, 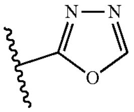, 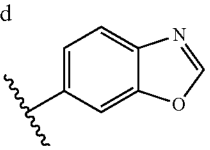,

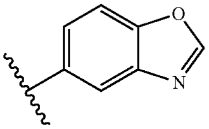, 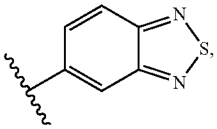

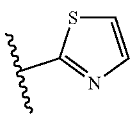, 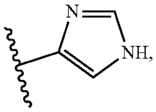 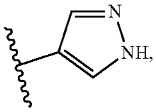

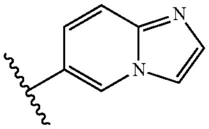, 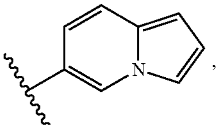,

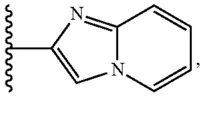, and 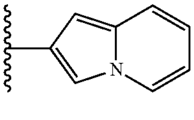, wherein n is 0, 1, or 2. In some embodiments, n is 0. In some embodiments, n is 1.

In some embodiments, $R^1$ is halo (e.g., fluoro or chloro), $C_1$-$C_6$ alkyl (e.g., Me), azido, cyclopropyl, 2-propynyloxy, cyano, —C(O)$R^D$ (e.g., —C(O)-(4-ethynyl)phenyl), or —$OR^B$ (e.g., —$OCH_3$ or —$OCF_3$). In some embodiments, $R^1$ is halo (e.g., fluoro or chloro).

In some embodiments, p is 0. In some embodiments, p is 1.

In some embodiments, $R^3$ is —$OR^B$ (e.g., —$OCH_3$ or —$OCF_3$) $C_1$-$C_6$ haloalkyl (e.g., —$CF_3$), halo (e.g., F or Cl), amino, azido, nitro, cyano, cycloalkyl (e.g., cyclopropyl), or $S(O)_xR^E$ (e.g., —$SO_2Me$). In some embodiments, $R^3$ is —$OR^B$ (e.g., —$OCH_3$ or $OCF_3$).

In some embodiments, each of $L^1$ and $L^2$ is independently —$C_1$-$C_6$ heteroalkyl-, —C(O)$NR^A$—, —$NR^A$C(O)—, —C(O)$NR^A$—$C_1$-$C_6$ alkyl-, —$C_1$-$C_6$ alkyl-C(O)$NR^A$—, —$NR^A$C(O)—$C_1$-$C_6$ alkyl-, or —$C_1$-$C_6$ alkyl-$NR^A$C(O)—, each of which is optionally substituted with 1-5 $R^4$. In some embodiments, each of $L^1$ and $L^2$ is independently $C_1$-$C_6$ heteroalkyl-, —C(O)$NR^A$—, or —$NR^A$C(O)—, each of which is optionally substituted with 1-5 $R^4$.

In some embodiments, $L^1$ is —$C_1$-$C_6$ heteroalkyl- (e.g., —$NHCH_2$—, —$NHCH_2CH_2$—, —N($CH_3$)$CH_2$)—, —N($R^4$)$CH_2$—, or —NHC$(R^4)_2$—) or —$NR^A$C(O)— (e.g., —NHC(O)—). In some embodiments, $L^1$ is —$C_1$-$C_6$ heteroalkyl- (e.g., —$NHCH_2$—, —$NHCH_2CH_2$—, —N($CH_3$) $CH_2$)—, —N($R^4$)$CH_2$—, or —NHC$(R^4)_2$—). In some embodiments, $L^1$ is —$NHCH_2$—. In some embodiments, $L^1$ is —$C_1$-$C_6$ heteroalkyl- substituted with at least one deuterium on one or more carbon atoms (e.g., —NHCHD-, —$NHCD_2$-, —$NHCD_2CH_2$—, —$NHCH_2CD_2$-, —$NHCD_2CD_2$-, —N($CH_3$)$CD_2$-, —N($R^4$)$CD_2$-). In some embodiments, $L^1$ is —$NR^A$C(O)— (e.g., —NHC(O)—).

In some embodiments, $R^4$, taken together with the atoms to which it is attached, forms a ring with Ring A (e.g., a 5-7 membered ring, e.g., a cyclopentyl ring fused to Ring A or a piperidinyl ring fused to Ring A). In some embodiments, one $R^4$ is taken together with the atoms to which it is attached to form a cyclopentyl ring fused to Ring A. In some embodiments, one $R^4$ is taken together with the atoms to which it is attached to form piperidinyl ring fused to Ring A.

In some embodiments, two $R^4$ are taken together with the atoms to which they are attached to form a heterocyclyl ring (e.g., a 4-membered heterocyclyl, e.g., oxetanyl).

In some embodiments, $L^2$ is C(O)$NR^A$—. In some embodiments, $R^A$ is $C_1$-$C_6$ alkyl (e.g., —$CH_2CH_3$) or $C_1$-$C_6$ haloalkyl (e.g., —$CH_2CF_3$). In some embodiments, $R^A$ is $C_1$-$C_6$ alkyl (e.g., —$CH_2CH_3$). In some embodiments, $R^A$ is $C_1$-$C_6$ haloalkyl (e.g., —$CH_2CF_3$).

In some embodiments, the compound of Formula (I) is a compound of Formula (I-l), Formula (I-j), or Formula (I-k):

Formula (I-i)

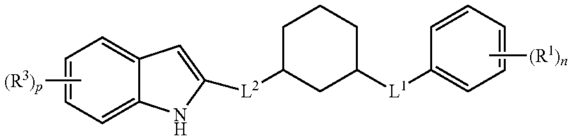

Formula (I-j)

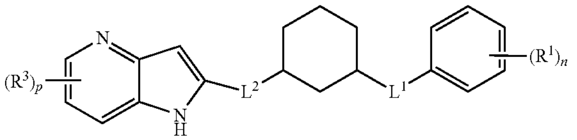

Formula (I-k)

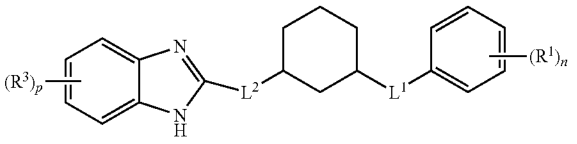

or a pharmaceutically acceptable salt thereof, wherein $L^1$, $L^2$, $R^1$, $R^2$, $R^3$, n, p, and subvariables thereof are as described in any of the preceding claims.

In some embodiments, the compound of Formula (I) is a compound of Formula (I-l):

Formula (I-l)

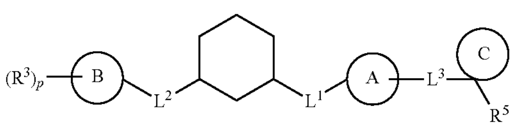

or a pharmaceutically acceptable salt thereof, wherein $L^1$, $L^2$, $R^2$, $R^3$, $R^5$, p, and subvariables thereof are as described in any of the preceding claims; $L^3$ is —$C_1$-$C_5$ heteroalkyl-; and Ring C is cycloalkyl or heterocyclyl.

In some embodiments, the compound of Formula (I) is a compound of Formula (I-m):

Formula (I-m)

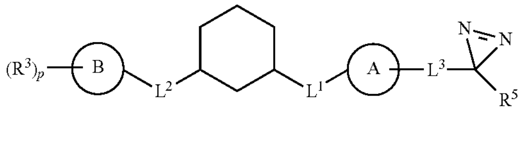

or a pharmaceutically acceptable salt thereof, wherein $L^1$, $L^2$, $R^2$, $R^3$, $R^5$, p, and subvariables thereof are as described in any of the preceding claims; and $L^3$ is —$C_1$-$C_5$ heteroalkyl-.

In some embodiments, n is 0. In some embodiments, n is 1.

In some embodiments, $R^1$ is halo (e.g., fluoro or chloro), $C_1$-$C_6$ alkyl (e.g., Me), azido, cyclopropyl, 2-propynyloxy, cyano, —C(O)$R^D$ (e.g., —C(O)-(4-ethynyl)phenyl), or —$OR^B$ (e.g., —$OCH_3$ or —$OCF_3$). In some embodiments, $R^1$ is halo (e.g., fluoro or chloro).

In some embodiments, p is 0. In some embodiments, p is 1.

In some embodiments, $R^3$ is —$OR^B$ (e.g., —$OCH_3$ or —$OCF_3$) $C_1$-$C_6$ haloalkyl (e.g., —$CF_3$), halo (e.g., F or Cl), amino, azido, nitro, cyano, cycloalkyl (e.g., cyclopropyl), or $S(O)_xR^E$ (e.g., —$SO_2$Me). In some embodiments, $R^3$ is —$OR^B$ (e.g., —$OCH_3$ or $OCF_3$).

In some embodiments, each of $L^1$ and $L^2$ is independently —$C_1$-$C_6$ heteroalkyl-, —C(O)$NR^A$—, —$NR^A$C(O)—, —C(O)$NR^A$—$C_1$-$C_6$ alkyl-, —$C_1$-$C_6$ alkyl-C(O)$NR^A$—, —$NR^A$C(O)—$C_1$-$C_6$ alkyl-, or —$C_1$-$C_6$ alkyl-$NR^A$C(O)—, each of which is optionally substituted with 1-5 $R^4$. In some embodiments, each of $L^1$ and $L^2$ is independently $C_1$-$C_6$ heteroalkyl-, —C(O)$NR^A$—, or —$NR^A$C(O)—, each of which is optionally substituted with 1-5 $R^4$.

In some embodiments, $L^1$ is —$C_1$-$C_6$ heteroalkyl- (e.g., —$NHCH_2$—, —$NHCH_2CH_2$—, —$N(CH_3)CH_2)$—, —$N(R^4)CH_2$—, or —$NHC(R^4)_2$—) or —$NR^A$C(O)— (e.g., —NHC(O)—). In some embodiments, $L^1$ is —$C_1$-$C_6$ heteroalkyl- (e.g., —$NHCH_2$—, —$NHCH_2CH_2$—, —$N(CH_3)$ $CH_2)$—, —$N(R^4)CH_2$—, or —$NHC(R^4)_2$—). In some embodiments, $L^1$ is —$NHCH_2$—. In some embodiments, $L^1$ is —$NR^A$C(O)— (e.g., —NHC(O)—). -. In some embodiments, $L^1$ is —$C_1$-$C_6$ heteroalkyl-substituted with at least one deuterium on one or more carbon atoms (e.g., —NHCHD-, —$NHCD_2$-, —$NHCD_2CH_2$—, —$NHCH_2CD_2$-, —$NHCD_2CD_2$-, —$N(CH_3)CD_2$-, —$N(R^4)$ $CD_2$-).

In some embodiments, $R^4$, taken together with the atoms to which it is attached, forms a ring with Ring A (e.g., a 5-7 membered ring, e.g., a cyclopentyl ring fused to Ring A or a piperidinyl ring fused to Ring A). In some embodiments, one $R^4$ is taken together with the atoms to which it is attached to form a cyclopentyl ring fused to Ring A. In some embodiments, one $R^4$ is taken together with the atoms to which it is attached to form piperidinyl ring fused to Ring A.

In some embodiments, two $R^4$ are taken together with the atoms to which they are attached to form a heterocyclyl ring (e.g., a 4-membered heterocyclyl, e.g., oxetanyl).

In some embodiments, $L^2$ is C(O)$NR^A$—. In some embodiments, $R^A$ is $C_1$-$C_6$ alkyl (e.g., —$CH_2CH_3$) or $C_1$-$C_6$ haloalkyl (e.g., —$CH_2CF_3$). In some embodiments, $R^A$ is $C_1$-$C_6$ alkyl (e.g., —$CH_2CH_3$). In some embodiments, $R^A$ is $C_1$-$C_6$ haloalkyl (e.g., —$CH_2CF_3$).

Figure 1A:
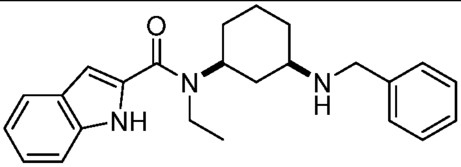
Figure 1A:
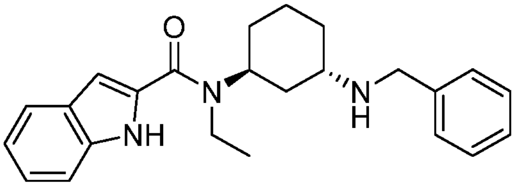
Figure 1A:
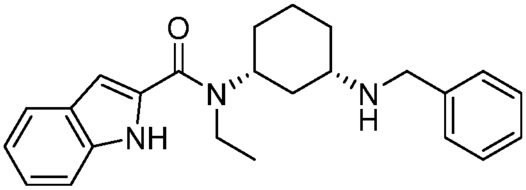
Figure 1A:
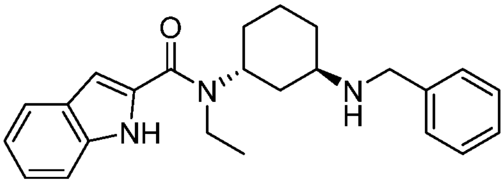
Figure 1A:
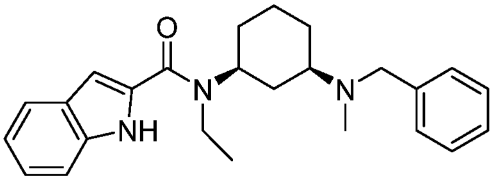
Figure 1A:
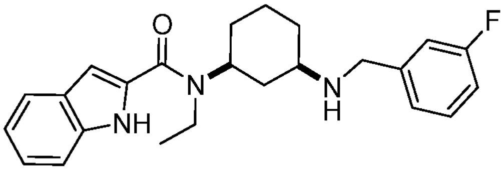
Figure 1A:
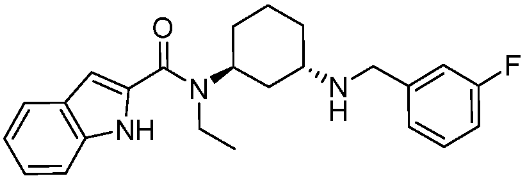
Figure 1B:
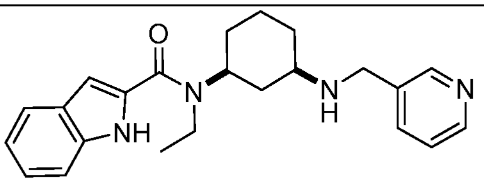
Figure 1B:
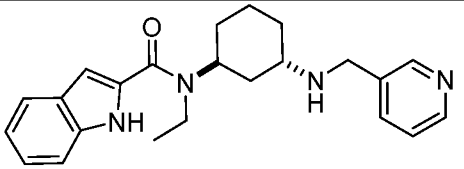
Figure 1B:
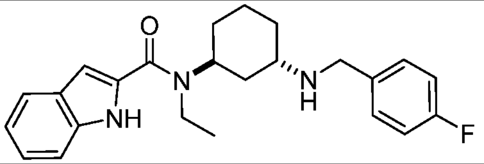
Figure 1B:
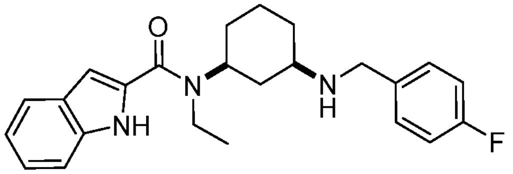
Figure 1B:
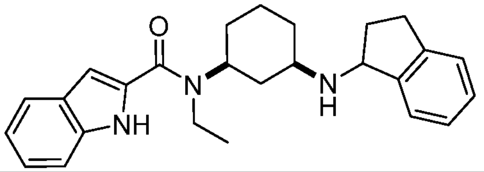
Figure 1B:
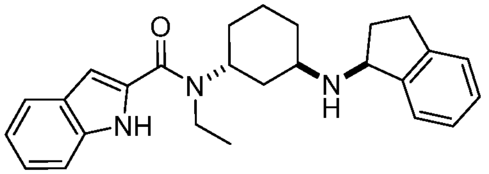
Figure 1B:
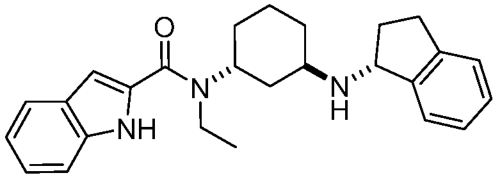
Figure 1B:
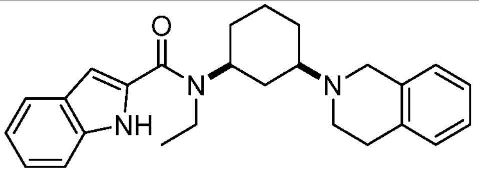
Figure 1B:
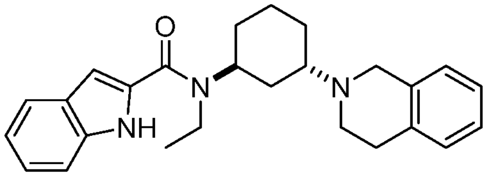
Figure 1C:
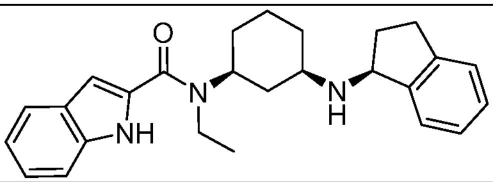
Figure 1C:
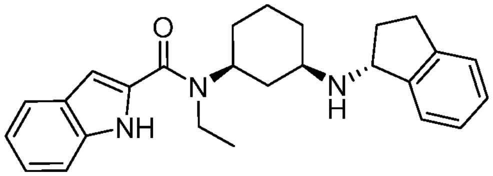
Figure 1C:
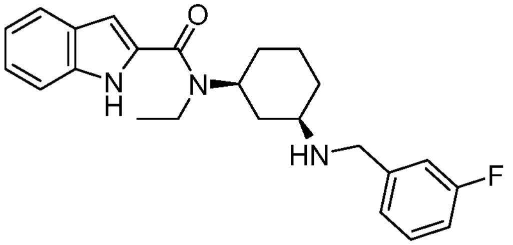
Figure 1C:
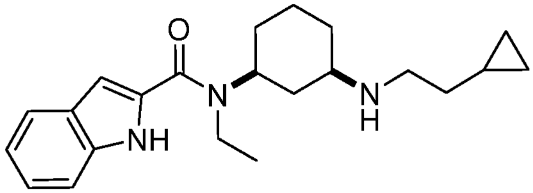
Figure 1C:
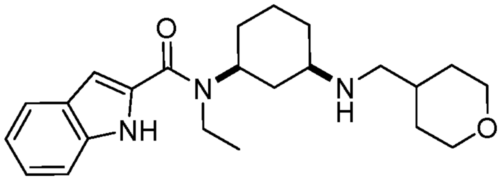
Figure 1C:
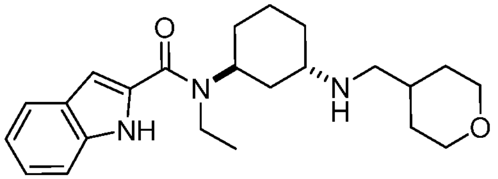
Figure 1C:
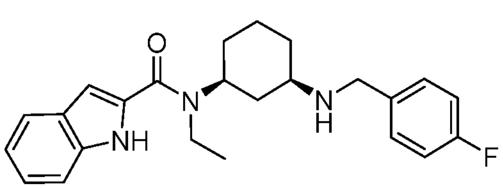
Figure 1D:
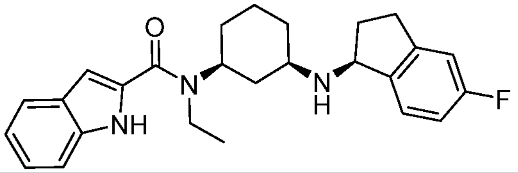
Figure 1D:
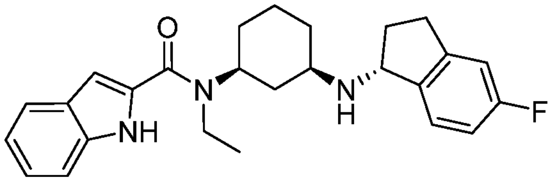
Figure 1D:
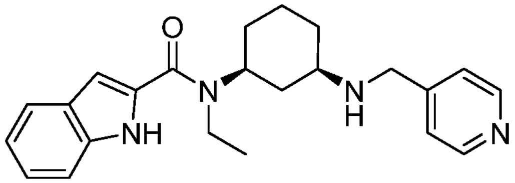
Figure 1D:
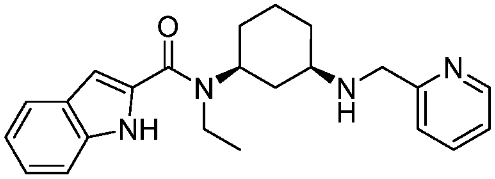
Figure 1D:
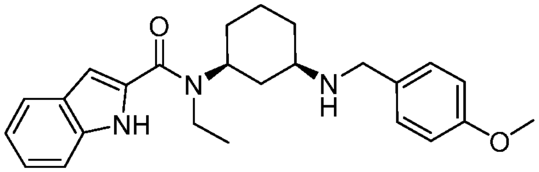
Figure 1D:
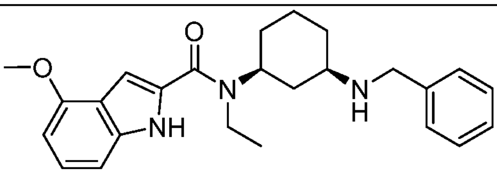
Figure 1D:
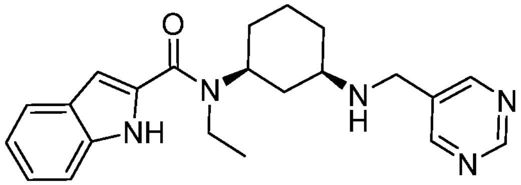
Figure 1E:
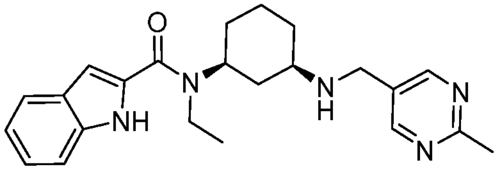
Figure 1E:
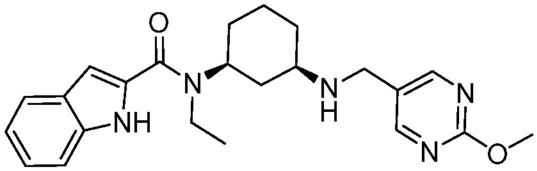
Figure 1E:
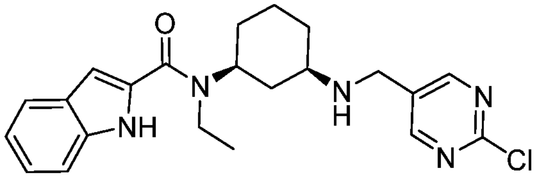
Figure 1E:
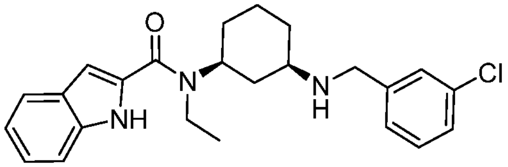
Figure 1E:
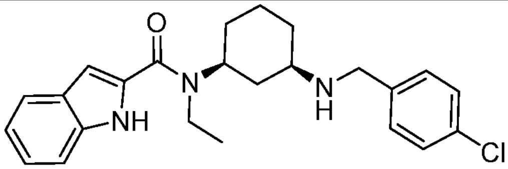
Figure 1E:
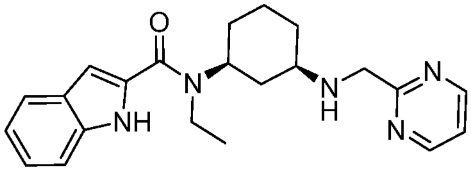
Figure 1E:
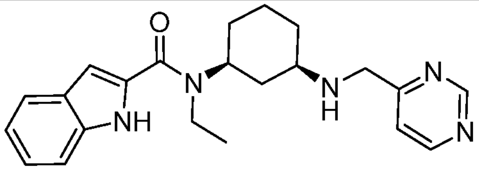
Figure 1E:
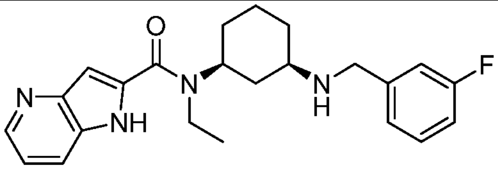
Figure 1F:
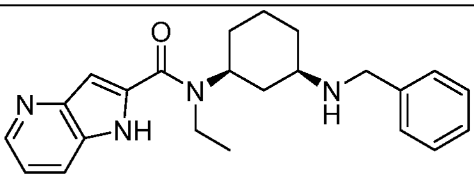
Figure 1F:
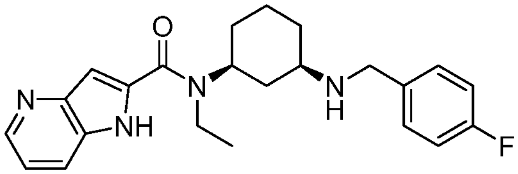
Figure 1F:
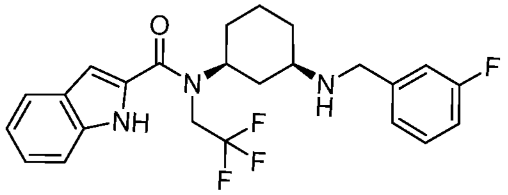
Figure 1F:
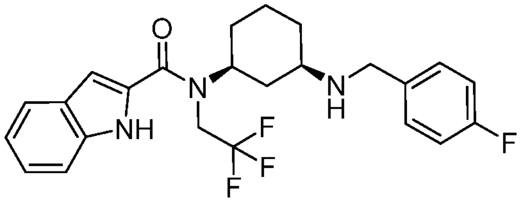
Figure 1F:
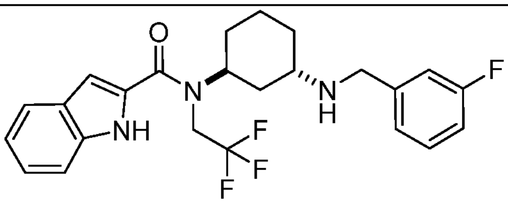
Figure 1F:
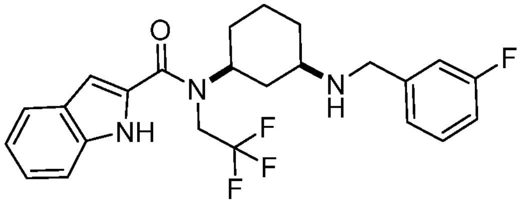
Figure 1F:
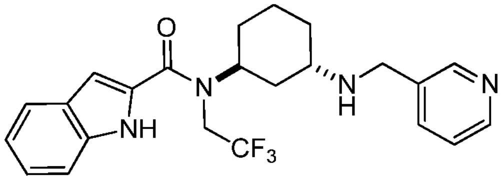
Figure 1G:
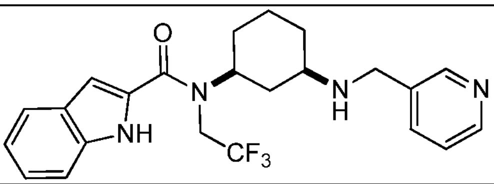
Figure 1G:
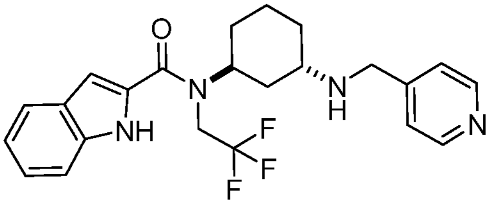
Figure 1G:
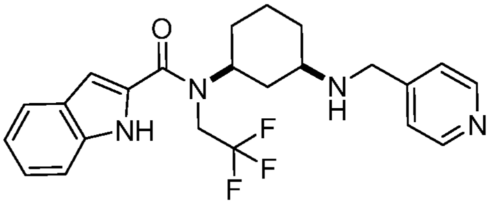
Figure 1G:
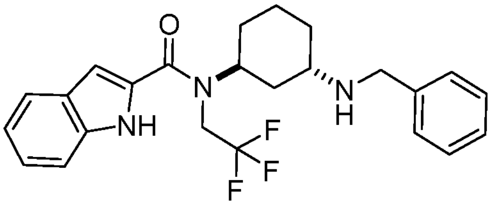
Figure 1G:
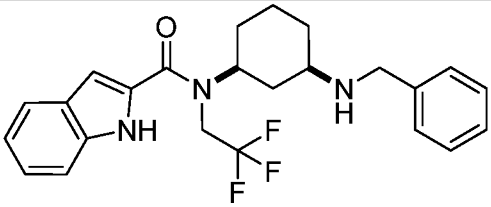
Figure 1G:
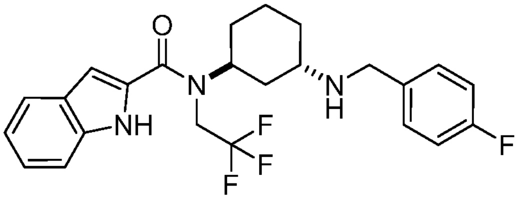
Figure 1G:
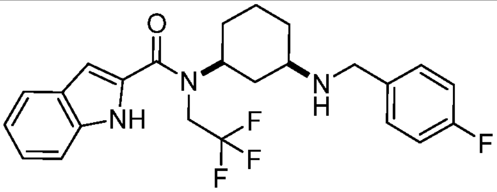
Figure 1H:
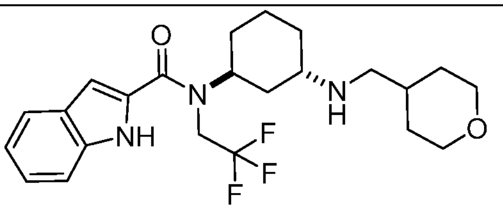
Figure 1H:
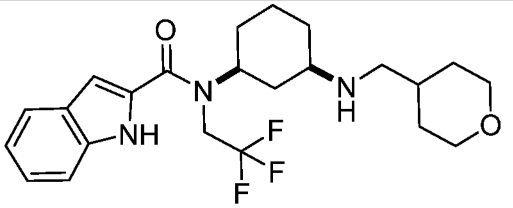
Figure 1H:
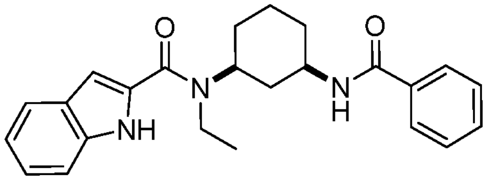
Figure 1H:
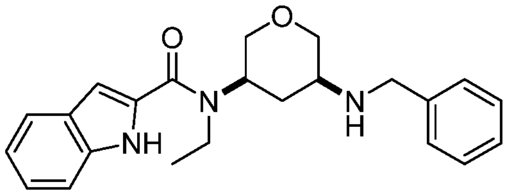
Figure 1H:
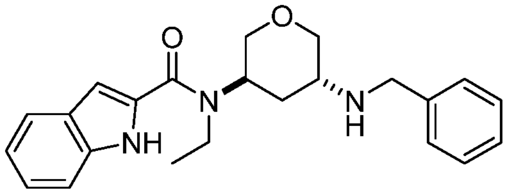
Figure 1H:
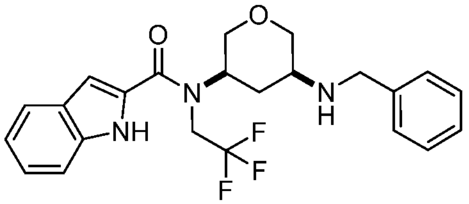
Figure 1H:
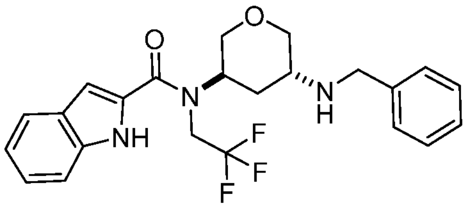
Figure 1I:
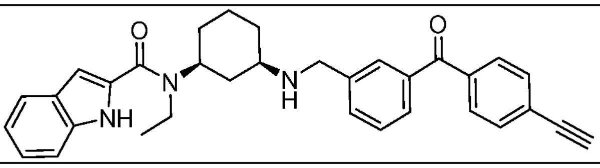
Figure 1I:
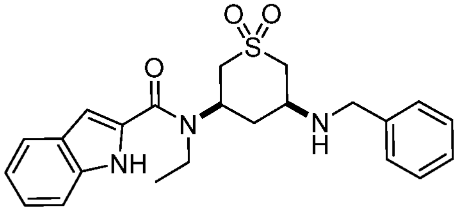
Figure 1I:
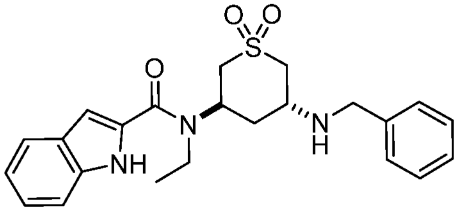
Figure 1I:
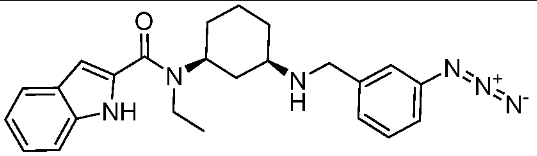
Figure 1I:
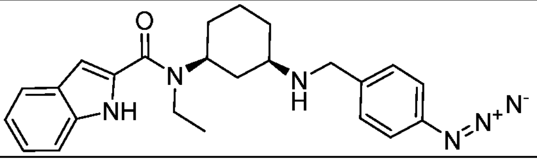
Figure 1I:
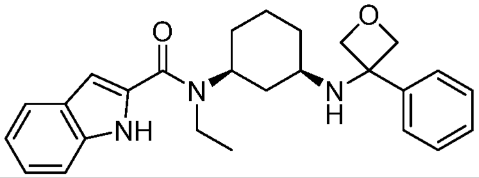
Figure 1I:
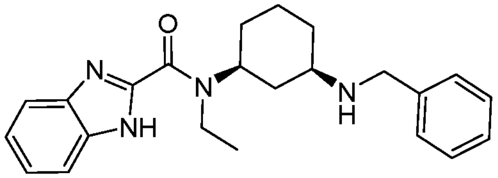
Figure 1I:
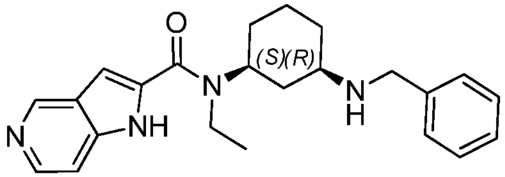
Figure 1J:
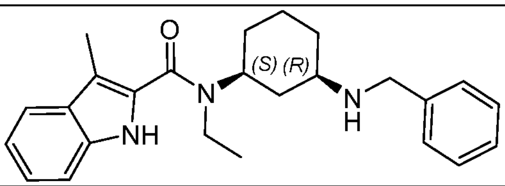
Figure 1J:
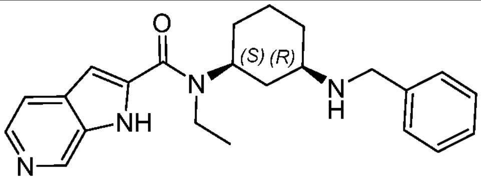
Figure 1J:
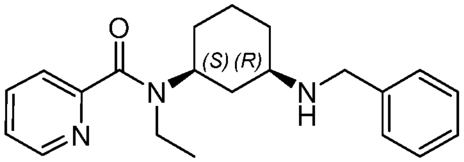
Figure 1J:
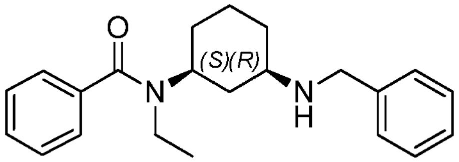
Figure 1J:
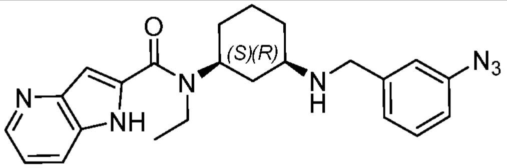
Figure 1J:
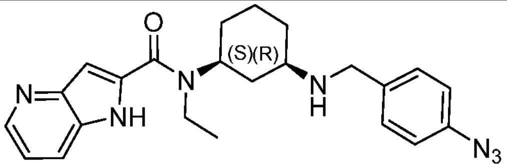
Figure 1J:
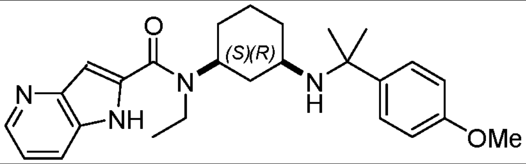
Figure 1J:
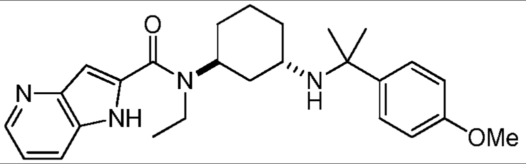
Figure 1J:
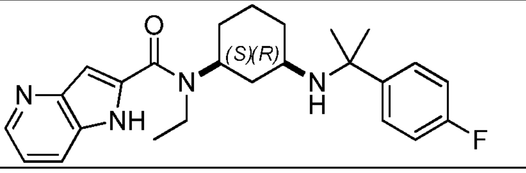
Figure 1K:
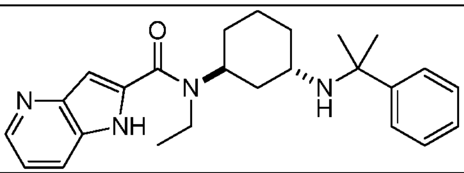
Figure 1K:
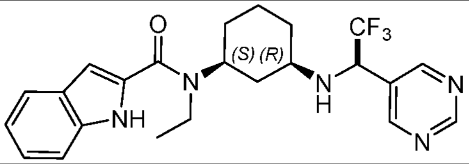
Figure 1K:
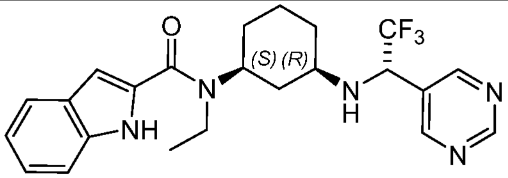
Figure 1K:
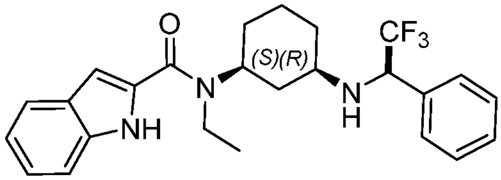
Figure 1K:
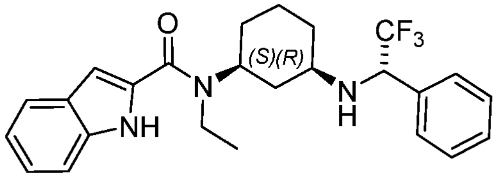
Figure 1K:
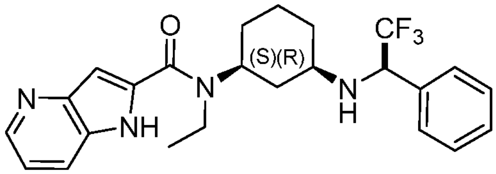
Figure 1K:
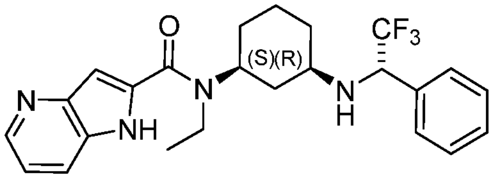
Figure 1K:
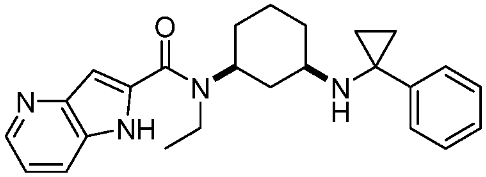
Figure 1L:
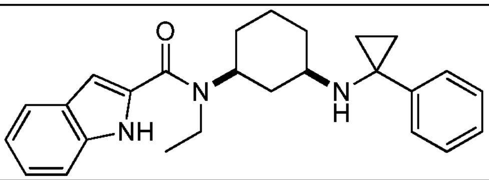
Figure 1L:
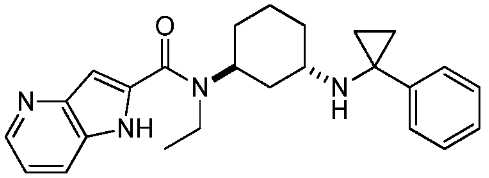
Figure 1L:
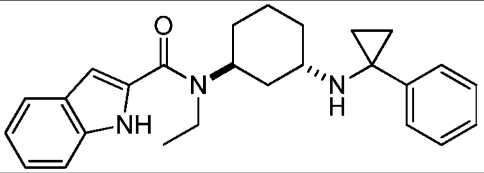
Figure 1L:
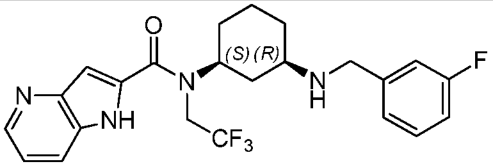
Figure 1L:
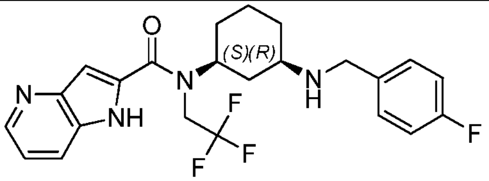
Figure 1L:
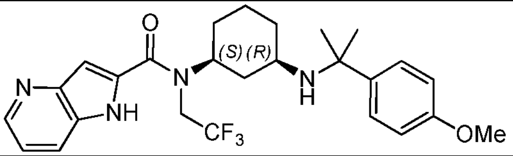
Figure 1L:
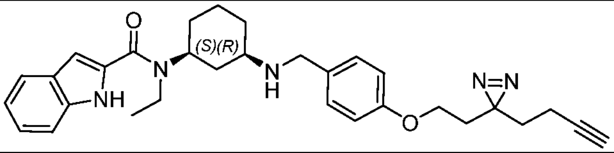
Figure 1L:
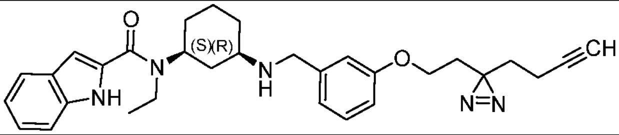
Figure 1L:
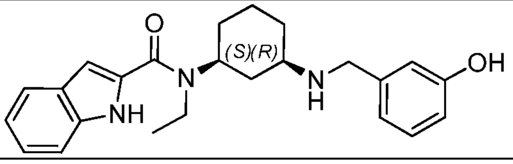
Figure 1M:
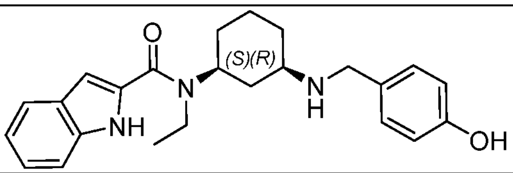
Figure 1M:
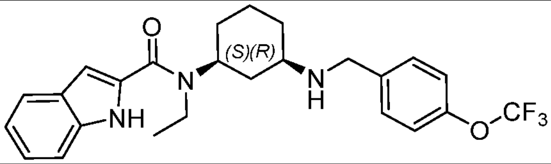
Figure 1M:
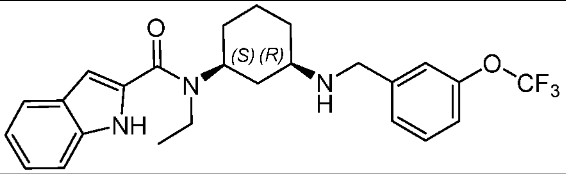
Figure 1M:
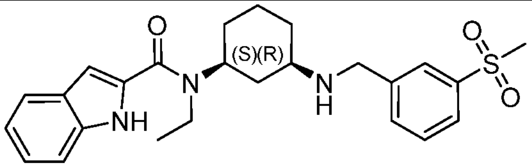
Figure 1M:
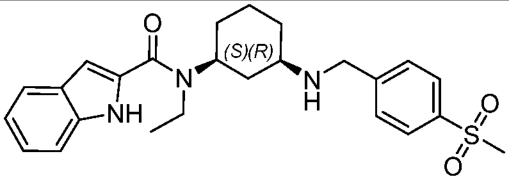
Figure 1M:
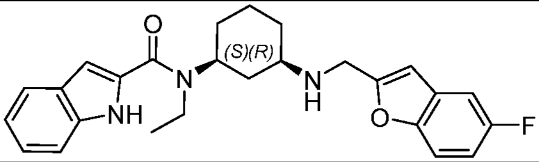
Figure 1M:
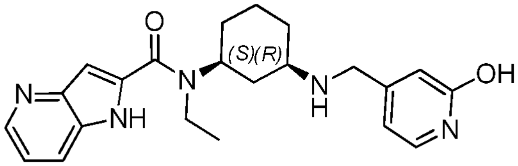
Figure 1M:
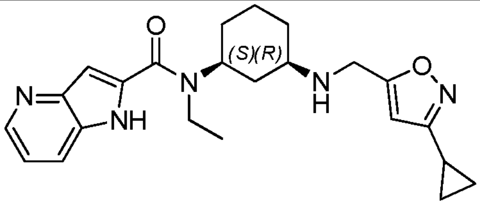
Figure 1M:
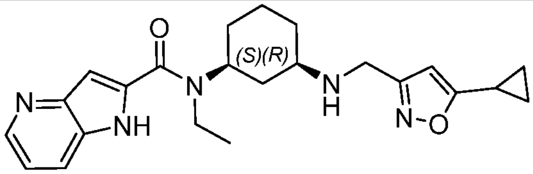
Figure 1N:
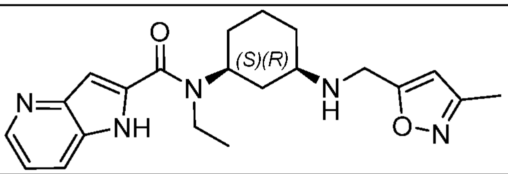
Figure 1N:
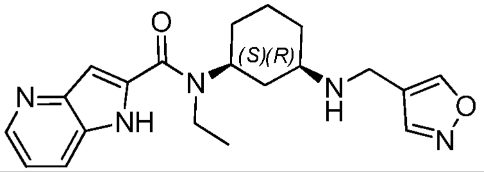
Figure 1N:
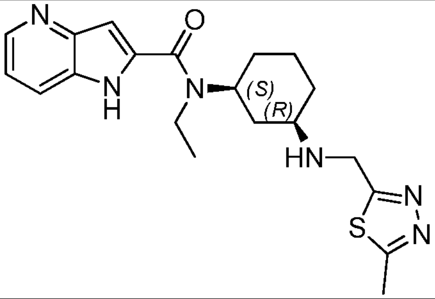
Figure 1N:
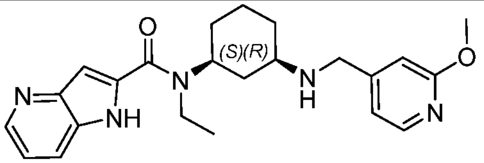
Figure 1N:
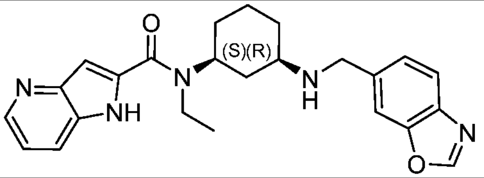
Figure 1N:
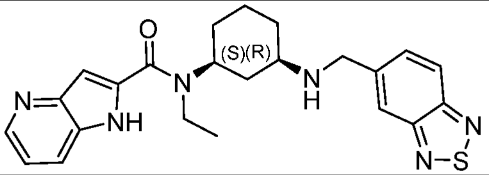
Figure 1N:
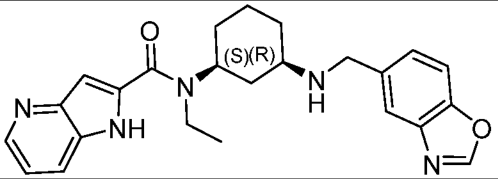
Figure 1N:
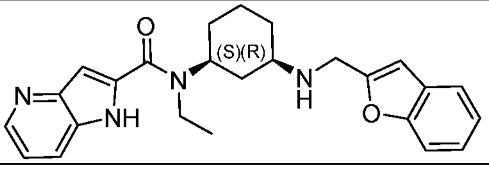
Figure 1O:
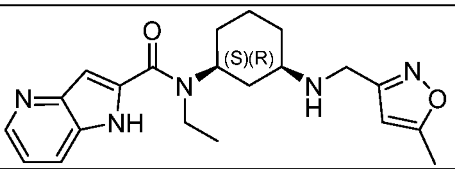
Figure 1O:
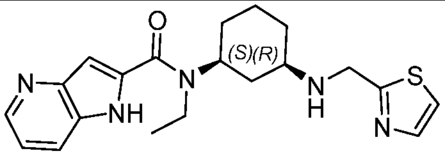
Figure 1O:
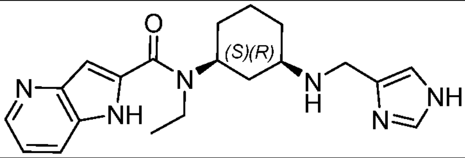
Figure 1O:
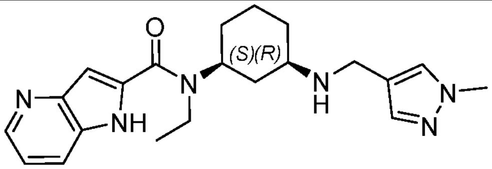
Figure 1O:
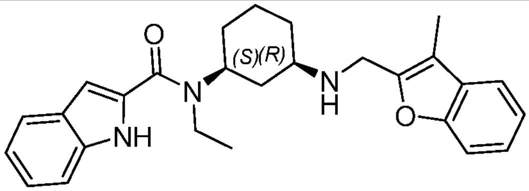
Figure 1O:
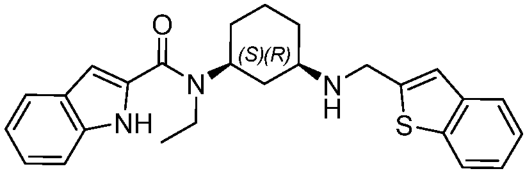
Figure 1O:
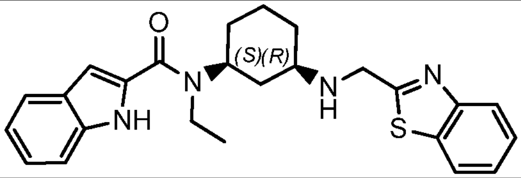
Figure 1O:
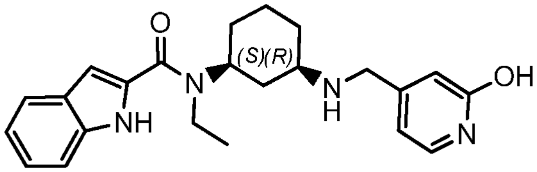
Figure 1O:
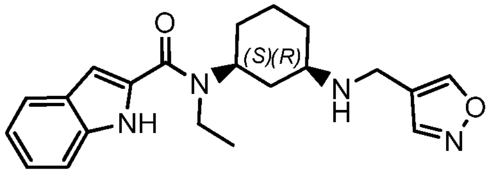
Figure 1P:
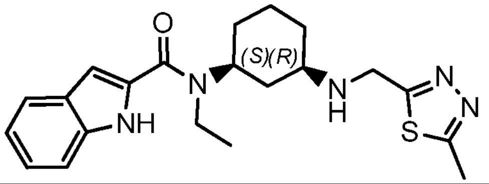
Figure 1P:
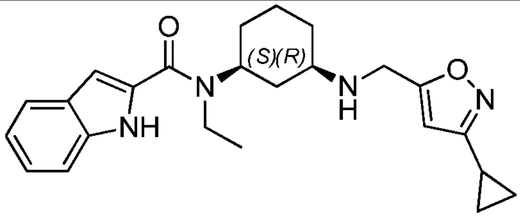
Figure 1P:
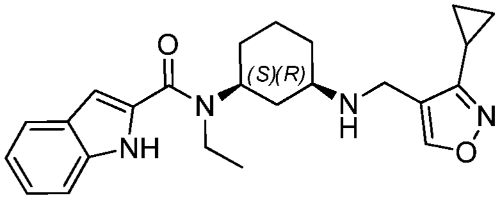
Figure 1P:
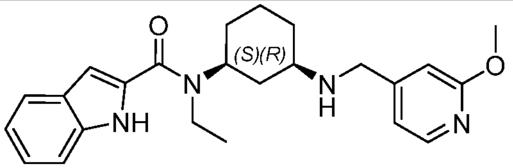
Figure 1P:
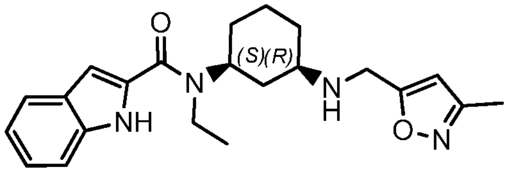
Figure 1P:
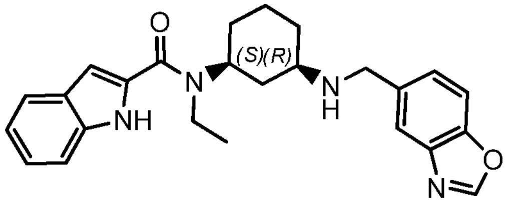
Figure 1P:
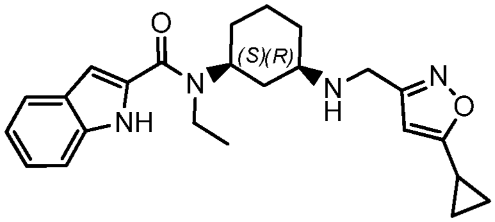
Figure 1P:
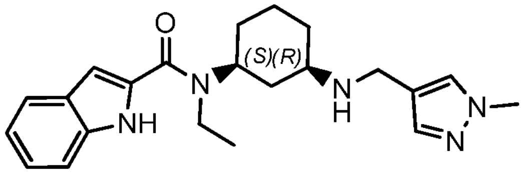
Figure 1Q:
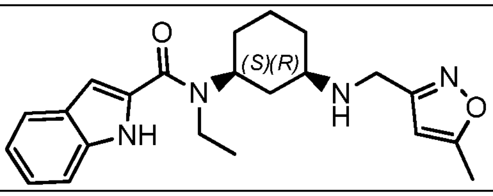
Figure 1Q:
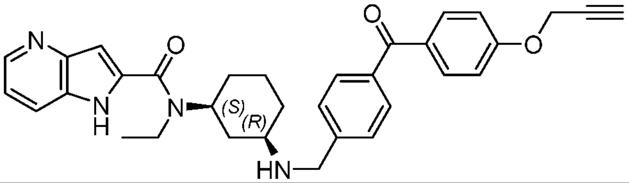
Figure 1Q:
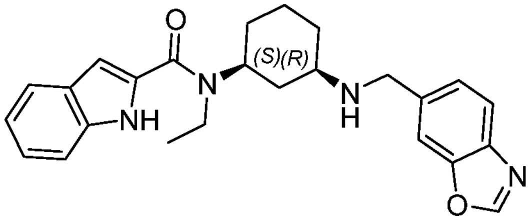
Figure 1Q:
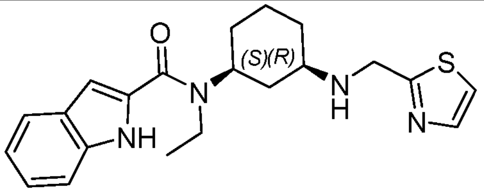
Figure 1Q:
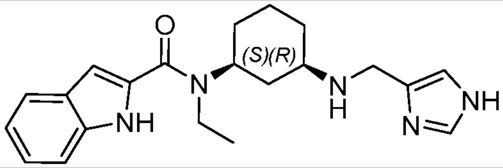
Figure 1Q:
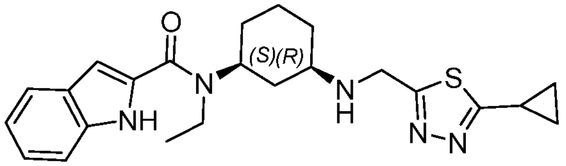
Figure 1Q:
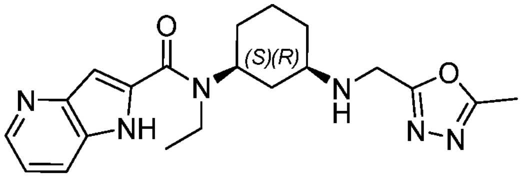
Figure 1Q:
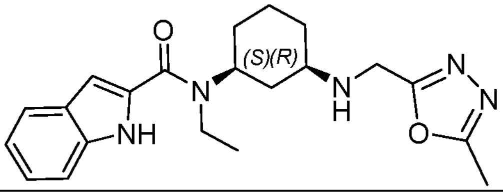
Figure 1R:
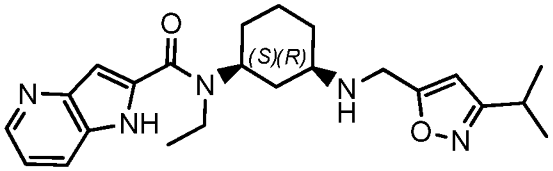
Figure 1R:
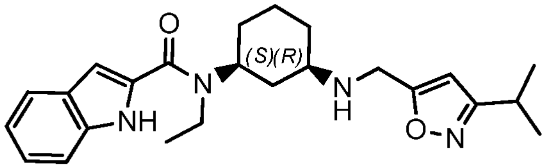
Figure 1R:
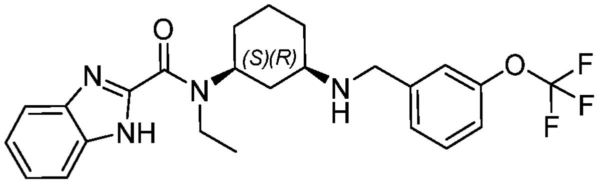
Figure 1R:
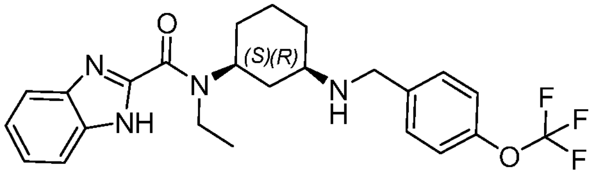
Figure 1R:
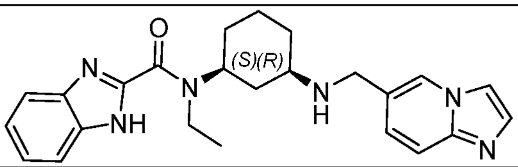
Figure 1R:
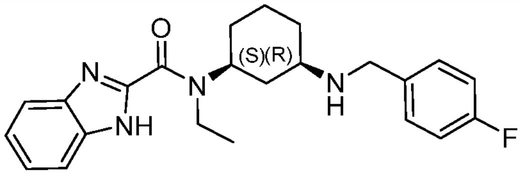
Figure 1R:
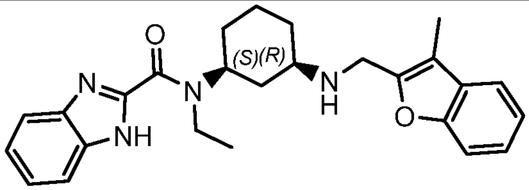
Figure 1R:
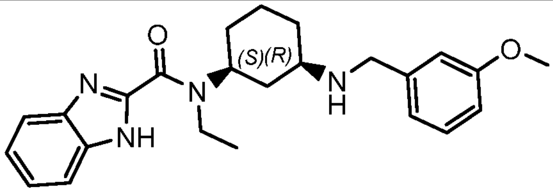
Figure 1S:
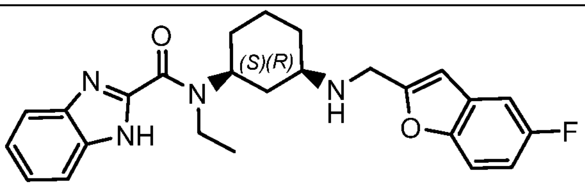
Figure 1S:
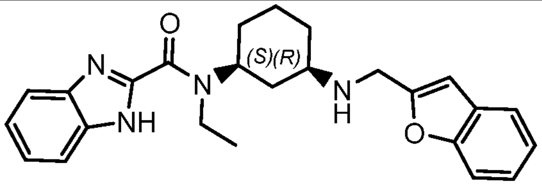
Figure 1S:
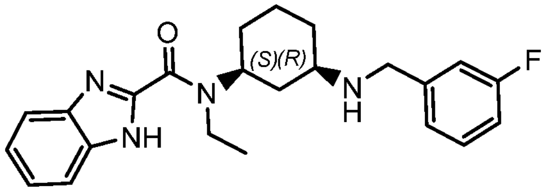
Figure 1S:
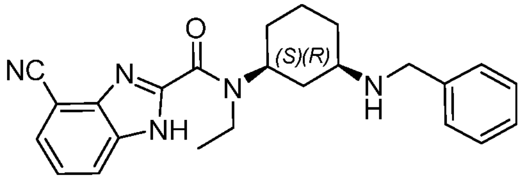
Figure 1S:
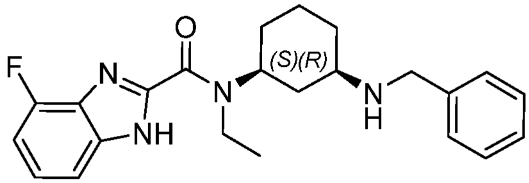
Figure 1S:
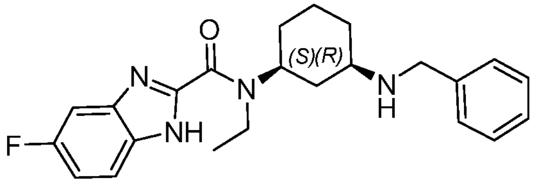
Figure 1S:
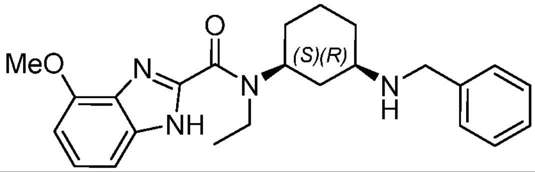
Figure 1S:
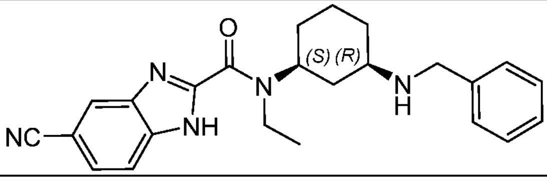
Figure 1T:
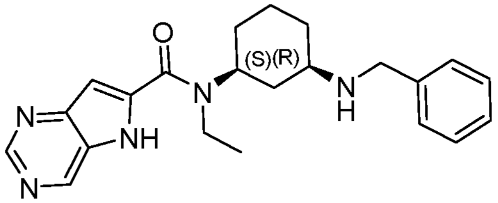
Figure 1T:
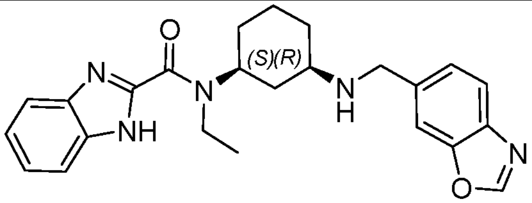
Figure 1T:
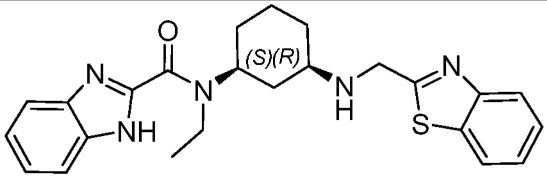
Figure 1T:
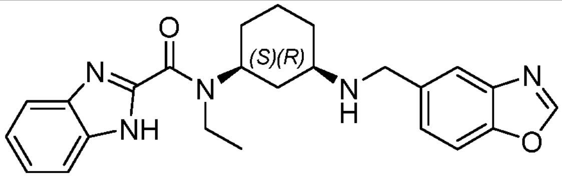
Figure 1T:
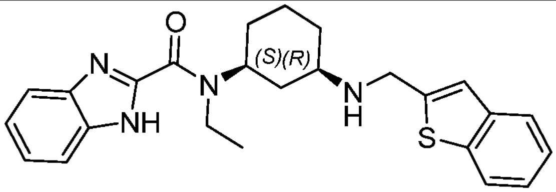
Figure 1T:
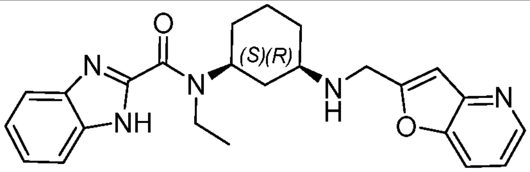
Figure 1T:
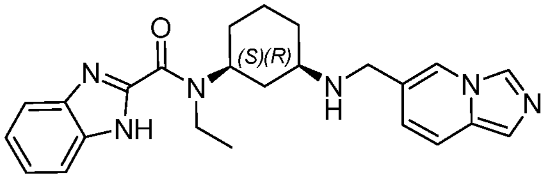
Figure 1T:
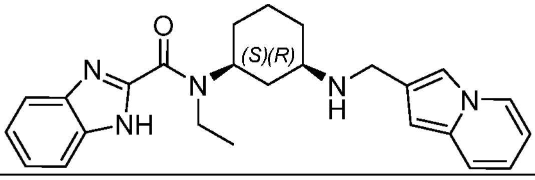
Figure 1U:
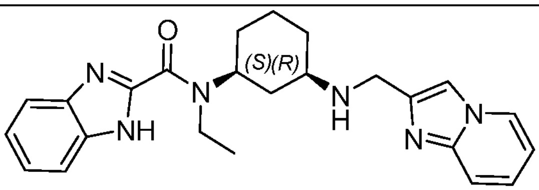
Figure 1U:
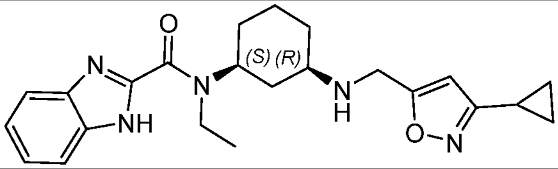
Figure 1U:
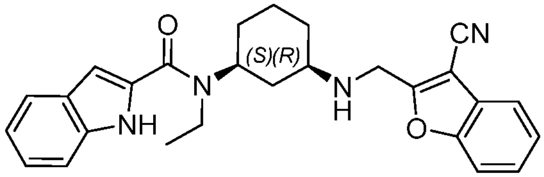
Figure 1U:
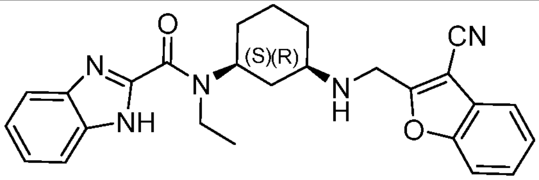
Figure 1U:
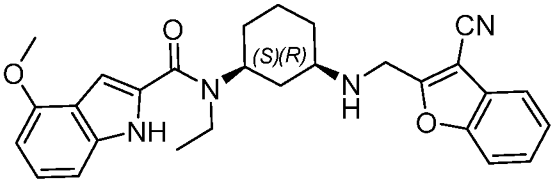
Figure 1U:
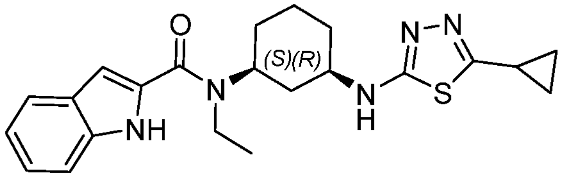
Figure 1U:
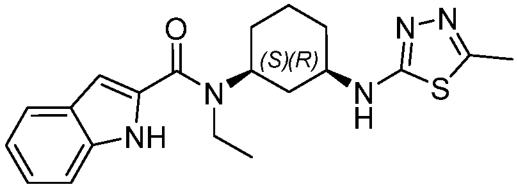
Figure 1U:
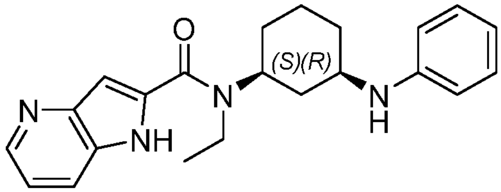
Figure 1V:
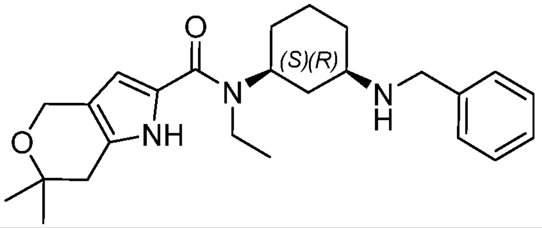
Figure 1V:
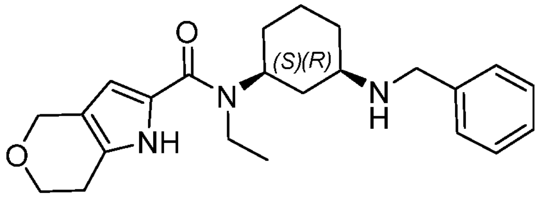
Figure 1V:
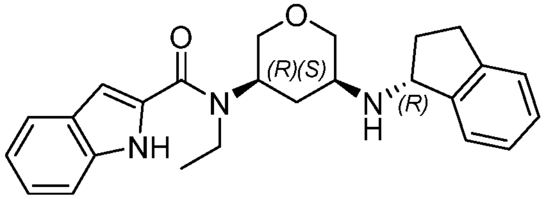
Figure 1V:
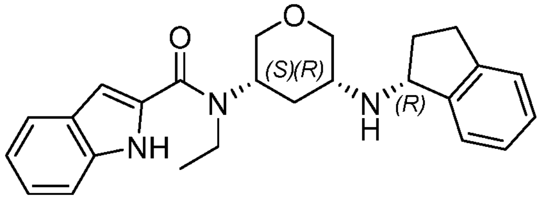
Figure 1V:
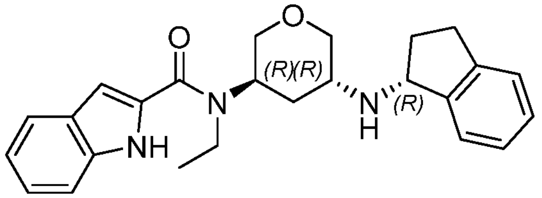
Figure 1V:
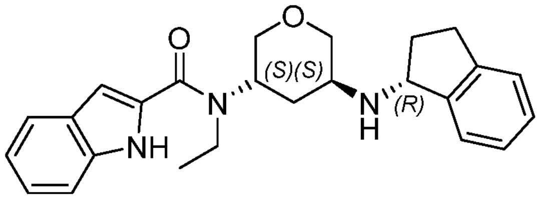
Figure 1V:
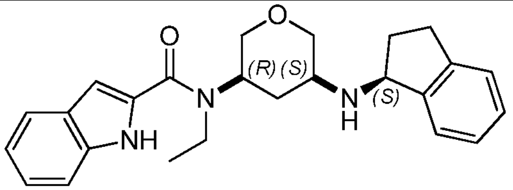
Figure 1W:
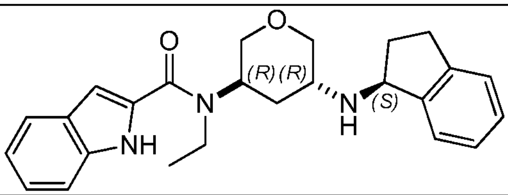
Figure 1W:
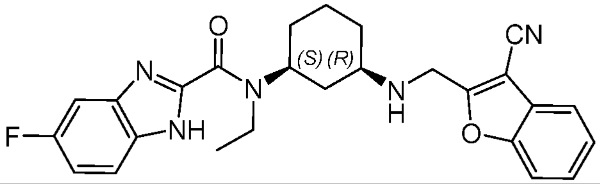
Figure 1W:
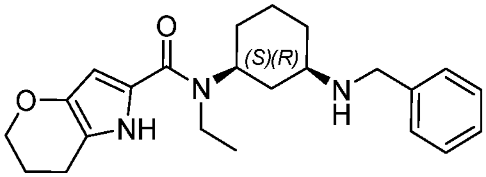
Figure 1W:
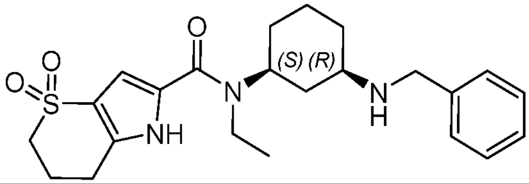
Figure 1W:
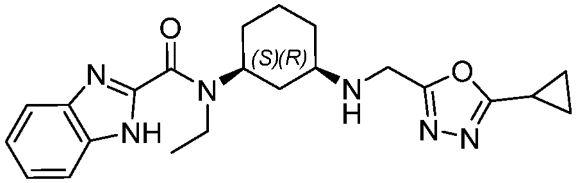
Figure 1W:
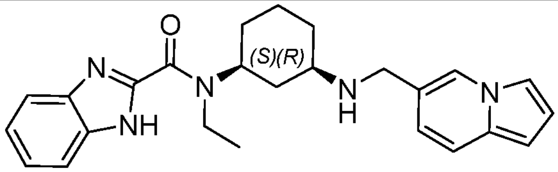
Figure 1W:
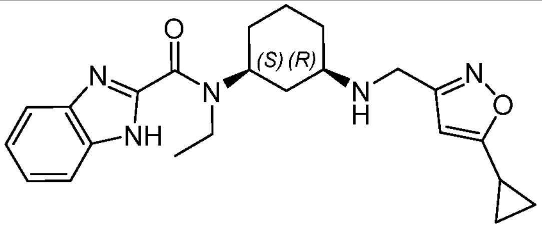
Figure 1W:
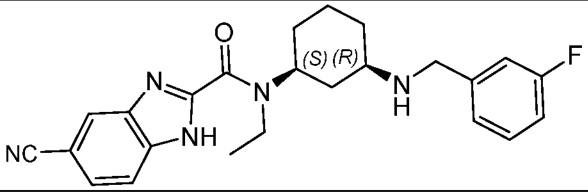
Figure 1X:
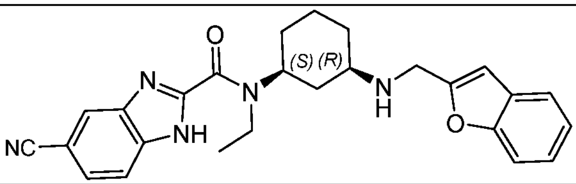
Figure 1X:
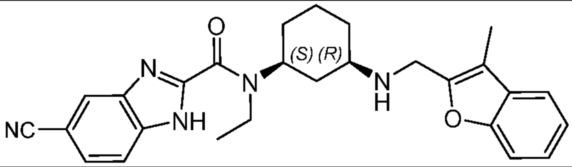
Figure 1X:
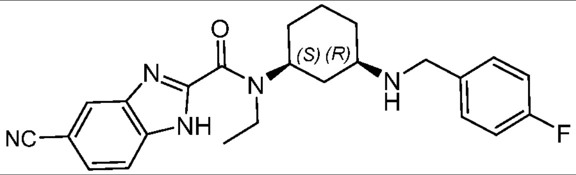
Figure 1X:
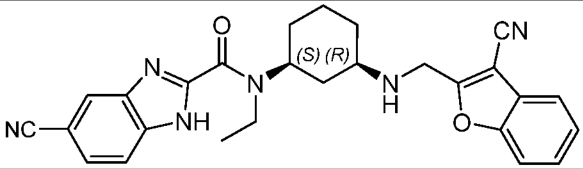
Figure 1X:
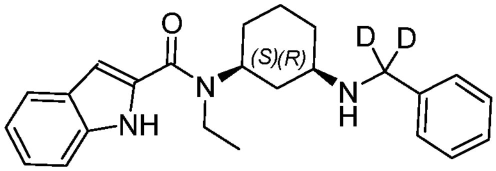
Figure 1X:
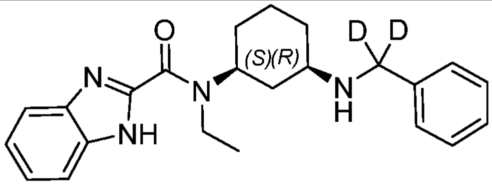
Figure 1X:
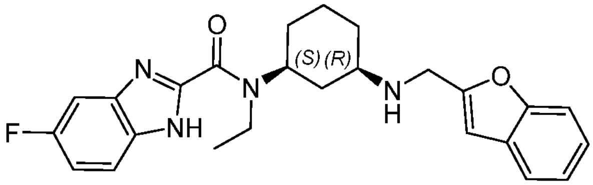
Figure 1X:
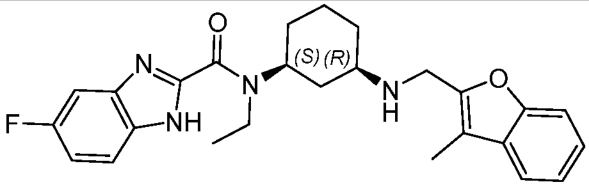
Figure 1Y:
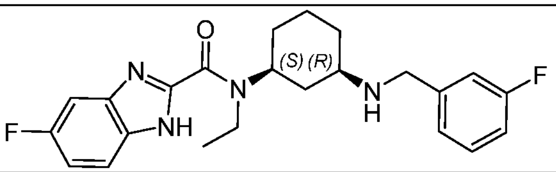
Figure 1Y:
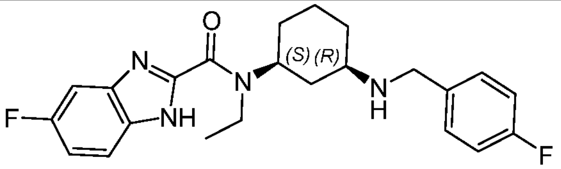
Figure 1Y:
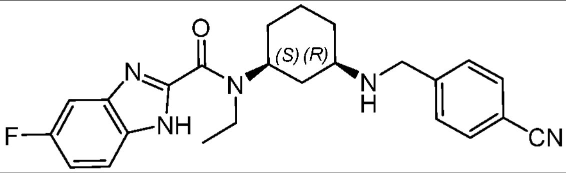
Figure 1Y:
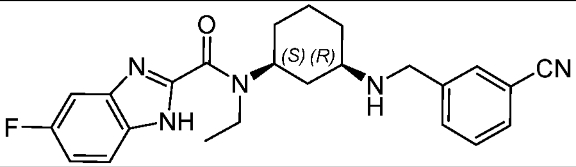
Figure 1Y:
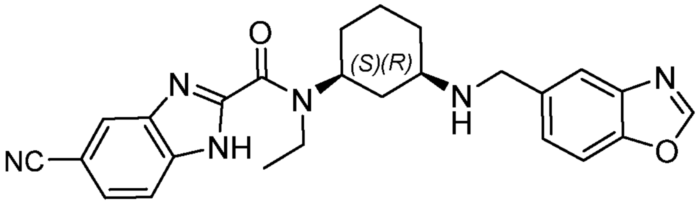
Figure 1Y:
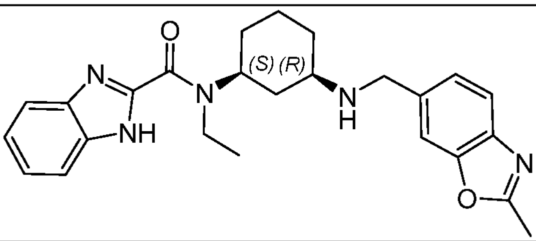
Figure 1Y:
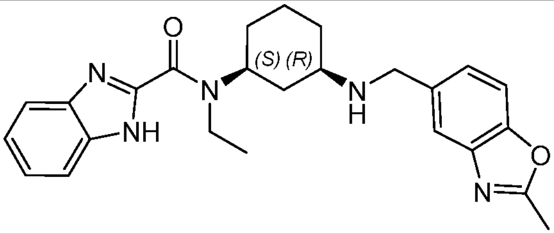
Figure 1Y:
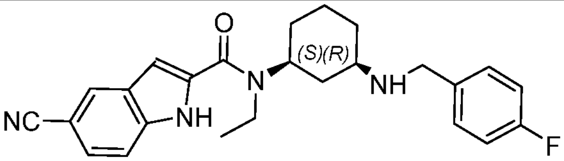
Figure 1Z:
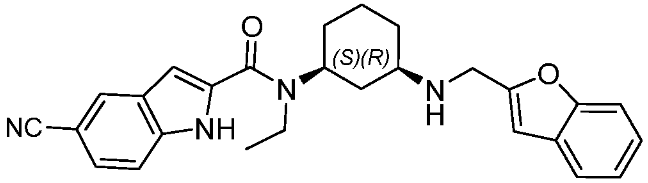
Figure 1Z:
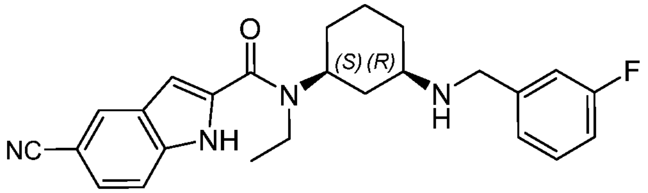
Figure 1Z:
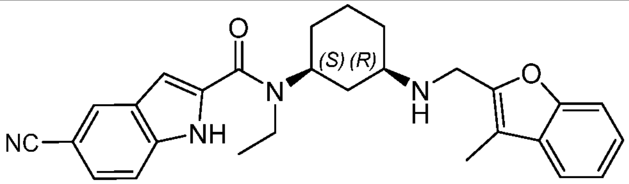
Figure 1Z:
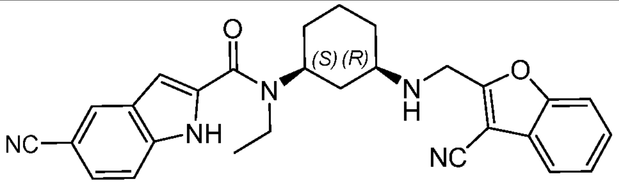
Figure 1Z:
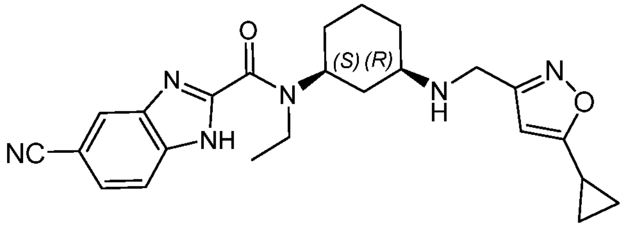
Figure 1Z:
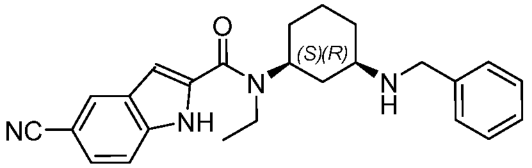
Figure 1Z:
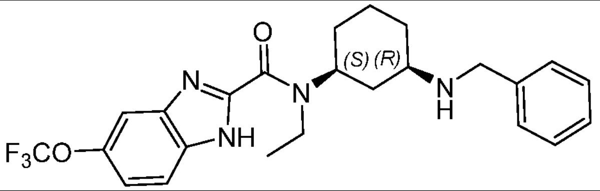
Figure 1Z:
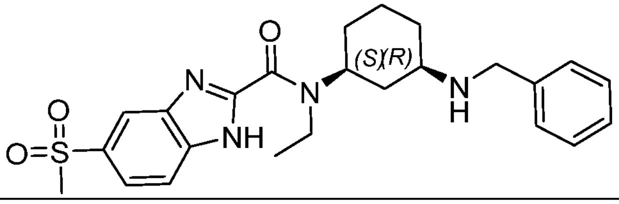
Figure 1A:
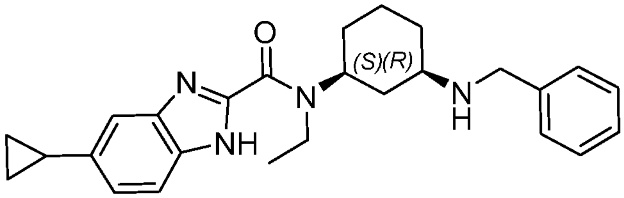
Figure 1A:
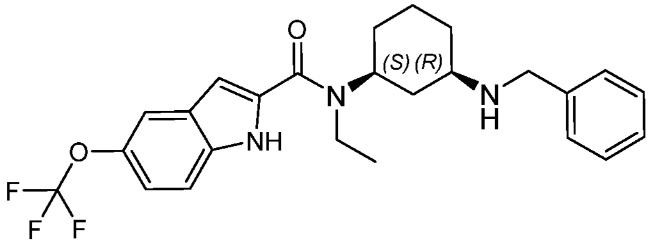
Figure 1A:
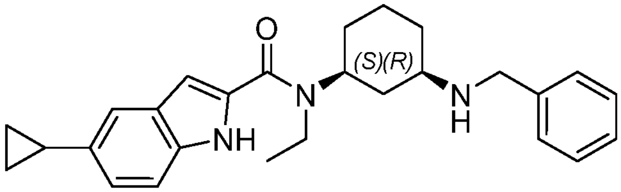
Figure 1A:
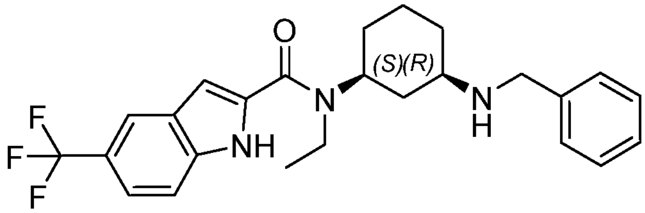
Figure 1A:
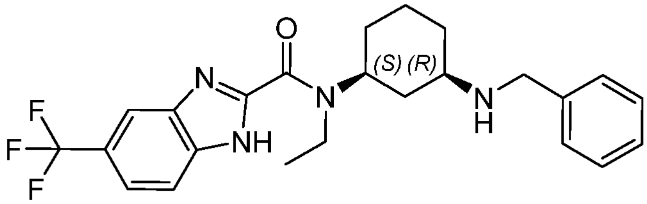
Figure 1A:
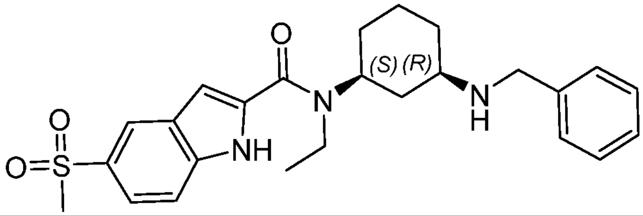
Figure 1A:
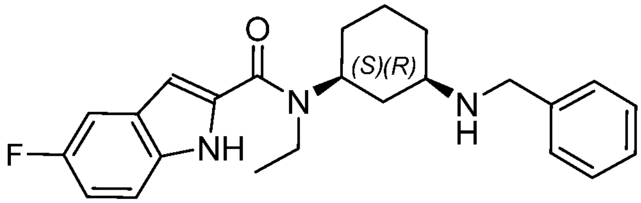
Figure 1B:
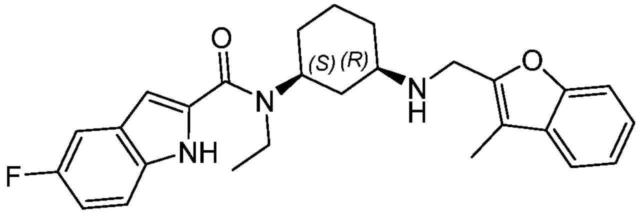
Figure 1B:
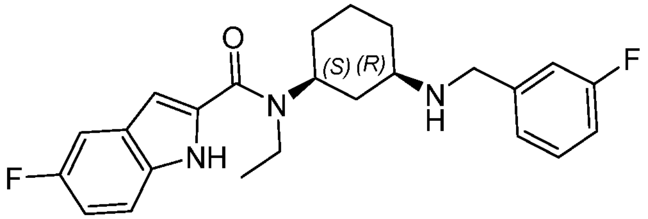
Figure 1B:
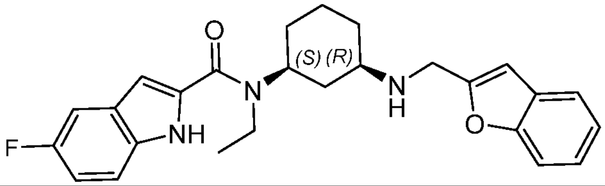
Figure 1B:
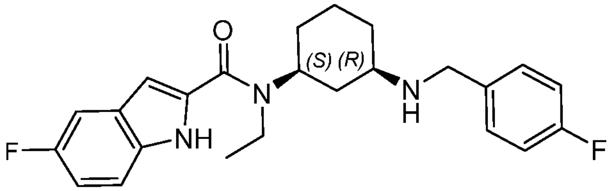
Figure 1B:
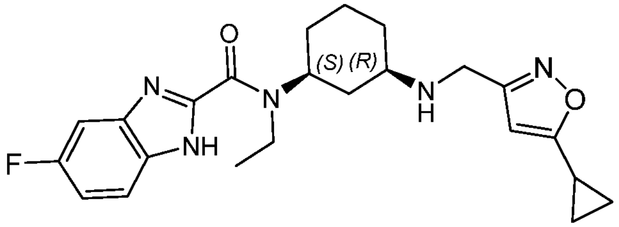
Figure 1B:
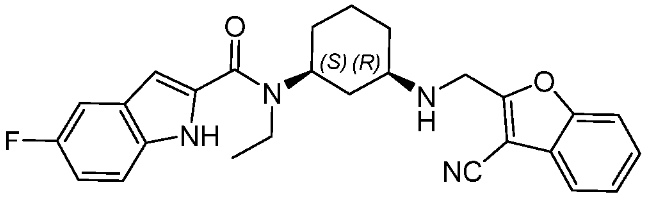
Figure 1B:
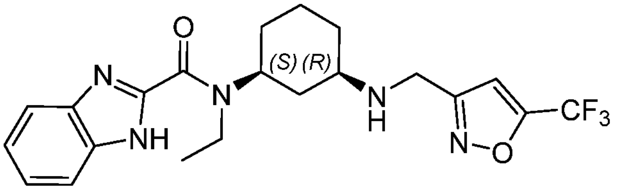
Figure 1C:
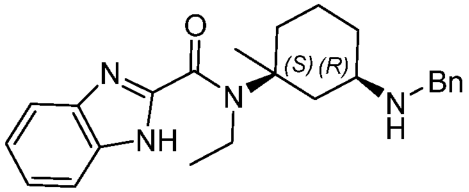
Figure 1C:
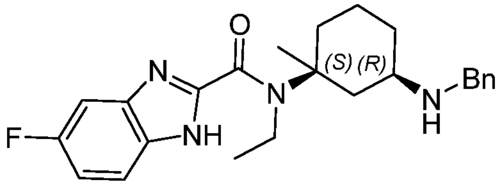
Figure 1C:
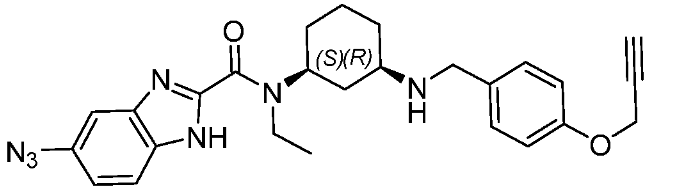
Figure 1C:
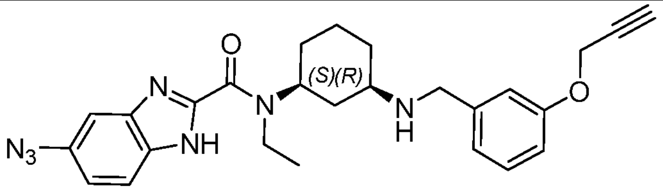
Figure 1C:
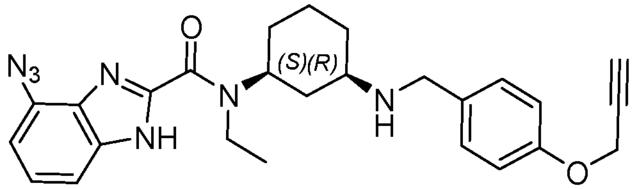
Figure 1C:
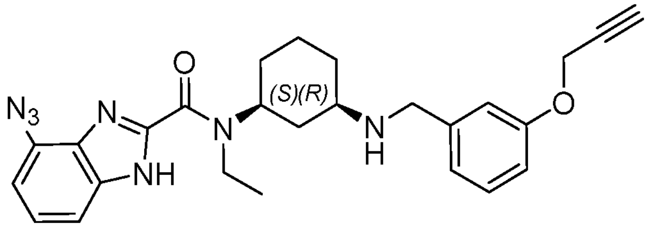
Figure 1C:
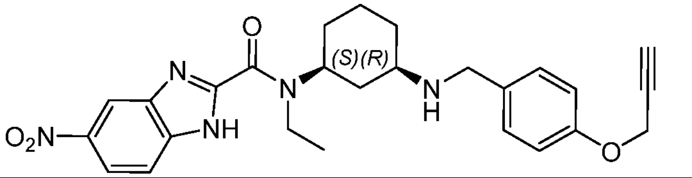
Figure 1C:
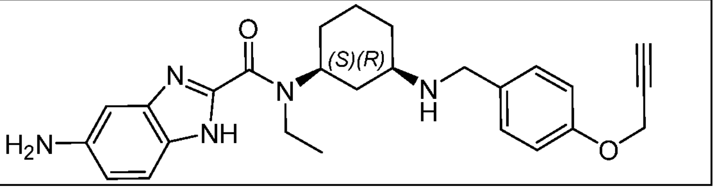
Figure 1D:
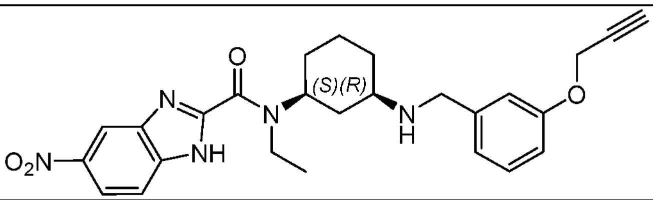
Figure 1D:
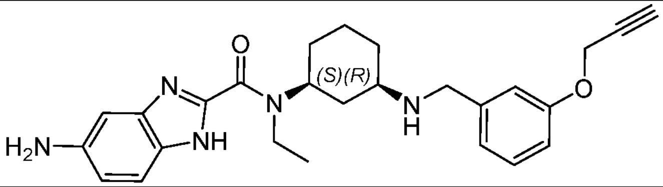
Figure 1D:
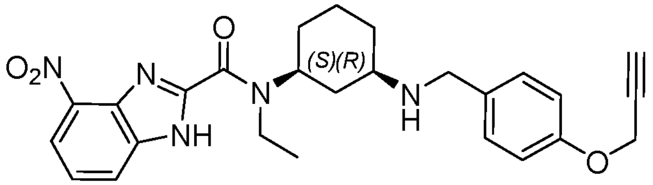
Figure 1D:
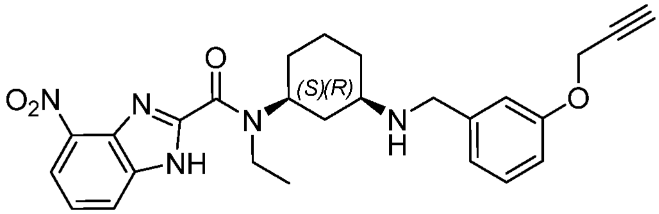
Figure 1D:
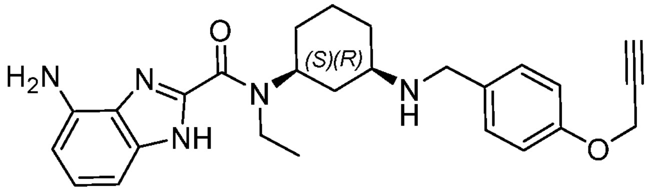
Figure 1D:
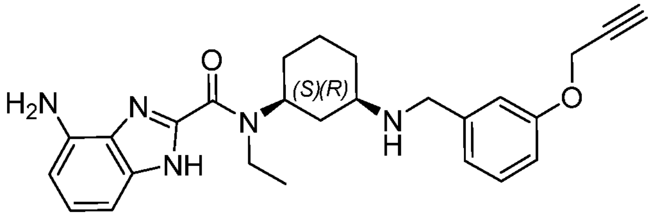
Figure 1D:
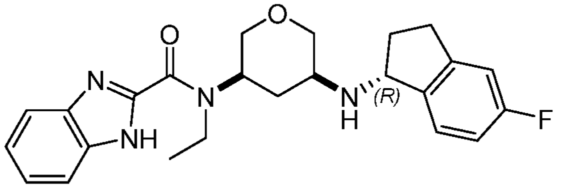

In some embodiments, the compound of Formula (I) (e.g., the compound of Formulas (I-a), (I-b), (I-c), (I-d), (I-e), (I-f), (I-g), (I-h), (I-i), (I-j), (I-k), (I-l), or (I-m)) is a compound described in FIG. 1.

In some embodiments, the compound of Formula (I) is selected from the group consisting of:

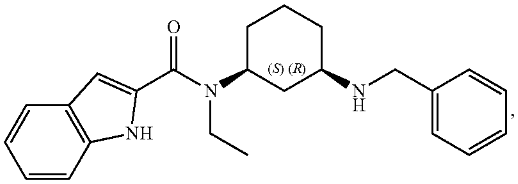
,

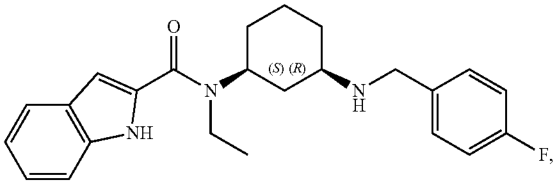
,

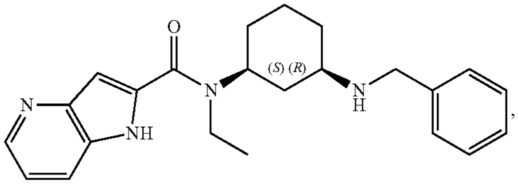
,

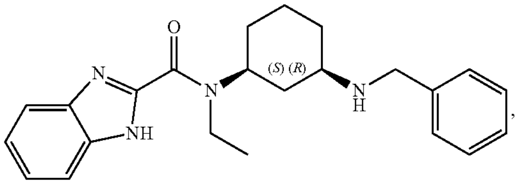
,

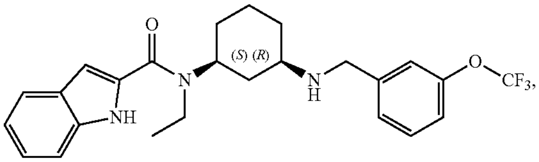
,

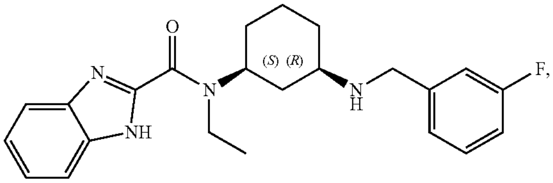
,

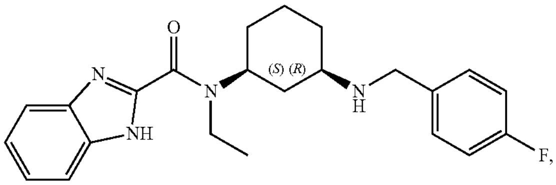
,

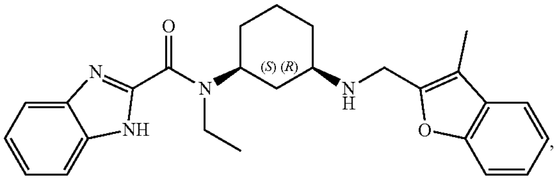
,

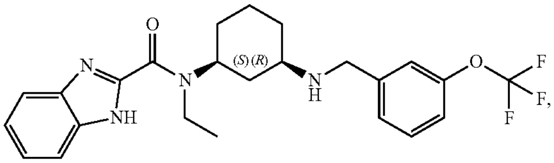
,

-continued
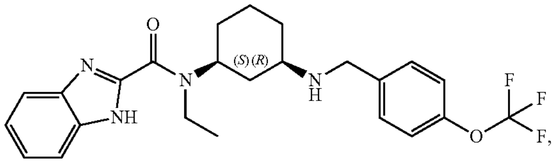
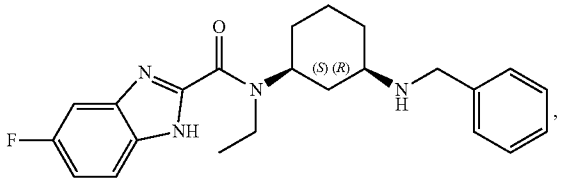
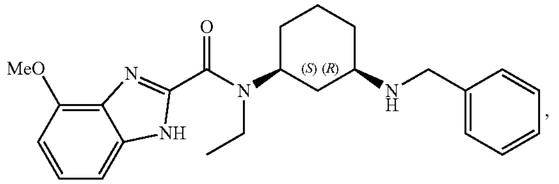
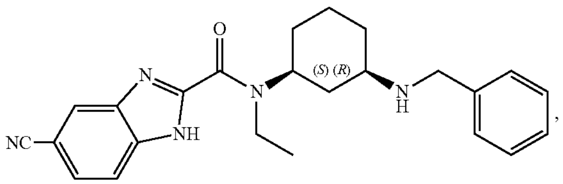
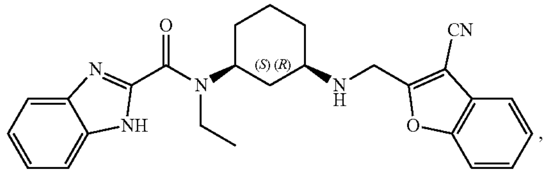
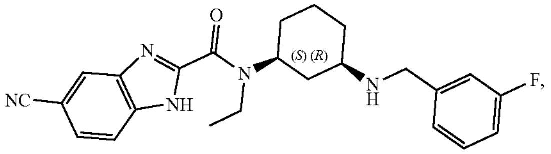
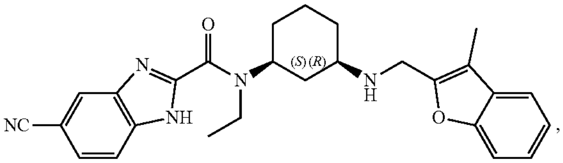
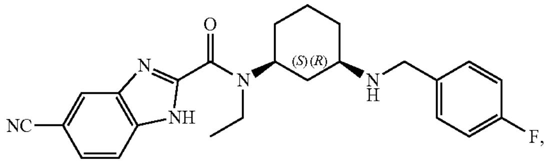
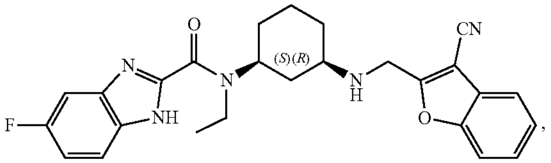
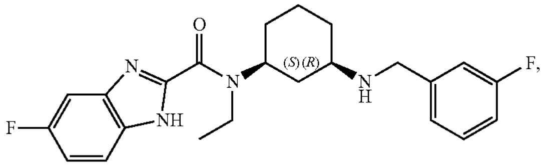
-continued
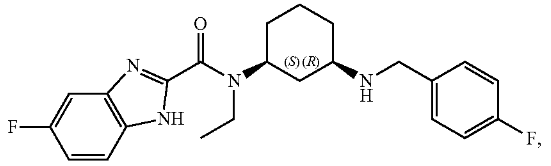
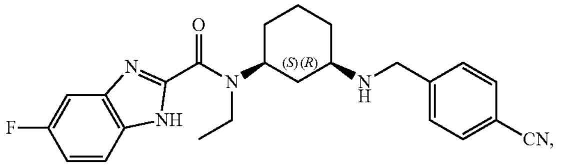
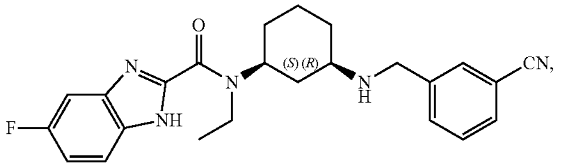
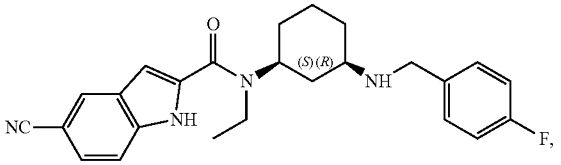
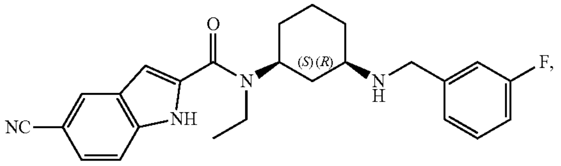
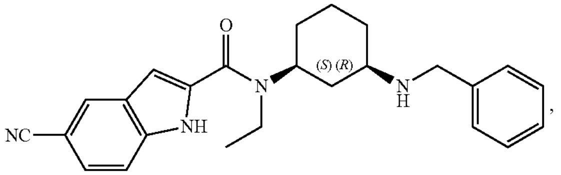
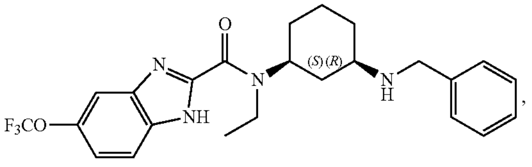
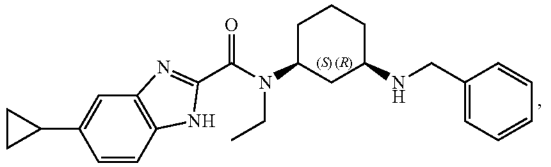
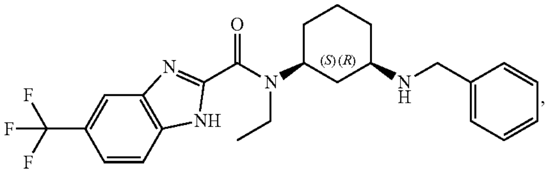
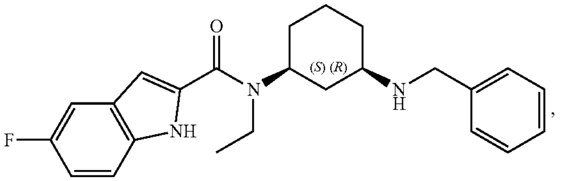

-continued

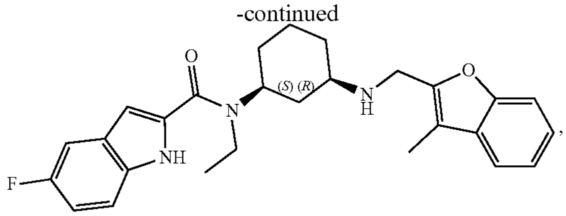

,

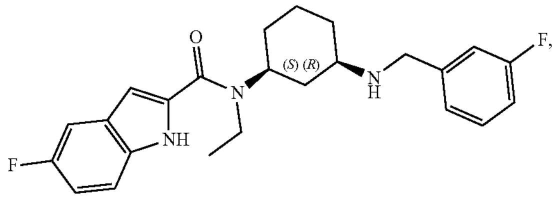

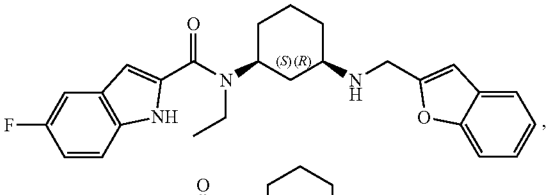

,

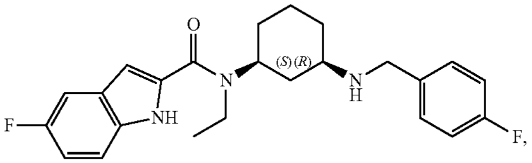

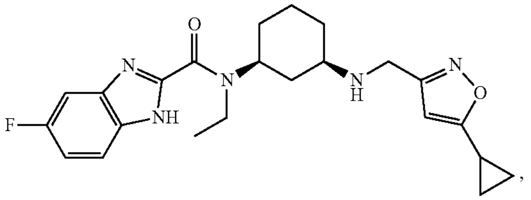

, and

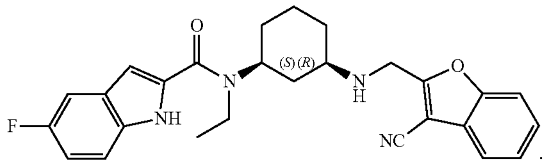

.

Deuterated Compounds

In some embodiments, compounds described herein (e.g., some compounds of Formula (I)) are deuterium-enriched.

Deuterium (D or $^2H$) is a stable, non-radioactive isotope of hydrogen and has an atomic weight of 2.0144. Hydrogen naturally occurs as a mixture of the isotopes $^1H$ (hydrogen or protium), D (H or deuterium), and T (H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015% should be considered unnatural and, as a result, novel over their non-enriched counterparts.

The effects of deuterium modification on a compound's metabolic properties are not predictable, even when deuterium atoms are incorporated at known sites of metabolism. Only by actually preparing and testing a deuterated compound can one determine if and how the rate of metabolism will differ from that of its non-deuterated counterpart. See, for example, Fukuto et al. (J. Med. Chem. 1991, 34, 2871-76). Many compounds have multiple sites where metabolism is possible. The site(s) where deuterium substitution is required and the extent of deuteration necessary to see an effect on metabolism, if any, will be different for each compound.

Unless otherwise stated, when a position is designated specifically as "H" or "hydrogen," the position is understood to have hydrogen at its natural abundance isotopic composition. Also unless otherwise stated, when a position is designated specifically as "D" or "deuterium," the position is understood to have deuterium at an abundance that is at least 3000 times greater than the natural abundance of deuterium, which is 0.015% (i.e., the term "D" or "deuterium" indicates at least 45% incorporation of deuterium).

The term "isotopic enrichment factor" as used herein means the ratio between the isotopic abundance of D at the specified position in a compound of this invention and the naturally occurring abundance of that isotope.

Increasing the amount of deuterium present in a compound (e.g., a compound of Formula (I)) is called "deuterium-enrichment," and such compounds are referred to as "deuterium-enriched" compounds. If not specifically noted, the percentage of enrichment refers to the percentage of deuterium present in the compound.

In other embodiments, a compound of this invention has an isotopic enrichment factor for each deuterium present at a site designated at a potential site of deuteration on the compound of at least 3500 (52.5.% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6466.7 (97% deuterium incorporation), at least 6633.3 (99.5% deuterium incorporation).

It is understood that the isotopic enrichment factor of each deuterium present at a site designated as a site of deuteration is independent of other deuterated sites. For example, if there are two sites of deuteration on a compound one site could be deuterated at 52.5% while the other could be deuterated at 75%. The resulting compound would be considered to be a compound wherein the isotopic enrichment factor is at least 3500 (52.5%).

Because the natural abundance of deuterium is about 0.015%, a small percentage of naturally occurring compounds of Formula (I) would be expected to have one naturally occurring compound with one deuterium present.

In some embodiments, the compounds of Formula (I) comprise an amount of deuterium-enrichment that is more than the amount of deuterium-enrichment present in naturally occurring compounds of Formula (I).

All percentages given for the amount of deuterium present are mole percentages.

It can be difficult in the laboratory to achieve 100% deuteration at any one site of a lab scale amount of compound (e.g., milligram or greater). When 100% deuteration is recited or a deuterium atom is specifically shown in a structure, it is assumed that a small percentage of hydrogen may still be present. Deuterium-enriched can be achieved by either exchanging protons with deuterium or by synthesizing the molecule with enriched starting materials.

Methods of Use

In another aspect, the invention provides a method of modulating stress granule formation, the method comprising contacting a cell with a compound of Formula (I). In some embodiments, stress granule formation is inhibited. In some embodiments, the stress granule is disaggregated. In some embodiments, stress granule formation is stimulated.

In some embodiments, a compound of Formula (I) inhibits the formation of a stress granule. The compound of Formula (I) can inhibit the formation of a stress granule by at least 10%, at least 20%, at least 30%, at least 40%, at least 50%, at least 60%, at least 70%, at least 80%, at least 90%, at least 95%, or 100% (i.e., complete inhibition) relative to a control.

In some embodiments, a compound of Formula (I) disaggregates a stress granule. The compound of Formula (I) can disperses or disaggregate a stress granule by at least 10%, at least 20%, at least 30%, at least 40%, at least 50%, at least 60%, at least 70%, at least 80%, at least 90%, at least 95%, or 100% (i.e., complete dispersal) relative to a control.

In some embodiments, the stress granule comprises tar DNA binding protein-43 (TDP-43), T-cell intracellular antigen 1 (TIA-1), TIA1 cytotoxic granule-associated RNA binding protein-like 1 (TIAR, TIAL1), GTPase activating protein binding protein 1 (G3BP-1), GTPase activating protein binding protein 2 (G3BP-2), tris tetraprolin (TTP, ZFP36), fused in sarcoma (FUS), or fragile X mental retardation protein (FMRP, FMR1).

In some embodiments, the stress granule comprises tar DNA binding protein-43 (TDP-43), T-cell intracellular antigen 1 (TIA-1), TIA1 cytotoxic granule-associated RNA binding protein-like 1 (TIAR, TIAL1), GTPase activating protein binding protein 1 (G3BP-1), GTPase activating protein binding protein 2 (G3BP-2), fused in sarcoma (FUS), or fragile X mental retardation protein (FMRP, FMR1).

In some embodiments, the stress granule comprises tar DNA binding protein-43 (TDP-43), T-cell intracellular antigen 1 (TIA-1), TIA1 cytotoxic granule-associated RNA binding protein-like 1 (TIAR, TIAL1), GTPase activating protein binding protein 1 (G3BP-1), GTPase activating protein binding protein 2 (G3BP-2), or fused in sarcoma (FUS).

In some embodiments, the stress granule comprises tar DNA binding protein-43 (TDP-43).

In some embodiments, the stress granule comprises T-cell intracellular antigen 1 (TIA-1).

In some embodiments, the stress granule comprises TIA-1 cytotoxic granule-associated RNA binding protein-like 1 (TIAR, TIAL1).

In some embodiments, the stress granule comprises GTPase activating protein binding protein 1 (G3BP-1).

In some embodiments, the stress granule comprises GTPase activating protein binding protein 2 (G3BP-2).

In some embodiments, the stress granule comprises tris tetraprolin (TTP, ZFP36).

In some embodiments, the stress granule comprises fused in sarcoma (FUS).

In some embodiments, the stress granule comprises fragile X mental retardation protein (FMRP, FMR1).

In another aspect, the invention provides a method of modulating TDP-43 inclusion formation, the method comprising contacting a cell with a compound of Formula (I). In some embodiments, TDP-43 inclusion formation is inhibited. In some embodiments, the TDP-43 inclusion is disaggregated. In some embodiments, TDP-43 inclusion formation is stimulated.

In some embodiments, a compound of Formula (I) inhibits the formation of a TDP-43 inclusion. The compound of Formula (I) can inhibit the formation of a TDP-43 inclusion by at least 10%, at least 20%, at least 30%, at least 40%, at least 50%, at least 60%, at least 70%, at least 80%, at least 90%, at least 95%, or 100% (i.e., complete inhibition) relative to a control.

In some embodiments, a compound of Formula (I) disaggregates a TDP-43 inclusion.

The compound of Formula (I) can disperses or disaggregate a TDP-43 inclusion by at least 10%, at least 20%, at least 30%, at least 40%, at least 50%, at least 60%, at least 70%, at least 80%, at least 90%, at least 95%, or 100% (i.e., complete dispersal) relative to a control.

In another aspect, the invention provides a method for treatment of a neurodegenerative disease or disorder, a musculoskeletal disease or disorder, a cancer, an ophthalmological disease or disorder (e.g., a retinal disease or disorder), and/or a viral infection, the method comprising administering an effective amount of a compound of Formula (I) to a subject in need thereof.

In some embodiments, the methods are performed in a subject suffering from a neurodegenerative disease or disorder, a musculoskeletal disease or disorder, a cancer, an ophthalmological disease or disorder (e.g., a retinal disease or disorder), and/or a viral infection.

In some embodiments, the methods are performed in a subject suffering from a neurodegenerative disease or disorder. In some embodiments, the methods are performed in a subject suffering from a musculoskeletal disease or disorder. In some embodiments, the methods are performed in a subject suffering from a cancer. In some embodiments, the methods are performed in a subject suffering from an ophthalmological disease or disorder (e.g., a retinal disease or disorder). In some embodiments, the methods are performed in a subject suffering from a viral infection or viral infections.

In some embodiments, the methods comprise administering a compound of Formula (I) to a subject in need thereof. In some embodiments, the subject is a mammal. In some embodiments, the subject is a nematode. In some embodiments, the subject is human.

In some embodiments, the methods further comprise the step of diagnosing the subject with a neurodegenerative disease or disorder, a musculoskeletal disease or disorder, a cancer, an ophthalmological disease or disorder (e.g., a retinal disease or disorder), or a viral infection prior to administration of a compound of Formula (I). In some embodiments, the methods further comprise the step of diagnosing the subject with a neurodegenerative disease or disorder prior to administration of a compound of Formula (I).

In some embodiments, the neurodegenerative disease is selected from the group consisting of Alzheimer's disease, frontotemporal dementia (FTD), FTLD-U, FTD caused by mutations in the progranulin protein or tau protein (e.g., progranulin-deficient FTLD), frontotemporal dementia with inclusion body myopathy (IBMPFD), frontotemporal dementia with motor neuron disease, amyotrophic lateral sclerosis (ALS), Huntington's disease (HD), Huntington's chorea, prion diseases (e.g., Creutzfeld-Jacob disease, bovine spongiform encephalopathy, Kuru, and scrapie), Lewy Body disease, diffuse Lewy body disease (DLBD), polyglutamine (polyQ)-repeat diseases, trinucleotide repeat diseases, cerebral degenerative diseases, presenile dementia, senile dementia, Parkinsonism linked to chromosome 17 (FTDP-17), progressive supranuclear palsy (PSP), progressive bulbar palsy (PBP), psuedobulbar palsy, spinal and bulbar muscular atrophy (SBMA), primary lateral sclerosis, Pick's disease, primary progressive aphasia, corticobasal dementia, HIV-associated dementia, Parkinson's disease, Parkinson's disease with dementia, dementia with Lewy bodies, Down's syndrome, multiple system atrophy, spinal muscular atrophy (SMA, e.g., SMA Type I (e.g., Werdnig- Hoffmann disease), SMA Type II, SMA Type III (e.g., Kugelberg-Welander disease), and congenital SMA with arthrogryposis), progressive spinobulbar muscular atrophy (e.g., Kennedy disease), post-polio syndrome (PPS), spinocerebellar ataxia, pantothenate kinase-associated neurodegeneration (PANK), spinal degenerative disease/motor neuron degenerative diseases, upper motor neuron disorder, lower motor neuron disorder, age-related disorders and dementias, Hallervorden-Spatz syndrome, cerebral infarction, cerebral trauma, chronic traumatic encephalopathy, transient ischemic attack, Lytigo-bodig (amyotrophic lateral sclerosis-parkinsonism dementia), Guam-Parkinsonism dementia, hippocampal sclerosis, corticobasal degeneration, Alexander disease, Apler's disease, Krabbe's disease, neuroborreliosis, neurosyphilis, Sandhoff disease, Tay-Sachs disease, Schilder's disease, Batten disease, Cockayne syndrome, Keams-Sayre syndrome, Gerstmann-Straussler-Scheinker syndrome and other transmissible spongiform encephalopathies, hereditary spastic paraparesis, Leigh's syndrome, demyelinating diseases, neuronal ceroid lipofuscinoses, epilepsy, tremors, depression, mania, anxiety and anxiety disorders, sleep disorders (e.g., narcolepsy, fatal familial insomnia), acute brain injuries (e.g., stroke, head injury) autism, other diseases or disorders relating to the aberrant expression of TDP-43 and altered proteostasis, and any combination thereof.

In some embodiments, the neurodegenerative disease is selected from the group consisting of Alzheimer's disease, frontotemporal dementia (FTD), FTLD-U, FTD caused by mutations in the progranulin protein or tau protein (e.g., progranulin-deficient FTLD), amyotrophic lateral sclerosis (ALS), Huntington's disease (HD), Huntington's chorea, Creutzfeld-Jacob disease, senile dementia, Parkinsonism linked to chromosome 17 (FTDP-17), progressive supranuclear palsy (PSP), Pick's disease, primary progressive aphasia, corticobasal dementia, Parkinson's disease, Parkinson's disease with dementia, dementia with Lewy bodies, Down's syndrome, multiple system atrophy, spinal muscular atrophy (SMA), spinocerebellar ataxia, spinal degenerative disease/motor neuron degenerative diseases, Hallervorden-Spatz syndrome, cerebral infarction, cerebral trauma, chronic traumatic encephalopathy, transient ischemic attack, Lytigo-bodig (amyotrophic lateral sclerosis-parkinsonism dementia), hippocampal sclerosis, corticobasal degeneration, Alexander disease, Cockayne syndrome, and any combination thereof.

In some embodiments, the neurodegenerative disease is frontotemporal dementia (FTD). In some embodiments, the neurodegenerative disease is Alzheimer's disease or amyotrophic lateral sclerosis (ALS).

In some embodiments, the musculoskeletal disease is selected from the group consisting of muscular dystrophy, facioscapulohumeral muscular dystrophy (e.g., FSHD1 or FSHD2), Freidrich's ataxia, progressive muscular atrophy (PMA), mitochondrial encephalomyopathy (MELAS), multiple sclerosis, inclusion body myopathy, inclusion body myositis (e.g., sporadic inclusion body myositis), post-polio muscular atrophy (PPMA), motor neuron disease, myotonia, myotonic dystrophy, sacropenia, multifocal motor neuropathy, inflammatory myopathies, paralysis, and other diseases or disorders relating to the aberrant expression of TDP-43 and altered proteostasis.

In some embodiments, compounds of Formula (I) may be used to prevent or treat symptoms caused by or relating to said musculoskeletal diseases, e.g., kyphosis, hypotonia, foot drop, motor dysfunctions, muscle weakness, muscle atrophy, neuron loss, muscle cramps, altered or aberrant gait, dystonias, astrocytosis (e.g., astrocytosis in the spinal cords), liver disease, respiratory disease or respiratory failure, inflammation, headache, and pain (e.g., back pain, neck pain, leg pain, or inflammatory pain).

In some embodiments, the cancer is selected from the group consisting of breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, ophthalmological cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, vulval cancer, and any combination thereof.

In some embodiments, the cancer is selected from the group consisting of blastoma, carcinoma, a glioblastoma, hepatic carcinoma, lymphoma, leukemia, and any combination thereof.

In some embodiments, the cancer is selected from Hodgkin's lymphoma or non-Hodgkin's lymphoma. In some embodiments, the cancer is a non-Hodgkin's lymphoma, selected from the group consisting of a B-cell lymphoma (e.g., diffuse large B-cell lymphoma, primary mediastinal B-cell lymphoma, intravascular large B-cell lymphoma, follicular lymphoma, chronic lymphocytic leukemia/small lymphocytic lymphoma, mantle cell lymphoma, marginal zone B-cell lymphomas, extranodal marginal B-cell lymphomas, mucosa-associated lymphoid tissue (MALT) lymphomas, modal marginal zone B-cell lymphoma, splenic marginal zone B-cell lymphoma, Burkitt lymphoma, lymphoplasmacytic lymphoma, Waldenström's macroglobulinemia, hairy cell leukemia, and primary central nervous system (CNS) lymphoma) and a T-cell lymphoma (e.g., precursor T-lymphoblastic lymphoma/leukemia, peripheral T-cell lymphoma, cutaneous T-cell lymphoma, adult T-cell lymphoma (e.g., smoldering adult T-cell lymphoma, chronic adult T-cell lymphoma, acute adult T-cell lymphoma, lymphomatous adult T-cell lymphoma), angioimmunoblastic T-cell lymphoma, extranodal natural killer T-cell lymphoma nasal type (ENKL), enteropathy-associated intestinal T-cell lymphoma (EATL) (e.g., Type I EATL and Type II EATL), and anaplastic large cell lymphoma (ALCL)).

In some embodiments, the ophthalmological disease or disorder (e.g., retinal disease or disorder) is selected from macular degeneration (e.g., age-related macular degeneration), diabetes retinopathy, histoplasmosis, macular hole, macular pucker, Bietti's crystalline dystrophy, retinal detachment, retinal thinning, retinoblastoma, retinopathy of prematurity, Usher's syndrome, vitreous detachment, Refsum disease, retinitis pigmentosa, onchocerciasis, choroideremia, Leber congenital amaurosis, retinoschisis (e.g., juvenile retinoschisis), Stargardt disease, ophthalmoplegia, and the like.

In some embodiments, the ophthalmological disease or disorder (e.g., retinal disease or disorder) is selected from macular degeneration (e.g., age-related macular degeneration), diabetes retinopathy, histoplasmosis, macular hole, macular pucker, Bietti's crystalline dystrophy, retinoblastoma, retinopathy of prematurity, Usher's syndrome, Refsum disease, retinitis pigmentosa, onchocerciasis, choroideremia, Leber congenital amaurosis, retinoschisis (e.g., juvenile retinoschisis), Stargardt disease, and the like.

In some embodiments, the viral infection is caused by a virus selected from the group consisting of West Nile virus, respiratory syncytial virus (RSV), herpes simplex virus 1, herpes simplex virus 2, Epstein-Barr virus (EBV), hepatitis virus A, hepatitis virus B, hepatitis virus C, influenza viruses, chicken pox, avian flu viruses, smallpox, polio viruses, HIV-1, HIV-2, Ebola virus, and any combination thereof.

In some embodiments, the viral infection is caused by a virus selected from the group consisting of herpes simplex virus 1, herpes simplex virus 2, Epstein-Barr virus (EBV), hepatitis virus A, hepatitis virus B, hepatitis virus C, HIV-1, HIV-2, Ebola virus, and any combination thereof.

In some embodiments, the viral infection is HIV-1 or HIV-2.

In some embodiments, the pathology of the neurodegenerative disease or disorder, musculoskeletal disease or disorder, cancer, ophthalmological disease or disorder (e.g., retinal disease or disorder), and/or viral infection comprises stress granules.

In some embodiments, pathology of the disease or disorder comprises stress granules. By comprising stress granules is meant that number of stress granules in a cell in the subject is changed relative to a control and/or healthy subject or relative to before onset of said disease or disorder. Exemplary diseases and disorders pathology of which incorporate stress granules include, but are not limited to, neurodegenerative diseases, musculoskeletal diseases, cancers, ophthalmological diseases (e.g., retinal diseases), and viral infections.

In another aspect, the invention provides methods of diagnosing a neurodegenerative disease, a musculoskeletal disease, a cancer, an ophthalmological disease (e.g., a retinal disease), or a viral infection in a subject, the method comprising administering a compound of Formula (I) to the subject. In some embodiments, the invention provides methods of diagnosing a neurodegenerative disease in a subject, the method comprising administering a compound of Formula (I) to the subject. For use in diagnosis, a compound of Formula (I) can be modified with a label.

In another aspect, the invention provides methods of modulating stress granules comprising contacting a cell with a compound of Formula (I).

In another aspect, the invention provides methods of modulating TDP-43 inclusion formation comprising contacting a cell with a compound of Formula (I). In some embodiments, TDP-43 is inducibly expressed. In some embodiments, the cell line is a neuronal cell line.

In some embodiments, the cell is treated with a physiochemical stressor. In some embodiments, the physicochemical stressor is selected from arsenite, nutrient deprivation, heat shock, osmotic shock, a virus, genotoxic stress, radiation, oxidative stress, oxidative stress, a mitochondrial inhibitor, and an endoplasmic reticular stressor. In some embodiments, the physicochemical stressor is ultraviolet or x-ray radiation. In some embodiments, the physicochemical stressor is oxidative stress induced by $FeCl_2$ or $CuCl_2$ and a peroxide.

In yet another aspect, the invention provides a method of screening for modulators of TDP-43 aggregation comprising contacting a compound of Formula (I) with a cell that expresses TDP-43 and develops spontaneous inclusions.

In some embodiments, the stress granule comprises TDP-43, i.e., is a TDP-43 inclusion.

Accordingly, in some embodiments, a compound of Formula (I) is a modulator of TDP-43 inclusions.

In some embodiments, the subject is a mammal. In some embodiments, the subject is human.

In some embodiments, the method further comprises the step of diagnosing the subject with the neurodegenerative disease or disorder, musculoskeletal disease or disorder, cancer, ophthalmological disease or disorder, or viral infection prior to onset of said administration. In some embodiments, the pathology of said neurodegenerative disease or disorder, said musculoskeletal disease or disorder, said cancer, said ophthalmological disease or disorder, and said viral infection comprises stress granules. In some embodiments, the pathology of said neurodegenerative disease, said musculoskeletal disease or disorder, said cancer, said ophthalmological disease or disorder, and said viral infection comprises TDP-43 inclusions.

TDP-43 and other RNA-binding proteins function in both the nucleus and cytoplasm to process mRNA, e.g., by splicing mRNA, cleaving mRNA introns, cleaving untranslated regions of mRNA or modifying protein translation at the synapse, axon, dendrite or soma. Therefore, targeting other proteins that function in an analogous manner to TDP-43 or by processing mRNA may also be beneficial to prevent and treat neurodegeneration resulting from disease. For instance, the fragile X mental retardation 1 (FMRP) protein is essential for normal cognitive development (Nakamoto, M., et al. (2007) *Proc Natl Acad Sci U.S.A.* 104: 15537-15542). The signaling systems that affect TDP-43 function might also affect this protein, thus improving cognitive function. This can be particularly important at the synapse where neurons communicate. Without wishing to be bound by a theory, the signaling systems that compounds of Formula (I) target may also modify these processes, which play a role in neurodegeneration or mental health illnesses (e.g., schizophrenia).

The cellular stress response follows a U-shaped curve. Overinduction of this pathway, such as observed in many neurodegenerative diseases, can be harmful for cells. However, a decreased stimulation of this pathway can also be harmful for cells, e.g., in the case of an acute stress, such as a stroke. Thus, the appropriate action for some diseases is the inhibition of stress granule formation, while for other diseases, stimulation of stress granule formation is beneficial.

In some embodiments, the TDP-43 protein in a stress granule may be wild-type or a mutant form of TDP-43. In some embodiments, the mutant form of TDP-43 comprises an amino acid addition, deletion, or substitution, e.g., relative to the wild type sequence of TDP-43. In some embodiments, the mutant form of TDP-43 comprises an amino acid substitution relative to the wild type sequence, e.g., a G294A, A135T, Q331K, or Q343R substitution. In some embodiments, the TDP-43 protein in a stress granule comprises a post-translational modification, e.g., phosphorylation of an amino acid side chain, e.g., T103, S104, S409, or S410. In some embodiments, post-translational modification of the TDP-43 protein in a stress granule may be modulated by treatment with a compound of the invention.

Methods of Treatment

Neurodegenerative diseases: Without wishing to be bound by a theory, compounds of Formula (I) can be used to delay the progression of neurodegenerative illnesses where the pathology incorporates stress granules. Such illnesses include ALS and frontotemporal dementia, in which TDP-43 is the predominant protein that accumulates to form the pathology. This group also includes Alzheimer's disease and FTLD-U, where TDP-43 and other stress granule proteins co-localize with tau pathology. Because modulators of TDP-43 inclusions, such as compounds of Formula (I), can act to block the enzymes that signal stress granule formation (e.g., the three enzymes that phosphorylate eIF2a: PERK, GCN2 and HRI), compounds of Formula (I) may also reverse stress granules that might not include TDP-43. Accordingly, compounds of Formula (I) can be used for treatment of neurodegenerative diseases and disorders in which the pathology incorporates stress granules, such as Huntington's chorea and Creutzfeld-Jacob disease. Compounds of Formula (I) may also be used for treatment of neurodegenerative diseases and disorders that involve TDP-43 multisystem proteinopathy.

The term "neurodegenerative disease" as used herein, refers to a neurological disease characterized by loss or degeneration of neurons. The term "neurodegenerative disease" includes diseases caused by the involvement of genetic factors or the cell death (apoptosis) of neurons attributed to abnormal protein accumulation and so on. Additionally, neurodegenerative diseases include neurodegenerative movement disorders and neurodegenerative conditions relating to memory loss and/or dementia. Neurodegenerative diseases include tauopathies and α-synucleopathies. Exemplary neurodegenerative diseases include, but are not limited to, Alzheimer's disease, frontotemporal dementia (FTD), FTLD-U, FTD caused by mutations in the progranulin protein or tau protein (e.g., progranulin-deficient FTLD), frontotemporal dementia with inclusion body myopathy (IBMPFD), frontotemporal dementia with motor neuron disease, amyotrophic lateral sclerosis (ALS), amyotrophic lateral sclerosis with dementia (ALSD), Huntington's disease (HD), Huntington's chorea, prion diseases (e.g., Creutzfeld-Jacob disease, bovine spongiform encephalopathy, Kuru, or scrapie), Lewy Body disease, diffuse Lewy body disease (DLBD), polyglutamine (polyQ)-repeat diseases, trinucleotide repeat diseases, cerebral degenerative diseases, presenile dementia, senile dementia, Parkinsonism linked to chromosome 17 (FTDP-17), progressive supranuclear palsy (PSP), progressive bulbar palsy (PBP), psuedobulbar palsy, spinal and bulbar muscular atrophy (SBMA), primary lateral sclerosis, Pick's disease, primary progressive aphasia, corticobasal dementia, HIV-associated dementia, Parkinson's disease, Parkinson's disease with dementia, dementia with Lewy bodies, Down's syndrome, multiple system atrophy, spinal muscular atrophy (SMA, e.g., SMA Type I (e.g., Werdnig-Hoffmann disease) SMA Type II, SMA Type III (e.g., Kugelberg-Welander disease), and congenital SMA with arthrogryposis), progressive spinobulbar muscular atrophy (e.g., Kennedy disease), post-polio syndrome (PPS), spinocerebellar ataxia, pantothenate kinase-associated neurodegeneration (PANK), spinal degenerative disease/motor neuron degenerative diseases, upper motor neuron disorder, lower motor neuron disorder, age-related disorders and dementias, Hallervorden-Spatz syndrome, Lytigo-bodig (amyotrophic lateral sclerosis-parkinsonism dementia), Guam-Parkinsonism dementia, hippocampal sclerosis, corticobasal degeneration, Alexander disease, Apler's disease, Krabbe's disease, neuroborreliosis, neurosyphilis, Sandhoff disease, Schilder's disease, Batten disease, Cockayne syndrome, Keams-Sayre syndrome, Gerstmann-Straussler-Scheinker syndrome, hereditary spastic paraparesis, Leigh's syndrome, demyelinating diseases, epilepsy, tremors, depression, mania, anxiety and anxiety disorders, sleep disorders (e.g., narcolepsy, fatal familial insomnia), acute brain injuries (e.g., stroke, head injury) and autism. As used herein, the term "α-synucleopathy" refers to a neurodegenerative disorder or disease involving aggregation of α-synuclein or abnormal α-synuclein in nerve cells in the brain (Ostrerova, N., et al. (1999) *J Neurosci* 19:5782:5791; Rideout, H. J., et al. (2004) *J Biol Chem* 279:46915-46920). α-Synucleopathies include, but are not limited to, Parkinson's disease, Parkinson's disease with dementia, dementia with Lewy bodies, Pick's disease, Down's syndrome, multiple system atrophy, amylotrophic lateral sclerosis (ALS), Hallervorden-Spatz syndrome, and the like.

As used herein, the term "tauopathy" refers to a neurodegenerative disease associated with the pathological aggregation of tau protein in the brain. Tauopathies include, but are not limited to, Alzheimer's disease, Pick's disease, corticobasal degeneration, Argyrophilic grain disease (AGD), progressive supranuclear palsy, Frontotemporal dementia, Frontotemporal lobar degeneration, or Pick's complex.

Musculoskeletal diseases: Musculoskeletal diseases and disorders as defined herein are conditions that affect the muscles, ligaments, tendons, and joints, as well as the skeletal structures that support them. Without wishing to be bound by a theory, aberrant expression of certain proteins, such as the full-length isoform of DUX4, has been shown to inhibit protein turnover and increase the expression and aggregation of cytotoxic proteins including insoluble TDP-43 in skeletal muscle cells (Homma, S. et al. *Ann Clin Transl Neurol* (2015) 2:151-166). As such, compounds of Formula (I), Formula (II), and Formula (III) may be used to prevent or treat a musculoskeletal disease, e.g., a musculoskeletal disease that results in accumulation of TDP-43 and other stress granule proteins, e.g., in the nucleus, cytoplasm, or cell bodies of a muscle cell or motor neuron. Exemplary musculoskeletal diseases include muscular dystrophy, facioscapulohumeral muscular dystrophy (e.g., FSHD1 or FSHD2), Freidrich's ataxia, progressive muscular atrophy (PMA), mitochondrial encephalomyopathy (MELAS), multiple sclerosis, inclusion body myopathy, inclusion body myositis (e.g., sporadic inclusion body myositis), post-polio muscular atrophy (PPMA), motor neuron disease, myotonia, myotonic dystrophy, sacropenia, spasticity, multifocal motor neuropathy, inflammatory myopathies, paralysis, and other diseases or disorders relating to the aberrant expression of TDP-43 and altered proteostasis. In addition, compounds of Formula (I) may be used to prevent or treat symptoms caused by or relating to said musculoskeletal diseases, e.g., kyphosis, hypotonia, foot drop, motor dysfunctions, muscle weakness, muscle atrophy, neuron loss, muscle cramps, altered or aberrant gait, dystonias, astrocytosis (e.g., astrocytosis in the spinal cords), liver disease, inflammation, headache, pain (e.g., back pain, neck pain, leg pain, inflammatory pain), and the like. In some embodiments, a musculoskeletal disease or a symptom of a musculoskeletal disease may overlap with a neurodegenerative disease or a symptom of a neurodegenerative disease.

Cancers: Cancer cells grow quickly and in low oxygen environments by activating different elements of the cellular stress response. Researchers have shown that drugs targeting different elements of the stress response can be anti-neoplastic. For example, rapamycin blocks mTOR, upregulates autophagy and inhibits some types of tumors. Proteasomal inhibitors, such as velcade (Millenium Pharma) are used to treat some cancers. HSP90 inhibitors, such as 17-allylaminogeldanamycin (17AAG), are currently in clinical trials for cancer. Without wishing to be bound by a theory, compounds of Formula (I) may also be used for treatment of cancer, as a greater understanding of the role of TDP-43 in RNA processing and transcription factor signaling has recently begun to emerge (Lagier-Tourenne, C., et al. (2010) *Hum Mol Genet* 19:R46-R64; Ayala, Y. M., et al. (2008) *Proc Natl Acad Sci U.S.A.* 105(10):3785-3789). Additionally, TDP-43 modulators can be combined with one or more cancer therapies, such as chemotherapy and radiation therapy.

A "cancer" in a subject refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. In some circumstances, cancer cells will be in the form of a tumor; such cells may exist locally within an animal, or circulate in the blood stream as independent cells, for example, leukemic cells. Examples of cancer include but are not limited to breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, ophthalmological cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, vulval cancer, and the like.

Other exemplary cancers include, but are not limited to, ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, ophthalmological cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva, Wilm's tumor, and the like.

Exemplary lymphomas include Hodgkin's lymphoma and non-Hodgkin's lymphoma. Further exemplification of non-Hodgkin's lymphoma include, but are not limited to, B-cell lymphomas (e.g., diffuse large B-cell lymphoma, primary mediastinal B-cell lymphoma, intravascular large B-cell lymphoma, follicular lymphoma, chronic lymphocytic leukemia/small lymphocytic lymphoma, mantle cell lymphoma, marginal zone B-cell lymphomas, extranodal marginal B-cell lymphomas, mucosa-associated lymphoid tissue (MALT) lymphomas, modal marginal zone B-cell lymphoma, splenic marginal zone B-cell lymphoma, Burkitt lymphoma, lymphoplasmacytic lymphoma, Waldenström's macroglobulinemia, hairy cell leukemia, and primary central nervous system (CNS) lymphoma) and T-cell lymphomas (e.g., precursor T-lymphoblastic lymphoma/leukemia, peripheral T-cell lymphoma, cutaneous T-cell lymphoma, adult T-cell lymphoma (e.g., smoldering adult T-cell lymphoma, chronic adult T-cell lymphoma, acute adult T-cell lymphoma, lymphomatous adult T-cell lymphoma), angioimmunoblastic T-cell lymphoma, extranodal natural killer T-cell lymphoma nasal type (ENKL), enteropathy-associated intestinal T-cell lymphoma (EATL) (e.g., Type I EATL and Type II EATL), and anaplastic large cell lymphoma (ALCL)).

Ophthalmological diseases: Ophthalmological diseases and disorders (e.g., retinal diseases and disorders) as defined herein affect the retina and other parts of the eye and may contribute to impaired vision and blindness. Several ophthalmological diseases (e.g., retinal diseases) are characterized by the accumulation of protein inclusions and stress granules within or between cells of the eye, e.g., retinal cells and nearby tissues. In addition, an ophthalmological disease (e.g., retinal disease) may also be a symptom of or precursor to neurogenerative diseases, such as ALS and FTD (Ward, M. E., et al. (2014) *J Exp Med* 211(10):1937). Therefore, use of compounds that may inhibit formation of protein inclusions and stress granules, including compounds of Formula (I), may play an important role in the prevention or treatment of ophthalmological diseases (e.g., retinal diseases).

Exemplary ophthalmological diseases (e.g., retinal diseases) include, but are not limited to, macular degeneration (e.g., age-related macular degeneration), diabetes retinopathy, histoplasmosis, macular hole, macular pucker, Bietti's crystalline dystrophy, retinal detachment, retinal thinning, retinoblastoma, retinopathy of prematurity, Usher's syndrome, vitreous detachment, Refsum disease, retinitis pigmentosa, onchocerciasis, choroideremia, Leber congenital amaurosis, retinoschisis (e.g., juvenile retinoschisis), Stargardt disease, ophthalmoplegia, and the like.

Viral infections: Stress granules often form during viral illnesses, as viral infections often involve hijacking the cellular reproductive machinery toward production of viral proteins. In this case, inhibitors of stress granules can be useful for interfering with viral function. Other viruses appear to inhibit SG formation to prevent the cell from mobilizing a stress response. In such a case, an inducer of stress granules can interfere with viral activity and help combat viral infections (e.g., Salubrinal, an eIF2a phosphatase inhibitor and stress granule inducer). Two viruses for which SG biology has been investigated include West Nile virus and respiratory syncytial virus (RSV) (Emara, M. E. and Brinton, M. A. (2007) *Proc. Nat. Acad. Sci. USA* 104(21): 9041-9046). Therefore, use of compounds that may inhibit formation of protein inclusions and stress granules, including compounds of Formula (I), may be useful for the prevention and/or treatment of a viral infection.

Exemplary viruses include, but are not limited to, West Nile virus, respiratory syncytial virus (RSV), Epstein-Barr virus (EBV), hepatitis A, B, C, and D viruses, herpes viruses, influenza viruses, chicken pox, avian flu viruses, smallpox, polio viruses, HIV, Ebola virus, and the like.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein, the terms “compounds” and “agent” are used interchangeably to refer to the inhibitors/antagonists/agonists of the invention. In certain embodiments, the compounds are small organic or inorganic molecules, e.g., with molecular weights less than 7500 amu, preferably less than 5000 amu, and even more preferably less than 2000, 1500, 1000, 750, 600, or 500 amu. In certain embodiments, one class of small organic or inorganic molecules are non-peptidyl, e.g., containing 2, 1, or no peptide and/or saccharide linkages.

Unless otherwise indicated, all numbers expressing quantities of ingredients or reaction conditions used herein should be understood as modified in all instances by the term “about.” The term “about” when used in connection with percentages may mean±1%.

The singular terms “a,” “an,” and “the” refer to one or to more than one, unless context clearly indicates otherwise. Similarly, the word “or” is intended to include “and” unless the context clearly indicates otherwise.

Although methods and materials similar or equivalent to those described herein can be used in the practice or testing of this disclosure, suitable methods and materials are described below.

As used herein, the term “administer” refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, intrathecal, and topical (including buccal and sublingual) administration.

The terms “decrease”, “reduced”, “reduction”, “decrease” or “inhibit” are all used herein generally to mean a decrease by a statistically significant amount. In some embodiments, the terms “reduced”, “reduction”, “decrease” or “inhibit” mean a decrease by at least 0.1% as compared to a reference level, for example a decrease by at least about 1%, or at least about 5%, or at least about 10%, or at least about 15%, or at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 1-100%, e.g., 10-100% as compared to a reference level.

The terms “increased”, “increase”, “enhance” or “activate” are all used herein to generally mean an increase by a statically significant amount. In some embodiments, the terms “increased”, “increase”, “enhance” or “activate” mean an increase by at least 0.1% as compared to a reference level, for example a decrease by at least about 1%, or at least about 5%, or at least about 10%, or at least about 15%, or at least about 20%, or at least about 30%, or at least about 40%, or at least about 50%, or at least about 60%, or at least about 70%, or at least about 80%, or at least about 90% or up to and including a 100% increase (e.g. absent level as compared to a reference sample), or any increase between 1-100%, e.g., 10-100% as compared to a reference level.

By “treatment”, “prevention” or “amelioration” of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, at least one symptom of a disease or disorder is alleviated by at least about 1%, or at least about 5%, or at least about 10%, or at least about 15%, or at least about 20%, or at least about 30%, or at least about 40%, or at least about 50%.

As used herein, an amount of a compound or combination effective to treat a disorder (e.g., a disorder as described herein), “therapeutically effective amount” or “effective amount” refers to an amount of the compound or combination which is effective, upon single or multiple dose administration(s) to a subject, in treating a subject, or in curing, alleviating, relieving or improving a subject with a disorder (e.g., a disorder as described herein) beyond that expected in the absence of such treatment. Determination of a therapeutically effective amount is well within the capability of those skilled in the art. Generally, a therapeutically effective amount can vary with the subject’s history, age, condition, sex, as well as the severity and type of the medical condition in the subject, and administration of other pharmaceutically active agents.

As used herein, a “subject” means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, “patient” and “subject” are used interchangeably herein. The terms, “patient” and “subject” are used interchangeably herein.

The term “nucleic acid” as used herein refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

As used herein, the terms “modulator of stress granule” and “stress granule modulator” refer to compounds and compositions of Formula (I) that modulate the formation and/or disaggregation of stress granules.

The term “TDP-43 inclusion” as used herein refers to protein aggregates that comprise TDP-43 proteins. The TDP-43 protein in the inclusion can be wild-type or a mutant form of TDP-43.

As used herein, the terms “modulator of TDP-43 inclusion” and “TDP-43 inclusion modulator” refer to compounds and compositions of Formula (I) and Formula (II) that modulate the formation and/or disaggregation of cytoplasmic TDP-43 inclusions.

Selected Chemical Definitions

At various places in the present specification, substituents of compounds of the invention are disclosed in groups or in ranges. It is specifically intended that the invention include each and every individual subcombination of the members of such groups and ranges. For example, the term “$C_{1-6}$ alkyl" is specifically intended to individually disclose methyl, ethyl, propyl, butyl, pentyl and hexyl.

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

If a compound of the present invention is depicted in the form of a chemical name and as a formula, in case of any discrepancy, the formula shall prevail.

The symbol ∿∿∿, whether utilized as a bond or displayed perpendicular to a bond indicates the point at which the displayed moiety is attached to the remainder of the molecule, solid support, etc.

The following terms are intended to have the meanings presented therewith below and are useful in understanding the description and intended scope of the present invention.

As used herein, "alkyl" refers to a radical of a straight-chain or branched saturated hydrocarbon group having from 1 to 24 carbon atoms ("$C_1$-$C_{24}$ alkyl"). In some embodiments, an alkyl group has 1 to 12 carbon atoms ("$C_1$-$C_{12}$ alkyl"). In some embodiments, an alkyl group has 1 to 8 carbon atoms ("$C_1$-$C_8$ alkyl"). In some embodiments, an alkyl group has 1 to 6 carbon atoms ("$C_1$-$C_6$ alkyl"). In some embodiments, an alkyl group has 1 to 5 carbon atoms ("$C_1$-$C_5$ alkyl"). In some embodiments, an alkyl group has 1 to 4 carbon atoms ("$C_1$-$C_4$alkyl"). In some embodiments, an alkyl group has 1 to 3 carbon atoms ("$C_1$-$C_3$ alkyl"). In some embodiments, an alkyl group has 1 to 2 carbon atoms ("$C_1$-$C_2$ alkyl"). In some embodiments, an alkyl group has 1 carbon atom ("$C_1$ alkyl"). In some embodiments, an alkyl group has 2 to 6 carbon atoms ("$C_2$-$C_6$alkyl"). Examples of $C_1$-$C_6$alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-6}$ alkyl.

As used herein, "alkenyl" refers to a radical of a straight-chain or branched hydrocarbon group having from 2 to 24 carbon atoms, one or more carbon-carbon double bonds, and no triple bonds ("$C_2$-$C_{24}$ alkenyl"). In some embodiments, an alkenyl group has 2 to 10 carbon atoms ("$C_2$-$C_{10}$ alkenyl"). In some embodiments, an alkenyl group has 2 to 8 carbon atoms ("$C_2$-$C_8$ alkenyl"). In some embodiments, an alkenyl group has 2 to 6 carbon atoms ("$C_2$-$C_6$ alkenyl"). In some embodiments, an alkenyl group has 2 to 5 carbon atoms ("$C_2$-$C_5$ alkenyl"). In some embodiments, an alkenyl group has 2 to 4 carbon atoms ("$C_2$-$C_4$ alkenyl"). In some embodiments, an alkenyl group has 2 to 3 carbon atoms ("$C_2$-$C_3$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-6}$ alkenyl.

As used herein, the term "alkynyl" refers to a radical of a straight-chain or branched hydrocarbon group having from 2 to 24 carbon atoms, one or more carbon-carbon triple bonds ("$C_2$-$C_{24}$ alkenyl"). In some embodiments, an alkynyl group has 2 to 10 carbon atoms ("$C_2$-$C_{10}$ alkynyl"). In some embodiments, an alkynyl group has 2 to 8 carbon atoms ("$C_2$-$C_8$ alkynyl"). In some embodiments, an alkynyl group has 2 to 6 carbon atoms ("$C_2$-$C_6$ alkynyl"). In some embodiments, an alkynyl group has 2 to 5 carbon atoms ("$C_2$-$C_5$ alkynyl"). In some embodiments, an alkynyl group has 2 to 4 carbon atoms ("$C_2$-$C_4$ alkynyl"). In some embodiments, an alkynyl group has 2 to 3 carbon atoms ("$C_2$-$C_3$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally substituted, i.e., unsubstituted (an "unsubstituted alkynyl") or substituted (a "substituted alkynyl") with one or more substituents e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-6}$ alkynyl.

As used herein, the term "heteroalkyl," refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any position of the heteroalkyl group. Exemplary heteroalkyl groups include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —NH$CH_2$—, —C(O)NH—, —C(O)N($CH_3$), —C(O)N($CH_2CH_3$)—, —C(O)N($CH_2CF_3$)—, —S(O)—$CH_3$, —$CH_2$—$CH_2$—S$(O)_2$—$CH_3$, —CH═CH—O—$CH_3$, —Si$(CH_3)_3$, —$CH_2$—CH═N—O$CH_3$, —CH═CH—N($CH_3$)—$CH_3$, —O—$CH_3$, and —O—$CH_2$—$CH_3$. Up to two or three heteroatoms may be consecutive, such as, for example, —$CH_2$—NH—O$CH_3$ and —$CH_2$—O—Si$(CH_3)_3$. Where "heteroalkyl" is recited, followed by recitations of specific heteroalkyl groups, such as —$CH_2$O, —N$R^CR^D$, or the like, it will be understood that the terms heteroalkyl and —$CH_2$O or —N$R^CR^D$ are not redundant or mutually exclusive. Rather, the specific heteroalkyl groups are recited to add clarity. Thus, the term "heteroalkyl" should not be interpreted herein as excluding specific heteroalkyl groups, such as —$CH_2O$, —$NR^CR^D$, or the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl and naphthyl. Each instance of an aryl group may be independently optionally substituted, i.e., unsubstituted (an "unsubstituted aryl") or substituted (a "substituted aryl") with one or more substituents. In certain embodiments, the aryl group is unsubstituted $C_6$-$C_{14}$ aryl. In certain embodiments, the aryl group is substituted $C_6$-$C_{14}$ aryl.

"aryl" also includes ring systems wherein the aryl ring, as defined above, is fused with one or more cycloalkyl or heterocycloalkyl groups wherein the point of attachment is on the aryl ring, and in such instances, the number of carbons continue to designate the number of carbons in the aryl ring system. Exemplary ring systems of this type include indanyl, tetrahydronaphthyl, and tetrahydroisoquinolinyl.

As used herein, "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Other exemplary heteroaryl groups include heme and heme derivatives. "heteroaryl" also includes ring systems wherein the heteroaryl ring, as defined above, is fused with one or more cycloalkyl or heterocycloalkyl groups wherein the point of attachment is on the heteroaryl ring, and in such instances, the number of carbons continue to designate the number of carbons in the heteroaryl ring system. Exemplary ring systems of this type include 7,8-dihydro-5H-pyrano[4,3-b]pyridine and 1,4,6,7-tetahydropyrano[4,3-b]pyrrole.

As used herein, "cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$cycloalkyl"). In some embodiments, a cycloalkyl group has 3 to 6 ring carbon atoms ("$C_3$-$C_6$ cycloalkyl"). In some embodiments, a cycloalkyl group has 3 to 6 ring carbon atoms ("$C_3$-$C_6$ cycloalkyl"). In some embodiments, a cycloalkyl group has 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_5$), bicyclo[2.2.2]octanyl ($C_8$), bicyclo [2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl or heteroaryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents. In certain embodiments, the cycloalkyl group is unsubstituted $C_3$-$C_{10}$ cycloalkyl. In certain embodiments, the cycloalkyl group is a substituted $C_3$-$C_{10}$ cycloalkyl.

"Heterocyclyl" as used herein refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

As used herein, "cyano" refers to the radical —CN.

As used herein, "halo" or "halogen," independently or as part of another substituent, mean, unless otherwise stated, a fluorine (F), chlorine ($C_1$), bromine (Br), or iodine (I) atom.

As used herein, "haloalkyl" can include alkyl structures that are substituted with one or more halo groups or with combinations thereof. For example, the terms "fluoroalkyl" includes haloalkyl groups in which the halo is fluorine (e.g., —$C_1$-$C_6$ alkyl-$CF_3$, —$C_1$-$C_6$ alkyl-$C_2F$). Non-limiting examples of haloalkyl include trifluoroethyl, trifluoropropyl, trifluoromethyl, fluoromethyl, diflurormethyl, and fluroisopropyl.

As used herein, "hydroxy" refers to the radical —OH.

As used herein, "nitro" refers to —$NO_2$.

As used herein, "oxo" refers to —C=O.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E.L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound.

In certain embodiments, the active ingredient can be formulated with little or no excipient or carrier.

Compound described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

Many of the terms given above may be used repeatedly in the definition of a formula or group and in each case have one of the meanings given above, independently of one another.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Contemplated equivalents of the compounds described above include compounds which otherwise correspond thereto, and which have the same general properties thereof (e.g., the ability to inhibit the formation of TDP-43 inclusions), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Pharmaceutical Compositions and Routes of Administration

Pharmaceutical compositions containing compounds described herein such as a compound of Formula (I) or pharmaceutically acceptable salt thereof can be used to treat or ameliorate a disorder described herein, for example, a neurodegenerative disease, a cancer, an ophthalmological disease (e.g., a retinal disease), or a viral infection.

The amount and concentration of compounds of Formula (I) in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of *Comprehensive Medicinal Chemistry* (Corwin Hansch; Chairman of Editorial Board), Pergamon Press 1990.

While it is possible for a compound of the present invention to be administered alone, it is preferable to administer the compound as a pharmaceutical formulation (composition), where the compound is combined with one or more pharmaceutically acceptable diluents, excipients or carriers. The compounds according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; (9) nasally; or (10) intrathecally. Additionally, compounds can be implanted into a patient or injected using a drug delivery system. See, for example, Urquhart, et al., (1994) *Ann Rev Pharmacol Toxicol* 24:199-236; Lewis, ed. "Controlled Release of Pesticides and Pharmaceuticals" (Plenum Press, New York, 1981); U.S. Pat. No. 3,773,919; and U.S. Pat. No. 35 3,270,960.

The phrase "therapeutically effective amount" as used herein means that amount of a compound, material, or composition comprising a compound of the present invention which is effective for producing some desired therapeutic effect, e.g., by inhibiting TDP-43 inclusions, in at least a sub-population of cells in an animal and thereby blocking the biological consequences of that function in the treated cells, at a reasonable benefit/risk ratio applicable to any medical treatment.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

The term "pharmaceutically acceptable salt" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al, *Journal of Pharmaceutical Science* 66: 1-19 (1977)). Certain specific compounds of the present invention contain both basic and acidic functionalities that allow the compounds to be converted into either base or acid addition salts. These salts may be prepared by methods known to those skilled in the art. Other pharmaceutically acceptable carriers known to those of skill in the art are suitable for the present invention.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal, vaginal, or urethral administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Alternatively or additionally, compositions can be formulated for delivery via a catheter, stent, wire, or other intraluminal device. Delivery via such devices may be especially useful for delivery to the heart, lung, bladder, urethra, ureter, rectum, or intestine. Furthermore, compositions can be formulated for delivery via a dialysis port.

Ophthalmic formulations, eye ointments, powders, solutions and the like, are also contemplated as being within the scope of this invention.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the compositions are administered by intravenous infusion or injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration. Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with neurodegenerative disease or disorder, cancer, or viral infections.

In addition, the methods described herein can be used to treat domesticated animals and/or pets. A subject can be male or female. A subject can be one who has been previously diagnosed with or identified as suffering from or having a neurodegenerative disease or disorder, a disease or disorder associated with cancer, a disease or disorder associated with viral infection, or one or more complications related to such diseases or disorders but need not have already undergone treatment.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

The compound and the pharmaceutically active agent can be administrated to the subject in the same pharmaceutical composition or in different pharmaceutical compositions (at the same time or at different times). When administrated at different times, the compound and the pharmaceutically active agent can be administered within 5 minutes, 10 minutes, 20 minutes, 60 minutes, 2 hours, 3 hours, 4, hours, 8 hours, 12 hours, 24 hours of administration of the other agent. When the inhibitor and the pharmaceutically active agent are administered in different pharmaceutical compositions, routes of administration can be different.

The amount of compound that can be combined with a carrier material to produce a single dosage form will generally be that amount of the inhibitor that produces a therapeutic effect. Generally out of one hundred percent, this amount will range from about 0.1% to 99% of inhibitor, preferably from about 5% to about 70%, most preferably from 10% to about 30%.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that the compound of Formula (I) is given at a dose from 1 ng/kg to 200 mg/kg, 10 ng/kg to 100 mg/kg, 10 ng/kg to 50 mg/kg, 100 ng/kg to 20 mg/kg, 100 ng/kg to 10 mg/kg, 100 ng/kg to 1 mg/kg, 1 μg/kg to 100 mg/kg, 1 μg/kg to 50 mg/kg, 1 μg/kg to 20 mg/kg, 1 μg/kg to 10 mg/kg, 1 μg/kg to 1 mg/kg, 10 μg/kg to 10 mg/kg, 10 μg/kg to 50 mg/kg, 10 μg/kg to 20 mg/kg, 10 μg/kg to 10 mg/kg, 10 μg/kg to 1 mg/kg, 100 μg/kg to 50 mg/kg, 100 μg/kg to 20 mg/kg, 1 mg/kg to 100 mg/kg, 1 mg/kg to 50 mg/kg, 1 mg/kg to 20 mg/kg, 1 mg/kg to 10 mg/kg, 1 μg/kg to 10 mg/kg, 10 mg/kg to 100 mg/kg, 10 mg/kg to 50 mg/kg, 10 mg/kg to 20 mg/kg, or 50 mg/kg to 100 mg/kg. It is to be understood that ranges given here include all intermediate ranges, e.g., the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the drugs. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The present invention contemplates formulation of the subject compounds in any of the aforementioned pharmaceutical compositions and preparations. Furthermore, the present invention contemplates administration via any of the foregoing routes of administration. One of skill in the art can select the appropriate formulation and route of administration based on the condition being treated and the overall health, age, and size of the patient being treated.

EXAMPLES

Examples are provided below to facilitate a more complete understanding of the invention. The following examples illustrate exemplary modes of making and practicing the invention. However, the scope of the invention is not limited to specific embodiments disclosed in these Examples, which are for purposes of illustration only, since alternative methods can be utilized to obtain similar results.

General. All oxygen and/or moisture sensitive reactions were carried out under $N_2$ atmosphere in glassware that was flame-dried under vacuum (0.5 mmHg) and purged with $N_2$ prior to use. All reagents and solvents were purchased from commercial vendors and used as received, or synthesized according to the footnoted references. NMR spectra were recorded on a Bruker 400 (400 MHz $^1H$, 75 MHz $^{13}C$) or Varian (400 MHz $^1H$, 75 MHz $^{13}C$) spectrometer. Proton and carbon chemical shifts are reported in ppm (δ) referenced to the NMR solvent. Data are reported as follows: chemical shifts, multiplicity (br=broad, s=singlet, t=triplet, q=quartet, m=multiplet; coupling constant (s) in Hz). Unless otherwise indicated NMR data were collected at 25° C. Flash chromatography was performed using 100-200 mesh Silica Gel. Liquid Chromatography/Mass Spectrometry (LCMS) was performed on Agilent 1200HPLC and 6110MS. Analytical thin layer chromatography (TLC) was performed on 0.2 mm silica gel plates. Visualization was accomplished with UV light and aqueous potassium permanganate ($KMnO_4$) stain followed by heating.

TABLE 1

| Abbreviations | |
|---|---|
| Bn | benzyl |
| Boc | t-butoxycarbonyl |
| t-BuXphos | 2-di-t-butylphosphino- 2',4',6'-triisopropylbiphenyl |
| t-BuOK | potassium tert-butoxide |
| Cbz | Carbobenzyloxy |
| COSY | correlation spectroscopy |
| DCE | 1,2-Dichloroethane |
| DCM | dichloromethane |
| DIBALH | diisobutylaluminum hydride |
| DMAP | N,N-4-dimethylaminopyridine |
| DMF | N,N-dimethylformamide |
| DMP | Dess-Martin periodinane |
| DMSO | dimethyl sulfoxide |
| ESI | Electrospray ionization |
| EtOAc | ethyl acetate |
| HATU | O-(7-azabenzotriazol-1-yl)-N,N,N',N'- tetramethyluronium hexafluorophosphate |
| HOAc | acetic acid |
| HPLC | High performance liquid chromatography |
| HSQC | Heteronuclear single quantum coherence spectroscopy |
| LCMS | liquid chromatography-mass specrtum |
| MCPBA | meta-chloroperbenzoic acid |
| Me | methyl |
| MeOH | methanol |
| MsCl | methanesulfonyl chloride |
| NOE | Nuclear Overhauser Effect |
| $Pd_2(dba)_3$ | tris(dibenzylideneacetone)dipalladium |
| PSI | pounds per square inch |
| Py or pyr | pyridine |
| TBAF | Tetrabutylammonium fluoride |
| TEA | triethylamine |
| TFA | trifluoroacetic acid |
| THF | tetrahydrofuran |
| TLC | Thin layer chromatography |

Example 1. Synthesis of N-((1S,3R)-3-(benzylamino)cyclohexyl)-N-ethyl-1H-indole-2-carboxamide (Compound 100)

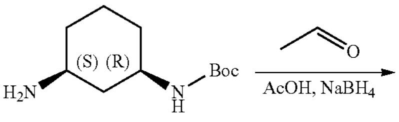

1

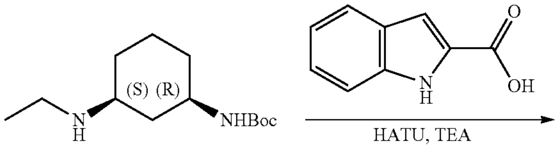

2

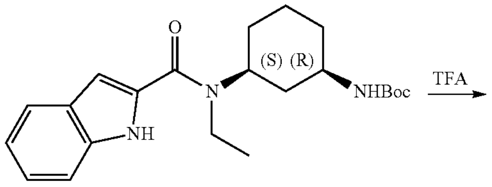

3

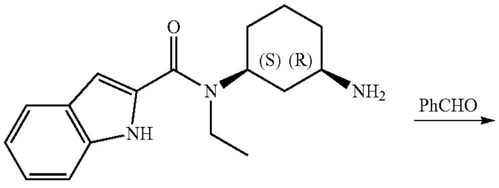

4

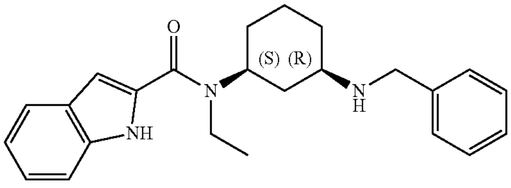

Compound 100

General procedure for preparation of Compound 2: To a mixture of tert-butyl ((1R,3S)-3-aminocyclohexyl)carbamate 1 (300 mg, 1.4 μmol, 1.0 eq), acetaldehyde (154 mg, 1.40 μmol, 1.00 eq) in 5 mL of $CHCl_3$ was added acetic acid (25. mg, 420 μmol, 0.30 equivalents) under $N_2$. The mixture was stirred for 0.5 hour at 25° C., then $NaBH_4$ (53 mg, 1.4 μmol, 1.0 eq) was added, then stirred at 25° C. for another 11.5 hours under $N_2$ atmosphere. The reaction was monitored by LCMS and allowed to run until complete. The reaction mixture was quenched with 5 ml of water and extracted with three 5 mL portions of dichloromethane. The combined organic layers were washed twice with 5 mL of brine, dried over $Na_2SO_4$, filtered and concentrated under reduced pressure to give a residue. The residue was purified by TLC (ethyl acetate:methanol=5/1) to afford 110 mg of ethyl amine 2 as a light yellow gum.

General procedure for preparation of compound 3: A mixture of 1H-indole-2-carboxylic acid (60 mg, 372 μmol, 1.0 eq), amine 2 (90 mg, 372 μmol, 1.0 eq), HATU (156 mg, 409 μmol, 1.1 eq), TEA (56 mg, 558 μmol, 1.5 eq) in 4 mL of DMF was degassed and purged three times. The mixture was stirred at 25° C. for 1 hour under $N_2$. The reaction was monitored by LCMS and allowed to run until complete. The reaction mixture was quenched with 15 ml of water and extracted with three 5 ml portions of ethyl acetate. The combined organic layers were washed twice with 5 ml of brine, dried over $Na_2SO_4$, filtered and concentrated under reduced pressure to give a residue. The residue was purified by TLC (petroleum ether:ethyl acetate=2:1) to afford 85 mg of amide 3 as colorless gum.

General procedure for preparation of compound 4: To a mixture of amide 3 (85 mg, 220 μmol, 1.0 eq) in 2 mL of ethyl acetate was added 5 mL of 4M HCl in ethyl acetate (91 eq). The mixture was stirred at 25° C. for 1 hour. The reaction was monitored by LCMS and allowed to run until complete. It was concentrated under reduced pressure to afford 70 mg of amine 4 (crude, as the HCl salt) as white solid. This material was used into the next step without further purification.

General procedure for preparation of Compound 100: To a mixture of amine 4 (55 mg, 171 μmol, 1.0 eq as the HCl salt) in 3 mL of methanol was added sequentially, TEA (17 mg, 171 μmol, 1.0 eq), benzaldehyde (22 mg, 205 μmol, 1.2 eq), acetic acid (10 mg, 171 μmol, 1.0 eq) and $NaBH_3CN$ (13 mg, 205 μmol, 1.2 eq). The mixture was stirred at 25° C. for 1 hour under $N_2$ atmosphere. The reaction was monitored by LCMS and allowed to run until complete. The mixture was filtered and the filtrate was purified by HPLC (TFA condition) to afford 52 mgs of compound 100 (62% yield, TFA salt) as a white solid.

$^1$H NMR (400 MHz, METHANOL-$d_4$) δ ppm 7.61-7.66 (m, 1H) 7.42-7.54 (m, 5H) 7.42-7.54 (m, 1H) 7.20-7.27 (m, 1H) 7.05-7.12 (m, 1H) 6.81 (br s, 1H) 4.27 (br s, 3H) 3.70 (br s, 2H) 3.30 (br s, 1H) 2.36 (br d, J=10.14 Hz, 1H) 2.22 (br d, J=8.60 Hz, 1H) 1.77-2.11 (m, 4H) 1.31-1.57 (m, 5H)

LCMS (ESI+): m/z 376.3 (M+H)

Rotation: $[\alpha]_D^{20}$=−63.22°±3.64° (c=1 g/100 mL methanol)

The following compounds could be prepared analogously:

Compound 101

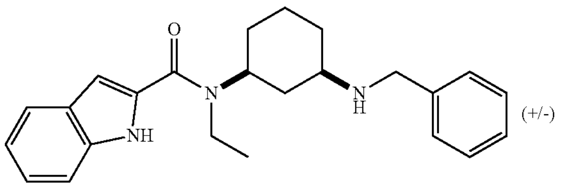

$^1$H NMR (400 MHz, METHANOL-$d_4$) δ ppm 7.60 (br s, 1H) 7.38-7.51 (m, 6H) 7.21 (br s, 1H) 7.06 (br s, 1H) 6.79 (br s, 1H) 4.52 (br d, J=13.45 Hz, 1H) 4.37 (br s, 1H) 4.20 (br d, J=13.01 Hz, 1H) 3.72 (br s, 2H) 3.46 (br s, 1H) 2.75 (br d, J=5.73 Hz, 3H) 2.01-2.29 (m, 4H) 1.82-1.95 (m, 2H) 1.63 (br d, J=13.67 Hz, 2H) 1.34 (br d, J=4.41 Hz, 3H)

LCMS (ESI+): m/z 376.3 (M+H)

Compound 102

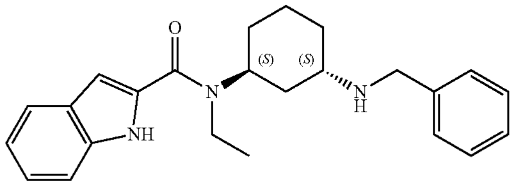

$^1$H NMR (400 MHz, METHANOL-$d_4$) δ ppm 7.51 (br d, J=8.16 Hz, 1H) 7.41 (d, J=8.60 Hz, 1H) 6.96-7.24 (m, 7H) 6.82 (s, 1H) 3.42-3.73 (m, 4H) 3.12 (br s, 1H) 1.94-2.01 (m, 1H) 1.69-1.92 (m, 6H) 1.60 (br s, 1H) 1.42-1.49 (m, 1H) 1.26 (br t, J=7.06 Hz, 3H)

LCMS (ESI+): m/z 376.3 (M+H)

Compound 103

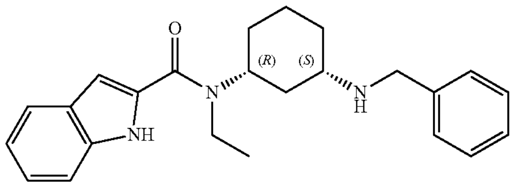

$^1$H NMR (400 MHz, METHANOL-$d_4$) δ ppm 7.60 (d, J=8.16 Hz, 1H) 7.58-7.63 (m, 1H) 7.58-7.63 (m, 1H) 7.40-7.50 (m, 6H) 7.20 (t, J=7.61 Hz, 1H) 7.02-7.09 (m, 1H) 6.78 (br s, 1H) 4.24 (s, 3H) 3.66 (br s, 2H) 3.22-3.28 (m, 1H) 2.33 (br d, J=11.25 Hz, 1H) 2.19 (br d, J=11.91 Hz, 1H) 2.13-2.24 (m, 1H) 1.76-2.08 (m, 4H) 1.29-1.53 (m, 5H)

LCMS (ESI+): m/z 376.0 (M+H)

Compound 104

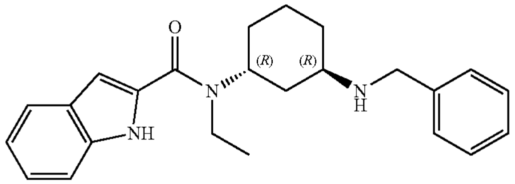

$^1$H NMR (400 MHz, METHANOL-$d_4$) δ ppm 7.52 (br d, J=7.94 Hz, 1H) 7.41 (d, J=8.38 Hz, 1H) 7.00-7.21 (m, 7H) 6.82 (s, 1H) 3.47-3.68 (m, 4H) 3.12 (br s, 1H) 1.97 (br d, J=12.57 Hz, 1H) 1.71-1.91 (m, 6H) 1.60 (br s, 1H) 1.46 (br d, J=11.69 Hz, 1H) 1.27-1.29 (m, 3H)

LCMS (ESI+): m/z 376.0 (M+H)

Compound 117

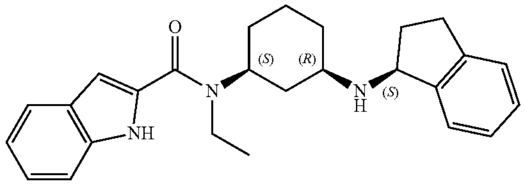

$^1$H NMR (400 MHz, CHLOROFORM-d) δ ppm 9.30 (br s, 1H) 7.60 (d, J=7.95 Hz, 1H) 7.29-7.40 (m, 2H) 7.20-7.24

(m, 1H) 7.11-7.18 (m, 3H) 7.04-7.09 (m, 1H) 6.71 (br s, 1H) 4.55 (br t, J=11.98 Hz, 1H) 4.34 (br t, J=6.30 Hz, 1H) 3.57 (br s, 1H) 2.80-3.03 (m, 2H) 2.67-2.79 (m, 1H) 2.30-2.42 (m, 1H) 2.09 (br d, J=11.62 Hz, 1H) 1.97-2.05 (m, 1H) 1.76-1.88 (m, 3H) 1.48-1.63 (m, 3H) 1.36-1.44 (m, 1H) 1.09-1.34 (m, 5H)

LCMS (ESI+): m/z 402.2 (M+H)

Compound 118

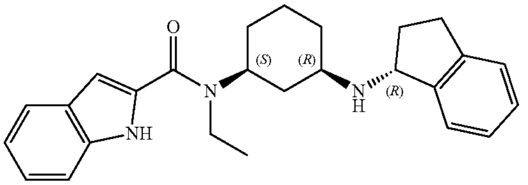

$^1$H NMR (400 MHz, CHLOROFORM-d) δ ppm 9.40 (br s, 1H) 7.59 (d, J=8.07 Hz, 1H) 7.37 (d, J=8.31 Hz, 1H) 7.24-7.30 (m, 1H) 7.19-7.24 (m, 1H) 7.10-7.17 (m, 3H) 7.04-7.09 (m, 1H) 6.70 (br s, 1H) 4.55 (br t, J=11.98 Hz, 1H) 4.30 (t, J=6.66 Hz, 1H) 3.57 (br s, 1H) 3.48-3.63 (m, 1H) 2.79-2.98 (m, 2H) 2.67-2.77 (m, 1H) 2.73 (dt, J=15.80, 7.81 Hz, 1H) 2.39 (dtd, J=12.38, 7.63, 7.63, 4.65 Hz, 1H) 2.16 (br d, J=10.15 Hz, 1H) 1.81-1.95 (m, 3H) 1.66-1.79 (m, 2H) 1.39-1.59 (m, 4H) 1.29 (br s, 3H) 1.06-1.20 (m, 1H)

LCMS (ESI+): m/z 402.2 (M+H)

Compound 119

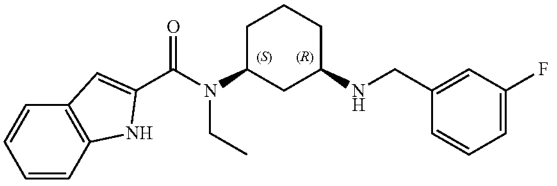

$^1$H NMR (400 MHz, CHLOROFORM-d) δ ppm 10.00 (br s, 1H) 9.67 (br s, 1H) 7.60 (br d, J=7.94 Hz, 1H) 7.27-7.42 (m, 2H) 7.01-7.23 (m, 5H) 6.90 (br s, 1H) 6.72 (br s, 1H) 3.91 (br s, 2H) 3.59 (br s, 3H) 3.01 (br s, 1H) 2.23 (br s, 1H) 1.76-2.14 (m, 5H) 1.31 (br s, 5H)

LCMS (ESI+): m/z 394.0 (M+H)

Example 2. Synthesis of N-((1S,3R)-3-(benzyl (methyl)amino)cyclohexyl)-N-ethyl-1H-indole-2-carboxamide (Compound 105)

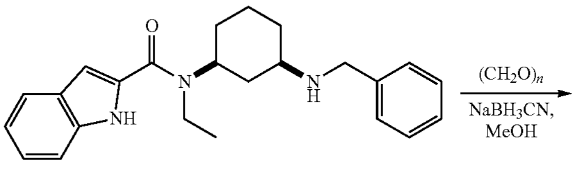

Compound 101

-continued

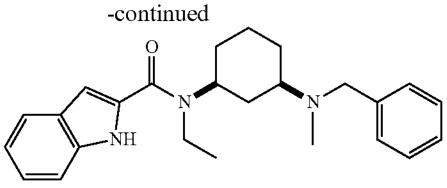

Compound 105

General procedure for preparation of Compound 105: To a mixture of compound 101 (80 mg, 213 μmol, 1.0 eq) and paraformaldehyde (19 mg, 213 μmol, 1.0 eq) in 1 mL of methanol was added acetic acid (1.3 mg, 21.3 μmol, 0.1 eq), $NaBH_3CN$ (14 mg, 213 μmol, 1.0 eq) in one portion at 25° C. under $N_2$. The mixture was stirred at 25° C. for 24 hrs. The reaction was monitored by LCMS and allowed to run until complete. The reaction mixture was filtered and mother liquor was concentrated under reduced pressure to give a residue. The residue was purified by prep-HPLC (TFA condition) to afford 14.8 mg of compound 105 (13.6% yield, TFA salt) as colorless oil.

$^1$H NMR (400 MHz, METHANOL-$d_4$) δ ppm 7.60 (br s, 1H) 7.38-7.51 (m, 6H) 7.21 (br s, 1H) 7.06 (br s, 1H) 6.79 (br s, 1H) 4.52 (br d, J=13.45 Hz, 1H) 4.37 (br s, 1H) 4.20 (br d, J=13.01 Hz, 1H) 3.72 (br s, 2H) 3.46 (br s, 1H) 2.75 (br d, J=5.73 Hz, 3H) 2.01-2.29 (m, 4H) 1.82-1.95 (m, 2H) 1.63 (br d, J=13.67 Hz, 2H) 1.34 (br d, J=4.41 Hz, 3H)

LCMS (ESI+): m/z 390.3 (M+H)

Example 3. Synthesis of N-ethyl-N-((1S,3R)-3-((3-fluorobenzyl)amino)cyclohexyl)-1H-indole-2-carboxamide (Compound 106) and N-ethyl-N-((1S, 3S)-3-((3-fluorobenzyl)amino)cyclohexyl)-1H-indole-2-carboxamide (Compound 107)

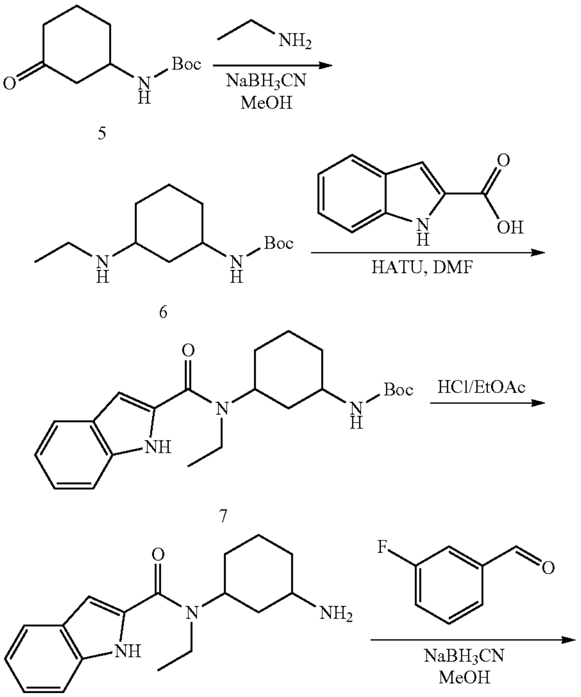

5

6

7

8

-continued

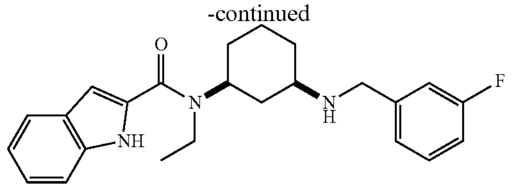

Compound 106

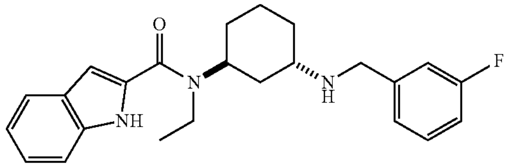

Compound 107

General procedure for preparation of compound 6: A mixture of compound 5 (3.0 g, 14.0 mmol, 1.0 eq), ethanamine (951 mg, 21 mmol, 1.5 eq), acetic acid (84.5 mg, 1.4 mmol, 81 μL, 0.1 eq) in 30 mL of methanol was stirred at 25° C. for 0.5 h. To the mix was added $NaBH_3CN$ (1.8 g, 28 mmol, 2.0 eq) and then the mixture was stirred at 25° C. for 11 hours. The reaction was monitored by TLC and allowed to run until complete. The reaction mixture was quenched by adding 10 mL of water, then concentrated under reduced pressure to remove methanol. It was extracted with three 20 mL portions of ethyl acetate. The combined organic layers were washed with 20 mL of brine, dried over $Na_2SO_4$, filtered and concentrated under reduced pressure to give 3.8 g of the desired compound 6 as a crude yellow oil.

General procedure for preparation of compound 7: To a mixture of 1H-indole-2-carboxylic acid (1.3 g, 8.3 mmol, 1.0 eq), HATU (3.1 g, 8.3 mmol, 1.0 eq), TEA (1.3 g, 12.4 mmol, 1.5 eq) in 25 mL of DMF stirred at 25° C. for 0.5 hour was added compound 6 (2.0 g, 8.3 μmol, 1.0 eq). The mixture was stirred at 25° C. for 11.5 hours. The reaction was monitored by TLC and allowed to run until complete. The reaction mixture was diluted with 30 mL of ethyl acetate and washed twice with 30 mL of water. The combined organic layers were washed five times with 50 mL of brine, dried over $Na_2SO_4$, filtered and concentrated under reduced pressure to give an oil. The residue was purified by column chromatography ($SiO_2$, petroleum ether:ethyl acetate=100:1 to 3:1) to give 1.3 g of compound 7 (39% yield) as a white solid.

General procedure for preparation of compound 8: A mixture of compound 7 (750 mg, 2.0 mmol, 1.0 eq) in 6 mL of 4M HCl in ethyl acetate was stirred at 25° C. for 0.5 hour. The reaction was monitored by TLC and allowed to run until complete. The reaction mixture was concentrated under reduced pressure to give 560 mg of compound 8 as a white solid (used crude as the HCl salt).

General procedure for preparation of Compounds 106 and 107: To a mixture of compound 8 (80.0 mg, 250 μmol, 1.0 eq, HCl), 3-fluorobenzaldehyde (46 mg, 373 μmol, 1.5 eq), acetic acid (7.5 mg, 124 μmol, 0.5 eq) and TEA (12.6 mg, 124 μmol, 0.5 eq) in 1 mL of methanol was added $NaBH_3CN$ (31.2 mg, 497 μmol, 2.0 eq) and the mixture was stirred at 25° C. for 12 hours. The reaction was monitored by LCMS and allowed to run until complete. The reaction mixture was concentrated under reduced pressure and then filtered. The residue was purified by prep-HPLC (neutral condition) to give 42.5 mg of Compound 106 (43% yield) as a white solid and 14.8 mg of compound 107 (14.5% yield) as a light yellow solid.

Compound 106

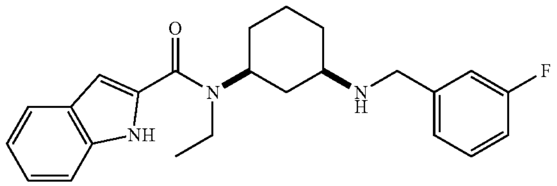

$^1H$ NMR (400 MHz, CHLOROFORM-d) δ ppm 9.23 (br s, 1H) 7.63 (br d, J=7.9 Hz, 1H) 7.41 (d, J=8.4 Hz, 1H) 7.31-7.25 (m, 2H) 7.15-7.10 (m, 1H) 7.09-7.02 (m, 2H) 6.93 (br t, J=8.5 Hz, 1H) 6.73 (br s, 1H) 4.54 (br t, J=12.5 Hz, 1H) 3.83 (s, 2H) 3.61 (br s, 2H) 2.67 (br s, 1H) 2.14 (br d, J=10.8 Hz, 1H) 1.97 (br d, J=11.7 Hz, 1H) 1.92-1.81 (m, 2H) 1.49-1.38 (m, 2H) 1.49-1.38 (m, 1H) 1.33 (br s, 3H) 1.23 (br s, 1H) 1.13-1.03 (m, 1H)

LCMS (ESI+): m/z 394.1 (M+H)

Compound 107

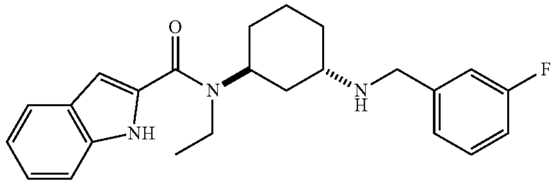

$^1H$ NMR (400 MHz, CHLOROFORM-d) δ ppm 9.26 (br s, 1H) 7.52 (br s, 1H) 7.40 (d, J=8.2 Hz, 1H) 7.28 (s, 1H) 7.18 (br s, 1H) 7.13-7.02 (m, 3H) 7.01-6.88 (m, 2H) 3.86-3.73 (m, 2H) 3.62-3.49 (m, 1H) 3.20 (br s, 1H) 1.98 (br d, J=11.7 Hz, 1H) 1.93-1.83 (m, 2H) 1.82-1.71 (m, 2H) 1.71-1.63 (m, 2H) 1.52 (br s, 3H) 1.47-1.41 (m, 1H) 1.35-1.24 (m, 3H)

LCMS (ESI+): m/z 394.1 (M+H)

The following compounds were prepared analogously:

Compound 108

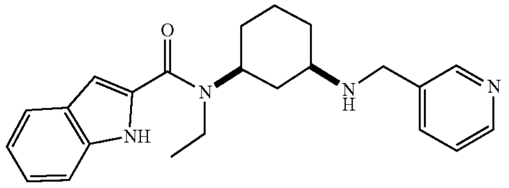

$^1H$ NMR (400 MHz, CHLOROFORM-d) δ ppm 9.55 (br s, 1H) 8.57 (d, J=1.1 Hz, 1H) 8.52-8.49 (m, 1H) 7.70-7.63 (m, 2H) 7.43 (d, J=8.2 Hz, 1H) 7.29-7.26 (m, 1H) 7.25-7.23 (m, 1H) 7.16-7.10 (m, 1H) 6.74 (br s, 1H) 4.62-4.52 (m, 1H) 3.85 (s, 2H) 3.63 (br s, 2H) 2.69 (br s, 1H) 2.16 (br d, J=11.7 Hz, 1H) 2.03-1.96 (m, 1H) 1.94-1.84 (m, 2H) 1.67 (br s, 3H) 1.52-1.40 (m, 2H) 1.35 (br s, 2H) 1.15-1.04 (m, 1H)

LCMS (ESI+): m/z 377.3 (M+H)

Compound 109

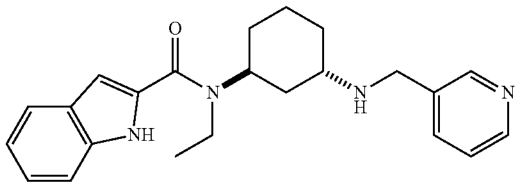

$^1$H NMR (400 MHz, CHLOROFORM-d) δ ppm 9.39 (br s, 1H) 8.54 (br s, 1H) 8.47 (br d, J=4.0 Hz, 1H) 7.54 (br s, 2H) 7.41 (d, J=8.4 Hz, 1H) 7.29-7.26 (m, 1H) 7.25 (br s, 1H) 7.12 (t, J=7.5 Hz, 1H) 6.93 (br s, 1H) 5.13 (br s, 1H) 3.82-3.72 (m, 2H) 3.57 (br s, 1H) 3.20 (br s, 1H) 2.00-1.88 (m, 3H) 1.87-1.79 (m, 2H) 1.75 (br d, J=14.8 Hz, 2H) 1.70 (br s, 1H) 1.51-1.41 (m, 2H) 1.32 (br s, 3H)

LCMS (ESI+): m/z 377.3 (M+H)

Compound 110

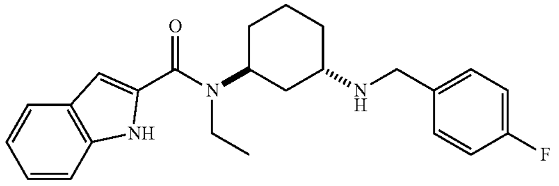

$^1$H NMR (400 MHz, CHLOROFORM-d) δ ppm 9.24 (br s, 1H) 7.50 (br s, 1H) 7.40 (d, J=7.7 Hz, 1H) 7.29-7.25 (m, 1H) 7.20 (br s, 2H) 7.13-7.07 (m, 1H) 6.99-6.80 (m, 3H) 3.80-3.65 (m, 2H) 3.54 (br s, 1H) 3.18 (br s, 1H) 1.96 (br d, J=13.7 Hz, 2H) 1.90-1.79 (m, 2H) 1.78-1.70 (m, 2H) 1.65 (br t, J=11.4 Hz, 3H) 1.49-1.38 (m, 2H) 1.36-1.21 (m, 3H)

LCMS (ESI+): m/z 394.1 (M+H)

Compound 111

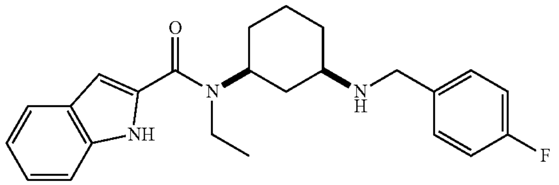

$^1$H NMR (400 MHz, CHLOROFORM-d) δ ppm 9.57 (br s, 1H) 7.63 (br d, J=7.9 Hz, 1H) 7.42 (d, J=7.9 Hz, 1H) 7.29-7.27 (m, 1H) 7.24 (br d, J=1.8 Hz, 2H) 7.15-7.09 (m, 1H) 6.99 (t, J=8.8 Hz, 2H) 6.83-6.58 (m, 1H) 4.56 (br t, J=11.8 Hz, 1H) 3.79 (s, 2H) 3.70-3.46 (m, 1H) 2.67 (br s, 1H) 2.19-2.12 (m, 1H) 1.97 (br d, J=12.3 Hz, 1H) 1.92-1.82 (m, 2H) 1.62-1.51 (m, 2H) 1.50-1.40 (m, 3H) 1.34 (br s, 3H) 1.14-1.02 (m, 1H)

LCMS (ESI+): m/z 394.2 (M+H)

Compound 112

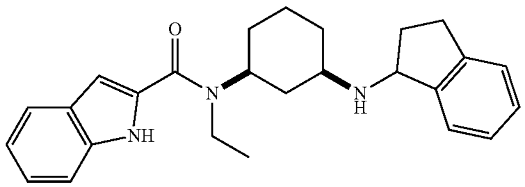

$^1$H NMR (400 MHz, CHLOROFORM-d) δ ppm 9.59 (br s, 1H) 7.67 (d, J=8.3 Hz, 1H) 7.45 (d, J=8.3 Hz, 1H) 7.38-7.32 (m, 1H) 7.31-7.27 (m, 1H) 7.25-7.18 (m, 3H) 7.17-7.10 (m, 1H) 6.77 (br s, 1H) 4.65 (br d, J=11.0 Hz, 1H) 4.37 (t, J=6.6 Hz, 1H) 3.65 (br s, 1H) 3.04-2.96 (m, 1H) 2.91 (br s, 1H) 2.80 (td, J=7.9, 15.8 Hz, 1H) 2.50-2.41 (m, 1H) 2.28-2.04 (m, 2H) 2.01-1.87 (m, 3H) 1.85-1.75 (m, 1H) 1.66-1.47 (m, 3H) 1.37 (br s, 3H) 1.28-1.11 (m, 1H) 1.28-1.11 (m, 1H)

LCMS (ESI+): m/z 402.3 (M+H)

Compound 113

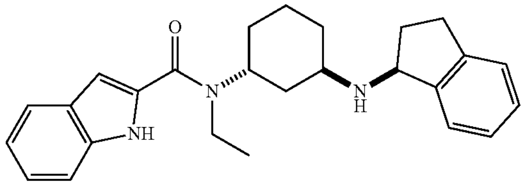

$^1$H NMR (400 MHz, CHLOROFORM-d) δ ppm 9.28 (br s, 1H) 7.59 (br d, J=7.9 Hz, 1H) 7.40 (d, J=8.3 Hz, 1H) 7.35-7.27 (m, 1H) 7.21-7.09 (m, 4H) 7.03-6.81 (m, 2H) 5.33 (br s, 1H) 4.30 (br s, 1H) 3.67-3.46 (m, 2H) 3.42 (br s, 1H) 3.00-2.89 (m, 1H) 2.78 (td, J=7.9, 15.8 Hz, 1H) 2.51 (br s, 1H) 2.09 (br d, J=11.8 Hz, 1H) 1.94 (br d, J=9.6 Hz, 2H) 1.73 (br s, 1H) 1.66 (br d, J=10.1 Hz, 4H) 1.61-1.52 (m, 2H) 1.32 (br s, 3H)

LCMS (ESI+): m/z 402.3 (M+H)

Compound 114

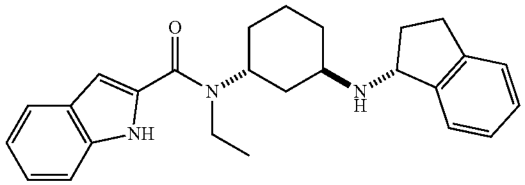

$^1$H NMR (400 MHz, CHLOROFORM-d) δ ppm 9.33 (br s, 1H) 7.52 (br d, J=6.6 Hz, 1H) 7.34 (br d, J=8.2 Hz, 2H) 7.22-7.19 (m, 1H) 7.22-7.19 (m, 1H) 7.17-7.09 (m, 3H) 7.08-7.02 (m, 1H) 4.22 (br t, J=6.8 Hz, 1H) 3.59-3.37 (m, 3H) 2.96-2.84 (m, 1H) 2.72 (td, J=8.0, 15.9 Hz, 1H) 2.45-2.32 (m, 1H) 1.95-1.78 (m, 5H) 1.73-1.53 (m, 4H) 1.46 (br s, 1H) 1.35 (br t, J=13.9 Hz, 1H) 1.25 (br s, 3H)

LCMS (ESI+): m/z 402.3 (M+H)

Compound 115

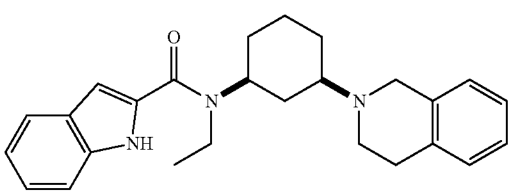

$^1$H NMR (400 MHz, CHLOROFORM-d) δ ppm 9.31 (br s, 1H) 7.70-7.62 (m, 1H) 7.45-7.38 (m, 1H) 7.33-7.26 (m, 2H) 7.20 (br d, J=7.3 Hz, 2H) 7.17-7.07 (m, 2H) 6.84 (br s, 1H) 4.61 (br d, J=14.3 Hz, 1H) 4.26 (br s, 1H) 3.76 (br s, 2H) 3.47-3.24 (m, 3H) 3.04 (br s, 1H) 2.49 (br s, 4H) 2.39-2.06 (m, 3H) 1.89 (br s, 2H) 1.71 (br d, J=13.2 Hz, 1H) 1.41 (br s, 3H)

LCMS (ESI+): m/z 402.3 (M+H)

Compound 116

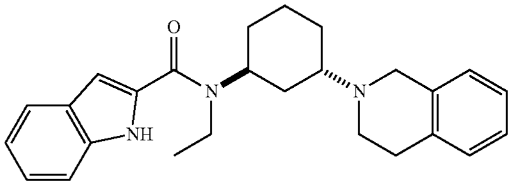

$^1$H NMR (400 MHz, CHLOROFORM-d) δ ppm 9.46 (br s, 1H) 7.66 (d, J=8.2 Hz, 1H) 7.42 (d, J=8.2 Hz, 1H) 7.33-7.27 (m, 2H) 7.26-7.22 (m, 1H) 7.18 (br d, J=7.3 Hz, 1H) 7.16-7.07 (m, 2H) 6.86 (s, 1H) 4.76 (s, 2H) 3.78 (br d, J=6.6 Hz, 3H) 3.57 (br s, 1H) 3.15 (br d, J=5.7 Hz, 1H) 2.60-2.37 (m, 1H) 2.44 (br s, 2H) 2.34-2.23 (m, 1H) 2.30 (br s, 1H) 2.17 (br d, J=15.9 Hz, 2H) 2.04 (br s, 2H) 1.94-1.67 (m, 2H) 1.43 (br t, J=7.1 Hz, 3H)

LCMS (ESI+): m/z 402.3 (M+H)

Compound 120

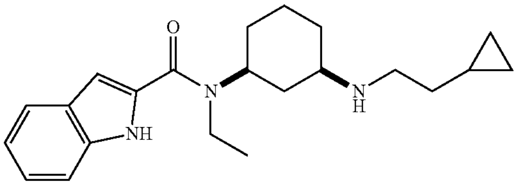

$^1$H NMR (400 MHz, CHLOROFORM-d) δ ppm 9.25 (br s, 1H) 7.64-7.62 (d, 1H) 7.40-7.38 (d, 1H) 7.26-7.24 (t, 1H) 7.12-7.10 (t, 1H) 6.72 (br s, 1H) 4.53 (t, 1H) 2.74-2.70 (t, 2H) 2.70 (m, 1H) 2.12-2.10 d, 1H) 1.95-1.85 (m, 3H) 1.57-1.45 (m, 11H) 1.16-0.95 (m, 1) 0.62-0.60 (m, 1H) 0.42-0.37 (d, 2H) 0.02-0.01 (d, 2H)

LCMS (ESI+): m/z 354.1 (M+H)

Compound 121

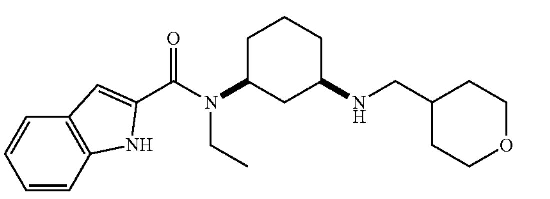

$^1$H NMR (400 MHz, CHLOROFORM-d) δ ppm 9.39 (br s, 1H) 7.59 (d, J=7.9 Hz, 1H) 7.37 (d, J=8.2 Hz, 1H) 7.24-7.20 (m, 1H) 7.10-7.03 (m, 1H) 7.10-7.03 (m, 1H) 6.69 (br s, 1H) 4.48 (br s, 1H) 3.88 (br dd, J=3.7, 11.2 Hz, 2H) 3.70-3.39 (m, 2H) 3.29 (br t, J=11.7 Hz, 2H) 2.65-2.54 (m, 1H) 2.49 (d, J=6.6 Hz, 2H) 2.11-2.03 (m, 2H) 1.93-1.78 (m, 3H) 1.65-1.52 (m, 3H) 1.47-1.35 (m, 2H) 1.31-1.16 (m, 5H) 1.03 (br d, J=11.9 Hz, 1H)

LCMS (ESI+): m/z 384.2 (M+H)

Compound 122

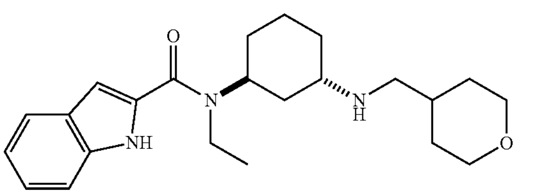

$^1$H NMR (400 MHz, CHLOROFORM-d) δ ppm 9.26 (br s, 1H) 7.62 (br d, J=7.7 Hz, 1H) 7.42 (br d, J=7.7 Hz, 1H) 7.28 (s, 1H) 7.16-7.09 (m, 1H) 6.92 (br s, 1H) 3.88 (br s, 1H) 3.72 (br dd, J=6.9, 14.2 Hz, 1H) 3.54 (br s, 2H) 3.30 (br s, 2H) 3.11 (br s, 1H) 2.45 (br s, 2H) 1.90 (br s, 3H) 1.82-1.66 (m, 6H) 1.55 (br s, 5H) 1.34-1.25 (m, 4H)

LCMS (ESI+): m/z 384.2 (M+H)

Example 4. Synthesis of N-((1S,3R)-3-benzamido-cyclohexyl)-N-ethyl-1H-indole-2-carboxamide (Compound 200)

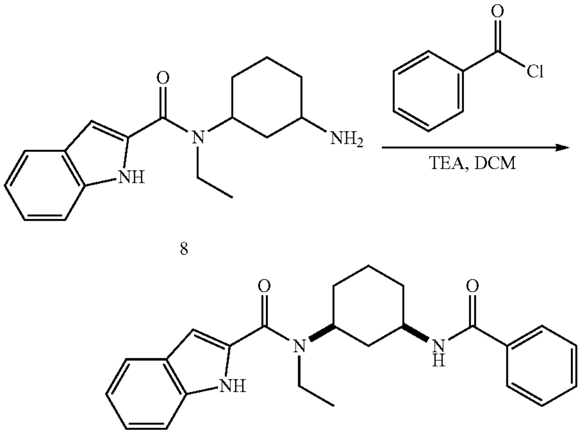

Compound 200

General procedure for preparation of compound 200: To a mixture of compound 8 (100 mg, 311 μmol, 1.0 eq, HCl), TEA (157 mg, 1.6 μmol, 215 μL, 5.0 eq) in 2 mL of dichloromethane was added benzoyl chloride (65.5 mg, 466 μmol, 54 μL, 1.5 eq) at 0° C. and the mixture was stirred at 25° C. for 12 hours. The reaction was monitored by LCMS and allowed to run until complete. The reaction mixture was concentrated under reduced pressure and then filtered. The residue was purified by prep-HPLC (neutral condition) to give 32.7 mg of compound 200 as a white solid (27% yield).

Compound 200

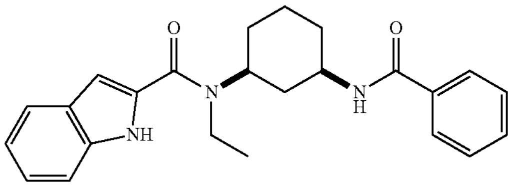

$^1H$ NMR (400 MHz, CHLOROFORM-d) δ ppm 9.28 (br s, 1H) 7.76 (d, J=7.5 Hz, 2H) 7.69 (br d, J=7.9 Hz, 1H) 7.52-7.47 (m, 1H) 7.43 (t, J=7.7 Hz, 3H) 7.31-7.27 (m, 1H) 7.17-7.11 (m, 1H) 6.81 (s, 1H) 6.02 (br d, J=7.3 Hz, 1H) 4.19-4.09 (m, 1H) 3.64 (br s, 1H) 2.36 (br s, 1H) 2.14 (br d, J=10.1 Hz, 1H) 1.93 (br t, J=15.0 Hz, 2H) 1.75 (br s, 3H) 1.56 (br d, J=13.0 Hz, 1H) 1.59-1.51 (m, 1H) 1.37 (br s, 3H) 1.28-1.17 (m, 1H)

LCMS (ESI+): m/z 390.2 (M+H)

Example 5. Synthesis of N-ethyl-N-((1S,3R)-3-((4-fluorobenzyl)amino)cyclohexyl)-1H-indole-2-carboxamide (Compound 123)

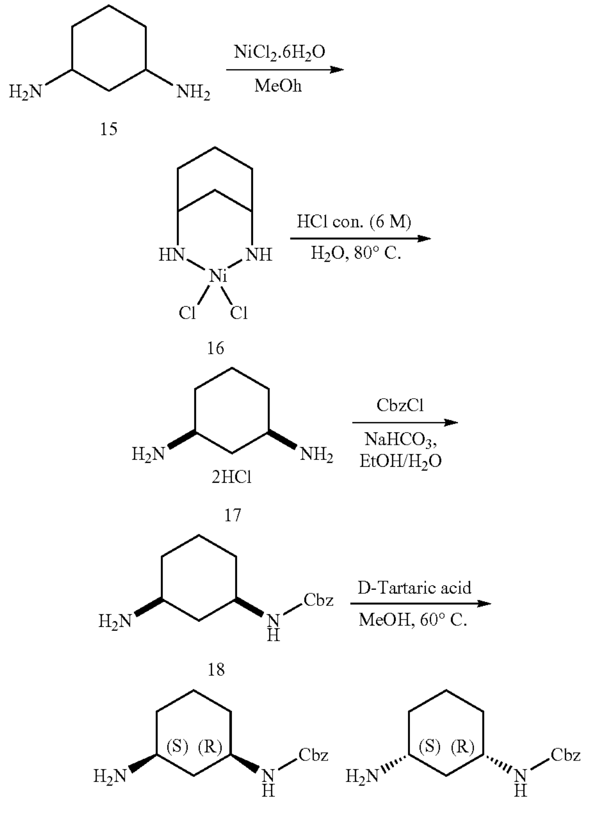

15

16

2HCl

17

18

19A

19B

-continued

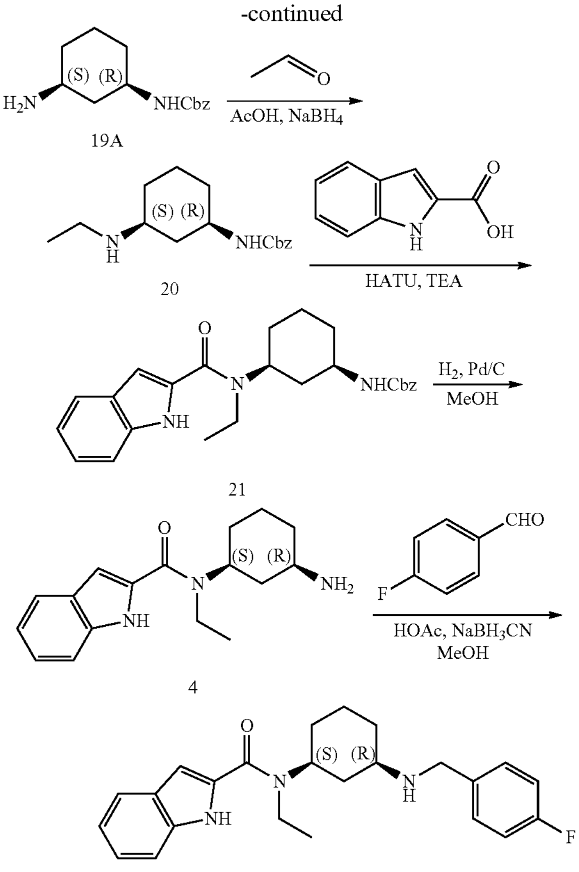

19A

20

21

4

Compound 123

General procedure for preparation of compound 16: To a mixture of compound 15 (95.0 g, 832.0 mmol, 1.0 eq) in 2.5 L of methanol was added $NiCl_2.6H_2O$ (197.8 g, 832.0 mmol, 1.0 eq) in 5 portions at 25° C. for 1 hour. Then the mixture was stirred at 25° C. for an additional 12 hours. The reaction was monitored by TLC and allowed to run until complete. The mixture was filtered to give 190.0 g of crude product compound 16 which was used without further purification.

General procedure for preparation of compound 17: A mixture of compound 16 (190.0 g, 785.9 mmol, 1.0 eq), HCl (238.8 g, 2.4 mol, 234.1 mL, 36% purity, 3.0 eq) in 900 mL of water was stirred at 70-80° C. for 4 hours. The reaction was monitored by HPLC and allowed to run until complete. The reaction mixture was concentrated under reduced pressure to remove water. The residue was diluted with 800 mL of ethanol and stirred at 25° C. for 0.5 hour, then filtered. The filter cake was washed with two 500 mL portions of ethanol to give 43.0 g of compound 17 (29% yield, 2HCl salt) as a pink solid which was used without further purification.

General procedure for preparation of compound 18: To a solution of compound 17 (71.0 g, 379.5 mmol, 1.0 eq, 2HCl salt) in 560 mL of ethanol and 350 mL of water was added $NaHCO_3$ (111.6 g, 1.3 mol, 3.5 eq). Then benzyl carbonochloridate (68.0 g, 398 mmol, 56.6 mL, 1.05 eq) in 70 mL of dioxane was added dropwise for 0.5 hour at 0° C. The mixture was stirred at 0° C. for 1.5 hours. The reaction was monitored by TLC and allowed to run until ~10% of reactant 17 remained. The reaction mixture was concentrated to remove the solvents. The mixture was made acidic by the addition 1N HCl to pH~1. The aqueous mixture was extracted with two 500 mL portions of dichloromethane. To the aqueous solution was made basic to pH~13 by the addition of added NaOH and then it extracted with four 800 mL portions of dichloromethane. The combined organic layers were washed with 1000 mL of brine, dried over $Na_2SO_4$, filtered and concentrated under reduced pressure to give 46 g of compound 18 (49% yield) as a white solid.

General procedure for preparation of compound 19A: To a solution of compound 18 (40.0 g, 161.1 mmol, 1.0 eq) in 600 mL of methanol was added L-tartaric acid (24.2 g, 161.1 mmol, 1.0 eq) and the mixture was stirred for 1 hour at 25° C. The mixture was heated to 60° C. and stirred at 60° C. for 5 hours. The mixture was cooled, filtered, and filter cake was washed with 200 mL of methanol. The filter cake was dissolved in 100 mL of water, and the pH adjusted to ~12 with 15% aq. NaOH. It was extracted with three 100 mL portions of dichloromethane. The combined organic phase was dried over $Na_2SO_4$, and concentrated to give 17 g of compound 19A (43% yield) as a white solid, which was used to do next reactions without purification.

General procedure for preparation of compound 20: A mixture of compound 19A (5.0 g, 20.1 mmol, 1.0 eq), acetaldehyde (2.2 g, 20.1 mmol, 2.8 mL, 1.0 eq), acetic acid (363 mg, 6.0 mmol, 0.34 mL, 0.3 eq) in 20 mL of $CHCl_3$ was stirred for 1 hour at 15° C. $NaBH_4$ (762 mg, 20.1 mmol, 1.0 eq) was added, the mixture was stirred at 15° C. for another 11 hours under $N_2$ atmosphere. The reaction was monitored by LCMS and allowed to run until complete. The reaction mixture was partitioned between 20 mL of water and 20 mL of dichloromethane. The organic phase was separated, washed with 20 mL of brine, dried over $Na_2SO_4$, filtered and concentrated under reduced pressure to give the crude product, which was purified by flash silica gel chromatography (ISCO®; 40 g SepaFlash® Silica Flash Column, eluent of 0~20% methanol:ethyl acetate gradient @ 60 mL/min) to give 3.7 g of compound 20 (66% yield) as a white solid.

General procedure for preparation of compound 21: A mixture of compound 20 (2.7 g, 9.8 mmol, 1.0 eq), 1H-indole-2-carboxylic acid (1.6 g, 9.8 mmol, 1.0 eq), HATU (4.5 g, 11.7 mmol, 1.2 eq), TEA (2.0 g, 19.5 mmol, 2.7 mL, 2.0 eq) in 30 mL of DMF was degassed and purged with $N_2$ three times, and then the mixture was stirred at 15° C. for 12 hours under $N_2$ atmosphere. The reaction was monitored by LCMS and allowed to run until complete. The reaction mixture was partitioned between 50 mL of water and 100 mL of ethyl acetate. The organic phase was separated, washed three times with 150 mL of water and 50 mL of brine, dried over $Na_2SO_4$, filtered and concentrated under reduced pressure to give the crude product, which was purified by flash silica gel chromatography (ISCO®; 80 g SepaFlash® Silica Flash Column, eluent of 0-40% ethyl acetate:petroleum ether gradient @ 60 mL/min) to give 2.8 g of crude compound 21 (64% yield) as a white foam which was used into the next step directly.

General procedure for preparation of compound 4: A mixture of compound 21 (2.7 g, 4.2 mmol, 1.0 eq), Pd/C (100 mg, 50% purity) in 5 mL of methanol was degassed and purged with $H_2$ three times. The mixture was stirred at 15° C. for 0.5 hour under $H_2$ atmosphere (15 psi). The reaction was monitored by LCMS and allowed to run until complete. The mixture was filtered and the filtrate was evaporated under reduced pressure to give 1.6 g of crude compound 4 as a white gum which was used into the next step without further purification.

General procedure for preparation of compound 123: A mixture of compound 4 (50.0 mg, 175.2 μmol, 1.0 eq), 4-fluorobenzaldehyde (21.7 mg, 175 μmol, 1.0 eq), acetic acid (10.5 mg, 175 μmol, 1.0 eq), $NaBH_3CN$ (22.0 mg, 350 μmol, 2.0 eq) in 2 mL of methanol was degassed and purged with $N_2$ three times. The mixture was stirred at 15° C. for 12 hours under $N_2$ atmosphere. The reaction was monitored by LCMS and allowed to run until complete. The mixture was filtered and the filtrate was purified by prep-HPLC (TFA condition) to give 60.8 mg of compound 123 (66.0% yield, TFA salt) as a white solid.

Compound 123

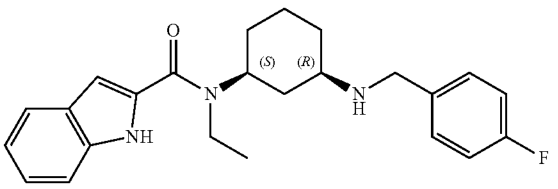

$^1H$ NMR (400 MHz, DMSO-$d_6$) δ ppm 11.52 (br s, 1H) 8.81 (br s, 2H) 7.58 (d, J=7.72 Hz, 1H) 7.48-7.55 (m, 2H) 7.39 (d, J=8.16 Hz, 1H) 7.21-7.29 (m, 2H) 7.15 (t, J=7.61 Hz, 1H) 7.01 (t, J=7.50 Hz, 1H) 6.70 (br s, 1H) 4.18 (br s, 3H) 3.42-3.60 (m, 2H) 3.19 (br s, 1H) 2.22 (br d, J=10.58 Hz, 1H) 2.05 (s, 1H) 1.60-1.90 (m, 4H) 1.14-1.39 (m, 5H)

LCMS (ESI+): m/z 394.2 (M+H)

The following compounds were prepared analogously.

Compound 124

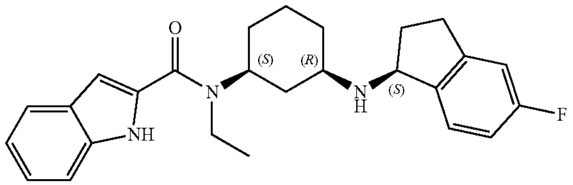

$^1H$ NMR (400 MHz, DMSO-$d_6$) δ ppm 11.51 (br s, 1H) 7.57 (d, J=7.94 Hz, 1H) 7.38 (d, J=8.38 Hz, 1H) 7.23 (br s, 1H) 7.14 (t, J=7.50 Hz, 1H) 6.95-7.04 (m, 2H) 6.87 (br s, 1H) 6.65 (br s, 1H) 4.24-4.34 (m, 1H) 4.19 (br s, 1H) 3.46 (br s, 1H) 2.85 (br s, 1H) 2.54-2.71 (m, 2H) 2.29 (br s, 1H) 1.86-2.00 (m, 1H) 1.38-1.80 (m, 6H) 1.12-1.34 (m, 5H) 0.96 (br d, J=11.25 Hz, 1H)

LCMS (ESI+): m/z 420.2 (M+H)

Compound 125

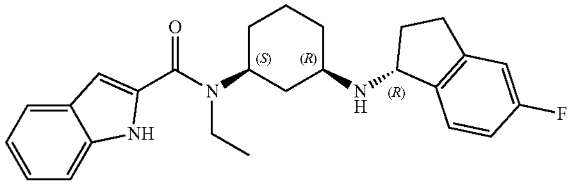

$^1H$ NMR (400 MHz, DMSO-$d_6$) δ ppm 11.50 (br s, 1H) 7.57 (d, J=7.94 Hz, 1H) 7.37 (d, J=8.38 Hz, 1H) 7.23-7.29 (m, 1H) 7.13 (t, J=7.50 Hz, 1H) 6.95-7.04 (m, 2H) 6.87-6.94 (m, 1H) 6.64 (br s, 1H) 4.26 (br s, 1H) 4.19 (br t, J=6.28 Hz, 1H) 3.48 (br s, 1H) 2.84 (br d, J=6.84 Hz, 1H) 2.58-2.71 (m, 2H) 2.28-2.34 (m, 1H) 2.07 (br d, J=9.92 Hz, 1H) 1.51-1.86 (m, 6H) 1.44 (q, J=11.54 Hz, 1H) 1.11-1.36 (m, 5H) 1.01 (br d, J=13.67 Hz, 1H)

LCMS (ESI+): m/z 420.2 (M+H)

Compound 126

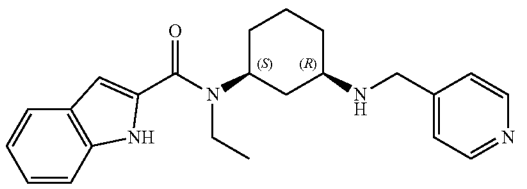

$^{1}$H NMR (400 MHz, DMSO-$d_6$) δ ppm 11.53 (br s, 1H) 9.26 (br s, 2H) 8.67 (br d, J=5.07 Hz, 2H) 7.58 (br d, J=5.73 Hz, 3H) 7.39 (br d, J=8.38 Hz, 1H) 7.10-7.19 (m, 1H) 7.01 (t, J=7.50 Hz, 1H) 6.70 (br s, 1H) 4.30 (br s, 2H) 3.50 (br s, 2H) 3.23 (br s, 1H) 2.55 (br s, 1H) 2.17-2.31 (m, 1H) 2.05 (br s, 1H) 1.60-1.94 (m, 4H) 1.32 (br t, J=8.93 Hz, 2H) 1.21 (br s, 3H)

LCMS (ESI+): m/z 377.1 (M+H)

Compound 127

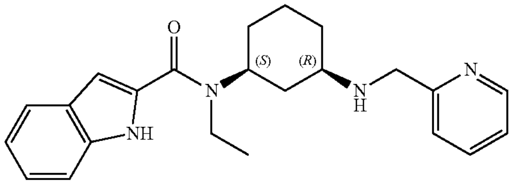

$^{1}$H NMR (400 MHz, DMSO-$d_6$) δ ppm 11.51 (br s, 1H) 8.44 (br d, J=4.41 Hz, 1H) 7.70 (td, J=7.66, 1.65 Hz, 1H) 7.55 (br d, J=8.16 Hz, 1H) 7.33-7.44 (m, 2H) 7.17-7.22 (m, 1H) 7.09-7.16 (m, 1H) 6.99 (t, J=7.28 Hz, 1H) 6.56 (br s, 1H) 4.22 (br t, J=12.13 Hz, 1H) 3.81 (s, 2H) 3.43 (br s, 2H) 2.42 (br s, 1H) 2.19-2.32 (m, 1H) 2.00 (br d, J=10.36 Hz, 1H) 1.63-1.86 (m, 3H) 1.37-1.61 (m, 2H) 1.09-1.27 (m, 4H) 0.89-1.03 (m, 1H)

LCMS (ESI+): m/z 377.2 (M+H)

Compound 128

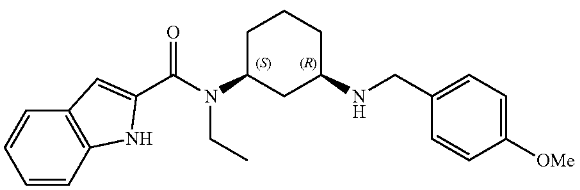

$^{1}$H NMR (400 MHz, DMSO-$d_6$) δ ppm 11.52 (br s, 1H) 8.77-8.92 (m, 2H) 7.59 (d, J=7.89 Hz, 1H) 7.36-7.44 (m, 3H) 7.16 (t, J=7.45 Hz, 1H) 7.03 (t, J=7.45 Hz, 1H) 6.97 (d, J=8.77 Hz, 2H) 6.70 (br s, 1H) 4.23 (br s, 1H) 4.12 (br s, 2H) 3.74 (s, 3H) 3.27-3.40 (m, 2H) 3.15 (br s, 1H) 2.23 (br d, J=10.96 Hz, 1H) 2.06 (br s, 1H) 1.60-1.94 (m, 4H) 1.16-1.40 (m, 5H)

LCMS (ESI+): m/z 406.2 (M+H)

Compound 129

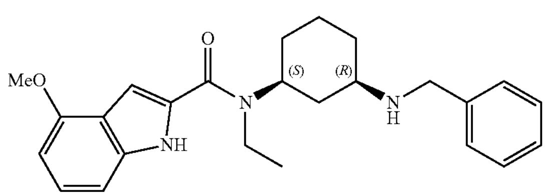

$^{1}$H NMR (400 MHz, CHLOROFORM-d) δ ppm 9.30 (br s, 1H) 7.32-7.37 (m, 4H) 7.21 (t, J=8.01 Hz, 1H) 7.04 (d, J=8.31 Hz, 1H) 6.89 (br s, 1H) 6.52 (d, J=7.82 Hz, 1H) 4.57 (br s, 1H) 3.97 (s, 3H) 3.85 (s, 2H) 3.51-3.75 (m, 2H) 3.65 (br s, 1H) 2.75 (br t, J=11.07 Hz, 1H) 2.11-2.26 (m, 1H) 2.02 (br d, J=11.49 Hz, 1H) 1.91 (br d, J=13.69 Hz, 2H) 1.58 (br d, J=12.23 Hz, 5H) 1.36 (br s, 3H) 1.15 (br d, J=11.49 Hz, 1H)

LCMS (ESI+): m/z 406.2 (M+H)

Compound 130

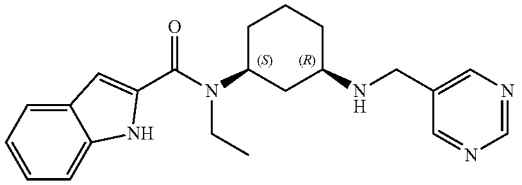

$^{1}$H NMR (400 MHz, CHLOROFORM-d) δ ppm 9.45 (br s, 1H) 9.13 (s, 1H) 8.73 (s, 2H) 7.66 (d, J=7.94 Hz, 1H) 7.43 (d, J=8.16 Hz, 1H) 7.24-7.29 (m, 1H) 7.08-7.17 (m, 1H) 6.76 (br s, 1H) 4.56 (br t, J=12.13 Hz, 1H) 3.86 (s, 2H) 3.64 (br s, 1H) 2.69 (br s, 1H) 2.16 (br d, J=11.47 Hz, 1H) 1.86-2.05 (m, 3H) 1.30-1.65 (m, 8H) 1.02-1.15 (m, 1H)

LCMS (ESI+): m/z 378.2 (M+H)

Compound 131

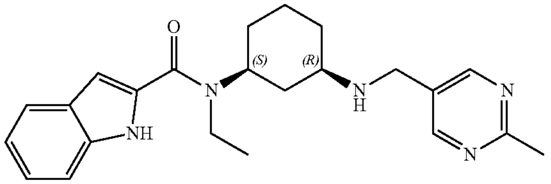

$^{1}$H NMR (400 MHz, CHLOROFORM-d) δ ppm 9.42 (br s, 1H) 8.59 (s, 2H) 7.64 (d, J=7.95 Hz, 1H) 7.40 (d, J=8.31 Hz, 1H) 7.20-7.26 (m, 1H) 7.06-7.14 (m, 1H) 6.73 (br s, 1H) 4.53 (br t, J=11.98 Hz, 1H) 3.79 (s, 2H) 3.62 (br s, 1H) 2.70 (s, 3H) 2.61-2.67 (m, 1H) 2.13 (br d, J=10.39 Hz, 1H) 1.81-2.02 (m, 3H) 1.29-1.61 (m, 8H) 0.98-1.12 (m, 1H)

LCMS (ESI+): m/z 392.3 (M+H)

Compound 132

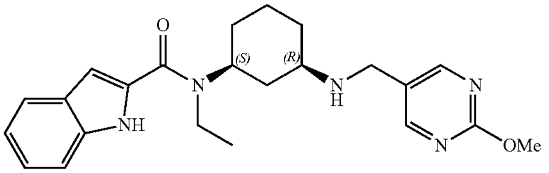

$^1$H NMR (400 MHz, CHLOROFORM-d) δ ppm 9.54 (br s, 1H) 8.46 (s, 2H) 7.64 (d, J=7.95 Hz, 1H) 7.41 (d, J=8.19 Hz, 1H) 7.22-7.26 (m, 1H) 7.08-7.15 (m, 1H) 6.73 (br s, 1H) 4.54 (br t, J=11.92 Hz, 1H) 3.98 (s, 3H) 3.75 (s, 2H) 3.62 (br s, 1H) 2.66 (br t, J=10.88 Hz, 1H) 2.13 (br d, J=8.93 Hz, 1H) 1.80-2.02 (m, 3H) 1.27-1.65 (m, 8H) 0.98-1.13 (m, 1H)

LCMS (ESI+): m/z 408.2 (M+H)

Compound 133

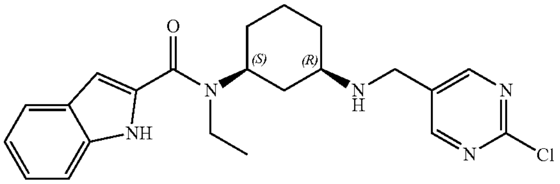

$^1$H NMR 400 MHz, CHLOROFORM-d) ppm 9.35 (br s, 1H) 8.63 (s, 2H) 7.67 (d, J=7.58 Hz, 1H) 7.44 (d, J=8.19 Hz, 1H) 7.27-7.33 (m, 1H) 7.12-7.18 (m, 1H) 6.77 (br s, 1H) 4.55 (br t, J=11.86 Hz, 1H) 3.86 (s, 2H) 3.66 (br s, 1H) 2.69 (br t, J=10.88 Hz, 1H) 2.11-2.21 (m, 1H) 1.86-2.05 (m, 3H) 1.31-1.67 (m, 8H) 1.00-1.14 (m, 1H)

LCMS (ESI+): m/z 412.1 (M+H)

Compound 134

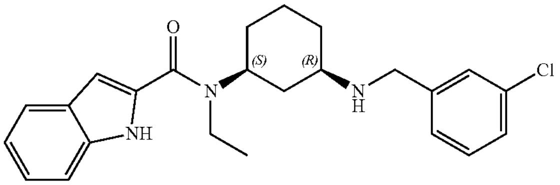

$^1$H NMR (400 MHz, CHLOROFORM-d) δ ppm 9.44 (br s, 1H), 7.65 (br d, J=8.2 Hz, 1H), 7.43 (br d, J=8.2 Hz, 1H), 7.34 (s, 1H), 7.30-7.18 (m, 4H), 7.13 (br t, J=7.3 Hz, 1H), 6.72 (br s, 1H), 4.57 (br t, J=11.8 Hz, 1H), 3.82 (s, 2H), 3.62 (br s, 2H), 2.68 (br s, 1H), 2.16 (br d, J=10.4 Hz, 1H), 1.99 (br d, J=11.7 Hz, 1H), 1.93-1.83 (m, 2H), 1.63-1.44 (m, 4H), 1.34 (br s, 3H), 1.15-1.03 (m, 1H)

LCMS (ESI+): m/z 410.2 (M+H)

Compound 135

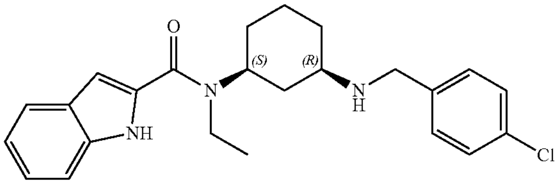

$^1$H NMR (400 MHz, CHLOROFORM-d) δ ppm 9.45 (br s, 1H), 7.65 (br d, J=7.9 Hz, 1H), 7.43 (br d, J=8.2 Hz, 1H), 7.32-7.23 (m, 5H), 7.17-7.10 (m, 1H), 6.70 (br s, 1H), 4.56 (br t, J=11.8 Hz, 1H), 3.81 (s, 2H), 3.64 (br s, 2H), 2.67 (br s, 1H), 2.16 (br d, J=11.2 Hz, 1H), 1.98 (br d, J=12.6 Hz, 1H), 1.93-1.83 (m, 2H), 1.62-1.42 (m, 4H), 1.35 (br s, 3H), 1.15-1.02 (m, 1H)

LCMS (ESI+): m/z 410.2 (M+H)

Compound 136

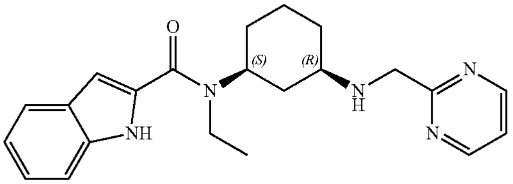

$^1$H NMR (400 MHz, METHANOL-$d_4$) δ ppm 8.85 (d, J=4.89 Hz, 2H) 7.62 (d, J=8.07 Hz, 1H) 7.41-7.52 (m, 2H) 7.22 (t, J=7.21 Hz, 1H) 7.03-7.11 (m, 1H) 6.81 (br s, 1H) 4.51-4.60 (m, 2H) 4.26-4.51 (m, 1H) 3.68 (br s, 2H) 3.41 (br s, 1H) 2.38 (br d, J=11.00 Hz, 1H) 2.23 (br s, 1H) 1.99-2.11 (m, 2H) 1.80-1.97 (m, 2H) 1.43-1.54 (m, 2H) 1.35 (br t, J=6.97 Hz, 3H)

LCMS (ESI+): m/z 378.1 (M+H)

Compound 137

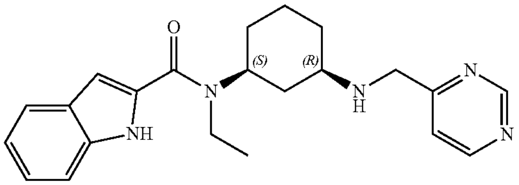

$^1$H NMR (400 MHz, METHANOL-$d_4$) δ ppm 9.23 (d, J=0.98 Hz, 1H) 8.82 (d, J=5.26 Hz, 1H) 7.55-7.65 (m, 2H) 7.44 (d, J=8.31 Hz, 1H) 7.18-7.25 (m, 1H) 7.04-7.11 (m, 1H) 6.75-6.85 (m, 1H) 6.81 (br s, 1H) 4.53 (s, 2H) 4.28-4.49 (m, 1H) 3.69 (br s, 2H) 3.38 (br s, 1H) 2.38 (br d, J=11.86 Hz, 1H) 2.22 (br s, 1H) 2.00-2.12 (m, 2H) 1.82-1.97 (m, 2H) 1.45-1.53 (m, 2H) 1.35 (br t, J=6.97 Hz, 3H)

LCMS (ESI+): m/z 378.1 (M+H)

Example 6. Synthesis of N-ethyl-N-((1S,3R)-3-((3-fluorobenzyl)amino)cyclohexyl)-1H-pyrrolo[3,2-b]pyridine-2-carboxamide (Compound 150)

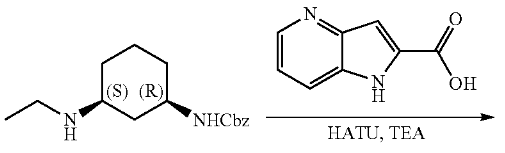

20

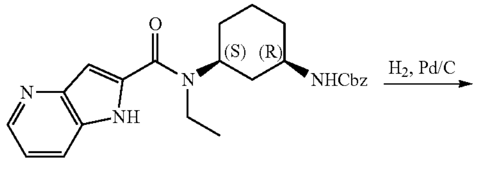

24

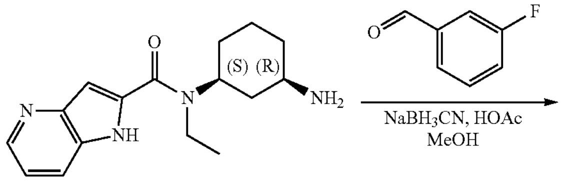

25

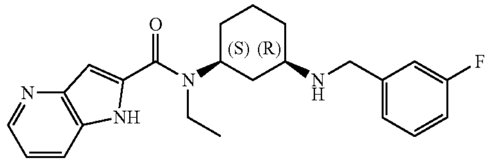

Compound 150

General procedure for preparation of compound 24: A mixture of compound 20 (200.0 mg, 723.7 μmol, 1.0 eq), 1H-pyrrolo[3, 2-b] pyridine-2-carboxylic acid (117.3 mg, 723.7 μmol, 1.0 eq), HATU (275 mg, 724 μmol, 1.0 eq), TEA (146.5 mg, 1.5 μmol, 2.0 eq) in 6 mL of DMF was degassed and purged with $N_2$ three times. The mixture was stirred at 15° C. for 12 hours under $N_2$ atmosphere. The reaction was monitored by LCMS and allowed to run until complete. The reaction mixture was partitioned between 10 mL of water and 20 mL of ethyl acetate. The organic phase was separated, washed three times with 30 mL of water and 10 mL of brine, dried over $Na_2SO_4$, filtered and concentrated under reduced pressure to give the crude product, which was purified by prep-TLC (ethyl acetate:petroleum ether=3:1) to give 100 mg of compound 24 (33% yield) as a colorless gum.

General procedure for preparation of compound 25: A mixture of compound 24 (100.0 mg, 238 μmol, 1.0 eq), Pd/C (100.0 mg, 50% purity), $NH_3.H_2O$ (0.5 mL) in 5 mL of methanol and 5 mL of ethyl acetate was degassed and purged with $H_2$ three times. The mixture was stirred at 15° C. for 0.5 hour under $H_2$ atmosphere (15 psi). The reaction was monitored by LCMS and allowed to run until complete. The mixture was filtered and the filtrate was evaporated under reduced pressure to give 60 mg of crude compound 25 as a white gum and to be used into the next step without further purification.

General procedure for preparation of compound 150: A mixture of crude compound 25 (20.0 mg, 69.8 μmol, 1.0 eq), 3-fluorobenzaldehyde (13.0 mg, 104.7 μmol, 1.5 eq), acetic acid (4.2 mg, 69.8 μmol, 1.0 eq), $NaBH_3CN$ (8.8 mg, 140 μmol, 2.0 eq) in 2 mL of methanol was degassed and purged with $N_2$ three times. The mixture was stirred at 18° C. for 12 hours under $N_2$ atmosphere. The reaction was monitored by LCMS and allowed to run until complete. The mixture was filtered and the filtrate was purified by prep-HPLC (TFA condition) to give 15.8 mg of compound 150 (43% yield, TFA salt) as a colorless gum.

Compound 150

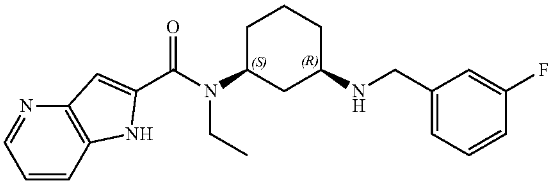

$^1H$ NMR (400 MHz, DMSO-$d_6$) δ ppm 13.09 (br s, 1H) 9.13 (br s, 2H) 8.72 (d, J=4.89 Hz, 1H) 8.46 (br d, J=8.19 Hz, 1H) 7.66 (dd, J=8.31, 5.50 Hz, 1H) 7.46-7.54 (m, 1H) 7.32-7.43 (m, 2H) 7.26 (br t, J=7.70 Hz, 1H) 7.07 (br s, 1H) 4.24 (br s, 2H) 4.07 (br s, 1H) 3.50 (br s, 2H) 3.18 (br s, 1H) 2.25-2.35 (m, 1H) 2.08 (br d, J=5.01 Hz, 1H) 1.63-1.95 (m, 4H) 1.14-1.42 (m, 5H)

LCMS (ESI+): m/z 395.2 (M+H)

The following compounds were prepared analogously.

Compound 151

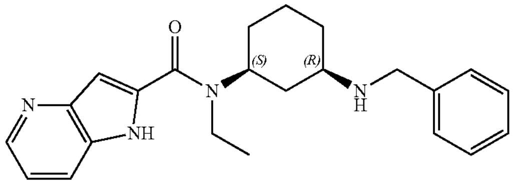

$^1H$ NMR (400 MHz, DMSO-$d_6$) δ ppm 11.76 (br s, 1H) 8.35 (d, J=4.41 Hz, 1H) 7.74 (d, J=8.38 Hz, 1H) 7.22-7.33 (m, 4H) 7.11-7.19 (m, 2H) 6.69 (br s, 1H) 4.16 (br s, 1H) 3.72 (br s, 2H) 3.37-3.47 (m, 2H) 2.34-2.44 (m, 1H) 2.02 (br s, 1H) 1.62-1.91 (m, 4H) 1.39-1.62 (m, 1H) 1.37-1.62 (m, 1H) 1.16 (br t, J=6.50 Hz, 4H) 0.96 (br d, J=12.35 Hz, 1H)

LCMS (ESI+): m/z 377.2 (M+H)

Compound 152

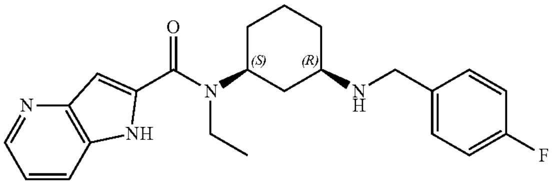

$^1H$ NMR (400 MHz, DMSO-$d_6$) δ ppm 12.99 (br s, 1H) 9.04 (br s, 2H) 8.70 (d, J=4.77 Hz, 1H) 8.41 (br d, J=8.19 Hz, 1H) 7.63 (dd, J=8.19, 5.50 Hz, 1H) 7.51-7.60 (m, 2H) 7.29 (br t, J=8.74 Hz, 2H) 7.05 (br s, 1H) 4.21 (br s, 2H) 4.07 (br s, 1H) 3.51 (br s, 1H) 3.41-3.57 (m, 1H) 3.18 (br s, 1H)

2.25-2.35 (m, 1H) 2.07 (br s, 1H) 1.62-1.92 (m, 4H) 1.27-1.41 (m, 1H) 1.33 (br s, 1H) 1.23 (br t, J=6.85 Hz, 3H)

LCMS (ESI+): m/z 395.2 (M+H)

Example 7. Synthesis of N-((1S,3R)-3-((3-fluorobenzyl)amino)cyclohexyl)-N-(2,2,2-trifluoroethyl)-1H-indole-2-carboxamide (Compound 170)

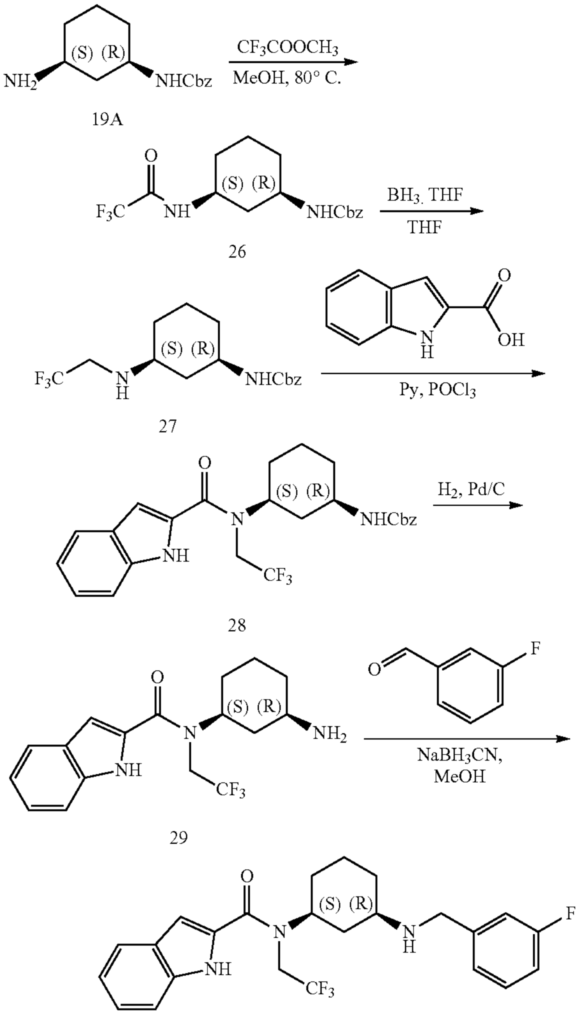

compound 170

General procedure for preparation of compound 26: A mixture of compound 19A (1.0 g, 4.0 mmol, 1.0 eq), methyl 2,2,2-trifluoroacetate (1.6 g, 12.1 mmol, 3.0 eq) in 10 mL of methanol was stirred at 80° C. for 12 hours. The reaction was monitored by LCMS and allowed to run until complete. The reaction mixture was concentrated under reduced pressure to give a solid. The solid was diluted with 10 mL of HCl (1M) and extracted twice with 20 mL of ethyl acetate. The combined organic layers were washed with 25 mL of brine, dried over $Na_2SO_4$, filtered and concentrated under reduced pressure to give 1.39 g of the desired compound 26 as a crude white solid.

General procedure for preparation of compound 27: To a mixture of compound 26 (1.39 g, 4.0 mmol, 1.0 eq) in 10 mL of THF was added $BH_3$.THF (1M, 12.1 mL, 3.0 eq) at 25° C., and then the mixture was stirred at 70° C. for 24 hours under $N_2$ atmosphere. The reaction was monitored by LCMS and allowed to run until complete. The mixture was quenched by adding 15 mL of methanol and 6 mL HCl (1M) and stirring at 70° C. for 1 hour. The mixture was concentrated to afford an oil. The oil was diluted with 20 mL of water and basified by $Na_2CO_3$ to pH=9-10, then extracted twice with 15 mL of ethyl acetate. The combined organic layers were washed with twice with 20 mL of brine, dried over $Na_2SO_4$, filtered and concentrated under reduced pressure to give an oil. The residue was purified by column chromatography ($SiO_2$, petroleum ether:ethyl acetate=50:1 to 2:1) to give 700 mg of compound 27 (53% yield) as a white solid.

General procedure for preparation of compound 28: A mixture of compound 27 (320 mg, 969 μmol, 1.0 eq), 1H-indole-2-carboxylic acid (156 mg, 969 μmol, 1.0 eq) in 5 mL of pyridine was added $POCl_3$ (446 mg, 2.9 mmol, 3.0 eq) at 0° C., and then the mixture was stirred at 25° C. for 1 hour. The reaction was monitored by TLC and allowed to run until complete. To the reaction mixture was added 13 mL of saturated $NH_4Cl$ dropwise to quench the $POCl_3$, then the mixture was concentrated under reduced pressure to remove pyridine and water. The resulting gum was diluted with 30 mL of ethyl acetate and washed twice with 40 mL of HCl (1M). The organic layers were washed with 50 mL of brine, dried over $Na_2SO_4$, filtered and concentrated under reduced pressure to give 560 mg of the desired compound 28 as a crude brown gum. This material was used without further purification.

General procedure for preparation of compound 29: A mixture of compound 28 (520 mg, 1.1 mmol, 1.0 eq), Pd/C (100 mg, 50% purity) in 10 mL of methanol was degassed and purged with $H_2$ three times. The mixture was stirred at 15° C. for 1 hour under $H_2$ atmosphere (15 psi). The reaction was monitored by LCMS and allowed to run until complete. The reaction mixture was filtered and then concentrated under reduced pressure to give 285 mg of the desired compound 28 as a crude yellow solid.

General procedure for preparation of compound 170: A mixture of compound 29 (100 mg, 295 μmol, 1.0 eq), 3-fluorobenzaldehyde (55 mg, 442 μmol, 1.5 eq), $NaBH_3CN$ (37 mg, 589 μmol, 2.0 eq), acetic acid (1.8 mg, 29.5 μmol, 0.1 eq) in 2 mL of methanol was stirred at 25° C. for 12 hours. The reaction was monitored by LCMS and allowed to run until complete. The reaction mixture was filtered. The residue was purified by prep-HPLC (TFA condition to give 52.9 mg of compound 170 (32% yield, TFA salt) as a white solid.

Compound 170

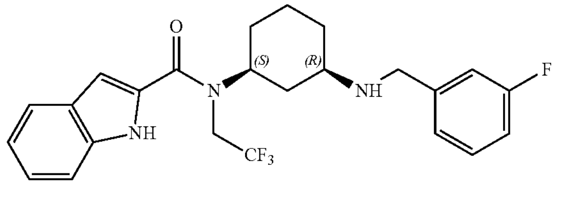

$^1H$ NMR (400 MHz, CHLOROFORM-d) δ ppm 9.81 (br d, J=8.2 Hz, 2H) 7.63 (d, J=8.1 Hz, 1H) 7.40 (d, J=8.2 Hz, 1H) 7.29 (t, J=7.6 Hz, 1H) 7.22 (q, J=7.3 Hz, 1H) 7.18-7.13 (m, 1H) 7.09 (br d, J=7.6 Hz, 2H) 6.95 (br t, J=8.0 Hz, 1H) 6.68 (s, 1H) 4.17 (br d, J=7.7 Hz, 3H) 3.93 (br s, 2H) 3.01 (br s, 1H) 2.30 (br d, J=11.4 Hz, 1H) 2.19-1.98 (m, 2H) 1.96-1.81 (m, 2H) 1.71 (br s, 1H) 1.38-1.21 (m, 2H)

LCMS (ESI+): m/z 448.2 (M+H)

The following compound can be prepared analogously:

Compound 171

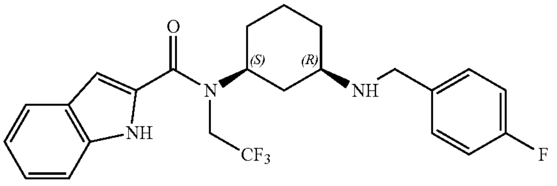

$^1H$ NMR (400 MHz, CHLOROFORM-d) δ ppm 9.72-9.46 (m, 1H) 7.64 (d, J=8.1 Hz, 1H) 7.41 (br d, J=8.3 Hz, 1H) 7.36-7.29 (m, 3H) 7.20-7.13 (m, 1H) 6.96 (br t, J=8.4 Hz, 2H) 6.69 (s, 1H) 4.21 (br d, J=8.3 Hz, 3H) 3.89 (br s, 2H) 3.02-2.70 (m, 2H) 2.30 (br d, J=10.3 Hz, 1H) 2.17 (s, 1H) 1.99-1.82 (m, 3H) 1.74 (br s, 1H) 1.27 (br s, 2H)

LCMS (ESI+): m/z 448.2 (M+H)

Example 8. Synthesis of N-((1S,3S)-3-((3-fluorobenzyl)amino)cyclohexyl)-N-(2,2,2-trifluoroethyl)-1H-indole-2-carboxamide (Compound 172) and N-((1S,3R)-3-((3-fluorobenzyl)amino)cyclohexyl)-N-(2,2,2-trifluoroethyl)-1H-indole-2-carboxamide (Compound 173)

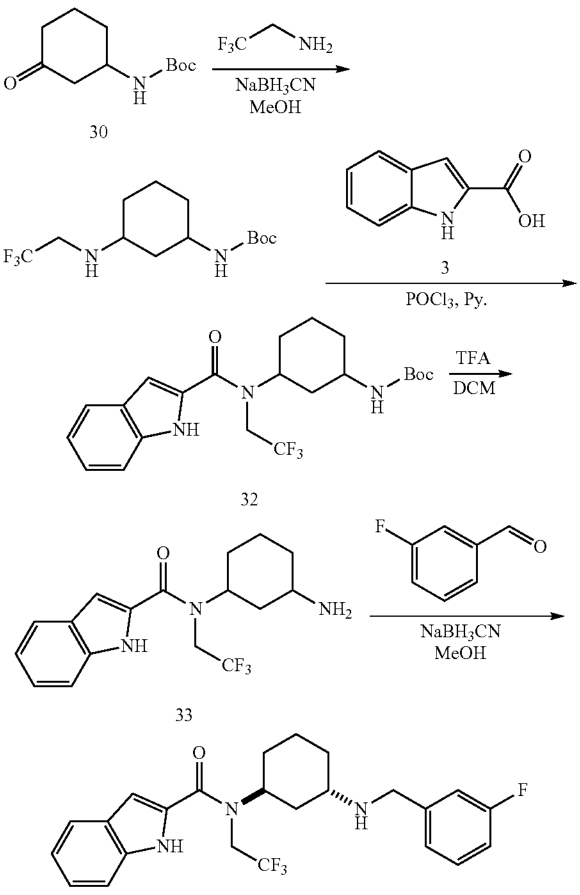

compound 172

-continued

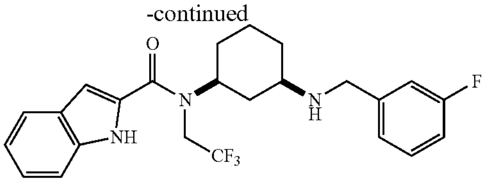

compound 173

General procedure for preparation of compound 31: A mixture of compound 30 (3.0 g, 14.1 mmol, 1.0 eq), 2,2,2-trifluoroethanamine (2.1 g, 21.1 mmol, 1.5 eq), acetic acid (167 mg, 2.8 mmol, 0.2 eq) in 30 mL of methanol was stirred at 25° C. for 0.5 hour. To the mix was added $NaBH_3CN$ (1.8 g, 28.1 mmol, 2.0 eq) and then the mixture was stirred at 25° C. for 11.5 hours. The reaction was monitored by TLC and allowed to run until complete. The reaction mixture was quenched by adding 10 mL water, then concentrated under reduced pressure to remove methanol. It was extracted with three 20 mL portions of ethyl acetate. The combined organic layers were washed with 20 mL of brine, dried over $Na_2SO_4$, filtered and concentrated under reduced pressure to give 4.2 g of the desired compound 31 as a crude yellow oil.

General procedure for preparation of compound 32: A mixture of compound 31 (500 mg, 1.7 mmol, 1.0 eq), compound 3 (272 mg, 1.7 mmol, 1.0 eq) in 10 mL of pyridine was added $POCl_3$ (777 mg, 5.1 mmol, 3.0 eq) at 0° C., and then the mixture was stirred at 25° C. for 1 hour. The reaction was monitored by TLC and allowed to run until complete. To the reaction mixture was added 10 mL of saturated $NH_4Cl$ dropwise to quench the $POCl_3$, then the mixture was concentrated under reduced pressure to remove pyridine and water. The resulting gum was diluted with 30 mL of ethyl acetate and washed twice with 40 mL of HCl (1M). The organic layers were washed with 50 mL of brine, dried over $Na_2SO_4$, filtered and concentrated under reduced pressure to give 390 mg of the desired compound 32 as a crude yellow gum which was used without further purification.

General procedure for preparation of compound 33: A mixture of compound 32 (30 mg, 68 μmol, 1.0 eq) in 250 μL of TFA and 2 mL of dichloromethane was stirred at 25° C. for 1 hour. The reaction was monitored by LCMS and allowed to run until complete. The reaction mixture was basified by 3 mL of saturated $NaHCO_3$, then the dichloromethane layer was dried over $Na_2SO_4$ and concentrated by $N_2$ to give 15 mg of the desired compound 33 as a crude yellow oil.

General procedure for preparation of compounds 172 and 173: A mixture of compound 33 (80 mg, 235.7 μmol, 1.0 eq), 3-fluorobenzaldehyde (44 mg, 354 μmol, 1.5 eq), $NaBH_3CN$ (30 mg, 472 μmol, 2.0 eq), acetic acid (7 mg, 118 μmol, 0.5 eq) in 2 mL of methanol was stirred at 25° C. for 12 hours. The reaction was monitored by LCMS and allowed to run until complete. The reaction mixture was filtered. The residue was purified by prep-HPLC (neutral condition) to give 29.7 mg of compound 172 (27.9% yield) as a white solid and 4.1 mg of compound 173 (3.6% yield) as a white solid.

Compound 172

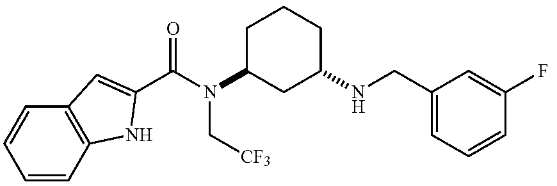

$^1H$ NMR (400 MHz, CHLOROFORM-d) δ ppm 9.53 (br s, 1H) 7.51 (d, J=8.2 Hz, 1H) 7.42 (dd, J=0.8, 8.3 Hz, 1H) 7.32-7.26 (m, 1H) 7.18-7.08 (m, 3H) 7.05-6.99 (m, 2H) 6.93 (dt, J=1.9, 8.4 Hz, 1H) 4.33-4.12 (m, 2H) 3.85-3.69 (m, 2H) 3.27-3.19 (m, 1H) 2.04 (br d, J=13.0 Hz, 1H) 1.97-1.83 (m, 2H) 1.81-1.62 (m, 5H) 1.53-1.42 (m, 1H) 1.10 (br s, 1H)

LCMS (ESI+): m/z 448.1 (M+H)

Compound 173

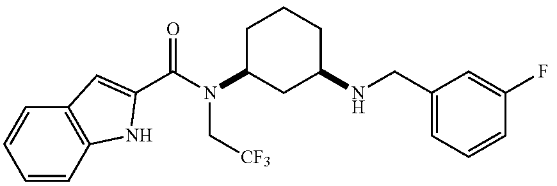

$^1H$ NMR (400 MHz, CHLOROFORM-d) δ ppm 9.30 (br s, 1H) 7.66 (d, J=8.2 Hz, 1H) 7.43 (dd, J=0.7, 8.2 Hz, 1H) 7.34-7.26 (m, 2H) 7.19-7.13 (m, 1H) 7.11-7.02 (m, 2H) 6.99-6.92 (m, 1H) 6.76 (d, J=1.3 Hz, 1H) 4.57 (br t, J=11.4 Hz, 1H) 4.31-4.18 (m, 2H) 3.84 (s, 2H) 2.72-2.61 (m, 1H) 2.27-2.17 (m, 1H) 2.05-1.89 (m, 3H) 1.66-1.56 (m, 3H) 1.44-1.34 (m, 1H) 1.16-1.03 (m, 1H)

LCMS (ESI+): m/z 448.2 (M+H)

The following compounds were prepared analogously:

Compound 174

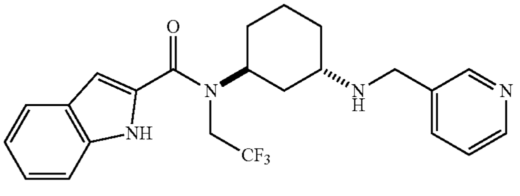

$^1H$ NMR (400 MHz, CHLOROFORM-d) δ ppm 9.51 (br s, 1H) 8.52 (d, J=1.8 Hz, 1H) 8.47 (dd, J=1.5, 4.9 Hz, 1H) 7.53 (d, J=8.2 Hz, 1H) 7.47 (br d, J=7.7 Hz, 1H) 7.41 (dd, J=0.8, 8.3 Hz, 1H) 7.30 (ddd, J=1.1, 7.0, 8.2 Hz, 1H) 7.13 (dt, J=0.9, 7.5 Hz, 1H) 7.07-6.99 (m, 2H) 4.22 (q, J=8.8 Hz, 2H) 3.74 (d, J=2.0 Hz, 2H) 3.23 (t, J=2.8 Hz, 1H) 2.04-1.93 (m, 3H) 1.92-1.78 (m, 2H) 1.77-1.65 (m, 4H) 1.53-1.42 (m, 1H)

LCMS (ESI+): m/z 431.1 (M+H)

Compound 175

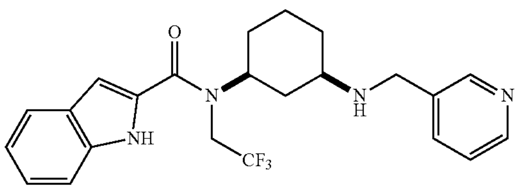

$^1H$ NMR (400 MHz, CHLOROFORM-d) δ ppm 9.33 (br s, 1H) 8.57 (d, J=1.8 Hz, 1H) 8.52 (dd, J=1.5, 4.9 Hz, 1H) 7.67 (d, J=7.9 Hz, 2H) 7.43 (d, J=8.2 Hz, 1H) 7.31 (dt, J=1.0, 7.7 Hz, 1H) 7.25 (br d, J=4.9 Hz, 1H) 7.19-7.13 (m, 1H) 6.77 (d, J=1.5 Hz, 1H) 4.57 (br s, 1H) 4.31-4.17 (m, 2H) 3.86 (s, 2H) 2.68 (tt, J=3.6, 11.1 Hz, 1H) 2.21 (br d, J=11.9 Hz, 1H) 2.02 (br d, J=12.1 Hz, 1H) 1.95 (br d, J=11.7 Hz, 2H) 1.62-1.56 (m, 3H) 1.49-1.37 (m, 1H) 1.15-1.04 (m, 1H)

LCMS (ESI+): m/z 431.1 (M+H)

Compound 176

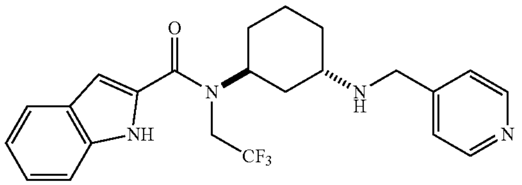

$^1H$ NMR (400 MHz, CHLOROFORM-d) δ ppm 9.78-9.64 (m, 1H) 8.37 (d, J=6.0 Hz, 2H) 7.48 (d, J=8.2 Hz, 1H) 7.42 (dd, J=0.7, 8.4 Hz, 1H) 7.30 (dt, J=1.1, 7.6 Hz, 1H) 7.16-7.10 (m, 3H) 7.03 (s, 1H) 4.22 (q, J=8.6 Hz, 2H) 3.74 (s, 2H) 3.21 (br s, 1H) 2.03-1.93 (m, 2H) 1.91 (br s, 1H) 1.91-1.83 (m, 1H) 1.79-1.63 (m, 4H) 1.53-1.41 (m, 1H) 1.11 (br s, 1H)

LCMS (ESI+): m/z 431.1 (M+H)

Compound 177

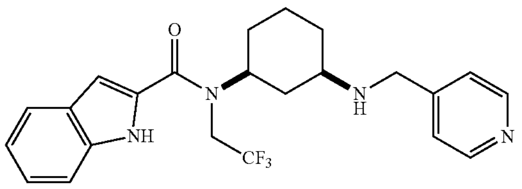

$^1H$ NMR (400 MHz, CHLOROFORM-d) δ ppm 9.38 (br s, 1H) 8.57-8.51 (m, 2H) 7.65 (dd, J=0.7, 7.9 Hz, 1H) 7.43 (dd, J=0.7, 8.2 Hz, 1H) 7.31 (ddd, J=1.1, 7.1, 8.3 Hz, 1H) 7.27 (s, 1H) 7.26 (s, 1H) 7.19-7.14 (m, 1H) 6.75 (d, J=1.5 Hz, 1H) 4.56 (br t, J=10.6 Hz, 1H) 4.30-4.20 (m, 2H) 3.86 (s, 2H) 2.65 (tt, J=3.7, 11.1 Hz, 1H) 2.25-2.18 (m, 1H) 2.04-1.90 (m, 3H) 1.66-1.55 (m, 3H) 1.46-1.35 (m, 1H) 1.15-1.01 (m, 1H)

LCMS (ESI+): m/z 431.1 (M+H)

Compound 178

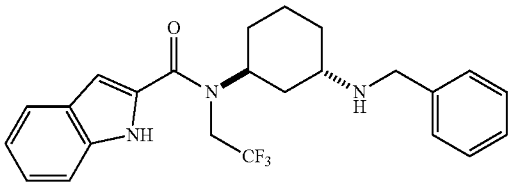

$^1$H NMR (400 MHz, CHLOROFORM-d) δ ppm 9.35 (br s, 1H) 7.48 (d, J=7.9 Hz, 1H) 7.40 (dd, J=0.9, 8.4 Hz, 1H) 7.28 (ddd, J=1.1, 7.0, 8.2 Hz, 1H) 7.25-7.21 (m, 2H) 7.21-7.16 (m, 2H) 7.14-7.08 (m, 2H) 4.29-4.10 (m, 2H) 3.81-3.69 (m, 2H) 3.22 (t, J=2.9 Hz, 1H) 2.04 (br d, J=13.0 Hz, 1H) 1.97-1.85 (m, 2H) 1.77-1.60 (m, 4H) 1.53-1.39 (m, 4H)

LCMS (ESI+): m/z 430.1 (M+H)

Compound 179

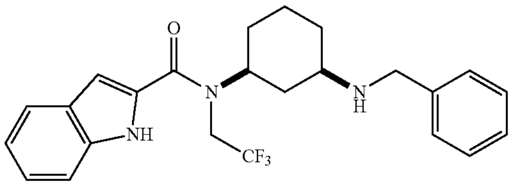

$^1$H NMR (400 MHz, CHLOROFORM-d) δ ppm 9.45 (br s, 1H) 7.64 (d, J=8.2 Hz, 1H) 7.41 (d, J=7.9 Hz, 1H) 7.34-7.31 (m, 3H) 7.30-7.27 (m, 1H) 7.26-7.22 (m, 1H) 7.17-7.12 (m, 1H) 6.74 (d, J=1.5 Hz, 1H) 4.57 (br t, J=11.7 Hz, 1H) 4.31-4.15 (m, 2H) 3.83 (s, 2H) 2.67 (tt, J=3.7, 11.0 Hz, 1H) 2.21 (br d, J=11.9 Hz, 1H) 2.03-1.88 (m, 3H) 1.64-1.56 (m, 3H) 1.54-1.35 (m, 2H) 1.15-1.03 (m, 1H)

LCMS (ESI+): m/z 430.1 (M+H)

Compound 180

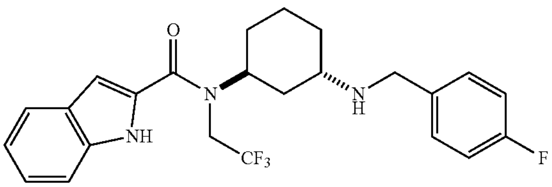

$^1$H NMR (400 MHz, CHLOROFORM-d) δ ppm 9.38 (br s, 1H) 7.50 (d, J=7.9 Hz, 1H) 7.41 (dd, J=0.7, 8.4 Hz, 1H) 7.30 (ddd, J=1.1, 7.1, 8.3 Hz, 1H) 7.16-7.10 (m, 2H) 7.16-7.10 (m, 1H), 7.06 (s, 1H) 6.82 (t, J=8.7 Hz, 2H) 4.20 (q, J=8.8 Hz, 2H) 3.74-3.63 (m, 2H) 3.21 (t, J=2.8 Hz, 1H) 2.04-1.92 (m, 2H) 1.91-1.82 (m, 1H) 1.76-1.61 (m, 4H) 1.51-1.41 (m, 3H)

LCMS (ESI+): m/z 448.1 (M+H)

Compound 181

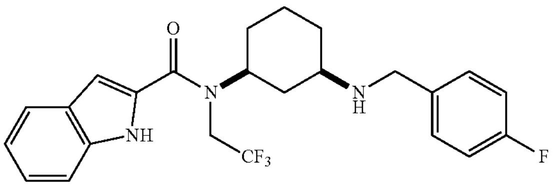

$^1$H NMR (400 MHz, CHLOROFORM-d) δ ppm 9.44 (br s, 1H) 7.63 (d, J=8.2 Hz, 1H) 7.42 (dd, J=0.7, 8.4 Hz, 1H) 7.32-7.25 (m, 3H) 7.15 (dt, J=0.9, 7.5 Hz, 1H) 7.02-6.96 (m, 2H) 6.74 (d, J=1.3 Hz, 1H) 4.56 (br t, J=11.5 Hz, 1H) 4.30-4.14 (m, 2H) 3.79 (s, 2H) 2.65 (tt, J=3.7, 11.1 Hz, 1H) 2.20 (br d, J=11.9 Hz, 1H) 2.01-1.89 (m, 3H) 1.66-1.57 (m, 3H) 1.50-1.40 (m, 1H) 1.14-1.02 (m, 1H)

LCMS (ESI+): m/z 448.2 (M+H)

Compound 182

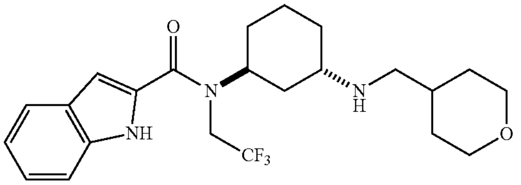

$^1$H NMR (400 MHz, CHLOROFORM-d) δ ppm 9.29 (br s, 1H) 7.63 (d, J=8.2 Hz, 1H) 7.42 (d, J=8.2 Hz, 1H) 7.29 (t, J=7.5 Hz, 1H) 7.17-7.11 (m, 1H) 7.05 (s, 1H) 4.28-4.12 (m, 2H) 3.87 (br dd, J=3.2, 10.9 Hz, 1H) 3.73 (br d, J=8.8 Hz, 1H) 3.32-3.20 (m, 2H) 3.10 (br s, 1H) 2.43-2.37 (m, 1H) 1.93 (br d, J=12.3 Hz, 2H) 1.87-1.78 (m, 1H) 1.73-1.62 (m, 4H) 1.57 (br d, J=12.3 Hz, 3H) 1.50-1.38 (m, 3H) 1.29-1.18 (m, 2H) 1.16-1.04 (m, 1H)

LCMS (ESI+): m/z 438.2 (M+H)

Compound 183

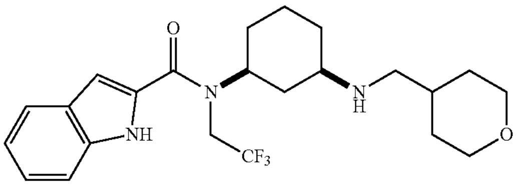

$^1$H NMR (400 MHz, CHLOROFORM-d) δ ppm 9.38 (br s, 1H) 7.68 (d, J=7.9 Hz, 1H) 7.44 (d, J=8.2 Hz, 1H) 7.31 (t, J=7.7 Hz, 1H) 7.16 (t, J=7.5 Hz, 1H) 6.81 (s, 1H) 4.60 (br s, 1H) 4.34-4.11 (m, 2H) 3.96 (br dd, J=3.9, 11.1 Hz, 2H) 3.37 (br t, J=11.4 Hz, 2H) 2.64-2.50 (m, 3H) 2.20-2.11 (m, 1H) 2.00-1.89 (m, 3H) 1.63 (br d, J=11.5 Hz, 3H) 1.51-1.38 (m, 3H) 1.37-1.22 (m, 3H) 1.11-0.98 (m, 1H)

LCMS (ESI+): m/z 438.2 (M+H)

Example 9: Synthesis of N-((3R,5S)-5-(benzylamino)tetrahydro-2H-pyran-3-yl)-N-ethyl-1H-indole-2-carboxamide (Compound 300) and N-((3R,5R)-5-(benzylamino)tetrahydro-2H-pyran-3-yl)-N-ethyl-1H-indole-2-carboxamide (Compound 301)

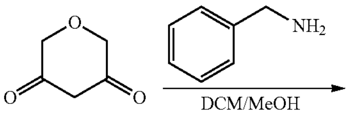

34

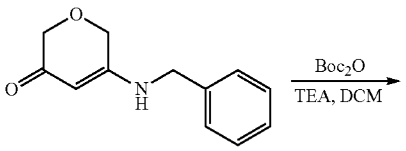

35

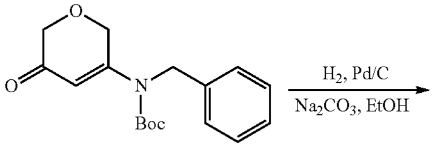

36

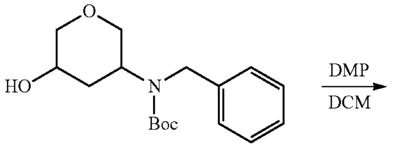

37

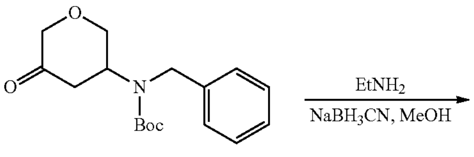

38

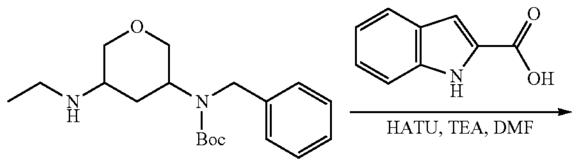

39

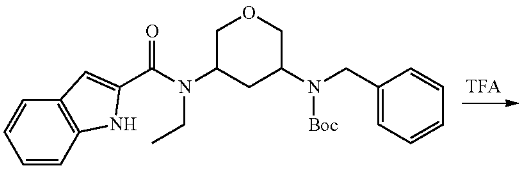

40

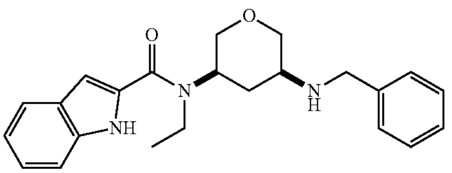

compound 300

-continued

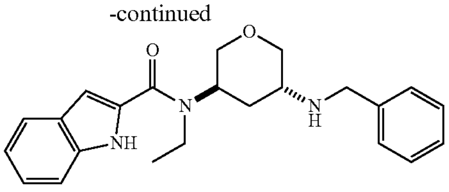

compound 301

General procedure for preparation of compound 35: To compound 34 (200 mg, 1.8 mmol, 1.0 eq) was added benzylamine (169 mg, 1.6 mmol, 0.9 eq) in 2 mL of dichloromethane and MeOH (200 μL) in one portion at 25° C. under $N_2$. The mixture was stirred at 25° C. for 5 hours. The reaction was monitored by TLC and allowed to run until complete. The reaction mixture was concentrated under reduced pressure to remove solvent to afford 350 mg of the crude product 3-(benzylamino)-2H-pyran-5-one 35 as yellow oil.

General procedure for preparation of compound 36: To a mixture of compound 35 (350 mg, 1.7 mmol, 1.0 eq) and $Boc_2O$ (564 mg, 2.6 mmol, 1.5 eq) in 5 mL of dichloromethane was added DMAP (21 mg, 172 μmol, 0.1 eq), $Et_3N$ (348 mg, 3.4 mmol, 2.0 eq) in one portion at 25° C. under $N_2$. The mixture was stirred at 25° C. for 2 hours. The reaction was monitored by TLC and allowed to run until complete. The reaction mixture was concentrated under reduced pressure to remove solvent. The residue was purified by prep-TLC ($SiO_2$, petroleum ether:ethyl acetate=3:1) to afford 250 mg of desired compound 36 (48% yield) as yellow oil.

General procedure for preparation of compound 37: To a solution of compound 36 (250 mg, 824 μmol, 1.0 eq) in 10 mL of ethanol was added $Na_2CO_3$ (87 mg, 824 μmol, 1.0 eq), Pd/C (200 mg, 10% purity) under $N_2$. The suspension was degassed under vacuum and purged with $H_2$ several times. The mixture was stirred under $H_2$ (45 psi) at 50° C. for 16 hours. The reaction was monitored by LCMS and allowed to run until complete. The reaction mixture was quenched with 10 ml of water and extracted with three 20 ml portions of dichloromethane. The combined organic layers were washed twice with 15 ml of brine, dried over $Na_2SO_4$, filtered and concentrated under reduced pressure to afford 230 mg of the desired crude compound 37 as colorless oil.

General procedure for preparation of compound 38: To a mixture of compound 37 (230 mg, 748 μmol, 1.0 eq) in 3 mL of dichloromethane was added (1,1-diacetoxy-3-oxo-1,2-benziodoxol-1-yl) acetate (317 mg, 748 μmol, 1.0 eq) in one portion at 0° C. under $N_2$. The mixture was stirred at 0° C. for 30 min, then heated to 25° C. and stirred for 3 hours. The reaction was monitored by LCMS and allowed to run until complete. The reaction mixture was quenched with 10 ml of aqueous $Na_2SO_3$ and then diluted with 5 mL of aqueous $NaHCO_3$ and extracted with three 5 ml portions of dichloromethane. The combined organic layers were washed twice with 10 ml of brine, dried over $Na_2SO_4$, filtered and concentrated under reduced pressure to give a residue. The residue was purified by prep-TLC ($SiO_2$, petroleum ether: ethyl acetate=1:1) to afford 160 mg of compound 38 (70% yield) as yellow oil.

General procedure for preparation of compound 39: To a mixture of compound 38 (65 mg, 213 μmol, 1.0 eq) and ethanamine (9.6 mg, 213 μmol, 1.0 eq) in 1 mL of methanol was added $NaBH_3CN$ (13.4 mg, 213 μmol, 1.0 eq) and acetic acid (1.3 mg, 21.3 μmol, 0.1 eq) in one portion at 25° C. under $N_2$. The mixture was stirred at 25° C. for 1 hour. The reaction was monitored by LCMS and allowed to run until complete. The reaction mixture was quenched with 2 ml of water and extracted with three 5 ml portions of dichloromethane. The combined organic layers were washed twice with 5 ml of brine, dried over $Na_2SO_4$, filtered and concentrated under reduced pressure to give a residue. The residue was purified by prep-TLC ($SiO_2$, petroleum ether:ethyl acetate=1:1) to afford 40 mg of compound 39 (56% yield) as light yellow oil.

General procedure for preparation of compound 40: To a mixture of 1H-indole-2-carboxylic acid (15 mg, 93 μmol, 1.0 eq) and compound 39 (28 mg, 84 μmol, 0.9 eq) in 1 mL of DMF was added HATU (39 mg, 102 μmol, 1.1 eq), $Et_3N$ (14. mg, 140 μmol, 1.5 eq) in one portion at 25° C. under $N_2$. The mixture was stirred at 40° C. for 16 hours. The reaction was monitored by LCMS and allowed to run until complete. The reaction mixture was quenched with 5 ml of water and extracted with three 5 ml portions of dichloromethane. The combined organic layers were washed twice with 5 ml of brine, dried over $Na_2SO_4$, filtered and concentrated under reduced pressure to afford 40 mg of compound 40 (90% yield) as white solid.

General procedure for preparation of compounds 300 and 301: To a mixture of compound 40 (40 mg, 84 μmol, 1.0 eq) in 2 mL of dichloromethane was added TFA (308 mg, 2.7 mmol, 200 μL, 32.3 eq) in one portion at 25° C. under $N_2$. The mixture was stirred at 25° C. for 0.5 hours. The reaction was monitored by LCMS and allowed to run until complete. The reaction mixture was quenched with 3 mL of aqueous $NaHCO_3$ and extracted with three 5 ml portions of dichloromethane. The combined organic layers were washed twice with 5 ml of brine, dried over $Na_2SO_4$, filtered and concentrated under reduced pressure to give a residue. The residue was purified by prep-HPLC (neutral condition) to afford 6.9 mg of compound 300 (19.4% yield) as white solid and 3.0 mg of compound 301 (9.3% yield,) as white solid.

Compound 300

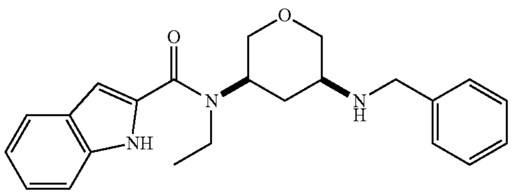

$^1$H NMR (400 MHz, CHLOROFORM-d) δ ppm 9.38 (br s, 1H), 7.64 (d, J=8.2 Hz, 1H), 7.41 (d, J=8.2 Hz, 1H), 7.35-7.32 (m, 1H), 7.31 (s, 2H), 7.30-7.23 (m, 3H), 7.15-7.10 (m, 1H), 6.78 (s, 1H), 4.07 (ddd, J=1.8, 4.2, 10.8 Hz, 1H), 3.99 (br d, J=7.3 Hz, 1H), 3.83 (d, J=4.0 Hz, 2H), 3.63 (br s, 2H), 3.54-3.46 (m, 1H), 3.09-3.01 (m, 1H), 2.98-2.89 (m, 1H), 2.29 (br d, J=11.7 Hz, 1H), 1.81-1.71 (m, 1H), 1.52 (br s, 2H), 1.32 (br s, 3H)

LCMS (ESI+): m/z 378.3 (M+H)

Compound 301

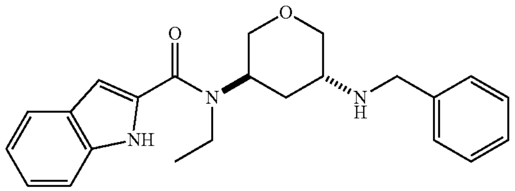

$^1$H NMR (400 MHz, CHLOROFORM-d) δ ppm 9.22 (br s, 1H), 7.55 (d, J=8.2 Hz, 1H), 7.36-7.33 (m, 1H), 7.29-7.25 (m, 2H), 7.25-7.20 (m, 3H), 7.20-7.17 (m, 2H), 7.09-7.03 (m, 1H), 3.95 (br dd, J=3.9, 10.7 Hz, 1H), 3.84 (s, 1H), 3.82-3.79 (m, 3H), 3.57 (br s, 3H), 3.46 (dd, J=1.8, 11.9 Hz, 1H), 2.95 (br s, 1H), 2.10 (br s, 2H), 1.31-1.23 (m, 3H)

LCMS (ESI+): m/z 378.3 (M+H)

The following compounds were prepared analogously.

Compound 302

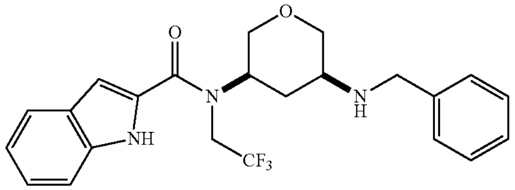

$^1$H NMR (400 MHz, CHLOROFORM-d) δ ppm 9.26 (br s, 1H), 7.66 (d, J=8.2 Hz, 1H), 7.41 (d, J=8.4 Hz, 1H), 7.34-7.27 (m, 5H), 7.25 (s, 1H), 7.17-7.12 (m, 1H), 6.86 (d, J=1.8 Hz, 1H), 4.63 (br s, 1H), 4.47-4.37 (m, 1H), 4.07 (br dd, J=2.6, 10.8 Hz, 3H), 3.82 (d, J=4.0 Hz, 2H), 3.54-3.45 (m, 1H), 3.10-3.02 (m, 1H), 2.97-2.87 (m, 1H), 2.29 (br d, J=11.7 Hz, 1H), 1.76 (q, J=11.4 Hz, 1H)

LCMS (ESI+): m/z 432.2 (M+H)

Compound 303

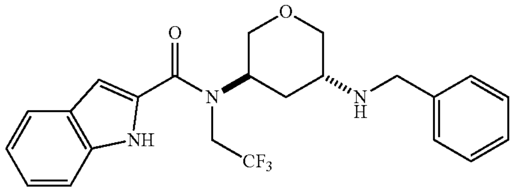

$^1$H NMR (400 MHz, CHLOROFORM-d) δ ppm 9.14 (br s, 1H), 7.56 (d, J=8.2 Hz, 1H), 7.37-7.33 (m, 1H), 7.27-7.25 (m, 1H), 7.24-7.21 (m, 2H), 7.19 (s, 2H), 7.18-7.16 (m, 2H), 7.11-7.06 (m, 1H), 4.33-4.21 (m, 1H), 4.15-4.06 (m, 1H), 4.00 (br dd, J=3.0, 12.0 Hz, 2H), 3.81 (d, J=2.4 Hz, 1H), 3.80-3.75 (m, 3H), 3.65-3.57 (m, 1H), 3.48 (dd, J=2.1, 12.0 Hz, 1H), 2.98 (br s, 1H), 2.14-2.04 (m, 2H)

LCMS (ESI+): m/z 432.0 (M+H)

Example 10: Synthesis of N-ethyl-N-((1S,3R)-3-((3-(4-ethynylbenzoyl)benzyl)-amino)cyclohexyl)-1H-indole-2-carboxamide (Compound 312)
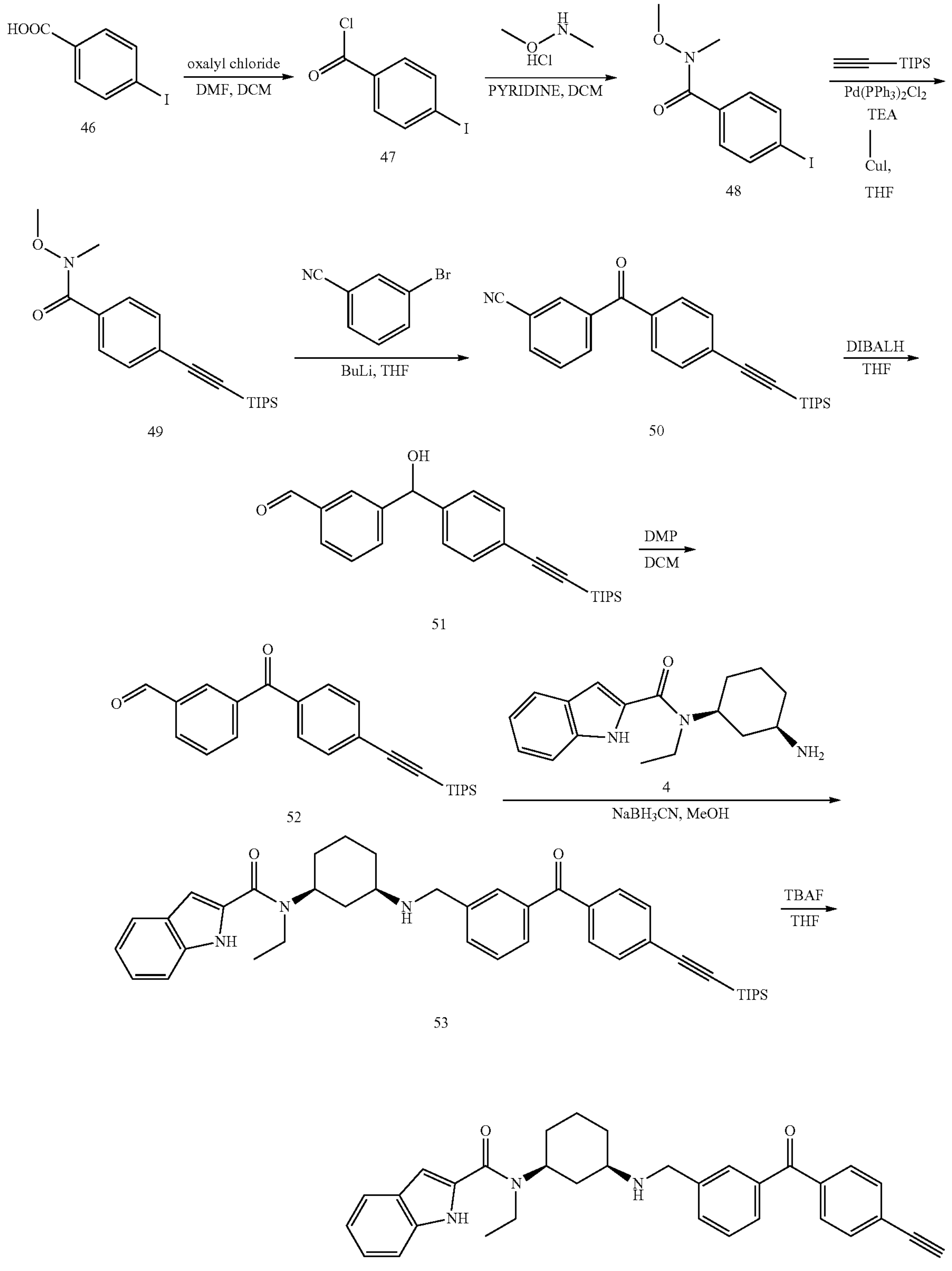
46 47 48 49 50 51 52 4 53
compound 312

General procedure for preparation of compound 47: To compound 48 (2.8 g, 11.3 mmol, 1.0 eq) in 40 mL of dichloromethane was added oxalyl dichloride (5.7 g, 45.2 mmol, 4.0 eq) and DMF (83 mg, 1.1 mmol, 0.1 eq). The mixture was stirred at 19° C. for 0.2 hour. The mixture was concentrated under reduced pressure to give 3.0 g of acid chloride 47 as a crude white solid.

General procedure for preparation of compound 48: To compound 47 (1.1 g, 11.3 mmol, 1.0 eq) in pyridine (17.8 g, 225 mmol, 20.0 eq) was added 4-iodobenzoyl chloride (3.0 g, 11.3 mmol, 1.0 eq) in 20 mL of dichloromethane. The mixture was stirred at 18° C. for 0.5 hour. The reaction was monitored by TLC and allowed to run until complete. The mixture was poured into 20 mL of water and then extracted twice with 25 mL portions of EtOAc. The combined organic layers were concentrated in vacuo to give a residue. The residue was purified by silica gel chromatography (petroleum ether:ethyl acetate=3:1 to 1:1) to give 2.8 g of compound 48 as a yellow oil.

General procedure for preparation of compound 49: To compound 48 (2.5 g, 8.6 mmol, 1.0 eq) and ethynyl(triisopropyl)silane (3.1 g, 17.2 mmol, 2.0 eq) in 20 mL of THF was added TEA (2.6 g, 25.8 mmol, 3.0 eq), $Pd(PPh_3)_2Cl_2$ (603 mg, 859 μmol, 0.1 eq) and CuI (164 mg, 859 μmol, 0.1 eq). The mixture was stirred at 55° C. for 12 hours under $N_2$. The reaction was monitored by TLC and allowed to run until complete. The mixture was poured into 20 mL of water, and then extracted with three 20 mL portions of ethyl acetate. The combined organic layers were concentrated to give a residue. The residue was purified by silica gel chromatography (silica gel, petroleum ether:ethyl acetate=3:1 to 1:1) to give 2.8 g of compound 49 as a crude yellow oil.

General procedure for preparation of compound 50: To 3-bromobenzonitrile (1.8 g, 9.8 mmol, 1.3 eq) and compound 49 (2.6 g, 7.5 mmol, 1.0 eq) in THF (30 mL) was added n-BuLi (2.5 M, 3.5 mL, 1.15 eq) at −78° C. under $N_2$. The mixture was stirred at −78° C. for 0.2 hour. The reaction was monitored by TLC and allowed to run until complete. The mixture was poured into 20 mL of water, and then extracted with three 20 mL portions of ethyl acetate. The organic layers were combined and concentrated to give a residue. The residue was purified by silica gel chromatography (100-200 mesh silica gel, petroleum ether:ethyl acetate=5:1 to 3:1) to give 2.2 g of compound 50 as a crude yellow oil.

General procedure for preparation of compound 51: To compound 50 (100 mg, 258 μmol, 1.0 eq) in 4 mL of THF was added DiBAL-H (1M, 1.0 mL, 4.0 eq) at −70° C. After the addition, the reaction mixture was warmed to 0° C., and stirred at 0° C. for 2 hours. The reaction was monitored by TLC and allowed to run until complete. The mixture was poured into 5 mL of MeOH and acetic acid (2:1), and stirred for 5 mins. Then 10 mL of water was added to the mixture. The mixture was extracted twice with 10 mL of ethyl acetate. The organic layers were combined and concentrated under reduced pressure to give a residue. The residue was purified by prep-TLC (petroleum ether:ethyl acetate=3:1) to give 80 mg of compound 51 as a yellow oil.

General procedure for preparation of compound 52: To compound 51 (80 mg, 204 μmol, 1.0 eq) in 3 mL of dichloromethane was added DMP (104 mg, 244 μmol, 1.2 eq). The mixture was stirred at 15° C. for 0.5 hour. The reaction was monitored by TLC and allowed to run until complete. The mixture was concentrated to give a residue. The residue was purified by prep-TLC (petroleum ether: ethyl acetate=5:1) to give 55 mg of compound 52 as a yellow solid.

General procedure for preparation of compound 53: To amine intermediate 4 (20 mg, 70 μmol, 1.0 eq) and compound 52 (27.4 mg, 70.1 μmol, 1.0 eq) in 2 mL of methanol was added $NaBH_3CN$ (8.8 mg, 140 μmol, 2.0 eq). The mixture was stirred at 10° C. for 12 hours. The mixture was stirred at 25° C. for 12 hours. The reaction was monitored by TLC and allowed to run until complete. The mixture was concentrated to give a residue. The residue was purified by prep-TLC (dichloromethane:methanol=10:1) to give 23 mg of compound 53 as a yellow solid.

General procedure for preparation of compound 312: To compound 53 (23 mg, 35 μmol, 1.0 eq) in 2 mL of THF was added TBAF (1 M, 3.0 eq). The mixture was stirred at 15° C. for 0.2 hour. The reaction was monitored by TLC and allowed to run until complete. The mixture was concentrated to give a residue. The residue was purified by prep-HPLC (TFA condition). The eluent (30 mL) was adjusted to pH=7.5, and extracted twice with 20 mL of ethyl acetate. The combined organic layers were concentrated to give 6.7 mg of compound 312 (36% yield) as a white solid.

Compound 312

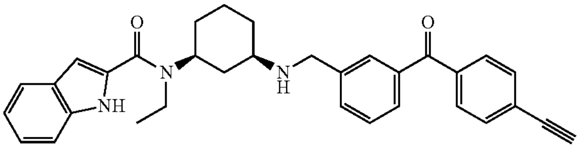

$^1H$ NMR (400 MHz, DMSO-$d_6$) δ ppm 11.49 (br s, 1H) 7.67-7.73 (m, 3H) 7.59-7.66 (m, 3H) 7.51-7.58 (m, 2H) 7.44-7.50 (m, 1H) 7.38 (d, J=8.16 Hz, 1H) 7.13 (t, J=7.61 Hz, 1H) 6.95-7.03 (m, 1H) 6.50-6.64 (m, 1H) 4.45 (s, 1H) 4.12-4.30 (m, 1H) 3.81 (br s, 2H) 3.46 (br s, 2H) 3.14 (s, 1H) 2.10-2.25 (m, 1H) 1.92-2.07 (m, 1H) 1.84 (br d, J=9.92 Hz, 1H) 1.64-1.77 (m, 2H) 1.49-1.64 (m, 1H) 1.37-1.48 (m, 1H) 1.11-1.31 (m, 6H)

LCMS (ESI+): m/z 504.2 (M+H)

Example 11: Synthesis of N-((3R,5S)-5-(benzylamino)-1,1-dioxidotetrahydro-2H-thiopyran-3-yl)-N-ethyl-1H-indole-2-carboxamide (Compound 313) and N-((3R,5R)-5-(benzylamino)-1,1-dioxidotetrahydro-2H-thiopyran-3-yl)-N-ethyl-1H-indole-2-carboxamide (Compound 314)

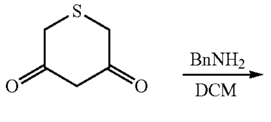

54

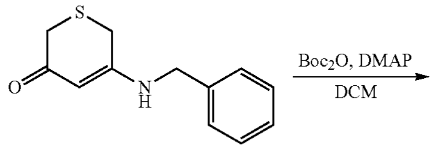

55

-continued

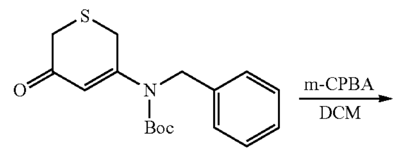

56

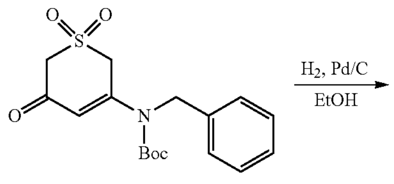

57

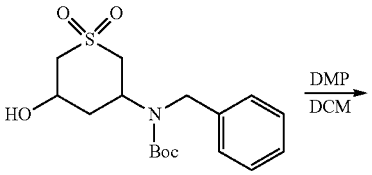

58

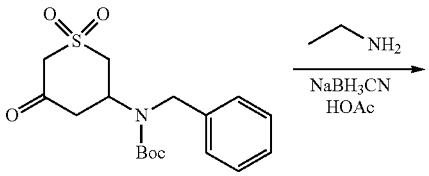

59

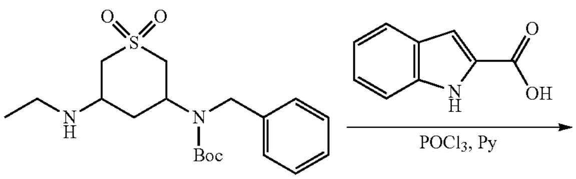

60

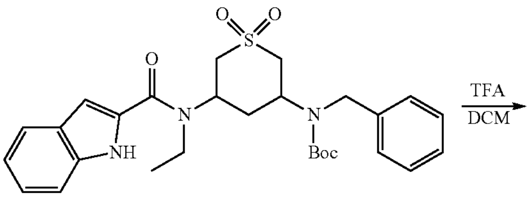

61

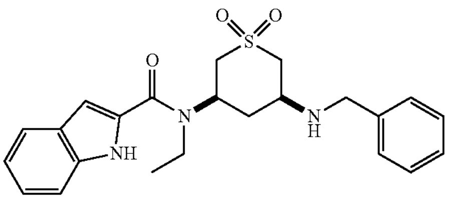

compound 313

-continued

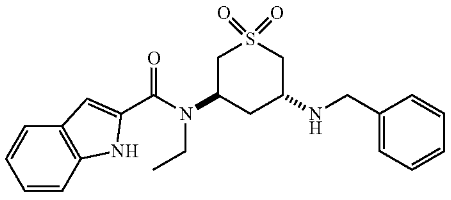

compound 314

General procedure for preparation of compound 55: A mixture of compound 54 (500 mg, 3.8 mmol, 1.0 eq), benzylamine (412 mg, 3.8 mmol, 1.0 eq) in 20 mL of dichloromethane was stirred at 25° C. for 1 hour under $N_2$ atmosphere. The reaction was monitored by TLC and allowed to run until complete. It was evaporated under reduced pressure to give the crude product which was purified by flash silica gel chromatography (ISCO©; 20 g SepaFlash© Silica Flash Column, eluent of 0-100% ethyl acetate:petroleum ether gradient @ 60 mL/min) to give 740 mg of compound 55 (88% yield) as brown foam.

General procedure for preparation of compound 56: A mixture of compound 55 (640 mg, 2.9 mmol, 1.0 eq), tert-butoxycarbonyl tert-butyl carbonate (955 mg, 4.4 mmol, 1.50 eq), TEA (591 mg, 5.8 mmol, 2.0 eq), DMAP (71.3 mg, 584 μmol, 0.2 eq) in 15 mL of dichloromethane was stirred at 25° C. for 12 hours. The reaction was monitored by TLC and allowed to run until complete. It was evaporated under reduced pressure to give the crude product, which was purified by flash silica gel chromatography (ISCO©; 20 g SepaFlash© Silica Flash Column, eluent of 0-20% ethyl acetate:petroleum ether gradient @ 60 mL/min) to give 440 mg of compound 56 (47% yield) as a brown gum.

General procedure for preparation of compound 57: A mixture of compound 56 (300 mg, 939 μmol, 1.0 eq) in 5 mL of dichloromethane was cooled to 0° C. m-CPBA (477 mg, 2.4 mmol, 85% purity, 2.5 eq) was added in portions, it was stirred for 1 hour at the temperature and then it was allowed to warm to 25° C. for another 1 hour. The reaction was monitored by TLC and allowed to run until complete. The reaction mixture was partitioned between 10 mL of saturated aqueous $Na_2SO_3$ and 15 mL of dichloromethane. The organic phase was separated, washed with 10 mL of saturated aqueous $NaHCO_3$ and 10 mL of brine, dried over $Na_2SO_4$, filtered and concentrated under reduced pressure to give 390 mg of crude compound 57 as yellow gum and to be used into the next step without further purification.

General procedure for preparation of compound 58: A mixture of compound 57 (300 mg, 854 μmol, 1.0 eq), Pd/C (900 mg, 50% purity) and $Na_2CO_3$ (91 mg, 854 μmol, 1.0 eq) in 15 mL of ethanol was degassed and purged with $H_2$ three times. The mixture was stirred at 25° C. for 12 hours under $H_2$ atmosphere (45 psi). The reaction was monitored by LCMS and TLC and allowed to run until complete. The mixture was filtered and the filtrate was evaporated under reduced pressure to give a residue which was partitioned between 10 mL of water and 15 mL of ethyl acetate. The organic phase was separated, washed with 10 mL of brine, dried over $Na_2SO_4$, filtered and concentrated under reduced pressure to give the crude product, which was purified by prep-TLC (petroleum ether:ethyl acetate=1:1) to give 170 mg of compound 58 (56% yield) as a white solid.

General procedure for preparation of compound 59: A mixture of compound 58 (120 mg, 338 μmol, 1.0 eq) in 6 mL of dichloromethane was added DMP (286 mg, 675 μmol, 2.0 eq) in two portions at 0° C. The mixture was stirred for 1 hour, then it was allowed to warm to 25° C. and stirred for another 1 hour under $N_2$ atmosphere. The reaction was monitored by TLC and allowed to run until complete. The reaction mixture was partitioned between 15 mL of saturated aqueous $Na_2SO_3$ and 15 mL of dichloromethane. The organic phase was separated, washed with 15 mL of saturated aqueous $NaHCO_3$ and 10 mL of brine, dried over $Na_2SO_4$, filtered and concentrated under reduced pressure to give the crude product which was purified by prep-TLC (petroleum ether:ethyl acetate=1:1) to give 120 mg of crude compound 59 as a colorless gum.

General procedure for preparation of compound 60: A mixture of compound 59 (100 mg, 283 μmol, 1.0 eq), ethanamine (38.3 mg, 849 μmol, 3.0 eq), acetic acid (17 mg, 283 μmol, 1.0 eq) in 3 mL of methanol was stirred for 0.5 hour. $NaBH_3CN$ (35.6 mg, 566 μmol, 2.0 eq) was added and the mixture was stirred at 25° C. for another 11.5 hours under $N_2$ atmosphere. The reaction was monitored by LCMS and allowed to run until complete. It was evaporated under reduced pressure to give a residue which was partitioned between 10 mL of 1N HCl and 10 mL of ethyl acetate. The aqueous layer was separated, extracted with two 10 mL portions of ethyl acetate. The combined organic layers were washed with 20 mL of saturated aqueous $NaHCO_3$ and 20 mL of brine, dried over $Na_2SO_4$, filtered and concentrated under reduced pressure to give 85 mg of crude compound 60 as a colorless gum and to be used into the next step without further purification.

General procedure for preparation of compound 61: To a mixture of compound 60 (50 mg, 131 μmol, 1.0 eq), 1H-indole-2-carboxylic acid (84.3 mg, 523 μmol, 4.0 eq) in 3 mL of pyridine was added $POCl_3$ (80 mg, 523 μmol, 4.0 eq) in portions (0.5 equivalents respectively per 20 min) at 25° C. under $N_2$ atmosphere. The reaction was monitored by LCMS and allowed to run until complete. The mixture was evaporated under reduced pressure and the residue was partitioned between 10 mL of saturated $NH_4Cl$ and 10 mL of ethyl acetate. The organic phase was separated, washed with 10 mL of brine, dried over $Na_2SO_4$, filtered and concentrated under reduced pressure to give 40 mg of crude compound 61 as brown gum to be used into the next step without further purification.

General procedure for preparation of compounds 313 and 314: To a mixture of crude compound 61 (50 mg, 95 μmol, 1.0 eq) in 4 mL of dichloromethane was added 1 mL of TFA. The mixture was stirred at 25° C. for 1 hour. The reaction was monitored by LCMS and allowed to run until complete. It was concentrated under reduced pressure to afford the crude product, which was purified by prep-HPLC (neutral condition) to afford 1.6 mg of compound 313 (3.7% yield) as a brown gum and 3.6 mg of compound 314 (8.9% yield) as a light yellow solid.

Compound 314

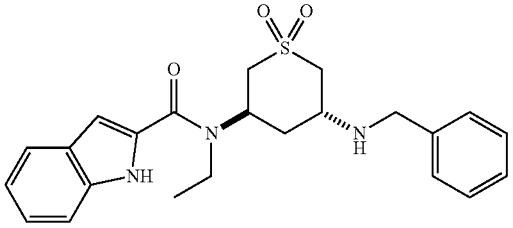

$^1$H NMR (400 MHz, DMSO-$d_6$) δ ppm 11.29 (br s, 1H) 7.50 (br d, J=8.33 Hz, 1H) 7.43 (d, J=8.33 Hz, 1H) 7.13-7.27 (m, 6H) 7.02 (t, J=7.45 Hz, 1H) 6.90 (s, 1H) 5.05-5.15 (m, 1H) 3.65-3.78 (m, 3H) 3.56 (br d, J=7.45 Hz, 2H) 3.41 (br s, 1H) 3.21-3.36 (m, 3H) 2.17-2.32 (m, 2H) 2.06 (br d, J=14.47 Hz, 1H) 1.22 (br t, J=7.02 Hz, 3H)

LCMS (ESI+): m/z 426.1 (M+H)

Compound 313

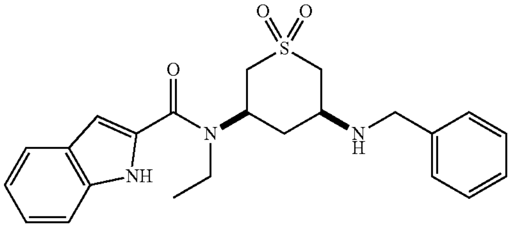

$^1$H NMR (400 MHz, CHLOROFORM-d) δ ppm 9.15 (br s, 1H) 7.67 (br d, J=8.33 Hz, 1H) 7.42 (brd, J=8.33 Hz, 1H) 7.27-7.37 (m, 6H) 7.11-7.17 (m, 1H) 6.84 (s, 1H) 3.82-3.88 (m, 2H) 3.75 (br s, 2H) 3.34-3.43 (m, 2H) 3.29 (br s, 1H) 3.16 (br d, J=10.09 Hz, 1H) 2.81 (br t, J=12.72 Hz, 1H) 2.28 (br s, 2H) 1.43 (br s, 4H)

LCMS (ESI+): m/z 426.1 (M+H)

Example 12. Synthesis of N-ethyl-N-((1S,3R)-3-((3-phenyloxetan-3-yl)amino)cyclohexyl)-1H-indole-2-carboxamide (Compound 318)

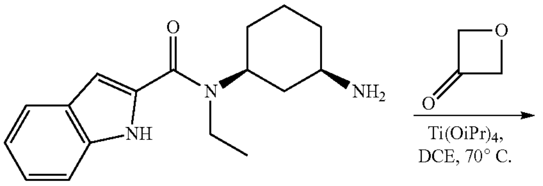

4

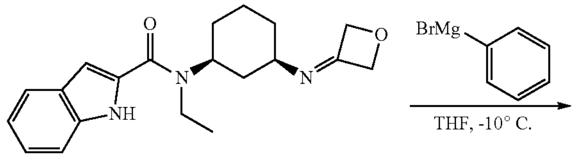

62

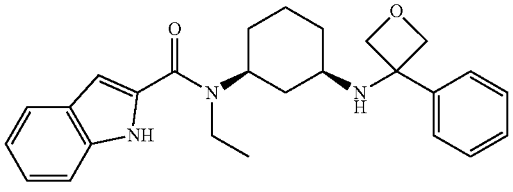

Compound 318

General procedure for preparation of compound 62: To a mixture of compound 4 (100 mg, 311 μmol, 1.0 eq, HCl salt) in 5 mL of 1, 1-dichloroethane was added TEA (63 mg, 621 μmol, 2.0 eq), then oxetan-3-one (67 mg, 932 μmol, 3.0 eq) and Ti(i-PrO)$_4$ (265 mg, 932 μmol, 3.0 eq). The mixture was stirred for 12 hours at 65° C. under $N_2$ atmosphere. The reaction was monitored by LCMS and allowed to run until complete. It was evaporated under reduced pressure to give 110 mg of crude compound 62 as a brown gum, which was used into the next step without further purification.

General procedure for preparation of compound 318: To a mixture of crude compound 62 (110 mg) in 4 mL of THF cooled to −10° C. under $N_2$ atmosphere was added bromo (phenyl)magnesium (3 M, 1.1 mL) dropwise, then the mixture was stirred at 11° C. for 1 hour. The reaction was monitored by LCMS and allowed to run until complete. The reaction mixture was partitioned between 10 mL of saturated aqueous $NH_4C_1$ and 10 mL of ethyl acetate. The organic phase was separated, washed with 10 mL of brine, dried over $Na_2SO_4$, filtered and concentrated under reduced pressure to give the crude product, which was purified by prep-HPLC (TFA condition) to give 11.1 mg of compound 318 (6.3% yield, TFA salt) as a white solid.

Compound 318

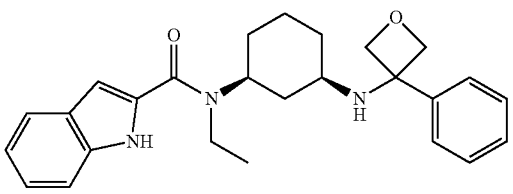

$^1$H NMR (400 MHz, CHLOROFORM-d) δ ppm 9.74 (br s, 1H) 7.40-7.65 (m, 7H) 7.26-7.31 (m, 1H) 7.13 (br t, J=7.50 Hz, 1H) 6.62-6.96 (m, 1H) 5.22-5.45 (m, 2H) 5.03 (br s, 2H) 3.98 (s, 1H) 3.57 (br s, 2H) 2.60 (br s, 1H) 2.01-2.20 (m, 1H) 1.51-1.96 (m, 7H) 1.29 (br s, 3H) 1.13 (br s, 1H)

LCMS (ESI+): m/z 418.2 (M+H)

Example 13. Synthesis of N-((1S,3R)-3-((3-azido-benzyl)amino)cyclohexyl)-N-ethyl-1H-indole-2-carboxamide (Compound 316)

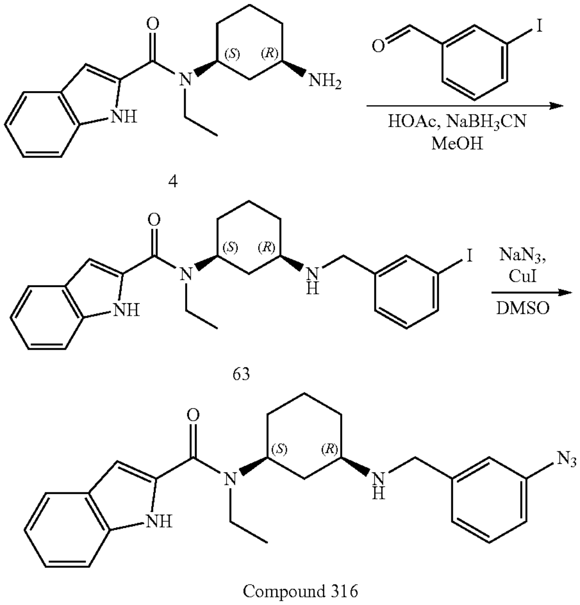

4

63

Compound 316

General procedure for preparation of compound 63: To a mixture of compound 4 (100 mg, 311 μmol, 1.0 eq, HCl) and 3-iodobenzaldehyde (72 mg, 311 μmol, 1.0 eq) in 2 mL of methanol was added acetic acid (1.9 mg, 31 μmol, 0.1 eq), triethylamine (3.1 mg, 31.1 μmol, 0.1 eq) in one portion at 20° C. under $N_2$. The mixture was stirred at 20° C. for 30 min, then $NaBH_3CN$ (19.5 mg, 310.7 μmol, 1.0 eq) was added. The mixture was stirred at 20° C. for 16 hours. The reaction was monitored by LCMS and allowed to run until complete. The reaction mixture was quenched by adding 5 mL water at 20° C., and extracted with three 5 ml portions of ethyl acetate. The combined organic layers were washed twice with 5 ml of brine, dried over $Na_2SO_4$, filtered and concentrated under reduced pressure to give a residue. The residue was purified by prep-TLC ($SiO_2$, petroleum ether: ethyl acetate=1:1) to afford 100 mg of compound 63 (64% yield) as light yellow solid.

General procedure for preparation of compound 316: To a mixture of compound 63 (80 mg, 160 μmol, 1.0 eq) and sodium azide (10.4 mg, 160 μmol, 1.0 eq) in 2 mL of DMSO was added CuI (6.1 mg, 32 μmol, 0.2 eq), N,N'-dimethyl-ethane-1,2-diamine (2.8 mg, 32 μmol, 0.2 eq), sodium (2R)-2-[(1S)-1,2-dihydroxyethyl]-4-hydroxy-5-oxo-2H-furan-3-olate (6.3 mg, 32 μmol, 0.2 eq) in one portion at 15° C. under $N_2$. The mixture was stirred at 15° C. for 10 min, then heated to 70° C. and stirred for 12 hours. The reaction was monitored by LCMS and allowed to run until complete. The reaction mixture was quenched by 2 mL NaClO at 15° C., and then diluted with 2 mL water and extracted with three 5 ml portions of ethyl acetate. The combined organic layers were washed twice with 5 ml of brine, dried over $Na_2SO_4$, filtered and concentrated under reduced pressure to give a residue. The residue was purified by prep-HPLC (TFA condition) to afford 7.2 mg of compound 316 (8.2% yield, TFA salt) as white solid.

$^1$H NMR (400 MHz, CHLOROFORM-d) δ ppm 10.15-9.75 (m, 2H), 7.54 (d, J=7.9 Hz, 1H), 7.32 (br d, J=8.2 Hz, 1H), 7.21-7.16 (m, 2H), 7.11-6.98 (m, 3H), 6.88 (br s, 1H), 6.71 (br s, 1H), 3.80 (br s, 2H), 3.55 (br s, 2H), 2.96 (br s, 1H), 2.21 (br s, 1H), 1.99 (br s, 1H), 1.88 (br d, J=10.8 Hz, 2H), 1.78 (br s, 2H), 1.26 (br s, 6H)

LCMS (ESI+): m/z 417.2 (M+H)

The following compound was prepared analogously:

Compound 317

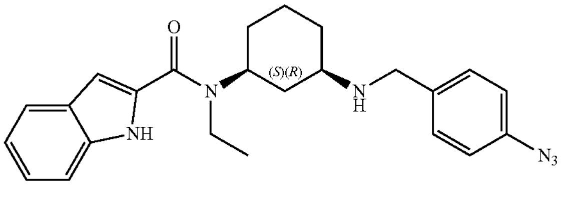

$^1$H NMR (400 MHz, CHLOROFORM-d) δ ppm 9.93 (br s, 1H), 9.69 (br s, 1H), 7.64 (br d, J=8.1 Hz, 1H), 7.40 (br d, J=8.3 Hz, 1H), 7.32-7.22 (m, 4H), 7.19-7.14 (m, 1H), 6.80 (br s, 2H), 3.89 (br s, 2H), 3.64 (br s, 2H), 3.07 (br s, 1H), 2.30 (br s, 1H), 2.15-1.79 (m, 5H), 1.35 (br s, 6H)

LCMS (ESI+): m/z 417.2 (M+H)

Example 14. Synthesis of N-((1S,3R)-3-(benzylamino)cyclohexyl)-N-ethyl-1H-benzo[d]imidazole-2-carboxamide (Compound 400)

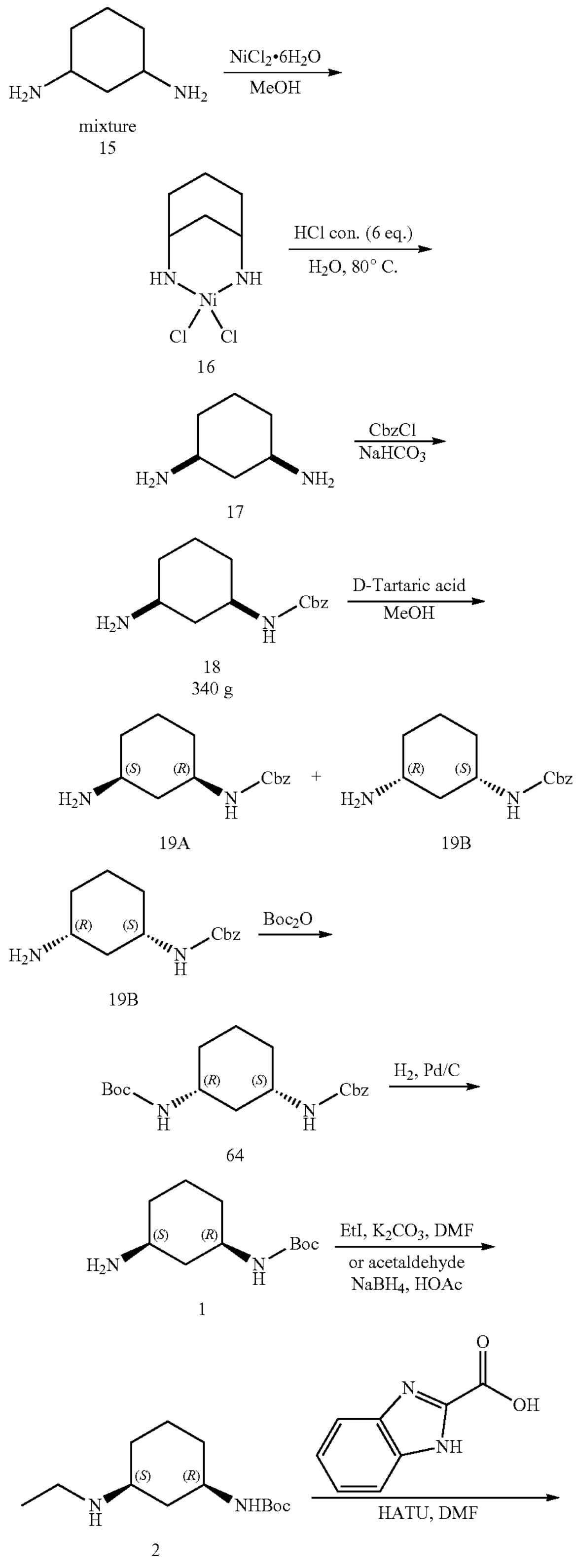

15, 16, 17, 18, 19A, 19B, 19B, 64, 1, 2

-continued

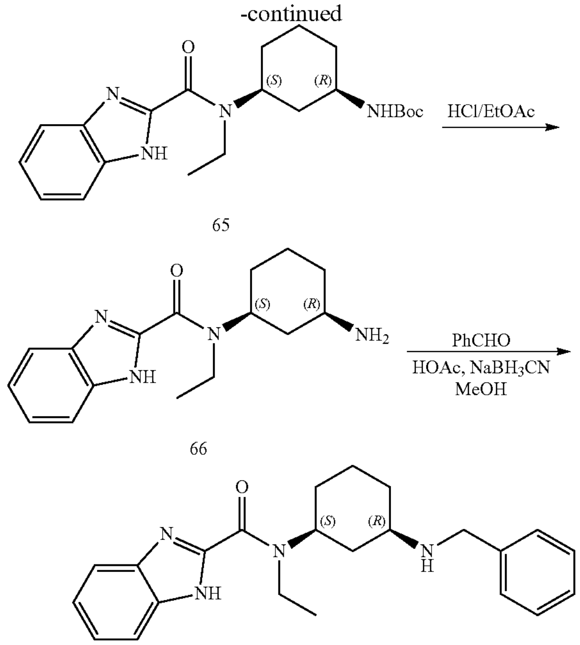

65, 66

Compound 400

General procedure for preparation of compound 16: To a mixture of diamine 15 (300 g, 2.6 mol, 1.0 eq) in 4 L of methanol was added $NiCl_2.6H_2O$ (625 g, 2.6 mol, 1.0 eq) in portions. The reaction mixture was stirred at 15° C. for 16 hours. The reaction mixture was filtered to give a residue. The residue was washed with 1.5 L of methanol and filtered to get 700 g of compound 16 (crude) as green solid.

General procedure for preparation of compound 17: To the mixture of compound 16 (350 g, 1.5 mol, 1.0 eq) in 3 L of $H_2O$ was added 12 M HCl (156 mL, 3.0 eq) in one portion at 15° C. The reaction mixture was stirred at 80° C. for 12 hours. The reaction mixture was concentrated in vacuo to reduce $H_2O$, then 2 L of EtOH was added to produce solids. The solids were filtered to give 200 g of compound 17 as the dihydrochloride salt (1.1 mol, 36.9% yield,) as light pink solid.

General procedure for preparation of compound 18: To a solution of compound 16 (200 g, 1.1 mol, 1.0 eq, 2HCl salt) in 1.6 L of EtOH and 1 L of $H_2O$ was added $NaHCO_3$ (314.3 g, 3.7 mol, 145.5 mL, 3.5 eq). CbzCl (218.8 g, 1.3 mol, 182.3 mL, 1.2 eq) in 220 mL of dioxane was added dropwise for 0.5 h at 0° C. The mixture was stirred at 0° C. for 1.5 h. The reaction mixture was quenched by addition 2 L of HCl (2M) to make pH ~1 at 15° C., and then extracted twice with 1.2 L of EtOAc. To the aqueous layer was added NaOH solid to make pH ~13, and then the mixture was extracted four times with 8 L of dichloromethane. The combined organic layers were washed with 1 L of brine, dried over $Na_2SO_4$, filtered and concentrated under reduced pressure to give 250 g of compound 18 (crude) as white solid.

General procedure for preparation of compounds 19A and 19B: To a mixture of compound 18 (220.0 g, 886 mmol, 1.0 eq) in 3 L of methanol was added 2,3-dihydroxybutanedioic acid (63.8 g, 425.3 mmol, 0.5 eq) in one portion at 15° C. under $N_2$. The mixture was stirred at 15° C. for 30 min, then heated to 50° C. and stirred for 3.5 hours. The reaction mixture was cooled and filtered and the filter cake was washed twice with 4 L of methanol to give 120 g of compound (301 mmol, 34.0% yield, D-tartrate salt) as white solid. The resolution was monitored by SFC. Resolved amine salt 19B was used into the next step without further purification.

In addition, concentration of the mother liquors gave 200 g of crude compound 19A was obtained as light pink solid.

General procedure for preparation of compound 64: To a mixture of compound 19B (120 g, 483 mmol, 1.0 eq) in 2 L of dichloromethane was added $(Boc)_2O$ (105.5 g, 483 mmol, 111.0 mL, 1.0 eq) in one portion at 15° C. under $N_2$. The mixture was stirred at 15° C. for 12 hours. The reaction mixture was quenched by addition of 500 mL of $NH_4Cl$ at 15° C., and then diluted with 500 mL of $H_2O$ and extracted three times with 3 L of dichloromethane. The combined organic layers were washed twice with 1 L of brine, dried over $Na_2SO_4$, filtered and concentrated under reduced pressure to give 150 g of compound 64 (431 mmol, 89% yield) obtained as white solid.

General procedure for preparation of compound 1: To a solution of compound 64 (75.0 g, 215 mmol, 1.0 eq) in 2 L of EtOH was added Pd/C (40 g, 10% purity) under $N_2$. The suspension was degassed under vacuum and purged with $H_2$ several times. The mixture was stirred under $H_2$ (15 psi) at 15° C. for 2 hours. The reaction mixture was filtered and concentrated under reduced pressure to give 66 g of compound 1 (308 mmol, 72% yield) as an off white solid.

General procedure for preparation of compound 2: A mixture of compound 1 (5 g, 23.3 mmol, 1 eq) in 30 mL of DMF and 30 mL of $CH_3CN$ was cooled to 0° C. $K_2CO_3$ (6.5 g, 46.7 mmol, 2 eq) was added, followed by the addition of EtI (3.5 g, 22.2 mmol, 1.8 mL, 0.95 eq). The mixture was stirred at 15° C. for 4 hour under $N_2$ atmosphere. The reaction mixture was partitioned between 100 mL of water and 60 mL of EtOAc. The organic phase was separated, washed three times with 90 mL of water and 30 mL of brine, dried over $Na_2SO_4$, filtered and concentrated under reduced pressure to give 3 g of crude compound 2 as a white gum and to be used into the next step without further purification.

Alternate method for preparation of compound 2: To a mixture of compound 1 (500 mg, 2.3 mmol, 1.0 eq) and acetaldehyde (231 mg, 2.1 mmol, 293 µL, 0.9 eq) in 5 mL of $CHCl_3$ was added acetic acid (28.0 mg, 467 µmol, 27 µL, 0.2 eq) in one portion at 15° C. under $N_2$. The mixture was stirred at 15° C. for 30 min, then $NaBH_4$ (88.3 mg, 2.3 mmol, 1.0 eq) was added at 15° C. and the mixture stirred for 16 hours. The reaction mixture was quenched by addition 5 mL of 1M aqueous HCl (to pH=1) at 15° C. and extracted with 5 mL of EtOAc. The aqueous phase was treated with saturated $Na_2CO_3$ to pH=10, then extracted four times with 40 mL of dichloromethane. The combined organic layers were washed three times with 30 mL of brine, dried over $Na_2SO_4$, filtered, and concentrated under reduced pressure to give 400 mg of crude compound 2 as colorless oil.

General procedure for preparation of compound 65: To a solution of 1H-benzo[d]imidazole-2-carboxylic acid (161 mg, 990 µmol, 1.2 eq) in 2 mL of DMF was added HATU (377 mg, 990 µmol, 1.2 eq) and TEA (167 mg, 1.6 mmol, 229 µL, 2.0 eq). The mixture was stirred at 15° C. for 0.5 hour, then tert-butyl N-[(1R,3S)-3-(ethylamino)cyclohexyl] carbamate, compound 2, (200 mg, 825 µmol, 1.0 eq) was added and the resulting reaction mixture was stirred at 15° C. for additional 15.5 hours. The reaction mixture was partitioned between 5 mL of water and 5 mL of ethyl acetate. The organic phase was separated, washed twice with 10 mL of brine, dried over anhydrous $Na_2SO_4$, filtered and concentrated under reduced pressure to give an oil. The oil was purified by prep-TLC ($SiO_2$, eluting with petroleum ether: ethyl acetate=1:1) to give 150 mg of compound 65 (388 µmol, 47% yield) as a colorless gum.

General procedure for preparation of compound 66: A mixture of compound 65 (150 mg, 388 µmol, 1.0 eq) in 2 mL of HCl/EtOAc (4M) was stirred at 15° C. for 1 hour. The reaction mixture was concentrated under reduced pressure to give 180 mg of crude compound 66 (HCl salt) as a white solid.

General procedure for preparation of compound 400: To a solution of compound 66 (180 mg, 558 µmol, 1.0 eq, HCl salt) and benzaldehyde (59 mg, 558 µmol, 56.4 µL, 1.0 eq) in 2 mL of methanol was added acetic acid (3.4 mg, 5 µmol, 0.1 eq). The mixture was stirred at 15° C. for 0.5 hour. To this mixture was added $NaBH_3CN$ (42 mg, 669 µmol, 1.2 eq) and the resulting reaction mixture was stirred at 15° C. for an additional 15.5 hours. The mixture was filtered and the filtrate was purified by prep-HPLC (TFA condition) to give 55.4 mg of compound 400 (111 µmol, 20% yield, 98.4% purity, TFA salt) as a white solid.

Compound 400

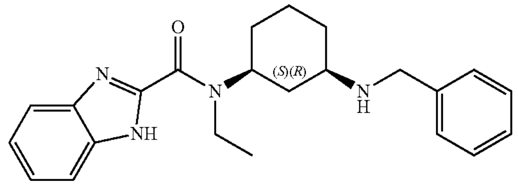

$^1H$ NMR (400 MHz, METHANOL-$d_4$) δ ppm 7.67 (s, 2H) 7.47-7.38 (m, 7H) 5.04 (s, 1H) 4.27-4.25 (m, 2H) 3.92-3.86 (m, 1H) 3.62-3.56 (m, 1H) 3.26 (s, 1H) 2.49-2.26 (m, 1H) 2.17-2.05 (m, 4H) 1.97-1.93 (m, 1H) 1.83-1.70 (m, 2H) 1.32-1.25 (d, J=26 Hz, 3H)

LCMS (ESI+): m/z 377.3 (M+H)

The following compounds were prepared analogously.

Compound 401

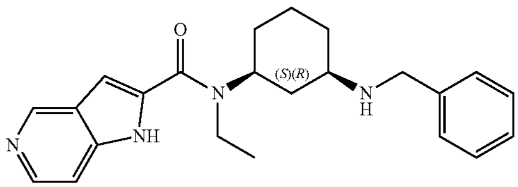

$^1H$ NMR (400 MHz, METHANOL-$d_4$) δ=9.27 (s, 1H), 8.44 (d, J=6.7 Hz, 1H), 7.99 (d, J=6.7 Hz, 1H), 7.55-7.45 (m, 5H), 7.38 (br s, 1H), 4.29 (s, 3H), 3.81-3.59 (m, 2H), 2.41 (br d, J=10.5 Hz, 1H), 2.25 (br s, 1H), 2.14-2.02 (m, 2H), 1.96 (br s, 2H), 1.61-1.41 (m, 2H), 1.37 (br t, J=6.8 Hz, 3H)

LCMS (ESI+): m/z 377.2 (M+H)

Compound 402

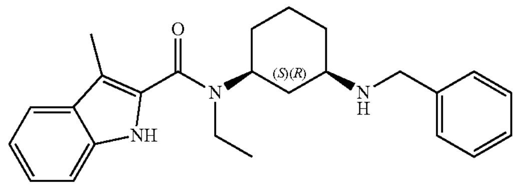

$^1H$ NMR (400 MHz, METHANOL-$d_4$) δ ppm 5.99 (d, J=7.9 Hz, 1H), 5.87 (br s, 5H), 5.80 (d, J=7.9 Hz, 1H), 5.63 (t, J=7.2 Hz, 1H), 5.54-5.49 (m, 1H), 2.65 (br s, 2H), 2.38 (br s, 1H), 2.06-1.85 (m, 2H), 1.76-1.72 (m, 3H), 1.56 (br s, 1H), 0.75 (s, 4H), 0.57 (br s, 1H), 0.47-0.35 (m, 2H), 0.27 (br s, 1H), −0.20 (br s, 2H), −0.34 (br s, 2H)

LCMS (ESI+): m/z 390.2 (M+H)

Compound 403

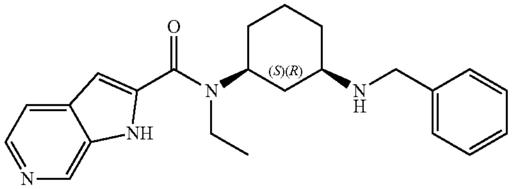

$^1H$ NMR (400 MHz, METHANOL-$d_4$) δ ppm 9.12 (s, 1H) 8.25 (dd, J=6, 31.6 Hz, 2H) 7.47 (d, J=19.2 Hz, 5H) 7.16 (d, J=32 Hz, 1H) 4.27 (s, 2H) 4.15-4.02 (m, 1H) 3.64-3.59 (m, 2H) 3.20 (s, 1H) 2.40 (d, J=9.6 Hz, 1H) 2.23-1.78 (m, 5H) 1.47-1.31 (m, 5H)

LCMS (ESI+): m/z 377.3 (M+H)

Compound 404

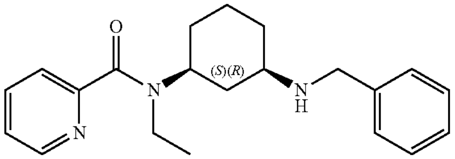

$^1H$ NMR (400 MHz, METHANOL-$d_4$) δ ppm 8.61 (s, 1H) 8.01-7.96 (m, 1H) 7.54-7.49 (m, 7H) 4.26 (d, J=27.2 Hz, 2H) 4.09-4.08 (m, 0.5H) 3.65-3.51 (m, 1.5H) 3.03-3.02 (m, 1H) 2.43-2.41 (m, 1H) 2.27-2.06 (m, 2H) 1.96-1.94 (m, 2H) 1.78-1.75 (m, 1H) 1.35-1.32 (m, 1H) 1.14-1.13 (m, 1H) 1.12-1.10 (m, 1H)

LCMS (ESI+): m/z 338.2 (M+H)

General Procedure for Preparation of Compound 405:

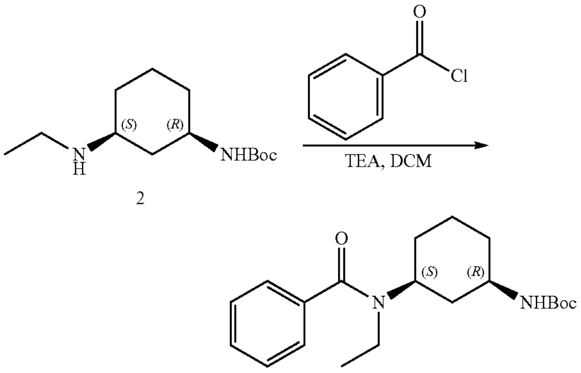

2

67

To a mixture of compound 2 (100 mg, 413 μmol, 1.0 eq), TEA (84 mg, 825 μmol, 114 μL, 2.0 eq) in 1 mL of dichloromethane was added benzoyl chloride (75 mg, 536 μmol, 1.3 eq) at 0° C., and then the mixture was stirred at 15° C. for 2 hours. The reaction mixture was diluted with 10 mL of $NH_4Cl$ and then extracted twice with 16 mL of dichloromethane. The combined organic layers were dried over $Na_2SO_4$, filtered and evaporated under reduced pressure to give a colorless oil which was purified by prep-TLC ($SiO_2$, eluting with petroleum ether:ethyl acetate=1:1) to give 95 mg of compound 11 (274 μmol, 67% yield) as a light yellow oil.

Compound 11 was deprotected and benzylated using the procedures described above to give:

Compound 405

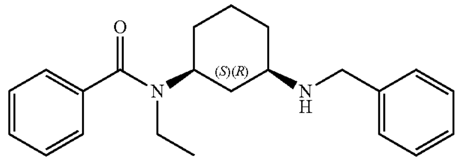

$^1H$ NMR (400 MHz, METHANOL-$d_4$) δ ppm 7.47 (t, J=3.2 Hz, 8H) 7.37-7.35 (m, 2H) 4.22 (s, 3H) 3.56-3.46 (m, 3H) 2.95 (s, 1H) 2.36-2.23 (m, 3H) 2.07-1.68 (m, 3H) 1.44-1.29 (m, 3H) 1.10 (s, 1H)

LCMS (ESI+): m/z 337.2 (M+H)

Example 15. Alternate Synthesis of N-((1S,3R)-3-(benzylamino)cyclohexyl)-N-ethyl-1H-benzo[d]imidazole-2-carboxamide (Compound 400)

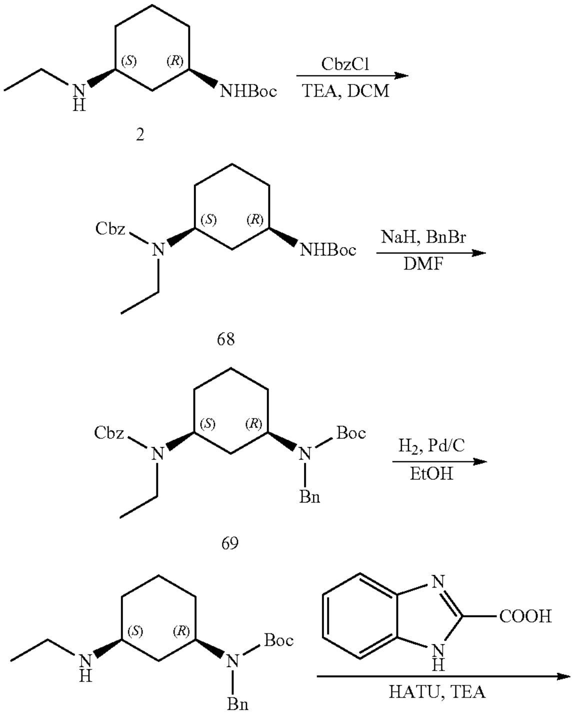

2

68

69

70

-continued

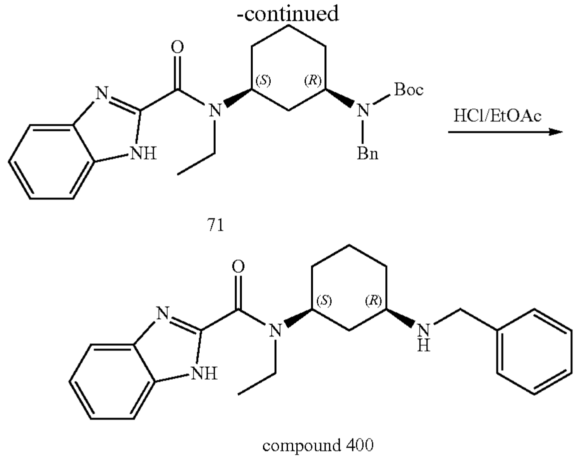

71 compound 400

General procedure for preparation of compound 68: To a solution of compound 2 (7.7 g, 32 mmol, 1 eq) in 150 mL of dichloromethane was added $Et_3N$ (9.6 g, 95 mmol, 13.2 mL, 3 eq) and CbzCl (6.5 g, 38 mmol, 5.4 mL, 1.2 eq) at 0° C. The mixture was stirred at 15° C. for 12 hours. The reaction mixture was concentrated under reduced pressure and the residue was purified by silica gel chromatography (column height: 250 mm, diameter: 100 mm, 100-200 mesh silica gel, eluting with a gradient of petroleum ether:ethyl acetate=30:1 to 5:1) to give 3.2 g of compound 68 (4.5 mmol, 14.3% yield, 53.3% purity) as colorless oil.

General procedure for preparation of compound 69: To a mixture of compound 68 (3.2 g, 8.5 mmol, 1 eq) in 40 mL of DMF cooled to 0° C. was added NaH (1.7 g, 42.5 mmol, 60% purity, 5 eq) in portions and the mixture was stirred for 0.5 hour at 15° C. Benzyl bromide (2.9 g, 17.0 mmol, 2.0 mL, 2 eq) was added slowly, then the mixture was stirred at 15° C. for another 1.5 hours under $N_2$ atmosphere. The reaction mixture was partitioned between 50 mL of water and 50 mL of EtOAc. The organic phase was separated, washed four times with 100 mL of water and 30 mL of brine, dried over $Na_2SO_4$, filtered and concentrated under reduced pressure to give a residue which was purified by column chromatography ($SiO_2$, eluting with a gradient of petroleum ether:ethyl acetate=15:1 to 5:1) to give 3.4 g of compound 69 (7.3 mmol, 86% yield) as a colorless gum.

General procedure for preparation of compound 70: A mixture of compound 69 (3.4 g, 7.3 mmol, 1 eq), 10% Pd/C (6 g) and $NH_3.H_2O$ (1.8 g, 13 mmol, 2 mL, 25% purity) in 50 mL of EtOH was degassed and purged with $H_2$ 3 times. The mixture was stirred at 15° C. for 2 hour under $H_2$ atmosphere (15 psi). The mixture was filtered, the filtrate was evaporated under reduced pressure to give 1.8 g of crude compound 70 as an off-white gum and to be used into the next step without further purification.

General procedure for preparation of compound 71: A mixture of compound 70 (0.7 g, 2.1 mmol, 1 eq), 1H-benzimidazole-2-carboxylic acid (358 mg, 2.2 mmol, 1.1 eq), HATU (881 mg, 2.3 mmol, 1.1 eq), TEA (426 mg, 4.2 mmol, 586 μL, 2 eq) in 10 mL of DMF was degassed and purged with $N_2$ 3 times, and then the mixture was stirred at 15° C. for 12 hours under $N_2$ atmosphere. The reaction mixture was partitioned between 20 mL of water and 20 mL of EtOAc. The organic phase was separated, washed three times with 45 mL of water and 15 mL of brine, dried over $Na_2SO_4$, filtered and concentrated under reduced pressure to give a residue which was purified by flash silica gel chromatography (ISCO®; 20 g SepaFlash® Silica Flash Column, Eluent of 0~20% ethyl acetate/petroleum ether gradient @ 60 mL/min) to give 0.37 g of compound 71 (745 μmol, 35% yield, 95.9% purity) as a white solid.

General procedure for alternate preparation of compound 400: A mixture of compound 71 (0.5 g, 1.1 mmol, 1 eq) in 15 mL of HCl/EtOAc (4 M) was stirred at 15° C. for 0.5 hour under $N_2$ atmosphere. The mixture was evaporated under reduced pressure to give 446 mg of compound 400 (1.0 mmol, 94% yield, 95.2% purity, HCl salt) as a light yellow solid.

Compound 400

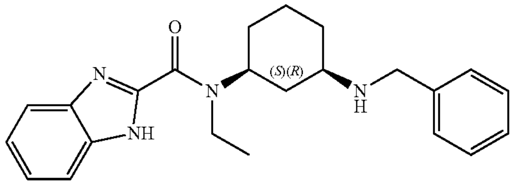

$^1H$ NMR (400 MHz, METHANOL-$d_4$) δ ppm 7.83-7.89 (m, 2H) 7.60-7.69 (m, 2H) 7.54 (br s, 2H) 7.45 (br s, 3H) 4.28 (br s, 2H) 4.07 (br s, 1H) 3.60 (br d, J=5.95 Hz, 2H) 3.31-3.42 (m, 1H) 2.52 (br s, 1H) 1.73-2.31 (m, 5H) 1.22-1.55 (m, 5H)

LCMS (ESI+): m/z 377.2 (M+H)

Example 16. Second Alternate Synthesis of N-((1S, 3R)-3-(benzylamino)cyclohexyl)-N-ethyl-1H-benzo[d]imidazole-2-carboxamide (Compound 400)

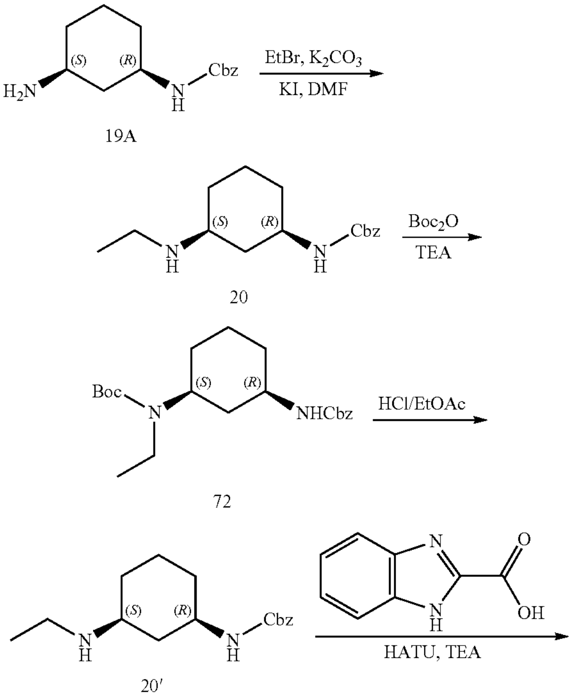

19A

20

72

20'

-continued

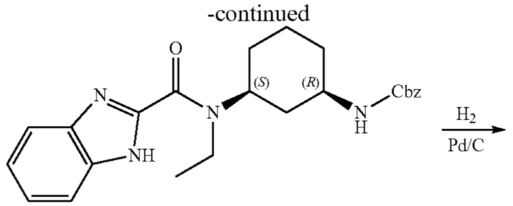

73

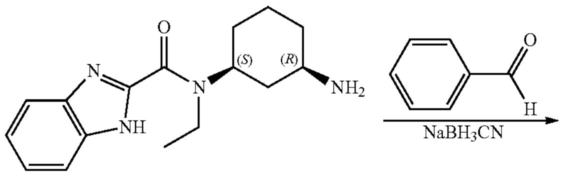

66

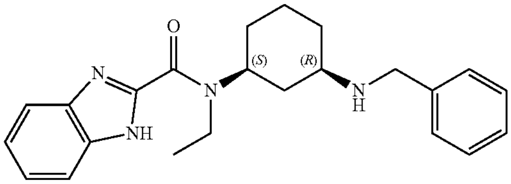

Compound 400

General procedure for preparation of compound 20: To a solution of compound 19A (100 g, 251 mmol, 1.0 eq, L-tartrate) in 1 L of DMF was added $K_2CO_3$ (104 g, 753 mmol, 3.0 eq) at 25° C. After the addition, the mixture was stirred at this temperature for 15 min, and then bromoethane (30.1 g, 276 mmol, 1.1 eq), and KI (4.2 g, 25 mmol, 0.1 eq) was added at 25° C. The resulting mixture was stirred at 25° C. for 12 hours. The reaction mixture was diluted with 1 L of water and extracted with three 500 mL portions of ethyl acetate. The combined organic layers were washed with twice with 500 mL of brine, dried over $Na_2SO_4$, filtered and concentrated under reduced pressure to afford the crude compound 20 (70 g, crude) as light pink solid which was used into the next step without further purification.

General procedure for preparation of compound 72: To a solution of compound 20 (70 g, 253 mmol, 1.0 eq) in 1 L of dichloromethane was added $Boc_2O$ (82.9 g, 380 mmol, 1.5 eq) at 25° C. After addition, $Et_3N$ (38.4 g, 380 mmol, 1.5 eq) was added at 25° C. The resulting mixture was stirred at 25° C. for 12 hours. The reaction mixture was quenched by addition 500 mL of 1N HCl at 25° C., and then diluted with 200 mL of water and extracted with three 500 mL portions of ethyl acetate. The combined organic layers were washed with three with 300 mL of brine, dried over $Na_2SO_4$, filtered and concentrated under reduced pressure to give a residue. The residue was purified by column chromatography ($SiO_2$, eluting with a gradient of petroleum ether:ethyl acetate=20:1 to 3:1) to afford 70 g of compound 72, 73% yield as colorless oil.

General procedure for preparation of compound 20': A mixture of compound 72 (15 g, 39.8 mmol, 1.0 eq) in 200 mL of HCl/ethyl acetate (4M) was stirred at 28° C. for 0.5 hour under $N_2$ atmosphere. The mixture was evaporated under reduced pressure to afford 10.7 g of compound 20' as HCl salt, 85.9% yield obtained as a white solid. The two-step process of converting to the N-Boc analog and deprotection was useful for purification of compound 20. The resulting product was pure enough to be used directly into the next step any additional purification.

General procedure for preparation of compound 73: To a solution of compound 20' (13 g, 42 mmol, 1.0 eq, HCl), 1H-benzimidazole-2-carboxylic acid (10.1 g, 62 mmol, 1.5 eq) in 100 mL of DMF was added $Et_3N$ (12.6 g, 125 mmol, 3 eq) at 28° C. After addition, HATU (23.7 g, 62.3 mmol, 1.5 eq) in 100 mL of DMF was added dropwise at 0° C. The resulting mixture was stirred at 28° C. for 12 hours. The reaction mixture was quenched by addition 200 mL of water and the mixture was extracted with three 200 mL portions of ethyl acetate. The combined organic layers were washed with twice with 200 mL of brine, dried over $Na_2SO_4$, filtered and concentrated under reduced pressure to give a residue. The residue was purified by column chromatography ($SiO_2$, eluting with a gradient of petroleum ether:ethyl acetate=20:1 to 1:1) to afford 16 g of compound 73 (92% yield) as a yellow oil.

General procedure for preparation of compound 66: To a solution of compound 73 (15 g, 36 mmol, 1.0 eq) in 200 mL of ethyl alcohol was added $Pd(OH)_2$ (6.7 g, 9.6 mmol, 20% purity, 0.27 eq) and $NH_3.H_2O$ (10.2 g, 72.7 mmol, 25% purity, 2.0 eq) under $N_2$. The suspension was degassed under vacuum and purged with $H_2$ several times. The mixture was stirred under $H_2$ (50 psi) at 20° C. for 3 hours. The reaction mixture was filtered and mother liquor was concentrated under reduced pressure to afford 10.2 g of crude compound 66 as a light yellow solid which was used into the next step without further purification.

General procedure for preparation of compound 400: To a solution of compound 66 (10 g, 35 mmol, 1.0 eq), benzaldehyde (3.5 g, 33 mmol, 0.95 eq) in 70 mL of dichloroethane and 35 mL of methyl alcohol was added acetic acid (210 mg, 3.5 mmol, 0.1 eq) at 20° C. After addition, the mixture was stirred at this temperature for 30 min, and then $NaBH_3CN$ (2.4 g, 38 mmol, 1.1 eq) was added at 0° C. The resulting mixture was stirred at 20° C. for 4 hours. The reaction mixture was quenched by addition 100 mL of water at 20° C., and then extracted with three 100 mL portions of ethyl acetate. The combined organic layers were washed with twice with 100 mL of brine, dried over $Na_2SO_4$, filtered and concentrated under reduced pressure to give a residue. The residue was purified by flash silica gel chromatography (ISCO®; 220 g SepaFlash® Silica Flash Column, eluting with a gradient of 0~100% ethyl acetate in petroleum ether @ 60 mL/min) to afford 8.4 g of compound 400.

Compound 400

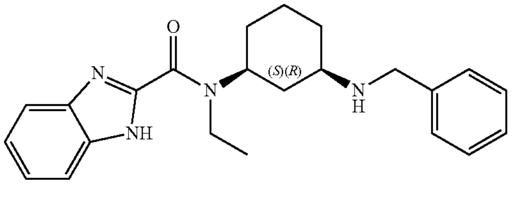

Example 17. Synthesis of N-((1S,3R)-3-((3-azidobenzyl)amino)cyclohexyl)-N-ethyl-1H-pyrrolo[3,2-b]pyridine-2-carboxamide (Compound 406)

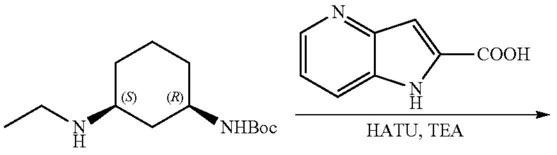

2

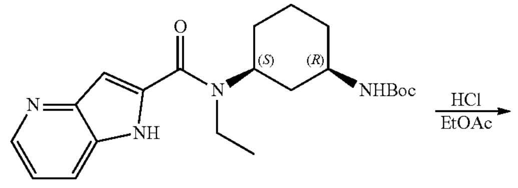

74

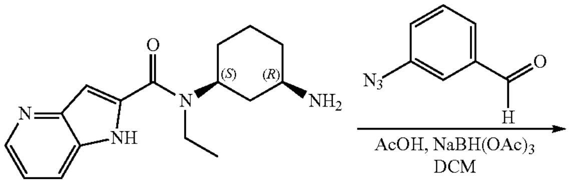

75

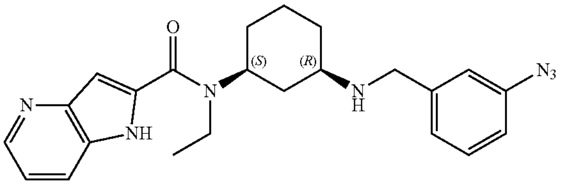

Compound 406

General procedure for preparation of compound 74: To a mixture of 1H-pyrrolo[3,2-b]pyridine-2-carboxylic acid (1.35 g, 8.3 mmol, 1.0 eq) and HATU (3.2 g, 8.3 mmol, 1.0 eq) in 10 mL of DMF was added TEA (1.3 g, 12.5 mmol, 1.7 mL, 1.5 eq) in one portion at 15° C. The mixture was stirred at 15° C. for 30 min, then amine 2 (2.0 g, 8.3 mmol, 1.0 eq) was added and the mixture was stirred at 15° C. for 12 hours. The reaction mixture was quenched by addition 20 mL of water, then extracted three times with 30 mL of EtOAc. The combined organic phases were washed three times with 30 mL of brine, dried over $Na_2SO_4$, filtered and concentrated under reduced pressure to give a residue, which was purified by column chromatography ($SiO_2$, eluting with a gradient of petroleum ether:ethyl acetate=15:1 to 0:1) to give 0.7 g of amide 74 (22% yield) as a light yellow solid.

General procedure for preparation of compound 75: A mixture of compound 74 (0.7 g, 1.8 mmol, 1.0 eq) in 10 mL of HCl/EtOAc (4 M) was stirred at 15° C. for 0.5 hour. The mixture was evaporated under reduced pressure to give 0.5 g of compound 75 (86% yield, HCl salt) as a white solid.

General Procedure for Preparation of 3-Azidobenzaldehyde:

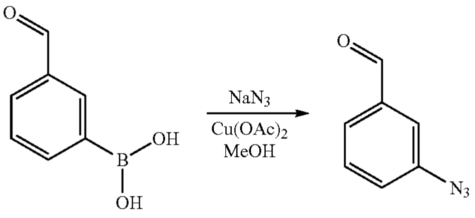 [SMILES: O=Cc1cccc(B(O)O)c1 ; [N-]=[N+]=Nc1cccc(C=O)c1 ; "NaN3"]

To a mixture of (3-formylphenyl)boronic acid (500 mg, 3.3 mmol, 1.0 eq) in 10.0 mL of MeOH was added $NaN_3$ (325 mg, 5.0 mmol, 1.5 eq) and $Cu(OAc)_2$ (60.5 mg, 333 μmol, 0.1 eq) in one portion at 15° C. under $N_2$. The mixture was stirred at 15° C. for 10 min, then heated to 55° C. and stirred for 12 hours. The reaction mixture was quenched by addition 2 mL of $H_2O$ at 15° C., and then extracted three times with 6 mL of DCM. The combined organic layers were washed twice with 6 mL of brine, dried over $Na_2SO_4$, filtered and concentrated under reduced pressure to give a residue. The residue was purified by prep-TLC ($SiO_2$, eluting with petroleum ether:ethyl acetate=2:1) to give 360 mg of 3-azidobenzaldehyde (74% yield) as yellow oil.

General procedure for preparation of compound 406: To a solution of compound 75 (50.0 mg, 155 μmol, 1.0 eq, HCl salt) in 1 mL of DCM was added 3-azidobenzaldehyde (25.1 mg, 170 μmol, 1.1 eq) and acetic acid (930.1 μg, 15.5 μmol, 0.1 eq) at 15° C. After the addition, the mixture was stirred at this temperature for 30 min, then $NaBH(OAc)_3$ (32.8 mg, 155 μmol, 1 eq) was added at 15° C. The resulting mixture was stirred at 15° C. for 12 hours. The reaction mixture was filtered and the mother liquor was concentrated under reduced pressure to give a residue which was purified by prep-HPLC (neutral condition) to give 9.8 mg of compound 406 as a white solid.

Compound 406

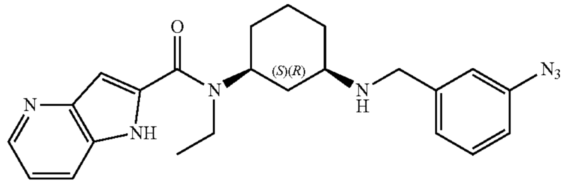

$^1H$ NMR (400 MHz, CHLOROFORM-d) δ ppm 9.45 (br s, 1H), 8.46 (dd, J=1.3, 4.6 Hz, 1H), 7.68 (d, J=8.2 Hz, 1H), 7.23 (t, J=7.8 Hz, 1H), 7.14 (dd, J=4.5, 8.3 Hz, 1H), 7.02 (d, J=7.5 Hz, 1H), 6.94 (s, 1H), 6.85 (br d, J=7.9 Hz, 1H), 4.50 (br s, 1H), 3.75 (s, 2H), 3.68 (br s, 1H), 3.48 (br s, 1H), 2.63 (br s, 1H), 2.09 (br d, J=10.1 Hz, 1H), 1.94 (br d, J=12.3 Hz, 1H), 1.84 (br d, J=14.1 Hz, 2H), 1.41-1.18 (m, 6H), 1.09-0.99 (m, 1H)

LCMS (ESI+): m/z 418.2 (M+H)

General Procedure for Preparation of Compound 4-Azidobenzaldehyde:

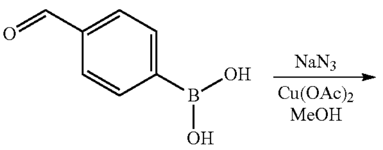

-continued

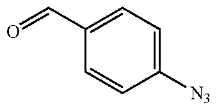

To a mixture of (4-formylphenyl)boronic acid (200 mg, 1.3 mmol, 1.0 eq) in 5.0 mL of MeOH was added $Cu(OAc)_2$ (24.2 mg, 133 μmol, 0.1 eq) and $NaN_3$ (129.7 mg, 2.0 mmol, 1.5 eq) in one portion at 15° C. under $N_2$. The mixture was stirred at 15° C. for 10 min, then heated to 55° C. and stirred for 12 hours. The reaction mixture was filtered and concentrated under reduced pressure to give a residue. The residue was purified by prep-TLC ($SiO_2$, eluting with petroleum ether:ethyl acetate=2:1) to give 100 mg of 4-azidobenzaldehyde (680 μmol, 51% yield) was obtained as yellow oil.

Compound 407 was prepared analogously to compound 406 using 4 azidobenzaldehyde:

Compound 407

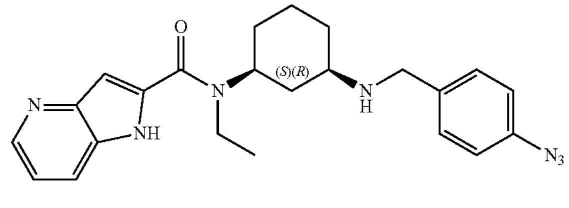

$^1$H NMR (400 MHz, CHLOROFORM-d) δ ppm 9.42 (br s, 1H), 8.46 (d, J=4.4 Hz, 1H), 7.68 (d, J=8.2 Hz, 1H), 7.24 (d, J=8.2 Hz, 2H), 7.15 (dd, J=4.6, 8.2 Hz, 1H), 6.92 (d, J=8.2 Hz, 2H), 4.49 (br t, J=11.8 Hz, 1H), 3.74 (s, 2H), 3.71-3.58 (m, 1H), 3.47 (br s, 1H), 2.62 (br s, 1H), 2.09 (br d, J=9.9 Hz, 1H), 1.92 (br d, J=13.2 Hz, 1H), 1.84 (br d, J=12.8 Hz, 2H), 1.39-1.18 (m, 6H), 1.08-0.96 (m, 1H)

LCMS (ESI+): m/z 418.2 (M+H)

Example 18. Synthesis of α,α-Disubstituted Amine Analogs

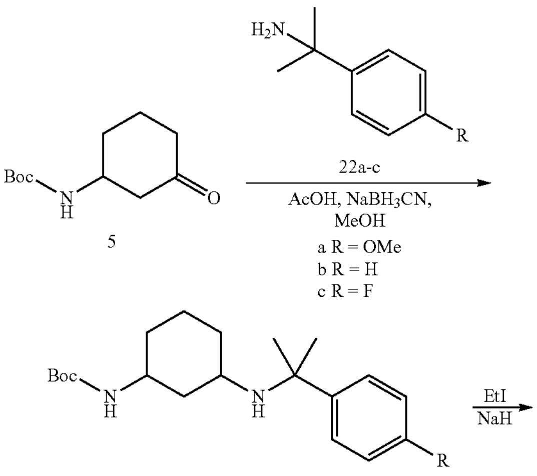

22a-c
5
75a-c

-continued

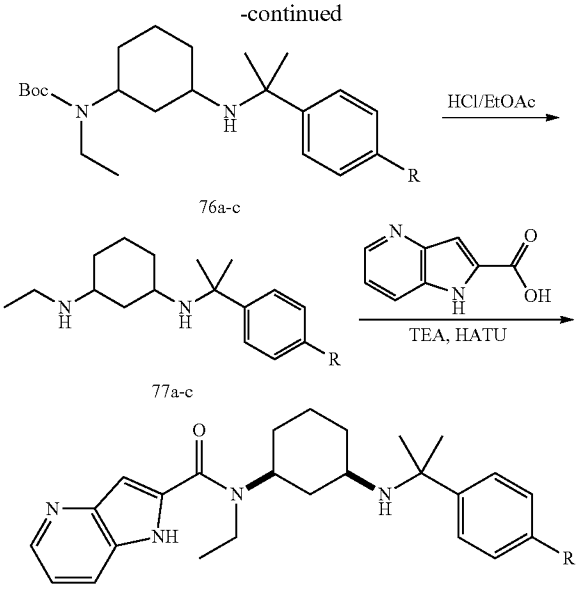

76a-c
77a-c
compounds

General procedure for preparation of compound 75a: A mixture of tert-butyl N-(3-oxocyclohexyl) carbamate 5 (372 mg, 1.7 mmol, 0.9 eq), 2-(4-methoxyphenyl)propan-2-amine (0.3, 1.9 mmol, 1 eq), AcOH (58.2 mg, 968 μmol, 55 μL, 0.5 eq) in 4 mL of MeOH was stirred at 15° C. for 0.5 hour, then $NaBH_3CN$ (243 mg, 3.9 mmol, 2 eq) was added at 15° C. and then the mixture was stirred at 70° C. for 11.5 hours. The reaction mixture was quenched by adding 1 mL of $H_2O$, then concentrated under reduced pressure, extracted three times with 6 mL of EtOAc. The combined organic layers were washed with 5 mL of brine, dried over $Na_2SO_4$, filtered and concentrated under reduced pressure to give an oil. The residue was purified by prep-TLC ($SiO_2$, eluting with ethyl acetate:methanol=10:1) to give 0.14 g of compound 75a as a colorless oil.

General procedure for preparation of compound 76a: A mixture of compound 75a (0.14 g, 386 μmol, 1 eq) in 2 mL of DMF was added NaH (309 mg, 7.7 mmol, 60% purity, 20 eq) at 0° C. and the mixture was stirred at 15° C. for 0.5 hour. Ethyl iodide (1.2 g, 7.7 mmol, 618 μL, 20 eq) was added and the mixture was stirred at 15° C. for 3.5 hours. The mixture was carefully quenched with 50 mL of icy saturated aqueous $NH_4C_1$ dropwise, then it was extracted three times with 20 mL of EtOAc. The combined organic layers were washed with 20 mL of brine, dried over $Na_2SO_4$, filtered and concentrated under reduced pressure to give an oil. The residue was purified by prep-TLC ($SiO_2$, eluting with ethyl acetate:methanol=10:1) to give 30 mg of compound 76a (trans) as a yellow oil and 16 mg of compound 76a (cis) was obtained as a yellow oil.

General procedure for preparation of compound 77a: A mixture of compound 76a (cis) (16 mg, 41 μmol, 1 eq) in 3 mL of HCl/EtOAc (4M) was stirred at 15° C. for 1 hour. The reaction mixture was concentrated under reduced pressure to give 17 mg of compound 77a (cis, HCl salt) as a cyan gum.

Trans Analogs were Prepared Analogously:

General procedure for preparation of compound 408: A mixture of 1H-pyrrolo[3,2-b]pyridine-2-carboxylic acid (9.5 mg, 58.5 μmol, 1 eq), HATU (22.3 mg, 58.5 μmol, 1 eq), TEA (11.9 mg, 117 μmol, 16.3 μL, 2 eq) in 1 mL of DMF was stirred at 15° C. for 0.5 hour, then compound 77a (cis) (17 mg, 58.5 μmol, 1 eq, HCl salt) was added and the mixture was stirred at 15° C. for 11.5 hours. The reaction mixture was filtered. The residue was purified by prep-HPLC (TFA condition) to give 11 mg of compound 408 (19.6 μmol, 34% yield, 97.9% purity, TFA salt) as a light yellow solid.

Compound 408

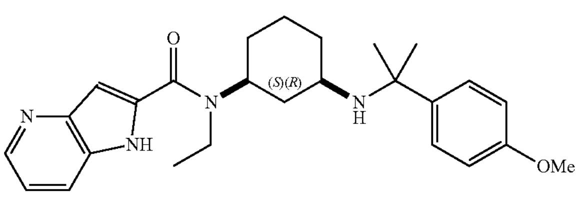

$^1$H NMR (400 MHz, METHANOL-$d_4$) δ=8.71 (br d, J=5.5 Hz, 1H), 8.62 (d, J=8.3 Hz, 1H), 7.80 (dd, J=5.8, 8.3 Hz, 1H), 7.58 (br s, 2H), 7.03 (br s, 3H), 3.93-3.77 (m, 4H), 3.53 (br d, J=6.4 Hz, 2H), 3.08 (br s, 1H), 2.17-1.75 (m, 10H), 1.67 (br s, 3H), 1.44-1.26 (m, 2H), 1.20 (br t, J=6.7 Hz, 3H)

LCMS (ESI+): m/z 435.2 (M+H)

The following compounds were prepared analogously:

Compound 409

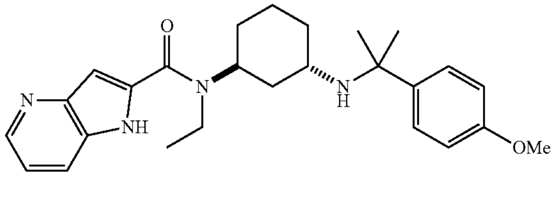

$^1$H NMR (400 MHz, METHANOL-$d_4$) δ=8.68 (d, J=5.6 Hz, 1H), 8.62 (d, J=8.3 Hz, 1H), 7.78 (dd, J=5.9, 8.3 Hz, 1H), 7.61 (br d, J=7.8 Hz, 2H), 7.12 (s, 1H), 7.01 (br d, J=8.7 Hz, 2H), 4.38 (br s, 1H), 3.80 (s, 3H), 3.53 (br d, J=6.7 Hz, 3H), 2.16-1.88 (m, 3H), 1.84 (br s, 6H), 1.78-1.49 (m, 5H), 1.21 (t, J=7.1 Hz, 3H)

LCMS (ESI+): m/z 435.3 (M+H)

Compound 410

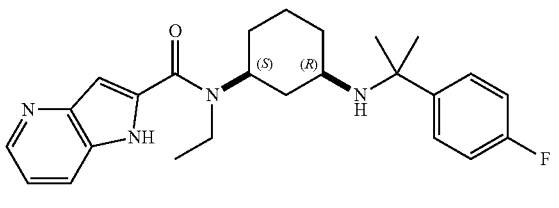

$^1$H NMR (400 MHz, METHANOL-$d_4$) δ ppm 8.67 (d, J=5.7 Hz, 1H), 8.59 (d, J=8.2 Hz, 1H), 7.77 (dd, J=5.8, 8.3 Hz, 1H), 7.68 (br s, 2H), 7.19 (br s, 2H), 7.00 (br s, 1H), 3.86 (br s, 1H), 3.50 (q, J=6.9 Hz, 2H), 3.06 (br s, 1H), 1.87-1.56 (m, 12H), 1.32 (br s, 2H), 1.18 (br t, J=6.9 Hz, 3H)

LCMS (ESI+): m/z 423.3 (M+H)

Compound 411

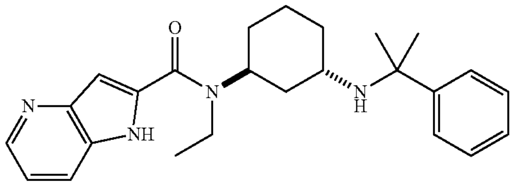

$^1$H NMR (400 MHz, CHLOROFORM-d) δ=9.86 (br s, 1H), 8.54 (d, J=4.4 Hz, 1H), 7.78 (d, J=8.0 Hz, 1H), 7.51 (d, J=7.6 Hz, 2H), 7.35-7.31 (m, 2H), 7.23-7.20 (m, 3H), 7.13-6.72 (m, H) 4.35 (br s, 1H), 3.63-3.50 (br s, 2H), 2.53 (br s, 1H), 1.86-1.84 (m, 3H), 1.77-1.73 (m, 2H), 1.66-1.63 (m, 6H), 1.48-1.45 (m, 2H) 1.27-1.25 (m, 3H) 1.05-1.02 (m, 1H)

LCMS (ESI+): m/z 405.2 (M+H)

Example 19. Synthesis of N-ethyl-N-((1S,3R)-3-(((R)-2,2,2-trifluoro-1-(pyrimidin-5-yl)ethyl)amino)cyclohexyl)-1H-indole-2-carboxamide (Compound 412) and N-ethyl-N-((1S,3R)-3-(((S)-2,2,2-trifluoro-1-(pyrimidin-5-yl)ethyl)amino)cyclohexyl)-1H-indole-2-carboxamide (Compound 413)

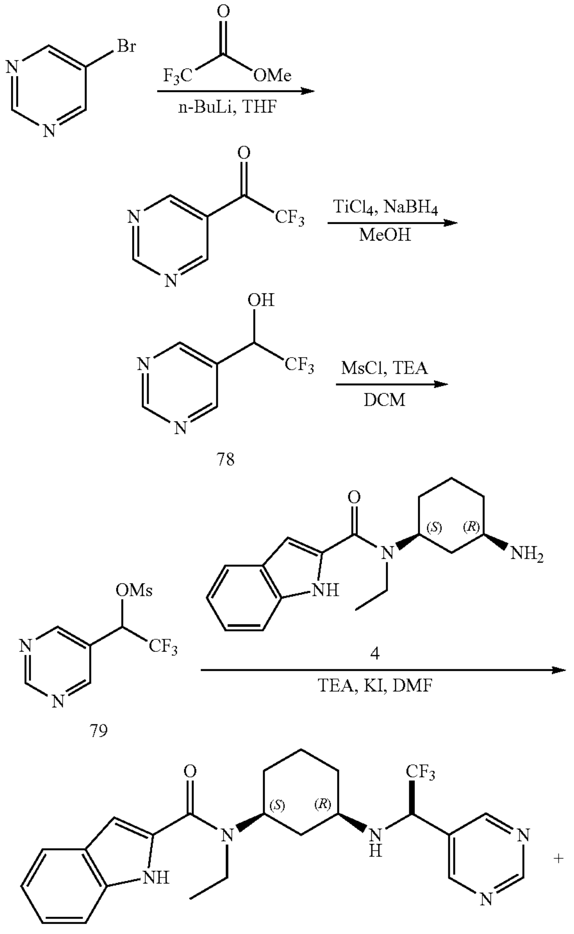

compound 412

-continued

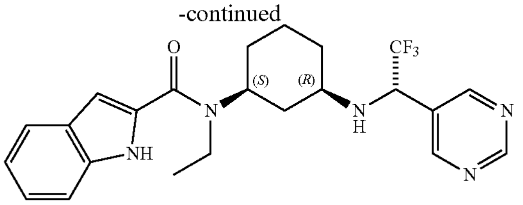

compound 413

General procedure for preparation of 2,2,2-trifluoro-1-(pyrimidin-5-yl)ethan-1-one: To a mixture of 5-bromopyrimidine (5.0 g, 31.5 mmol, 1.0 eq) in THF (40 mL) was added n-BuLi (2.5 M, 13.2 mL, 1.1 eq) dropwise at −107° C. (EtOH/liquid nitrogen bath cooling). The mixture was stirred at −107° C. for 0.5 hour, then to the mixture was added methyl 2,2,2-trifluoroacetate (4.0 g, 31.5 mmol, 3.2 mL, 1.0 eq) in THF (5 mL) at −107° C. The resulting light yellow solution was slowly warmed to −60° C. over 1 hour, the cooling bath was removed, and the reaction was allowed to warm to 15° C. over 0.5 hour. The reaction was monitored by TLC. The reaction mixture was quenched by adding 50 mL of aq. sat. $NH_4Cl$, extracted twice with 50 mL portions of ethyl acetate. The combined organic phases were washed once with 100 mL of brine, dried with anhydrous $Na_2SO_4$, filtered and concentrated in vacuo. To the residue was added 20 mL of DCM and 10 mL of petroleum ether until precipitation. The solids were filtered to give 2.5 g of 2,2,2-trifluoro-1-(pyrimidin-5-yl)ethan-1-one as a white solid.

General procedure for preparation of compound 78: To a mixture of 2,2,2-trifluoro-1-(pyrimidin-5-yl)ethan-1-one (1.0 g, 5.7 mmol, 1.0 eq) in MeOH (15 mL) was added $TiCl_4$ (32.3 mg, 170 μmol, 0.03 eq) at 0° C., followed by the addition of $NaBH_4$ (430 mg, 11.4 mmol, 2.0 eq) in batches at 0° C. Then the reaction mixture was stirred at 15° C. for 0.5 hour. The reaction mixture was quenched by adding 20 mL of $H_2O$ and extracted with three 20 mL portions of ethyl acetate. The combined organic phases were dried with anhydrous $Na_2SO_4$, filtered and concentrated in vacuo to give 0.9 g of crude compound 78 as a yellow oil which was used directly into the next step without purification.

General procedure for preparation of compound 79: To a mixture of compound 78 (540 mg, 3.0 mmol, 1.0 eq) and TEA (920 mg, 9.1 mmol, 1.3 mL, 3.0 eq) in DCM (10 mL) was added MsCl (417 mg, 3.6 mmol, 1.2 eq) dropwise at 0° C. The mixture was stirred at 15° C. for 0.5 hour. The reaction mixture was quenched by adding 20 mL of $H_2O$, and extracted twice with 15 mL portions of DCM. The combined organic phases were dried with anhydrous $Na_2SO_4$, filtered and concentrated in vacuo. The residue was purified by prep-TLC ($SiO_2$, eluting with petroleum ether: ethyl acetate=1:2) to give 0.6 g of compound 79 as a yellow oil.

General procedure for preparation of compounds 412 and 413: To a mixture of compound 4 (50 mg, 155 μmol, 1.0 eq, HCl salt) and TEA (78.6 mg, 777 μmol, 5.0 eq) in acetonitrile (1 mL) was added compound 79 (159 mg, 621 μmol, 4.0 eq) and KI (7.7 mg, 47 μmol, 0.3 eq) at 15° C. under $N_2$. The reaction mixture was stirred at 40° C. for 16 hours, and then stirred at 50° C. for 24 hours. The reaction was monitored by LCMS. The reaction mixture was concentrated in vacuo to reduce acetonitrile and then 3 mL of DCM was added. The mixture was filtered and the filtrate was concentrated in vacuo. The residue was purified by prep-TLC ($SiO_2$, eluting with ethyl acetate:methanol=10:1), and then re-purified by reverse phase prep-HPLC (TFA condition) to give 1.2 mg of compound 412 (1.3% yield, TFA salt) as a white solid and 1.9 mg of compound 413 (2.0% yield, TFA salt) as a white solid. Note, the configuration of the two isomers at the newly formed chiral center were assigned arbitrarily.

Compound 412

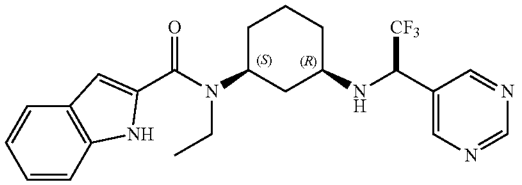

$^1H$ NMR (400 MHz, DMSO-$d_6$) δ ppm 11.54 (br s, 1H) 8.25 (s, 2H) 7.63 (d, J=7.82 Hz, 1H) 7.42 (d, J=8.07 Hz, 1H) 7.35 (br d, J=7.70 Hz, 1H) 7.18 (t, J=7.64 Hz, 1H) 7.01-7.08 (m, 1H) 6.79 (s, 1H) 4.36 (br s, 1H) 3.77 (br s, 1H) 3.47 (br d, J=11.49 Hz, 3H) 2.07 (br s, 1H) 1.73-1.93 (m, 3H) 1.56-1.72 (m, 2H) 1.38 (br d, J=11.86 Hz, 1H) 1.16-1.29 (m, 4H)

LCMS (ESI+): m/z 446.2 (M+H)

Compound 413

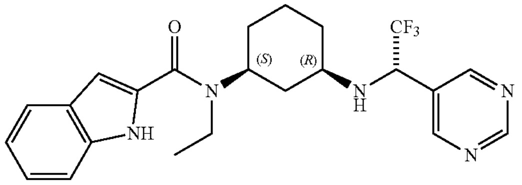

$^1H$ NMR (400 MHz, METHANOL-$d_4$) δ ppm 8.68 (s, 1H) 8.22 (s, 1H) 7.64 (br d, J=8.16 Hz, 1H) 7.44 (br d, J=8.16 Hz, 1H) 7.22 (br t, J=7.50 Hz, 1H) 7.08 (br t, J=7.61 Hz, 1H) 6.82 (br s, 1H) 4.46 (br s, 2H) 3.71 (q, J=10.44 Hz, 3H) 3.02 (d, J=7.72 Hz, 1H) 2.19 (br d, J=9.92 Hz, 1H) 1.89-2.05 (m, 4H) 1.82 (br s, 1H) 1.43-1.60 (m, 2H) 1.32 (br s, 3H)

LCMS (ESI+): m/z 446.2 (M+H)

The following compounds were prepared analogously:

Compound 414

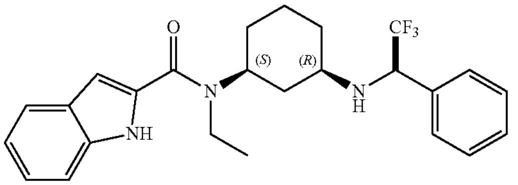

$^1H$ NMR (400 MHz, METHANOL-$d_4$) δ ppm 7.40-7.65 (m, 7H) 7.23 (t, J=7.21 Hz, 1H) 7.06-7.13 (m, 1H) 6.33-6.71 (m, 1H) 5.05 (br s, 1H) 4.17 (br s, 1H) 3.51-3.74 (m, 2H) 2.73 (br s, 1H) 2.29 (br d, J=10.39 Hz, 1H) 1.91 (br s, 2H) 1.65-1.84 (m, 3H) 1.33 (br t, J=6.97 Hz, 5H)

LCMS (ESI+): m/z 444.2 (M+H)

Compound 415

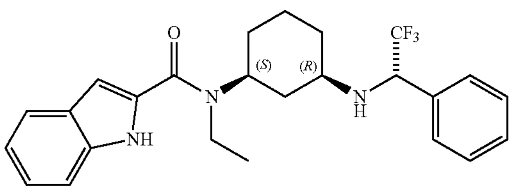

$^1$H NMR (400 MHz, METHANOL-$d_4$) δ ppm 7.40-7.64 (m, 7H) 7.22 (t, J=7.64 Hz, 1H) 7.03-7.12 (m, 1H) 6.65 (br s, 1H) 4.92-5.02 (m, 1H) 4.24 (br s, 1H) 3.60 (br s, 2H) 2.69 (br d, J=8.80 Hz, 1H) 2.09 (br d, J=10.51 Hz, 2H) 1.91 (br d, J=10.88 Hz, 1H) 1.64-1.85 (m, 3H) 1.13-1.37 (m, 5H)

LCMS (ESI+): m/z 444.2 (M+H)

Example 20. Synthesis of N-ethyl-N-((1S,3R)-3-(((R)-2,2,2-trifluoro-1-phenylethyl)amino)cyclohexyl)-1H-pyrrolo[3,2-b]pyridine-2-carboxamide (Compound 416) and N-ethyl-N-((1S,3R)-3-(((S)-2,2,2-trifluoro-1-phenylethyl)amino)cyclohexyl)-1H-pyrrolo[3,2-b]pyridine-2-carboxamide (Compound 417)

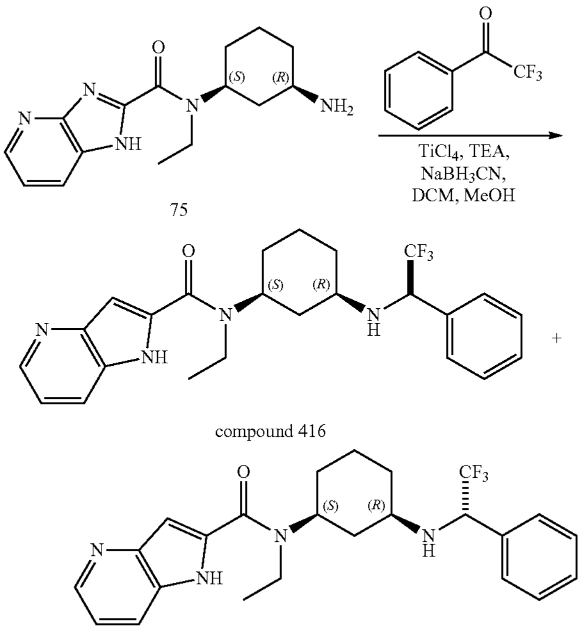

75 compound 416 compound 417

General procedure for preparation of compounds 416 and 417 To a mixture of compound 75 (50 mg, 175 μmol, 1.0 eq) and 2,2,2-trifluoro-1-phenylethan-1-one (36.6 mg, 210 μmol, 1.2 eq) in DCM (1 mL) was added $TiCl_4$ (16.6 mg, 88 μmol, 0.5 eq) at 15° C., followed by the addition of TEA (53.2 mg, 526 μmol, 3.0 eq) dropwise and the mixture was stirred for 12 hours at 15° C. To this mixture was added slowly $NaBH_3CN$ (22.0 mg, 350 μmol, 2.0 eq) in MeOH (1 mL), then the mixture was stirred at 15° C. for another 2 hours under $N_2$ atmosphere. The reaction was monitored by LCMS. The mixture was evaporated under reduced pressure to give a residue which was purified by prep-HPLC (TFA condition) to give 14.3 mg of compound 416 (15% yield, TFA salt) as a white solid and 10.2 mg of compound 417 (10.4% yield, TFA salt) as a white solid. Note, the configuration of the two isomers at the newly formed chiral center were assigned arbitrarily.

Compound 416

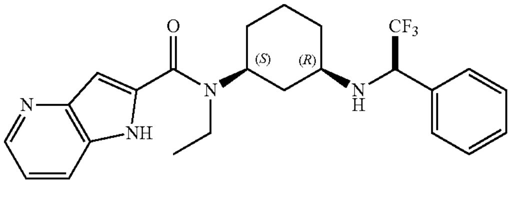

$^1$H NMR (400 MHz, METHANOL-$d_4$) δ ppm 8.69 (d, J=5.7 Hz, 1H), 8.64 (d, J=8.3 Hz, 1H), 7.80 (dd, J=5.9, 8.3 Hz, 1H), 7.66-7.37 (m, 5H), 7.11 (br s, 1H), 3.94 (br s, 1H), 3.65-3.53 (m, 2H), 2.96 (br s, 1H), 2.77-2.48 (m, 1H), 2.26 (br d, J=11.2 Hz, 1H), 2.09-1.87 (m, 4H), 1.73 (br s, 1H), 1.40-1.16 (m, 5H)

LCMS (ESI+): m/z 445.1 (M+H)

Compound 417

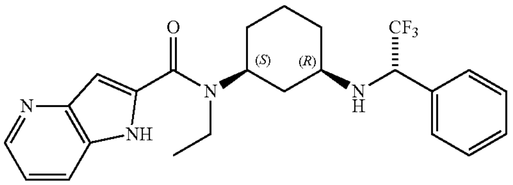

$^1$H NMR (400 MHz, METHANOL-$d_4$) δ ppm 8.67 (br d, J=5.5 Hz, 1H), 8.61 (br d, J=8.4 Hz, 1H), 7.82-7.76 (m, 1H), 7.55 (br s, 5H), 7.09 (br s, 1H), 4.12-3.80 (m, 1H), 3.64-3.52 (m, 2H), 3.02-2.84 (m, 1H), 2.76-2.54 (m, 1H), 2.16 (br s, 2H), 1.96-1.63 (m, 4H), 1.34-1.19 (m, 5H)

LCMS (ESI+): m/z 445.2 (M+H)

Example 21. Synthesis of N-ethyl-N-((1S,3R)-3-((1-phenylcyclopropyl)amino)cyclohexyl)-1H-pyrrolo[3,2-b]pyridine-2-carboxamide (Compound 418)

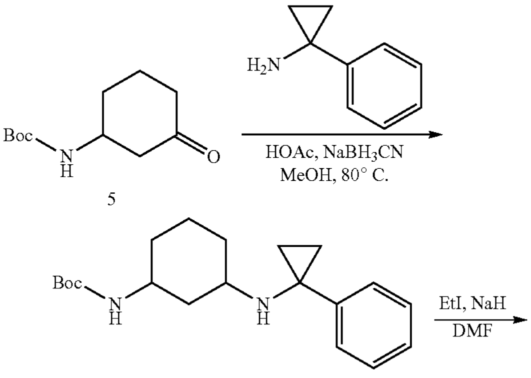

5

80

-continued

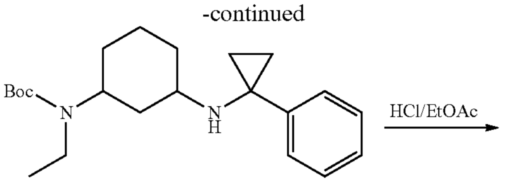

81

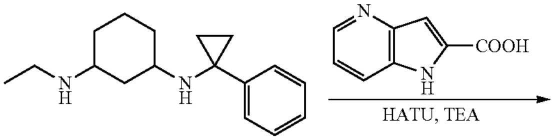

81

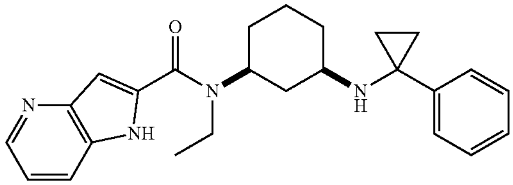

Compound 418

General procedure for preparation of compound 80: A mixture of 1-phenylcyclopropanamine hydrochloride (477 mg, 2.8 mmol, 1 eq), TEA (142 mg, 1.4 mmol, 196 μL, 0.5 eq) in 10 mL of MeOH was stirred via ultrasound equipment for 1 min, then compound 5 (0.6 g, 2.8 mmol, 1 eq) and AcOH (84.5 mg, 1.4 mmol, 0.5 eq) was added and the mixture was stirred at 15° C. for 29 mins. $NaBH_3CN$ (354 mg, 5.6 mmol, 2 eq) was added and the mixture was stirred at 70° C. for 11.5 hours. The reaction mixture was quenched by 6 mL of $H_2O$, then concentrated under reduced pressure and extracted twice with 10 mL of EtOAc. The combined organic layers were washed with 10 mL of brine, dried over $Na_2SO_4$, filtered and concentrated under reduced pressure to give an oil which was purified by column chromatography ($SiO_2$, eluting with a gradient of petroleum ether:ethyl acetate=5:1 to 1:1) to give 0.8 g of crude compound 80 as a light yellow oil.

General procedure for preparation of compound 81: To a mixture of compound 80 (780 mg, 2.3 mmol, 1 eq) in 10 mL of DMF was added NaH (466 mg, 11.7 mmol, 60% purity, 5 eq) at 0° C. and the mixture was stirred at 15° C. for 0.5 hour. Ethyl iodide (1.8 g, 11.7 mmol, 932 μL, 5 eq) was added at 15° C. and the mixture was stirred at 15° C. for 1.5 hours. To the reaction mixture was added 50 mL of icy saturated aqueous $NH_4Cl$ dropwise to quench NaH, then the mixture was extracted twice with 20 mL of EtOAc. The combined organic layers were washed with 20 mL of brine, dried over $Na_2SO_4$, filtered and concentrated under reduced pressure to give an oil which was purified by column chromatography ($SiO_2$, eluting with a gradient of petroleum ether:ethyl acetate=50:1 to 1:1) to give 280 mg of trans compound 81a (629 μmol, 27% yield, 80.6% purity) as a yellow oil and 400 mg of cis compound 81 (970 μmol, 42% yield, 87.0% purity) as a yellow oil.

General procedure for preparation of compound 82: A mixture of compound 81 (400 mg, 1.1 mmol, 1 eq) in 10 mL of HCl/EtOAc (4M) was stirred at 15° C. for 1 hour. The reaction mixture was concentrated under reduced pressure to give 330 mg of crude compound 82 (HCl salt) as a yellow solid.

General procedure for preparation of compound 418: A mixture of 1H-pyrrolo[3,2-b]pyridine-2-carboxylic acid (69 mg, 426 μmol, 1 eq), HATU (162 mg, 426 μmol, 1 eq), TEA (86 mg, 851 μmol, 119 μL, 2 eq) in 2 mL of DMF was stirred at 15° C. for 0.5 hour, then compound 30 (110 mg, 426 μmol, 1 eq, HCl salt) was added at 15° C. and the mixture was stirred at 15° C. for 11.5 hours. The mixture was filtered and the filtrate was purified by prep-HPLC (TFA condition) to give 53.5 mg of compound 418 (98 μmol, 23% yield, 95.0% purity, TFA salt) as a brown solid.

Compound 418

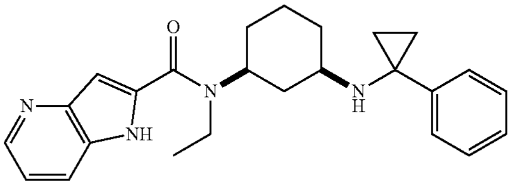

$^1H$ NMR (400 MHz, METHANOL-$d_4$) δ=8.67 (d, J=5.6 Hz, 1H), 8.62 (d, J=8.3 Hz, 1H), 7.78 (dd, J=5.7, 8.3 Hz, 1H), 7.69-7.27 (m, 5H), 7.22-6.90 (m, 1H), 3.90 (br s, 1H), 3.66-3.48 (m, 2H), 3.07-2.76 (m, 1H), 2.38-2.03 (m, 2H), 2.01-1.67 (m, 4H), 1.44 (br t, J=3.7 Hz, 2H), 1.42-1.30 (m, 4H), 1.27 (br t, J=7.0 Hz, 2H), 1.29-1.24 (m, 1H)

LCMS (ESI+): m/z 403.3 (M+H)

The following compounds were made analogously:

Compound 419

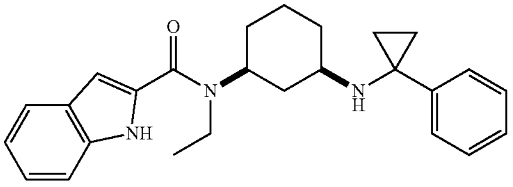

$^1H$ NMR (400 MHz, METHANOL-$d_4$) δ=7.57 (br d, J=7.9 Hz, 1H), 7.44 (br d, J=7.7 Hz, 3H), 7.31 (br t, J=7.2 Hz, 2H), 7.27-7.19 (m, 2H), 7.12-7.05 (m, 1H), 6.51 (br s, 1H), 4.23 (br t, J=11.9 Hz, 1H), 3.58 (br s, 2H), 2.50 (br s, 1H), 2.25-2.09 (m, 1H), 1.91-1.72 (m, 3H), 1.68-1.47 (m, 2H), 1.28 (t, J=7.0 Hz, 3H), 1.20-1.05 (m, 2H), 1.03-0.94 (m, 3H), 0.91 (br s, 1H)

LCMS (ESI+): m/z 402.2 (M+H)

Compound 420

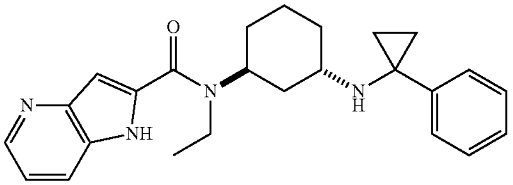

$^1H$ NMR (400 MHz, METHANOL-$d_4$) δ=8.68 (d, J=5.4 Hz, 1H), 8.61 (d, J=8.3 Hz, 1H), 7.78 (dd, J=5.7, 8.3 Hz, 1H), 7.63 (br d, J=6.0 Hz, 2H), 7.50-7.42 (m, 3H), 7.13 (s, 1H), 4.49 (br s, 1H), 3.57 (br d, J=6.8 Hz, 2H), 3.50 (br s, 1H), 2.15 (br s, 2H), 2.00-1.76 (m, 5H), 1.74-1.59 (m, 2H), 1.56-1.29 (m, 3H), 1.25 (t, J=7.1 Hz, 3H)

LCMS (ESI+): m/z 403.2 (M+H)

Compound 421

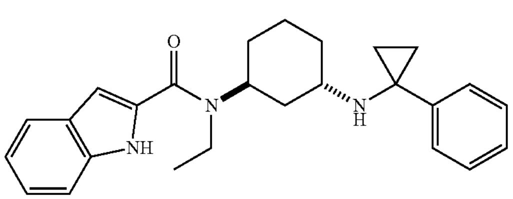

$^1$H NMR (400 MHz, METHANOL-$d_4$) δ=7.63 (d, J=7.9 Hz, 1H), 7.44 (d, J=8.3 Hz, 1H), 7.29 (br s, 2H), 7.21 (br t, J=7.0 Hz, 3H), 7.16-7.04 (m, 2H), 6.82 (s, 1H), 3.50 (br s, 2H), 2.98 (br s, 1H), 1.82 (br d, J=9.2 Hz, 2H), 1.76-1.49 (m, 4H), 1.74-1.49 (m, 1H), 1.31-1.14 (m, 5H), 0.73 (br s, 4H)

LCMS (ESI+): m/z 402.2 (M+H)

Example 22. Synthesis of N-((1S,3R)-3-((3-fluorobenzyl)amino)cyclohexyl)-N-(2,2,2-trifluoroethyl)-1H-pyrrolo[3,2-b]pyridine-2-carboxamide (Compound 422)

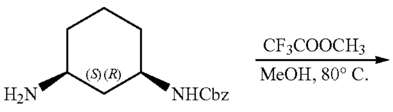

19A

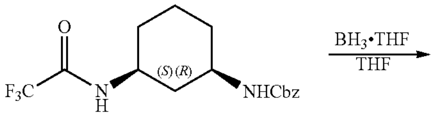

83

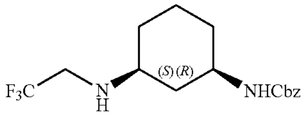

84

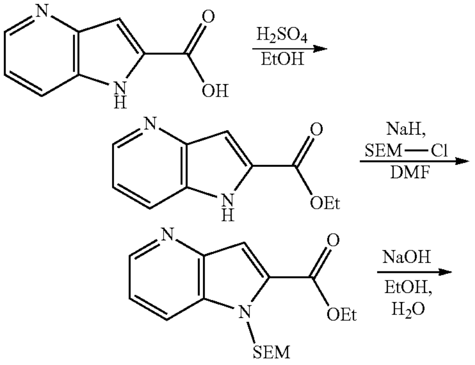

85

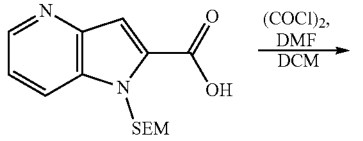

86

-continued

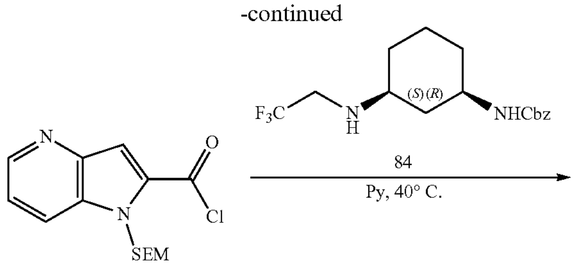

87

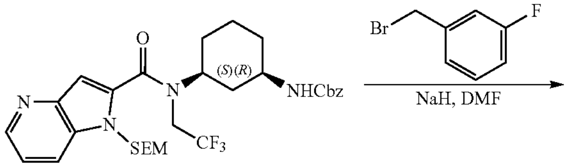

88

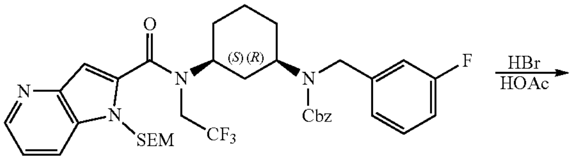

89

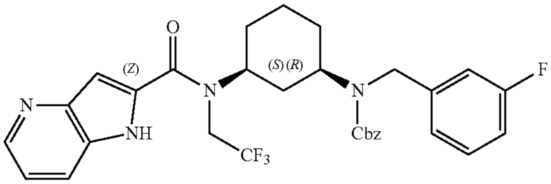

compound 422

General procedure for preparation of compound 83: A mixture of compound 19A (2 g, 8.1 mmol, 1.0 eq) and methyl 2,2,2-trifluoroacetate (3.1 g, 24.2 mmol, 3.0 eq) in 20 mL of MeOH was stirred at 80° C. for 12 hour. The reaction mixture was concentrated under reduced pressure to give a solid. The solid was diluted with 10 mL of HCl (1M) and extracted twice with 20 mL of ethyl acetate. The combined organic layers were washed with 25 mL of brine, dried over $Na_2SO_4$, filtered and concentrated under reduced pressure to afford compound 83 (2.2 g, crude) as a white solid.

General procedure for preparation of compound 84: A mixture of compound 83 (2.2 g, 6.4 mmol, 1.0 eq) in 20 mL of THF was added $BH_3$.THF (1 M, 44.7 mL, 7.0 eq) at 25° C., and then the mixture was stirred at 70° C. for 36 hours under $N_2$ atmosphere. The mixture was quenched with 15 mL of methanol and 6 mL of HCl (1M), then the mixture was stirred at 70° C. for 1 hour. It was concentrated to afford an oil. The oil was diluted with 20 mL of water and basified by $Na_2CO_3$ to pH=9-10, and extracted twice with 15 mL portions of ethyl acetate. The combined organic layers were washed twice with 20 mL portions of brine, dried over $Na_2SO_4$, filtered and concentrated under reduced pressure to give an oil. The residue was purified by column chromatography ($SiO_2$, eluting with a gradient of petroleum ether: ethyl acetate=20/1 to 2:1) to afford amine 84 (810 mg, 2.5 mmol, 38% yield) as a white solid.

General procedure for preparation of ethyl 1H-pyrrolo[3,2-b]pyridine-2-carboxylate: To a mixture of 1H-pyrrolo[3,2-b]pyridine-2-carboxylic acid (5 g, 30.8 mmol, 1 eq) in 50 mL of ethyl alcohol was added $H_2SO_4$ (15.4 g, 154 mmol, 98% purity, 5 eq) at 15° C., and the mixture was stirred at 80° C. for 12 hours. To the reaction mixture was added NaOH (15% in water) to neutralize $H_2SO_4$ until the pH~7-8. A precipitate formed which was filtered. The filter cake was washed with 50 mL of water to get the crude product (part 1). The mother liquors were concentrated under reduced pressure and the aqueous phase was extracted with three 20 mL portions of ethyl acetate. The combined organic layers were concentrated under reduced pressure to give a solid (part 2). The mixture of solids from part 1 and part 2 were combined to produce the ethyl ester as a white solid which could be used directly into the next step without further purification.

General procedure for preparation of compound 85: To a mixture of ethyl 1H-pyrrolo[3,2-b]pyridine-2-carboxylate (3.95 g, 20.8 mmol, 1 eq) in 40 mL of DMF was added NaH (1.3 g, 31.2 mmol, 60% purity, 1.5 eq) at 0° C. and the mixture was stirred at 15° C. for 0.5 hour. SEM-$C_1$ (5.2 g, 31.2 mmol, 1.5 eq) was added and the mixture was stirred at 15° C. for 0.5 hour under $N_2$ atmosphere. To the reaction mixture was added in 150 mL of icy saturated $NH_4Cl$ dropwise to quench NaH, then the mixture was extracted with twice 100 mL portions of ethyl acetate. The combined organic layers were washed with 100 mL of brine, dried over $Na_2SO_4$, filtered and concentrated under reduced pressure to afford compound 85 (12.9 g, crude) as a brown oil.

General procedure for preparation of compound 86: A mixture of compound 85 (6 g, 18.7 mmol, 1 eq), NaOH (2.3 g, 56.2 mmol, 3 eq) in 30 mL of ethyl alcohol and 30 mL of water was stirred at 15° C. for 12 hours. The reaction mixture was concentrated under reduced pressure and the resulting oil was diluted with 30 mL of water and extracted twice with 20 mL portions of dichloromethane. The combined organic layers were concentrated under reduced pressure to give an oil. The oil was diluted with 30 mL of water and acidified to pH=6 by HCl (1 N) and then extracted with three 20 mL portions of ethyl acetate. The combined organic layers were dried over $Na_2SO_4$, filtered and concentrated under reduced pressure to get the part 1 (4.3 g, crude) as a brown solid after filtration. The acidified aqueous layers were extracted again with three 10 mL portions of ethyl acetate, the combined organic layers were dried over $Na_2SO_4$, filtered and concentrated under reduced pressure to get the part 2 (130 mg, crude) as a yellow solid. The mixture of part 1 and part 2 was obtained as a white solid 86 which could be used directly into the next step without further purification.

General procedure for preparation of compound 87: To a mixture of compound 86 (300 mg, 1.0 mmol, 1 eq) in 3 mL of dichloromethane was added DMF (37.5 mg, 513 μmol, 0.5 eq) and $(COCl)_2$ (261 mg, 2.1 mmol, 2 eq), and then the mixture was stirred at 15° C. for 1 hour. The reaction mixture was concentrated under reduced pressure to afford compound 87 (350 mg, crude) as a black brown solid.

General procedure for preparation of compound 88: To a mixture of benzyl N-[(1R,3S)-3-(2,2,2-trifluoroethylamino) cyclohexyl]carbamate 87 (140 mg, 424 μmol, 1 eq) in 1.5 mL of pyridine was added compound 84 (263.5 mg, 848 μmol, 2 eq) in 1 mL of dichloromethane at 0° C., and the mixture was stirred at 40° C. for 2 hours. The reaction mixture was concentrated under reduced pressure to give an oil. The residue was purified by prep-TLC ($SiO_2$, eluting with petroleum ether:ethyl acetate=1:1) to afford compound 88 (70 mg, 100 μmol, 24% yield, 86.0% purity) as a yellow oil.

General procedure for preparation of compound 89: To a mixture of compound 88 (80 mg, 132 μmol, 1 eq) in 1.5 mL of DMF was added NaH (6.4 mg, 159 μmol, 60% purity, 1.2 eq) at 0° C. and the mixture was stirred at 15° C. for 0.5 hour. 1-(Bromomethyl)-3-fluoro-benzene (27.5 mg, 146 μmol, 1.1 eq) was added and ten the mixture was stirred at 15° C. for 0.5 hour. The reaction mixture was added to 10 mL of icy saturated $NH_4C_1$ dropwise to quench NaH, then the mixture was extracted twice with 5 mL portions of ethyl acetate. The combined organic layers were washed with 10 mL of brine, dried over $Na_2SO_4$, filtered and concentrated under reduced pressure to afford 100 mg of compound 89 as a crude yellow oil.

General procedure for preparation of compound 422: A mixture of compound 89 (100 mg, 140 μmol, 1 eq) in 1 mL of AcOH and HBr (1 mL) was stirred at 15° C. for 1 hour. The reaction mixture was basified by NaOH (4M in water) to pH ~7-8. The mixture was concentrated under reduced pressure to give a solid. The residue was purified by prep-HPLC (TFA condition) to afford compound 422 (7.6 mg, 13.0 μmol, 9% yield, 96.2% purity, TFA) as a white solid.

Compound 422

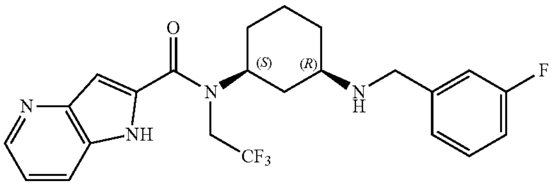

$^1H$ NMR (400 MHz, METHANOL-$d_4$) δ=8.71 (d, J=5.7 Hz, 1H), 8.62 (d, J=8.3 Hz, 1H), 7.80 (dd, J=5.7, 8.3 Hz, 1H), 7.53-7.42 (m, 1H), 7.34-7.25 (m, 2H), 7.23-7.15 (m, 2H), 4.48-4.37 (m, 2H), 4.27 (s, 2H), 4.14 (br s, 1H), 3.30-3.24 (m, 1H), 2.45 (br d, J=11.8 Hz, 1H), 2.21 (br s, 1H), 2.13-1.82 (m, 4H), 1.50-1.37 (m, 2H)

LCMS (ESI+): m/z 449.1 (M+H)

The following compounds were prepared analogously.

Compound 423

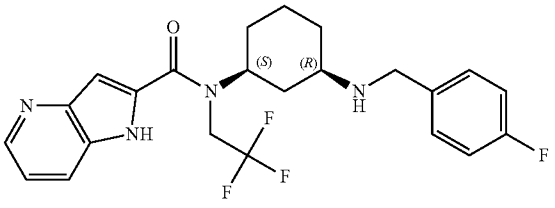

$^1H$ NMR (400 MHz, DMSO-$d_6$) δ ppm 13.08 (s, 1H) 9.11 (s, 2H) 8.71 (d, J=5.2 Hz, 1H) 8.39 (d, J=7.2 Hz, 1H) 7.64 (d, J=5.2 Hz, 1H) 7.55 (dd, J=5.6, 8.8 Hz, 2H) 7.27 (t, J=8.8 Hz, 2H) 7.15 (s, 1H) 4.46-4.41 (m, 2H) 4.19 (s, 3H) 3.16 (s, 1H) 2.32 (d, J=11.6 Hz, 1H) 2.05 (s, 1H) 1.88-1.77 (m, 4H) 1.33 (s, 2H)

LCMS (ESI+): m/z 449.2 (M+H)

Example 23. Synthesis of N-((1S,3R)-3-((2-(4-methoxyphenyl)propan-2-yl)amino)cyclohexyl)-N-(2,2,2-trifluoroethyl)-1H-pyrrolo[3,2-b]pyridine-2-carboxamide (Compound 424)

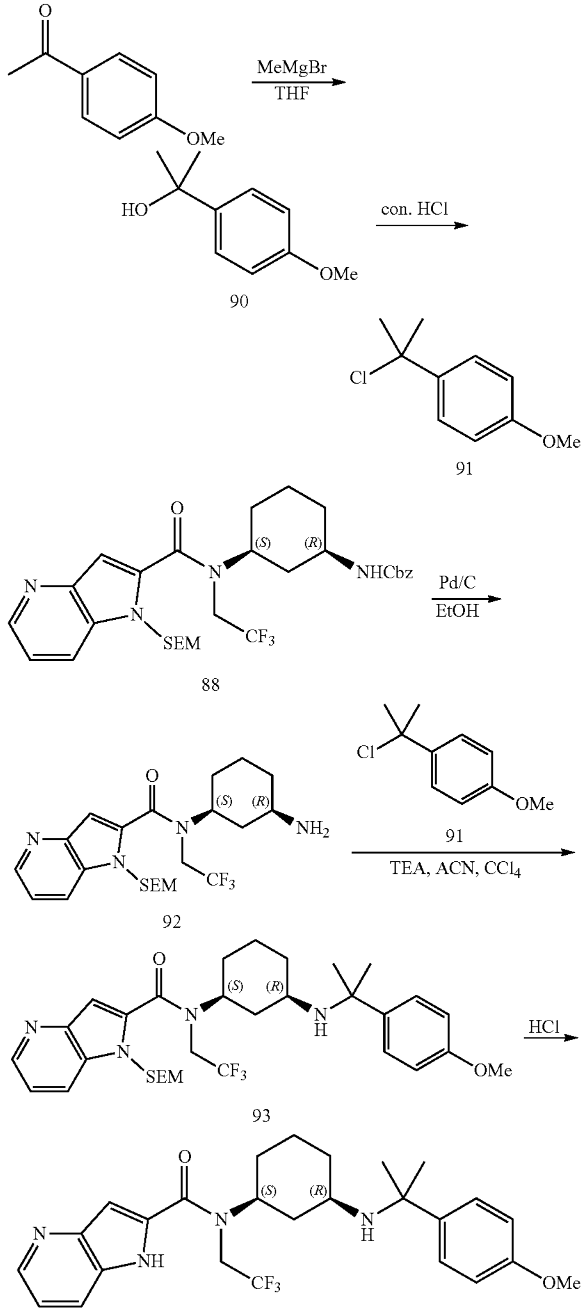

90

91

88

92

91

93 compound 424

General procedure for preparation of compound 90: To a mixture of 4-methoxyacetophenone (3.0 g, 20.0 mmol, 1 eq) in 30 mL of THF was added dropwise MeMgBr (3 M, 20.0 mL, 3 eq) a t 5° C., and then the mixture was stirred at 15° C. for 12 hours under $N_2$ atmosphere. The reaction was monitored by TLC and allowed to run until one major new spot with larger polarity was detected. The reaction mixture was quenched by 80 mL of icy saturated $NH_4Cl$ solution, extracted twice with 30 mL portions of ethyl acetate. The combined organic layers were washed with 50 mL of brine, dried over $Na_2SO_4$, filtered and concentrated under reduced pressure to give an oil. The residue was purified by prep-TLC ($SiO_2$, eluting with petroleum ether:ethyl acetate=3:1) to afford compound 90 (2.1 g, crude) as a yellow oil.

General procedure for preparation of compound 91: To a mixture of compound 90 (260 mg, 1.6 mmol, 1 eq) in 1.5 mL of $CCl_4$ was added HCl (12M, 521 μL, 4 eq) at 0° C., and then the mixture was stirred at 0° C. for 5 min. TLC indicated two new spots with lower polarity were detected. The organic layer was separated. The crude product compound 91 in the organic layer ($CCl_4$) was used in the next step without further purification.

General procedure for preparation of compound 92: A mixture of compound 88 (100 mg, 169 μmol, 1 eq), Pd/C (0.2 g, 50% purity), $NH_3.H_2O$ (11.9 mg, 84.6 μmol, 25% purity, 0.5 eq) in 20 mL of ethyl alcohol was degassed and purged with $H_2$ 3 times. The mixture was stirred at 15° C. for 1 hour under $H_2$ atmosphere (15 psi). The reaction mixture was filtered and then concentrated under reduced pressure to afford compound 92 (70 mg, 145 μmol, 86% yield, 97.7% purity). This compound was used into the next step without further purification.

General procedure for preparation of compound 93: A mixture of compound 92 (60 mg, 128 μmol, 1 eq) and TEA (258 mg, 2.6 mmol, 20 eq) in 1 mL of acetonitrile was cooled to 0° C. and then crude compound 91 (47.1 mg, 255 μmol, 2 eq) in 3 mL of $CCl_4$ was added at 0° C., The mixture was stirred at 15° C. for 0.5 hour. The reaction mixture was diluted with 10 mL of saturated $NH_4Cl$ solution, and extracted twice with 6 mL portions of dichloromethane. The combined organic layers were washed with 8 mL of brine, dried over $Na_2SO_4$, filtered and concentrated under reduced pressure to give an oil. The residue was purified by prep-TLC ($SiO_2$, eluting with ethyl acetate:methanol=10:1) to afford compound 93 (12 mg, 19.4 μmol, 15% yield) as a colorless oil.

General procedure for preparation of compound 424: A mixture of compound 93 (12 mg, 19 μmol, 1 eq) in 1 mL of HCl (6M) was stirred at 30° C. for 12 hours. The reaction mixture was basified by NaOH (solid) to pH ~9-10. The mixture was concentrated under reduced pressure to give a solid. The residue was purified by prep-HPLC (TFA condition) to afford compound 424 (5 mg, 7.9 μmol, 410% yield, 94.8% purity, TFA) as a white solid.

Compound 424

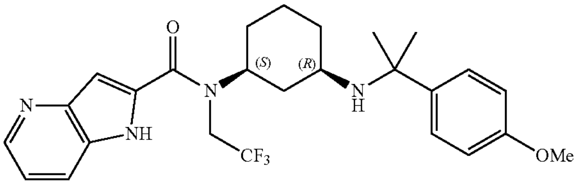

$^1H$ NMR (400 MHz, METHANOL-$d_4$) δ=8.71 (br d, J=5.4 Hz, 1H), 8.56 (d, J=8.2 Hz, 1H), 7.78 (dd, J=5.7, 8.1 Hz, 1H), 7.55 (br d, J=8.7 Hz, 2H), 7.06-6.95 (m, 3H), 4.34 (q, J=8.7 Hz, 2H), 4.00-3.75 (m, 4H), 3.05 (br t, J=11.3 Hz, 1H), 2.05-1.71 (m, 11H), 1.64 (br d, J=11.7 Hz, 1H), 1.38-1.21 (m, 2H)

LCMS (ESI+): m/z 341.1 (M+H)

Example 24. Additional Synthesis of Left-Hand-Side (LHS) Heterocyclic Analogs; Synthesis of Intermediate N-((1S,3R)-3-aminocyclohexyl)-N-ethyl-1H-indole-2-carboxamide (4)

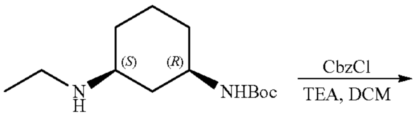

2

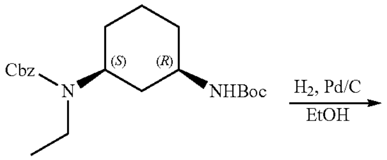

94

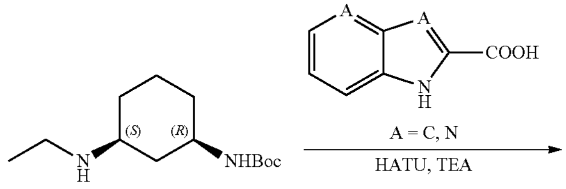

2'

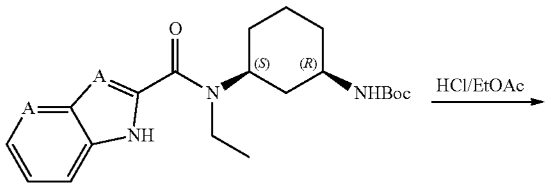

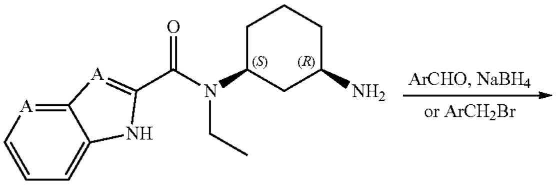

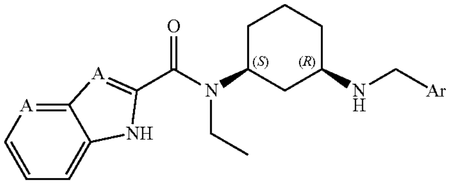

compounds

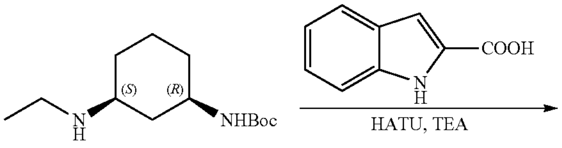

2'

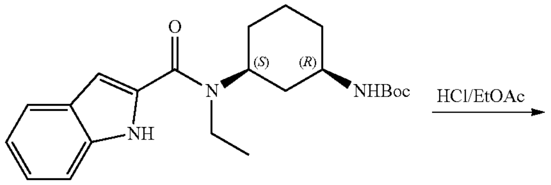

3

-continued

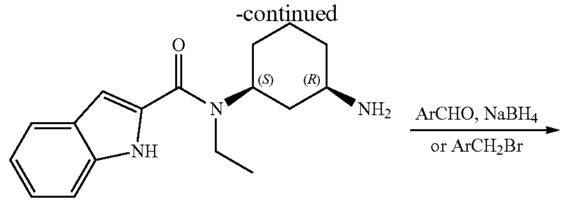

4

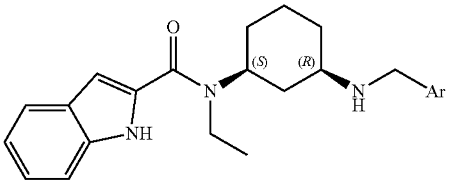

compounds

In this route, two steps (from Compound 2 to Compound 2') were carried out for purification.

General procedure for preparation of compound 94: To a solution of compound 2 (7.7 g, 31.7 mmol, 1 eq) in 150 mL of DCM was added $Et_3N$ (9.6 g, 95 mmol, 13.2 mL, 3 eq) and CbzCl (6.5 g, 38 mmol, 5.4 mL, 1.2 eq) at 0° C. The mixture was stirred at 15° C. for 12 hours. The reaction mixture was concentrated under reduced pressure to remove solvent. The residue was purified by silica gel chromatography (column height: 250 mm, diameter: 100 mm, 100-200 mesh silica gel, eluting with a gradient of petroleum ether: ethyl acetate=30:1-5:1) to give 3.2 g of compound 94 (4.5 mmol, 14% yield, 53.3% purity) as colorless oil.

General procedure for preparation of compound 2': To a solution of compound 94 (1 g, 2.7 mmol, 1 eq) in 15 mL of MeOH was added Pd/C (1 g, 10% purity) under $N_2$. The suspension was degassed under vacuum and purged with $H_2$ several times. The mixture was stirred under $H_2$ (15 psi) at 15° C. for 2 hours. The reaction mixture was filtered and filtrate was concentrated under reduced pressure to give 0.79 g of crude compound 2' as colorless oil which was used into subsequent steps without further purification.

General procedure for preparation of compound 3: A mixture of compound 2' (3.0 g, 12.4 mmol, 1 eq), 1H-indole-2-carboxylic acid (2.0 g, 12.4 mmol, 1 eq), HATU (4.7 g, 12.4 mmol, 1 eq), TEA (2.5 g, 24.8 mmol, 3.5 mL, 2 eq) in 40 mL of DMF was degassed and purged with $N_2$ three times. The mixture was stirred at 15° C. for 2 hours under $N_2$ atmosphere. The reaction mixture was partitioned between 50 mL of water and 60 mL of EtOAc. The organic phase was separated, washed four times with 100 mL of water and 30 mL of brine, dried over $Na_2SO_4$, filtered and concentrated under reduced pressure to give a residue which was purified by column chromatography ($SiO_2$, eluting with petroleum ether:ethyl acetate=10:1 to 4:1) to give 1.4 g of crude compound 3 as a light yellow solid.

General procedure for preparation of compound 4: A mixture of compound 3 (0.7 g, 1.8 mmol, 1 eq) in 10 mL of HCl/EtOAc (4 M) was stirred at 15° C. for 0.5 hour. The mixture was evaporated under reduced pressure to give 0.47 g of compound 4 (1.5 mmol, 80% yield, HCl salt) as a white solid.

Example 25. Synthesis of Aldehyde Intermediates A-1 and A-2

General Procedure for Preparation of Aldehyde A-1:

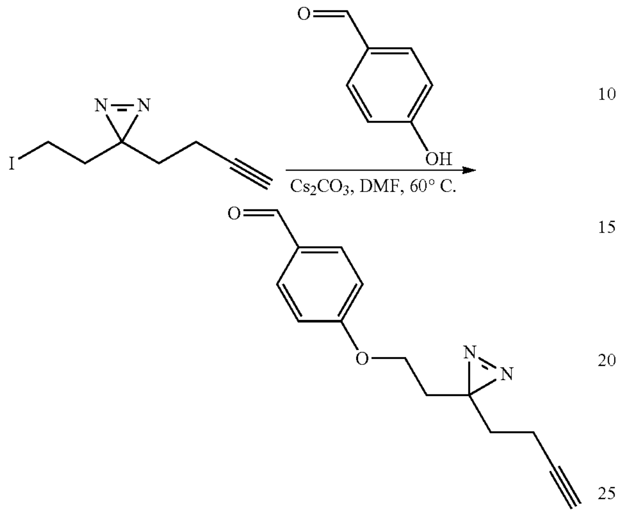

A-1

To a mixture of 3-(but-3-yn-1-yl)-3-(2-iodoethyl)-3H-diazirine (70 mg, 282 μmol, 1 eq) and 4-hydroxybenzaldehyde (34.5 mg, 282 μmol, 1 eq) in 1 mL of DMF was added $Cs_2CO_3$ (276 mg, 847 μmol, 3 eq) in one portion at 15° C. under $N_2$. The mixture was stirred at 60° C. for 12 hours. The residue was poured into 2 mL water. The aqueous phase was extracted with three 1 mL portions of ethyl acetate. The combined organic phases were washed twice with 2 mL of brine, dried with anhydrous $Na_2SO_4$, filtered and concentrated in vacuo to give 40 mg of crude aldehyde A-1 as yellow oil which was used into the next step without further purification.

General Procedure for Preparation of Aldehyde A-2:

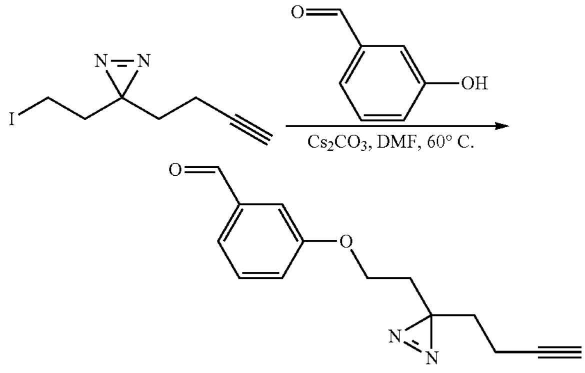

A-2

To a mixture of 3-(but-3-yn-1-yl)-3-(2-iodoethyl)-3H-diazirine (70 mg, 282 μmol, 1 eq) and 3-hydroxybenzaldehyde (34.5 mg, 282 μmol, 1 eq) in 1 mL of DMF was added $Cs_2CO_3$ (276 mg, 847 μmol, 3 eq) in one portion at 15° C. under $N_2$. The mixture was stirred at 60° C. for 12 hours.

The reaction mixture was diluted with 3 mL of $H_2O$ and extracted three times with 9 mL of EtOAc. The combined organic layers were washed twice with 6 mL of brine, dried over $Na_2SO_4$, filtered and concentrated under reduced pressure to give a residue. The residue was purified by prep-TLC ($SiO_2$, eluting with petroleum ether:ethyl acetate=3:1) to give 40 mg of crude A-2 as colorless oil.

Example 26. Synthesis of Aldehyde Intermediate A-3

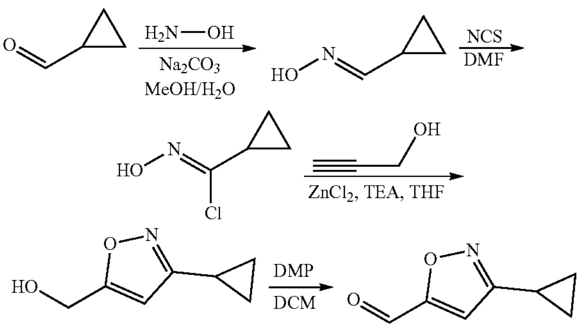

A-3

General procedure for preparation of cyclopropanecarbaldehyde oxime: A mixture of cyclopropanecarboxaldehyde (1.0 g, 14.3 mmol, 1.1 mL, 1.0 eq) in 25 mL of MeOH and 25 mL of water was cooled to 0° C., then $NH_2OH.HCl$ (1.2 g, 17.1 mmol, 1.2 eq), $Na_2CO_3$ (907 mg, 8.6 mmol, 0.6 eq) were added. The mixture was stirred at 12° C. for 12 hours under $N_2$ atmosphere. It was concentrated under reduced pressure to remove the MeOH and the remaining aqueous portion was extracted twice with 50 mL of EtOAc. The combined organic layers were washed with brine, dried over $Na_2SO_4$, filtered and evaporated under reduced pressure to give 900 mg of crude cyclopropanecarbaldehyde oxime as a white solid.

General procedure for preparation of N-hydroxycyclopropanecarbimidoyl chloride: To a mixture of cyclopropanecarbaldehyde oxime (900 mg, 10.6 mmol, 1.0 eq) in 15 mL of DMF was added NCS (1.6 g, 11.6 mmol, 1.1 eq) at 40° C., then the mixture was stirred at 40° C. for 2 hours under $N_2$ atmosphere. The reaction mixture was partitioned between 20 mL of water and 25 mL of EtOAc. The organic phase was separated, washed three times with 30 mL of water and 10 mL of brine, dried over $Na_2SO_4$, filtered and concentrated under reduced pressure to give 1.0 g of crude N-hydroxycyclopropanecarbimidoyl chloride as a colorless liquid.

General procedure for preparation of (3-cyclopropylisoxazol-5-yl)methanol: A mixture of prop-2-yn-1-ol (1.3 g, 23 mmol, 1.3 mL, 3.0 eq) in 15 mL of THF was cooled to 0° C., then N-hydroxycyclopropanecarbimidoyl chloride (900 mg, 7.5 mmol, 1.0 eq), $ZnCl_2$ (2.1 g, 15 mmol, 705 μL, 2.0 eq), TEA (2.7 g, 26 mmol, 3.7 mL, 3.5 eq) were added successively at that temperature. The mixture was stirred at 30° C. for 12 hour under $N_2$ atmosphere. The reaction mixture was partitioned between 15 mL of water and 15 mL of EtOAc and the mixture was filtered. The organic phase was separated, washed with 15 mL of brine, dried over $Na_2SO_4$, filtered and concentrated under reduced pressure to give 1.0 g of crude (3-cyclopropylisoxazol-5-yl)methanol as a light yellow liquid General procedure for preparation of aldehyde A-3: To a mixture of (3-cyclopropylisoxazol-5-yl) methanol (50.0 mg, 359 μmol, 1.0 eq) in 2 mL of DCM was added DMP (229 mg, 539 μmol, 167 μL, 1.5 eq). The mixture was stirred at 15° C. for 2 hours under $N_2$ atmosphere. The reaction solution containing A-3 was used directly into the next step without purification.

Example 27. Synthesis of Aldehyde Intermediates A-4 and A-5

General Procedure for Preparation of Aldehyde A-4:

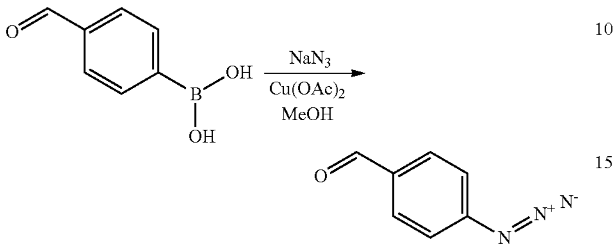

A-4

To a mixture of (4-formylphenyl)boronic acid (200 mg, 1.3 mmol, 1.0 eq) in 5.0 mL of MeOH was added $Cu(OAc)_2$ (24.2 mg, 133 μmol, 0.1 eq), $NaN_3$ (130 mg, 2.0 mmol, 1.5 eq) in one portion at 15° C. under $N_2$. The mixture was stirred at 15° C. for 10 min, then heated to 55° C. and stirred for 12 hours. The reaction mixture was filtered and concentrated under reduced pressure to give a residue. The residue was purified by prep-TLC ($SiO_2$, eluting with petroleum ether:ethyl acetate=2:1) to give 100 mg of 4-azidobenzaldehyde (A-4) (680 μmol, 51% yield) obtained as yellow oil.

General Procedure for Preparation of Aldehyde A-5:

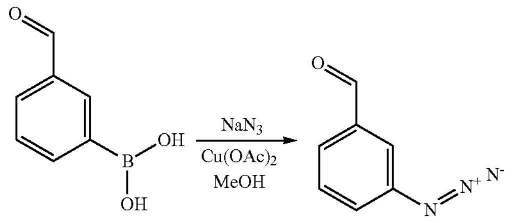

A-5

To a mixture of (3-formylphenyl)boronic acid (500 mg, 3.3 mmol, 1.0 eq) in 10 mL of MeOH was added $NaN_3$ (325 mg, 5.0 mmol, 1.5 eq) $Cu(OAc)_2$ (61 mg, 333 μmol, 0.1 eq) in one portion at 15° C. under $N_2$. The mixture was stirred at 15° C. for 10 min, then heated to 55° C. and stirred for 12 hours. The reaction mixture was quenched by addition 2 mL of $H_2O$ at 15° C. and extracted three times with 6 mL of DCM. The combined organic layers were washed twice with 6 mL of brine, dried over $Na_2SO_4$, filtered and concentrated under reduced pressure to give a residue. The residue was purified by prep-TLC ($SiO_2$, eluting with petroleum ether: ethyl acetate=2:1) to give 360 mg of aldehyde A-5 (2.5 mmol, 74% yield) as yellow oil.

Example 28. Synthesis of Aldehyde Intermediate A-6

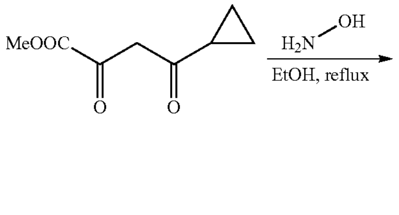

-continued

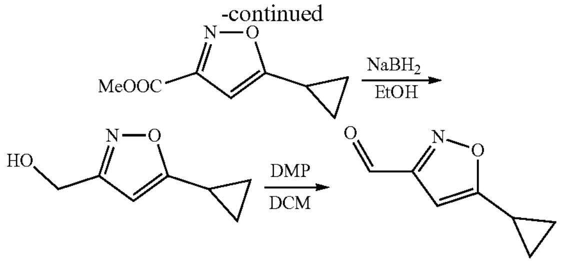

A-6

General procedure for preparation of methyl 5-cyclopropylisoxazole-3-carboxylate: A mixture of methyl 4-cyclopropyl-2,4-dioxo-butanoate (900 mg, 5.3 mmol, 1.0 eq), hydroxylamine (1.1 g, 16 mmol, 3.0 eq, HCl salt) in 10 mL of EtOH was stirred at 70° C. for 1 hour. The reaction mixture was concentrated under reduced pressure to give an oil. The oil was diluted with 10 mL of water and extracted twice with 16 mL of EtOAc. The combined organic layers were washed with 10 mL of brine, dried over $Na_2SO_4$, filtered and evaporated under reduced pressure to give a colorless oil which was purified by column chromatography ($SiO_2$, eluting with a gradient of petroleum ether:ethyl acetate=100:1 to 20:1) to give 175 mg of methyl 5-cyclopropylisoxazole-3-carboxylate (1.05 mmol, 20% yield) as a colorless oil.

General procedure for preparation of (5-cyclopropylisoxazol-3-yl)methanol: To a mixture of methyl 5-cyclopropylisoxazole-3-carboxylate (175 mg, 1.1 mmol, 1.0 eq) in 2 mL of EtOH was added $NaBH_4$ (99 mg, 2.6 mmol, 2.5 eq) at 0° C. and then the mixture was stirred at 15° C. for 12 hours. The reaction mixture was quenched by 10 mL of $H_2O$, then concentrated under reduced pressure and extracted twice with 20 mL of EtOAc. The combined organic layers were washed with 10 mL of brine, dried over $Na_2SO_4$, filtered and concentrated under reduced pressure to give 106 mg of crude (5-cyclopropylisoxazol-3-yl)methanol as a colorless oil.

General procedure for preparation of aldehyde A-6: To a mixture of (5-cyclopropylisoxazol-3-yl)methanol (20.0 mg, 143.7 μmol, 1.0 eq) in 1.0 mL of DCM was added DMP (61 mg, 144 μmol, 45 μL, 1.0 eq) and the mixture was stirred at 15° C. for 2.5 hours. Another portion of DMP (61 mg, 144 μmol, 45 μL, 1.0 eq) was added and then the mixture was stirred at 15° C. for 11.5 hours. The crude product 5-cyclopropylisoxazole-3-carbaldehyde A-6 in the solvent was used into the subsequent steps without further purification.

Example 29. Synthesis of Aldehyde Intermediate A-7

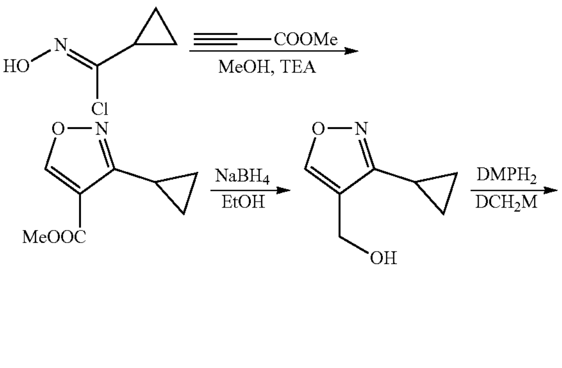

-continued

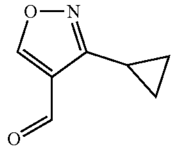

A-7

General procedure for preparation of methyl 3-cyclopropylisoxazole-4-carboxylate: A mixture of methyl propiolate (774 mg, 9.2 mmol, 766 μL, 1.0 eq), TEA (1.9 g, 18.4 mmol, 2.6 mL, 2.0 eq) in 10 mL of MeOH was cooled to 0° C. N-hydroxycyclopropanecarboximidoyl chloride (1.1 g, 9.2 mmol, 1.0 eq) in 5 mL of MeOH was added dropwise, then the mixture was stirred at 14° C. for 12 hours under $N_2$ atmosphere. The mixture was evaporated under reduced pressure and the resulting residue was diluted with 15 mL of EtOAc, washed with 15 mL of 1N HCl, 15 mL of saturated aqueous $NaHCO_3$ and 15 mL of brine, dried over $Na_2SO_4$, filtered and evaporated under reduced pressure to give 0.6 g of crude methyl 3-cyclopropylisoxazole-4-carboxylate as light-yellow liquid.

General procedure for preparation of (3-cyclopropylisoxazol-4-yl)methanol: To a mixture of methyl 3-cyclopropylisoxazole-4-carboxylate (500 mg, 3.0 mmol, 1.0 eq) in 5 mL of EtOH cooled to 0° C., was added in portions $NaBH_4$ (283 mg, 7.5 mmol, 2.5 eq), then the mixture was allowed to warm to 15° C. gradually and stirred for 12 hours under $N_2$ atmosphere. It was quenched by adding 5 mL of water, and then concentrated under reduced pressure. The remaining aqueous layer was extracted three times with 15 mL of EtOAc and the combined the organic layers were washed with 10 mL of brine, dried over $Na_2SO_4$, filtered and evaporated under reduced pressure to give 0.3 g of crude (3-cyclopropylisoxazol-4-yl)methanol as colorless liquid.

General procedure for the preparation of aldehyde A-7: A mixture of (3-cyclopropylisoxazol-4-yl)methanol (120 mg, 862 μmol, 1.0 eq) in 2 mL of DCM was added DMP (549 mg, 1.3 mmol, 400 μL, 1.5 eq) in portions at 15° C. and the mixture was stirred at 15° C. for 1 hour. The reaction mixture containing A-7 was used directly in the subsequent reaction step.

Example 30. Synthesis of N-((1S,3R)-3-((4-(2-(3-(but-3-yn-1-yl)-3H-diazirin-3-yl)ethoxy)benzyl)amino)cyclohexyl)-N-ethyl-1H-indole-2-carboxamide (Compound 425)

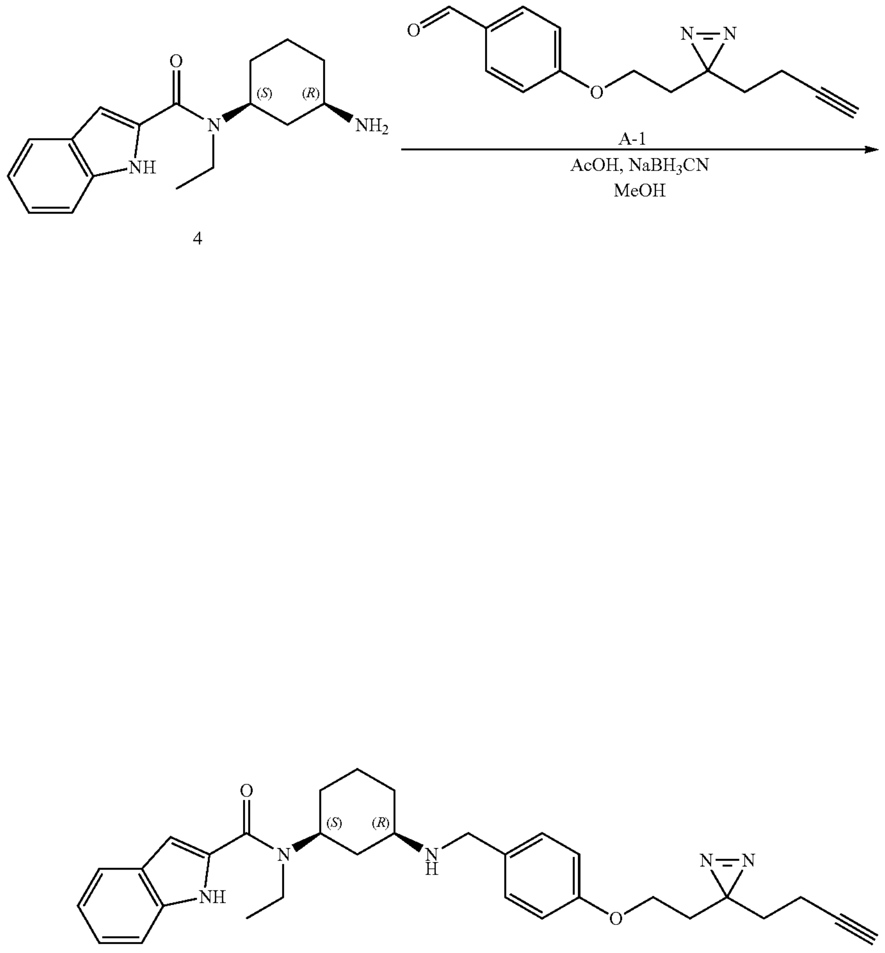

4 compound 425

To a solution of compound 4 (40.0 mg, 124 μmol, 1.0 eq, HCl salt) in 1 mL of MeOH was added 4-[2-(3-but-3-ynyldiazirin-3-yl)ethoxy]benzaldehyde A-1 (36.1 mg, 149 μmol, 1.2 eq), AcOH (746 μg, 12.4 μmol, 0.1 eq) at 15° C. After addition, the mixture was stirred at this temperature for 30 min, and then $NaBH_3CN$ (7.8 mg, 124 μmol, 1 eq) was added at 15° C. The resulting mixture was stirred at 15° C. for 12 hours. The reaction mixture was filtered and mother liquor was concentrated under reduced pressure to give a residue which was purified by prep-HPLC (TFA condition) to give 16.8 mg of compound 425 (26.5 μmol, 21% yield, 98.5% purity, TFA salt) as a light yellow solid.

Compound 425

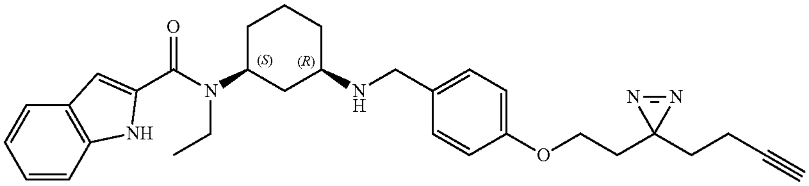

$^1$H NMR (400 MHz, METHANOL-$d_4$) δ ppm 7.62 (d, J=7.9 Hz, 1H), 7.45-7.38 (m, 3H), 7.25-7.19 (m, 1H), 7.07 (t, J=7.5 Hz, 1H), 6.98 (br d, J=8.6 Hz, 2H), 6.79 (br s, 1H), 4.34 (br s, 1H), 4.18 (s, 2H), 3.87-3.83 (m, 2H), 3.68 (br s, 2H), 3.24 (br s, 1H), 2.33 (br d, J=11.2 Hz, 1H), 2.26 (t, J=2.6 Hz, 1H), 2.18 (br d, J=11.2 Hz, 1H), 2.05 (dt, J=2.8, 7.4 Hz, 3H), 1.91-1.83 (m, 4H), 1.67 (t, J=7.4 Hz, 2H), 1.41 (br d, J=11.2 Hz, 1H), 1.38-1.29 (m, 4H)

LCMS (ESI+): m/z 512.2 (M+H)

The following compounds were prepared analogously:

Compound 426

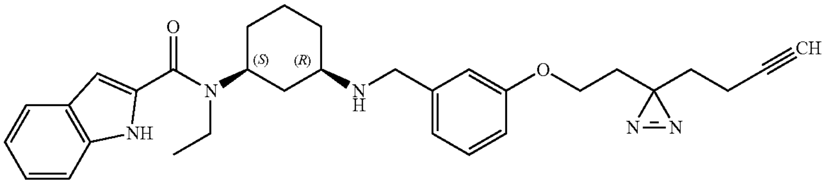

$^1$H NMR (400 MHz, METHANOL-$d_4$) δ ppm 7.62 (d, J=8.2 Hz, 1H), 7.45-7.35 (m, 2H), 7.21 (d, J=7.1 Hz, 1H), 7.09-6.99 (m, 4H), 6.80 (br d, J=9.0 Hz, 1H), 4.34 (s, 1H), 4.23 (s, 2H), 3.90-3.83 (m, 2H), 3.66 (br s, 2H), 3.36-3.32 (m, 1H), 2.35 (br d, J=10.8 Hz, 1H), 2.26 (s, 1H), 2.22 (br s, 1H), 2.05 (dt, J=2.6, 7.5 Hz, 3H), 1.97-1.85 (m, 4H), 1.70-1.64 (m, 2H), 1.51-1.38 (m, 2H), 1.34 (br t, J=6.7 Hz, 4H)

LCMS (ESI+): m/z 512.2 (M+H)

Compound 427

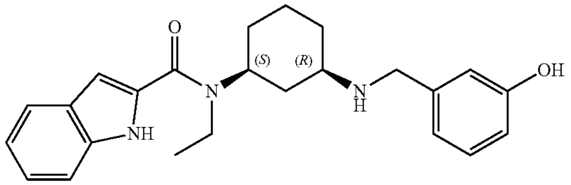

$^{1}H$ NMR (400 MHz, METHANOL-$d_4$) δ ppm 7.63 (d, J=7.95 Hz, 1H) 7.44 (dd, J=8.31, 0.73 Hz, 1H) 7.17-7.31 (m, 2H) 7.03-7.11 (m, 1H) 6.90-6.96 (m, 2H) 6.86 (dt, J=8.74, 1.31 Hz, 1H) 6.79 (br s, 1H) 4.22-4.48 (m, 1H) 4.11-4.22 (m, 2H) 3.67 (br s, 2H) 3.26 (br s, 1H) 2.34 (br d, J=11.25 Hz, 1H) 2.19 (br d, J=10.27 Hz, 1H) 1.97-2.09 (m, 1H) 1.88-1.97 (m, 2H) 1.84 (br s, 1H) 1.37-1.53 (m, 2H) 1.34 (br t, J=6.97 Hz, 3H)

LCMS (ESI+): m/z 392.2 (M+H)

Compound 428

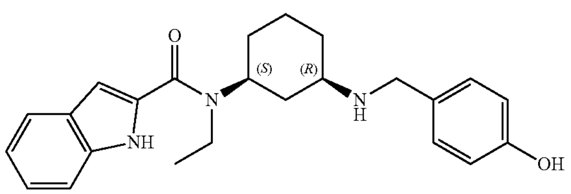

$^{1}H$ NMR (400 MHz, METHANOL-$d_4$) δ ppm 7.65 (d, J=7.9 Hz, 1H), 7.46 (d, J=8.3 Hz, 1H), 7.33 (d, J=8.6 Hz, 2H), 7.24 (dt, J=1.0, 7.6 Hz, 1H), 7.12-7.07 (m, 1H), 6.89-6.85 (m, 2H), 6.81 (br s, 1H), 4.36 (br s, 1H), 4.16 (s, 2H), 3.69 (br s, 2H), 3.29-3.22 (m, 1H), 2.35 (br d, J=11.4 Hz, 1H), 2.20 (br d, J=11.2 Hz, 1H), 2.09-2.01 (m, 1H), 1.99-1.80 (m, 3H), 1.54-1.41 (m, 2H), 1.36 (br t, J=7.0 Hz, 4H)

LCMS (ESI+): m/z 392.2 (M+H)

Compound 429

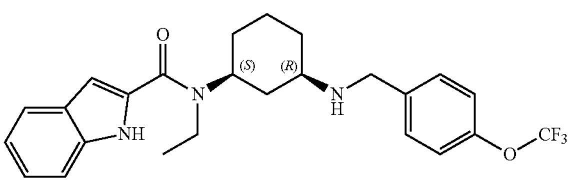

$^{1}H$ NMR (400 MHz, METHANOL-$d_4$) δ ppm 7.57-7.64 (m, 3H) 7.42-7.46 (m, 1H) 7.37 (br d, J=8.38 Hz, 2H) 7.22 (td, J=7.61, 1.10 Hz, 1H) 7.04-7.10 (m, 1H) 6.80 (br s, 1H) 4.23-4.45 (m, 3H) 3.69 (br s, 2H) 3.34 (br s, 1H) 2.36 (br d, J=11.47 Hz, 1H) 2.21 (br d, J=11.69 Hz, 1H) 2.02-2.09 (m, 1H) 1.78-2.01 (m, 3H) 1.38-1.56 (m, 2H) 1.34 (br t, J=6.95 Hz, 3H)

LCMS (ESI+): m/z 460.2 (M+H)

Compound 430

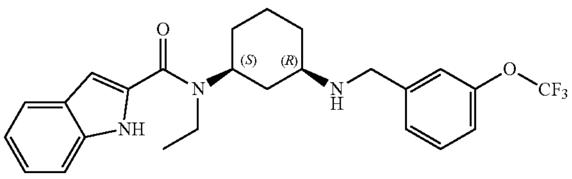

$^{1}H$ NMR (400 MHz, METHANOL-$d_4$) δ ppm 7.55-7.64 (m, 2H) 7.46-7.53 (m, 2H) 7.42-7.45 (m, 1H) 7.39 (br d, J=8.16 Hz, 1H) 7.22 (td, J=7.61, 1.10 Hz, 1H) 7.03-7.10 (m, 1H) 6.80 (br s, 1H) 4.25-4.44 (m, 3H) 3.69 (br s, 2H) 3.33 (br s, 1H) 2.36 (br d, J=11.69 Hz, 1H) 2.22 (br d, J=12.13 Hz, 1H) 2.02-2.11 (m, 1H) 1.80-2.01 (m, 3H) 1.38-1.56 (m, 2H) 1.35 (br t, J=6.95 Hz, 3H)

LCMS (ESI+): m/z 460.2 (M+H)

Compound 431

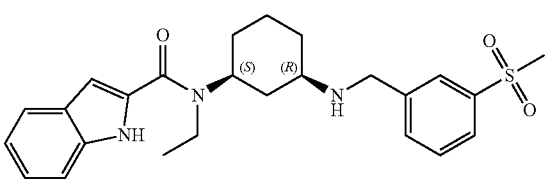

$^{1}H$ NMR (400 MHz, METHANOL-$d_4$) δ ppm 8.14 (s, 1H), 8.05 (br s, 1H), 7.84 (br d, J=7.7 Hz, 1H), 7.73 (br d, J=7.1 Hz, 1H), 7.62 (d, J=7.9 Hz, 1H), 7.44 (d, J=8.4 Hz, 1H), 7.22 (t, J=7.6 Hz, 1H), 7.10-7.04 (m, 1H), 6.80 (br s, 1H), 4.39 (br s, 2H), 3.68 (br s, 2H), 3.34 (br s, 1H), 3.13 (s, 3H), 2.37 (br d, J=10.4 Hz, 1H), 2.23 (br s, 1H), 2.10-1.81 (m, 4H), 1.50-1.39 (m, 2H), 1.34 (br s, 3H)

LCMS (ESI+): m/z 454.2 (M+H)

Compound 432

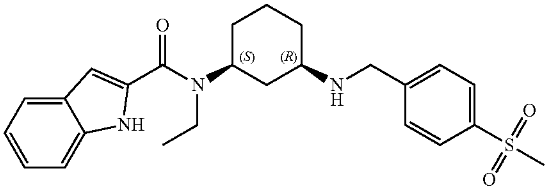

$^{1}H$ NMR (400 MHz, METHANOL-$d_4$) δ ppm 8.05 (d, J=8.31 Hz, 2H) 7.76 (d, J=8.31 Hz, 2H) 7.63 (d, J=8.07 Hz, 1H) 7.44 (dd, J=8.31, 0.86 Hz, 1H) 7.19-7.27 (m, 1H) 7.22 (dd, J=8.25, 7.09, 1.04 Hz, 1H) 7.05-7.11 (m, 1H) 6.81 (br s, 1H) 4.40 (s, 3H) 3.70 (br s, 2H) 3.34 (br s, 1H) 3.14 (s, 3H) 2.37 (br d, J=10.64 Hz, 1H) 2.23 (br d, J=11.00 Hz, 1H) 2.02-2.13 (m, 1H) 1.80-2.01 (m, 1H) 1.80-2.01 (m, 2H) 1.41-1.57 (m, 2H) 1.35 (br t, J=6.97 Hz, 3H)

LCMS (ESI+): m/z 454.2 (M+H)

Compound 433

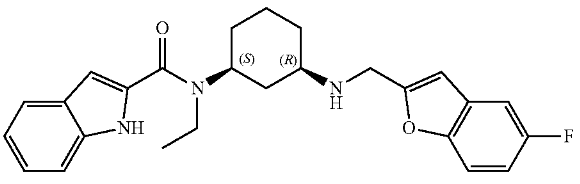

$^{1}H$ NMR (400 MHz, METHANOL-$d_4$) δ ppm 7.59 (br d, J=7.06 Hz, 1H) 7.40-7.53 (m, 2H) 7.33 (br s, 1H) 7.18-7.26 (m, 1H) 7.01-7.16 (m, 3H) 6.78 (br s, 1H) 4.51 (br d, J=4.41 Hz, 2H) 4.36 (br s, 1H) 3.67 (br s, 2H) 3.23-3.29 (m, 1H) 2.35 (br s, 1H) 2.19 (br s, 1H) 1.81-2.09 (m, 4H) 1.44 (br s, 2H) 1.33 (br d, J=5.73 Hz, 3H)

LCMS (ESI+): m/z 434.2 (M+H)

Compound 434

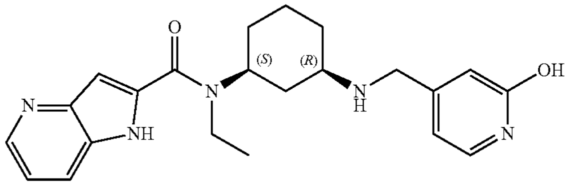

$^1H$ NMR (400 MHz, CHLOROFORM-d) δ ppm 10.61-10.39 (m, 1H), 8.52 (d, J=3.6 Hz, 1H), 7.79 (d, J=8.0 Hz, 1H), 7.31 (s, 1H), 7.21-7.18 (m, 1H), 7.08-6.90 (m, 1H), 6.57 (s, 1H), 6.29 (d, J=6.8 Hz, 2H), 4.56 (br s, 1H), 3.72-3.61 (m, 4H), 2.66 (br s, 1H), 2.15-2.13 (m, 1H), 2.00-1.90 (m, 3H), 1.64-1.62 (m, 1H), 1.52-1.38 (m, 6H), 1.09-1.07 (m, 1H)

LCMS (ESI+): m/z 394.2 (M+H)

Compound 435

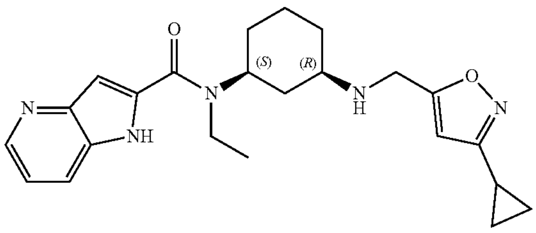

$^1H$ NMR (400 MHz, METHANOL-$d_4$) δ ppm 8.68 (d, J=5.73 Hz, 1H) 8.62 (d, J=8.38 Hz, 1H) 7.78 (dd, J=8.38, 5.73 Hz, 1H) 7.11 (s, 1H) 6.37 (br s, 1H) 4.47 (br s, 2H) 4.09 (br s, 1H) 3.62 (br d, J=7.06 Hz, 2H) 2.37 (br d, J=10.58 Hz, 1H) 1.86-2.24 (m, 6H) 1.24-1.58 (m, 6H) 1.02-1.12 (m, 2H) 0.81 (br s, 2H)

LCMS (ESI+): m/z 408.2 (M+H)

Compound 436

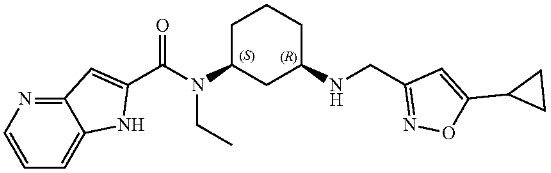

$^1H$ NMR (400 MHz, METHANOL-$d_4$) δ ppm 8.65 (d, J=5.7 Hz, 1H), 8.54 (d, J=8.2 Hz, 1H), 7.73 (dd, J=5.6, 8.3 Hz, 1H), 7.08 (br s, 1H), 6.19 (s, 1H), 4.35 (s, 2H), 4.11 (br s, 1H), 3.63 (br d, J=6.6 Hz, 2H), 2.37 (br d, J=10.4 Hz, 1H), 2.22-1.98 (m, 4H), 1.93 (br s, 2H), 1.43 (br s, 2H), 1.32 (t, J=7.1 Hz, 3H), 1.13 (br dd, J=2.2, 8.2 Hz, 2H), 0.97-0.97 (m, 1H), 0.93 (br s, 2H)

LCMS (ESI+): m/z 408.3 (M+H)

Compound 437

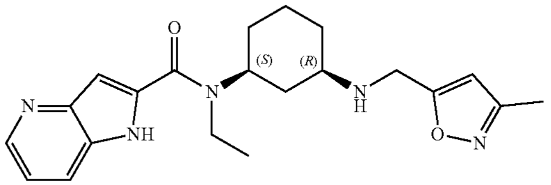

$^1H$ NMR (400 MHz, METHANOL-$d_4$) δ ppm 8.67 (d, J=6 Hz, 1H) 8.60 (d, J=8.4 Hz, 1H) 7.79-7.76 (m, 1H) 7.12 (s, 1H) 6.52 (s, 1H) 4.50 (s, 2H) 4.11 (s, 1H) 3.62 (d, J=6 Hz, 2H) 3.53 (s, 1H) 2.38 (d, J=11.6 Hz, 1H) 2.31 (s, 3H) 2.15-1.95 (m, 5H) 1.42 (s, 2H) 1.32 (t, J=7.2 Hz, 3H)

LCMS (ESI+): m/z 382.2 (M+H)

Compound 438

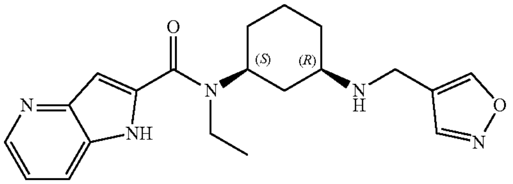

$^1H$ NMR (400 MHz, METHANOL-$d_4$) δ=8.91 (br s, 1H), 8.70-8.68 (d, J=5.6 Hz, 1H), 8.63-8.58 (m, 2H), 7.80-7.77 (m, 1H), 7.13 (s, 1H), 4.29 (br s, 1H), 4.15-4.11 (m, 2H), 3.65-3.64 (m, 2H), 2.42-2.39 (m, 1H), 2.19-1.95 (m, 6H), 1.45-1.44 (m, 2H), 1.35-1.32 (m, 3H)

LCMS (ESI+): m/z 368.1 (M+H)

Compound 439

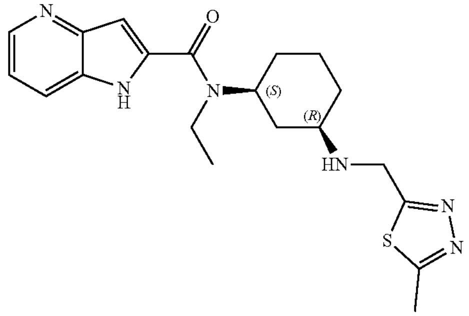

$^1H$ NMR (400 MHz, METHANOL-$d_4$) δ=8.69 (br d, J=5.5 Hz, 1H), 8.61 (d, J=8.3 Hz, 1H), 7.78 (dd, J=5.7, 8.3 Hz, 1H), 7.16 (s, 1H), 4.83 (s, 2H), 4.15 (br s, 1H), 3.65 (br d, J=6.8 Hz, 2H), 3.54-3.36 (m, 1H), 2.83 (s, 3H), 2.45 (br s, 1H), 2.27-2.01 (m, 3H), 1.96 (br d, J=7.6 Hz, 2H), 1.50 (br s, 2H), 1.34 (br t, J=7.0 Hz, 3H)

LCMS (ESI+): m/z 399.1 (M+H)

Compound 440

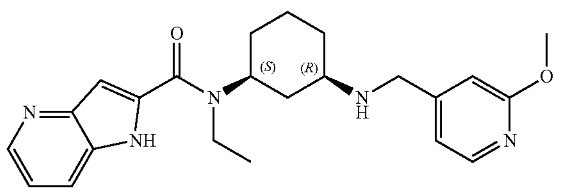

$^{1}$H NMR (400 MHz, METHANOL-$d_4$) δ ppm 8.68 (d, J=5.81 Hz, 1H) 8.63 (d, J=7.74 Hz, 1H) 8.21 (br d, J=4.41 Hz, 1H) 7.79 (t, J=6.62 Hz, 1H) 7.03-7.17 (m, 2H) 6.96 (br s, 1H) 4.28 (br s, 2H) 4.04-4.22 (m, 1H) 3.93 (s, 3H) 3.63 (br d, J=6.39 Hz, 2H) 3.33-3.43 (m, 1H) 2.41 (br d, J=10.80 Hz, 1H) 2.19 (br s, 2H) 1.74-2.09 (m, 2H) 1.38-1.60 (m, 2H) 1.32 (br t, J=6.73 Hz, 3H)

LCMS (ESI+): m/z 408.3 (M+H)

Compound 441

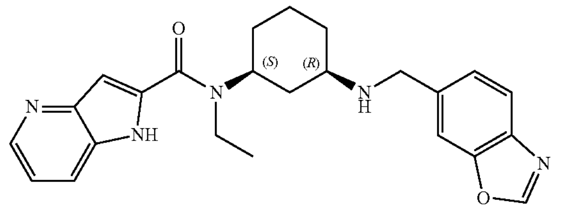

$^{1}$H NMR (400 MHz, CHLOROFORM-d) δ ppm 9.57 (br s, 1H), 8.52 (dd, J=1.1, 4.6 Hz, 1H), 8.06 (s, 1H), 7.77-7.70 (m, 2H), 7.59 (s, 1H), 7.35-7.31 (m, 1H), 7.21 (dd, J=4.4, 8.3 Hz, 1H), 7.12-6.84 (m, 1H), 4.56 (br s, 1H), 3.97 (s, 2H), 3.84-3.51 (m, 2H), 2.74 (br t, J=11.0 Hz, 1H), 2.18 (br d, J=12.3 Hz, 1H), 2.07-1.98 (m, 3H), 1.91 (br d, J=13.6 Hz, 1H), 1.67-1.52 (m, 2H), 1.50-1.24 (m, 4H), 1.18-1.06 (m, 1H)

LCMS (ESI+): m/z 418.2 (M+H)

Compound 442

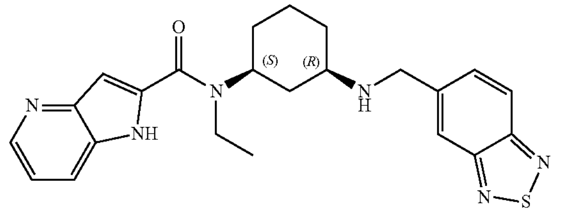

$^{1}$H NMR (400 MHz, METHANOL-$d_4$) δ ppm 8.70 (d, J=5.7 Hz, 1H), 8.63 (d, J=8.3 Hz, 1H), 8.24 (br s, 1H), 8.14 (br d, J=8.9 Hz, 1H), 7.79 (dd, J=5.6, 8.3 Hz, 2H), 7.14 (s, 1H), 4.56-4.49 (m, 2H), 4.17 (br s, 1H), 3.71-3.60 (m, 2H), 3.42 (br s, 1H), 2.48 (br d, J=10.3 Hz, 1H), 2.28 (br s, 1H), 2.13-1.93 (m, 3H), 1.51 (br s, 2H), 1.35 (t, J=7.0 Hz, 3H)

LCMS (ESI+): m/z 435.2 (M+H)

Compound 443

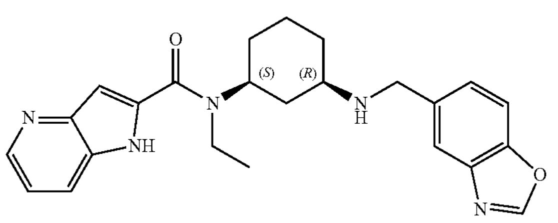

$^{1}$H NMR (400 MHz, CHLOROFORM-d) δ ppm 9.62 (br s, 1H), 8.45 (d, J=4.6 Hz, 1H), 8.01 (s, 1H), 7.71-7.65 (m, 2H), 7.46 (d, J=8.4 Hz, 1H), 7.31 (d, J=8.4 Hz, 1H), 7.13 (dd, J=4.5, 8.3 Hz, 1H), 7.05-6.78 (m, 1H), 4.49 (br s, 1H), 3.89 (s, 2H), 3.76-3.45 (m, 2H), 2.67 (br s, 1H), 2.12 (br d, J=11.5 Hz, 1H), 1.97 (br d, J=11.2 Hz, 1H), 1.85 (br d, J=13.7 Hz, 2H), 1.57-1.45 (m, 2H), 1.41-1.19 (m, 4H), 1.12-1.00 (m, 1H)

LCMS (ESI+): m/z 418.2 (M+H)

Compound 444

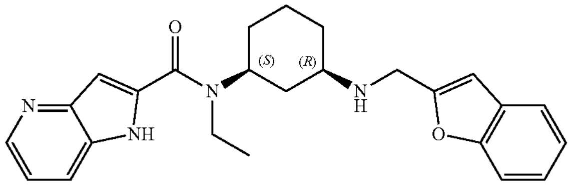

$^{1}$H NMR (400 MHz, METHANOL-$d_4$) δ ppm 8.69 (d, J=5.6 Hz, 1H), 8.62 (d, J=8.3 Hz, 1H), 7.79 (dd, J=5.7, 8.3 Hz, 1H), 7.66 (br d, J=7.6 Hz, 1H), 7.54 (br d, J=6.1 Hz, 1H), 7.38 (br t, J=7.6 Hz, 1H), 7.33-7.27 (m, 1H), 7.13 (s, 1H), 7.07 (br s, 1H), 4.55 (br s, 2H), 4.14 (br s, 1H), 3.69-3.59 (m, 2H), 2.43 (br d, J=11.0 Hz, 1H), 2.29-1.90 (m, 5H), 1.49 (br s, 2H), 1.33 (t, J=7.0 Hz, 3H)

LCMS (ESI+): m/z 417.2 (M+H)

Compound 445

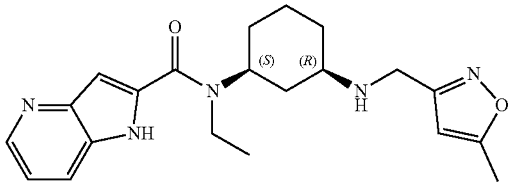

$^{1}$H NMR (400 MHz, METHANOL-$d_4$) δ ppm 8.62 (d, J=5.3 Hz, 1H), 8.47 (d, J=8.2 Hz, 1H), 7.68 (dd, J=5.6, 8.3 Hz, 1H), 7.06 (br s, 1H), 6.27 (s, 1H), 4.37 (s, 2H), 4.18-4.09 (m, 1H), 3.63 (br d, J=5.7 Hz, 2H), 2.45 (s, 3H), 2.38 (br d, J=11.0 Hz, 1H), 2.21-1.89 (m, 5H), 1.43 (br s, 2H), 1.32 (t, J=6.9 Hz, 3H)

LCMS (ESI+): m/z 382.1 (M+H)

Compound 446

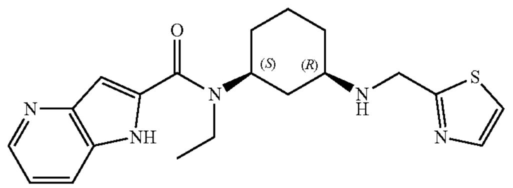

$^1$H NMR (400 MHz, METHANOL-$d_4$) δ ppm 8.69 (d, J=5.6 Hz, 1H) 8.62 (d, J=8 Hz, 2H) 7.91 (s, 1H) 7.81-7.74 (m, 2H) 7.14 (s, 1H) 7.14 (s, 1H) 4.72 (s, 1H) 4.15-4.11 (m, 1H) 3.65 (d, J=6.8 Hz, 2H) 3.41-3.33 (m, 3H) 2.42 (d, J=10.4 Hz, 1H) 2.22-1.96 (m, 5H) 1.49 (s, 2H) 1.34 (t, J=7.2 Hz, 3H)

LCMS (ESI+): m/z 384.2 (M+H)

Compound 447

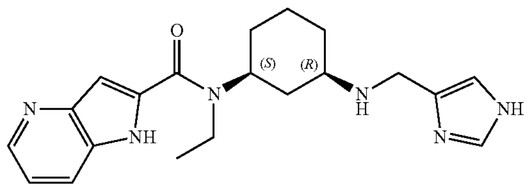

$^1$H NMR (400 MHz, METHANOL-$d_4$) δ ppm 8.69 (d, J=5.2 Hz, 2H) 8.62 (d, J=8.4 Hz, 2H) 7.81-7.78 (m, 1H) 7.66 (m, 1H) 7.13 (m, 1H) 4.46 (s, 2H) 4.16-4.06 (m, 1H) 3.64 (d, J=6.4 Hz, 2H) 3.53 (s, 3H) 2.42 (d, J=10.8 Hz, 1H) 2.22-1.96 (m, 5H) 1.48 (s, 2H) 1.34 (t, J=6.8 Hz, 3H)

LCMS (ESI+): m/z 367.3 (M+H)

Compound 448

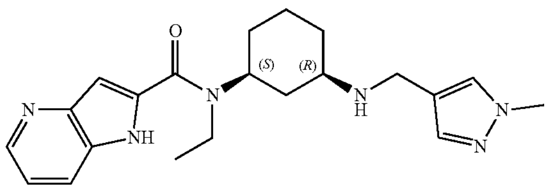

$^1$H NMR (400 MHz, METHANOL-$d_4$) δ ppm 8.70 (d, J=5.6 Hz, 1H) 8.64 (d, J=8.4 Hz, 1H) 7.80 (d, J=5.6, 8 Hz, 1H) 7.72 (s, 1H) 7.14 (s, 1H) 4.18 (s, 1H) 3.64 (d, J=4.8 Hz, 2H) 3.33 (s, 2H) 2.43-2.36 (m, 4H) 2.21-1.95 (m, 1H) 1.44 (s, 2H) 1.34 (t, J=7.2 Hz, 3H)

LCMS (ESI+): m/z 381.2 (M+H)

Compound 449

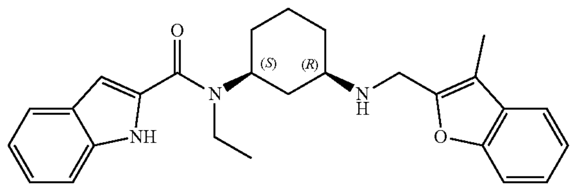

$^1$H NMR (400 MHz, CHLOROFORM-d) δ ppm 9.26 (br s, 1H) 7.59 (br s, 1H) 7.38-7.51 (m, 3H) 7.28-7.32 (m, 1H) 7.21-7.26 (m, 1H) 7.13 (t, J=7.22 Hz, 1H) 6.68 (br s, 1H) 4.53-4.62 (m, 1H) 3.97 (s, 2H) 3.63 (br s, 2H) 2.62-2.79 (m, 1H) 2.09-2.29 (m, 4H) 1.80-2.04 (m, 3H) 1.50-1.69 (m, 4H) 1.24-1.47 (m, 4H) 1.05-1.24 (m, 1H)

LCMS (ESI+): m/z 430.2 (M+H)

Compound 450

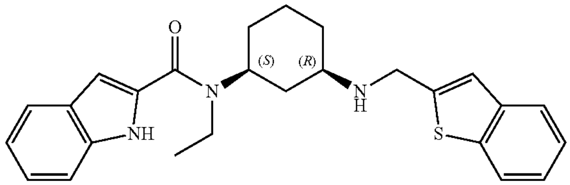

$^1$H NMR (400 MHz, METHANOL-$d_4$) δ ppm 7.80-7.91 (m, 2H) 7.53-7.61 (m, 2H) 7.37-7.47 (m, 3H) 7.18-7.26 (m, 1H) 7.03-7.10 (m, 1H) 6.79 (br s, 1H) 4.56-4.66 (m, 2H) 4.26-4.44 (m, 1H) 3.56-3.79 (m, 2H) 3.33 (br s, 1H) 2.38 (br d, J=10.80 Hz, 1H) 2.21 (br d, J=9.70 Hz, 1H) 1.78-2.09 (m, 4H) 1.39-1.55 (m, 2H) 1.34 (t, J=7.06 Hz, 3H)

LCMS (ESI+): m/z 432.3 (M+H)

Compound 451

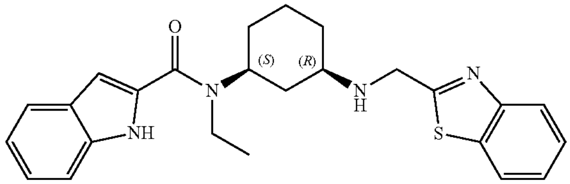

$^1$H NMR (400 MHz, METHANOL-$d_4$) δ ppm 8.05 (t, J=7.17 Hz, 2H) 7.54-7.60 (m, 2H) 7.47-7.53 (m, 1H) 7.44 (d, J=8.38 Hz, 1H) 7.21 (t, J=7.50 Hz, 1H) 7.06 (t, J=7.17 Hz, 1H) 6.80 (br s, 1H) 4.83 (s, 2H) 4.39 (br s, 1H) 3.69 (br s, 2H) 3.40-3.57 (m, 1H) 2.42 (br d, J=11.47 Hz, 1H) 2.24 (br s, 1H) 1.98-2.11 (m, 2H) 1.78-1.97 (m, 2H) 1.49 (br t, J=9.59 Hz, 2H) 1.26-1.42 (m, 3H)

LCMS (ESI+): m/z 433.3 (M+H)

Compound 452

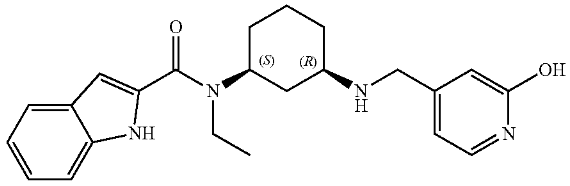

$^1$H NMR (400 MHz, CHLOROFORM-d) δ ppm 9.57 (br s, 1H) 7.59 (d, J=8.0 Hz, 1H) 7.37 (d, J=8.4 Hz, 1H) 7.20-7.26 (m, 1H) 7.04 (m, 1H) 6.67 (br s, 1H) 6.48 (s, 1H) 6.20 (dd, J=1.2, 5.6 Hz, 1H) 4.47 (br t, J=12 Hz, 1H) 3.65-3.46 (m, 4H) 2.58 (m, 1H) 2.07 (br d, J=11.6 Hz, 1H) 1.90-1.82 (m, 3H) 1.51-1.40 (m, 2H) 1.41-1.28 (m, 5H) 1.01-0.98 (m, 1H)

LCMS (ESI+): m/z 393.2 (M+H)

Compound 453

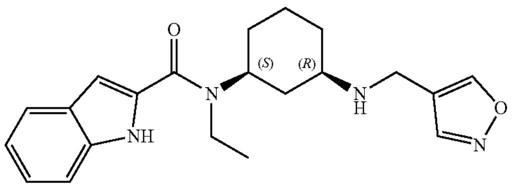

$^1$H NMR (400 MHz, METHANOL-$d_4$) δ ppm 8.91 (s, 1H), 8.57 (s, 1H), 7.66 (d, J=8.4 Hz, 1H), 7.47 (d, J=8.4 Hz, 1H), 7.24 (t, J=7.2 Hz, 1H), 7.09 (t, J=6.8 Hz, 2H), 6.82 (br s, 1H), 4.37-4.27 (m, 3H), 3.70 (br s, 2H), 3.31-3.28 (m, 1H), 2.37 (br d, J=11.2 Hz, 1H), 2.21 (br d, J=11.6 Hz, 1H), 2.08-1.95 (m, 4H), 1.49-1.43 (m, 2H) 1.38-1.35 (t, J=6.8 Hz, 3H)

LCMS (ESI+): m/z 367.2 (M+H)

Compound 454

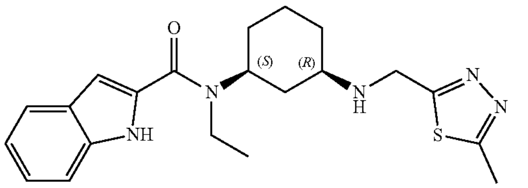

$^1$H NMR (400 MHz, METHANOL-$d_4$) δ ppm 7.66 (br d, J=8.1 Hz, 1H), 7.46 (br d, J=8.2 Hz, 1H), 7.24 (br t, J=7.6 Hz, 1H), 7.13-7.05 (m, 1H), 6.83 (br s, 1H), 4.81 (s, 2H), 4.39 (br s, 1H), 3.69 (br s, 2H), 3.43 (br s, 1H), 2.82 (s, 3H), 2.40 (br d, J=10.3 Hz, 1H), 2.23 (br s, 1H), 2.05 (s, 2H), 1.99-1.82 (m, 2H), 1.49 (br d, J=7.0 Hz, 2H), 1.36 (br t, J=6.8 Hz, 3H)

LCMS (ESI+): m/z 398.1 (M+H)

Compound 455

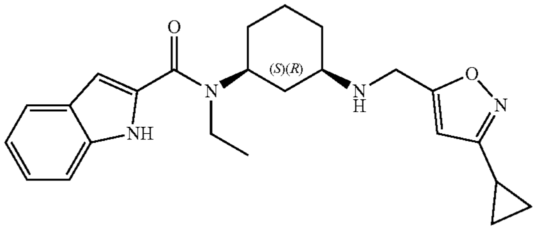

$^1$H NMR (400 MHz, CHLOROFORM-d) δ ppm 9.30 (br s, 1H) 7.60 (br d, J=7.72 Hz, 1H) 7.39 (br d, J=7.28 Hz, 1H) 7.20-7.26 (m, 1H) 7.07 (br t, J=7.17 Hz, 1H) 6.70 (br s, 1H) 5.80 (br s, 1H) 4.40 (br s, 1H) 3.87 (br s, 2H) 3.56 (br s, 2H) 2.66 (br s, 1H) 2.07 (br s, 1H) 1.77-1.95 (m, 4H) 1.54 (br s, 1H) 1.24-1.43 (m, 4H) 1.09 (br s, 1H) 0.94 (br d, J=7.50 Hz, 3H) 0.73 (br s, 2H)

LCMS (ESI+): m/z 407.2 (M+H)

Compound 456

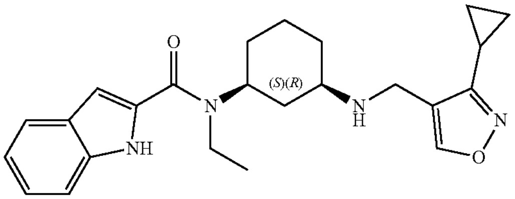

$^1$H NMR (400 MHz, CHLOROFORM-d) δ ppm 9.31 (br s, 1H) 8.15 (s, 1H) 7.60 (d, J=7.94 Hz, 1H) 7.36 (d, J=8.38 Hz, 1H) 7.20-7.25 (m, 1H) 7.04-7.10 (m, 1H) 6.71 (br s, 1H) 4.50 (br t, J=11.80 Hz, 1H) 3.42-3.76 (m, 4H) 2.64 (br s, 1H) 2.09 (br d, J=11.47 Hz, 1H) 1.82-1.97 (m, 3H) 1.71-1.77 (m, 1H) 1.48-1.59 (m, 2H) 1.40 (br dd, J=16.43, 12.46 Hz, 4H) 0.99-1.09 (m, T H) 0.87-0.97 (m, 4H)

LCMS (ESI+): m/z 407.2 (M+H)

Compound 457

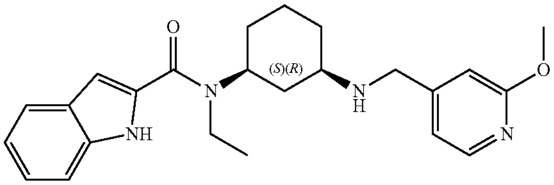

$^1$H NMR (400 MHz, METHANOL-$d_4$) δ ppm 8.21 (br d, J=5.29 Hz, 1H) 7.62 (br d, J=7.94 Hz, 1H) 7.44 (br d, J=8.16 Hz, 1H) 7.22 (t, J=7.61 Hz, 1H) 7.02-7.11 (m, 2H) 6.95 (s, 1H) 6.79 (br s, 1H) 4.30-4.51 (m, 1H) 4.26 (s, 2H) 3.93 (s, 3H) 3.67 (br s, 2H) 3.24-3.30 (m, 1H) 2.36 (br d, J=11.03 Hz, 1H) 2.20 (br s, 1H) 1.79-2.08 (m, 4H) 1.38-1.53 (m, 2H) 1.33 (br t, J=6.62 Hz, 3H)

LCMS (ESI+): m/z 407.2 (M+H)

Compound 458

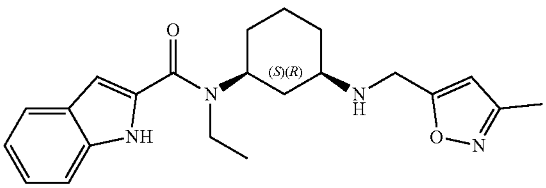

$^1$H NMR (400 MHz, METHANOL-$d_4$) δ ppm 7.63 (d, J=8 Hz, 1H) 7.44 (d, J=8.4 Hz, 1H) 7.22 (t, J=8 Hz, 1H) 7.07 (t, J=8 Hz, 1H) 6.81 (s, 1H) 6.51 (s, 1H) 4.53 (s, 2H) 4.36 (s, 1H) 3.68 (s, 2H) 3.58 (s, 1H) 2.36-2.31 (m, 3H) 2.18 (d, J=10.8 Hz, 1H) 2.04 (d, J=13.2 Hz, 1H) 2.02-1.92 (m, 3H) 1.49-1.42 (m, 2H) 1.38-1.33 (m, 3H)

LCMS (ESI+): m/z 381.2 (M+H)

Compound 459

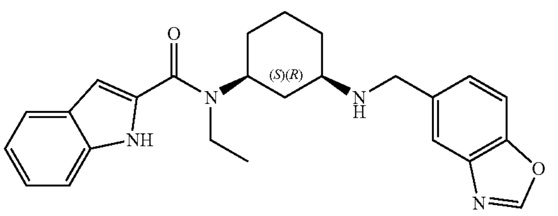

$^1$H NMR (400 MHz, CHLOROFORM-d) δ ppm 9.46 (br s, 1H), 9.53-9.41 (m, 1H), 8.06 (s, 1H), 7.73 (s, 1H), 7.60 (br d, J=7.5 Hz, 1H), 7.50 (d, J=8.3 Hz, 1H), 7.43-7.32 (m, 2H), 7.25-7.21 (m, 1H), 7.10 (t, J=7.5 Hz, 1H), 6.70 (br s, 1H), 4.53 (br t, J=11.9 Hz, 1H), 3.94 (s, 2H), 3.60 (br s, 2H), 2.70 (br s, 1H), 2.15 (br d, J=11.1 Hz, 1H), 2.03-1.95 (m, 1H), 1.92-1.81 (m, 2H), 1.60-1.38 (m, 3H), 1.32 (br s, 3H), 1.16-1.03 (m, 1H)

LCMS (ESI+): m/z 417.2 (M+H)

Compound 460

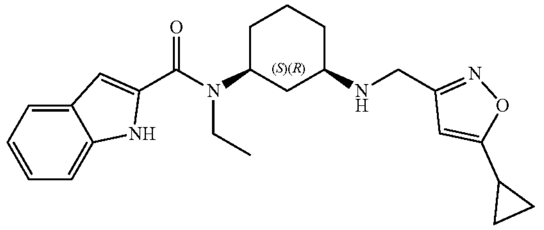

$^1$H NMR (400 MHz, METHANOL-$d_4$) δ ppm 7.65 (d, J=8.1 Hz, 1H), 7.46 (d, J=8.2 Hz, 1H), 7.24 (t, J=7.6 Hz, 1H), 7.13-7.06 (m, 1H), 6.83 (br s, 1H), 6.21 (s, 1H), 4.37 (s, 2H), 3.69 (br s, 2H), 3.37 (s, 2H), 2.38 (br d, J=10.9 Hz, 1H), 2.22-2.12 (m, 2H), 2.09-1.91 (m, 3H), 1.87 (br s, 1H), 1.55-1.40 (m, 2H), 1.36 (br t, J=6.8 Hz, 3H), 1.19-1.10 (m, 2H), 1.00-0.92 (m, 2H)

LCMS (ESI+): m/z 407.3 (M+H)

Compound 461

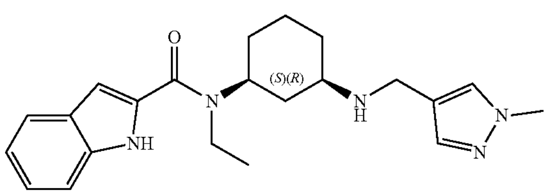

$^1$H NMR (400 MHz, CHLOROFORM-d) δ ppm 9.41 (s, 1H), 7.59 (d, J=8 Hz, 1H), 7.36 (d, J=12.4 Hz, 2H), 7.23-7.19 (m, 2H), 7.06 (t, J=7.6 Hz, 1H), 6.68 (s, 1H), 4.51 (t, J=12 Hz, 1H), 3.62 (s, 4H), 2.63 (s, 1H), 2.20 (s, 3H), 2.08 (d, J=13.6 Hz, 1H), 1.93-1.83 (m, 3H), 1.54-1.28 (m, 6H), 1.06 (dd, J=11.2, 22.8 Hz, 1H)

LCMS (ESI+): m/z 380.2 (M+H)

Compound 462

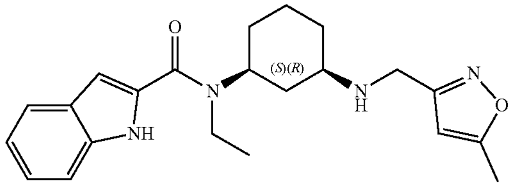

$^1$H NMR (400 MHz, CHLOROFORM-d) δ ppm 9.29 (s, 1H), 7.68 (d, J=8 Hz, 1H), 7.43 (d, J=9.2 Hz, 1H), 7.29 (t, J=7.2 Hz, 2H), 7.15 (t, J=7.6 Hz, 1H), 6.76 (s, 1H), 5.96 (s, 1H), 4.56 (t, J=12 Hz, 1H), 3.89 (s, 2H), 3.72 (s, 2H), 2.70 (t, J=10.8 Hz, 1H), 2.41 (s, 3H), 2.16 (d, J=12.4 Hz, 1H), 2.00 (d, J=12 Hz, 1H), 1.93-1.89 (m, 2H), 1.50 (s, 1H), 1.47-1.36 (m, 5H), 1.33-1.07 (m, 1H)

LCMS (ESI+): m/z 381.1 (M+H)

Example 31. Synthesis of N-ethyl-N-((1S,3R)-3-((4-(4-(prop-2-yn-1-yloxy)benzoyl)benzyl)amino)cyclohexyl)-1H-pyrrolo[3,2-b]pyridine-2-carboxamide (Compound 463)

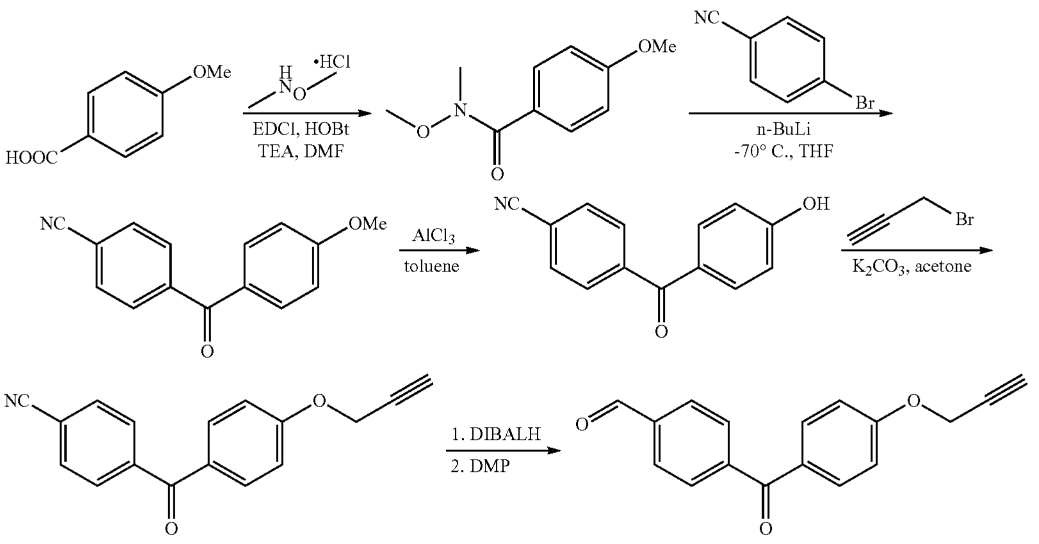

A-8

-continued

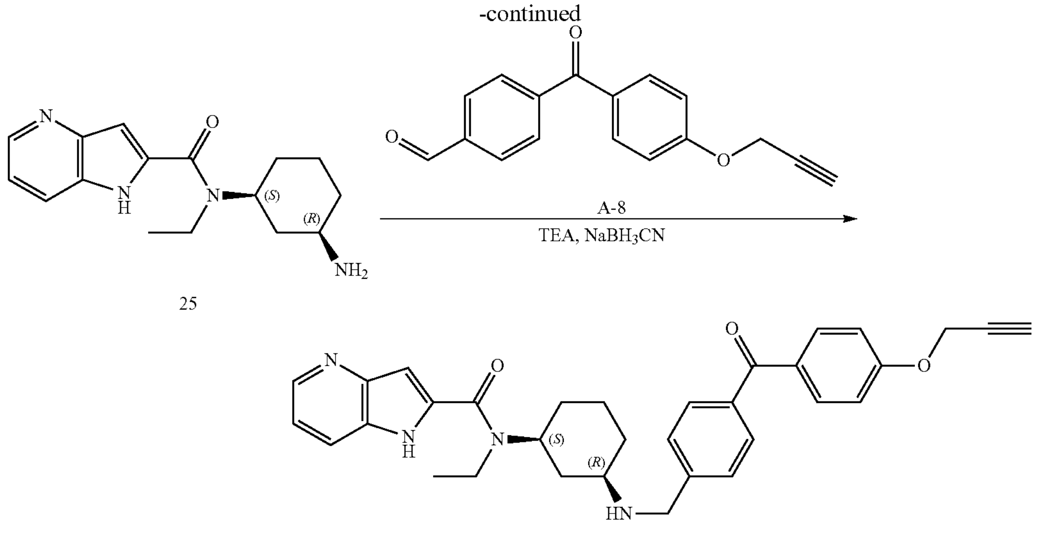

25 compound 463

General procedure for preparation of N,4-dimethoxy-N-methylbenzamide: A mixture of 4-methoxybenzoic acid (5.0 g, 33 mmol, 1.0 eq), EDCI (7.6 g, 39 mmol, 1.2 eq), HOBt (6.7 g, 49 mmol, 1.5 eq) and TEA (6.7 g, 66 mmol, 9.1 mL, 2.0 eq) in 75 mL of DMF was stirred for 10 min, then N-methoxymethanamine hydrochloride (3.9 g, 39.4 mmol, 1.2 eq) was added. The mixture was stirred at 15° C. for another 12 hours under $N_2$ atmosphere. The reaction mixture was partitioned between 100 mL of water and 100 mL of EtOAc. The organic phase was separated, washed three times with 150 mL of water and 50 mL of brine, dried over $Na_2SO_4$, filtered and concentrated under reduced pressure to give 5 g of crude N,4-dimethoxy-N-methylbenzamide as colorless liquid which was used into the next step without further purification General procedure for preparation of 4-(4-methoxybenzoyl)benzonitrile: A mixture of 4-bromobenzonitrile (932 mg, 5.1 mmol, 1.0 eq) in 10 mL of THF was cooled to −70° C. n-BμLi (2.5 M, 2.1 mL, 1.0 eq) was added dropwise and the mixture was stirred for 30 min, then N,4-dimethoxy-N-methylbenzamide (1.0 g, 5.1 mmol, 1.0 eq) in 5.0 mL of THF was added slowly. The mixture was stirred for 30 min at that temperature, then it was allowed to warm to 15° C. and stirred for another 1 hour under $N_2$ atmosphere. It was quenched by 10 mL of ice water, extracted twice with 30 mL of EtOAc. The combined organic layers were washed with 15 mL of brine, dried over $Na_2SO_4$, filtered and evaporated under reduced pressure to give the crude product which was purified by column chromatography ($SiO_2$, eluting with a gradient of petroleum ether:ethyl acetate=30:1 to 20:1) to give 1.1 g of crude 4-(4-methoxybenzoyl)benzonitrile as a light yellow solid which was used into the next step without further purification.

General procedure for preparation of 4-(4-hydroxybenzoyl)benzonitrile: A mixture of 4-(4-methoxybenzoyl)benzonitrile (1.0 g, 4.2 mmol, 1.0 eq), $AlCl_3$ (1.7 g, 12.6 mmol, 690 μL, 3.0 eq) in 15.0 mL of toluene was degassed and purged with $N_2$ three times. The mixture was stirred at 110° C. for 1 hour under $N_2$ atmosphere. The reaction mixture was poured into 20 mL of water, filtered to give 530 mg of crude 4-(4-hydroxybenzoyl)benzonitrile as a light purple solid and was used into the next step without further purification.

General procedure for preparation of 4-(4-(prop-2-yn-1-yloxy)benzoyl)benzonitrile: A mixture of 4-(4-hydroxybenzoyl)benzonitrile (530 mg, 2.4 mmol, 1.0 eq), 3-bromoprop-1-yne (1.4 g, 11.9 mmol, 1.0 mL, 5.0 eq), $K_2CO_3$ (983 mg, 7.1 mmol, 3.0 eq) in 8.0 mL of acetone was stirred at 30° C. for 72 hour. The reaction mixture was partitioned between 10 mL of water and 10 mL of EtOAc. The organic phase was separated, washed with 10 mL of brine, dried over $Na_2SO_4$, filtered and concentrated under reduced pressure to give a residue which was purified by prep-TLC (eluting with petroleum ether:ethyl acetate=3:1) to give 310 mg of 4-(4-(prop-2-yn-1-yloxy)benzoyl)benzonitrile (1.19 mmol, 50% yield) as a yellow solid.

General procedure for preparation of 4-(hydroxy(4-(prop-2-yn-1-yloxy)phenyl)methyl)benzaldehyde: A mixture of 4-(4-(prop-2-yn-1-yloxy)benzoyl)benzonitrile (100 mg, 383 μmol, 1.0 eq) in 2.0 mL of THF was cooled to −70° C. DIBAL-H (1 M, 1.5 mL, 4.0 eq) was added dropwise. The mixture was stirred at 0° C. for 1.5 hour under $N_2$ atmosphere. It was quenched by adding 0.5 mL of MeOH/HOAc (2/1, v/v), 4 mL of water, filtered, and the resulting filtrate was extracted twice with 10 mL of EtOAc, the combined organic layers were washed with 5 mL of brine, dried over $Na_2SO_4$, filtered and evaporated under reduced pressure to give 80 mg of crude 4-(hydroxy(4-(prop-2-yn-1-yloxy)phenyl)methyl)benzaldehyde as a light yellow gum which was used in the next step without further purification.

General procedure for preparation of aldehyde A-8: To a mixture of 4-(hydroxy(4-(prop-2-yn-1-yloxy)phenyl)methyl)benzaldehyde (80 mg, 300 μmol, 1.0 eq) in 2.0 mL of DCM was added DMP (191 mg, 451 μmol, 1.5 eq) in portions, then the mixture was stirred at 15° C. for 1.5 hour under $N_2$ atmosphere. The reaction mixture containing A-8 was used directly into the next step.

General procedure for preparation of compound 463: To a mixture of compound 25 (50 mg, 155 μmol, 1.0 eq, HCl salt) in 1 mL of MeOH was added TEA (15.7 mg, 155 μmol, 1.0 eq), 4-(4-prop-2-ynoxybenzoyl)benzaldehyde (A-8) (41 mg, 155 μmol, 1 eq, crude from the reaction mixture). The mixture was stirred for 30 min at 15° C. and $NaBH_3CN$ (19.5 mg, 310 μmol, 2.0 eq) was added. The mixture was stirred at 15° C. for another 2 hours under $N_2$ atmosphere. It was filtered and the filtrate was purified by prep-HPLC (TFA condition) firstly, and then re-purified by prep-HPLC (neutral condition) to give 5.6 mg of compound 463 (10 μmol, 7% yield, 99.2% purity) as a white solid.

Compound 463

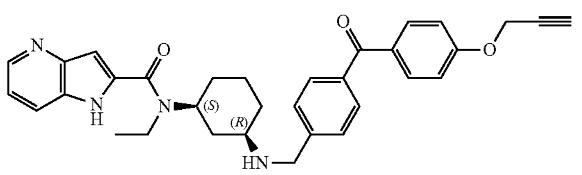

$^1$H NMR (400 MHz, METHANOL-$d_4$) δ ppm 8.38 (br d, J=3.79 Hz, 1H) 7.91 (d, J=8.31 Hz, 1H) 7.79 (br d, J=8.68 Hz, 2H) 7.71 (br d, J=6.72 Hz, 2H) 7.53 (br d, J=6.85 Hz, 2H) 7.27 (dd, J=8.19, 4.52 Hz, 1H) 7.12 (d, J=8.80 Hz, 2H) 6.85 (br s, 1H) 4.29 (br s, 1H) 3.94 (br s, 2H) 3.64 (br s, 2H) 3.04 (t, J=2.38 Hz, 1H) 2.60 (br s, 1H) 2.21 (br d, J=11.62 Hz, 1H) 1.83-2.12 (m, 4H) 1.54-1.82 (m, 2H) 1.54-1.82 (m, 1H) 1.33 (br t, J=6.97 Hz, 4H) 1.17 (br d, J=11.13 Hz, 1H)

LCMS (ESI+): m/z 535.3 (M+H)

Example 32. Synthesis of N-((1S,3R)-3-((benzo[d]oxazol-6-ylmethyl)amino)cyclohexyl)-N-ethyl-1H-indole-2-carboxamide (Compound 464)

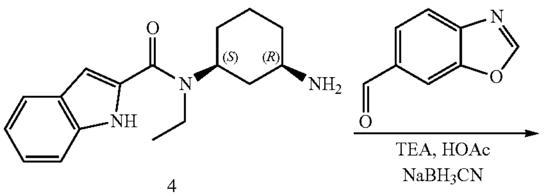

4

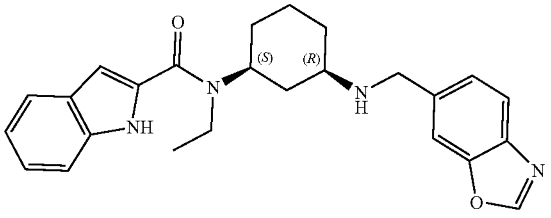

compound 464

General procedure for the preparation of compound 464: A mixture of compound 4 (50.0 mg, 155.4 μmol, 1.0 eq, HCl salt), 1,3-benzoxazole-6-carbaldehyde (27.4 mg, 186 μmol, 1.2 eq), TEA (7.9 mg, 78 μmol, 0.5 eq) and AcOH (4.7 mg, 78 μmol, 4.4 μL, 0.5 eq) in 2.0 mL of MeOH was stirred at 15° C. for 0.5 hour, then $NaBH_3CN$ (19.5 mg, 311 μmol, 2.0 eq) was added and the mixture was stirred at 15° C. for 11 hour. The reaction mixture was filtered and the residue was purified by prep-HPLC (neutral condition) to give 12.8 mg of compound 464 (29.9 μmol, 19% yield, 97.3% purity) as a brown solid.

Compound 464

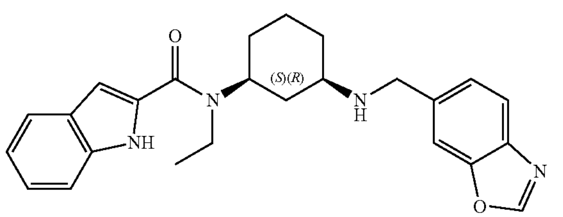

$^1$H NMR (400 MHz, CHLOROFORM-d) δ ppm 9.19 (br s, 1H), 7.99 (s, 1H), 7.66 (d, J=8.2 Hz, 1H), 7.58-7.51 (m, 2H), 7.35 (d, J=8.3 Hz, 1H), 7.27 (dd, J=1.2, 8.2 Hz, 1H), 7.23-7.20 (m, 1H), 7.09-7.03 (m, 1H), 6.66 (br s, 1H), 4.54-4.42 (m, 1H), 3.91 (s, 2H), 3.56 (br s, 2H), 2.65 (br t, J=10.7 Hz, 1H), 2.12 (br d, J=11.2 Hz, 1H), 1.95 (br d, J=12.2 Hz, 1H), 1.88-1.78 (m, 2H), 1.50-1.33 (m, 4H), 1.31-1.22 (m, 1H), 1.28 (br s, 2H), 1.10-0.99 (m, 1H)

LCMS (ESI+): m/z 417.1 (M+H)

Example 33. Synthesis of N-ethyl-N-((1S,3R)-3-((thiazol-2-ylmethyl)amino)cyclohexyl)-1H-indole-2-carboxamide (Compound 465)

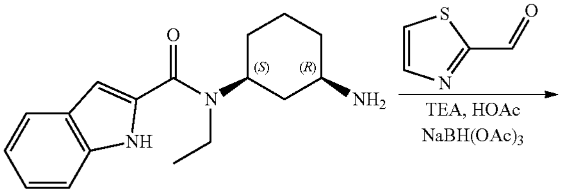

4

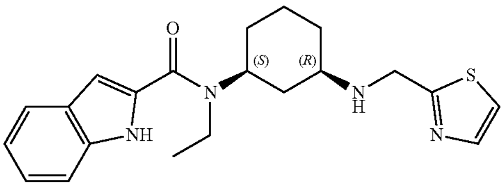

compound 465

General procedure for preparation of compound 465: To a mixture of compound 4 (20.0 mg, 62 μmol, 1.0 eq, HCl salt) in 1.0 mL of DCE and 1.0 mL of MeOH was added TEA (6.3 mg, 62.1 μmol, 1.0 eq), then thiazole-2-carbaldehyde (7.7 mg, 68 μmol, 1.1 eq), HOAc (4.5 mg, 75 μmol, 1.2 eq) were added and the mixture was stirred for 4 hours at 10° C. $NaBH(OAc)_3$ (19.8 mg, 93 μmol, 1.5 eq) was added and the mixture was stirred for another 8 hours under $N_2$ atmosphere. The mixture was stirred at 25° C. and stirred for another 12 hours. It was evaporated under reduced pressure and purified by prep-HPLC (TFA condition) to give 5.8 mg of compound 465 (11.2 μmol, 18% yield, 96.1% purity, TFA salt) as a white solid.

Compound 465

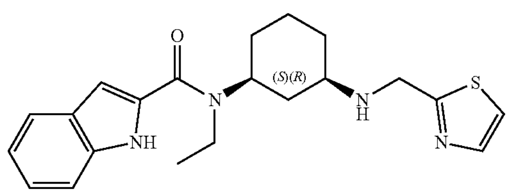

$^1$H NMR (400 MHz, METHANOL-$d_4$) δ ppm 7.90 (d, J=3.31 Hz, 1H) 7.72 (d, J=3.31 Hz, 1H) 7.62 (d, J=7.94 Hz, 1H) 7.43 (d, J=8.38 Hz, 1H) 7.21 (t, J=7.72 Hz, 1H) 7.03-7.10 (m, 1H) 6.80 (br s, 1H) 4.64-4.74 (m, 2H) 4.36 (br s, 1H) 3.67 (br s, 2H) 3.38 (br s, 1H) 2.36 (br d, J=10.80 Hz, 1H) 2.19 (br d, J=9.04 Hz, 1H) 1.79-2.09 (m, 4H) 1.40-1.54 (m, 2H) 1.27-1.38 (m, 3H)

LCMS (ESI+): m/z 383.2 (M+H)

The following compound was prepared analogously:

Compound 466

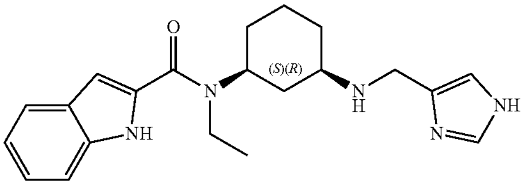

$^1$H NMR (400 MHz, METHANOL-$d_4$) δ ppm 8.57 (s, 1H) 7.56-7.64 (m, 2H) 7.39-7.46 (m, 1H) 7.21 (td, J=7.61, 0.88 Hz, 1H) 6.80 (br s, 1H) 4.40 (s, 3H) 3.67 (br s, 2H) 2.35 (br d, J=10.58 Hz, 1H) 2.19 (br d, J=9.48 Hz, 1H) 1.79-2.09 (m, 4H) 1.39-1.54 (m, 2H) 1.25-1.38 (m, 4H)

LCMS (ESI+): m/z 366.2 (M+H)

Example 34. Synthesis of N-((1S,3R)-3-(((5-cyclopropyl-1,3,4-thiadiazol-2-yl)methyl)amino)cyclohexyl)-N-ethyl-1H-indole-2-carboxamide (Compound 467)

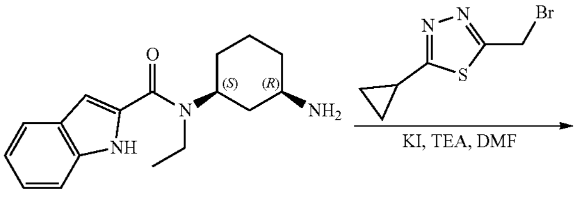

4

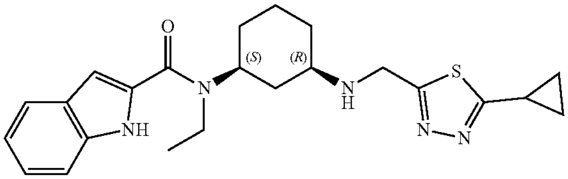

compound 467

General procedure for the preparation of compound 467: To a mixture of compound 4 (30 mg, 93 μmol, 1 eq, HCl salt), 2-(bromomethyl)-5-cyclopropyl-1,3,4-thiadiazole (61.3 mg, 280 μmol, 3 eq) and KI (7.7 mg, 47 μmol, 0.5 eq) in 1 mL of DMF was added $Et_3N$ (28.3 mg, 280 μmol, 39 μL, 3 eq). The mixture was degassed and purged with $N_2$ three times, and then the mixture was stirred at 15° C. for 12 hours under $N_2$ atmosphere. The reaction mixture was filtered and the mother liquor was purified by prep-HPLC (TFA condition) to give 16 mg of compound 467 (29 μmol, 31% yield, 97.6% purity, TFA salt) as white solid.

Compound 467

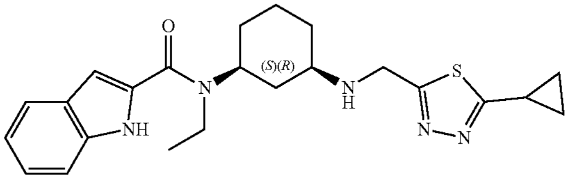

$^1$H NMR (400 MHz, METHANOL-$d_4$) δ ppm 7.66 (d, J=7.9 Hz, 1H), 7.46 (d, J=8.2 Hz, 1H), 7.24 (t, J=7.6 Hz, 1H), 7.12-7.07 (m, 1H), 6.84 (br s, 1H), 4.78 (s, 2H), 4.39 (br s, 1H), 3.70 (br s, 2H), 3.48-3.38 (m, 1H), 2.57-2.49 (m, 1H), 2.40 (br d, J=10.6 Hz, 1H), 2.22 (br d, J=9.4 Hz, 1H), 2.11-1.81 (m, 4H), 1.53-1.43 (m, 2H), 1.39-1.31 (m, 5H), 1.17-1.13 (m, 2H)

LCMS (ESI+): m/z 424.2 (M+H)

Example 35. Synthesis of 2-(bromomethyl)-5-cyclopropyl-1,3,4-thiadiazole (the Bromide Used in the Synthesis of Compound 467)

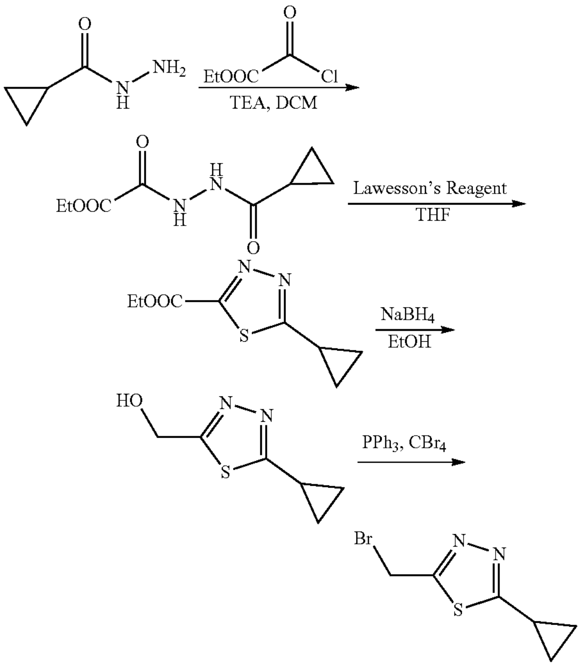

General procedure for preparation of ethyl 2-(2-(cyclopropanecarbonyl)hydrazineyl)-2-oxoacetate: To a mixture of cyclopropanecarbohydrazide (5 g, 50 mmol, 1 eq) and $Et_3N$ (15.2 g, 150 mmol, 20.9 mL, 3 eq) in 100 mL of DCM was added ethyl 2-chloro-2-oxo-acetate (6.8 g, 50 mmol, 5.6 mL, 1 eq) drop-wise at 0° C. The reaction mixture was stirred at 15° C. for 2 hours. The reaction mixture was filtered and the filtrate was concentrated in vacuo. The residue was purified by column chromatography ($SiO_2$, eluting with a gradient of petroleum ether:ethyl acetate=20:1 to 1:1) to give 9.1 g of ethyl 2-(2-(cyclopropanecarbonyl) hydrazineyl)-2-oxoacetate (45.5 mmol, 91% yield) as colorless oil.

General procedure for preparation of ethyl 5-cyclopropyl-1,3,4-thiadiazole-2-carboxylate: A mixture of ethyl 2-(2-(cyclopropanecarbonyl)hydrazineyl)-2-oxoacetate (9.1 g, 45.5 mmol, 1 eq) and Lawesson's Reagent (18.4 g, 45.5 mmol, 1 eq) in 100 mL of THF was degassed and purged with $N_2$ three times. The mixture was stirred at 15° C. for 12 hours under $N_2$ atmosphere. The reaction mixture was quenched by addition 150 mL of $H_2O$ at 15° C., and then extracted three times with 300 mL of DCM. The combined organic layers were washed twice with 200 mL of brine, dried over $Na_2SO_4$, filtered and concentrated under reduced pressure to give a residue. The residue was purified by column chromatography ($SiO_2$, eluting with a gradient of petroleum ether:ethyl acetate=20:1 to 8:1) to give 8.5 g of ethyl 5-cyclopropyl-1,3,4-thiadiazole-2-carboxylate (43 mmol, 94% yield) as light yellow oil.

General procedure for preparation of (5-cyclopropyl-1,3,4-thiadiazol-2-yl)methanol: To a solution of ethyl 5-cyclopropyl-1,3,4-thiadiazole-2-carboxylate (5 g, 25.2 mmol, 1 eq) in 50 mL of EtOH was added $NaBH_4$ (1.9 g, 50.4 mmol, 2 eq) in portions at 0° C. The mixture was stirred at 15° C. for 12 hours. The reaction mixture was concentrated under reduced pressure to remove solvent. The residue was diluted with 30 mL of $H_2O$ and extracted three times with 90 mL of EtOAc. The combined organic layers were washed twice with 60 mL of brine, dried over $Na_2SO_4$, filtered and concentrated under reduced pressure to give 1.5 g of crude (5-cyclopropyl-1,3,4-thiadiazol-2-yl)methanol (9.6 mmol, 38% yield) as colorless oil which was used into the next step without further purification.

General procedure for preparation of 2-(bromomethyl)-5-cyclopropyl-1,3,4-thiadiazole: A mixture of (5-cyclopropyl-1,3,4-thiadiazol-2-yl)methanol (1 g, 6.4 mmol, 1 eq) and $PPh_3$ (1.9 g, 7.0 mmol, 1.1 eq), $CBr_4$ (2.3 g, 7.0 mmol, 1.1 eq) in 15 mL of THF was degassed and purged with $N_2$ three times, and then the mixture was stirred at 15° C. for 0.5 hours under $N_2$ atmosphere. The reaction mixture was concentrated under reduced pressure to remove solvent. The residue was purified by prep-TLC ($SiO_2$, eluting with petroleum ether:ethyl acetate=1:1) to give 550 mg of 2-(bromomethyl)-5-cyclopropyl-1,3,4-thiadiazole (2.25 mmol, 35% yield, 89.6% purity) as yellow solid.

Example 36. Synthesis of N-ethyl-N-((1S,3R)-3-(((5-methyl-1,3,4-oxadiazol-2-yl)methyl)amino) cyclohexyl)-1H-pyrrolo[3,2-b]pyridine-2-carboxamide (Compound 468)

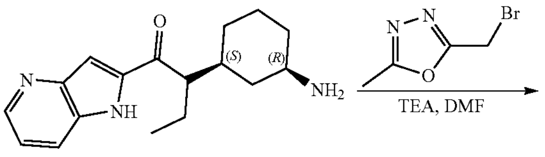

25

-continued

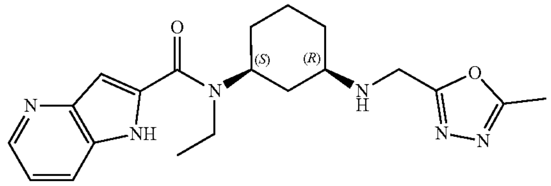

compound 468

General procedure for the preparation of compound 468: To a mixture of compound 25 (30 mg, 93 µmol, 1 eq, HCl salt) and TEA (28 mg, 279 µmol, 3 eq) in 1 mL of DMF was added 2-(bromomethyl)-5-methyl-1,3,4-oxadiazole (49.3 mg, 279 µmol, 3 eq) at 15° C. The reaction mixture was stirred at 15° C. for 12 hours under $N_2$ atmosphere. The reaction mixture was filtered and the filtrate was purified by prep-HPLC (TFA condition) to give 20.9 mg of compound 468 (41 µmol, 38% yield, 97.4% purity, TFA salt) as a white solid.

Compound 468

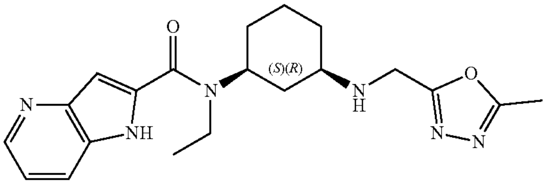

$^1H$ NMR (400 MHz, METHANOL-$d_4$) δ ppm 8.69 (d, J=5.62 Hz, 1H) 8.62 (d, J=8.31 Hz, 1H) 7.78 (dd, J=8.31, 5.75 Hz, 1H) 7.14 (s, 1H) 4.66 (s, 2H) 4.12 (br s, 1H) 3.63 (br d, J=6.60 Hz, 2H) 3.42-3.55 (m, 1H) 2.58 (s, 3H) 2.42 (br s, 1H) 2.16-2.27 (m, 1H) 2.01 (br d, J=5.38 Hz, 2H) 1.89-1.97 (m, 2H) 1.37-1.55 (m, 2H) 1.32 (br t, J=6.91 Hz, 4H)

LCMS (ESI+): m/z 383.2 (M+H)

The following compounds were prepared analogously:

Compound 469

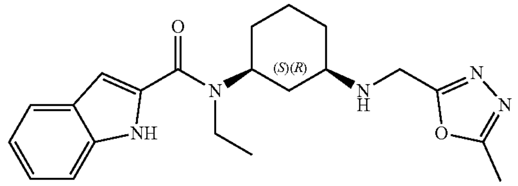

$^1H$ NMR (400 MHz, METHANOL-$d_4$) δ ppm 7.64 (d, J=8.07 Hz, 1H) 7.44 (d, J=8.31 Hz, 1H) 7.22 (t, J=7.58 Hz, 1H) 7.03-7.12 (m, 1H) 6.82 (br s, 1H) 4.65 (s, 2H) 4.36 (br s, 1H) 3.68 (br s, 2H) 3.43 (br s, 1H) 3.37-3.50 (m, 1H) 2.58 (s, 3H) 2.37 (br d, J=10.64 Hz, 1H) 2.12-2.27 (m, 1H) 1.97-2.11 (m, 2H) 1.92 (br s, 2H) 1.39-1.52 (m, 2H) 1.35 (br t, J=6.72 Hz, 3H)

LCMS (ESI+): m/z 382.2 (M+H)

Compound 470

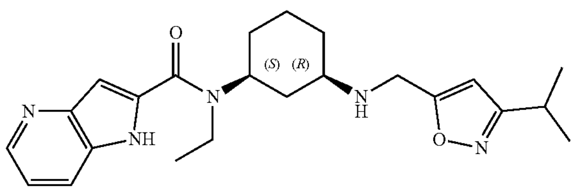

$^{1}$H NMR (400 MHz, METHANOL-$d_4$) δ ppm 8.41 (d, J=4.2 Hz, 1H), 7.93 (d, J=8.3 Hz, 1H), 7.30 (dd, J=4.8, 8.3 Hz, 1H), 6.86 (br s, 1H), 6.29 (s, 1H), 4.39-4.24 (m, 1H), 4.31 (br s, 1H), 3.94 (s, 2H), 3.63 (br s, 2H), 3.11-2.95 (m, 1H), 2.60 (br s, 1H), 2.15 (br d, J=12.3 Hz, 1H), 2.01-1.86 (m, 3H), 1.74 (br d, J=12.0 Hz, 1H), 1.60 (br d, J=12.2 Hz, 1H), 1.32 (br t, J=6.9 Hz, 3H), 1.26 (br d, J=6.5 Hz, 6H), 1.18-1.06 (m, 1H)

LCMS (ESI+): m/z 410.2 (M+H)

Compound 471

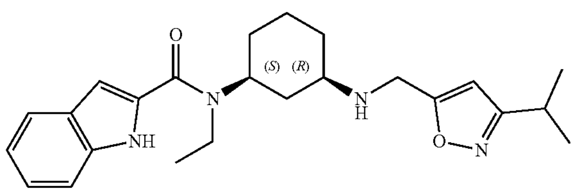

$^{1}$H NMR (400 MHz, METHANOL-$d_4$) δ ppm 7.63 (d, J=7.9 Hz, 1H), 7.43 (d, J=8.4 Hz, 1H), 7.21 (t, J=7.6 Hz, 1H), 7.10-7.03 (m, 1H), 6.81 (br s, 1H), 6.57 (s, 1H), 4.49 (s, 2H), 4.36 (br s, 1H), 3.67 (br s, 2H), 3.30 (br s, 1H), 3.06 (td, J=6.9, 13.9 Hz, 1H), 2.33 (br d, J=11.2 Hz, 1H), 2.17 (br d, J=11.5 Hz, 1H), 2.08-2.00 (m, 1H), 1.97-1.77 (m, 3H), 1.50-1.37 (m, 2H), 1.33 (br t, J=6.9 Hz, 3H), 1.28 (d, J=7.1 Hz, 6H)

LCMS (ESI+): m/z 409.2 (M+H)

Example 37. Synthesis of 2-(bromomethyl)-5-methyl-1,3,4-oxadiazole (the bromomethyl intermediate for the synthesis of compounds 468 and 469)

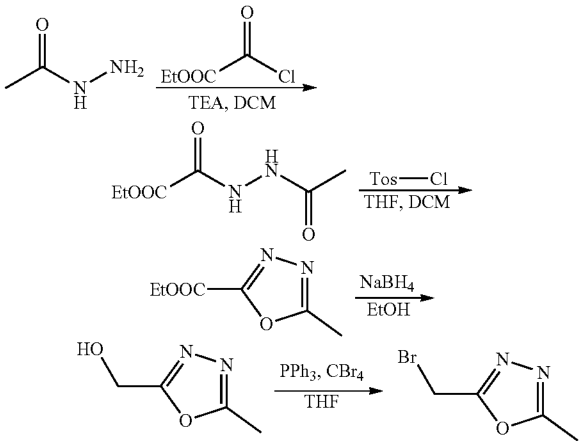

General procedure for preparation of ethyl 2-(2-acetylhydrazineyl)-2-oxoacetate: To a mixture of acetohydrazide (5.0 g, 68 mmol, 1.0 eq) and TEA (20.5 g, 203 mmol, 28.1 mL, 3.0 eq) in 100 mL of DCM was added ethyl 2-chloro-2-oxo-acetate (9.2 g, 68 mmol, 7.6 mL, 1.0 eq) dropwise at 0° C. The reaction mixture was stirred at 15° C. for 16 hours. The reaction mixture was filtered and the filtrate was concentrated in vacuo. The residue was purified by column chromatography ($SiO_2$, eluting with a gradient of ethyl acetate:MeOH=100:1 to 20:1) to give 9.5 g of crude ethyl 2-(2-acetylhydrazineyl)-2-oxoacetate as a white solid.

General procedure for preparation of ethyl 5-methyl-1,3,4-oxadiazole-2-carboxylate: To a mixture of ethyl 2-(2-acetylhydrazineyl)-2-oxoacetate (6.1 g, 35.0 mmol, 1.0 eq) in 60 mL of DCM was added TEA (4.6 g, 45.5 mmol, 6.3 mL, 1.3 eq) and TosCl (8.0 g, 42.0 mmol, 1.2 eq) at 0° C. The reaction mixture was stirred at 15° C. for 3 hours. The reaction mixture was washed twice with 140 mL of saturated aqueous $NH_4Cl$. The organic phase was dried with anhydrous $Na_2SO_4$, filtered and concentrated in vacuo. The residue was purified by flash silica gel chromatography (ISCO®; 80 g SepaFlash® Silica Flash Column, eluting with a gradient of 10-30% ethyl acetate in petroleum ether @ 50 mL/min) to give 3.5 g of ethyl 5-methyl-1,3,4-oxadiazole-2-carboxylate (22.4 mmol, 64% yield) as a white solid.

General procedure for preparation of (5-methyl-1,3,4-oxadiazol-2-yl)methanol: A mixture of ethyl 5-methyl-1,3,4-oxadiazole-2-carboxylate (2.5 g, 16.0 mmol, 1.0 eq) in 30 mL of EtOH was added $NaBH_4$ (1.2 g, 32.0 mmol, 2 eq) at 0° C. and then the mixture was stirred at 15° C. for 12 hours. The reaction mixture was quenched by 30 mL of $H_2O$, then concentrated under reduced pressure, and extracted three times with 90 mL of EtOAc. The combined organic layers were dried over $Na_2SO_4$, filtered and concentrated under reduced pressure to give 1.2 g of (5-methyl-1,3,4-oxadiazol-2-yl)methanol (10.5 mmol, 66% yield) as a colorless oil.

General procedure for preparation of 2-(bromomethyl)-5-methyl-1,3,4-oxadiazole: A mixture of (5-methyl-1,3,4-oxadiazol-2-yl)methanol (1.2 g, 10.5 mmol, 1 eq), $CBr_4$ (3.5 g, 10.5 mmol, 1 eq) in 15 mL of THF was stirred at 15° C. for 0.5 hour, then $PPh_3$ (2.8 g, 10.5 mmol, 1 eq) was added and the mixture stirred at 15° C. for 11.5 hours. The reaction mixture was concentrated in vacuo. The residue was purified by column chromatography ($SiO_2$, eluting with petroleum ether:ethyl acetate=10:1 to 2:1) to give 400 mg of 2-(bromomethyl)-5-methyl-1,3,4-oxadiazole (2.2 mmol, 20.5% yield, 95.5% purity) as a light yellow oil.

Example 38. Synthesis of 5-(bromomethyl)-3-isopropyl-isoxazole (the Bromomethyl Intermediate for the Synthesis of Compounds 470 and 471)

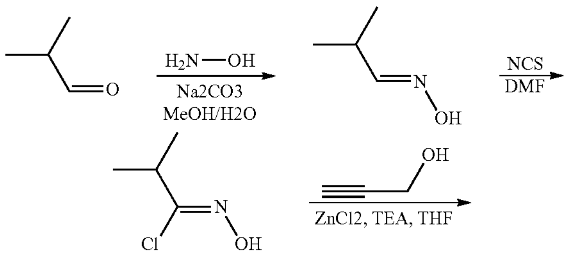

-continued

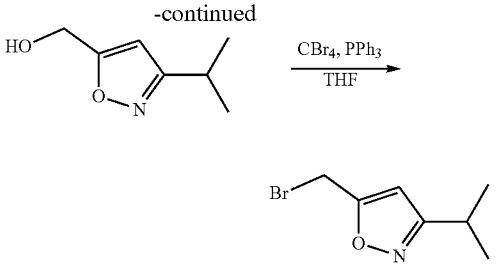

General procedure for preparation of isobutyraldehyde oxime: A mixture of 2-methylpropanal (5.0 g, 69.3 mmol, 6.3 mL, 1.0 eq) in 30 mL of MeOH and 30 mL of $H_2O$ was cooled to 0° C., then hydroxylamine hydrochloride (5.8 g, 83 mmol, 1.2 eq) and $Na_2CO_3$ (4.4 g, 42 mmol, 0.6 eq) was added and the mixture was stirred at 15° C. for 12 hours. It was concentrated under reduced pressure and the remaining aqueous portion was extracted twice with 50 mL of EtOAc. The combined organic layers were washed with 30 mL of brine, dried over $Na_2SO_4$, filtered and evaporated under reduced pressure to give 2.8 g of crude isobutyraldehyde oxime as a colorless oil.

General procedure for preparation of N-hydroxyisobutyrimidoyl chloride: To a mixture of isobutyraldehyde oxime (2.7 g, 30.4 mmol, 1.0 eq) in 30.0 mL of DMF was added NCS (4.5 g, 33.5 mmol, 1.1 eq) at 40° C., and the mixture was stirred at 40° C. for 12 hours. The reaction mixture was partitioned between 50 mL of water and 30 mL of EtOAc. The organic phase was separated, washed twice with 40 mL of water and 20 mL of brine, dried over $Na_2SO_4$, filtered and concentrated under reduced pressure to give 3.0 g of crude N-hydroxyisobutyrimidoyl chloride as a colorless oil.

General procedure for preparation of (3-isopropylisoxazol-5-yl)methanol: A mixture of prop-2-yn-1-ol (4.3 g, 77 mmol, 4.5 mL, 3.0 eq) in 30 mL of THF was cooled to 0° C., then N-hydroxyisobutyrimidoyl chloride (3.1 g, 26 mmol, 1.0 eq), $ZnCl_2$ (7.0 g, 51 mmol, 2.4 mL, 2.0 eq), TEA (9.0 g, 89 mmol, 12.4 mL, 3.5 eq) were added successively at the temperature and the mixture was stirred at 40° C. for 12 hours. The reaction mixture was partitioned between 30 mL of water and 30 mL of EtOAc and the resulting mixture was filtered. The organic phase was separated, washed with 15 mL of brine, dried over $Na_2SO_4$, filtered and concentrated under reduced pressure to give 3.1 g of crude (3-isopropylisoxazol-5-yl)methanol as a colorless oil.

General procedure for preparation of 5-(bromomethyl)-3-isopropyl-isoxazole: A mixture of (3-isopropylisoxazol-5-yl)methanol (1.2 g, 8.5 mmol, 1 eq), $CBr_4$ (3.1 g, 9.4 mmol, 1.1 eq) in 15 mL of THF was stirred at 15° C. for 0.5 hour, then $PPh_3$ (2.5 g, 9.4 mmol, 1.1 eq) was added and the mixture was stirred at 15° C. for 1.5 hours. The reaction mixture was concentrated under reduced pressure to give an oil. The oil was purified by column chromatography ($SiO_2$, eluting with petroleum ether:ethyl acetate=100:1 to 40:1) to give 0.63 g of 5-(bromomethyl)-3-isopropyl-isoxazole (3.1 mmol, 36% yield) as a colorless oil.

Example 39. Additional Compounds

The following compounds were prepared using reductive aminations as described above in Example 30:

Compound 472

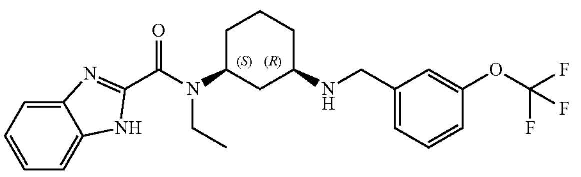

$^1H$ NMR (400 MHz, METHANOL-$d_4$) δ ppm 7.62-7.69 (m, 2H) 7.46-7.60 (m, 3H) 7.30-7.43 (m, 3H) 5.23 (br t, J=11.47 Hz, 1H) 4.29-4.38 (m, 2H) 4.23 (br s, 1H) 3.86-4.09 (m, 1H) 3.46-3.68 (m, 1H) 3.32-3.44 (m, 1H) 2.33-2.56 (m, 1H) 2.15-2.30 (m, 1H) 1.88-2.14 (m, 3H) 1.67-1.87 (m, 1H) 1.36-1.62 (m, 2H) 1.24-1.36 (m, 3H)

LCMS (ESI+): m/z 461.2 (M+H)

Compound 473

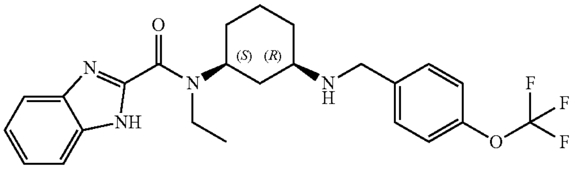

$^1H$ NMR (400 MHz, METHANOL-$d_4$) δ ppm 7.56-7.69 (m, 4H) 7.29-7.44 (m, 4H) 5.24 (br t, J=11.80 Hz, 1H) 4.31 (br s, 2H) 4.22 (br s, 1H) 3.87-4.08 (m, 1H) 3.46-3.68 (m, 1H) 3.36 (br d, J=11.91 Hz, 1H) 2.33-2.56 (m, 1H) 2.19 (br d, J=11.03 Hz, 1H) 1.88-2.14 (m, 3H) 1.65-1.86 (m, 1H) 1.35-1.62 (m, 2H) 1.24-1.34 (m, 3H)

LCMS (ESI+): m/z 461.2 (M+H)

Compound 474

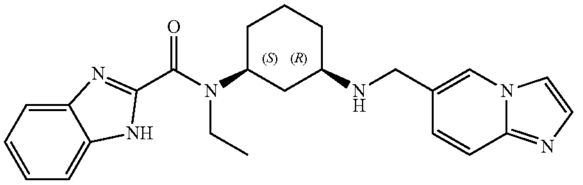

$^1H$ NMR (400 MHz, METHANOL-$d_4$) δ ppm 9.01 (br s, 1H) 8.21-8.35 (m, 1H) 7.97-8.15 (m, 3H) 7.65 (br s, 2H) 7.37 (br s, 2H) 5.12 (br s, 1H) 4.44-4.56 (m, 2H) 4.24 (br s, 1H) 3.92 (br d, J=15.66 Hz, 1H) 3.60 (br d, J=9.04 Hz, 1H) 3.39 (br s, 1H) 2.39-2.58 (m, 1H) 2.21 (br s, 1H) 1.64-2.12 (m, 4H) 1.40-1.61 (m, 2H) 1.22-1.36 (m, 3H)

LCMS (ESI+): m/z 417.2 (M+H)

Compound 475

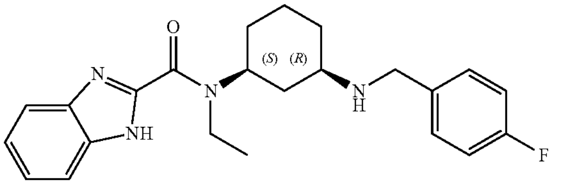

$^1$H NMR (400 MHz, METHANOL-$d_4$) δ ppm 7.67 (br s, 2H), 7.52 (br d, J=4.2 Hz, 2H), 7.37 (dd, J=3.1, 6.0 Hz, 2H), 7.23-7.13 (m, 2H), 5.11-5.00 (m, 1H), 5.11-5.00 (m, 1H), 4.30-4.22 (m, 2H), 3.89 (br dd, J=7.2, 18.4 Hz, 1H), 3.67-3.52 (m, 1H), 3.27 (br s, 1H), 2.52-2.34 (m, 1H), 2.27-2.13 (m, 1H), 2.11-1.88 (m, 3H), 1.86-1.66 (m, 1H), 1.56-1.36 (m, 2H), 1.34-1.21 (m, 3H)

LCMS (ESI+): m/z 395.2 (M+H)

Compound 476

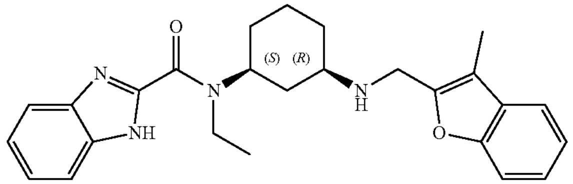

$^1$H NMR (400 MHz, METHANOL-$d_4$) δ ppm 7.57-7.72 (m, 3H) 7.44-7.56 (m, 1H) 7.29-7.42 (m, 4H) 5.27 (br s, 1H) 4.53 (br s, 2H) 4.24 (br s, 1H) 3.86-4.07 (m, 1H) 3.52-3.70 (m, 1H) 3.34-3.45 (m, 1H) 2.20-2.57 (m, 5H) 1.91-2.18 (m, 3H) 1.70-1.89 (m, 1H) 1.39-1.62 (m, 2H) 1.25-1.37 (m, 3H)

LCMS (ESI+): m/z 431.2 (M+H)

Compound 477

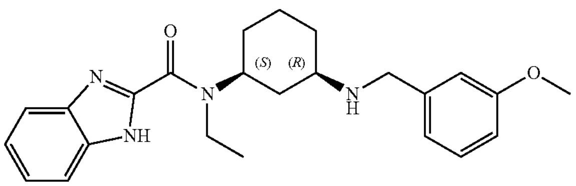

$^1$H NMR (400 MHz, METHANOL-$d_4$) δ ppm 7.66 (br d, J=2.43 Hz, 2H) 7.30-7.41 (m, 3H) 6.97-7.10 (m, 3H) 5.14 (br s, 1H) 4.23 (br s, 2H) 3.76-4.02 (m, 4H) 3.50-3.66 (m, 1H) 3.31 (br s, 1H) 2.33-2.53 (m, 1H) 2.12-2.28 (m, 1H) 1.87-2.12 (m, 3H) 1.66-1.86 (m, 1H) 1.36-1.59 (m, 2H) 1.21-1.34 (m, 3H)

LCMS (ESI+): m/z 407.2 (M+H)

Compound 478

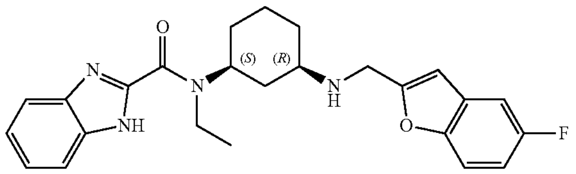

$^1$H NMR (400 MHz, METHANOL-$d_4$) δ ppm 7.47-7.73 (m, 3H) 7.31-7.43 (m, 3H) 7.03-7.20 (m, 2H) 5.17 (br s, 1H) 4.55 (br s, 2H) 4.23 (br s, 1H) 3.94 (br dd, J=18.46, 6.60 Hz, 1H) 3.61 (td, J=14.37, 7.09 Hz, 1H) 3.34-3.45 (m, 1H) 2.38-2.58 (m, 1H) 2.22 (br s, 1H) 1.91-2.15 (m, 3H) 1.69-1.89 (m, 1H) 1.39-1.61 (m, 2H) 1.24-1.37 (m, 3H)

LCMS (ESI+): m/z 435.2 (M+H)

Compound 479

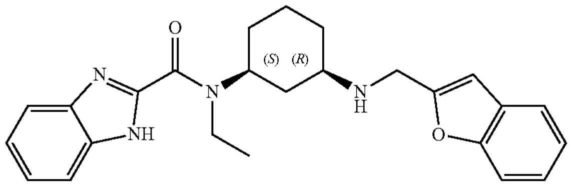

$^1$H NMR (400 MHz, CHLOROFORM-d) δ ppm 10.91-11.20 (m, 1H) 7.59-7.79 (m, 1H) 7.41-7.49 (m, 2H) 7.36 (br d, J=7.34 Hz, 1H) 7.19-7.30 (m, 2H) 7.09-7.18 (m, 2H) 6.49 (s, 1H) 5.79-5.90 (m, 1H) 4.51 (brt, J=12.17 Hz, 1H) 4.16-4.26 (m, 1H) 3.88-3.96 (m, 2H) 3.52 (q, J=6.89 Hz, 1H) 2.65-2.84 (m, 1H) 2.07-2.29 (m, 1H) 1.75-1.98 (m, 3H) 1.33-1.58 (m, 3H) 1.26 (td, J=6.91, 3.42 Hz, 3H) 0.99-1.13 (m, 1H)

LCMS (ESI+): m/z 417.2 (M+H)

Compound 480

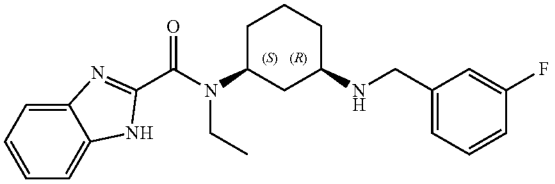

$^1$H NMR (400 MHz, METHANOL-$d_4$) δ ppm 7.70 (br s, 2H) 7.49 (br d, J=6.24 Hz, 1H) 7.29-7.44 (m, 4H) 7.22 (br s, 1H) 5.10 (br d, J=11.62 Hz, 1H) 4.30 (br s, 2H) 4.23 (br s, 1H) 3.92 (br d, J=19.32 Hz, 1H) 3.54-3.71 (m, 1H) 3.34-3.43 (m, 1H) 2.37-2.57 (m, 1H) 1.91-2.31 (m, 4H) 1.66-1.88 (m, 1H) 1.38-1.62 (m, 2H) 1.22-1.37 (m, 3H)

LCMS (ESI+): m/z 395.2 (M+H)

Example 40. Synthesis of 3-methylbenzofuran-2-carbaldehyde (the Aldehyde for the Synthesis of Compound 476)

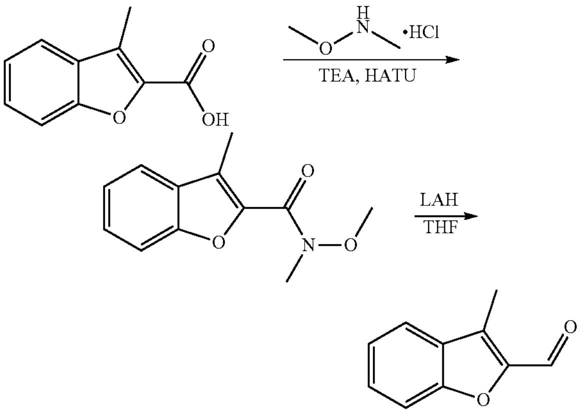

General procedure for preparation of N-methoxy-N,3-dimethylbenzofuran-2-carboxamide: A mixture of 3-methylbenzofuran-2-carboxylic acid (0.5 g, 2.8 mmol, 1 eq), N,O-dimethylhydroxylamine hydrochloride (415 mg, 4.3 mmol, 1.5 eq), HATU (1.2 g, 3.1 mmol, 1.1 eq), TEA (718.0 mg, 7.1 mmol, 987.6 μL, 2.5 eq) in 5 mL of DMF was degassed and purged with $N_2$ three times. The mixture was stirred at 15° C. for 12 hours under $N_2$ atmosphere. The reaction mixture was partitioned between 10 mL of water and 10 mL of EtOAc. The organic phase was separated, washed four times with 20 mL of water and 5 mL of brine, dried over $Na_2SO_4$, filtered and concentrated under reduced pressure to give 0.62 g of crude N-methoxy-N,3-dimethylbenzofuran-2-carboxamide as a yellow gum which was used into the next step without further purification.

General procedure for preparation of 3-methylbenzofuran-2-carbaldehyde: To a mixture of N-methoxy-N,3-dimethylbenzofuran-2-carboxamide (0.6 g, 2.8 mmol, 1 eq) in 10 mL of THF cooled to −70° C. was added LAH (215 mg, 5.7 mmol, 2 eq) in portions, then the mixture was stirred at −70° C. for 1 hour under $N_2$ atmosphere. It was quenched by adding 0.25 mL of water slowly, followed by the addition of 0.25 mL of 15% aqueous NaOH and 0.75 mL of water. The mixture was filtered and the filtrate was dried over $Na_2SO_4$, filtered and evaporated under reduced pressure to give the crude product which was purified by prep-TLC ($SiO_2$, eluting with petroleum ether:ethyl acetate=3:1) to give 250 mg of 3-methylbenzofuran-2-carbaldehyde (1.6 mmol, 55% yield) as a yellow solid.

Example 41. Synthesis of 5-fluorobenzofuran-2-carbaldehyde (the Aldehyde for the Synthesis of Compound 478)

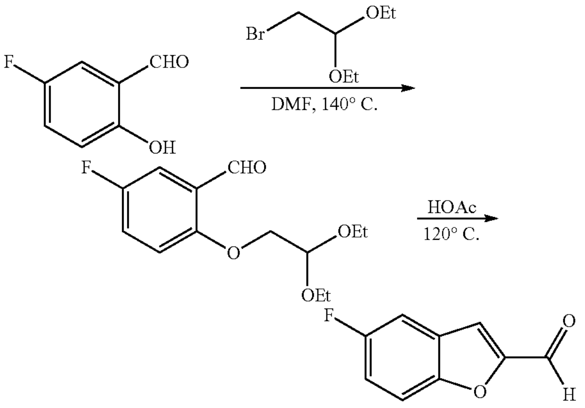

General procedure for preparation of 2-(2,2-diethoxyethoxy)-5-fluorobenzaldehyde: To a mixture of 5-fluoro-2-hydroxy-benzaldehyde (0.5 g, 3.6 mmol, 1 eq), $K_2CO_3$ (986 mg, 7.1 mmol, 2 eq) in 10 mL of DMF was added 2-bromo-1,1-diethoxy-ethane (774 mg, 3.9 mmol, 591 μL, 1.1 eq) dropwise at 15° C. The mixture was stirred at 140° C. for 4 hours under $N_2$ atmosphere. The reaction mixture was partitioned between 10 mL of water and 10 mL of EtOAc. The organic phase was separated, washed three times with 30 mL of water and 10 mL of brine, dried over $Na_2SO_4$, filtered and concentrated under reduced pressure to give 1.0 g of crude product 2-(2,2-diethoxyethoxy)-5-fluorobenzaldehyde as brown liquid and to be used into the next step without further purification.

General procedure for preparation of 5-fluorobenzofuran-2-carbaldehyde: A mixture of crude 2-(2,2-diethoxyethoxy)-5-fluorobenzaldehyde (1 g, 3.9 mmol, 1 eq) in 15 mL of HOAc was degassed and purged with $N_2$ three times. The mixture was stirred at 100° C. for 12 hours under $N_2$ atmosphere. The mixture was evaporated under reduced pressure to give the crude product. The residue was purified by column chromatography ($SiO_2$, eluting with a gradient of petroleum ether:ethyl acetate=10:1 to 5:1) to give 0.4 g of 5-fluorobenzofuran-2-carbaldehyde (2.4 mmol, 63% yield) as a yellow solid.

Example 42. Synthesis of N-((1S,3R)-3-(benzylamino)cyclohexyl)-4-cyano-N-ethyl-1H-benzo[d]imidazole-2-carboxamide (Compound 481)

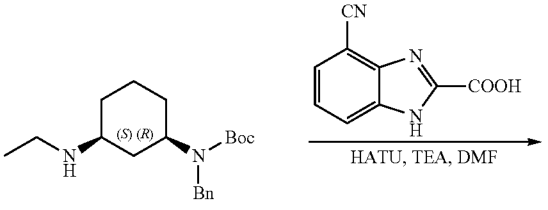

70

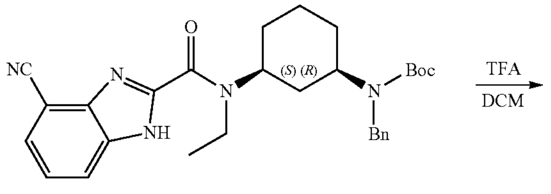

95

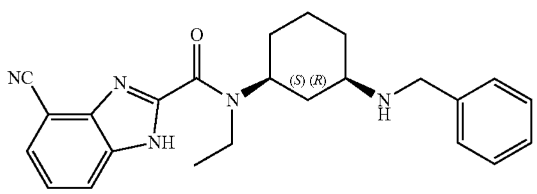

compound 481

General procedure for preparation of intermediate 95: A mixture of compound 70 (35.0 mg, 105 μmol, 1.0 eq), 5-cyanobenzimidazole-2-carboxylic acid (70.6 mg, 316 μmol, 3.0 eq, HCl), TEA (54 mg, 526 μmol, 5.0 eq), HATU (80.1 mg, 211 μmol, 2.0 eq) in DMF (1.5 mL) was degassed and purged with $N_2$ three times. The mixture was stirred at 30° C. for 2 hours under $N_2$ atmosphere. The reaction mixture was partitioned between 3 mL of water and 3 mL of EtOAc. The organic phase was separated, washed three times with 3 mL of water and once with 2 mL of brine, dried over $Na_2SO_4$, filtered and concentrated under reduced pressure to give a residue. The residue was purified by prep-TLC (eluting with petroleum ether:ethyl acetate=1:1) to give 15.0 mg of crude compound 95 as a colorless gum which was used in the next step without further purification.

General procedure for preparation of compound 481: A mixture of compound 95 (15.0 mg, 29.9 μmol, 1.0 eq), TFA (154 mg, 1.4 mmol, 0.1 mL, 45 eq) in DCM (0.5 mL) was stirred at 18° C. for 0.5 hour. It was evaporated under reduced pressure to give the crude product. The residue was purified by prep-HPLC (TFA condition) to give 5.8 mg of compound 481 (37% yield, TFA salt) as a white solid.

Compound 481

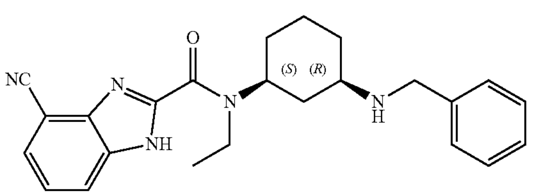

$^1$H NMR (400 MHz, METHANOL-$d_4$) δ ppm 7.91 (br d, J=7.94 Hz, 1H) 7.70-7.78 (m, 1H) 7.43-7.53 (m, 6H) 5.38 (br s, 1H) 4.36 (s, 2H) 4.22-4.31 (m, 1H) 3.42-3.73 (m, 2H) 3.36 (br s, 1H) 2.83 (br s, 1H) 2.39 (br d, J=10.36 Hz, 1H) 2.25 (br d, J=12.57 Hz, 1H) 1.89-2.13 (m, 3H) 1.74-1.87 (m, 2H) 1.39-1.59 (m, 2H) 1.30-1.37 (m, 3H)

LCMS (ESI+): m/z 402.2 (M+H)

The following compounds were prepared analogously:

Compound 482

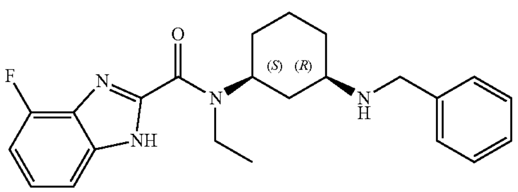

$^1$H NMR (400 MHz, METHANOL-$d_4$) δ ppm 7.23-7.45 (m, 7H) 6.97-7.09 (m, 1H) 4.61 (br s, 2H) 4.30 (brs, 1H) 3.90-4.00 (m, 3H) 3.50-3.68 (m, 2H) 2.21-2.38 (m, 1H) 1.77-2.13 (m, 4H) 1.56-1.72 (m, 2H) 1.15-1.38 (m, 1H) 1.15-1.40 (m, 6H)

LCMS (ESI+): m/z 395.1 (M+H)

Compound 483

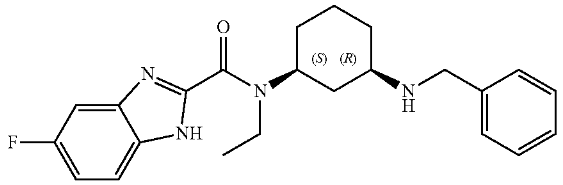

$^1$H NMR (400 MHz, METHANOL-$d_4$) δ ppm 7.59-7.66 (m, 1H) 7.63 (dd, J=8.93, 4.74 Hz, 1H) 7.40-7.53 (m, 5H) 7.33 (dd, J=9.04, 2.20 Hz, 1H) 7.07-7.17 (m, 1H) 5.25 (br t, J=11.58 Hz, 1H) 4.26 (br s, 2H) 3.89-4.11 (m, 1H) 3.48-3.66 (m, 1H) 3.34 (br s, 1H) 2.32-2.53 (m, 1H) 2.16-2.27 (m, 1H) 1.88-2.12 (m, 3H) 1.64-1.86 (m, 1H) 1.24-1.53 (m, 7H)

LCMS (ESI+): m/z 395.2 (M+H)

Compound 484

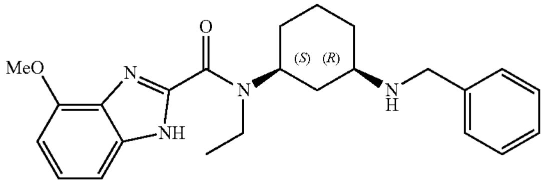

$^1$H NMR (400 MHz, METHANOL-$d_4$) δ ppm 7.45 (br d, J=16.10 Hz, 5H) 7.18-7.30 (m, 2H) 6.82 (br d, J=7.50 Hz, 1H) 4.95-4.97 (m, 1H) 4.25 (br s, 3H) 4.00 (s, 3H) 3.80-3.97 (m, 1H) 3.51-3.66 (m, 1H) 3.18-3.29 (m, 1H) 2.33-2.58 (m, 1H) 1.88-2.27 (m, 5H) 1.65-1.85 (m, 2H) 1.27-1.46 (m, 5H) 1.18-1.24 (m, 1H)

LCMS (ESI+): m/z 407.2 (M+H)

Compound 485

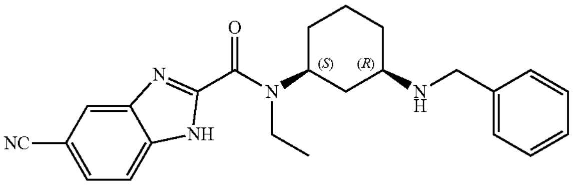

$^1$H NMR (400 MHz, METHANOL-$d_4$) δ ppm 8.09 (d, J=10.52 Hz, 1H) 7.78 (d, J=8.77 Hz, 1H) 7.60-7.67 (m, 1H) 7.42-7.54 (m, 5H) 5.27 (br t, J=11.84 Hz, 1H) 4.20-4.32 (m, 2H) 3.92-4.14 (m, 1H) 3.52-3.71 (m, 1H) 3.36 (br s, 1H) 2.34-2.56 (m, 1H) 2.18-2.29 (m, 1H) 1.89-2.12 (m, 3H) 1.67-1.88 (m, 1H) 1.38-1.57 (m, 2H) 1.32 (t, J=7.02 Hz, 3H)

LCMS (ESI+): m/z 402.2 (M+H)

Compound 486

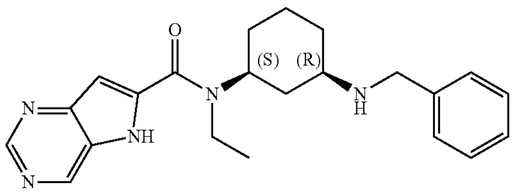

$^1$H NMR (400 MHz, METHANOL-$d_4$) δ ppm 9.10 (s, 1H), 8.98 (s, 1H), 7.51-7.44 (m, 5H), 7.01 (br s, 1H), 4.26 (br s, 2H), 4.11 (br s, 1H), 3.69-3.52 (m, 2H), 3.13 (br s, 1H), 2.39 (br d, J=11.0 Hz, 1H), 2.25-1.73 (m, 6H), 1.42 (br s, 2H), 1.32 (br t, J=6.9 Hz, 3H)

LCMS (ESI+): m/z 378.2 (M+H)

Example 43. Synthesis of 4-cyanobenzimidazol-2-carboxylic (Intermediate Used to Synthesize Compound 481)

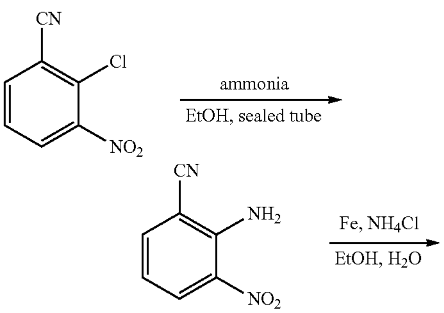

-continued

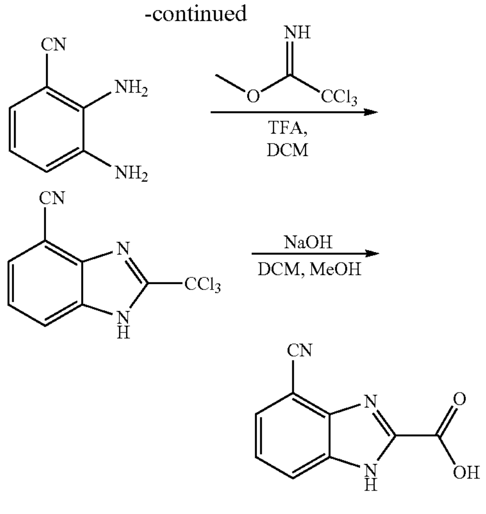

General procedure for preparation of 2-amino-3-nitrobenzonitrile: A solution of anhydrous EtOH (20 mL) was bubbled through $NH_3$ at 0° C. to obtain 7M $NH_3$/EtOH. It was transferred into a sealed tube containing 2-chloro-3-nitrobenzonitrile (0.5 g, 2.7 mmol, 1.0 eq). The mixture was allowed to warm to 18° C. gradually and then stirred at 110° C. for 12 hours. The mixture was evaporated under reduced pressure to remove the most solvent to give 0.5 g of crude 2-amino-3-nitrobenzonitrile as a yellow solid which was used in the next step without further purification.

General procedure for preparation of 2,3-diaminobenzonitrile: A mixture of crude 2-amino-3-nitrobenzonitrile (150.0 mg, 920 μmol, 1.0 eq), Fe (257 mg, 4.6 mmol, 5.0 eq), $NH_4C_1$ (246 mg, 4.6 mmol, 5.0 eq) in EtOH (3 mL) and water (1.5 mL) was stirred at 60° C. for 0.5 hour. The mixture was filtered and the filtrate was evaporated under reduced pressure to give a residue. It was diluted with 5 mL of water and 5 mL of EtOAc, the organic layer was separated and washed once with 2 mL of brine, dried over $Na_2SO_4$, filtered and evaporated under reduced pressure to give 50.0 mg of crude 2,3-diaminobenzonitrile as a brown solid which was used in the next step without further purification.

General procedure for preparation of 2-(trichloromethyl)-1H-benzo[d]imidazole-4-carbonitrile: To a mixture of 2,3-diaminobenzonitrile (50.0 mg, 376 μmol, 1.0 eq) in DCM (1 mL) was added methyl 2,2,2-trichloroethanimidate (86.1 mg, 488 μmol, 1.3 eq), followed by the addition of TFA (107.0 mg, 939 μmol, 2.5 eq). The mixture was stirred at 18° C. for 2 hours under $N_2$ atmosphere. The mixture was diluted with 5 mL of DCM and filtered. The filtrate was used directly into the next step without further purification. The 97.8 mg of crude 2-(trichloromethyl)-1H-benzo[d]imidazole-4-carbonitrile in 5 mL of DCM was obtained as a brown solution and used in the next step directly.

General procedure for preparation of 4-cyano-1H-benzo[d]imidazole-2-carboxylic acid: To a solution of crude 2-(trichloromethyl)-1H-benzo[d]imidazole-4-carbonitrile (97.8 mg, 375.5 μmol, 1.0 eq) in DCM (5 mL) was added NaOH (2.0 M, 376 μL, 2.0 eq). The mixture was 5 evaporated under reduced pressure to remove the most of DCM. To the resulting mixture was added MeOH (2 mL), then it was stirred at 17° C. for 0.5 hour. The mixture was concentrated in vacuo to remove the solvent and the resulting residue was diluted with 1 mL of water and 2 mL of EtOAc and filtered. The EtOAC layer was removed from the filtrate and the aqueous layer, acidified by concentrated HCl until pH~3, was evaporated under reduced pressure to give the crude product. This residue was diluted with 1 mL of MeOH, filtered to remove the salt, and the filtrate was concentrated to give 85.0 mg crude 4-cyano-1H-benzo[d]imidazole-2-carboxylic acid (HCl salt) as a yellow solid which was used in the next step without further purification.

Example 44. Synthesis of N-((1S,3R)-3-((benzo[d]oxazol-6-ylmethyl)amino)cyclohexyl)-N-ethyl-1H-benzo[d]imidazole-2-carboxamide (Compound 487)

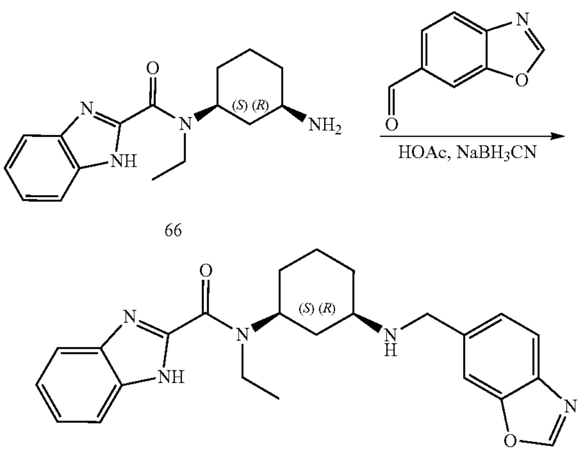

66 compound 487

General procedure for preparation of Compound 487: A mixture of compound 66 (35 mg, 122 μmol, 1.0 eq), 1,3-benzoxazole-6-carbaldehyde (18.0 mg, 122 μmol, 1.0 eq), HOAc (7.3 mg, 122 μmol, 1 eq) in 1 mL of MeOH was stirred at 25° C. for 30 min, then $NaBH_3CN$ (15.4 mg, 244 μmol, 2.0 eq) was added and the mixture was stirred for another 11.5 hours at 25° C. It was quenched by adding 1 drop of water, filtered to give the filtrate. The filtrate was purified by prep-HPLC (neutral condition) to afford 3.2 mg of compound 487 (6.8 μmol, 5.6% yield, 88.7% purity) as a white solid.

Compound 487

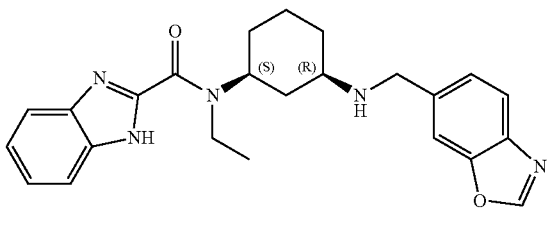

$^1H$ NMR (400 MHz, CHLOROFORM-d) δ ppm 10.75 (br s, 1H) 8.06 (s, 1H) 7.57-7.62 (m, 1H) 7.48-7.84 (m, 3H) 7.29-7.36 (m, 2H) 7.29-7.36 (m, 1H) 5.92 (br t, J=11.36 Hz, 1H) 4.51 (br t, J=12.57 Hz, 1H) 4.26 (q, J=6.91 Hz, 1H) 3.99 (d, J=4.85 Hz, 2H) 3.56 (q, J=6.98 Hz, 1H) 2.72-2.90 (m, 1H) 2.14-2.34 (m, 1H) 2.02 (br d, J=12.13 Hz, 1H) 1.91 (br d, J=11.47 Hz, 2H) 1.41-1.61 (m, 3H) 1.27-1.34 (m, 3H) 1.06-1.19 (m, 1H)

LCMS (ESI+): m/z 418.2 (M+H)

The following compounds could be prepared analogously from compound 66:

Compound 488

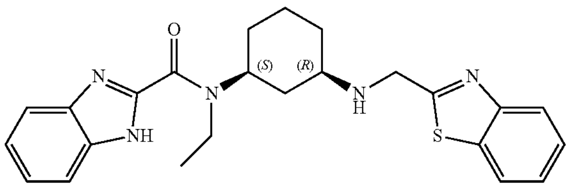

$^{1}$H NMR (400 MHz, METHANOL-$d_4$) δ ppm 7.99-8.13 (m, 2H) 7.47-7.72 (m, 4H) 7.34 (br s, 2H) 5.18 (br s, 1H) 4.84 (br s, 2H) 4.26 (br s, 1H) 3.96 (br dd, J=17.79, 7.15 Hz, 1H) 3.41-3.71 (m, 2H) 2.38-2.61 (m, 1H) 2.11-2.35 (m, 2H) 1.83-2.10 (m, 3H) 1.75 (br d, J=12.10 Hz, 1H) 1.41-1.59 (m, 2H) 1.23-1.36 (m, 3H)

LCMS (ESI+): m/z 434.1 (M+H)

Compound 489

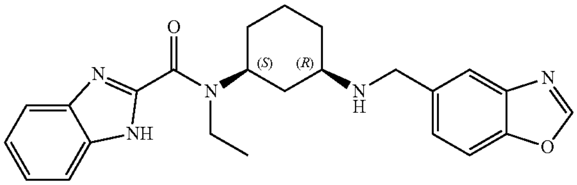

$^{1}$H NMR (400 MHz, CHLOROFORM-d) δ ppm 10.87-11.36 (m, 1H) 8.01 (s, 1H) 7.61-7.81 (m, 2H) 7.44 (br dd, J=8.31, 2.69 Hz, 2H) 7.14-7.35 (m, 3H) 5.79-5.92 (m, 1H) 4.50 (br s, 1H) 4.20 (q, J=6.81 Hz, 1H) 3.90 (d, J=5.99 Hz, 2H) 3.52 (q, J=6.97 Hz, 1H) 2.60-2.84 (m, 1H) 2.08-2.27 (m, 1H) 1.75-2.00 (m, 4H) 1.36-1.62 (m, 4H) 1.26 (td, J=6.85, 4.16 Hz, 3H) 0.98-1.14 (m, 1H)

LCMS (ESI+): m/z 418.2 (M+H)

Compound 490

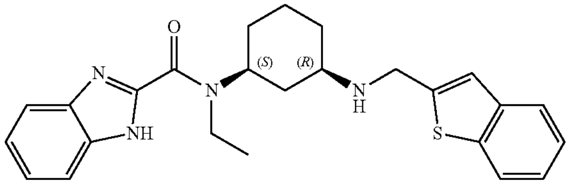

$^{1}$H NMR (400 MHz, CHLOROFORM-d) δ ppm 10.55-10.79 (m, 1H) 7.68-7.79 (m, 1H) 7.56-7.65 (m, 1H) 7.40-7.48 (m, 1H) 7.17-7.32 (m, 4H) 7.07 (s, 1H) 5.84 (brt, J=11.69 Hz, 1H) 4.46 (br t, J=12.57 Hz, 1H) 4.21 (q, J=6.98 Hz, 1H) 4.07 (d, J=4.41 Hz, 2H) 3.51 (q, J=6.91 Hz, 1H) 2.68-2.88 (m, 1H) 2.07-2.29 (m, 1H) 1.74-2.00 (m, 3H) 1.38-1.62 (m, 6H) 1.25 (dt, J=10.58, 7.06 Hz, 3H) 0.97-1.13 (m, 1H)

LCMS (ESI+): m/z 433.1 (M+H)

Compound 491

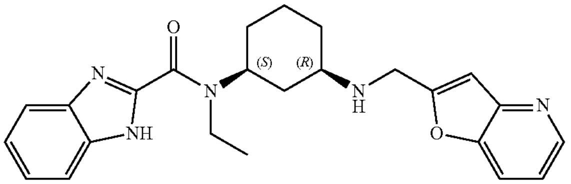

$^{1}$H NMR (400 MHz, CHLOROFORM-d) δ ppm 10.89-11.14 (m, 1H) 8.50 (br d, J=3.31 Hz, 1H) 7.63-7.84 (m, 2H) 7.51 (br d, J=7.50 Hz, 1H) 7.27-7.37 (m, 2H) 7.16 (dd, J=8.16, 4.85 Hz, 1H) 6.81 (d, J=5.07 Hz, 1H) 5.92 (br t, J=11.36 Hz, 1H) 4.56 (br t, J=12.02 Hz, 1H) 4.27 (q, J=6.91 Hz, 1H) 4.00-4.09 (m, 2H) 3.58 (q, J=6.98 Hz, 1H) 2.71-2.90 (m, 1H) 2.13-2.34 (m, 1H) 1.83-2.04 (m, 3H) 1.41-1.65 (m, 3H) 1.32 (q, J=6.76 Hz, 3H) 1.06-1.20 (m, 1H)

LCMS (ESI+): m/z 418.2 (M+H)

Compound 492

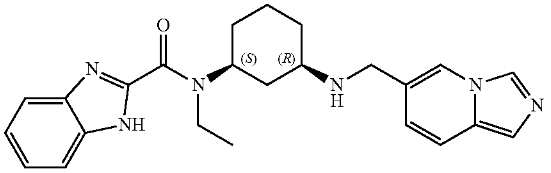

$^{1}$H NMR (400 MHz, METHANOL-$d_4$) δ ppm 8.12-8.33 (m, 2H) 7.46-7.73 (m, 3H) 7.26-7.39 (m, 3H) 6.80-6.94 (m, 1H) 4.74-4.88 (m, 2H) 4.37 (br t, J=12.04 Hz, 1H) 3.91-4.00 (m, 1H) 3.72-3.83 (m, 2H) 3.55-3.64 (m, 1H) 2.68-2.77 (m, 1H) 2.57 (br t, J=11.13 Hz, 1H) 2.17-2.32 (m, 1H) 1.80-2.11 (m, 3H) 1.41-1.74 (m, 2H) 1.32 (br t, J=6.97 Hz, 2H) 1.22 (br t, J=6.85 Hz, 1H) 1.04-1.18 (m, 1H)

LCMS (ESI+): m/z 417.3 (M+H)

Compound 493

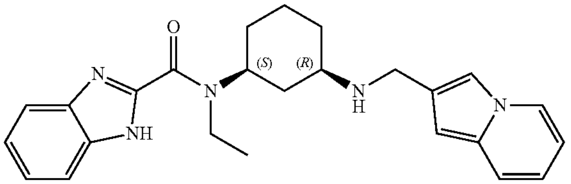

$^{1}$H NMR (400 MHz, DMSO-$d_6$) δ ppm 8.85 (br d, J=19.93 Hz, 2H) 8.29 (dd, J=13.88, 6.91 Hz, 1H) 7.61-7.69 (m, 2H) 7.52-7.58 (m, 1H) 7.43 (br t, J=10.21 Hz, 1H) 7.24-7.32 (m, 2H) 6.74 (dd, J=8.56, 6.60 Hz, 1H) 6.58 (t, J=6.72 Hz, 1H) 6.52 (br d, J=6.24 Hz, 1H) 5.28 (br t, J=11.92 Hz, 1H) 4.29 (br d, J=3.91 Hz, 2H) 3.95-4.21 (m, 2H) 3.44-3.54 (m, 1H) 3.13-3.29 (m, 1H) 2.39 (br s, 1H) 2.26 (br d, J=10.27 Hz, 1H) 2.12 (br s, 1H) 1.72-1.94 (m, 3H) 1.56-1.71 (m, 1H) 1.29-1.44 (m, 2H) 1.24 (q, J=7.09 Hz, 2H) 1.19-1.27 (m, 1H)

LCMS (ESI+): m/z 416.2 (M+H)

Example 45. Synthesis of furo[3,2-b]pyridine-2-carbaldehyde (the Aldehyde used in the Synthesis of Compound 491)

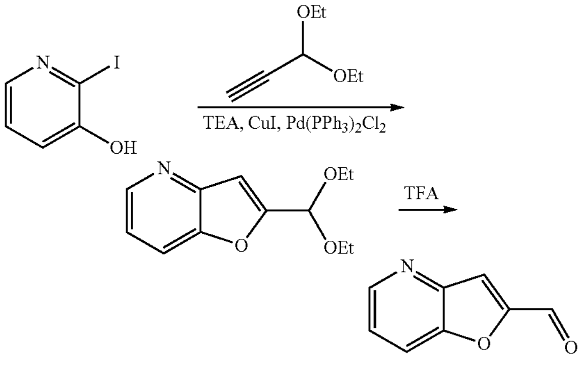

General procedure for preparation of 2-(diethoxymethyl) furo[3,2-b]pyridine: A mixture of 2-iodo-3-hydroxypyridine (1 g, 4.5 mmol, 1.0 eq), 3,3-diethoxyprop-1-yne (754.0 mg, 5.9 mmol, 1.3 eq), TEA (4.1 g, 41 mmol, 9.0 eq), CuI (172 mg, 905 μmol, 0.2 eq) and $Pd(PPh_3)_2Cl_2$ (318 mg, 453 μmol, 0.1 eq) in 10 mL of THF was degassed and purged with $N_2$ three times. The mixture was stirred at 70° C. for 14 hours under $N_2$ atmosphere. The reaction mixture was concentrated in vacuo. The residue was purified by column chromatography ($SiO_2$, eluting with petroleum ether:ethyl acetate=100:1 to 2:1) to afford 820 mg of 2-(diethoxymethyl)furo[3,2-b]pyridine (3.7 mmol, 82% yield) as yellow oil.

General procedure for preparation of furo[3,2-b]pyridine-2-carbaldehyde: To a mixture of 2-(diethoxymethyl)furo[3,2-b]pyridine in 2 mL of THF and 0.5 mL of water was added TFA (770.0 mg, 6.8 mmol, 7.5 eq), the mixture was stirred at 60° C. for 1 hour under $N_2$ atmosphere. It was diluted with 2 mL of water, basified by 2N NaOH solution until pH=9, then extracted twice with 9 mL of ethyl acetate. The combined organic layers were washed with 2 mL of brine, dried over $Na_2SO_4$, filtered and evaporated under reduced pressure to afford 130 mg of crude furo[3,2-b]pyridine-2-carbaldehyde as a light-yellow oil which was used in the next step without further purification to prepare compound 491.

Example 46. Synthesis of imidazo[1,5-a]pyridine-6-carbaldehyde (the Aldehyde used in the Synthesis of Compound 492)

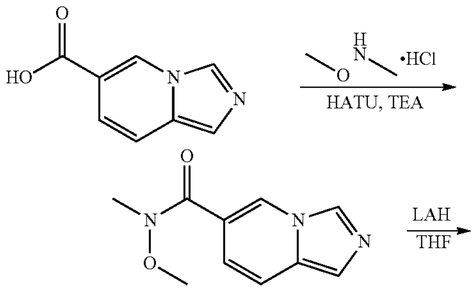

-continued

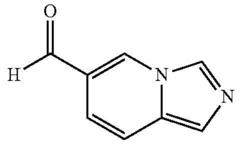

General procedure for the preparation of N-methoxy-N-methylimidazo[1,5-a]pyridine-6-carboxamide: To a solution of imidazo[1,5-a]pyridine-6-carboxylic acid (70 mg, 432 μmol, 1.0 eq) and HATU (197 mg, 518 μmol, 1.2 eq) in 1 mL of DMF was added TEA (131 mg, 1.3 mmol, 3 eq). The mixture was stirred at 25° C. for 10 min, and then N-methoxymethanamine hydrochloride (50.5 mg, 518 μmol, 1.2 eq) was added. The mixture was stirred at 25° C. for 12 hours. The reaction mixture was poured into 5 mL of ice-water and extracted with five 3 mL portions of ethyl acetate. The combined organic layers were dried with anhydrous $Na_2SO_4$, filtered and concentrated in vacuo. The residue was purified by prep-TLC ($SiO_2$) to afford 110 mg of crude N-methoxy-N-methylimidazo[1,5-a]pyridine-6-carboxamide as yellow oil.

General procedure for preparation of imidazo[1,5-a]pyridine-6-carbaldehyde: To a solution of N-methoxy-N-methylimidazo[1,5-a]pyridine-6-carboxamide (110 mg, 536 μmol, 1.0 eq) in 2 mL of THF was added LAH (30.5 mg, 804 μmol, 1.5 eq) in portions at 0° C. After addition, the resulting mixture was stirred at 0° C. for 0.5 hour. The reaction mixture was quenched by addition 1 mL of water at 0° C., and then diluted with 5 mL of water and finally extracted with four 3 mL portions of ethyl acetate. The combined organic layers were dried over anhydrous $Na_2SO_4$, filtered and concentrated under reduced pressure to afford 70 mg of crude imidazo[1,5-a]pyridine-6-carbaldehyde as an orange oil which was used to prepare compound 492 without further purification.

Example 47. Synthesis of indolizine-2-carbaldehyde (the Aldehyde Used in the Synthesis of Compound 493)

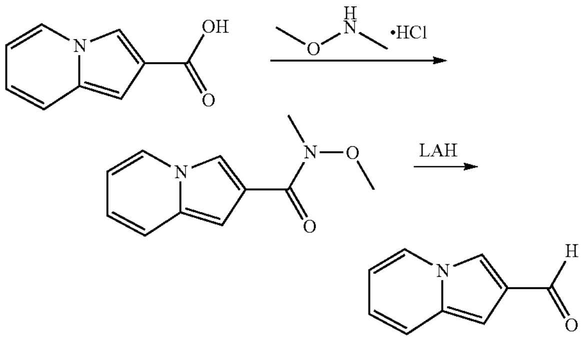

General procedure for preparation of N-methoxy-N-methylindolizine-2-carboxamide: A mixture of indolizine-2-carboxylic acid (0.2 g, 1.2 mmol, 1 eq), N-methoxymethanamine (182 mg, 1.9 mmol, 1.5 eq, HCl), HATU (566 mg, 1.5 mmol, 1.2 eq), TEA (251 mg, 2.5 mmol, 2 eq) in 3 mL of DMF was degassed and purged with $N_2$ three times. The mixture was stirred at 28° C. for 12 hours under $N_2$ atmosphere. The reaction mixture was partitioned between 5 mL of water and 5 mL of EtOAc. The organic phase was separated, washed twice with 5 mL of water and 5 mL of brine, dried over $Na_2SO_4$, filtered and concentrated under reduced pressure to afford 190 mg of crude N-methoxy-N-methylindolizine-2-carboxamide as black brown oil which was used in the next step without further purification.

Procedure for the preparation of indolizine-2-carbaldehyde: To a solution of N-methoxy-N-methylindolizine-2-carboxamide (190 mg, 930 μmol, 1.0 eq) in 2 mL of THF was added LAH (53.0 mg, 1.4 mmol, 1.5 eq) in portions at 0° C. After addition, the resulting mixture was stirred at 25° C. for 2 hours. The reaction mixture was quenched by the addition of 1.5 mL of water and 4.5 mL NaOH (15%) solution at 0° C. It was diluted with 15 mL of water and extracted with three 7 ml portions of ethyl acetate. The combined organic layers were washed with 7 mL of brine, dried over anhydrous $Na_2SO_4$, filtered and concentrated under reduced pressure to afford 182 mg of crude indolizine-2-carbaldehyde as a black brown solid.

Example 48. Synthesis of N-ethyl-N-((1S,3R)-3-((imidazo[1,2-a]pyridin-2-ylmethyl)amino)cyclohexyl)-1H-benzo[d]imidazole-2-carboxamide (Compound 494)

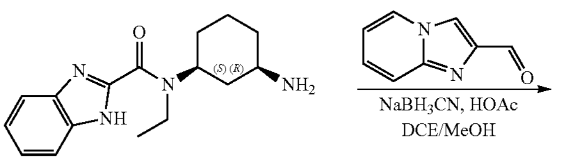

66

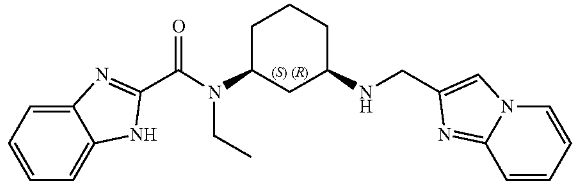

compound 494

General procedure for preparation of Compound 494: A mixture of compound 66 (20 mg, 70 μmol, 1.0 eq), imidazo[1,2-a]pyridine-2-carbaldehyde (8.2 mg, 56 μmol, 0.8 eq), HOAc (4.2 mg, 70 μmol, 1 eq) in 1 mL of DCE and 0.5 mL of MeOH was stirred for 30 min at 25° C., then $NaBH_3CN$ (8.8 mg, 140 μmol, 2 eq) was added and the mixture stirred for another 1 hour under $N_2$ atmosphere. It was quenched by adding 2 drops of water, then filtered to give the filtrate. The filtrate was concentrated and purified by prep-HPLC (neutral condition) to afford 9.2 mg of compound 494 (21.8 μmol, 31. % yield, 98.9% purity) as a white solid.

Compound 494

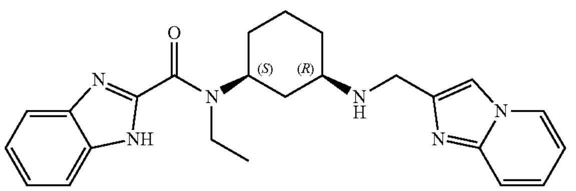

$^1$H NMR (400 MHz, CHLOROFORM-d) δ ppm 10.87-11.53 (m, 1H) 8.02 (t, J=7.72 Hz, 1H) 7.44-7.86 (m, 4H) 7.30 (br s, 2H) 7.09-7.17 (m, 1H) 6.73 (t, J=6.73 Hz, 1H) 5.84-5.94 (m, 1H) 4.61 (br t, J=12.13 Hz, 1H) 4.18-4.34 (m, 1H) 4.01 (s, 2H) 3.58 (q, J=6.98 Hz, 1 H) 2.75-2.90 (m, 1H) 2.18-2.34 (m, 1H) 2.03 (br d, J=12.13 Hz, 3H) 1.40-1.66 (m, 3H) 1.28-1.35 (m, 3H) 1.07-1.21 (m, 1H)

LCMS (ESI+): m/z 417.2 (M+H)

Example 49. Synthesis of N-((1S,3R)-3-(((3-cyclopropylisoxazol-5-yl)methyl)amino)cyclohexyl)-N-ethyl-1H-benzo[d]imidazole-2-carboxamide (Compound 495)

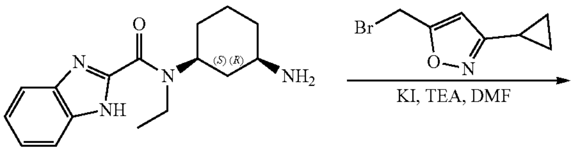

66

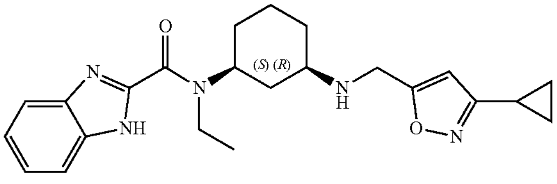

compound 495

General procedure or preparation of Compound 495: A mixture of compound 66 (35 mg, 122 μmol, 1.0 eq), 5-(bromomethyl)-3-cyclopropylisoxazole (49.4 mg, 244 μmol, 2.0 eq), $Et_3N$ (37.1 mg, 367 μmol, 3.0 eq) and KI (10.1 mg, 61.1 μmol, 0.5 eq) in 1 mL of DMF was degassed and purged with $N_2$ three times. The mixture was stirred at 20° C. for 12 hours under $N_2$ atmosphere. The reaction mixture was filtered and filter liquor was concentrated under reduced pressure to give a residue. The residue was purified by prep-HPLC (TFA condition) to afford 24.4 mg of compound 495 (46.7 μmol, 38.2% yield, 99.9% purity, TFA salt) as a white solid.

Compound 495

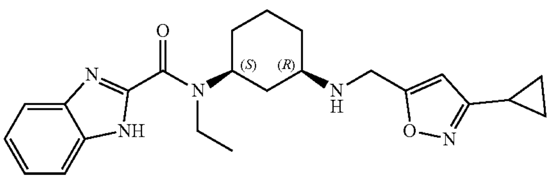

$^1$H NMR (400 MHz, METHANOL-$d_4$) δ ppm 7.69 (br s, 2H) 7.39 (m, 2H) 6.38-6.36 (m, 1H) 4.92-4.95 (m, 0.5H) 4.48-4.45 (m, 2H) 4.19-4.18 (m, 0.5H) 3.86-3.83 (m, 1H) 3.82-3.81 (m, 1H) 3.62-3.54 (m, 1H) 2.47-2.45 (m, 1H) 2.19-1.83 (m, 6H) 1.40-1.24 (m, 5H) 1.07-1.06 (m, 2H) 0.80-0.77 (m, 2H)

LCMS (ESI+): m/z 408.2 (M+H)

The following compounds were prepared analogously:

Compound 496

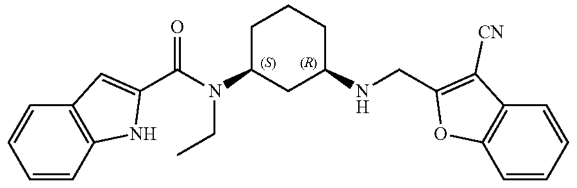

$^1$H NMR (400 MHz, CHLOROFORM-d) δ ppm 9.31 (br s, 1H), 7.67-7.64 (m, 1H), 7.60 (br s, 1H), 7.52-7.50 (m, 1H), 7.42-7.34 (m, 3H), 7.28-7.25 (m, 1H), 7.13-7.09 (t, J=8.0 Hz, 1H), 6.75 (br s, 1H), 4.56-4.51 (br t, J=11.6 Hz, 1H), 4.22-4.14 (m, 2H), 3.63 (br s, 2H), 2.72 (br s, 1H), 2.16 (br d, J=10.8 Hz, 1H), 2.06 (br d, J=12.1 Hz, 1H), 1.94-1.86 (m, 2H), 1.29-1.50 (m, 2H), 1.44-1.25 (m, 4H), 1.16-1.06 (m, 1H)

LCMS (ESI+): m/z 441.2 (M+H)

Conmpound 497

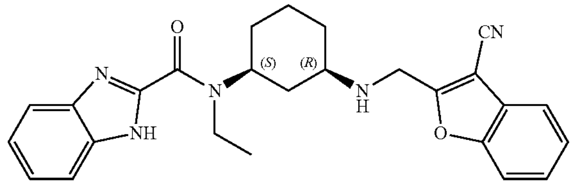

$^1$H NMR (400 MHz, CHLOROFORM-d) δ ppm 11.26-11.34 (d, J=86 Hz 1H), 7.84-7.60 (m, 2H), 7.53-7.49 (m, 2H), 7.41-7.22 (m, 4H), 5.96-5.91 (m, 1H), 4.58 (br t, J=12.2 Hz, 1H), 4.31-4.27 (m, 1H), 4.24-4.14 (m, 2H), 3.62 (q, J=7.0 Hz, 1H), 2.87-2.74 (m, 1H), 2.31-2.17 (m, 1H), 2.08 (br d, J=12.1 Hz, 1H), 1.97-1.88 (m, 2H), 1.67-1.46 (m, 3H), 1.35 (t, J=7.1 Hz, 3H), 1.20-1.09 (m, 1H)

LCMS (ESI+): m/z 442.2 (M+H)

Compound 498

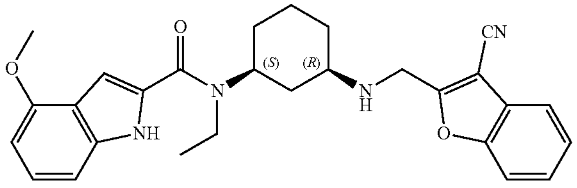

$^1$H NMR (400 MHz, CHLOROFORM-d) δ ppm 9.35 (br s, 1H), 7.67 (dd, J=2.6, 6.0 Hz, 1H), 7.54-7.51 (m, 1H), 7.41-7.35 (m, 2H), 7.22-7.18 (m, 1H), 7.03 (d, J=8.4 Hz, 1H), 6.88 (br s, 1H), 6.50 (d, J=7.7 Hz, 1H), 4.56 (br s, 1H), 4.23-4.15 (m, 2H), 3.94 (s, 2H), 3.66 (br s, 2H), 2.78-2.73 (m, 1H), 2.22-2.06 (m, 2H), 1.94 (br d, J=13.9 Hz, 2H), 1.60-1.45 (m, 3H), 1.36 (br s, 3H), 1.17-1.07 (m, 1H)

LCMS (ESI+): m/z 471.3 (M+H)

Compound 510

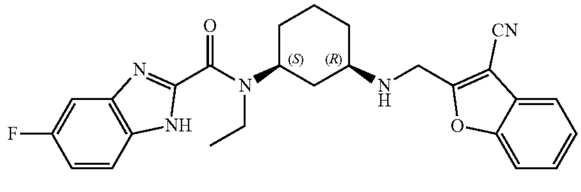

$^1$H NMR (400 MHz, METHANOL-$d_4$) δ ppm 7.77-7.67 (m, 5H), 7.57-7.52 (m, 1H), 7.11 (br t, J=9.3 Hz, 1H), 5.35 (br t, J=11.8 Hz, 1H), 4.78-4.74 (m, 2H), 4.06-3.98 (m, 1H), 3.64-3.43 (m, 2H), 2.54-2.45 (m, 1H), 2.12-2.07 (m, 1H), 2.13-1.85 (m, 4H), 1.51-1.46 (m, 2H), 1.35-1.31 (m, 3H)

LCMS (ESI+): m/z 460.2 (M+H)

Example 50. Synthesis of 5-(bromomethyl)-3-cyclopropylisoxazole (the Bromide Used in the Synthesis of Compound 495)

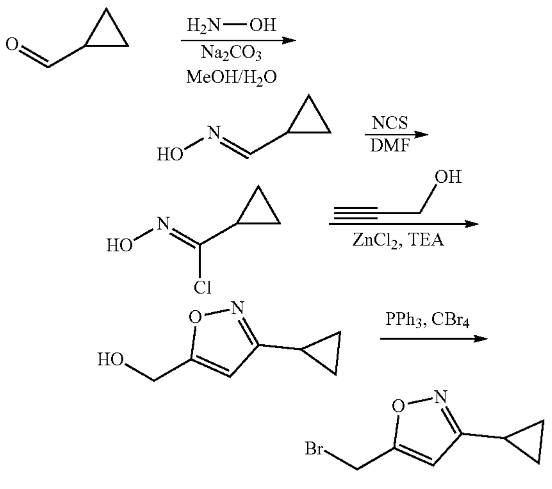

5-(bromomethyl)-3-cyclopropylisoxazole

General procedure for preparation of cyclopropanecarbaldehyde oxime: To a solution of cyclopropanecarbaldehyde (5 g, 71 mmol, 1.0 eq) in 50 mL MeOH and 50 mL of water was added hydroxylamine-hydrochloride (6.0 g, 86 mmol, 1.2 eq) and $Na_2CO_3$ (4.5 g, 43 mmol, 0.6 eq) at 0° C. The mixture was stirred at 20° C. for 12 hours. The reaction mixture was concentrated under reduced pressure to remove solvent. The residue was diluted with 30 mL of water and extracted with four 50 ml portions of ethyl acetate. The combined organic layers were washed twice with 50 mL of brine, dried over $Na_2SO_4$, filtered and concentrated under reduced pressure to afford 4.7 g of crude cyclopropanecarbaldehyde oxime as a colorless oil.

General procedure for preparation of N-hydroxycyclopropanecarbimidoyl chloride: To a mixture of cyclopropanecarbaldehyde oxime (4.7 g, 55 mmol, 1.0 eq) in 60 mL of DMF was added NCS (8.1 g, 61 mmol, 1.1 eq) at 25° C., then the mixture was stirred at 25° C. for 2 hours under $N_2$ atmosphere. The reaction mixture was partitioned between 100 mL of water and extracted with three 50 mL portions of ethyl acetate. The organic phase was separated, washed three with 50 mL of brine, dried over $Na_2SO_4$, filtered and concentrated under reduced pressure to afford 6.6 g of crude N-hydroxycyclopropanecarbimidoyl chloride as light green oil.

General procedure for preparation of (3-cyclopropylisoxazol-5-yl)methanol: A mixture of prop-2-yn-1-ol (1.4 g, 25 mmol, 3 eq) in 10 mL of was cooled to 0° C., then N-hydroxycyclopropanecarbimidoyl chloride (1 g, 8.4 mmol, 1.0 eq), $ZnCl_2$ (2.3 g, 17 mmol, 2.0 eq), TEA (3.0 g, 29 mmol, 3.5 eq) were added sequentially. The mixture was stirred at 25° C. for 12 hours under $N_2$ atmosphere. The reaction mixture was diluted with 15 mL of water and 15 mL of EtOAc, the mixture was filtered. The organic phase was separated, washed with 15 mL of brine, dried over $Na_2SO_4$, filtered and concentrated under reduced pressure to afford 860 mg of crude (3-cyclopropylisoxazol-5-yl)methanol as yellow oil.

General procedure for preparation of 5-(bromomethyl)-3-cyclopropylisoxazole: A mixture of (3-cyclopropylisoxazol-5-yl)methanol (100 mg, 719 μmol, 1.0 eq) and $CBr_4$ (262 mg, 791 μmol, 1.1 eq) $PPh_3$ (207 mg, 791 μmol, 1.1 eq) in 2 mL of THF was degassed and purged with $N_2$ three times. The mixture was stirred at 20° C. for 12 hours under $N_2$ atmosphere. The reaction mixture was quenched by the addition 2 mL of water, and then extracted with three 2 mL portions of ethyl acetate. The combined organic layers were washed twice with 2 mL of brine, dried over $Na_2SO_4$, filtered and concentrated under reduced pressure to afford 100 mg of 5-(bromomethyl)-3-cyclopropylisoxazole (495 μmol, 69% yield) as yellow solid.

Example 51. Synthesis of 2-(bromomethyl)benzofuran-3-carbonitrile (the Bromide Used in the Synthesis of Compounds 496, 497 and 498)

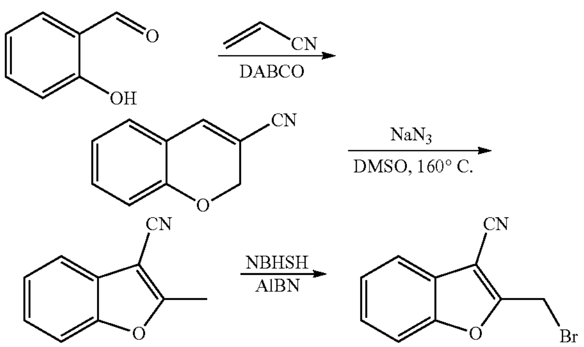

General procedure for preparation of 2H-chromene-3-carbonitrile: A mixture of 2-hydroxybenzaldehyde (5 g, 41 mmol, 4.4 mL, 1 eq), prop-2-enenitrile (10.9 g, 205 mmol, 13.6 mL, 5 eq), DABCO (1.0 g, 9.0 mmol, 991 μL, 0.2 eq) was stirred at 90° C. for 12 hours under $N_2$ atmosphere. The mixture was evaporated under reduced pressure to give the crude product. The residue was purified by column chromatography ($SiO_2$, eluting with petroleum ether:ethyl acetate=20:1) to give 5.6 g of 2H-chromene-3-carbonitrile (36 mmol, 87% yield) as a light yellow solid.

General procedure for preparation of 2-methylbenzofuran-3-carbonitrile: A mixture of 2H-chromene-3-carbonitrile (3 g, 19.1 mmol, 1 eq), $NaN_3$ (1.4 g, 21.0 mmol, 1.1 eq) in 30 mL of DMSO was degassed and purged with $N_2$ three times, and then the mixture was stirred at 160° C. for 30 min under $N_2$ atmosphere. The reaction mixture was partitioned between 30 mL of water and 30 mL of EtOAc. The organic phase was separated, washed three times with 60 mL of water and 20 mL of brine, dried over $Na_2SO_4$, filtered and concentrated under reduced pressure to give a residue. The residue was purified by column chromatography ($SiO_2$, eluting with a gradient of petroleum ether:ethyl acetate=30:1 to 15:1) to give 1.7 g of 2-methylbenzofuran-3-carbonitrile (10.8 mmol, 57% yield) as a light-yellow solid.

General procedure for preparation of 2-(bromomethyl)benzofuran-3-carbonitrile: A mixture of 2-methylbenzofuran-3-carbonitrile (2.3 g, 14.6 mmol, 1.0 eq), AIBN (479 mg, 2.9 mmol, 0.2 eq) and NBS (2.9 g, 16.0 mmol, 1.1 eq) in 23 mL of $CCl_4$ was degassed and purged with $N_2$ three times, and then the mixture was stirred at 80° C. for 12 hours under $N_2$ atmosphere. The mixture was evaporated under reduced pressure to give the crude product. The crude product was purified by column chromatography ($SiO_2$, eluting with petroleum ether:ethyl acetate=20:1) to give 0.9 g of 2-(bromomethyl)benzofuran-3-carbonitrile (3.8 mmol, 26% yield) as a yellow solid.

Example 52. Synthesis of N-((1S,3R)-3-((5-cyclopropyl-1,3,4-thiadiazol-2-yl)amino)cyclohexyl)-N-ethyl-1H-indole-2-carboxamide (Compound 499)

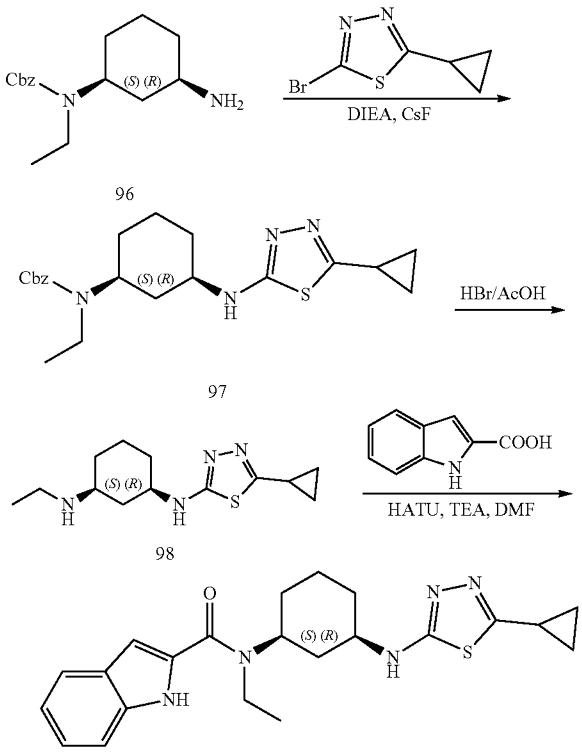

96

97

98 compound 499

General procedure for preparation of compound 97: To a solution of compound 96 (500 mg, 1.8 mmol, 1 eq) prepared from compound 68 and HCl in EtOAc, 2-bromo-5-cyclopropyl-1,3,4-thiadiazole (557 mg, 2.7 mmol, 1.5 eq) in 8 mL of DMSO was added DIEA (1.2 g, 9.1 mmol, 5 eq) and CsF (1.4 g, 9.1 mmol, 5 eq). The mixture was stirred at 100° C. for 12 hours. The residue was poured into 10 mL of water. The aqueous phase was extracted with three 10 mL portions of ethyl acetate. The combined organic phase was washed with twice with 10 mL of brine, dried with anhydrous $Na_2SO_4$, filtered and concentrated in vacuo. The residue was purified by prep-TLC ($SiO_2$, eluting with petroleum ether: ethyl acetate=10:1) to afford compound 97 (130 mg, 325 μmol, 18% yield) as a yellow oil.

General procedure for preparation of compound 98: A mixture of compound 97 (110 mg, 275 μmol, 1 eq) in 2 mL of acetic acid containing 0.2 mL of HBr (40%) was degassed and purged with $N_2$ three times, and then the mixture was stirred at 15° C. for 2 hours under $N_2$ atmosphere. The reaction mixture was partitioned between 10 mL of 4 M aqueous NaOH solution (pH=12) and 5 mL of ethyl acetate. The organic phase was separated, washed with 5 mL of brine, dried over $Na_2SO_4$, filtered and concentrated under reduced pressure to give a residue. The crude product compound 98 (23 mg) was used into the next step without further purification as a yellow oil.

General procedure for preparation of compound 499: To a solution of 1H-indole-2-carboxylic acid (13 mg, 81 μmol, 1.0 eq) in 1 mL of DMF was added HATU (37 mg, 97 μmol, 1.2 eq), $Et_3N$ (12 mg, 121 μmol, 1.5 eq) at 15° C. After addition, the mixture was stirred at this temperature for 30 min, and then compound 98 (21 mg, 81 μmol, 1.0 eq) was added at 15° C. The resulting mixture was stirred at 15° C. for 1 hour. The reaction mixture was filtered. The filtrate was purified by prep-HPLC (TFA condition) to afford compound 499 (7.7 mg, 15 μmol, 18% yield, 100% purity, TFA) as a white solid.

Compound 499

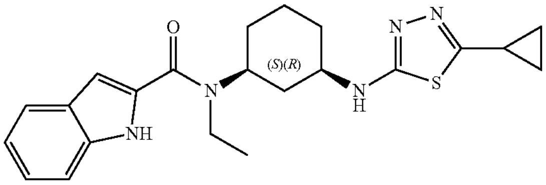

$^1H$ NMR (400 MHz, METHANOL-$d_4$) δ ppm 7.62 (d, J=8.2 Hz, 1H), 7.45-7.41 (m, 1H), 7.21 (dt, J=1.1, 7.6 Hz, 1H), 7.09-7.04 (m, 1H), 6.80 (s, 1H), 4.41 (br s, 1H), 3.60 (br d, J=17.9 Hz, 3H), 2.31-2.17 (m, 2H), 2.08 (br d, J=11.5 Hz, 1H), 1.98-1.86 (m, 2H), 1.83-1.69 (m, 2H), 1.48 (br d, J=12.8 Hz, 1H), 1.31 (br t, J=6.9 Hz, 4H), 1.18-1.11 (m, 2H), 1.01-0.93 (m, 2H)

LCMS (ESI+): m/z 410.1 (M+H)

The following compounds were prepared analogously:

Compound 500

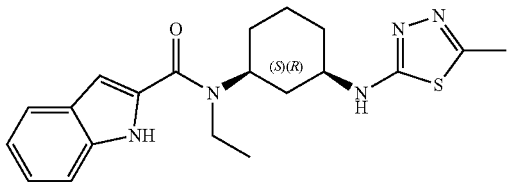

$^1H$ NMR (400 MHz, METHANOL-$d_4$) δ ppm 7.63 (d, J=7.9 Hz, 1H), 7.43 (d, J=8.3 Hz, 1H), 7.21 (t, J=7.7 Hz, 1H), 7.06 (t, J=7.7 Hz, 1H), 6.81 (br s, 1H), 4.43 (br s, 1H), 3.62 (br s, 3H), 2.54 (s, 3H), 2.27 (br d, J=11.0 Hz, 1H), 2.09 (br d, J=10.5 Hz, 1H), 2.01-1.87 (m, 2H), 1.79 (br d, J=13.2 Hz, 2H), 1.49 (br d, J=12.3 Hz, 1H), 1.31 (br t, J=6.8 Hz, 4H)

LCMS (ESI+): m/z 384.1 (M+H)

Compound 501

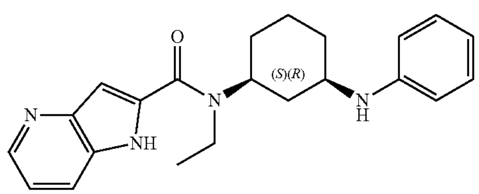

$^1H$ NMR (400 MHz, METHANOL-$d_4$) δ ppm 8.69 (d, J=5.6 Hz, 1H), 8.62 (d, J=8.3 Hz, 1H), 7.79 (dd, J=5.9, 8.3 Hz, 1H), 7.57 (br s, 5H), 7.12 (br s, 1H), 4.12 (br s, 1H), 3.62 (q, J=7.0 Hz, 3H), 2.21 (br d, J=6.1 Hz, 1H), 2.11-1.73 (m, 4H), 1.48 (br dd, J=7.0, 14.2 Hz, 1H), 1.30 (br s, 3H)

LCMS (ESI+): m/z 363.0 (M+H)

Example 53. Synthesis of N-((1S,3R)-3-(benzylamino)cyclohexyl)-N-ethyl-6,6-dimethyl-1,4,6,7-tetrahydropyrano[4,3-b]pyrrole-2-carboxamide (Compound 502)

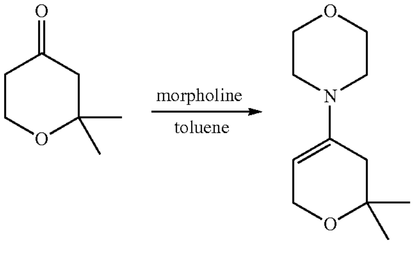

I-1

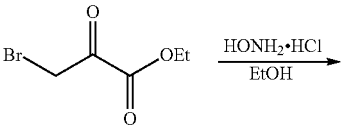

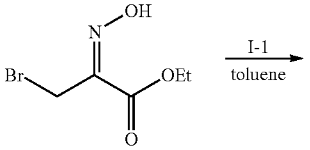

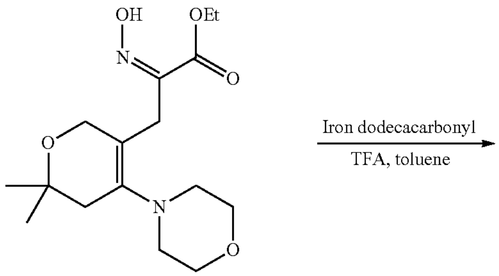

I-2

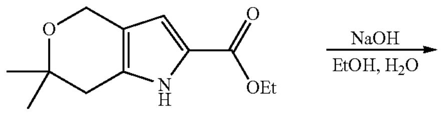

-continued

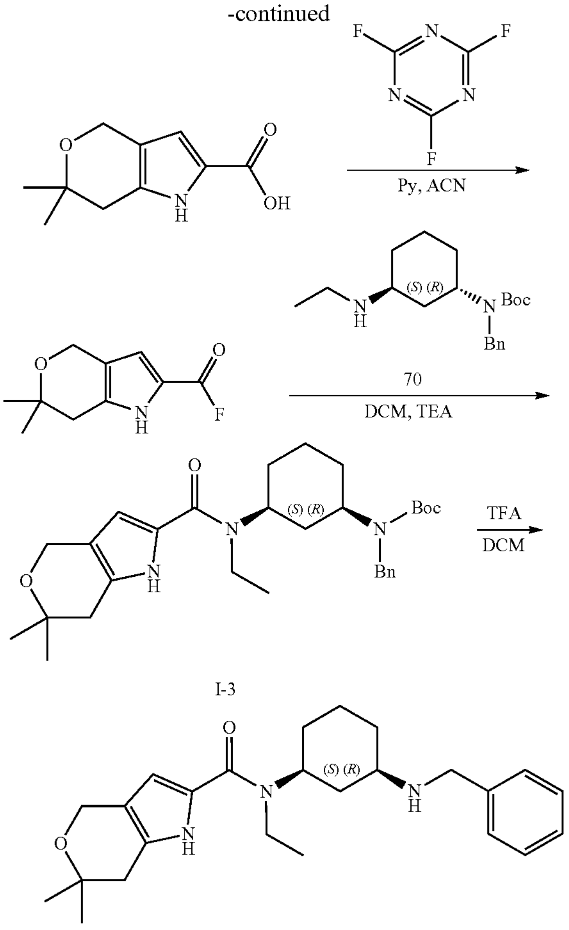

I-3 compound 502

General procedure for preparation of compound I-1: To a solution of 2,2-dimethyltetrahydro-4H-pyran-4-one (1.0 g, 7.8 mmol, 1.0 eq) in toluene (10 mL) was added morpholine (1.0 g, 11.7 mmol, 1.0 mL, 1.5 eq) and PTSA (134 mg, 780 μmol, 0.1 eq). The mixture was stirred at 110° C. for 12 hours. The reaction mixture was concentrated under reduced pressure to remove solvent to give 1.3 g of crude compound I-1 as a yellow oil, which was used in the next step without further purification.

General procedure for preparation of ethyl 3-bromo-2-(hydroxyimino)propanoate: To a mixture of ethyl 3-bromo-2-oxopropanoate (5.0 g, 25.6 mmol, 1.0 eq) in EtOH (50 mL) was added hydroxylamine hydrochloride (1.8 g, 25.6 mmol, 1.0 eq) at 20° C., and then the mixture was stirred at 80° C. for 12 hours. It was concentrated under reduced pressure to remove the EtOH. To the remaining aqueous portion was added 20 mL of $H_2O$ and it was extracted with twice with 30 mL portions of EtOAc. The combined organic layers were washed once with 30 mL of brine, dried over $Na_2SO_4$, filtered and evaporated under reduced pressure to give 4.63 g of ethyl 3-bromo-2-(hydroxyimino)propanoate as a white solid, which was used directly in the next step without purification.

General procedure for preparation of compound I-2: A mixture of ethyl 3-bromo-2-(hydroxyimino)propanoate (680 mg, 3.2 mmol, 1.0 eq), compound I-1 (1.3 g, 6.5 mmol, 2.0 eq), 4 A MS (0.7 g) in toluene (5 mL) was stirred at 15° C. for 0.5 hour. The reaction mixture was filtered and filtrate was concentrated under reduced pressure to give 1.0 g of crude compound I-2 as a yellow oil, which was used in the next step without further purification.

General procedure for preparation of ethyl 6,6-dimethyl-1,4,6,7-tetrahydropyrano[4,3-b]pyrrole-2-carboxylate: To a solution of compound I-2 (1.0 g, 3.1 mmol, 1.0 eq) in toluene (5 mL) was added TFA (559 mg, 4.9 mmol, 1.6 eq) 4 A MS (1.0 g) and carbon monoxide; 4,5,6triferratricyclo-pentane-1-dione (772 mg, 1.5 mmol, 0.5 eq). The mixture was stirred at 110° C. for 12 hours. The reaction mixture was filtered and filtrate was concentrated under reduced pressure to give a residue. The residue was purified by column chromatography ($SiO_2$, eluting with petroleum ether:ethyl acetate=15:1 to 3:1) to give 250 mg of ethyl 6,6-dimethyl-1,4,6,7-tetrahydropyrano[4,3-b]pyrrole-2-carboxylate as a yellow oil.

General procedure for preparation of 6,6-dimethyl-1,4,6,7-tetrahydropyrano[4,3-b]pyrrole-2-carboxylic acid: A mixture of ethyl 6,6-dimethyl-1,4,6,7-tetrahydropyrano[4,3-b]pyrrole-2-carboxylate (250 mg, 1.1 mmol, 1.0 eq) and NaOH (134.4 mg, 3.4 mmol, 3.0 eq) in EtOH (1.5 mL) and $H_2O$ (1.5 mL) was degassed and purged with $N_2$ three times. The mixture was stirred at 15° C. for 0.5 hour under $N_2$ atmosphere, then heated to 40° C. for 12 hours. The reaction mixture was concentrated in vacuo and the residue was diluted with 1 mL of HCl (1 M) (pH=3) and extracted with three 2 mL portions of EtOAc. The combined organic layers were concentrated under reduced pressure to give 0.2 g of crude 6,6-dimethyl-1,4,6,7-tetrahydropyrano[4,3-b]pyrrole-2-carboxylic acid as a yellow solid, which was used in the next step without further purification.

General procedure for preparation of 6,6-dimethyl-1,4,6,7-tetrahydropyrano[4,3-b]pyrrole-2-carbonylfluoride: A mixture of 6,6-dimethyl-1,4,6,7-tetrahydropyrano[4,3-b]pyrrole-2-carboxylic acid (50.0 mg, 256 μmol, 1.0 eq), pyridine (12.2 mg, 154 μmol, 0.6 eq) and 2,4,6-trifluoro-1,3,5-triazine (17.3 mg, 128 μmol, 0.5 eq) in ACN (1 mL) was degassed and purged with $N_2$ three times, and then the mixture was stirred at 20° C. for 2 hours under $N_2$ atmosphere. The reaction mixture was quenched by adding 2 mL of $H_2O$, and then extracted with three 2 mL portions of EtOAc. The combined organic layers were concentrated under reduced pressure to give 35.0 mg of crude 6,6-dimethyl-1,4,6,7-tetrahydropyrano[4,3-b]pyrrole-2-carbonyl fluoride as a yellow oil, which was used in the next step without further purification.

General procedure for preparation of compound I-3: A mixture of 6,6-dimethyl-1,4,6,7-tetrahydropyrano[4,3-b]pyrrole-2-carbonyl fluoride (35.0 mg, 178 μmol, 1 eq) and compound 70 (59.0 mg, 178 μmol, 1.0 eq), $Et_3N$ (19.8 mg, 195 μmol, 1.1 eq) in DCM (1 mL) was degassed and purged with $N_2$ three times. The mixture was stirred at 20° C. for 12 hours under $N_2$ atmosphere. The reaction mixture was concentrated under reduced pressure to remove solvent. The residue was purified by prep-TLC ($SiO_2$, eluting with petroleum ether:ethyl acetate=1:1) to give 35.0 mg of crude compound I-3 as a yellow gum, which was used in the next step without further purification.

General procedure for preparation of compound 502: A mixture of compound I-3 (35.0 mg, 68.7 μmol, 1.0 eq) and TFA (154 mg, 1.4 mmol, 0.1 mL, 19.7 eq) in DCM (1 mL) was degassed and purged with $N_2$ three times. The mixture was stirred at 20° C. for 1 hour under $N_2$ atmosphere. The reaction mixture was quenched by adding 1 mL of aq. saturated $Na_2CO_3$ (to 15 pH~12) at 0° C., and then extracted with three 2 mL portions of DCM. The combined organic layers were concentrated under reduced pressure to give a residue. The residue was purified by prep-HPLC (neutral condition) to give 4.0 mg of compound 502 (13% yield) as a white solid.

Compound 502

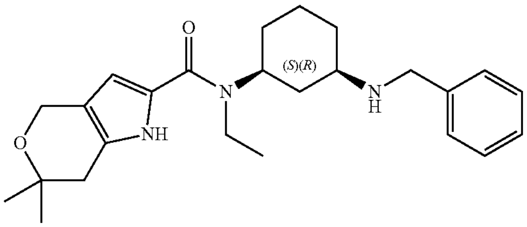

$^1H$ NMR (400 MHz, CHLOROFORM-d) δ ppm 9.25 (br s, 1H), 7.36-7.30 (m, 4H), 7.28-7.22 (m, 1H), 6.16 (br s, 1H), 4.64 (s, 2H), 4.44 (br s, 1H), 3.83 (s, 2H), 3.51 (br s, 2H), 2.68 (br s, 1H), 2.58 (s, 2H), 2.11 (br d, J=10.6 Hz, 1H), 1.98 (br d, J=11.9 Hz, 1H), 1.89-1.79 (m, 2H), 1.51-1.38 (m, 3H), 1.33-1.23 (m, 9H), 1.16-1.04 (m, 1H)

LCMS (ESI+): m/z 410.2 (M+H)

Compound 503 was prepared via an analogous two step procedure involving coupling of 1,4,6,7-tetrahydropyrano[4,3-b]pyrrole-2-carboxylic acid to amine 66 and deprotection with TFA in DCM.

Compound 503

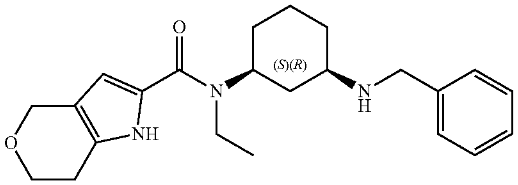

$^1H$ NMR (400 MHz, CHLOROFORM-d) δ ppm 9.36 (br s, 1H) 7.18-7.34 (m, 5H) 6.09 (br s, 1H) 4.58 (s, 2H) 4.31 (br s, 1H) 3.88 (t, J=5.56 Hz, 2H) 3.80 (s, 2H) 3.44 (br s, 3H) 2.67 (br t, J=5.38 Hz, 3H) 1.93-2.14 (m, 2H) 1.67-1.86 (m, 2H) 1.40-1.62 (m, 2H) 1.10-1.36 (m, 5H)

LCMS (ESI+): m/z 382.2 (M+H)

Example 54. Synthesis of 1,4,6,7-tetrahydropyrano[4,3-b]pyrrole-2-carboxylic acid (Used to Synthesize Compounds 502 and 503)

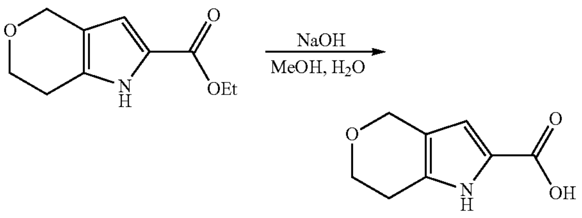

General procedure for preparation of 1,4,6,7-tetrahydropyrano[4,3-b]pyrrole-2-carboxylic acid: To a mixture of 1,4,6,7-tetrahydropyrano[4,3-b]pyrrole-2-carboxylic acid ethyl ester (80 mg, 410 μmol, 1.0 eq) in MeOH (1 mL) and $H_2O$ (0.3 mL) was added NaOH (49 mg, 1.2 mmol, 3.0 eq) in one portion at 15° C. The reaction mixture was stirred at 30° C. for 3 hours. The reaction mixture was concentrated in vacuo to reduce MeOH, then the mixture was adjusted by HCl (1 N) to pH~4 producing some solids. The solids were isolated by filtration to give 60 mg of compound 1,4,6,7-tetrahydropyrano[4,3-b]pyrrole-2-carboxylic acid as a light red solid, which was used directly in the next step without purification.

Example 55. Synthesis of N-((1S,3R)-3-(benzylamino)cyclohexyl)-N-ethyl-1,5,6,7-tetrahydropyrano[3,2-b]pyrrole-2-carboxamide (Compound 511)

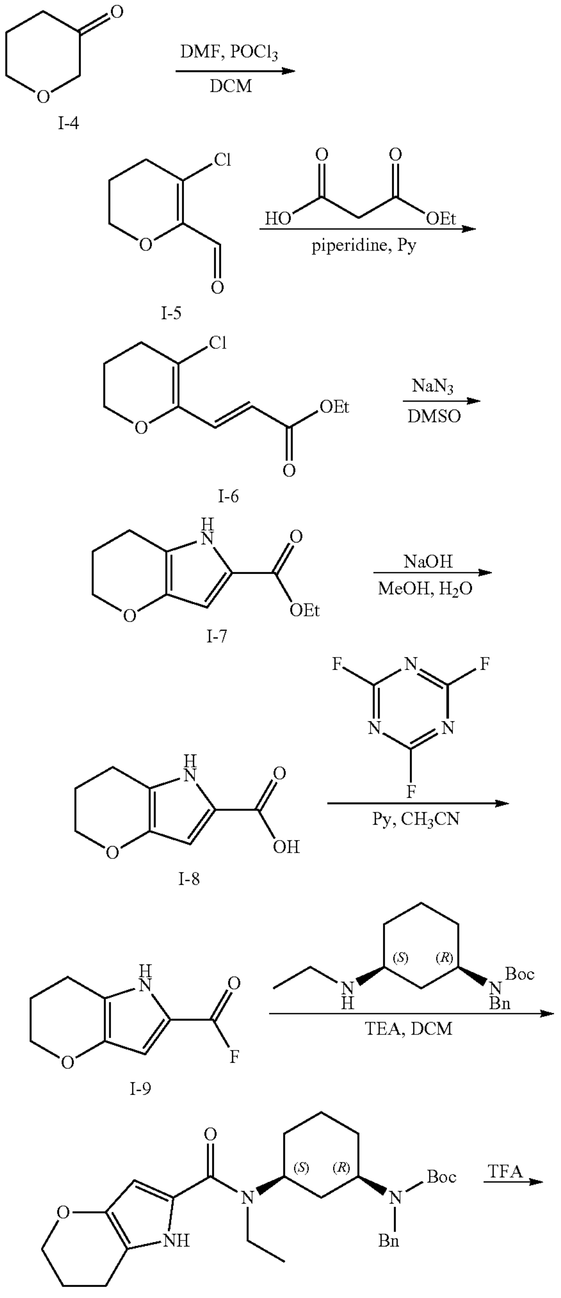

-continued

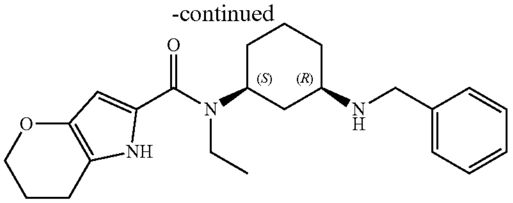

Compound 511

General Procedure for preparation of compound I-5: $POCl_3$ (3.1 g, 20.0 mmol, 1 eq) was added dropwise to DMF (1.46 g, 20.0 mmol, 1 eq) over 5 minutes at 0° C. Dichloromethane (10 mL) was added and then the ice-bath was removed. The reaction was kept at 25° C. for 1 hour, then it was cooled to 0° C. again. Dihydro-2H-pyran-3(4H)-one I-4 (2 g, 20.0 mmol, 1 eq) in 5 mL of dichloromethane was added dropwise within 5 minutes. The reaction was kept at 0° C. for 1 hour. The reaction mixture was quenched by adding 20 mL of sat. $NH_4Cl$, and extracted three times with 30 mL of DCM. The combined organic phases were washed with 20 mL of brine, dried over anhydrous $Na_2SO_4$, filtered and concentrated in vacuo. The residue was purified by column chromatography ($SiO_2$ eluting with a gradient of petroleum ether:ethyl acetate=50:1 to 20:1) to give 470 mg of compound I-5 as a yellow oil.

General procedure for preparation of compound I-6: To a mixture of compound I-5 (470 mg, 3.2 mmol, 1 eq) and 3-ethoxy-3-oxo-propanoic acid (847 mg, 6.4 mmol, 2.0 eq) in 5 mL of pyridine was added piperidine (54.6 mg, 641 μmol, 0.2 eq) at 25° C. The reaction mixture was stirred at 110° C. for 3 hours. To the reaction mixture was added 20 mL of 2N HCl, then the mixture was extracted three times with 15 mL of ethyl acetate. The combined organic phases were washed with 10 mL of 1N HCl, dried over anhydrous $Na_2SO_4$, filtered and concentrated in vacuo to give 0.6 g of crude compound I-6 as brown oil, which was used directly into the next step without purification.

General procedure for preparation of compound I-7. The mixture of compound I-6 (0.6 g, 2.8 mmol, 1 eq) in 10 mL of DMSO was added $NaN_3$ (360 mg, 5.5 mmol, 2 eq) at 25° C. The reaction mixture was stirred at 110° C. for 12 hours. To the reaction mixture was added 30 mL of $H_2O$. The mixture was extracted three times with 30 mL of ethyl acetate. The combined organic phases were washed with 20 mL of brine, dried over anhydrous $Na_2SO_4$, filtered and concentrated in vacuo. The residue was purified by prep-TLC ($SiO_2$ eluting with petroleum ether:ethyl acetate=5:1) to give 160 mg of compound I-7 as a light yellow solid.

General procedure for preparation of compound I-8: The mixture of compound I-7 (150 mg, 768 μmol, 1 eq) in 2 mL of MeOH and 0.5 mL of $H_2O$ was added NaOH (92 mg, 2.3 mmol, 3 eq) in one portion at 25° C. The mixture was stirred at 40° C. for 12 hours. The reaction mixture was adjusted by 4N HCl to pH~3, The resulting solids were filtered to give 80 mg of compound I-8 (62% yield) as a red solid.

General procedure for preparation of compound I-9: To a solution of compound I-8 (56 mg, 335 μmol, 1.0 eq), pyridine (15.9 mg, 201 μmol, 0.6 eq) in 6 mL of $CH_3CN$ was added 2,4,6-trifluoro-1,3,5-triazine (18.1 mg, 134 μmol, 0.4 eq). The mixture was stirred at 25° C. for 1 hour. The reaction mixture was concentrated under reduced pressure. The residue was diluted with 6 mL of $H_2O$ and extracted three times with 24 mL of ethyl acetate. The combined organic layers were dried over $Na_2SO_4$, filtered and concentrated under reduced pressure to give 58 mg of crude compound I-9 as yellow oil.

General procedure for preparation of compound I-10: To a solution of compound I-9 (58 mg, 343 μmol, 1.0 eq) in 2 mL of DCM was added $Et_3N$ (52 mg, 514 μmol, 1.5 eq) and tert-butyl N-benzyl-N-[(1R,3S)-3-(ethylamino)cyclohexyl] carbamate (114 mg, 343 μmol, 1.0 eq). The mixture was stirred at 25° C. under the atmosphere of $N_2$ for 12 hours. The reaction mixture was concentrated under reduced pressure. The residue was purified by prep-TLC ($SiO_2$ eluting with petroleum ether:ethyl acetate=1:1) to give 40 mg of compound I-10 as a yellow oil.

General procedure for preparation of compound 511: To a solution of compound I-10 (40 mg, 83 μmol, 1 eq) in 1 mL of DCM was added 0.2 mL of TFA. The mixture was stirred at 25° C. for 1 hour. The reaction mixture was concentrated under reduced pressure. The residue was purified by prep-HPLC (TFA condition) to get 26.4 mg of compound 511 (62% yield, TFA salt) as a yellow solid.

Compound 511

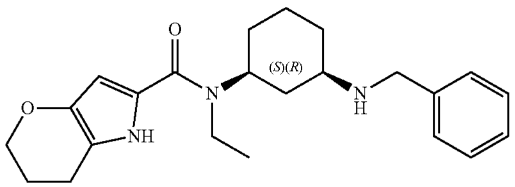

$^1H$ NMR (400 MHz, METHANOL-$d_4$) δ ppm 7.50-7.46 (m, 5H), 6.06 (s, 1H), 4.34 (br s, 1H), 4.25 (s, 2H), 4.06-4.04 (m, 2H), 3.57 (td, J=6.7, 13.3 Hz, 2H), 3.30-3.27 (m, 1H), 2.68 (t, J=6.4 Hz, 2H), 2.29-2.019 (m, 2H), 2.05-1.95 (m, 3H), 1.88-1.71 (m, 3H), 1.49-1.36 (m, 2H), 1.28 (t, J=7.1 Hz, 3H)

LCMS (ESI+): m/z 382.2 (M+H)

Example 56. Synthesis of N-((1S,3R)-3-(benzylamino)cyclohexyl)-N-ethyl-1,5,6,7-tetrahydrothiopyrano[3,2-b]pyrrole-2-carboxamide 4,4-dioxide (Compound 512)

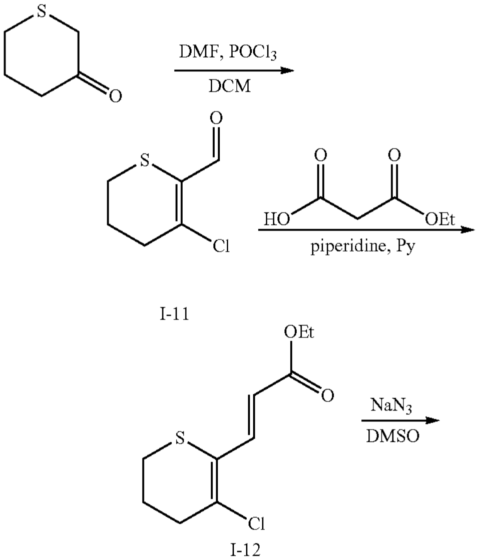

-continued

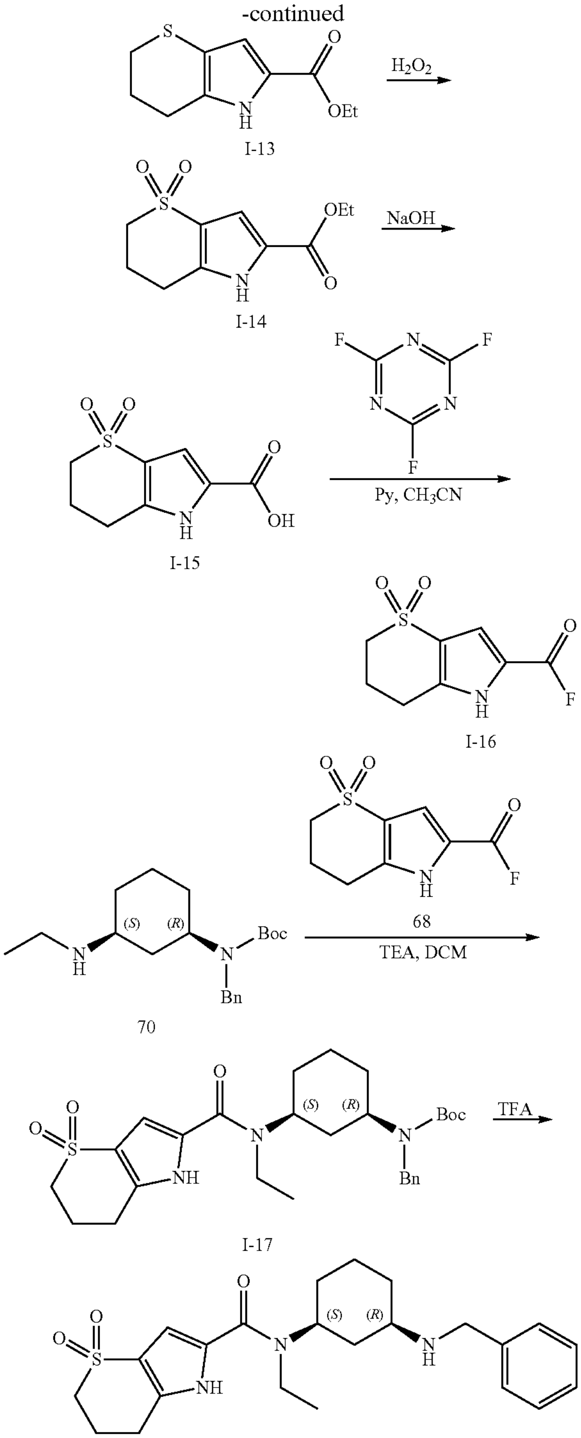

Compound 512

General procedure for preparation of compound I-11: $POCl_3$ (2.0 g, 12.9 mmol, 1.2 mL, 1.5 eq) was added dropwise to DMF (944 mg, 12.9 mmol, 1.5 eq) over 5 minutes at 0° C. To this mixture was added 5 mL of DCM and then the ice-bath was removed. The reaction was kept at 20° C. for 1 hour. The mixture was cooled to 0° C. Dihydro-2H-thiopyran-3(4H)-one (1 g, 8.6 mmol, 1 eq) in 5 mL of DCM was added dropwise over 5 minutes. The reaction was kept at 20° C. for 5 hours. The reaction mixture was quenched by addition 10 mL of ice water at 0° C., and then extracted three times with 30 mL of ethyl acetate. The combined organic layers were washed three times with 30 mL of brine, dried over $Na_2SO_4$, filtered and concentrated under reduced pressure to give a residue. The residue was purified by prep-TLC ($SiO_2$ eluting with petroleum ether: ethyl acetate=5:1) to afford 0.5 g of compound I-11 (36% yield) as a yellow oil.

General procedure for preparation of compound I-12: A mixture of compound I-11 (0.5 g, 3.1 mmol, 1 eq), 3-ethoxy-3-oxo-propanoic acid (812 mg, 6.2 mmol, 2 eq) and piperidine (52.4 mg, 615 μmol, 0.2 eq) in 3 mL of pyridine was degassed and purged with $N_2$ three times. The mixture was stirred at 110° C. for 3 hours under $N_2$ atmosphere. The reaction mixture was concentrated under reduced pressure to give 0.7 g of crude compound I-12 as yellow oil, which was used into the next step without further purification.

General Procedure for preparation of compound I-13: A mixture of compound I-12 (0.6 g, 2.6 mmol, 1 eq) and sodium azide (335 mg, 5.2 mmol, 2 eq) in 6 mL of DMSO was degassed and purged with $N_2$ three times. The mixture was stirred at 110° C. for 3 hours under $N_2$ atmosphere. The reaction mixture was quenched by the addition of 2 mL of water, and then extracted three times with 6 mL of ethyl acetate. The combined organic layers were washed three times with 6 mL of brine, dried over $Na_2SO_4$, filtered and concentrated under reduced pressure to give a residue. The residue was purified by prep-TLC ($SiO_2$ eluting with petroleum ether:ethyl acetate=3:1) to afford 50 mg of compound I-13 (9% yield) as a yellow solid.

General Procedure for preparation of compound I-14: To a solution of compound I-13 (50 mg, 237 μmol, 1 eq) in 1 mL of EtOH was added $H_2O_2$ (223 mg, 2.4 mmol, 35% purity, 10 eq), NaOAc (1.9 mg, 23.7 μmol, 0.1 eq), disodium; dioxido(dioxo)tungsten (13.9 mg, 47.3 μmol, 0.2 eq) at 0° C. After the addition, the mixture was stirred at 20° C. for 12 hours. The reaction mixture was quenched by addition 1 mL of saturated $Na_2SO_3$ aq, and then extracted three times with 3 mL of ethyl acetate. The combined organic layers were dried over $Na_2SO_4$, filtered and concentrated under reduced pressure to give 50 mg of crude compound I-14 as yellow oil.

General Procedure for preparation of compound I-15: A mixture of compound I-14 (40 mg, 164 μmol, 1 eq) and NaOH (19.7 mg, 493 μmol, 3 eq) in 0.2 mL of EtOH and 0.2 mL of water was degassed and purged with $N_2$ three times. The mixture was stirred at 25° C. for 0.5 hour under $N_2$ atmosphere, then it was heated to 40° C. and stirred for 12 hours. The residue was diluted with 1 mL of 1M HCl (to pH=3) and extracted three times with 3 mL of ethyl acetate. The combined organic layers were concentrated under reduced pressure to give 30 mg of crude compound I-15 as yellow oil, which was used into the next step without further purification.

General procedure for the preparation of compound I-16: A mixture of compound I-15 (30 mg, 139 μmol, 1 eq), pyridine (5.5 mg, 70 μmol, 0.5 eq) and 2,4,6-trifluoro-1,3,5-triazine (11 mg, 84 μmol, 0.6 eq) in 0.5 mL of acetonitrile was degassed and purged with $N_2$ three times. The mixture was stirred at 25° C. for 1 hour under $N_2$ atmosphere. The reaction mixture was concentrated under reduced pressure to give 30 mg of crude compound I-16 as yellow solid, which was used into the next step without further purification.

General procedure for the preparation of compound I-17: A mixture of compound I-16 (30 mg, 138 μmol, 1 eq), compound 70 (37 mg, 111 μmol, 0.8 eq) and $Et_3N$ (28 mg, 276 μmol, 2 eq) in 0.5 mL of DCM was degassed and purged with $N_2$ three times. The mixture was stirred at 25° C. for 12 hours under $N_2$ atmosphere. The reaction mixture was concentrated under reduced pressure. The residue was purified by prep-TLC ($SiO_2$ eluting with ethyl acetate) to afford 20 mg of crude compound I-17 as a yellow solid.

General procedure for preparation of compound 512: A mixture of compound I-17 (20 mg, 38 µmol, 1 eq) and TFA (1.4 mmol, 0.1 mL) in 1 mL of DCM was degassed and purged with $N_2$ three times. The mixture was stirred at 20° C. for 10 min under $N_2$ atmosphere. The reaction mixture was concentrated under reduced pressure. The residue was purified by prep-HPLC (TFA condition) to afford 4.6 mg of compound 512 (20% yield, TFA salt) as a yellow solid.

Compound 512

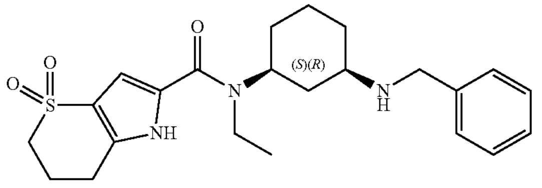

$^1H$ NMR (400 MHz, METHANOL-$d_4$) δ ppm 7.51-7.44 (m, 5H), 6.76 (br s, 1H), 4.31-4.22 (m, 3H), 3.58 (br s, 2H), 3.35 (br s, 1H), 2.86 (t, J=6.3 Hz, 2H), 2.50-2.39 (m, 3H), 2.30 (br d, J=10.6 Hz, 1H), 2.21 (br d, J=11.7 Hz, 1H), 2.06-2.00 (m, 1H), 1.95-1.72 (m, 3H), 1.54-1.33 (m, 3H), 1.30 (br t, J=6.7 Hz, 3H)

LCMS (ESI+): m/z 430.1 (M+H)

Example 57. Synthesis of N-((3R,5S)-5-(((R)-2,3-dihydro-1H-inden-1-yl)amino)tetrahydro-2H-pyran-3-yl)-N-ethyl-1H-indole-2-carboxamide (Compound 504), N-((3S,5R)-5-(((R)-2,3-dihydro-1H-inden-1-yl)amino)tetrahydro-2H-pyran-3-yl)-N-ethyl-1H-indole-2-carboxamide (Compound 505), N-((3R,5R)-5-(((R)-2,3-dihydro-1H-inden-1-yl)amino)tetrahydro-2H-pyran-3-yl)-N-ethyl-1H-indole-2-carboxamide (Compound 506) and N-((3S,5S)-5-(((R)-2,3-dihydro-1H-inden-1-yl)amino)tetrahydro-2H-pyran-3-yl)-N-ethyl-1H-indole-2-carboxamide (Compound 507)

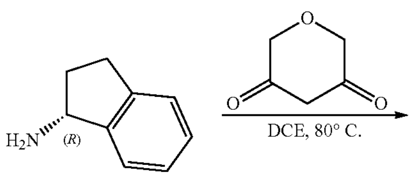

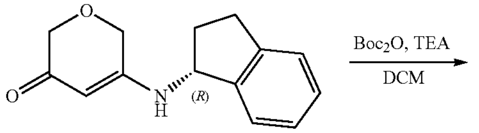

I-18

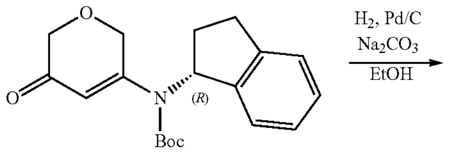

I-19

-continued

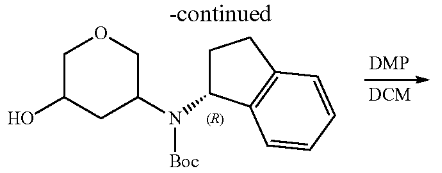

I-20

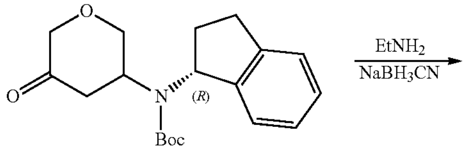

I-21

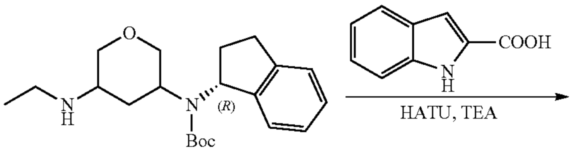

I-22

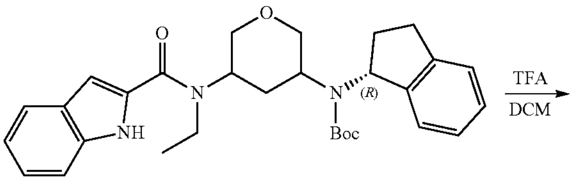

I-23

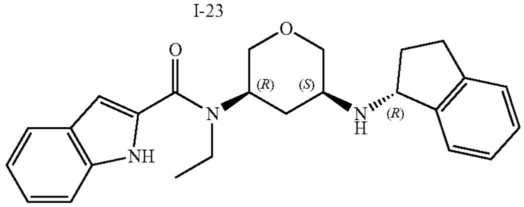

compound 504

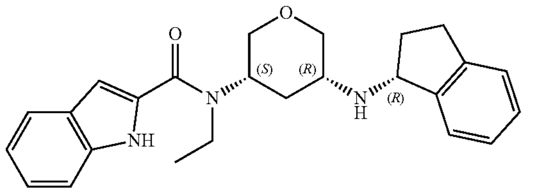

compound 505

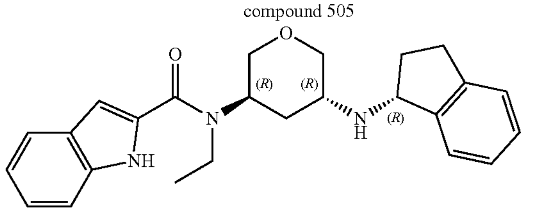

compound 506

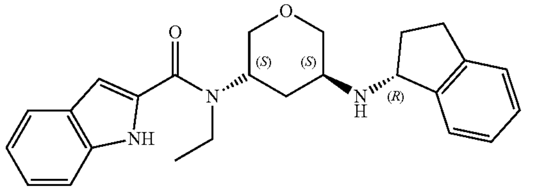

compound 507

General procedure for preparation of compound I-18: A mixture of tetrahydropyran-3,5-dione (214 mg, 1.9 mmol, 1.0 eq), (R)-2,3-dihydro-1H-inden-1-amine (3×250 mg, 1.9 mmol, 1.0 eq) and AcOH (11.3 mg, 188 µmol, 0.1 eq) in 3 mL of DCE was stirred at 80° C. for 16 hours. The reaction mixture was partitioned between 10 mL of water and 10 mL of dichloromethane. The organic phase was separated, washed with 10 mL of brine, dried over anhydrous $Na_2SO_4$, filtered and concentrated under reduced pressure to afford the crude compound I-18 (1.3 g, crude) as a black solid.

General procedure for preparation of compound I-19: A mixture of compound I-18 (1.3 g, 5.7 mmol, 1.0 eq), $Boc_{2}O$ (2.5 g, 11.3 mmol, 2.0 eq), TEA (1.2 g, 11.3 mmol, 2.0 eq) and DMAP (69.3 mg, 567.0 μmol, 0.1 eq) in 15 mL of dichloromethane was stirred at 15° C. for 16 hours. The reaction mixture was concentrated under reduced pressure to remove the solvent to afford a black brown oil. The residue was purified by column chromatography ($SiO_2$, eluting with petroleum ether:ethyl acetate=1:0 to 20:1) to afford compound I-19 (1.1 g, 3.3 mmol, 59% yield) as a brown oil.

General procedure for preparation of compound I-20: To a solution of compound I-19 (1 g, 3.0 mmol, 1.0 eq) in 10 mL of EtOH was added $Na_2CO_3$ (322 mg, 3.0 mmol, 1.0 eq) and Pd/C (10 mg, 10% purity). The suspension was degassed under vacuum and purged with $H_2$ several times. The mixture was stirred under $H_2$ (50 psi) at 25° C. for 16 hours. The reaction mixture was filtered and concentrated under reduced pressure to remove the solvent to afford a yellow oil. The reaction mixture was partitioned between 10 mL of ethyl acetate and 10 mL of water. The organic phase was separated, washed with 10 mL of brine, dried over anhydrous $Na_2SO_4$, filtered and concentrated under reduced pressure to afford the crude compound I-20 (880 mg, crude) as a light-yellow oil.

General procedure for preparation of compound I-21: To a solution of compound I-20 (880 mg, 2.6 mmol, 1.0 eq) in 10 mL of dichloromethane was added DMP (1.1 g, 2.6 mmol, 1.0 eq) at 0° C. The mixture was allowed to stir at 30° C. for 16 hours. The reaction mixture was quenched by addition 15 mL of saturated $Na_2SO_3$ solution at 0° C., and then diluted with 15 mL of ethyl acetate and extracted with 15 mL of ethyl acetate. The combined organic layers were washed with 15 mL of brine, dried over anhydrous $Na_2SO_4$, filtered and concentrated under reduced pressure to afford the crude compound I-21 (1 g) as a yellow oil.

General procedure for preparation of compound I-22: To a solution of compound I-21 (1 g, 3.0 mmol, 1.0 eq) and ethanamine (136 mg, 3.0 mmol, 1.0 eq) in 10 mL of methyl alcohol was added AcOH (18.1 mg, 302 μmol, 0.1 eq). The mixture was stirred at 15° C. for 0.5 hour, then $NaBH_3CN$ (228 mg, 3.6 mmol, 1.2 eq) was added and the resulting reaction mixture was stirred for additional 15.5 hours at 15° C. The reaction mixture was quenched by addition 10 mL of water at 0° C., and then diluted with ethyl acetate 10 mL and extracted with 10 mL of ethyl acetate. The combined organic layers were washed with 10 mL of brine, dried over anhydrous $Na_2SO_4$, filtered and concentrated under reduced pressure to afford the crude compound I-22 (700 mg) as a light-yellow oil.

General procedure for preparation of compound I-23: To a solution of 1H-indole-2-carboxylic acid (376 mg, 2.3 mmol, 1.2 eq) in 10 mL of DMF was added HATU (886 mg, 2.3 mmol, 1.2 eq) and TEA (393 mg, 3.9 mmol, 2.0 eq). The mixture was stirred at 15° C. for 0.5 hour. Then compound I-22 (700 mg, 1.9 mmol, 1.0 eq) was added, and the resulting reaction mixture was stirred at 15° C. for additional 15.5 hours. The reaction mixture was partitioned between 10 mL of water and 10 mL of ethyl acetate. The organic phase was separated, washed with 10 mL of brine, dried over anhydrous $Na_2SO_4$, filtered and concentrated under reduced pressure to give an oil. The residue was purified by prep-TLC ($SiO_2$, eluting with petroleum ether:ethyl acetate=1:1) to afford compound I-23 (380 mg, 755 μmol, 39% yield) as a yellow oil.

General procedure for preparation of compounds 504, 505, 506, 507: A mixture of compound I-23 (380 mg, 755 μmol, 1.0 eq) in 4 mL of dichloromethane and 1 mL of TFA was stirred at 15° C. for 1 hour. The reaction mixture was concentrated under reduced pressure to remove the solvent to afford a yellow oil. The residue was purified by prep-HPLC (TFA condition) to afford compound 504 (17 mg, 32 μmol, 4% yield, 98.2% purity, TFA) as a white solid, compound 505 (500 μg, 0.80 μmol, 0.1% yield, 82.9% purity, TFA) as a white solid, compound 506 (3.2 mg, 5.8 μmol, 0.8% yield, 94.2% purity, TFA) as a white solid, and compound 507 (2.5 mg, 4.4 μmol, 0.6% yield, 90.2% purity, TFA) as a white solid.

Compound 504

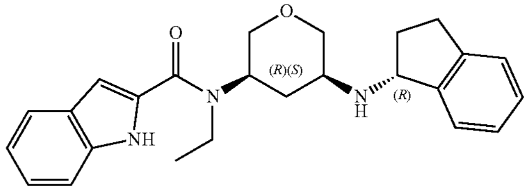

$^1$H NMR (400 MHz, METHANOL-$d_4$) δ ppm 7.66 (dd, J=3.2 Hz, 4.8 Hz, 1H), 7.59 (m, 1H), 7.48-7.42 (m, 4H), 7.26 (m, 1H), 7.10 (m, 1H), 6.88 (s, 1H), 5.05-4.97 (m, 1H), 4.47-4.28 (m, 2H), 4.08-4.06 (m, 1H), 3.95-3.86 (m, 1H), 3.75-3.68 (m, 3H), 3.47 (t, J=10.8 Hz, 1H), 3.44-3.05 (m, 2H), 2.67-2.27 (m, 4H), 1.41-1.37 (m, 3H)

LCMS (ESI+): m/z 404.2 (M+H)

Compound 505

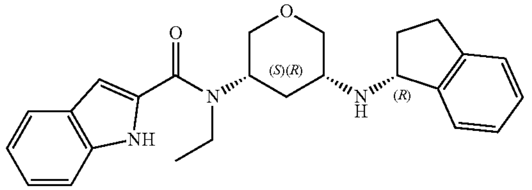

$^1$H NMR (400 MHz, METHANOL-$d_4$) δ ppm 7.58 (d, J=8 Hz, 1H) 7.42 (d, J=8 Hz, 1H) 7.23-7.21 (m, 1H) 7.19-7.14 (m, 3H) 7.09-7.07 (m, 1H) 7.05 (s, 1H) 6.88 (d, J=8.4 Hz, 1H) 4.01-3.93 (m, 2H) 3.67-3.61 (m, 3H) 2.99 (s, 2H) 2.81 (s, 3H) 2.34 (s, 2H) 1.82 (s, 2H) 0.89 (d, J=7.6 Hz, 3H)

LCMS (ESI+): m/z 404.2 (M+H)

Compound 506

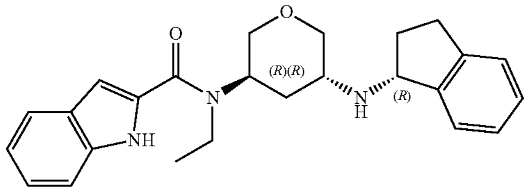

$^1H$ NMR (400 MHz, METHANOL-$d_4$) δ ppm 7.25 (dd, J=8.4, 19.6 Hz, 2H) 7.07-6.94 (m, 4H) 6.80-6.74 (m, 3H) 4.47 (dd, J=7.2, 16 Hz, 1H) 3.92-3.80 (m, 3H) 3.40-3.37 (m, 3H) 3.02-2.92 (m, 4H) 2.44-2.17 (m, 4H) 1.11 (t, J=6.8, 3H)

LCMS (ESI+): m/z 404.2 (M+H)

Compound 507

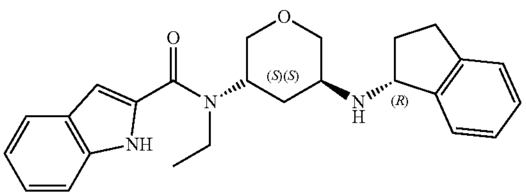

$^1H$ NMR (400 MHz, METHANOL-$d_4$) δ ppm 7.28-7.20 (m, 2H) 7.07-6.94 (m, 4H) 6.80-6.72 (m, 3H) 4.49-4.28 (m, 1H) 3.90-3.75 (m, 4H) 3.60 (t, J=8.4 Hz, 2H) 3.40-3.36 (m, 2H) 3.02-2.90 (m, 2H) 2.44-2.41 (m, 2H) 2.27-2.25 (m, 2H) 2.04-2.01 (m, 1H)

LCMS (ESI+): m/z 404.1 (M+H)

The following compounds were made analogously starting with the (S)-2,3-dihydro-1H-inden-1-amine:

Compound 508

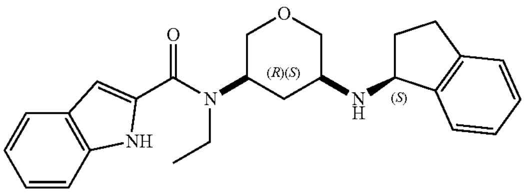

$^1H$ NMR (400 MHz, CHLOROFORM-d) δ ppm 9.21 (br s, 1H), 7.60 (d, J=7.9 Hz, 1H), 7.37-7.32 (m, 1H), 7.28 (br s, 1H), 7.22 (t, J=7.6 Hz, 1H), 7.17-7.12 (m, 3H), 7.10-7.05 (m, 1H), 6.76 (br s, 1H), 4.27 (br d, J=7.1 Hz, 1H), 4.12-3.88 (m, 2H), 3.58 (br s, 2H), 3.51-3.41 (m, 1H), 3.07 (br s, 2H), 2.94 (br s, 1H), 2.74 (td, J=7.7, 15.7 Hz, 1H), 2.48-2.26 (m, 2H), 2.19 (br d, J=9.7 Hz, 1H), 1.75 (br s, 2H), 1.42 (br d, J=13.5 Hz, 1H), 1.28 (br s, 3H)

LCMS (ESI+): m/z 404.2 (M+H)

Compound 509

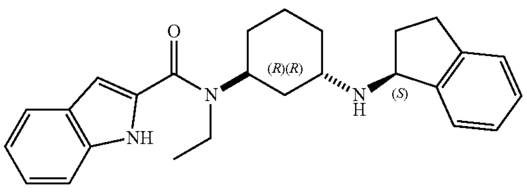

$^1H$ NMR (400 MHz, CHLOROFORM-d) δ ppm 7.27 (br dd, J=7.8, 16.6 Hz, 2H), 7.15-7.06 (m, 2H), 7.02-6.94 (m, 1H), 6.89-6.79 (m, 3H), 4.57-4.45 (m, 1H), 3.85-3.66 (m, 1H), 3.42 (br s, 3H), 3.10-2.91 (m, 2H), 2.82 (br s, 1H), 2.45 (br d, J=7.7 Hz, 1H), 2.36-2.28 (m, 1H), 2.12 (br d, J=13.0 Hz, 3H), 1.98 (br s, 2H), 1.14-1.03 (m, 4H)

LCMS (ESI+): m/z 404.2 (M+H)

Example 58. Synthesis of N-((1S,3R)-3-(((5-cyclopropyl-1,3,4-oxadiazol-2-yl)methyl)amino)cyclohexyl)-N-ethyl-1H-benzo[d]imidazole-2-carboxamide (Compound 513)

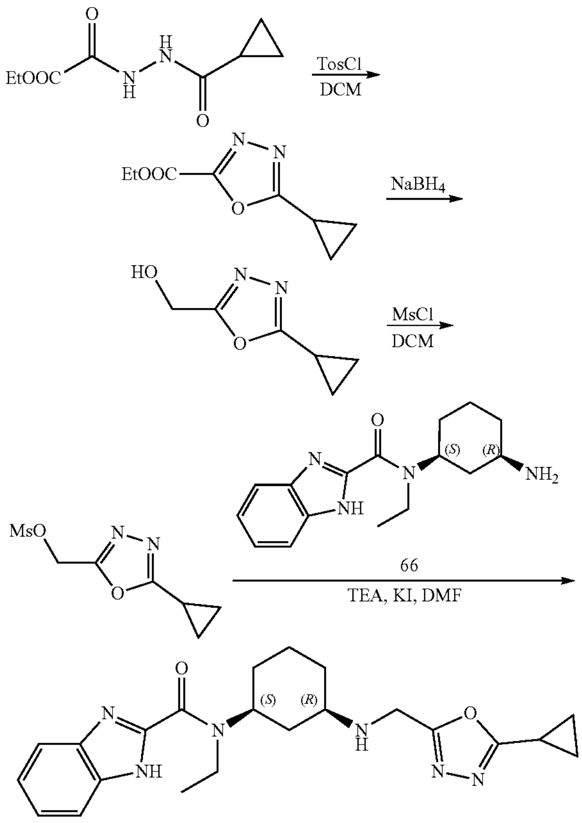

Compound 513

General procedure for preparation of ethyl 5-cyclopropyl-1,3,4-oxadiazole-2-carboxylate: To a solution of ethyl 2-(2-(cyclopropanecarbonyl)hydrazineyl)-2-oxoacetate (3 g, 15.0 mmol, 1 eq) in 30 mL of DCM was added $Et_3N$ (2.0 g, 19.5 mmol, 1.3 eq) and TosCl (3.4 g, 18.0 mmol, 1.2 eq) at 0° C. The mixture was stirred at 20° C. for 2 hours. The reaction mixture was quenched by addition 30 mL of water at 20° C., and then extracted three times with 90 mL of ethyl acetate. The combined organic layers were washed three times with 90 mL of brine, dried over $Na_2SO_4$, filtered and concentrated under reduced pressure to give a residue. The residue was purified by column chromatography ($SiO_2$ eluting with a gradient of petroleum ether:ethyl acetate=20:1 to 3:1) to afford 1 g of ethyl 5-cyclopropyl-1,3,4-oxadiazole-2-carboxylate (37% yield) as a colorless oil.

General procedure for preparation of (5-cyclopropyl-1,3,4-oxadiazol-2-yl)methanol: To a solution of ethyl 5-cyclopropyl-1,3,4-oxadiazole-2-carboxylate (300 mg, 1.7 mmol, 1 eq) in 3 mL of EtOH was added $NaBH_4$ (156 mg, 4.1 mmol, 2.5 eq) at 0° C. The mixture was stirred at 20° C. for 12 hours. The reaction mixture was quenched by addition 2 mL of water at 0° C., and then extracted three times with 6 mL of ethyl acetate. The combined organic layers were washed twice with 4 mL of brine, dried over $Na_2SO_4$, filtered and concentrated under reduced pressure to give 140 mg of crude (5-cyclopropyl-1,3,4-oxadiazol-2-yl)methanol as colorless oil, which was used into the next step without further purification.

General procedure for the preparation of (5-cyclopropyl-1,3,4-oxadiazol-2-yl)methyl methanesulfonate: To a solution of (5-cyclopropyl-1,3,4-oxadiazol-2-yl)methanol (50 mg, 356.8 μmol, 1 eq) in 0.5 mL of DCM was added $Et_3N$ (36 mg, 357 μmol, 1 eq) and MsCl (41 mg, 357 μmol, 1 eq). The mixture was stirred at 20° C. for 2 hours. The reaction mixture was concentrated under reduced pressure to give 50 mg of crude (5-cyclopropyl-1,3,4-oxadiazol-2-yl)methyl methanesulfonate as colorless oil, which was used into the next step without further purification.

General procedure for preparation of compound 513: A mixture of (5-cyclopropyl-1,3,4-oxadiazol-2-yl)methyl methanesulfonate (50 mg, 229 μmol, 1 eq) and N-[(1S,3R)-3-aminocyclohexyl]-N-ethyl-1H-benzimidazole-2-carboxamide 66 (66 mg, 229 μmol, 1 eq), KI (3.8 mg, 23 μmol, 0.1 eq), TEA (46.4 mg, 458 μmol, 2 eq) in 1 mL of DMF was degassed and purged with $N_2$ three times. The mixture was stirred at 20° C. for 12 hours under $N_2$ atmosphere. The reaction mixture was diluted with 1 mL of water and extracted three times with 3 mL of ethyl acetate. The combined organic layers were washed twice with 2 mL of brine, dried over $Na_2SO_4$, filtered and concentrated under reduced pressure to give a residue. The residue was purified by prep-TLC ($SiO_2$ eluting with ethyl acetate), then further purified by prep-HPLC (neutral condition) to afford 2.4 mg of compound 513 (2.5% yield) as a white solid.

Compound 513

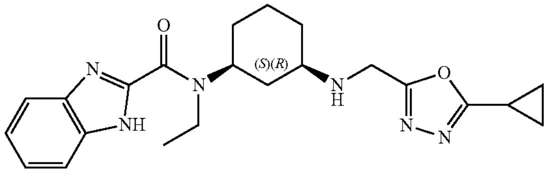

$^1$H NMR (400 MHz, CHLOROFORM-d) δ ppm 10.53-10.38 (m, 1H), 7.77-7.70 (m, 1H), 7.44 (br s, 1H), 7.31-7.21 (m, 2H), 5.85 (br s, 1H), 4.50-4.40 (m, 1H), 4.22-4.16 (m, 1H), 3.98-3.93 (m, 2H), 3.48 (q, J=7.1 Hz, 1H), 2.80-2.62 (m, 1H), 2.19-1.99 (m, 2H), 1.96-1.73 (m, 3H), 1.49-1.34 (m, 3H), 1.25 (td, J=7.1, 16.5 Hz, 3H), 1.09-0.97 (m, 5H)

LCMS (ESI+): m/z 409.2 (M+H)

Example 59. Synthesis of N-ethyl-N-((1S,3R)-3-((indolizin-6-ylmethyl)amino)cyclohexyl)-1H-benzo[d]imidazole-2-carboxamide (Compound 514)

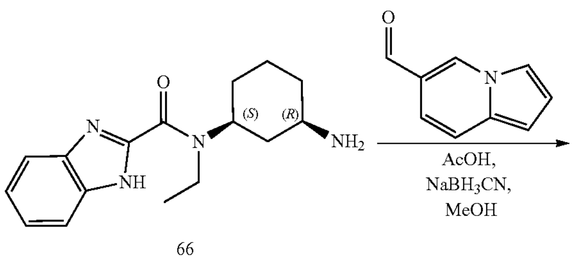

66

-continued

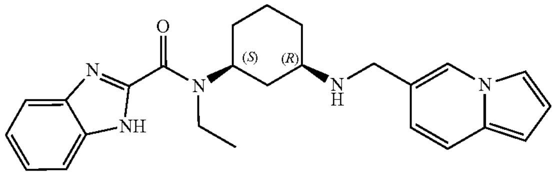

compound 514

General procedure for preparation of compound 514: To a solution of compound 66 (40 mg, 140 μmol, 1 eq) in 1 mL of MeOH was added indolizine-6-carbaldehyde (26.4 mg, 182 μmol, 1.3 eq) and HOAc (0.8 mg, 14 μmol, 0.1 eq) at 25° C. The mixture was stirred at this temperature for 30 min, then $NaBH_3CN$ (8.8 mg, 140 μmol, 1 eq) was added at 25° C. The resulting mixture was stirred at 25° C. for 3 hours. The mixture was filtered to give the filtrate which was purified by prep-HPLC (TFA condition) to give 39.1 mg of compound 514 (53% yield, TFA salt) as a black brown solid.

Compound 514

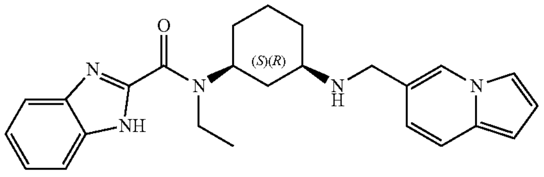

$^1$H NMR (400 MHz, DMSO-$d_6$) δ ppm 8.80-8.99 (m, 2H) 8.41 (br d, J=8.56 Hz, 1H) 7.54-7.69 (m, 3H) 7.49 (t, J=9.23 Hz, 1H) 7.29 (dt, J=5.99, 2.75 Hz, 2H) 6.77-6.84 (m, 2H) 6.44 (d, J=3.79 Hz, 1H) 5.32 (br t, J=11.74 Hz, 1H) 4.13-4.18 (m, 1H) 4.15 (br d, J=4.52 Hz, 2H) 3.95-4.09 (m, 1H) 3.49 (br d, J=6.97 Hz, 1H) 3.15-3.36 (m, 1H) 2.20-2.44 (m, 5H) 2.13 (br s, 2H) 1.56-2.03 (m, 4H) 1.30-1.47 (m, 2H) 1.20-1.27 (m, 3H)

LCMS (ESI+): m/z 416.2 (M+H)

Example 60. Synthesis of N-((1S,3R)-3-(((5-cyclopropylisoxazol-3-yl)methyl)amino)cyclohexyl)-N-ethyl-1H-benzo[d]imidazole-2-carboxamide (Compound 515)

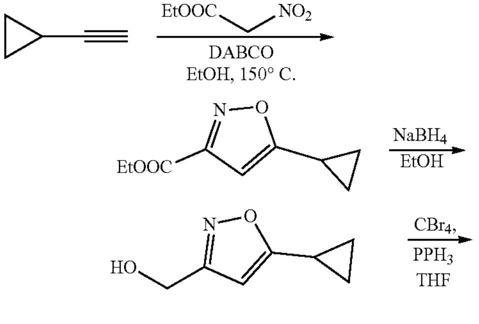

-continued

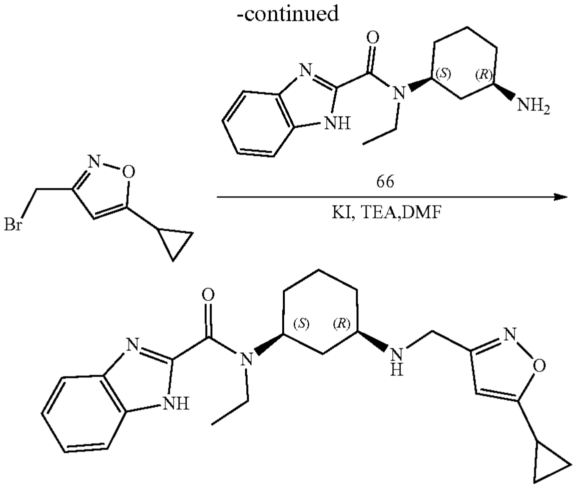

compound 515

General procedure for preparation of ethyl 5-cyclopropylisoxazole-3-carboxylate: A mixture of ethyl 2-nitroacetate (1.0 g, 7.6 mmol, 2.5 eq), ethynylcyclopropane (0.2 g, 3.0 mmol, 1 eq), DABCO (33.9 mg, 303 μmol, 0.1 eq) in 2 mL of EtOH was degassed and purged with $N_2$ three times. The mixture was stirred at 150° C. for 30 min under microwave condition. It was evaporated under reduced pressure to give a residue. The residue was purified by column chromatography ($SiO_2$ eluting with petroleum ether:ethyl acetate=30:1) to give 0.4 g of ethyl 5-cyclopropylisoxazole-3-carboxylate as a colorless liquid.

General procedure for preparation of (5-cyclopropylisoxazol-3-yl)methanol: To a solution of ethyl 5-cyclopropylisoxazole-3-carboxylate (100 mg, 552 μmol, 1.0 eq) in 2.0 mL of EtOH was added $NaBH_4$ (52.2 mg, 1.4 mmol, 2.5 eq) at 0° C. After addition, the resulting mixture was stirred at 25° C. for 16 hours. The reaction mixture was quenched by 3 mL of $H_2O$ at 25° C., then extracted three times with 9 mL of ethyl acetate. The combined organic layers were dried over $Na_2SO_4$, filtered and concentrated under reduced pressure to give a residue. The residue was purified by prep-TLC ($SiO_2$, eluting with petroleum ether:ethyl acetate=2:1) to give 70.0 mg of (5-cyclopropylisoxazol-3-yl)methanol as a yellow oil.

General procedure for preparation of 3-(bromomethyl)-5-cyclopropylisoxazole: To a solution of (5-cyclopropylisoxazol-3-yl)methanol (70.0 mg, 503 μmol, 1.0 eq) in 1 mL of THF was added $PPh_3$ (145 mg, 553 μmol, 1.1 eq) and $CBr_4$ (184 mg, 553 μmol, 1.1 eq). The mixture was stirred at 25° C. for 12 hours. The reaction mixture was concentrated under reduced pressure. The residue was purified by prep-TLC ($SiO_2$, eluting with petroleum ether:ethyl acetate=3:1) to give 32.6 mg of 3-(bromomethyl)-5-cyclopropylisoxazole (32% yield) as a white solid.

General procedure for preparation of compound 515: A mixture of 3-(bromomethyl)-5-cyclopropylisoxazole (32.6 mg, 161 μmol, 2.0 eq), N-[(1S,3R)-3-aminocyclohexyl]-N-ethyl-1H-benzimidazole-2-carboxamide 66 (23.1 mg, 80.7 μmol, 1.0 eq), $Et_3N$ (24.5 mg, 242 μmol, 3 eq) and KI (6.7 mg, 40 μmol, 0.5 eq) in 1 mL of DMF was degassed and purged with $N_2$ three times. The mixture was stirred at 25° C. for 5 hours under $N_2$ atmosphere. The reaction mixture was concentrated under reduced pressure. The residue was purified by prep-HPLC (neutral condition) to give 7.3 mg of compound 515 (22% yield) as a white solid.

Compound 515

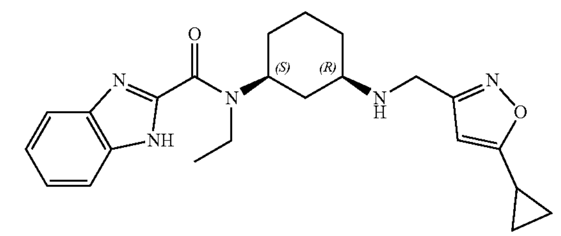

$^1$H NMR (400 MHz, CHLOROFORM-d) δ ppm 10.98-10.85 (d, J=50.8 Hz 1H), 7.82 (br t, J=8.9 Hz, 1H), 7.53 (br d, J=7.9 Hz, 1H), 7.34-7.29 (m, 2H), 5.95-5.89 (m, 1H), 4.60-4.55 (m, 1H), 4.28 (tt, J=6.9, 13.4 Hz, 1H), 3.87-3.86 (m, 2H), 3.58 (q, J=7.0 Hz, 1H), 2.82-2.70 (m, 1H), 2.27-2.24 (m, 1H), 2.03-2.00 (m, 4H), 1.54-1.43 (m, 3H), 1.37-1.30 (m, 3H), 1.14-0.99 (m, 3H), 0.96-0.89 (m, 2H)

LCMS (ESI+): m/z 408.2 (M+H)

Example 61. Synthesis of 5-cyano-N-ethyl-N-((1S, 3R)-3-((3-fluorobenzyl)amino)cyclohexyl)-1H-benzo[d]imidazole-2-carboxamide (Compound 516)

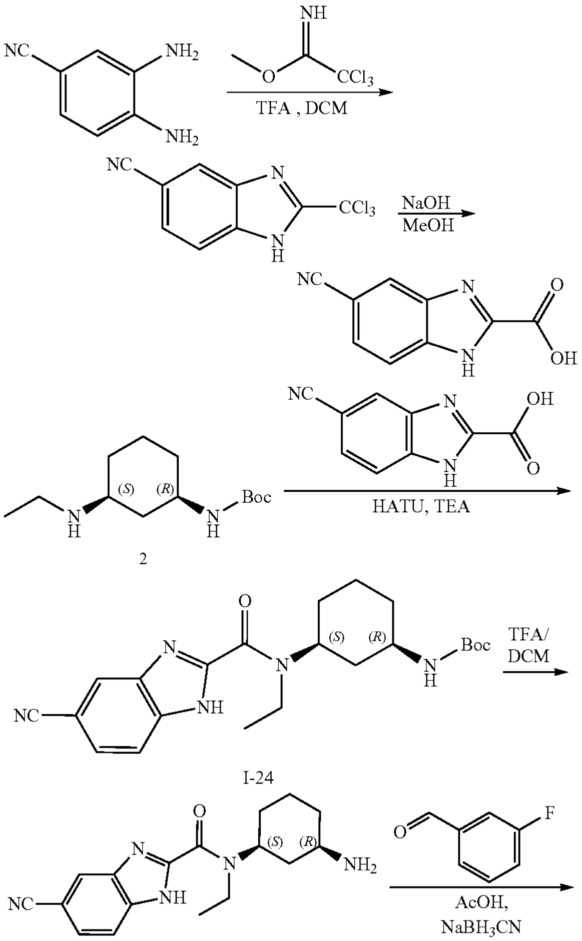

-continued

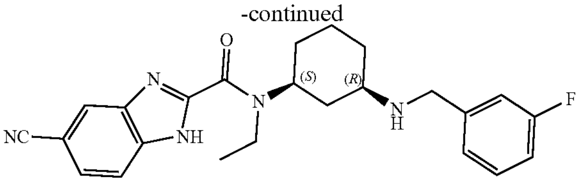

compound 516

General procedure for preparation of 2-(trichloromethyl)-1H-benzo[d]imidazole-5-carbonitrile: To a solution of 3,4-diaminobenzonitrile (2 g, 15.0 mmol, 1 eq) in 20 mL of DCM was added methyl 2,2,2-trichloroethanimidate (3.5 g, 19.5 mmol, 1.3 eq), followed by the addition of TFA (4.3 g, 37.6 mmol, 2.5 eq) at 25° C. The reaction mixture was stirred at 25° C. for 3 hours. The reaction mixture was filtered, and the orange filtrate containing the crude product, 2-(trichloromethyl)-1H-benzo[d]imidazole-5-carbonitrile, was used into next step without treatment.

General procedure for preparation of 5-cyano-1H-benzo[d]imidazole-2-carboxylic acid: To the crude mixture of 2-(trichloromethyl)-1H-benzo[d]imidazole-5-carbonitrile (3.9 g, 15.0 mmol, 1 eq) in DCM was added NaOH (1.5 M, 30 mL, 3.0 eq). The DCM was removed in vacuo, then 30 mL of methanol was added. The reaction mixture was stirred at 25° C. for 12 hours. The reaction mixture was diluted with 5 mL of 1N HCl (pH=2). The reaction mixture was filtered to give 2 g of 5-cyano-1H-benzo[d]imidazole-2-carboxylic acid (60% yield, HCl salt) as yellow solid, which was used into the next step without further purification.

General procedure for preparation of compound I-24: To a solution of 5-cyano-1H-benzo[d]imidazole-2-carboxylic acid (0.5 g, 2.2 mmol, 1 eq, HCl salt) in 5 mL of DMF was added HATU (1.0 g, 2.7 mmol, 1.2 eq), $Et_3N$ (453 mg, 4.5 mmol, 2 eq) at 20° C. After the addition, compound 2 (596 mg, 2.5 mmol, 1.1 eq) was added at 20° C. The resulting mixture was stirred at 40° C. for 12 hours. The reaction was quenched by ice water slowly and then extracted with extracted three times with 15 mL of ethyl acetate. The combined organic layers were washed twice with 10 mL of brine, dried over $Na_2SO_4$, filtered and concentrated under reduced pressure to give a residue. The residue was purified by column chromatography ($SiO_2$, eluting with a gradient of petroleum ether:ethyl acetate=10:1 to 1:1) to afford 480 mg of compound I-24 (52% yield) as a yellow gum.

General procedure for preparation of compound I-25: A mixture of compound I-24 (50 mg, 122 μmol, 1 eq) and TFA (6.8 mmol, 0.5 mL) in 5 mL of DCM was degassed and purged with $N_2$ three times. The mixture was stirred at 25° C. for 10 min under $N_2$ atmosphere. The reaction mixture was concentrated under reduced pressure to give 50 mg of crude compound I-25 (TFA salt) as colorless gum which was used into the next step without further purification.

General procedure for preparation of compound 516: To a solution of compound I-25 (30 mg, 71 μmol, 1 eq, TFA salt) in 1 mL of MeOH was added 3-fluorobenzaldehyde (7.9 mg, 64 μmol, 0.9 eq), AcOH (0.4 mg, 7.1 μmol, 0.1 eq) at 25° C. After the addition, the mixture was stirred at this temperature for 30 min, then $NaBH_3CN$ (4.4 mg, 71 μmol, 1 eq) was added at 25° C. The resulting mixture was stirred at 25° C. for 12 hours. The reaction mixture was filtered and filtrate was concentrated under reduced pressure to give a residue. The residue was purified by prep-HPLC (TFA condition) to afford 16.1 mg of compound 516 (43% yield, TFA salt) as white solid.

Compound 516

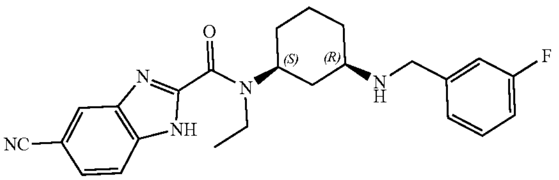

$^1H$ NMR (400 MHz, METHANOL-$d_4$) δ ppm 8.09 (br s, 1H), 7.78 (br d, J=8.4 Hz, 1H), 7.67-7.61 (m, 1H), 7.53-7.46 (m, 1H), 7.35-7.28 (m, 2H), 7.25-7.18 (m, 1H), 5.37-5.26 (m, 1H), 4.30 (s, 2H), 4.22 (br s, 1H), 4.12-3.93 (m, 1H), 3.67-3.48 (m, 1H), 3.36 (br d, J=9.5 Hz, 1H), 2.57-2.33 (m, 1H), 2.23 (br s, 1H), 2.13-1.85 (m, 3H), 1.83-1.65 (m, 1H), 1.58-1.38 (m, 2H), 1.32 (t, J=7.1 Hz, 3H)

LCMS (ESI+): m/z 420.1 (M+H)

The following compounds were prepared analogously:

Compound 517

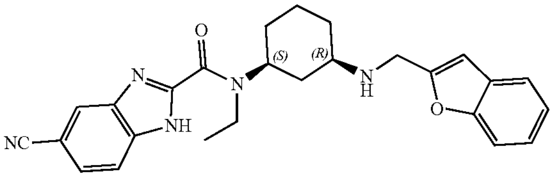

$^1H$ NMR (400 MHz, METHANOL-$d_4$) δ ppm 7.96-8.15 (m, 1H) 7.73 (d, J=8.44 Hz, 1H) 7.61-7.70 (m, 2H) 7.51-7.60 (m, 1H) 7.40 (brt, J=7.76 Hz, 1H) 7.28-7.36 (m, 1H) 7.06-7.11 (m, 1H) 5.26-5.37 (m, 1H) 4.57 (s, 2H) 4.25 (br t, J=11.74 Hz, 1H) 3.95-4.15 (m, 1H) 3.63 (tq, J=13.98, 6.86 Hz, 1H) 3.34-3.44 (m, 1H) 2.36-2.61 (m, 1H) 2.20-2.31 (m, 1H) 1.91-2.17 (m, 3H) 1.70-1.88 (m, 1H) 1.41-1.61 (m, 2H) 1.33 (br t, J=6.97 Hz, 3H) 1.20 (t, J=7.09 Hz, 1H)

LCMS (ESI+): m/z 442.2 (M+H)

Compound 518

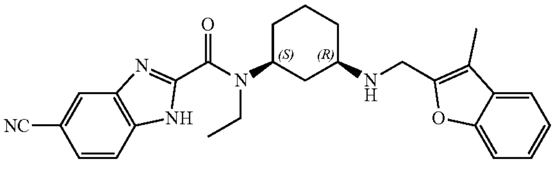

$^1H$ NMR (400 MHz, METHANOL-$d_4$) δ ppm 7.81-8.03 (m, 1H) 7.57-7.71 (m, 1H) 7.45-7.56 (m, 2H) 7.34-7.42 (m, 1H) 7.17-7.32 (m, 2H) 5.19-5.28 (m, 1H) 4.42 (s, 2H) 4.09-4.18 (m, 1H) 3.83-4.02 (m, 1H) 3.40-3.60 (m, 1H) 3.28 (br s, 1H) 2.29-2.45 (m, 1H) 2.17-2.28 (m, 3H) 2.07-2.16 (m, 1H) 1.79-2.05 (m, 3H) 1.59-1.79 (m, 1H) 1.30-1.53 (m, 2H) 1.21 (t, J=7.03 Hz, 3H)

LCMS (ESI+): m/z 456.2 (M+H)

Compound 519

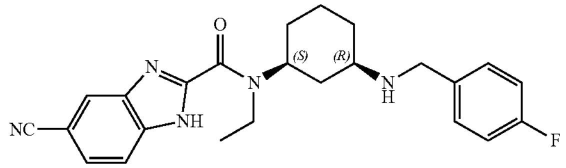

$^1$H NMR (400 MHz, METHANOL-$d_4$) δ ppm 8.00 (s, 1H) 7.68 (d, J=8.44 Hz, 1H) 7.50-7.56 (m, 1H) 7.44 (dt, J=8.25, 5.65 Hz, 2H) 7.04-7.15 (m, 2H) 5.16 (br t, J=11.80 Hz, 1H) 4.07-4.23 (m, 2H) 3.83-4.02 (m, 1H) 3.40-3.60 (m, 1H) 3.22-3.31 (m, 1H) 2.24-2.46 (m, 1H) 2.07-2.19 (m, 1H) 1.78-2.03 (m, 3H) 1.57-1.75 (m, 1H) 1.29-1.51 (m, 2H) 1.22 (br t, J=6.91 Hz, 3H)

LCMS (ESI+): m/z 420.2 (M+H)

Compound 520

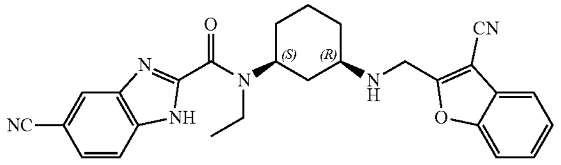

$^1$H NMR (400 MHz, METHANOL-$d_4$) δ ppm 7.94-8.10 (m, 1H) 7.77 (br d, J=8.16 Hz, 1H) 7.66-7.74 (m, 2H) 7.54-7.65 (m, 2H) 7.47-7.53 (m, 1H) 5.33 (br t, J=11.80 Hz, 1H) 4.73 (s, 2H) 4.17-4.29 (m, 1H) 3.94-4.09 (m, 1H) 3.33-3.71 (m, 3H) 2.38-2.56 (m, 1H) 2.15-2.31 (m, 1H) 1.69-2.14 (m, 4H) 1.44-1.62 (m, 1H) 1.42-1.60 (m, 1H) 1.27-1.34 (m, 2H) 1.24-1.35 (m, 1H)

LCMS (ESI+): m/z 467.1 (M+H)

Compound 529

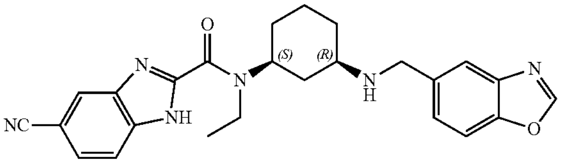

$^1$H NMR (400 MHz, CHLOROFORM-d) 6) 6 ppm 8.11 (d, J=16.66 Hz, 2H) 7.76 (d, J=8.77 Hz, 1H) 7.68 (br s, 1H) 7.49-7.59 (m, 2H) 7.38 (d, J=8.33 Hz, 1H) 5.76 (br t, J=11.62 Hz, 1 H) 4.52 (br s, 1H) 4.23 (q, J=6.58 Hz, 1H) 3.99 (d, J=7.02 Hz, 2H) 3.56-3.67 (m, 1H) 2.73-2.88 (m, 1H) 2.17-2.36 (m, 1H) 2.02-2.11 (m, 1H) 1.95-2.02 (m, 1H) 1.90 (br s, 1H) 1.42-1.68 (m, 4H) 1.35 (q, J=7.31 Hz, 3H) 1.12-1.26 (m, 1H)

LCMS (ESI+): m/z 443.2 (M+H)

Example 62. Synthesis of Deuterated Analog N-ethyl-N-((1S,3R)-3-((phenylmethyl-d2)amino) cyclohexyl)-1H-indole-2-carboxamide (Compound 521)

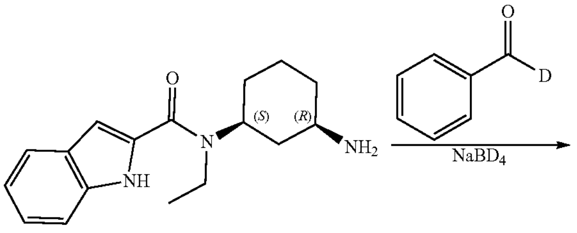

4

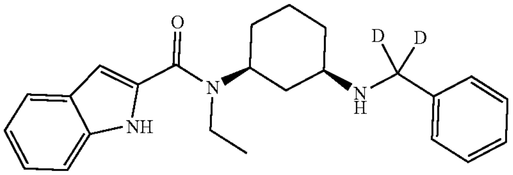

compound 521

General procedure for preparation of compound 521: To a solution of compound 4 (30 mg, 105 μmol, 1 eq) in 1 mL of MeOD was added dropwise deuterio(phenyl)methanone (13.5 mg, 126 μmol, 1.2 eq) at 25° C. After the addition, the mixture was stirred at this temperature for 3 hours. $NaBD_4$ (6.0 mg, 158 μmol, 1.5 eq) was added at 25° C. The resulting mixture was stirred at 25° C. for 12 hours. The mixture was filtered and the filtrate was concentrated and purified by prep-HPLC (TFA condition) to give 22.6 mg of compound 521 (41% yield, TFA salt) as a white solid.

Compound 521

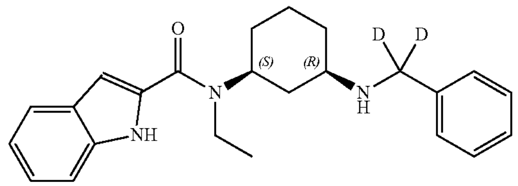

$^1$H NMR (400 MHz, METHANOL-$d_4$) δ ppm 7.62 (d, J=8.33 Hz, 1H) 7.41-7.52 (m, 6H) 7.19-7.25 (m, 1H) 7.04-7.11 (m, 1H) 6.80 (br s, 1H) 4.35 (br s, 1H) 3.68 (br s, 2H) 3.22-3.30 (m, 1H) 2.35 (br d, J=10.96 Hz, 1H) 2.20 (br d, J=10.09 Hz, 1H) 1.75-2.07 (m, 4H) 1.27-1.53 (m, 5H)

LCMS (ESI+): m/z 378.2 (M+H)

Example 63. Synthesis of Deuterated Analog N-ethyl-N-((1S,3R)-3-((phenylmethyl-d2)amino)cyclohexyl)-1H-benzo[d]imidazole-2-carboxamide (Compound 522)

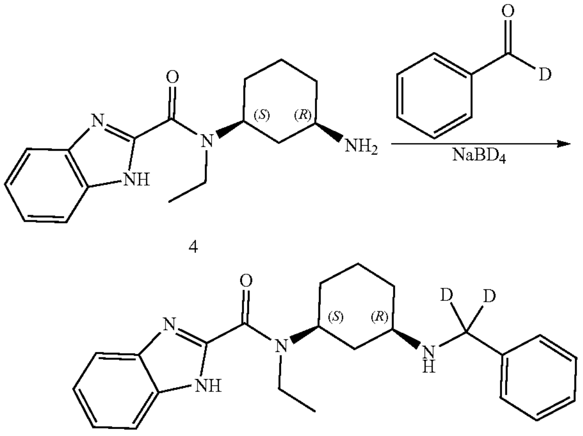

4 compound 522

General procedure for preparation of compound 522: To a solution of compound 4 (30 mg, 105 μmol, 1 eq) in 1 mL of MeOD was added dropwise deuterio(phenyl)methanone (13.5 mg, 126 μmol, 1.2 eq) at 25° C. After the addition, the mixture was stirred at this temperature for 3 hours, then $NaBD_4$ (5.9 mg, 157 μmol, 1.5 eq) was added at 25° C. The resulting mixture was stirred at 25° C. for 12 hours. The mixture was filtered and the resulting filtrate was concentrated and purified by prep-HPLC (TFA condition) to give 46.8 mg of compound 522 (90% yield, TFA salt) as a white solid.

Compound 522

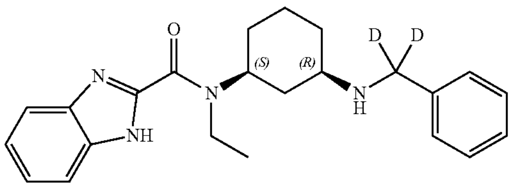

$^1$H NMR (400 MHz, METHANOL-$d_4$) δ ppm 7.73 (br s, 2H) 7.32-7.58 (m, 7H) 4.82 (br s, 1H) 4.21 (br s, 1H) 3.51-3.90 (m, 2H) 3.17-3.34 (m, 1H) 2.38-2.57 (m, 1H) 1.65-2.31 (m, 5H) 1.18-1.62 (m, 5H)

LCMS (ESI+): m/z 379.2 (M+H)

Example 64: Synthesis of Fluorinated Compounds (Compounds 523-528)

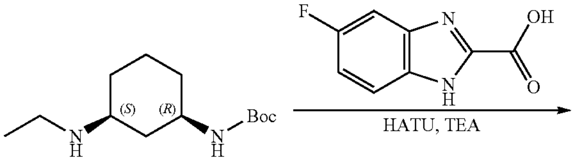

2

-continued

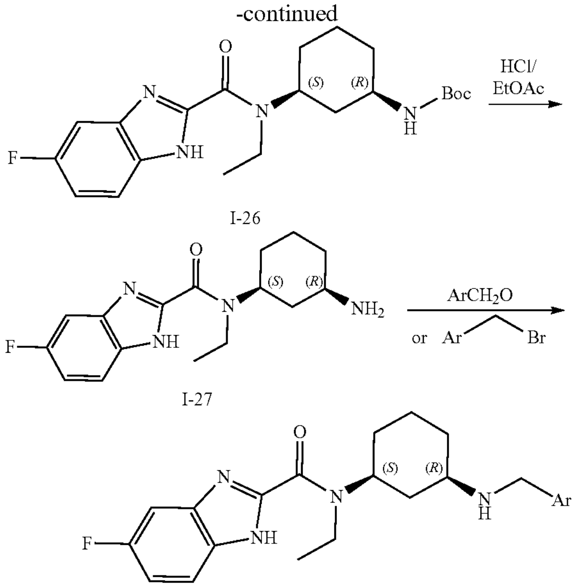

I-26

I-27 compound 523-528

General procedure for preparation of compound I-26: To a solution of compound 2 (330 mg, 1.8 mmol, 1 eq) in 3 mL of DMF was added TEA (278 mg, 2.8 mmol, 1.5 eq) at 25° C. After the addition, HATU (836 mg, 2.2 mmol, 1.2 eq) in 3 mL of DMF was added dropwise at 0° C. The mixture was stirred at 25° C. for 12 hours. The reaction mixture was diluted with 5 mL of water and extracted three times with 15 mL of ethyl acetate. The combined organic phases were washed twice with 10 mL of brine, dried over anhydrous $Na_2SO_4$, filtered and concentrated under reduced pressure to give a residue which was purified by prep-TLC ($SiO_2$, eluting with petroleum ether:ethyl acetate=1:1) to give 450 mg of compound I-26 (yield 61%) as a yellow oil.

General procedure for preparation of compound I-27: A mixture of compound I-26 (450 mg, 1.1 mmol, 1.0 eq) in 2 mL of 4M HCl/EtOAc was stirred at 25° C. for 2 hours. The reaction mixture was concentrated under reduced pressure to give 349 mg of compound I-27 (HCl salt, yield 92%) as a white solid.

General procedure for preparation of compound 523: Compound I-27 (40 mg, 117 μmol, 1 eq, HCl salt) was dissolved in 0.3 mL of MeOH and 0.6 mL of DCE. To the mixture was added $Et_3N$ (1.2 mg, 12 μmol, 0.1 eq) to reach pH~8, and then benzofuran-2-carbaldehyde (17.2 mg, 117 μmol, 1 eq) was added. To the mixture was added HOAc (0.7 mg, 12 μmol, 0.1 eq) adjusting the pH to ~5. The mixture was stirred for 0.5 hour at 25° C. To the mixture was added $NaBH_3CN$ (7.4 mg, 117 μmol, 1 eq). The mixture was stirred at 25° C. for 12 hours. The reaction mixture was concentrated under reduced pressure. The residue was purified by prep-HPLC (TFA condition) to give 9.8 mg of compound 523 (15% yield, TFA salt) as white solid.

Compound 523

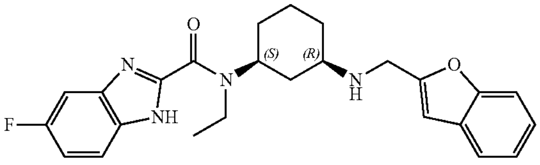

$^1$H NMR (400 MHz, METHANOL-$d_4$) δ ppm 7.64-7.62 (m, 1H), 7.54-7.48 (m, 2H), 7.36-7.34 (m, 1H), 7.30-7.28 (m, 2H), 7.26-7.04 (m, 2H), 5.29 (br t, J=11.4 Hz, 1H), 4.53 (s, 2H), 4.21 (br s, 1H), 4.09-3.92 (m, 1H), 3.62-3.56 (m, 1H), 3.54-3.53 (m, 1H), 2.51-2.49 (m, 1H), 2.22 (br s, 1H), 2.06-1.97 (m, 3H), 1.83-1.70 (m, 1H), 1.44-1.42 (m, 2H), 1.29 (q, J=7.5 Hz, 3H).

LCMS (ESI+): m/z 435.2 (M+H)

General Procedure for Preparation of Compound 524:

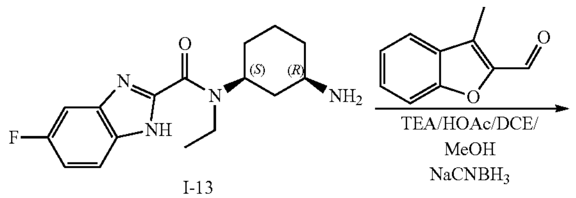

I-13

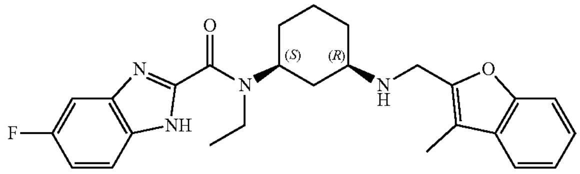

compound 524

Compound I-13 (30 mg, 88.0 μmol, 1 eq, HCl) was dissolved in 0.3 mL of MeOH and 0.6 mL DCE. To the mixture was added $Et_3N$ (0.9 mg, 8.8 μmol, 0.1 eq) to reach pH ~8, then 3-methylbenzofuran-2-carbaldehyde (14.1 mg, 88.0 μmol, 1 eq) was added. To the mixture was added HOAc (0.53 mg, 8.8 μmol, 0.1 eq) adjusting the pH to ~5. The mixture was stirred for 0.5 hour at 25° C. To the mixture was added $NaBH_3CN$ (5.5 mg, 88.0 μmol, 1 eq). The mixture was stirred at 25° C. for 12 hours. The reaction mixture was concentrated under reduced pressure. The residue was purified by prep-HPLC (TFA condition) to get 7.9 mg of compound 524 (15% yield, TFA salt) as a white solid.

Compound 524

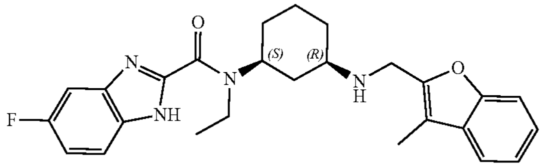

$^1$H NMR (400 MHz, METHANOL-$d_4$) δ ppm 7.58-7.52 (m, 3H), 7.43-7.35 (m, 3H), 7.32-7.11 (m, 1H), 5.34 (br d, J=12.6 Hz, 1H), 4.51 (s, 2H), 4.04 (br s, 1H), 3.69-3.54 (m, 2H), 2.49 (br d, J=10.1 Hz, 1H), 2.36-2.34 (m, 2H), 2.29 (s, 2H), 2.24 (br s, 1H), 2.07-2.05 (m, 2H), 1.98-1.84 (m, 1H), 1.49-1.44 (m, 2H), 1.32-1.29 (m, 3H)

LCMS (ESI+): m/z 449.2 (M+H)

The following compounds were prepared analogously:

Compound 525

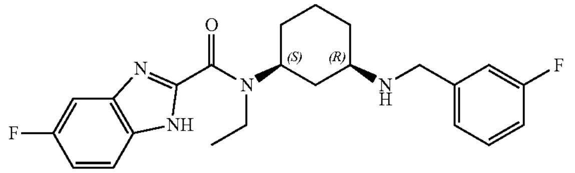

$^1$H NMR (400 MHz, 400 MHz, CHLOROFORM-d) δ ppm 11.23 (m, 1H), 7.45 (br s, 1H), 7.26-7.23 (m, 2H), 7.09 (br d, J=7.1 Hz, 3H), 6.97-6.92 (m, 1H), 5.87 (br t, J=11.2 Hz, 1H), 4.25 (q, J=7.1 Hz, 1H), 3.85 (d, J=6.6 Hz, 2H), 3.59 (q, J=6.8 Hz, 1H), 2.81-2.77 (m, 1H), 2.24-1.94 (m, 1H), 1.93-1.90 (m, 2H), 1.57-1.51 (m, 3H), 1.35-1.31 (m, 3H), 1.29-1.11 (m, 1H)

LCMS (ESI+): m/z 413.3 (M+H)

Compound 526

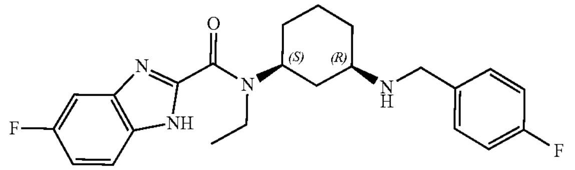

$^1$H NMR (400 MHz, METHANOL-$d_4$) δ ppm 7.64 (br dd, J=4.7, 8.7 Hz, 1H), 7.53 (br d, J=5.5 Hz, 2H), 7.33 (dd, J=2.4, 9.0 Hz, 1H), 7.20-7.15 (m, 3H), 5.28 (br t, J=11.7 Hz, 1H), 4.26 (br s, 2H), 4.07-3.96 (m, 1H), 3.63-3.53 (m, 1H), 3.39-3.31 (m, 1H), 2.50-2.47 (m, 1H), 2.21 (br s, 1H), 2.09-1.94 (m, 2H), 1.82-1.72 (m, 2H), 1.47-1.40 (m, 2H), 1.32-1.30 (m, 3H)

LCMS (ESI+): m/z 413.3 (M+H)

Compound 527

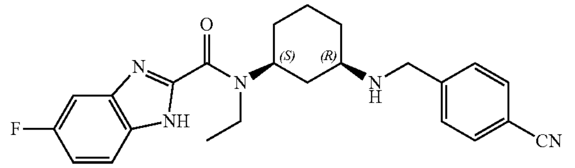

$^1$H NMR (400 MHz, METHANOL-$d_4$) δ ppm 7.85-7.79 (m, 2H), 7.71-7.69 (m, 3H), 7.65 (dd, J=2.4, 9.0 Hz, 1H), 7.35-7.13 (m, 1H), 5.27 (br t, J=11.7 Hz, 1H), 4.36 (br s, 2H), 4.05-3.96 (m, 1H), 3.63-3.60 (m, 1H), 3.35 (s, 2H), 2.51-2.48 (m, 1H), 2.22-2.08 (m, 1H), 2.05-2.01 (m, 1H), 1.94-1.92 (m, 3H), 1.46-1.44 (m, 1H), 1.33-1.31 (m, 2H), 1.29-1.28 (m, 3H)

LCMS (ESI+): m/z 420.3 (M+H)

Compound 528

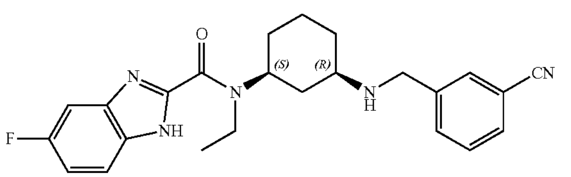

$^1$H NMR (400 MHz, METHANOL-$d_4$) δ ppm 7.91 (br s, 1H), 7.83 (br s, 2H), 7.67-7.61 (m, 2H), 7.35 (dd, J=1.5, 8.8 Hz, 1H), 7.14 (br t, J=9.2 Hz, 1H), 5.23 (br t, J=11.2 Hz, 1H), 4.34 (br s, 2H), 4.03-3.96 (m, 1H), 3.63-3.54 (m, 1H), 3.35 (br s, 1H), 2.52-2.34 (m, 1H), 2.22 (br s, 1H), 2.11-1.95 (m, 3H), 1.87-1.70 (m, 1H), 1.49-1.43 (m, 2H), 1.33-1.28 (m, 3H)

LCMS (ESI+): m/z 420.2 (M+H)

Example 65. Synthesis of N-ethyl-N-((1S,3R)-3-(((2-methylbenzo[d]oxazol-6-yl)methyl)amino)cyclohexyl)-1H-benzo[d]imidazole-2-carboxamide (Compound 530)

Compound 531

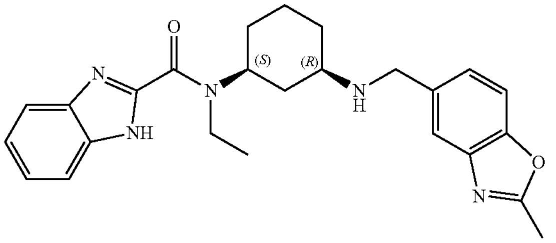

To a solution of compound 66 (50 mg, 174.6 μmol, 1 eq) in 1 mL of MeOH was added 2-methyl-1,3-benzoxazole-6-carbaldehyde (30.9 mg, 192.1 μmol, 1.1 eq) and HOAc (1.1 mg, 17.5 μmol, 0.1 eq). The mixture was stirred for 0.5 hour at 25° C. Then $NaBH_3CN$ (16.5 mg, 261.9 μmol, 1.5 eq) was added and the mixture was stirred for 11.5 hours. The reaction mixture was filtered and the filtrate was purified by prep-HPLC (neutral condition) to get 30.9 mg of compound 530 (40.6% yield, 99.1% purity) as a white solid.

$^1$H NMR (400 MHz, CHLOROFORM-d) δ ppm 11.34-11.21 (m, 1H), 7.77-7.70 (m, 1H), 7.53-7.48 (m, 2H), 7.42 (d, J=5.5 Hz, 1H), 7.27 (br s, 2H), 7.21-7.19 (m, 1H), 5.91-5.85 (m, 1H), 4.54 (br t, J=11.9 Hz, 1H), 4.24 (q, J=6.9 Hz, 1H), 3.91-3.89 (m, 2H), 3.55 (q, J=7.0 Hz, 1H), 2.79-2.76 (m, 1H), 2.57 (s, 3H), 2.31-2.11 (m, 1H), 1.97-1.82 (m, 3H), 1.54-1.47 (m, 3H), 1.29 (t, J=7.0 Hz, 3H), 1.27-1.09 (m, 1H).

LCMS (ESI+): m/z 432.2 (M+H)

The following compounds were prepared analogously

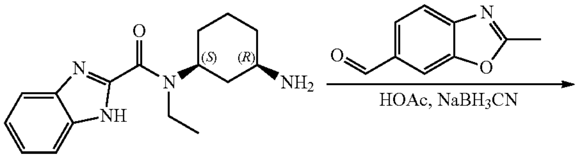

66

-continued

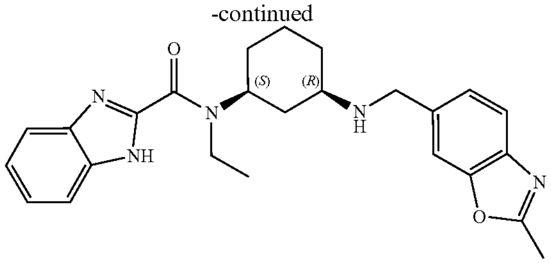

compound 530

$^1$H NMR (400 MHz, METHANOL-$d_4$) δ ppm 7.55-7.66 (m, 3H) 7.38-7.52 (m, 1H) 7.24-7.37 (m, 3H) 4.75 (br t, J=11.91 Hz, 1H) 4.24-4.38 (m, 1H) 3.83-3.95 (m, 3H) 3.47-3.62 (m, 1H) 2.44-2.75 (m, 4H) 2.12-2.24 (m, 1H) 1.91-2.06 (m, 1H) 1.36-1.87 (m, 4H) 1.15-1.32 (m, 4H) 0.99-1.14 (m, 1H)

LCMS (ESI+): m/z 432.2 (M+H)

Example 66. Synthesis of 5-cyano-N-ethyl-N-((1S, 3R)-3-((4-fluorobenzyl)amino)cyclohexyl)-1H-indole-2-carboxamide (Compound 532

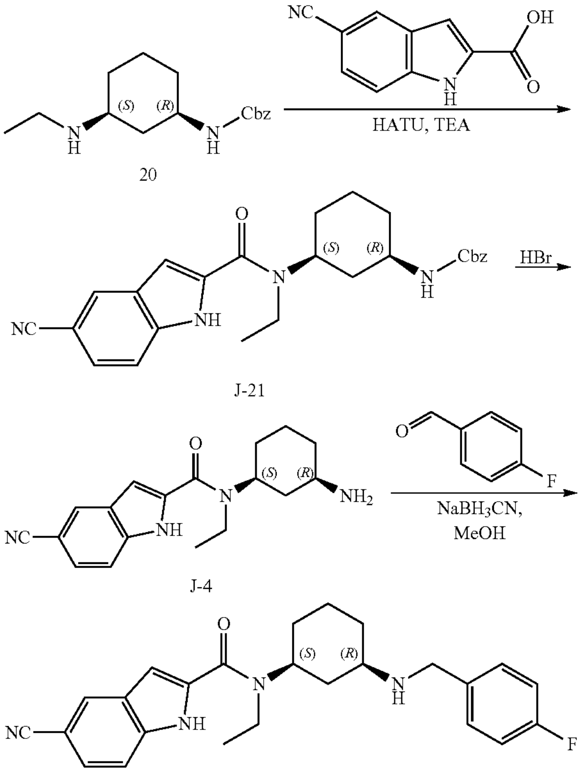

Compound 532

General procedure for preparation of compound J-21: To a solution of 5-cyano-1H-indole-2-carboxylic acid (0.5 g, 2.7 mmol, 1 eq) and compound 20 (840 mg, 2.7 mmol, 1 eq, HCl salt) in 10 mL of DMF was added TEA (815 mg, 8.0 mmol, 1.1 mL, 3 eq) at 20° C. The mixture was stirred at 20° C. for 0.5 hour. HATU (1.8 g, 4.8 mmol, 1.8 eq) in 2 mL of DMF was added to the mixture at 0° C. and the mixture was stirred at 20° C. for 11.5 hours. Then it was partitioned between 10 mL of water and 60 mL of ethyl acetate. The organic phase was separated, washed with 15 mL of brine, dried over $Na_2SO_4$, filtered and concentrated under reduced pressure to give the crude product, which was purified by column chromatography ($SiO_2$, eluting with a gradient of petroleum ether:ethyl acetate=5:1 to 1:1) to give ~1 g of compound J-21 (41% yield, 49% purity) as a yellow solid.

General procedure for preparation of compound J-4: To a solution of compound J-21 (0.5 g, 551 μmol, 1 eq) was added HBr (7.3 g, 36 mmol, 4.9 mL, 40% purity, 65 eq). The mixture was stirred at 20° C. for 0.5 hour. The reaction mixture was basified by 4M NaOH until pH~11, extracted with 100 mL of ethyl acetate. The organic layers were combined, washed with 15 mL of brine, dried over $Na_2SO_4$, filtered and evaporated under reduced pressure to give 0.2 g of compound J-4 as a yellow solid, which was used into the next step without further purification.

General procedure for preparation of compound 532: To a solution of compound J-4 (40 mg, 129 μmol, 1 eq) and 4-fluorobenzaldehyde (24.0 mg, 193 μmol, 1.5 eq) in 1 mL of MeOH was added HOAc (774 μg, 12.9 μmol, 0.1 eq) at 20° C. The mixture was stirred at 20° C. for 0.5 hour. $NaBH_3CN$ (12.1 mg, 193 μmol, 1.5 eq) was added to the mixture. The mixture was stirred at 20° C. for 11.5 hours. The reaction mixture was quenched by addition 1 mL of water at 20° C., and then the mixture filtered and concentrated under reduced pressure to give the crude product which was purified by prep-HPLC (HCl condition) to give 25 mg of compound 532 (40% yield, 93.2% purity, HCl salt) as a white solid.

$^1$H NMR (400 MHz, METHANOL-$d_4$) δ ppm 8.13 (s, 1H) 7.49-7.63 (m, 4H) 7.23 (t, J=8.68 Hz, 2H) 6.97 (br s, 1H) 4.96 (br s, 1H) 4.28 (s, 3H) 3.71 (br s, 2H) 2.38 (br d, J=10.15 Hz, 1H) 2.23 (br d, J=9.29 Hz, 1H) 1.76-2.14 (m, 4H) 1.41-1.61 (m, 2H) 1.37 (br t, J=6.85 Hz, 3H)

LCMS (ESI+): m/z 419.1 (M+H)

The following compounds were prepared analogously using different aldehydes:

Compound 533

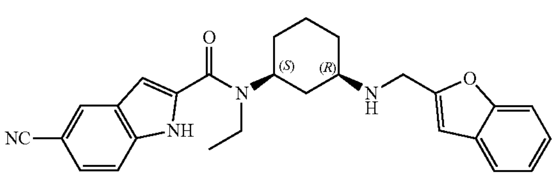

$^1$H NMR (400 MHz, CHLOROFORM-d) δ ppm 10.17 (br s, 1H) 7.60-8.15 (m, 1H) 7.41-7.57 (m, 4H) 7.27 (s, 2H) 6.59 (s, 2H) 4.46 (br t, J=11.49 Hz, 1H) 4.03 (s, 2H) 3.56 (br s, 2H) 2.74 (br s, 1H) 1.99-2.13 (m, 2H) 1.80-1.97 (m, 2H) 1.61 (quin, J=11.46 Hz, 2H) 1.25-1.43 (m, 3H) 1.24-1.25 (m, 1H) 1.09-1.23 (m, 1H)

LCMS (ESI+): m/z 441.2 (M+H)

Compound 534

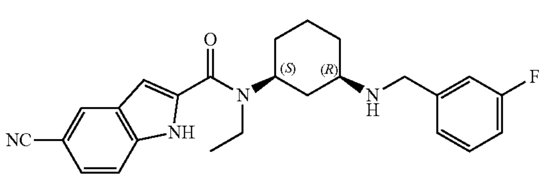

$^1$H NMR (400 MHz, METHANOL-$d_4$) δ ppm 8.10 (s, 1H), 7.58 (d, J=8.6 Hz, 1H), 7.57-7.47 (m, 2H), 7.33-7.27 (m, 2H), 7.21 (dt, J=2.2, 8.5 Hz, 1H), 6.93 (br s, 1H), 4.28 (s, 3H), 3.67 (br s, 3H), 2.35 (br d, J=11.5 Hz, 1H), 2.20 (br d, J=9.3 Hz, 1H), 2.06-1.92 (m, 4H), 1.45-1.39 (m, 2H), 1.34 (br t, J=6.9 Hz, 3H)

LCMS (ESI+): m/z 419.2 (M+H)

Compound 535

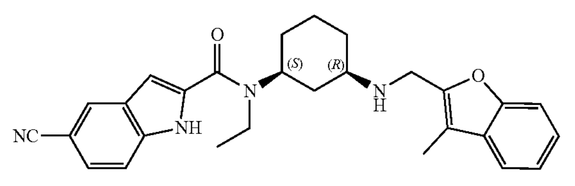

$^1$H NMR (400 MHz, METHANOL-$d_4$) δ ppm 8.07 (br s, 1H) 7.59-7.64 (m, 2H) 7.46-7.54 (m, 2H) 7.39 (t, J=7.46 Hz, 1H) 7.29-7.35 (m, 1H) 6.93 (br s, 1H) 4.75-4.87 (m, 1H) 4.52 (s, 2H) 4.33 (br d, J=7.58 Hz, 1H) 3.70 (br s, 2H) 2.31-2.42 (m, 4H) 2.20-2.29 (m, 1H) 1.83-2.11 (m, 4H) 1.43-1.56 (m, 2H) 1.29-1.39 (m, 3H)

LCMS (ESI+): m/z 455.1 (M+H)

Example 67. Synthesis of 5-cyano-N-((1S,3R)-3-(((3-cyanobenzofuran-2-yl)methyl)amino)cyclohexyl)-N-ethyl-1H-indole-2-carboxamide (Compound 536)

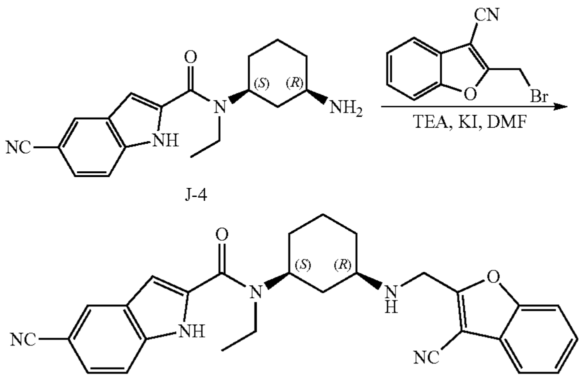

Compound 536

To a solution of compound J-4 (29 mg, 93 μmol, 1 eq) in 0.5 mL of DMF was added 2-(bromomethyl)benzofuran-3-carbonitrile (26 mg, 112 μmol, 1.2 eq), KI (7.8 mg, 47 μmol, 0.5 eq) and TEA (28 mg, 280 μmol, 3 eq). The mixture was stirred at 25° C. for 12 hours. The reaction mixture was filtered to give the filtrate, which was purified by prep-HPLC (TFA condition) to give 15.7 mg of compound 536 (29% yield, 99.0% purity, TFA salt) as a white solid.

$^1$H NMR (400 MHz, METHANOL-$d_4$) δ ppm 8.08 (s, 1H), 7.77 (d, J=7.7 Hz, 1H), 7.71 (br d, J=8.1 Hz, 1H), 7.59-7.57 (m, 2H), 7.53-7.48 (m, 2H), 6.94 (br s, 1H), 4.74 (s, 2H), 4.30 (br s, 1H), 3.68 (br s, 2H), 3.48-3.43 (m, 1H), 2.41 (br d, J=11.2 Hz, 1H), 2.24 (br d, J=8.8 Hz, 1H), 2.09-2.06 (m, 2H), 1.99-1.94 (m, 2H), 1.51-1.42 (m, 2H), 1.35 (br t, J=6.8 Hz, 3H)

LCMS (ESI+): m/z 466.1 (M+H) Compound 537 was prepared analogously using 3-(bromomethyl)-5-cyclopropyl-isoxazole.

Compound 537

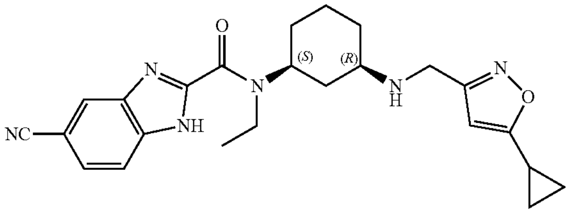

$^1$H NMR (400 MHz, METHANOL-$d_4$) δ ppm 8.12 (s, 1H), 7.60-7.58 (m, 1H), 7.51-7.49 (m, 1H), 6.95 (br s, 1H), 6.20 (s, 1H), 4.40-4.28 (m, 3H), 3.66-3.59 (m, 2H), 3.45-3.40 (m, 1H), 2.37 (br d, J=9.3 Hz, 1H), 2.19-2.17 (m, 2H), 2.14 (br d, J=11.9 Hz, 1H), 1.91 (br s, 3H), 1.42-1.36 (m, 2H), 1.34 (br t, J=6.8 Hz, 3H), 1.16-1.13 (m, 2H), 0.96-0.94 (m, 2H)

LCMS (ESI+): m/z 432.2 (M+H)

Example 68. Synthesis of N-((1S,3R)-3-(benzylamino)cyclohexyl)-5-cyano-N-ethyl-1H-indole-2-carboxamide (Compound 538)

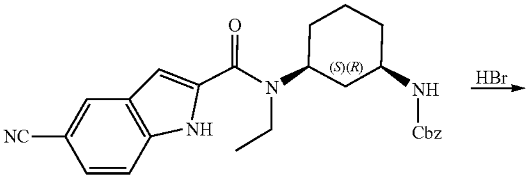

J-21

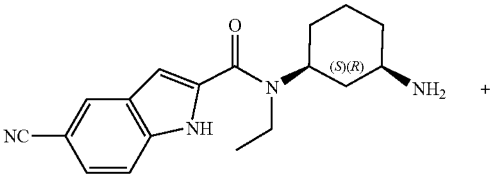

J-4

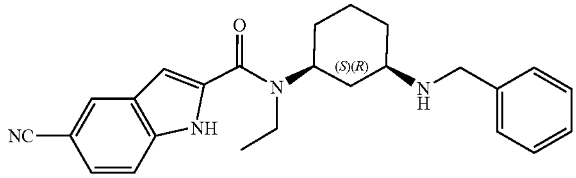

Compound 538

To a solution of compound J-21 (0.5 g, 1.1 mmol, 1 eq) was added HBr (44.7 g, 221 mmol, 30 mL, 40% purity). The mixture was stirred at 20° C. for 0.5 hour. The reaction mixture was basified by addition 4M NaOH until pH~11 and extracted with 100 mL of ethyl acetate. The organic layers were separated, washed with 15 mL of brine, dried over $Na_2SO_4$, filtered and evaporated under reduced pressure to give a mixture of the two products, which was then purified by prep-HPLC (neutral condition) to give 100 mg of compound J-4 (322 μmol, 29% yield) as a yellow solid and 38.2 mg of compound 538 (8.3% yield, 98.3% purity) as a white solid.

$^1$H NMR (400 MHz, CHLOROFORM-d) δ ppm 9.67 (br s, 1H) 7.94 (br s, 1H) 7.42 (s, 2H) 7.23-7.30 (m, 4H) 7.22 (br s, 1H) 6.42-6.88 (m, 1H) 4.41 (br s, 1H) 3.78 (s, 2H) 3.34-3.68 (m, 2H) 2.64 (br s, 1H) 2.10 (br d, J=9.66 Hz, 1H) 1.95 (br d, J=12.72 Hz, 1H) 1.73-1.88 (m, 2H) 1.16-1.46 (m, 6H) 0.97-1.12 (m, 1H)

LCMS (ESI+): m/z 401.1 (M+H)

Example 69. Synthesis of N-((1S,3R)-3-(benzylamino)cyclohexyl)-N-ethyl-5-(trifluoromethoxy)-1H-benzo[d]imidazole-2-carboxamide (Compound 539

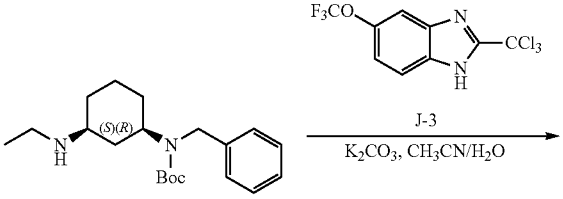

14

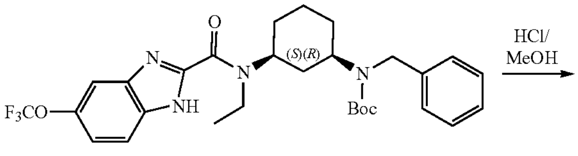

J-5

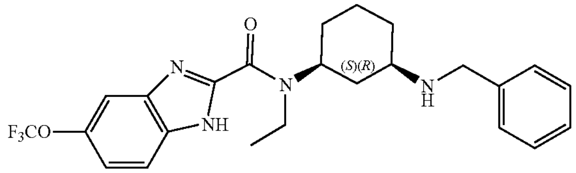

Compound 539

General procedure for preparation of compound J-3: To a mixture of 4-(trifluoromethoxy)benzene-1,2-diamine (0.1 g, 521 μmol, 1 eq) in 2 mL of dichloromethane cooled to 0° C. was added methyl 2,2,2-trichloroethanimidate (119 mg, 676 μmol, 1.3 eq), TFA (148 mg, 1.3 mmol, 2.5 eq) successively. The mixture was stirred at 25° C. for 12 hours under $N_2$ atmosphere. The mixture was filtered and the filtrate was purified by prep-TLC ($SiO_2$, eluting with petroleum ether: ethyl acetate=2:1) to give a 0.1 g of compound J-3 (44% yield, TFA salt) as a yellow solid.

General procedure for preparation of compound J-5: A mixture of 2-(trichloromethyl)-5-(trifluoromethoxy)-1H-benzimidazole J-3 (0.1 g, 231 μmol, 1 eq, TFA salt), compound 14 (69 mg, 208 μmol, 0.9 eq), $K_2CO_3$ (319 mg, 2.3 mmol, 10 eq) in 4 mL of acetonitrile and 2 mL of water was stirred at 50° C. for 12 hours under $N_2$ atmosphere. To the mixture was added 5 mL of water; it was extracted twice with 10 mL of ethyl acetate. The combined organic layers was washed with 5 mL of brine, dried over $Na_2SO_4$, filtered and evaporated under reduced pressure to give the crude product, which was purified by prep-TLC ($SiO_2$, eluting with petroleum ether:ethyl acetate=2:1) to give 65 mg of compound J-5 (50% yield) as a colorless gum.

General procedure for preparation of compound 539: A mixture of compound J-5 (60 mg, 107 μmol, 1 eq) in 0.3 mL of TFA and 2 mL of dichloromethane was stirred at 25° C. for 0.5 hour under $N_2$ atmosphere. It was evaporated under reduced pressure to give 60 mg of compound 539 (93% yield, 95.8% purity, TFA salt) as a light-yellow foam.

$^1H$ NMR (400 MHz, METHANOL-$d_4$) δ ppm 7.70 (d, J=8.82 Hz, 1H) 7.56 (s, 1H) 7.40-7.53 (m, 5H) 7.22-7.30 (m, 1H) 5.29 (br t, J=11.80 Hz, 1H) 4.26 (br s, 2H) 3.91-4.11 (m, 1H) 3.51-3.66 (m, 1H) 3.31-3.39 (m, 1H) 2.32-2.54 (m, 1H) 2.20 (br d, J=13.01 Hz, 1H) 1.87-2.12 (m, 3H) 1.66-1.85 (m, 1H) 1.35-1.59 (m, 2H) 1.27-1.34 (m, 3H)

LCMS (ESI+): m/z 461.3 (M+H)

The following compounds were prepared from the analogous corresponding diamines via the trichloromethyl analogues and coupling with intermediate 14 followed by deprotection as detailed above (diamine preparations included below):

Compound 540

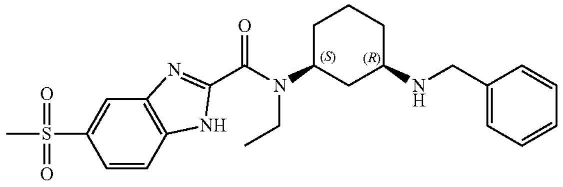

$^1H$ NMR (400 MHz, METHANOL-$d_4$) δ ppm 8.36 (s, 1H) 7.85-8.02 (m, 2H) 7.41-7.60 (m, 5H) 5.04-5.17 (m, 1H) 4.17-4.38 (m, 2H) 3.86-4.09 (m, 1H) 3.38-3.75 (m, 2H) 3.20 (s, 3H) 2.37-2.63 (m, 1H) 1.68-2.32 (m, 5H) 1.40-1.63 (m, 2H) 1.27-1.38 (m, 3H)

LCMS (ESI+): m/z 445.2 (M+H)

Compound 541

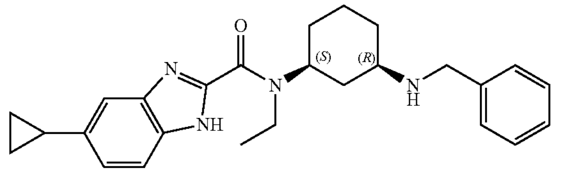

$^1H$ NMR (400 MHz, METHANOL-$d_4$) δ ppm 7.44-7.59 (m, 6H) 7.35 (s, 1H) 7.14 (br d, J=8.44 Hz, 1H) 5.24 (br s, 1H) 4.28 (br s, 2H) 3.84-4.09 (m, 1H) 3.63 (br s, 1H) 2.35-2.56 (m, 1H) 2.22 (br s, 1H) 1.91-2.14 (m, 3H) 1.91-2.14 (m, 1H) 1.67-1.88 (m, 1H) 1.42 (br d, J=13.20 Hz, 2H) 1.21-1.36 (m, 3H) 1.03 (br d, J=7.70 Hz, 2H) 0.75 (q, J=5.14 Hz, 2H)

LCMS (ESI+): m/z 417.2 (M+H)

Example 70. Synthesis of Compounds J-6 and J-7

General Procedure for Preparation of Compound J-6:

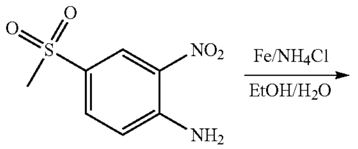

-continued

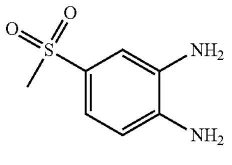

J-6

To a solution of 4-(methylsulfonyl)-2-nitroaniline (0.1 g, 463 μmol, 1 eq) in 2 mL of EtOH and 0.8 mL of $H_2O$ was added iron powder (129 mg, 2.3 mmol, 5 eq) and $NH_4Cl$ (247 mg, 4.6 mmol, 10 eq). The mixture was stirred at 80° C. for 1 hour. The reaction mixture was filtered and concentrated under reduced pressure to give 80 mg of crude compound J-6 as a brown solid, which was used directly into the next step without purification.

General Procedure for Preparation of Compound J-7:

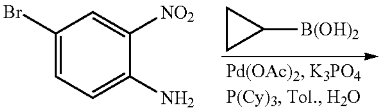

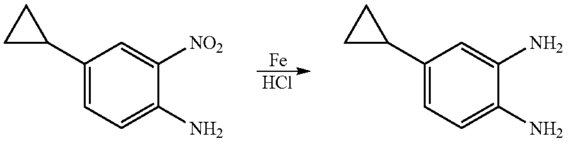

J-7

A mixture of 4-bromo-2-nitroaniline (300 mg, 1.4 mmol, 1 eq), cyclopropylboronic acid (154 mg, 1.8 mmol, 1.3 eq), $Pd(OAc)_2$ (15.5 mg, 69.1 μmol, 0.05 eq), $P(Cy)_3$ (194 mg, 138 μmol, 20% purity, 0.1 eq) and $K_3PO_4$ (1.0 g, 4.8 mmol, 3.5 eq) in 0.3 mL of $H_2O$ and 6 mL of toluene was degassed and purged with $N_2$ 3 times, and then the mixture was stirred at 100° C. for 12 hours under $N_2$ atmosphere. The reaction mixture was filtered and concentrated under reduced pressure to give the crude product, which was purified by column chromatography ($SiO_2$, eluting with a gradient of petroleum ether:ethyl acetate=15:1 to 7:1) to give 220 mg of 4-cyclopropyl-2-nitro-aniline (1.2 mmol, 89% yield) as a as a red gum.

The obtained nitroaniline was then reduced using iron powder to give the required diamine J-7 which was used directly in the next reaction.

Example 71. Synthesis of N-((1S,3R)-3-(benzylamino)cyclohexyl)-N-ethyl-5-(trifluoromethoxy)-1H-indole-2-carboxamide (Compound 542)

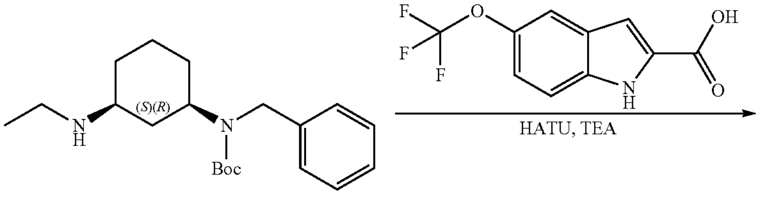

14

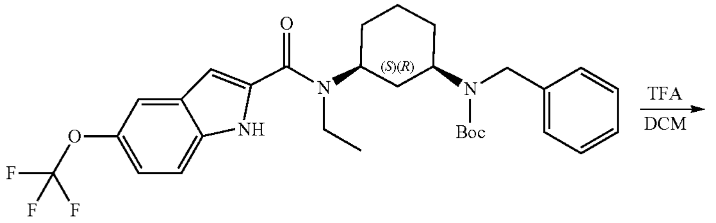

J-8

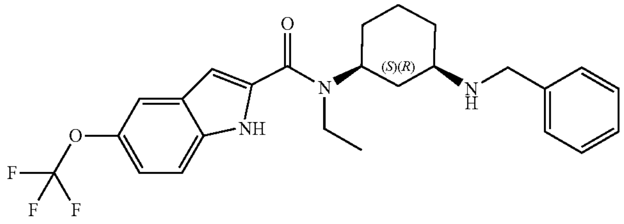

Compound 542

General procedure for preparation of compound J-8: To a solution of compound 14 (80 mg, 241 μmol, 1 eq) in 1 mL of DMF was added 5-(trifluoromethoxy)-1H-indole-2-carboxylic acid (71 mg, 289 μmol, 1.2 eq) and $Et_3N$ (36.5 mg, 360.9 μmol, 1.5 eq). To the mixture was added HATU (101 mg, 265 μmol, 1.1 eq) dropwise in 1 mL of DMF at 0° C. The mixture was stirred at 25° C. for 12 hours. To the reaction mixture was added 1 mL of $H_2O$ at 25° C. and it extracted three times with 3 mL of ethyl acetate. The combined organic layers were washed with 3 mL of $H_2O$, 1 mL of brine, dried over $Na_2SO_4$, filtered and concentrated under reduced pressure to give a residue, which was purified by prep-TLC ($SiO_2$, eluting with petroleum ether: ethyl acetate=2:1) to get 55 mg of compound J-8 (41% yield) as a white solid.

General procedure for preparation of compound 542: To a solution of compound J-8 (55 mg, 98 μmol, 1 eq) in 1 mL of dichloromethane was added 0.2 mL of TFA. The mixture was stirred at 25° C. for 1 hour. Then it was concentrated under reduced pressure. The residue was purified by prep-TLC ($SiO_2$, eluting with ethyl acetate:methanol=8:1) to get 23 mg of compound 542 (38% yield, 94.4% purity, TFA salt) as a white solid.

$^1H$ NMR (400 MHz, METHANOL-$d_4$) δ ppm 7.50-7.46 (m, 2H), 7.36-7.25 (m, 5H), 7.13 (br d, J=8.8 Hz, 1H), 6.65 (br s, 1H), 4.28 (br s, 1H), 3.85-3.78 (m, 2H), 3.60 (br s, 2H), 2.59 (br s, 1H), 2.16 (br d, J=11.2 Hz, 1H), 1.98-1.81 (m, 2H), 1.70-1.57 (m, 2H), 1.31-1.27 (m, 4H), 1.12 (br d, J=10.4 Hz, 1H)

LCMS (ESI+): m/z 460.3 (M+H)

General Procedure for Preparation of J-9

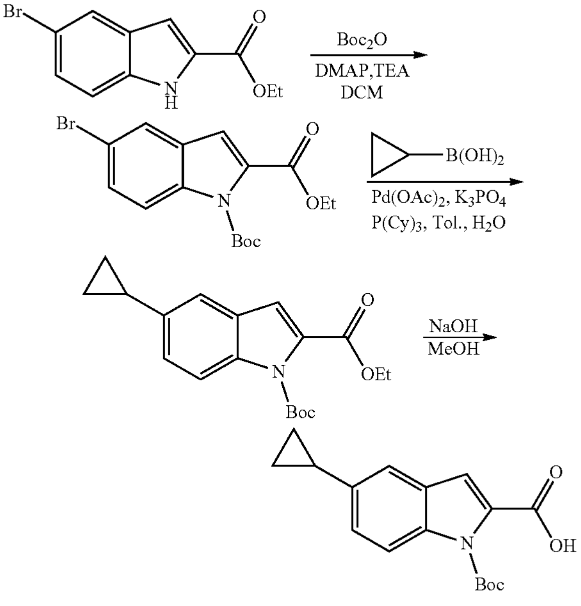

J-9

General procedure for preparation of compound 1-(tert-butyl) 2-ethyl 5-bromo-1H-indole-1,2-dicarboxylate: To a solution of ethyl 5-bromo-1H-indole-2-carboxylate (300 mg, 1.1 mmol, 1 eq) in 2 mL of dichloromethane was added TEA (226 mg, 2.2 mmol, 2 eq), DMAP (13.7 mg, 112 μmol, 0.1 eq) and $Boc_{2}O$ (366 mg, 1.7 mmol, 1.5 eq). The mixture was stirred at 0° C. for 1 hour. Then it was partitioned between 5 mL of water and 15 mL of ethyl acetate. The organic phase was separated, washed with 5 mL of brine, dried over $Na_2SO_4$, filtered and concentrated under reduced pressure to give the crude product which was purified by column chromatography ($SiO_2$, eluting with a gradient of petroleum ether:ethyl acetate=50:1 to 7:1) to give 350 mg of 1-(tert-butyl) 2-ethyl 5-bromo-1H-indole-1,2-dicarboxylate (85% yield) as a yellow oil.

General procedure for preparation of compound 1-(tert-butyl) 2-ethyl 5-cyclopropyl-1H-indole-1,2-dicarboxylate: A mixture of 1-(tert-butyl) 2-ethyl 5-bromo-1H-indole-1,2-dicarboxylate (0.3 g, 815 μmol, 1 eq), cyclopropylboronic acid (91 mg, 1.1 mmol, 1.3 eq), $Pd(OAc)_2$ (9.1 mg, 41 μmol, 0.05 eq), $K_3PO_4$ (432 mg, 2.0 mmol, 2.5 eq) and $P(Cy)_3$ (114 mg, 82 μmol, 20% purity, 0.1 eq) in 10 mL of toluene and 0.5 mL of $H_2O$ was degassed and purged with $N_2$ three times. Then the mixture was stirred at 120° C. for 3 hours under $N_2$ atmosphere. The reaction mixture was filtered and concentrated under reduced pressure to give the crude product, which was purified by column chromatography ($SiO_2$, eluting with a gradient of petroleum ether:ethyl acetate=30:1 to 10:1) to give 220 mg of 1-(tert-butyl) 2-ethyl 5-cyclopropyl-1H-indole-1,2-dicarboxylate (82% yield) as a yellow solid.

General procedure for preparation of compound J-9: To a solution of 1-(tert-butyl) 2-ethyl 5-cyclopropyl-1H-indole-1,2-dicarboxylate (220 mg, 668 μmol, 1 eq) in 5 mL of MeOH was added NaOH (2 M, 1.6 mL, 5 eq). The mixture was stirred at 40° C. for 2 hours. The reaction mixture was concentrated under reduced pressure to give the crude product, which was diluted with 10 mL of water and acidified by 1M HCl until pH~2, then extracted with 30 mL of ethyl acetate. The combined organic layers were washed with 15 mL of brine, dried over $Na_2SO_4$, filtered and concentrated under reduced pressure to give 150 mg of crude compound J-9 as a yellow solid, which was used directly into the next step without purification.

The following compounds were prepared analogously to compound 542 by coupling the appropriate acid with the amine 14 using the HATU procedure, followed by deprotection:

Compound 543

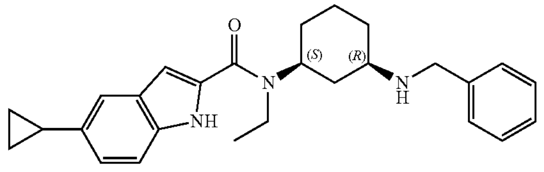

$^1H$ NMR (400 MHz, METHANOL-$d_4$) δ ppm 7.44-7.56 (m, 5H) 7.31-7.41 (m, 2H) 7.03 (d, J=8.80 Hz, 1H) 6.73 (br s, 1H) 4.21-4.45 (m, 3H) 3.70 (br s, 2H) 3.23 (br d, J=7.09 Hz, 1H) 2.37 (br d, J=10.76 Hz, 1H) 2.23 (br d, J=10.27 Hz, 1H) 1.82-2.11 (m, 5H) 1.41-1.58 (m, 2H) 1.36 (br t, J=6.85 Hz, 3H) 0.89-0.98 (m, 2H) 0.68 (q, J=5.14 Hz, 2H)

LCMS (ESI+): m/z 416.3 (M+H)

Compound 544

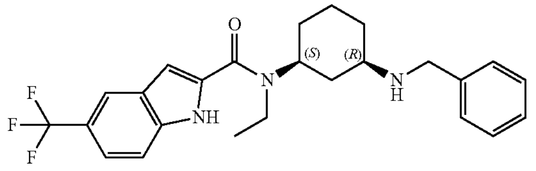

$^1H$ NMR (400 MHz, METHANOL-$d_4$) δ ppm 8.02 (s, 1H) 7.61 (d, J=8.80 Hz, 1H) 7.59-7.64 (m, 1H) 7.45-7.54 (m, 6H) 6.96 (br s, 1H) 4.28 (s, 3H) 3.71 (br s, 2H) 3.35 (br s, 1H) 2.38 (br d, J=11.86 Hz, 1H) 2.23 (br d, J=11.74 Hz, 1H) 1.82-2.13 (m, 4H) 1.41-1.57 (m, 2H) 1.30-1.40 (m, 3H)

LCMS (ESI+): m/z 444.1 (M+H)

Compound 545

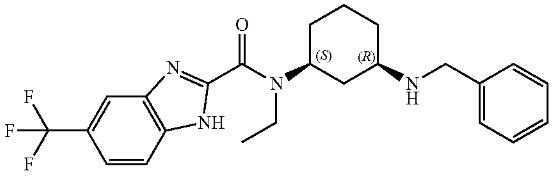

$^1H$ NMR (400 MHz, METHANOL-$d_4$) δ ppm 8.10 (br s, 1H) 7.91 (br d, J=7.58 Hz, 1H) 7.74 (br d, J=8.31 Hz, 1H) 7.41-7.61 (m, 5H) 4.77-4.87 (m, 1H) 4.26-4.36 (m, 2H) 4.22 (br s, 1H) 3.88 (td, J=14.09, 7.64 Hz, 1H) 3.61-3.69 (m, 1H) 3.38 (br d, J=13.45 Hz, 1H) 2.39-2.62 (m, 1H) 2.18-2.31 (m, 1H) 1.94-2.08 (m, 3H) 1.68-1.82 (m, 1H) 1.44-1.62 (m, 2H) 1.26-1.39 (m, 3H)

LCMS (ESI+): m/z 445.3 (M+H)

Compound 546

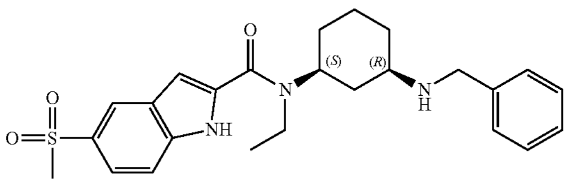

$^1H$ NMR (400 MHz, METHANOL-$d_4$) δ ppm 8.35 (s, 1H) 7.79 (dd, J=8.74, 1.41 Hz, 1H) 7.67 (d, J=8.68 Hz, 1H) 7.41-7.57 (m, 5H) 7.01 (br s, 1H) 4.28 (s, 3H) 3.52-3.81 (m, 2H) 3.22-3.31 (m, 1H) 3.15 (s, 3H) 2.39 (br d, J=10.76 Hz, 1H) 2.23 (br d, J=6.11 Hz, 1H) 1.81-2.11 (m, 4H) 1.29-1.54 (m, 5H)

LCMS (ESI+): m/z 454.2 (M+H)

Example 72. Synthesis of N-((1S,3R)-3-(benzylamino)cyclohexyl)-N-ethyl-5-fluoro-1H-indole-2-carboxamide (Compound 547)

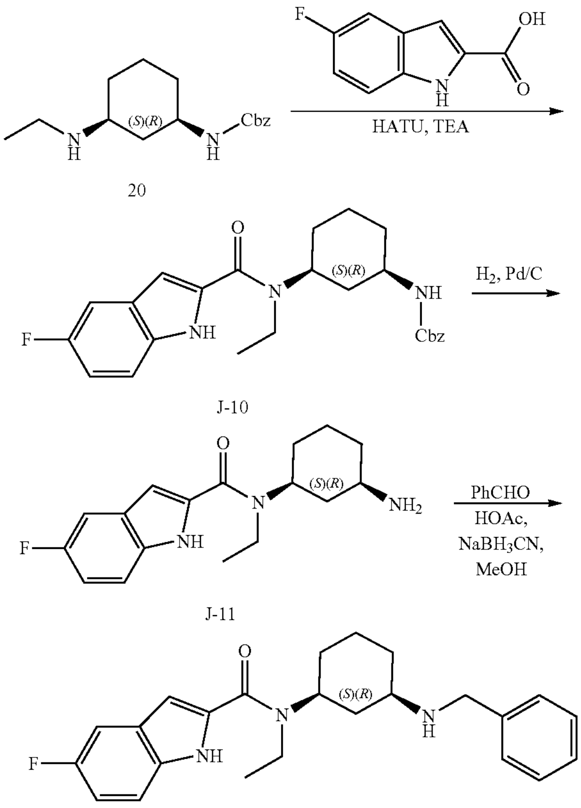

20

J-10

J-11

Compound 547

General procedure for preparation of compound J-10: To a solution of compound 20 (450 mg, 1.4 mmol, 1 eq, HCl salt), 5-fluoro-1H-indole-2-carboxylic acid (284 mg, 1.6 mmol, 1.1 eq) and TEA (437 mg, 4.3 mmol, 3 eq) in 3 mL of DMF was added dropwise HATU (656 mg, 1.7 mmol, 1.2 eq) in 1.5 mL of DMF at 0° C. The resulting mixture was stirred at 25° C. for 12 hours. Then it was quenched by addition 5 mL of water and 5 mL of ethyl acetate. The aqueous layer was separated and extracted three times with 12 mL of ethyl acetate. The combined organic layers were washed with 8 mL of brine, dried over anhydrous $Na_2SO_4$, filtered and concentrated under reduced pressure to give a residue, which was purified by column chromatography ($SiO_2$, eluting with a gradient of petroleum ether:ethyl acetate=6:1 to 2:1) to give 621 mg of compound J-10 (1.4 mmol, 98% yield) as a yellow solid.

General procedure for preparation of compound J-11: To a solution of compound J-10 (600 mg, 1.4 mmol, 1 eq) and $NH_3.H_2O$ (385 mg, 2.7 mmol, 25% purity, 2 eq) in 8 mL of EtOH was added Pd/C (10%, 0.8 g) under $N_2$. The suspension was degassed under vacuum and purged with $H_2$ several times, and then stirred at 25° C. for 0.5 hour under $H_2$ (15 psi). The reaction mixture was filtered and the filtrate was concentrated under vacuum to give 350 mg of compound J-11 (84% yield) as a yellow oil.

General procedure for preparation of compound 547: To a solution of compound J-11 (30 mg, 99 μmol, 1 eq) in 1 mL of MeOH was added HOAc (594 μg, 9.9 μmol, 0.1 eq) and benzaldehyde (12.6 mg, 119 μmol, 1.2 eq) at 25° C. After addition, the mixture was stirred at this temperature for 30 min, and then $NaBH_3CN$ (6.2 mg, 99 μmol, 1 eq) was added. The resulting mixture was stirred at 25° C. for 11.5 hours. Then it was filtered and the filtrate was purified by prep-HPLC (TFA condition) to give 24.7 mg of compound 547 (48% yield, 98.5% purity, TFA salt) as a white solid.

$^1H$ NMR (400 MHz, METHANOL-$d_4$) δ ppm 7.46-7.55 (m, 5H) 7.43 (dd, J=8.93, 4.40 Hz, 1H) 7.31 (dd, J=9.60, 2.38 Hz, 1H) 7.03 (td, J=9.17, 2.57 Hz, 1H) 6.80 (br s, 1H) 4.22-4.44 (m, 3H) 3.69 (br s, 2H) 3.24-3.32 (m, 1H) 2.37 (br d, J=10.64 Hz, 1H) 2.23 (br d, J=11.98 Hz, 1H) 2.03-2.13 (m, 1H) 1.95 (br s, 3H) 1.40-1.58 (m, 2H) 1.36 (br t, J=6.97 Hz, 3H)

LCMS (ESI+): m/z 394.2 (M+H)

The following compounds were prepared analogously to compound 547 using the appropriate aldehydes:

Compound 548

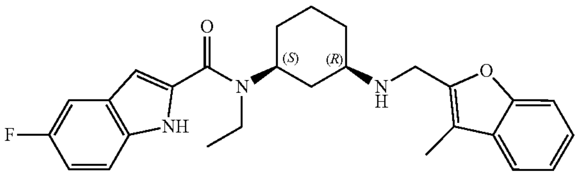

$^1H$ NMR (400 MHz, METHANOL-$d_4$) δ ppm 7.62 (d, J=7.58 Hz, 1H) 7.35-7.52 (m, 3H) 7.22-7.35 (m, 2H) 7.03 (td, J=9.17, 2.45 Hz, 1H) 6.79 (br s, 1H) 4.52 (s, 2H) 4.33 (br s, 1H) 3.69 (br s, 2H) 3.34-3.41 (m, 1H) 2.30-2.43 (m, 4H) 2.18-2.28 (m, 1H) 1.79-2.12 (m, 4H) 1.28-1.59 (m, 5H)

LCMS (ESI+): m/z 448.2 (M+H)

Compound 549

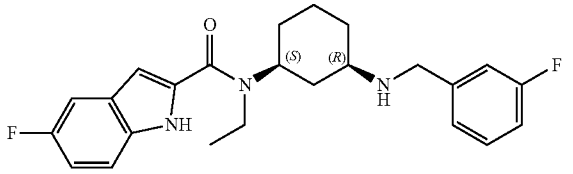

$^1H$ NMR (400 MHz, METHANOL-$d_4$) δ ppm 7.48-7.56 (m, 1H) 7.43 (dd, J=8.99, 4.46 Hz, 1H) 7.28-7.37 (m, 3H) 7.23 (td, J=8.56, 2.57 Hz, 1H) 7.03 (td, J=9.17, 2.45 Hz, 1H) 6.80 (br s, 1H) 4.30 (s, 3H) 3.69 (br s, 2H) 3.35-3.43 (m, 1H) 2.37 (br d, J=11.00 Hz, 1H) 2.23 (br d, J=10.88 Hz, 1H) 2.07 (br d, J=13.20 Hz, 1H) 1.94 (br s, 3H) 1.40-1.59 (m, 2H) 1.36 (br t, J=7.03 Hz, 3H)

LCMS (ESI+): m/z 412.1 (M+H)

Compound 550

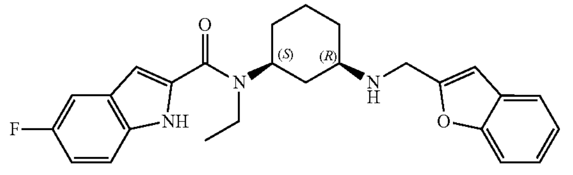

$^1$H NMR (400 MHz, METHANOL-$d_4$) δ ppm 7.64 (d, J=7.58 Hz, 1H) 7.48-7.57 (m, 1H) 7.33-7.46 (m, 2H) 7.22-7.32 (m, 2H) 7.05 (s, 1H) 7.01 (td, J=9.17, 2.57 Hz, 1H) 6.76 (br s, 1H) 4.50-4.55 (m, 1H) 4.33 (br d, J=10.03 Hz, 1H) 3.66 (br s, 2H) 3.32 (br s, 1H) 2.36 (br d, J=9.54 Hz, 1H) 2.21 (br d, J=10.03 Hz, 1H) 1.77-2.09 (m, 4H) 1.38-1.54 (m, 2H) 1.33 (t, J=6.97 Hz, 3H)

LCMS (ESI+): m/z 434.1 (M+H)

Compound 551

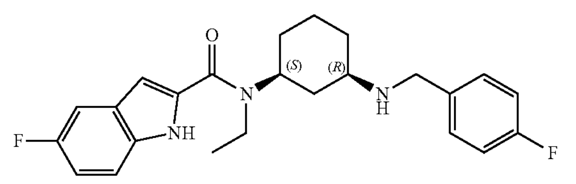

$^1$H NMR (400 MHz, CHLOROFORM-d) δ ppm 9.60 (br s, 1H) 7.29 (dd, J=8.93, 4.30 Hz, 1H) 7.17-7.24 (m, 3H) 6.89-6.99 (m, 3H) 6.40-6.80 (m, 1H) 4.41-4.55 (m, 1H) 3.73 (s, 2H) 3.35-3.69 (m, 2H) 2.61 (br s, 1H) 2.08 (br d, J=11.25 Hz, 1H) 1.92 (br d, J=12.57 Hz, 1H) 1.74-1.87 (m, 2H) 1.36-1.63 (m, 5H) 1.18 (s, 1H) 0.95-1.09 (m, 1H)

LCMS (ESI+): m/z 412.2 (M+H)

Example 73. Synthesis of N-((1S,3R)-3-(((5-cyclopropylisoxazol-3-yl)methyl)amino)cyclohexyl)-N-ethyl-5-fluoro-1H-benzo[d]imidazole-2-carboxamide (Compound 552

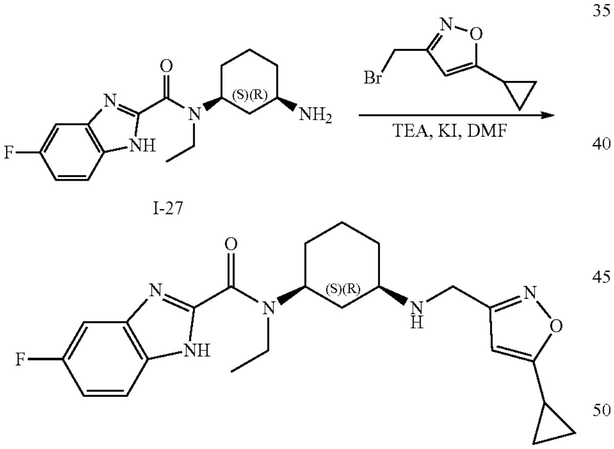

I-27

Compound 552

A mixture of compound I-27 (30 mg, 98.9 μmol, 1 eq), 3-(bromomethyl)-5-cyclopropyl-isoxazole (29.9 mg, 148 μmol, 1.5 eq), TEA (30.0 mg, 297 μmol, 3 eq) and KI (8.2 mg, 49 μmol, 0.5 eq) in 1 mL of DMF was degassed and purged with $N_2$ 3 times, and then the mixture was stirred at 25° C. for 12 hours under $N_2$ atmosphere. It was filtered, and the filtrate was purified by prep-HPLC (TFA condition) to give 17.1 mg of compound 552 (29% yield, 91.4% purity, TFA salt) as a white solid.

$^1$H NMR (400 MHz, METHANOL-$d_4$) δ ppm 7.41 (dd, J=4.5, 8.9 Hz, 1H), 7.30 (dd, J=2.4, 9.6 Hz, 1H), 7.00 (dt, J=2.6, 9.2 Hz, 1H), 6.79 (br s, 1H), 6.18 (s, 1H), 4.35 (d, J=1.1 Hz, 3H), 3.65 (br s, 2H), 3.36-3.31 (m, 1H), 2.34 (br d, J=10.9 Hz, 1H), 2.18-2.10 (m, 2H), 2.07-2.00 (m, 1H), 1.90 (br s, 3H), 1.34-1.32 (m, 2H), 1.31 (br t, J=7.0 Hz, 3H), 1.14-1.11 (m, 2H), 0.95-0.93 (m, 2H)

LCMS (ESI+): m/z 425.2 (M+H)

Compound 553 was prepared analogously using 2-(bromomethyl)benzofuran-3-carbonitrile:

Compound 553

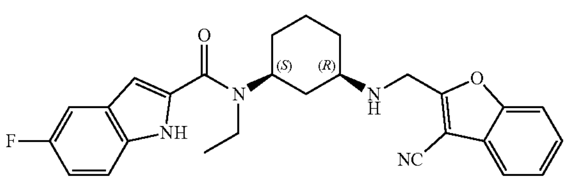

$^1$H NMR (400 MHz, METHANOL-$d_4$) δ ppm 7.67 (d, J=7.5 Hz, 1H), 7.58 (br d, J=8.2 Hz, 1H), 7.47-7.40 (m, 2H), 7.33 (dd, J=4.4, 8.9 Hz, 1H), 7.18 (dd, J=2.3, 9.5 Hz, 1H), 6.90 (dt, J=2.4, 9.2 Hz, 1H), 6.68 (br s, 1H), 4.63 (s, 2H), 4.21 (br s, 1H), 3.57 (br s, 2H), 3.33 (br s, 1H), 2.29 (br d, J=9.7 Hz, 1H), 2.13 (br d, J=7.8 Hz, 1H), 1.98-1.83 (m, 4H), 1.40-1.34 (m, 2H), 1.25-1.18 (m, 3H)

LCMS (ESI+): m/z 459.1 (M+H)

Example 74. Synthesis of N-ethyl-N-((1S,3R)-3-(((5-(trifluoromethyl)isoxazol-3-yl)methyl)amino)cyclohexyl)-1H-benzo[d]imidazole-2-carboxamide (Compound 554

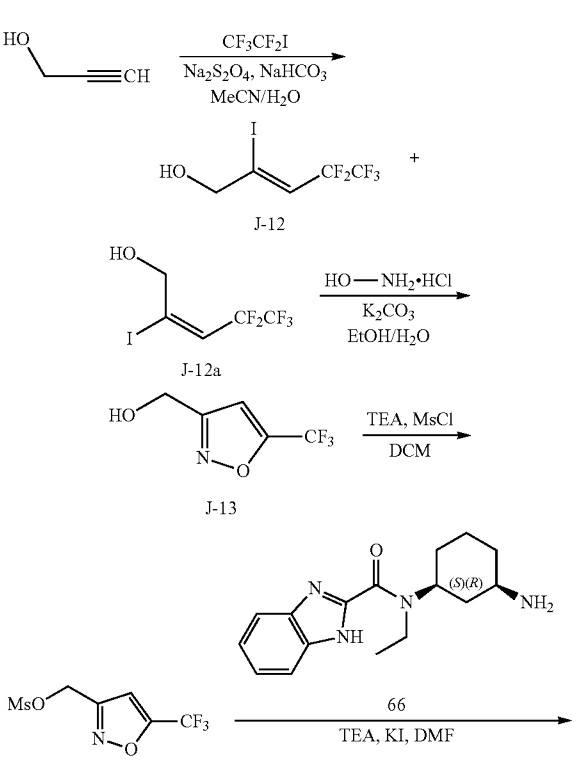

J-12

J-12a

J-13

66

J-14

-continued

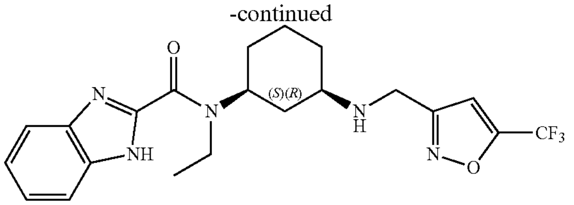

Compound 554

General procedure for preparation of compounds J-12, J-12a: 1,1,1,2,2-pentafluoro-2-iodo-ethane (4.4 g, 17.8 mmol, 1 eq) was added into a stirring mixture in a sealed tube of 35 mL of acetonitrile and 30 mL of water at −20° C., followed by prop-2-yn-1-ol (1 g, 17.8 mmol, 1.1 mL, 1 eq). To this mixture was added sodium hydrosulfite (3.1 g, 17.8 mmol, 1 eq) and $NaHCO_3$ (1.5 g, 17.8 mmol, 1 eq). After addition, the mixture was stirred at 0° C. for 4 hours. Then it was partitioned between 20 mL of water and 40 mL of dichloromethane. The organic phase was separated, washed with 20 mL of brine, dried over $Na_2SO_4$, filtered and concentrated under reduced pressure (at about 25° C.) to give 5.4 g of compound J-12 and J-12a as a light-yellow liquid, which was used into the next step without further purification.

General procedure for preparation of compound J-13: To a mixture of (E)-4,4,5,5,5-pentafluoro-2-iodo-pent-2-en-1-ol and (Z)-4,4,5,5,5-pentafluoro-2-iodo-pent-2-en-1-ol (5.0 g, 16.6 mmol, 1 eq) in 35 mL of EtOH (75% purity) was added hydroxylamine hydrochloride (2.3 g, 33.1 mmol, 2 eq), $K_2CO_3$ (11.4 g, 82.8 mmol, 5 eq), and then the mixture was stirred at 60° C. for 12 hours under $N_2$ atmosphere. The reaction mixture was partitioned between 30 mL of water and 30 mL of ethyl acetate. The organic phase was separated, washed with 15 mL of brine, dried over $Na_2SO_4$, filtered and concentrated under reduced pressure to give the crude product, which was purified by column chromatography ($SiO_2$, eluting with a gradient of petroleum ether:ethyl acetate=10:1 to 5:1) to give 350 mg of compound J-13 (13% yield) as a light yellow liquid.

General procedure for preparation of compound J-14: To a mixture of [5-(trifluoromethyl)isoxazol-3-yl]methanol (50 mg, 299 μmol, 1 eq), TEA (60.6 mg, 599 μmol, 2 eq) in 1 mL of dichloromethane was cooled to 0° C. was added MsCl (41 mg, 359 μmol, 1.2 eq). The mixture was stirred at 25° C. for 1 hour under $N_2$ atmosphere. The reaction mixture was partitioned between 3 mL of sat. aqueous $NH_4Cl$ solution and 5 mL of dichloromethane. The organic phase was separated, washed with 2 mL of brine, dried over $Na_2SO_4$, filtered and concentrated under reduced pressure to give 59 mg of crude compound J-14 as a light-yellow liquid, which was used directly into the next step without purification.

General procedure for preparation of compound 554: To a mixture of compound 66 (45 mg, 157 μmol, 1 eq) and [5-(trifluoromethyl)isoxazol-3-yl]methyl methanesulfonate (58 mg, 236 μmol, 1.5 eq) in 2 mL of DMF was added TEA (31.8 mg, 314 μmol, 2 eq) and KI (2.6 mg, 15.7 μmol, 0.1 eq). The reaction was stirred at 25° C. for 2 hours under $N_2$ atmosphere. The mixture was filtered and the filtrate was purified by prep-HPLC (TFA condition) to give a white solid. The solid was re-purified by prep-TLC ($SiO_2$, eluting with ethyl acetate:methanol=10:1) to give 9.7 mg of compound 554 (11% yield, 99.3% purity, TFA salt) as a white solid.

$^1H$ NMR (400 MHz, METHANOL-$d_4$) δ ppm 7.55-7.72 (m, 1H) 7.55-7.72 (m, 1H) 7.62 (br s, 1H) 7.55-7.72 (m, 1H) 7.31 (br dd, J=5.73, 2.87 Hz, 2H) 7.03-7.12 (m, 1H) 4.72-4.81 (m, 1H) 4.34 (br t, J=11.80 Hz, 1H) 3.86-4.01 (m, 3H) 3.57 (q, J=6.98 Hz, 1H) 2.48-2.72 (m, 1H) 2.11-2.26 (m, 1H) 1.76-2.05 (m, 3H) 1.57-1.69 (m, 1H) 1.40-1.54 (m, 1H) 1.18-1.35 (m, 4H) 0.98-1.15 (m, 1H)

LCMS (ESI+): m/z 436.1 (M+H)

Example 75. Synthesis of N-((1S,3R)-3-(benzylamino)-1-methylcyclohexyl)-N-ethyl-1H-benzo[d]imidazole-2-carboxamide (Compound 555) and N-((1S,3R)-3-(benzylamino)-1-methylcyclohexyl)-N-ethyl-5-fluoro-1H-benzo[d]imidazole-2-carboxamide (Compound 556)

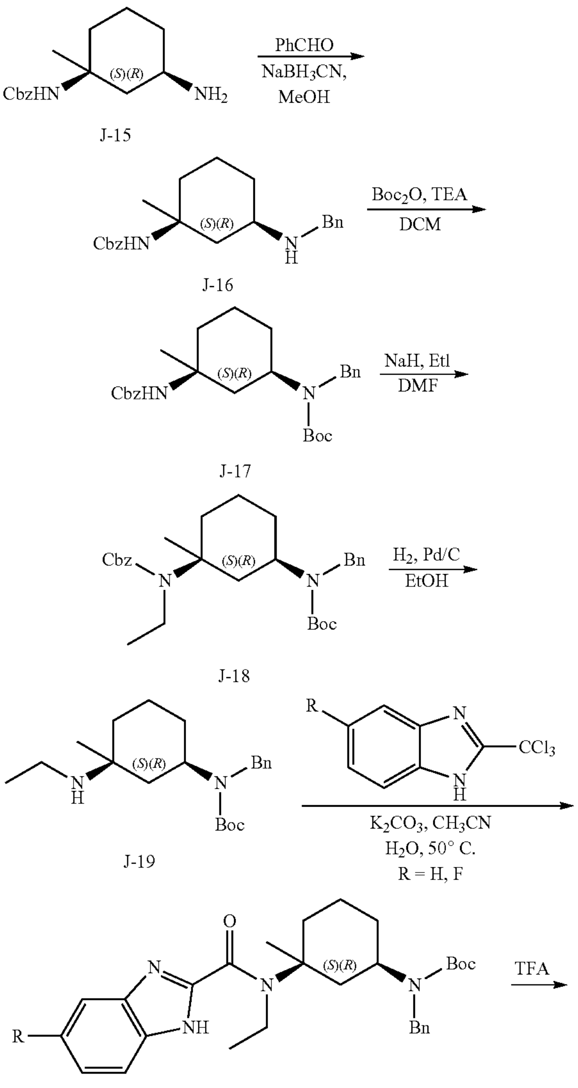

J-15

J-16

J-17

J-18

J-19

J-22a, R = H
J-22b, R = F

-continued

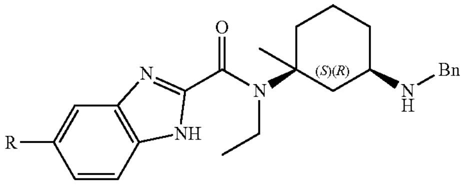

Compound 555, R = H
Compound 556, R = F

General procedure for preparation of compound J-16: A mixture of benzyl N-[(1S,3R)-3-amino-1-methyl-cyclohexyl]carbamate J-15 (150 mg, 571.8 μmol, 1 eq), benzaldehyde (79 mg, 743 μmol, 1.3 eq), HOAc (34 mg, 572 μmol, 1 eq) in 3 mL of MeOH was stirred for 30 min at 25° C., then $NaBH_3CN$ (71.9 mg, 1.1 mmol, 2 eq) was added and the mixture was stirred at 25° C. for another 11.5 hours under $N_2$ atmosphere. It was quenched by adding 5 mL of saturated $NaHCO_3$ aqueous solution, extracted twice with 10 mL of ethyl acetate, the combined organic layers were washed with 3 mL of brine, dried over $Na_2SO_4$, filtered and evaporated under reduced pressure to give 180 mg of crude compound J-16 as light yellow gum, which was used into the next step without further purification.

General procedure for preparation of compound J-17: A mixture of compound J-16 (180 mg, 511 μmol, 1 eq), $Boc_{20}$ (167 mg, 766 μmol, 1.5 eq), TEA (103.3 mg, 1.0 mmol, 2 eq) in 5 mL of dichloromethane was stirred at 25° C. for 12 hours under $N_2$ atmosphere. It was quenched by adding 5 mL of 1N HCl aqueous solution, extracted twice with 10 mL of dichloromethane, the combined organic layers was washed with 5 mL of brine, dried over $Na_2SO_4$, filtered and evaporated under reduced pressure to give the crude product which was purified by prep-TLC ($SiO_2$, eluting with petroleum ether:ethyl acetate=5:1) to give 180 mg of compound J-17 (78% yield) as a colorless gum.

General procedure for preparation of compound J-18: To a mixture of compound J-17 (130 mg, 287 μmol, 1 eq) in 3 mL of DMF was cooled to 0° C. was added NaH (57.4 mg, 1.4 mmol, 60% purity, 5 eq) and the mixture was stirred for 30 min at 0° C. EtI (134.4 mg, 862 μmol, 3 eq) was added. The mixture was allowed to warm to 25° C. gradually and stirred for another 11.5 hours under $N_2$ atmosphere. The reaction mixture was partitioned between 5 mL of water and 10 mL of ethyl acetate. The organic phase was separated, washed three times with 15 mL of water and 5 mL of brine, dried over $Na_2SO_4$, filtered and concentrated under reduced pressure to give 140 mg of crude compound J-18 as a yellow oil, which was used into the next step without further purification.

General procedure for preparation of compound J-19: A mixture of compound J-18 (140 mg, 291 μmol, 1 eq), Pd/C (0.1 g, 10% purity) in 10 mL of EtOH and 0.5 mL of $NH_3.H_2O$ (25% purity) was degassed and purged with $H_2$ for 3 times, and then the mixture was stirred at 25° C. for 0.5 hour under $H_2$ atmosphere (15 psi). The mixture was filtered, the filtrate was evaporated under reduced pressure to give 93 mg of the crude compound J-19 as a white gum, which was used into the next step without further purification.

General Procedure for Preparation of Compound J-20a:

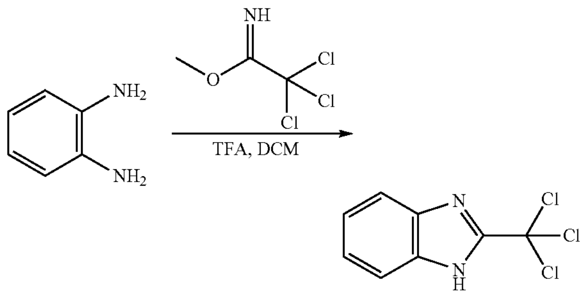

J-20a

To a mixture of benzene-1,2-diamine (0.1 g, 924.7 μmol, 1 eq) in 3 mL of dichloromethane cooled to 0° C. was added methyl 2,2,2-trichloroethanimidate (212 mg, 1.2 mmol, 1.3 eq) and TFA (264 mg, 2.3 mmol, 2.5 eq) successively. Then the mixture was stirred at 25° C. for 12 hours under $N_2$ atmosphere. The mixture was filtered, the filtrate was evaporated under reduced pressure to give 280 mg crude compound J-20a (TFA salt) as a yellow gum.

General procedure for preparation of compound J-22a: A mixture of compound J-19 (20 mg, 58 μmol, 1 eq), 2-(trichloromethyl)-1H-benzimidazole J-20a (24.2 mg, 69.3 μmol, 1.2 eq, TFA salt), and $K_2CO_3$ (79.8 mg, 577 μmol, 10 eq) in 1 mL of acetonitrile and 0.5 mL of water was stirred at 50° C. for 1 hour under $N_2$ atmosphere. To the mixture was added 3 mL of water; it was extracted twice with 5 mL of ethyl acetate. The combined organic layers were washed with 2 mL of brine, dried over $Na_2SO_4$, filtered and evaporated under reduced pressure to give the crude product which was purified by prep-TLC ($SiO_2$, eluting with petroleum ether: ethyl acetate=3:1) to give 25 mg of compound J-22a (51 μmol, 88% yield) as a colorless gum.

General procedure for preparation of compound 555: A mixture of compound J-22a (25 mg, 51 μmol, 1 eq) in 0.3 mL of TFA and 2 mL of dichloromethane was stirred at 25° C. for 1 hour under $N_2$ atmosphere. It was evaporated under reduced pressure to give 22 mg of compound 555 (80% yield, 93.9% purity, TFA salt) as a white solid.

$^1H$ NMR (400 MHz, METHANOL-$d_4$) δ ppm 7.62-7.69 (m, 2H) 7.41-7.54 (m, 5H) 7.32-7.40 (m, 2H) 4.19-4.32 (m, 2H) 3.76-3.90 (m, 2H) 3.36-3.49 (m, 1H) 3.09 (brd, J=11.69 Hz, 1H) 2.26 (br d, J=10.80 Hz, 1H) 1.93-2.17 (m, 4H) 1.61-1.76 (m, 4H) 1.47 (qd, J=12.53, 3.86 Hz, 1H) 1.16-1.30 (m, 3H)

LCMS (ESI+): m/z 391.3 (M+H)

Compound 556 was prepared analogously coupling 5-fluoro-2-(trichloromethyl)-1H-benzoimidazole with the amine J-19, followed by deprotection. 5-fluoro-2-(trichloromethyl)-1H-benzoimidazole was obtained using the procedures described above to give:

Compound 556

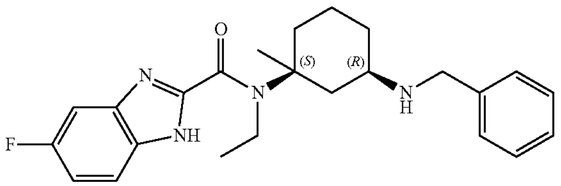

$^{1}$H NMR (400 MHz, METHANOL-$d_4$) δ ppm 7.62 (dd, J=8.82, 4.63 Hz, 1H) 7.44-7.53 (m, 5H) 7.32 (dd, J=8.93, 2.32 Hz, 1H) 7.12 (td, J=9.32, 2.54 Hz, 1H) 4.20-4.32 (m, 2H) 3.84-3.98 (m, 2H) 3.36-3.50 (m, 1H) 3.10 (br d, J=11.69 Hz, 1H) 2.26 (br d, J=11.69 Hz, 1H) 2.09-2.18 (m, 2H) 1.93-2.08 (m, 2H) 1.63-1.76 (m, 4H) 1.46 (qd, J=12.50, 4.19 Hz, 1H) 1.18-1.29 (m, 3H)

LCMS (ESI+): m/z 409.3 (M+H)

Example 76. Synthesis of 5-azido-N-ethyl-N-((1S, 3R)-3-((4-(prop-2-yn-1-yloxy)benzyl)amino)cyclohexyl)-1H-benzo[d]imidazole-2-carboxamide (Compound 557)

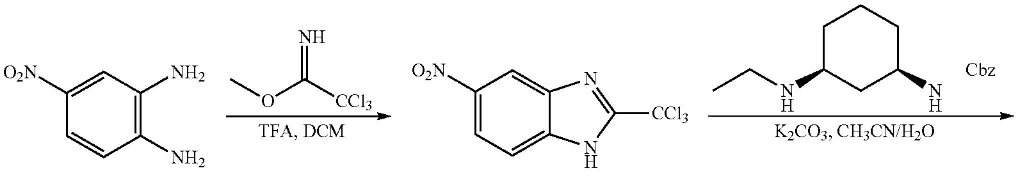

J-23

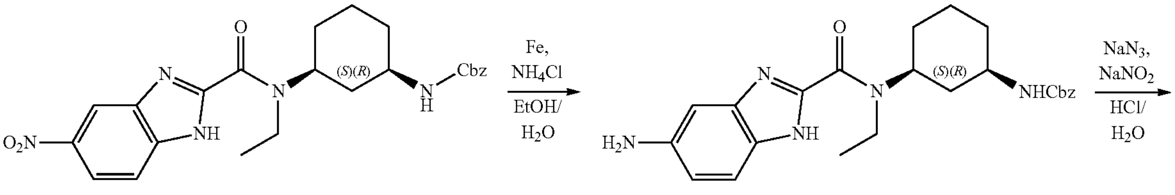

J-24

J-25

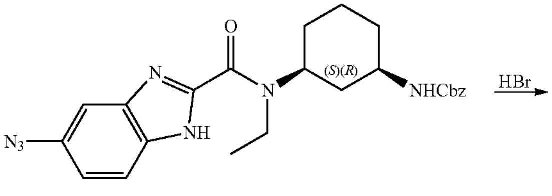

J-26

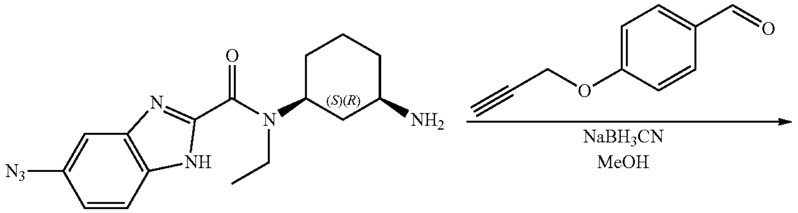

J-27

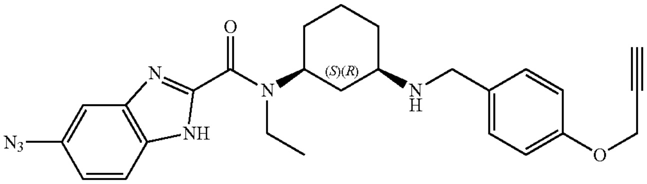

Compound 557

General procedure for preparation of compound J-23: To a solution of 4-nitrobenzene-1,2-diamine (1 g, 6.5 mmol, 1 eq) in 15 mL of dichloromethane was added methyl 2,2,2-trichloroethanimidate (1.5 g, 8.5 mmol, 1.1 mL, 1.3 eq) and TFA (1.8 g, 16.3 mmol, 1.2 mL, 2.5 eq) at 0° C. The mixture was stirred at 25° C. for 12 hours. It was evaporated under reduced pressure to give the crude product, which was purified by column chromatography ($SiO_2$, eluting with a gradient of petroleum ether:ethyl acetate=10:1 to 8:1) to give 1.8 g of compound J-23 (71% yield, TFA salt) as a white solid.

General procedure for preparation of compound J-24: A mixture of benzyl N-[(1R,3S)-3-(ethylamino)cyclohexyl]carbamate 20 (260 mg, 831.1 μmol, 1 eq, HCl salt), compound J-23 (393 mg, 997 μmol, 1.2 eq, TFA salt), $K_2CO_3$ (1.7 g, 12.4 mmol, 15 eq) in 10 mL of acetonitrile and 5 mL of $H_2O$ was degassed and purged with $N_2$ for 3 times, and then the mixture was stirred at 60° C. for 4 hours under $N_2$ atmosphere. The reaction mixture was partitioned between 10 mL of ice-water and 60 mL of ethyl acetate. The combined organic layers were washed with 15 mL of brine, dried over $Na_2SO_4$, filtered and concentrated under reduced pressure to give 0.4 g of crude compound J-24 as a brown solid, which was used into the next step without further purification.

General procedure for preparation of compound J-25: To a solution of compound J-24 (150 mg, 322 μmol, 1 eq) in 5 mL of EtOH and 2 mL of $H_2O$ was added Fe (89.9 mg, 1.6 mmol, 5 eq) and $NH_4Cl$ (172 mg, 3.2 mmol, 10 eq). The mixture was stirred at 80° C. for 0.5 hour. The reaction mixture was filtered and concentrated under reduced pressure to give a residue. The residue was dissolved in $H_2O$ and extracted by 30 mL of ethyl acetate. The organic phase was concentrated under reduced pressure to give 140 mg of crude compound J-25 as a brown gum, which was used into the next step without further purification.

General procedure for preparation of compound J-26: To a mixture of compound J-25 (140 mg, 321 μmol, 1 eq) in 3 mL of HCl (6M) cooled to 0° C. was added dropwise $NaNO_2$ (44.3 mg, 643 μmol, 2 eq) in 0.6 mL of $H_2O$ and the mixture was stirred for 30 min. The resulting diazonium salt was added to a cooled solution of $NaN_3$ (104.5 mg, 1.6 mmol, 5 eq), NaOAc (264 mg, 3.2 mmol, 10 eq) in 2.4 mL of $H_2O$. The mixture was warmed to 25° C. gradually and stirred for another 1.5 hours. It was partitioned between 15 mL of ethyl acetate and water. The organic phase was separated, washed with 10 mL of brine, dried over $Na_2SO_4$, filtered and concentrated under reduced pressure to give 160 mg of crude compound J-26 (HCl salt) as a red gum, which was used into the next step without further purification.

General procedure for preparation of compound J-27: To a solution of compound J-26 (160 mg, 321 μmol, 1 eq, HCl salt) was added HBr (15.7 g, 78.0 mmol, 10.6 mL, 40% purity, 243 eq). The mixture was stirred at 20° C. for 0.5 hour. It was basified by 4M NaOH until pH~11, extracted with 80 mL of ethyl acetate, and the combined organic layers were washed with 15 mL of brine, dried over $Na_2SO_4$, filtered and evaporated under reduced pressure to give 0.1 g of crude compound J-27 as a brown solid, which was used into the next step without further purification.

General procedure for preparation of compound 557: To a solution of compound J-27 (50 mg, 153 μmol, 1 eq) and 4-prop-2-ynoxybenzaldehyde (24.4 mg, 153 μmol, 1 eq) in 1 mL of MeOH was added HOAc (9.1 mg, 153 μmol, 1 eq). The mixture was stirred for 0.5 hour at 25° C. $NaBH_3CN$ (14.4 mg, 229 μmol, 1.5 eq) was added to the mixture, and the mixture was stirred at 25° C. for 11.5 hours. The reaction mixture was partitioned between 6 mL of water and 12 mL of ethyl acetate. The organic phase was separated, washed with 5 mL of brine, dried over $Na_2SO_4$, filtered and concentrated under reduced pressure to give the crude product, which was purified by prep-HPLC (neutral condition) to give 14.7 mg of compound 557 (18% yield, 90.3% purity) as a pink solid.

$^1H$ NMR (400 MHz, CHLOROFORM-d) δ ppm 7.42-7.78 (m, 1H) 7.09-7.24 (m, 3H) 6.94 (br d, J=8.68 Hz, 1H) 6.85 (br d, J=8.31 Hz, 2H) 5.83 (br t, J=11.74 Hz, 1H) 4.60 (dd, J=4.77, 2.20 Hz, 2H) 4.51 (br t, J=12.04 Hz, 1H) 4.18 (q, J=6.81 Hz, 1H) 3.71 (d, J=5.62 Hz, 2H) 3.52 (q, J=6.81 Hz, 1H) 2.62-2.80 (m, 1H) 2.43 (br s, 1H) 2.03-2.25 (m, 1H) 1.74-1.99 (m, 4H) 1.40-1.50 (m, 2H) 1.23-1.31 (m, 3H) 0.95-1.11 (m, 1H)

LCMS (ESI+): m/z 472.2 (M+H)

Compound 558 was prepared analogously by reductive amination using 3-(prop-2-yn-1-yloxy)benzaldehyde:

Compound 558

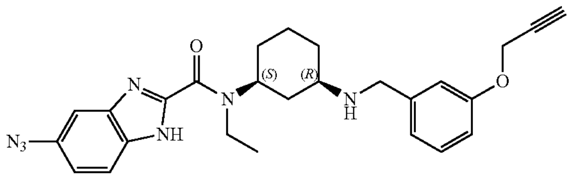

$^1H$ NMR (400 MHz, CHLOROFORM-d) δ ppm 7.42-7.76 (m, 1H) 7.09-7.27 (m, 2H) 6.93 (dd, J=8.68, 1.71 Hz, 1H) 6.83-6.90 (m, 2H) 6.79 (br t, J=7.58 Hz, 1H) 5.81 (br t, J=11.31 Hz, 1H) 4.60 (s, 2H) 4.43-4.54 (m, 1H) 4.18 (q, J=6.68 Hz, 1H) 3.76 (br d, J=7.09 Hz, 2H) 3.53 (q, J=6.93 Hz, 1H) 2.61-2.80 (m, 1H) 2.45 (br d, J=1.96 Hz, 1H) 2.05-2.25 (m, 1H) 1.73-2.00 (m, 4H) 1.35-1.62 (m, 2H) 1.27 (br t, J=6.48 Hz, 3H) 0.94-1.13 (m, 1H)

Compounds 559 and 560 were synthesized analogously to compound 558 by using 3-nitrobenzene-1,2-diamine as starting material.

Compound 559

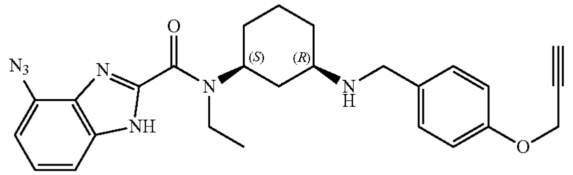

$^1H$ NMR (400 MHz, CHLOROFORM-d) δ ppm 7.21-7.27 (m, 1H) 7.13-7.19 (m, 3H) 6.81-6.88 (m, 2H) 6.77 (br s, 1H) 5.96 (br s, 1H) 4.60 (d, J=2.43 Hz, 2H) 4.46-4.56 (m, 1H) 4.15 (q, J=6.91 Hz, 1H) 3.66-3.74 (m, 2H) 3.47-3.55 (m, 1H) 3.51 (q, J=6.98 Hz, 1H) 2.78 (br t, J=11.03 Hz, 1H) 2.63-2.71 (m, 1H) 2.41-2.46 (m, 1H) 2.11 (br dd, J=17.75, 12.02 Hz, 1H) 1.93 (br d, J=11.47 Hz, 1H) 1.77-1.85 (m, 2H) 1.42-1.57 (m, 3H) 1.22-1.32 (m, 3H) 0.97-1.11 (m, 1H)

LCMS (ESI+): m/z 472.2 (M+H)

Compound 560

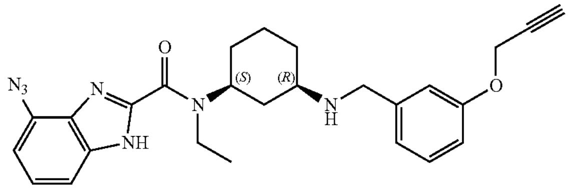

$^1H$ NMR (400 MHz, CHLOROFORM-d) δ ppm 7.12-7.22 (m, 3H) 6.85-6.90 (m, 2H) 6.71-6.82 (m, 2H) 5.97 (br s, 1H) 4.60 (dd, J=10.91, 2.32 Hz, 2H) 4.51 (br t, J=11.69 Hz, 1H) 4.15 (q, J=7.06 Hz, 1H) 3.75 (d, J=4.19 Hz, 2H) 3.47-3.57 (m, 1H) 2.78 (br t, J=10.80 Hz, 1H) 2.66 (br t, J=11.14 Hz, 1H) 2.45 (dt, J=16.59, 2.29 Hz, 1H) 2.07-2.17 (m, 1H) 1.92-1.97 (m, 1H) 1.76-1.87 (m, 2H) 1.40-1.58 (m, 3H) 1.22-1.32 (m, 3H) 0.95-1.11 (m, 1H)

LCMS (ESI+): m/z 472.2 (M+H)

Example 77. Synthesis of N-ethyl-5-nitro-N-((1S,3R)-3-((4-(prop-2-yn-1-yloxy)benzyl)amino)cyclohexyl)-1H-benzo[d]imidazole-2-carboxamide (Compound 561) and 5-amino-N-ethyl-N-((1S,3R)-3-((4-(prop-2-yn-1-yloxy)benzyl)amino)cyclohexyl)-1H-benzo[d]imidazole-2-carboxamide (Compound 562

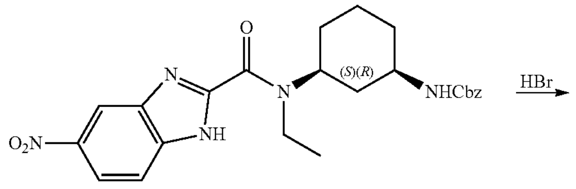

J-24

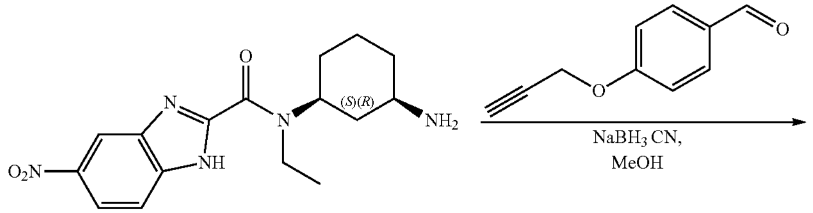

J-28

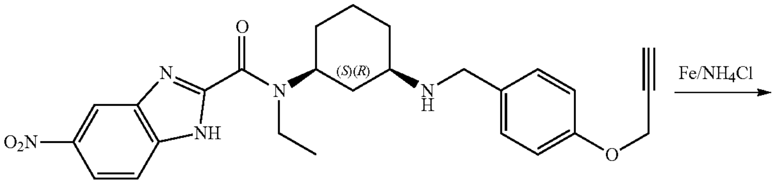

Compound 561

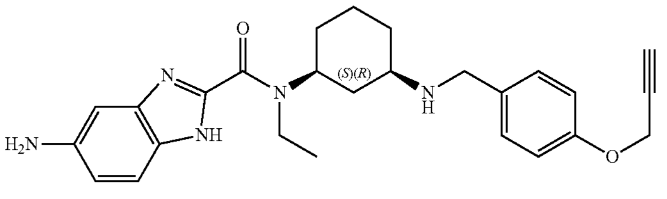

Compound 562

General procedure for preparation of compound J-28: To a solution of compound J-24 (0.2 g, 430 μmol, 1 eq) was added HBr (21.1 g, 104 mmol, 14.1 mL, 40% purity, 243 eq). The mixture was stirred at 20° C. for 0.5 hour. The reaction mixture was basified by 4M NaOH until pH~11, partitioned between 15 mL of water and 90 mL of ethyl acetate. The organic phase was separated, washed with 15 mL of brine, dried over $Na_2SO_4$, filtered and concentrated under reduced pressure to give 0.1 g of crude compound J-28 as a yellow solid, which was used directly into the next step without purification.

General procedure for preparation of compound 561: To a solution of compound J-28 (0.1 g, 302 μmol, 1 eq) and 4-prop-2-ynoxybenzaldehyde (48.3 mg, 302 μmol, 1 eq) in 2 mL of MeOH was added HOAc (18.1 mg, 302 μmol, 1 eq) at 25° C. The mixture was stirred for 0.5 hour at 25° C. $NaBH_3CN$ (28.4 mg, 453 μmol, 1.5 eq) was added to the mixture, and the mixture was stirred at 25° C. for 11.5 hours. The reaction mixture was partitioned between 6 mL of water and 12 mL of ethyl acetate. The organic phase was separated, washed with 5 mL of brine, dried over $Na_2SO_4$, filtered and concentrated under reduced pressure to give 120 mg of crude compound 561. 40 mg of the crude product was purified by prep-TLC ($SiO_2$, eluting with ethyl acetate: methanol=10:1) to give 10.6 mg of compound 561 (7% yield, 98.1% purity) as a yellow solid.

$^1$H NMR (400 MHz, CHLOROFORM-d) δ ppm 8.60 (br s, 1H) 8.19 (dd, J=8.82, 2.20 Hz, 1H) 7.58-7.69 (m, 1H) 7.14-7.19 (m, 2H) 6.78-6.92 (m, 2H) 5.75 (brt, J=11.91 Hz, 1H) 4.60 (dd, J=12.90, 2.32 Hz, 2H) 4.48-4.56 (m, 1H) 4.19 (q, J=6.91 Hz, 1H) 3.72 (d, J=7.06 Hz, 2H) 3.57 (q, J=7.13 Hz, 1H) 2.66-2.79 (m, 2H) 2.40-2.45 (m, 1H) 2.07-2.26 (m, 1H) 1.78-2.02 (m, 3H) 1.50-1.65 (m, 2H) 1.25-1.35 (m, 3H) 0.97-1.22 (m, 2H)

LCMS (ESI+): m/z 476.3 (M+H)

Additionally: 80 mg of the crude product was purified by prep-TLC ($SiO_2$, eluting with ethyl acetate:methanol=10:1) to give 60 mg of compound 561, which was used directly into the next step.

General procedure for preparation of compound 562: A mixture of compound 561 (60 mg, 126 μmol, 1 eq), Fe (35.2 mg, 631 μmol, 5 eq), $NH_4Cl$ (67.5 mg, 1.2 mmol, 10 eq) in 2 mL of EtOH and 0.8 mL of $H_2O$ was degassed and purged with $N_2$ 3 times, and then the mixture was stirred at 80° C. for 0.5 hour under $N_2$ atmosphere. The reaction mixture was filtered and the filter liquor was concentrated under reduced pressure to give the crude product, which was purified by prep-HPLC (neutral condition) to give 21.8 mg of compound 562 (37% yield, 94.6% purity) as a white solid.

$^1$H NMR (400 MHz, METHANOL-$d_4$) δ ppm 7.40-7.55 (m, 3H) 7.06 (br s, 2H) 6.80-6.94 (m, 2H) 4.48-4.81 (m, 3H) 4.20 (br s, 2H) 4.00 (br s, 1H) 3.48-3.70 (m, 1H) 3.37 (br s, 1H) 3.11-3.28 (m, 1H) 2.97 (t, J=2.38 Hz, 1H) 2.31-2.50 (m, 1H) 2.19 (br s, 1H) 1.63-2.12 (m, 4H) 1.44 (br s, 2H) 1.19-1.38 (m, 3H)

LCMS (ESI+): m/z 446.3 (M+H)

Compounds 563 and 564 were prepared analogously by reductive amination using 3-(prop-2-yn-1-yloxy)benzaldehyde, and then reduced by iron powder.

Compound 563

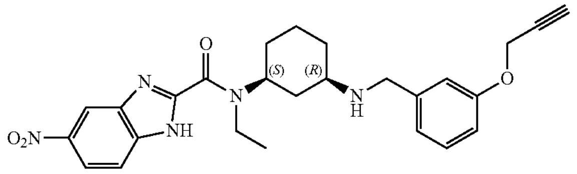

$^1$H NMR (400 MHz, METHANOL-$d_4$) δ ppm 8.53-8.65 (m, 1H) 8.23 (dd, J=8.93, 1.96 Hz, 1H) 7.69-7.80 (m, 1H) 7.20-7.34 (m, 1H) 6.87-7.08 (m, 3H) 4.67-4.82 (m, 3H) 4.28-4.41 (m, 1H) 3.93-4.01 (m, 1H) 3.81-3.92 (m, 2H) 3.54-3.68 (m, 1H) 2.87-3.00 (m, 1H) 2.58-2.85 (m, 1H) 2.17-2.34 (m, 1H) 1.84-2.00 (m, 3H) 1.49-1.81 (m, 2H) 1.24-1.37 (m, 4H) 1.05-1.22 (m, 1H)

LCMS (ESI+): m/z 476.1 (M+H)

Compound 564

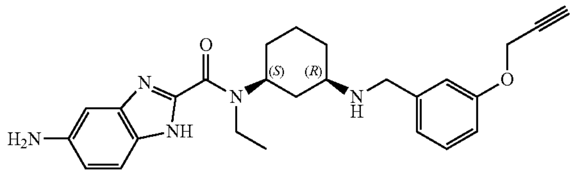

$^1$H NMR (400 MHz, CHLOROFORM-d) δ ppm 10.26 (br s, 1H) 7.57 (br dd, J=17.97, 7.83 Hz, 1H) 7.21-7.26 (m, 1H) 6.92-6.99 (m, 2H) 6.87 (br d, J=9.04 Hz, 1H) 6.67-6.76 (m, 2H) 5.91 (br s, 1H) 4.69 (dd, J=8.93, 1.87 Hz, 2H) 4.50 (br s, 1H) 4.24 (br d, J=6.84 Hz, 1H) 3.84 (br d, J=3.31 Hz, 2H) 3.69-3.79 (m, 1H) 3.53 (br d, J=7.06 Hz, 1H) 2.67-2.87 (m, 1H) 2.54 (br d, J=7.06 Hz, 1H) 2.10-2.32 (m, 1H) 1.78-2.06 (m, 4H) 1.39-1.49 (m, 1H) 1.22-1.36 (m, 4H) 1.13 (br d, J=8.60 Hz, 1H)

LCMS (ESI+): m/z 446.3 (M+H)

Compounds 565, 566, 567, and 568 were synthesized analogously by using 4-nitro substituted benzimidazole intermediate as starting material.

Compound 565

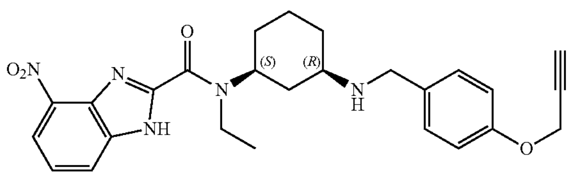

$^1$H NMR (400 MHz, CHLOROFORM-d) δ ppm 8.21 (d, J=8.38 Hz, 1H) 8.02-8.12 (m, 1H) 7.37 (td, J=8.05, 3.31 Hz, 1H) 7.18 (br d, J=2.87 Hz, 2H) 6.86 (t, J=8.93 Hz, 2H) 5.57 (br t, J=11.69 Hz, 1H) 4.57-4.63 (m, 2H) 4.44 (br s, 1H) 4.11 (q, J=7.13 Hz, 1H) 3.72 (s, 2H) 3.50 (q, J=7.06 Hz, 1H) 2.64-2.73 (m, 1H) 2.43-2.46 (m, 1H) 2.18 (br d, J=9.48 Hz, 1H) 2.09 (br d, J=9.92 Hz, 1H) 1.93 (br d, J=12.79 Hz, 1H) 1.77-1.86 (m, 2H) 1.37-1.57 (m, 3H) 1.26 (dt, J=16.37, 7.14 Hz, 3H) 0.97-1.12 (m, 1H)

LCMS (ESI+): m/z 476.2 (M+H)

Compound 566

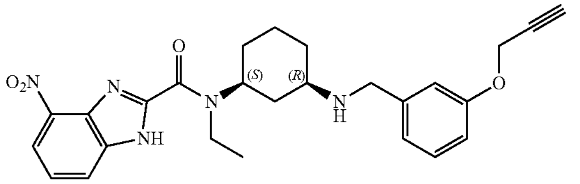

$^1$H NMR (400 MHz, CHLOROFORM-d) δ ppm 8.21 (d, J=8.16 Hz, 1H) 8.03-8.12 (m, 1H) 7.37 (t, J=8.16 Hz, 1H) 7.15-7.19 (m, 1H) 7.15-7.19 (m, 1H) 6.77-6.92 (m, 3H) 5.57 (br t, J=12.24 Hz, 1H) 4.62 (dd, J=13.23, 1.98 Hz, 2H) 4.43 (br t, J=12.02 Hz, 1H) 4.11 (q, J=6.84 Hz, 1H) 3.77 (s, 2H) 3.50 (q, J=6.98 Hz, 1H) 2.63-2.75 (m, 1H) 2.46 (br d, J=13.23 Hz, 1H) 2.05-2.23 (m, 1H) 2.05-2.23 (m, 1H) 1.74-1.97 (m, 3H) 1.34-1.61 (m, 3H) 1.18-1.31 (m, 3H) 0.97-1.11 (m, 1H)

LCMS (ESI+): m/z 476.2 (M+H)

Compound 567

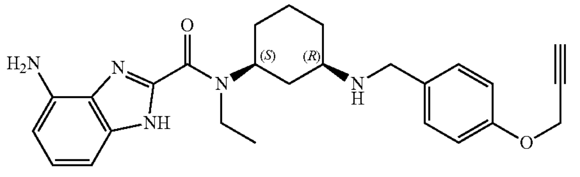

$^1$H NMR (400 MHz, CHLOROFORM-d) δ ppm 10.78-11.13 (m, 1H) 7.17 (br d, J=8.60 Hz, 2H) 7.04 (t, J=7.83 Hz, 1H) 6.77-6.87 (m, 3H) 6.45 (br d, J=7.72 Hz, 1H) 5.84 (br t, J=11.80 Hz, 1H) 4.57-4.62 (m, 2H) 4.46-4.56 (m, 1H) 4.29 (br s, 1H) 4.10-4.22 (m, 1H) 3.71 (d, J=8.16 Hz, 2H) 3.45-3.55 (m, 1H) 2.62-2.74 (m, 1H) 2.44 (q, J=2.43 Hz, 1H) 2.41-2.46 (m, 1H) 2.04-2.25 (m, 1H) 1.93 (br d, J=13.45 Hz, 1H) 1.76-1.87 (m, 2H) 1.35-1.56 (m, 3H) 1.17-1.31 (m, 3H) 0.98-1.12 (m, 1H)

LCMS (ESI+): m/z 446.3 (M+H)

Compound 568
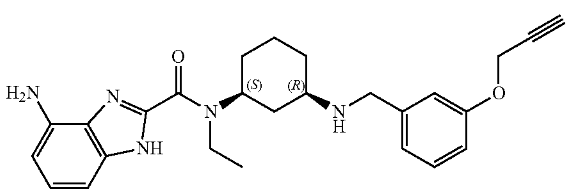
$^1$H NMR (400 MHz, CHLOROFORM-d) δ ppm 10.62-10.94 (m, 1H) 7.14-7.19 (m, 1H) 7.04 (br t, J=7.83 Hz, 1H) 6.85-6.90 (m, 2H) 6.76-6.85 (m, 2H) 6.46 (dd, J=7.50, 2.87 Hz, 1H) 5.82 (br t, J=11.69 Hz, 1H) 4.61 (dd, J=7.83, 2.32 Hz, 2H) 4.45-4.55 (m, 1H) 4.11-4.33 (m, 2H) 3.76 (d, J=7.28 Hz, 2H) 3.49 (q, J=6.76 Hz, 1H) 2.62-2.75 (m, 1H) 2.41-2.48 (m, 1H) 2.05-2.26 (m, 1H) 1.86-1.96 (m, 2H) 1.75-1.86 (m, 1H) 1.35-1.56 (m, 3H) 1.20-1.31 (m, 3H) 0.98-1.11 (m, 1H)
LCMS (ESI+): m/z 446.3 (M+H)
Example 78. Synthesis of N-ethyl-N-((3R,5S)-5-(((R)-5-fluoro-2,3-dihydro-1H-inden-1-yl)amino) tetrahydro-2H-pyran-3-yl)-1H-benzo[d]imidazole-2-carboxamide (Compound 569)
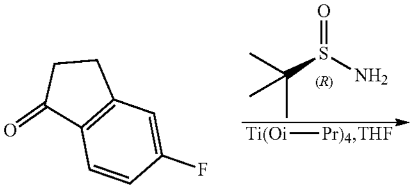
J-29
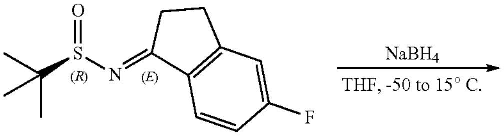
J-30
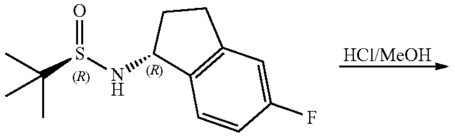
J-31
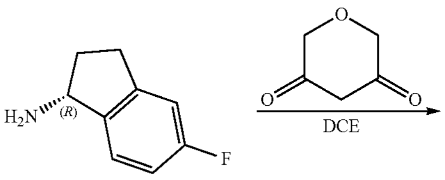
J-32
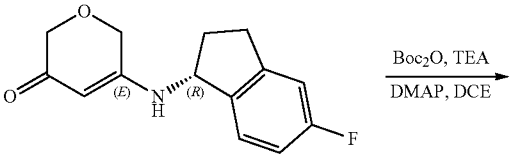
J-33
-continued
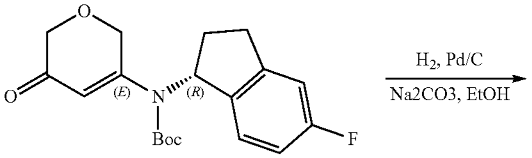
J-34
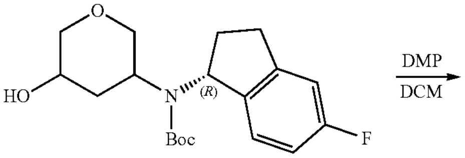
J-35
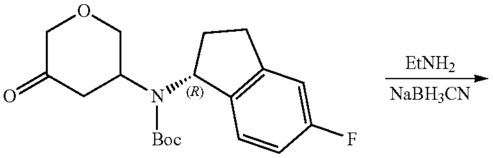
J-36
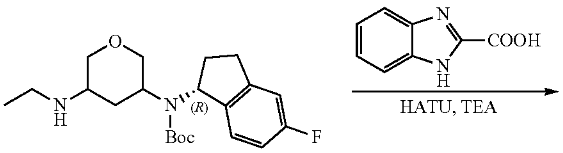
J-37
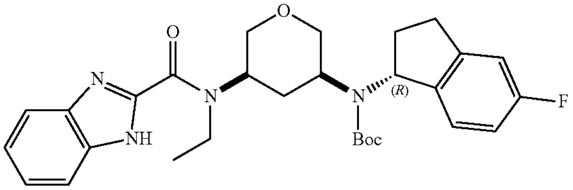
J-38a
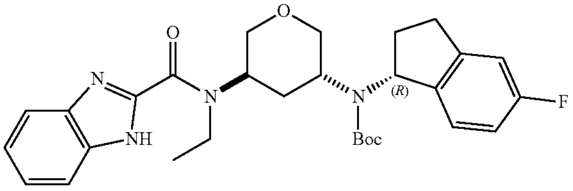
J-38b
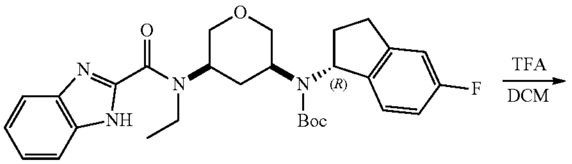
J-38a
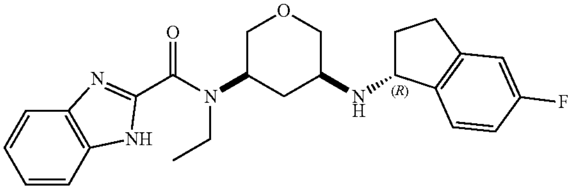
Compound 569

General procedure for preparation of compound J-30: A mixture of 5-fluoroindan-1-one, J-29, (5 g, 33 mmol, 1 eq), (R)-2-methylpropane-2-sulfinamide (5 g, 41 mmol, 1.2 eq) and $Ti(Oi\text{-}Pr)_4$ (11.4 g, 40.0 mmol, 11.8 mL, 1.2 eq) in 50 mL of THF was stirred for 28 hours at 70° C. The reaction mixture was concentrated, and the residue was diluted with 200 mL of ethyl acetate and 5 mL of brine. The reaction mixture was filtered, and the filtrate was concentrated under reduced pressure to give the crude product, which was purified by column chromatography ($SiO_2$, petroleum ether: ethyl acetate=8:1 to 5:1) to give 1.7 g of compound J-30 (20% yield) as a black solid.

General procedure for preparation of compound J-31: To a solution of (NE)-N-(5-fluoroindan-1-ylidene)-2-methyl-propane-2-sulfinamide (1.7 g, 6.7 mmol, 1.0 eq) and $Ti(i\text{-}PrO)_4$ (191 mg, 671 μmol, 198.7 μL, 0.1 eq) in 15.0 mL of THF was added $NaBH_4$ (762 mg, 20.1 mmol, 3.0 eq) in portions at −50° C. and the reaction was warmed to 15° C. and stirred for 12 hours. The reaction mixture was quenched by addition 1 mL of MeOH and then concentrated to give the residue. Then the residue was dissolved into 10 mL of dichloromethane and was washed with 20 mL of saturated $NH_4Cl$, dried over $Na_2SO_4$, filtered and concentrated under reduced pressure to give 1.8 g of crude compound J-31 as a grey solid, which was used into the next step without further purification.

General procedure for preparation of compound J-32: A solution of N-[(1R)-5-fluoroindan-1-yl]-2-methyl-propane-2-sulfinamide (1.5 g, 5.9 mmol, 1.0 eq) in 20 mL of HCl/MeOH (4M) was stirred for 1 hours at 15° C. The reaction mixture was concentrated under reduced pressure to give 1.1 g of crude compound J-32 (HCl salt) as a yellow solid, which was used into the next step without further purification.

General procedure for preparation of compound J-33: To a solution of (1R)-5-fluoroindan-1-amine, J-32, (980 mg, 5.2 mmol, 1 eq, HCl salt) in 10 mL of 1,2-dichloroethane was added TEA (529 mg, 5.2 mmol, 727 μL, 1 eq) for neutralization at 15° C. Then tetrahydropyran-3,5-dione (596 mg, 5.2 mmol, 1 eq) and HOAc (31.4 mg, 522 μmol, 0.1 eq) was added. The reaction was stirred for 1 hour at 80° C. The reaction mixture was concentrated under reduced pressure to give the crude product, which was purified by column chromatography ($SiO_2$, eluting with a gradient of petroleum ether:ethyl acetate=10:1 to 0:1) to give 820 mg of compound J-33 (63% yield) as a yellow solid.

General procedure for preparation of compound J-34: To a solution of 3-[[(1R)-5-fluoroindan-1-yl]amino]-2H-pyran-5-one, J-33, (350 mg, 1.4 mmol, 1 eq), TEA (430 mg, 4.3 mmol, 589 μL, 3 eq) and DMAP (34.6 mg, 283.1 μmol, 0.20 eq) in 2 mL of 1,2-dichloroethane was added $Boc_{20}$ (618 mg, 2.8 mmol, 650 μL, 2 eq) at 15° C. and the reaction was stirred for 12 hours at 30° C. The reaction mixture was concentrated under reduced pressure to give the crude product, which was purified by column chromatography ($SiO_2$, eluting with a gradient of petroleum ether:ethyl acetate=15:1 to 8:1) to give 800 mg of compound J-34 (74% yield, 91% purity) as a red-brown gum.

General procedure for preparation of compound J-35: To a solution of tert-butyl N-[(1R)-5-fluoroindan-1-yl]-N-(5-oxo-2H-pyran-3-yl) carbamate, J-34, (650 mg, 1.9 mmol, 1 eq) and $Na_2CO_3$ (198 mg, 1.9 mmol) in 15 mL of EtOH was added Pd/C (0.3 g, 10% purity) under $N_2$. The suspension was degassed under vacuum and purged with $H_2$ several times and stirred under $H_2$ (50 psi) at 30° C. for 12 hours. The reaction mixture was filtered and the filtrate was concentrated under reduced pressure to give the crude product, which was purified by column chromatography ($SiO_2$, eluting with a gradient of petroleum ether:ethyl acetate=100:1 to 3:1) to give 340 mg of compound J-35 (52% yield) as a yellow oil.

General procedure for preparation of compound J-36: To a solution of tert-butyl N-[(1R)-5-fluoroindan-1-yl]-N-(5-hydroxytetrahydropyran-3-yl)carbamate, J-35, (450 mg, 1.3 mmol, 1 eq) in 5 mL of dichloromethane was added DMP (1.1 g, 2.6 mmol, 2 eq) portionwise at 0° C. After addition, the resulting mixture was stirred at 40° C. for 12 hours. The reaction mixture was filtered and the filtrate was washed with 5 mL of saturated $Na_2SO_3$ and 5 mL of saturated $NaHCO_3$, dried over $Na_2SO_4$, filtered and concentrated under reduced pressure to give the crude product, which was purified by column chromatography ($SiO_2$, eluting with a gradient of petroleum ether:ethyl acetate=50:1 to 8:1) to give 290 mg of compound J-36 (65% yield) as a yellow oil.

General procedure for preparation of compound J-37: To a solution of tert-butyl N-[(1R)-5-fluoroindan-1-yl]-N-(5-oxotetrahydropyran-3-yl)carbamate, J-36, (200 mg, 572 μmol, 1 eq) in 2 mL of MeOH was added AcOH (3.4 mg, 57.2 μmol, 0.1 eq) and ethanamine (51.6 mg, 1.1 mmol, 2 eq) at 25° C. After addition, the mixture was stirred at this temperature for 30 min, and then $NaBH_3CN$ (54.0 mg, 859 μmol, 1.5 eq) was added. The resulting mixture was stirred at 25° C. for 1 hour. Then it was filtered and the filtrate was concentrated under reduced pressure to give the crude product, which was purified by prep-TLC ($SiO_2$, eluting with petroleum ether:ethyl acetate=3:1) to give 160 mg of compound J-37 (74% yield) as a yellow oil.

General procedure for preparation of compounds J-38a and J-38b: To a solution of compound J-37 (170 mg, 449 μmol, 1 eq), 1H-benzimidazole-2-carboxylic acid (80.1 mg, 494 μmol, 1.1 eq) and TEA (136.4 mg, 1.4 mmol, 188 μL, 3 eq) in 2 mL of DMF was added dropwise HATU (205 mg, 539 μmol, 1.2 eq) in 1 mL of DMF at 0° C. The resulting mixture was stirred at 20° C. for 5 hours. Then it was partitioned between 2 mL of water and 6 mL of ethyl acetate. The organic phase was separated, washed with 9 mL of water and 6 mL of brine, dried over $Na_2SO_4$, filtered and concentrated under reduced pressure to give the crude product, which was purified by prep-TLC ($SiO_2$, eluting with petroleum ether: ethyl acetate=1:1) to give 110 mg of cis-form compound J-38a (47% yield) as a colorless gum and 25 mg of trans-form compound J-38b (11% yield) as a colorless gum. (Note: the configuration of two isomers were assigned randomly) General procedure for preparation of compound 569: A mixture of compound J-38a (110 mg, 211 μmol, 1 eq) and TFA (308 mg, 2.7 mmol, 0.2 mL) in 1 mL of dichloromethane was degassed and purged with $N_2$ for 3 times, and then the mixture was stirred at 25° C. for 1 hour under $N_2$ atmosphere. The reaction mixture was concentrated under reduced pressure to give the crude product, which was purified by prep-HPLC (TFA condition) to give 20.1 mg of compound 569 (20% yield, TFA salt) as a white solid. (Note: the configuration was assigned randomly)

$^1H$ NMR (400 MHz, METHANOL-$d_4$) δ ppm 7.68 (br s, 2H) 7.30-7.53 (m, 3H) 7.03 (br s, 2H) 5.36 (br s, 1H) 4.48-4.69 (m, 1H) 3.93-4.41 (m, 3H) 3.52-3.90 (m, 3H) 3.05-3.21 (m, 2H) 2.92 (br s, 1H) 2.35-2.70 (m, 2H) 1.79-2.31 (m, 2H) 1.21-1.37 (m, 3H)

LCMS (ESI+): m/z 423.3 (M+H)

Example 79: In Vitro Efficacy Assay of Exemplary Compounds

Exemplary compounds of the invention were evaluated for efficacy in inhibiting TDP-43 inclusions using a concentration-response assay. Briefly, PC12 cells stably expressing a GFP-tagged mutant form of TDP-43 (TDP-43$^{Q331K}$::eGFP) were pre-treated for 1 hour with exemplary compounds and stressed with 15 μM sodium arsenite for 23 hours to induce TDP-43 aggregation. The inhibitory effect on TDP-43 aggregation was measured using fluorescence microscopy. The ratio of cells with TDP-43 aggregates was calculated based on the total number of cells with detectable GFP expression. A 10-point dose response curve was generated, and the $IC_{50}$ for each compound tested was determined and is summarized in Table 2 below. In the table, "A" indicates an $IC_{50}$ of less than 100 nM, "B" indicates an $IC_{50}$ range from 100 nM to 500 nM; "C" indicates an $IC_{50}$ range from 500 nM to 2 μM; and "D" indicates an $IC_{50}$ greater than 2 μM.

TABLE 2

Efficacy of exemplary compounds of the invention

| Compound No. | Average $IC_{50}$ (nM) |
|---|---|
| 100 | A |
| 101 | A |
| 102 | C |
| 103 | C |
| 104 | C |
| 105 | B |
| 106 | A |
| 107 | C |
| 108 | B |
| 109 | C |
| 110 | B |
| 111 | A |
| 112 | A |
| 113 | C |
| 114 | D |
| 115 | C |
| 116 | C |
| 117 | A |
| 118 | B |
| 119 | A |
| 120 | C |
| 121 | D |
| 122 | D |
| 123 | A |
| 124 | A |
| 125 | B |
| 126 | B |
| 127 | A |
| 128 | A |
| 129 | A |
| 130 | C |
| 131 | B |
| 132 | A |
| 133 | B |
| 134 | A |
| 135 | A |
| 136 | B |
| 137 | B |
| 150 | A |
| 151 | A |
| 152 | A |
| 170 | A |
| 171 | A |
| 172 | C |
| 173 | A |
| 174 | D |
| 175 | A |
| 176 | D |
| 177 | B |
| 178 | C |
| 179 | A |
| 180 | C |
| 181 | A |
| 182 | C |
| 183 | D |
| 200 | D |

TABLE 2-continued

Efficacy of exemplary compounds of the invention

| Compound No. | Average $IC_{50}$ (nM) |
|---|---|
| 300 | B |
| 301 | D |
| 302 | B |
| 303 | D |
| 312 | C |
| 313 | D |
| 314 | D |
| 316 | A |
| 317 | A |
| 318 | C |
| 400 | A |
| 401 | B |
| 402 | A |
| 403 | B |
| 404 | D |
| 405 | D |
| 406 | A |
| 407 | A |
| 408 | A |
| 409 | C |
| 410 | A |
| 411 | A |
| 412 | B |
| 413 | C |
| 414 | C |
| 415 | D |
| 416 | C |
| 417 | B |
| 418 | B |
| 419 | B |
| 420 | C |
| 421 | D |
| 422 | A |
| 423 | A |
| 424 | A |
| 425 | B |
| 426 | A |
| 427 | A |
| 428 | A |
| 429 | A |
| 430 | A |
| 431 | A |
| 432 | B |
| 433 | A |
| 434 | D |
| 435 | A |
| 436 | A |
| 437 | A |
| 438 | D |
| 439 | D |
| 440 | A |
| 441 | A |
| 442 | A |
| 443 | A |
| 444 | A |
| 445 | B |
| 446 | C |
| 447 | B |
| 448 | A |
| 449 | A |
| 450 | A |
| 451 | B |
| 452 | D |
| 453 | B |
| 454 | A |
| 455 | A |
| 456 | A |
| 457 | A |
| 458 | B |
| 459 | A |
| 460 | A |
| 461 | C |
| 462 | A |
| 463 | A |
| 464 | A |
| 465 | C |

TABLE 2-continued

Efficacy of exemplary compounds of the invention

| Compound No. | Average $IC_{50}$ (nM) |
|---|---|
| 466 | D |
| 467 | A |
| 468 | C |
| 469 | B |
| 470 | A |
| 471 | A |
| 472 | A |
| 473 | A |
| 474 | B |
| 475 | A |
| 476 | A |
| 477 | A |
| 478 | A |
| 479 | A |
| 480 | A |
| 481 | A |
| 482 | A |
| 483 | A |
| 484 | A |
| 485 | A |
| 486 | B |
| 487 | A |
| 488 | A |
| 489 | A |
| 490 | A |
| 491 | A |
| 492 | A |
| 493 | A |
| 494 | A |
| 495 | A |
| 496 | A |
| 497 | A |
| 498 | A |
| 499 | D |
| 500 | D |
| 501 | D |
| 502 | C |
| 503 | B |
| 504 | A |
| 505 | D |
| 506 | C |
| 507 | D |
| 508 | D |
| 509 | D |
| 510 | A |
| 511 | B |
| 512 | B |
| 513 | B |
| 514 | A |
| 515 | A |
| 516 | A |
| 517 | A |
| 518 | A |
| 519 | A |
| 520 | A |
| 521 | A |
| 522 | A |
| 523 | A |
| 524 | A |
| 525 | A |
| 526 | A |
| 527 | A |
| 528 | A |
| 529 | A |
| 530 | A |
| 531 | B |
| 532 | A |
| 533 | A |
| 534 | A |
| 535 | A |
| 536 | A |
| 537 | A |
| 538 | A |
| 539 | A |
| 540 | A |
| 541 | A |

TABLE 2-continued

Efficacy of exemplary compounds of the invention

| Compound No. | Average $IC_{50}$ (nM) |
|---|---|
| 542 | A |
| 543 | A |
| 544 | A |
| 545 | A |
| 546 | B |
| 547 | A |
| 548 | A |
| 549 | A |
| 550 | A |
| 551 | A |
| 552 | A |
| 553 | A |
| 554 | A |
| 555 | D |
| 556 | D |
| 557 | A |
| 558 | |
| 559 | |
| 560 | A |
| 561 | A |
| 562 | C |
| 563 | A |
| 564 | B |
| 565 | A |
| 566 | A |
| 567 | A |
| 568 | A |
| 569 | |

EQUIVALENTS

It will be recognized that one or more features of any embodiments disclosed herein may be combined and/or rearranged within the scope of the invention to produce further embodiments that are also within the scope of the invention.

Those skilled in the art will recognize, or be able to ascertain using no more than routine experimentation, many equivalents to the specific embodiments of the invention described herein. Such equivalents are intended to be within the scope of the present invention.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and/or rearranged in various ways within the scope and spirit of the invention to produce further embodiments that are also within the scope of the invention. Those skilled in the art will recognize, or be able to ascertain, using no more than routine experimentation, numerous equivalents to the specific embodiments described specifically in this disclosure. Such equivalents are intended to be encompassed in the scope of the following claims.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

What is claimed is:

1. A compound of Formula (I):

Formula (I)

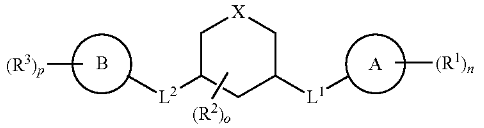

or a pharmaceutically acceptable salt thereof, wherein:

Ring A is cycloalkyl or aryl;

Ring B is indolyl or benzimidazolyl;

X is C(R')(R");

$L^1$ is —$NHCH_2$;

$L^2$ is —C(O)$NR^A$—;

each of $R^1$ and $R^3$ is independently $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, halo, cyano, nitro, azido, cycloalkyl, —$OR^B$, —C(O)$R^D$, —C(O)$OR^B$, —$NR^AR^C$, —$NR^A$C(O)$R^D$, —$S(O)_xR^E$, —$OS(O)_xR^E$, —C(O)$NR^AS(O)_xR^E$, —$NR^AS(O)_xR^E$, or —$S(O)_xNR^A$, each of which is optionally substituted with 1-5 $R^5$; or each $R^2$ is independently $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, halo, cyano, or nitro;

each of R' and R" is independently H, $C_1$-$C_6$ alkyl, or $C_1$-$C_6$ heteroalkyl;

each $R^5$ is independently $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, halo, cyano, or oxo;

or two $R^5$, taken together with the atoms to which they are attached, form a ring, optionally substituted with 1-5 $R^6$;

each $R^A$, $R^B$, $R^C$, $R^D$, or $R^E$ is independently H, $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, cycloalkyl, heterocyclyl, aryl, or heteroaryl, each of which is optionally substituted with 1-4 $R^6$;

or $R^A$ and $R^C$, together with the atoms to which each is attached, form a heterocyclyl ring;

each $R^6$ is independently $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_1$-$C_6$ haloalkyl, cycloalkyl, heterocyclyl, aryl, heteroaryl, halo, cyano, or nitro;

each of n, o, and p is independently 0, 1, 2, 3, 4, 5, or 6; and x is 0, 1, or 2.

2. The compound of claim 1, wherein Ring A is aryl.

3. The compound of claim 1, wherein Ring A is phenyl.

4. The compound of claim 1, wherein Ring A is cycloalkyl.

5. The compound of claim 4, wherein Ring A is cyclopropyl or indanyl.

6. The compound of claim 1, wherein Ring A is selected from the group consisting of:

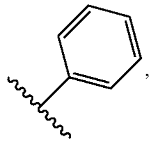,
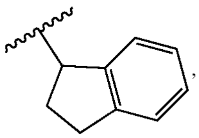, and
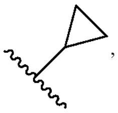, each of which is substituted with n R groups, wherein n is 0, 1, or 2.

7. The compound of claim 1, wherein n is 1.

8. The compound of claim 1, wherein o is 0.

9. The compound of claim 1, wherein each $R^1$ is independently $C_1$-$C_6$ alkyl, halo, azido, cyclopropyl, 2-propynyloxy, cyano, —C(O)$R^D$, or —$OR^B$.

10. The compound of claim 1, wherein p is 0.

11. The compound of claim 1, wherein p is 1.

12. The compound of claim 1, wherein each $R^3$ is independently —$OR^B$, $C_1$-$C_6$ haloalkyl, halo, amino, azido, nitro, cyano, cycloalkyl, or $S(O)_xR^E$.

13. The compound of claim 1, wherein X is $CH_2$.

14. The compound of claim 1, wherein $R^A$ is $C_1$-$C_6$ alkyl or $C_1$-$C_6$ haloalkyl.

15. The compound of claim 1, wherein the compound of Formula (I) is a compound of Formula (I-f):

Formula (I-f)

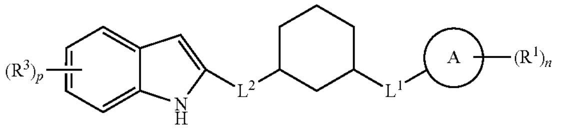

or a pharmaceutically acceptable salt thereof.

16. The compound of claim 1, wherein the compound of Formula (I) is a compound of Formula (I-h):

Formula (I-h)

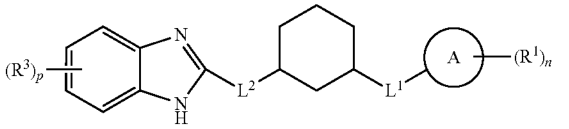

or a pharmaceutically acceptable salt thereof.

17. The compound of claim 1, wherein the compound of Formula (I) is selected from the group consisting of

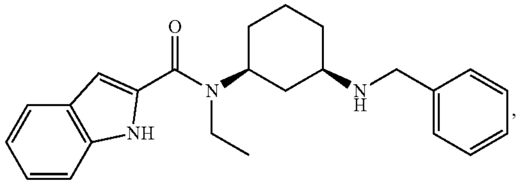,

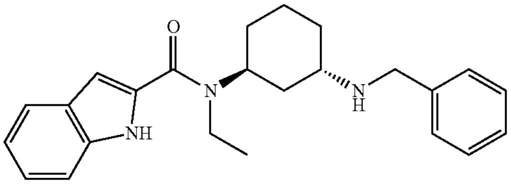,

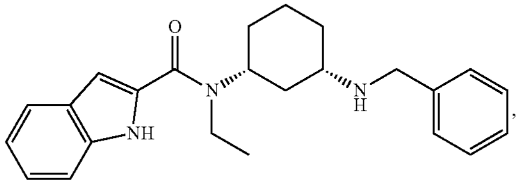,

-continued
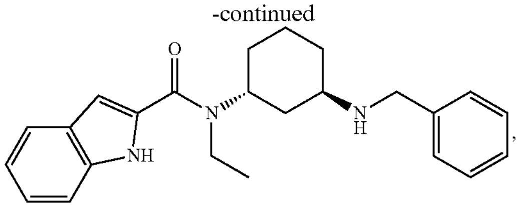
,
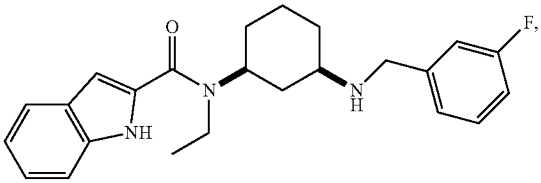
,
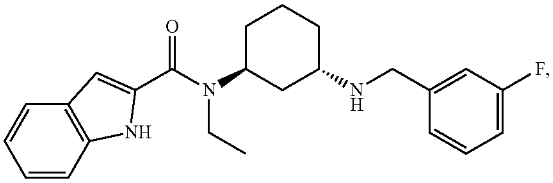
,
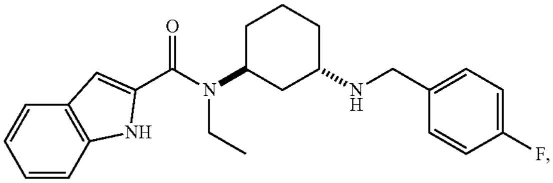
,
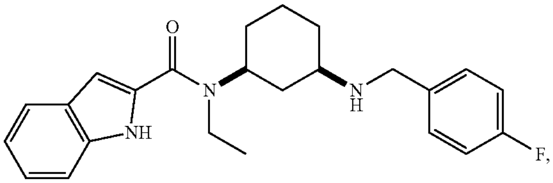
,
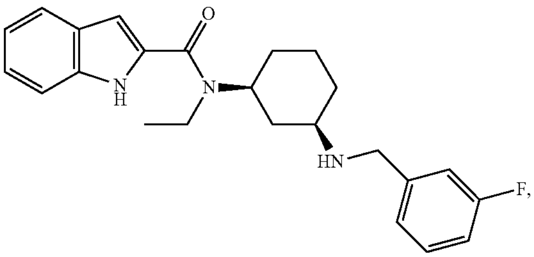
,
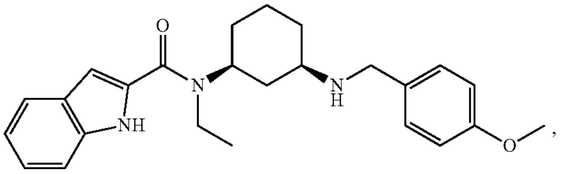
,
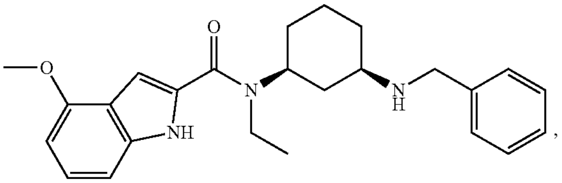
,
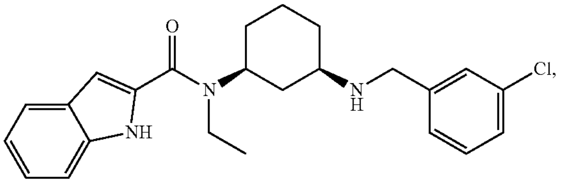
,
-continued
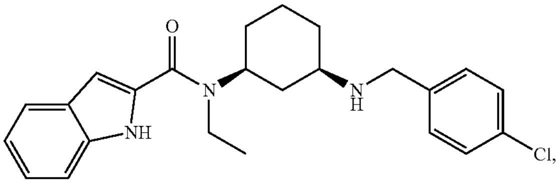
,
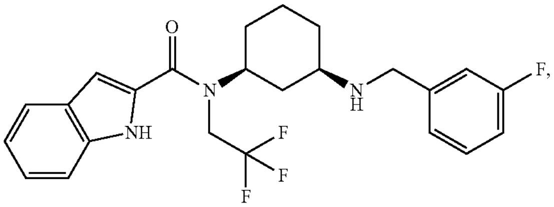
,
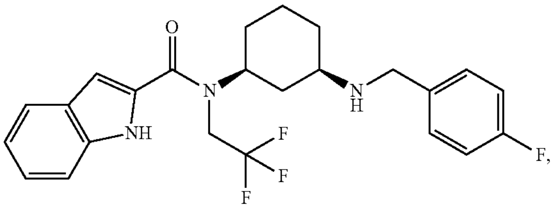
,
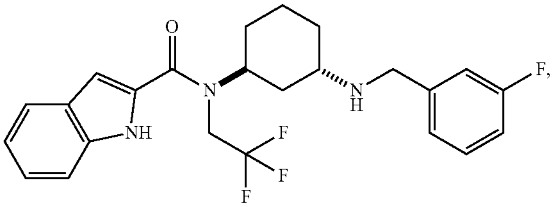
,
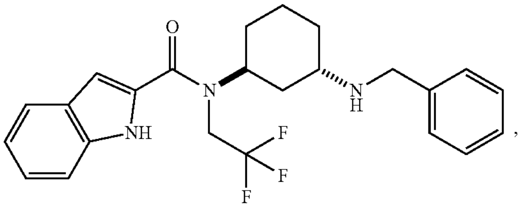
,
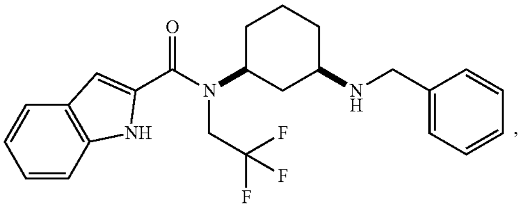
,
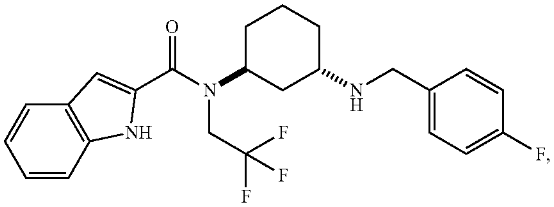
,
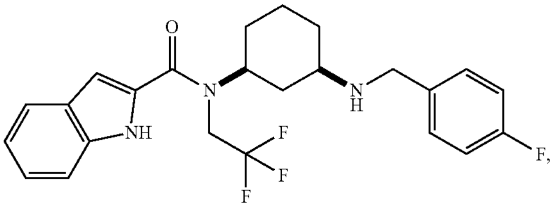
, -continued
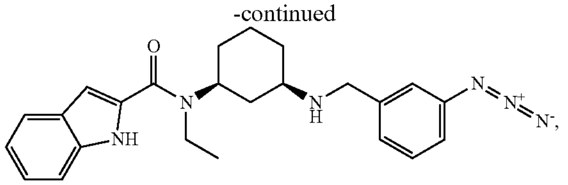
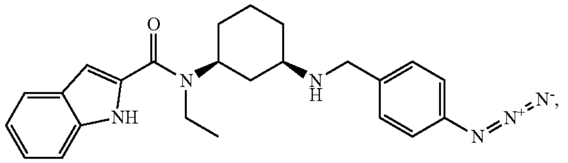
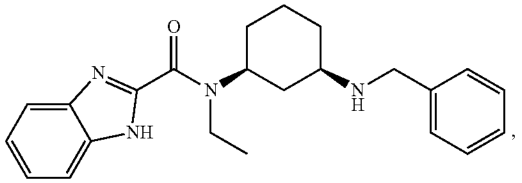
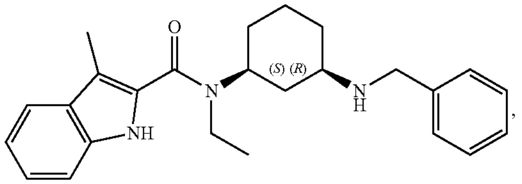
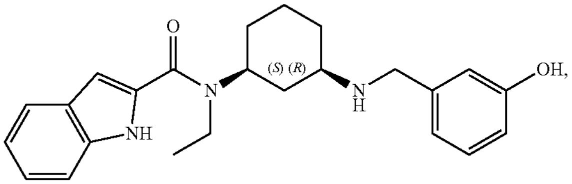
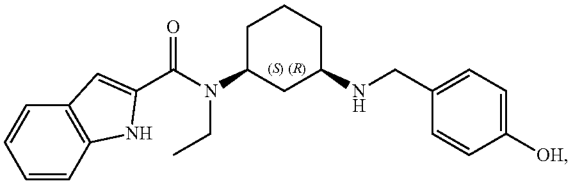
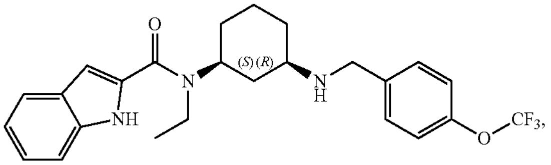
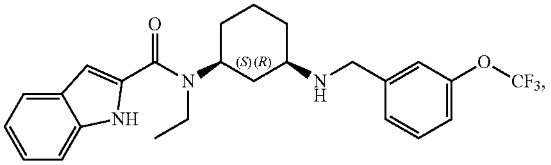
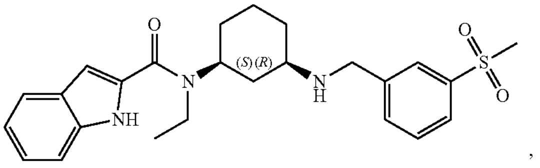
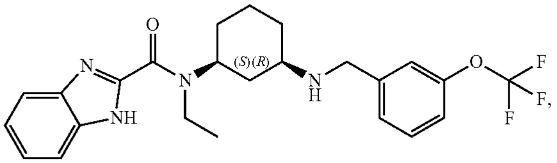
-continued
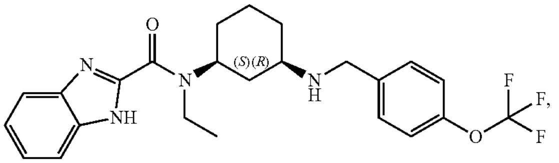
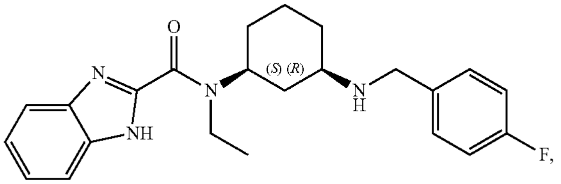
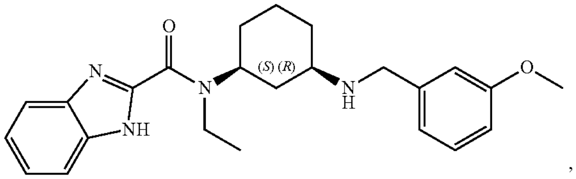
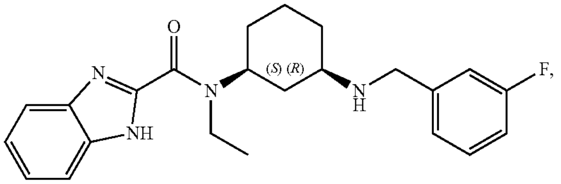
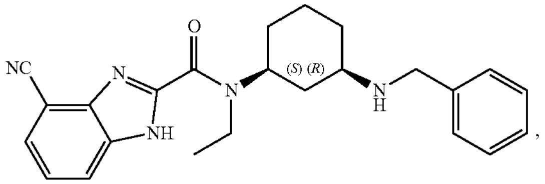
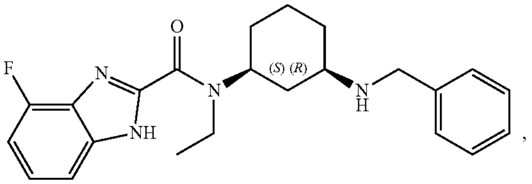
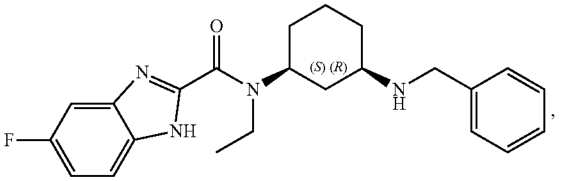
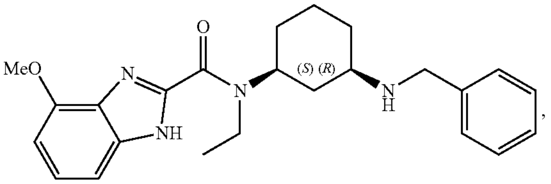
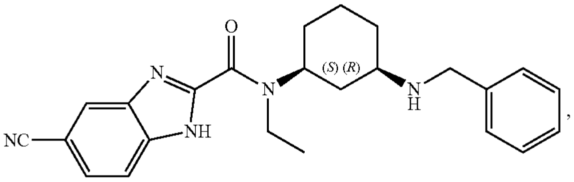

-continued
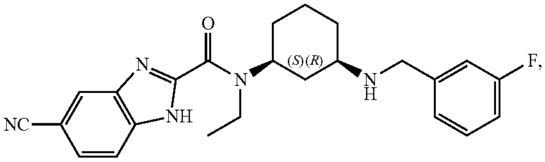
,
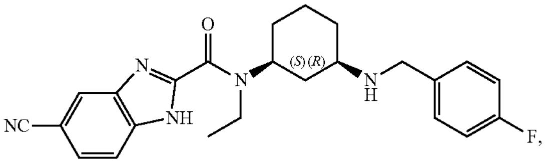
,
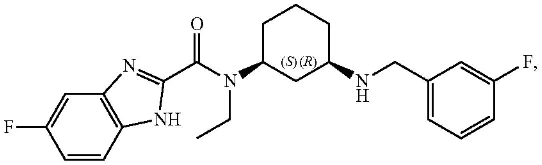
,
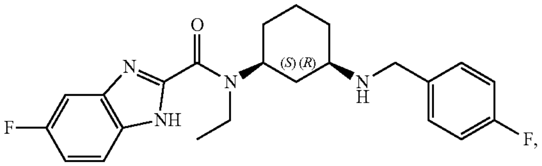
,
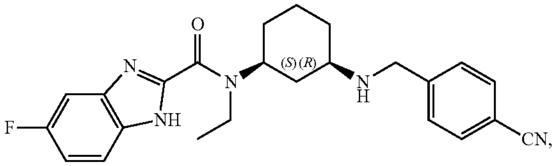
,
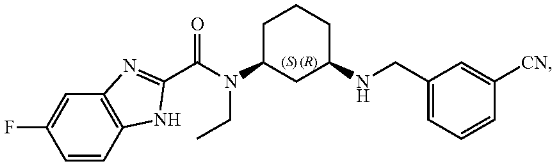
,
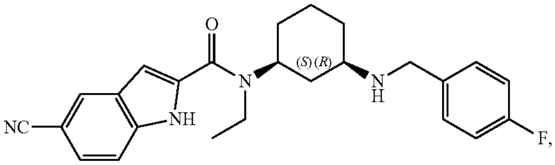
,
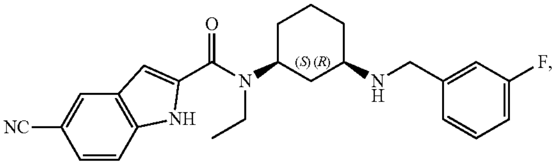
,
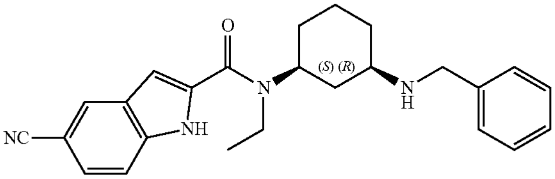
,
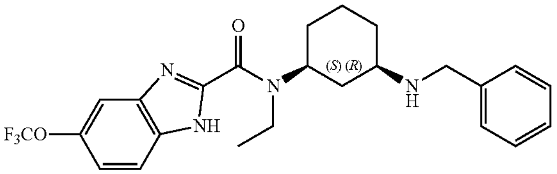
,
-continued
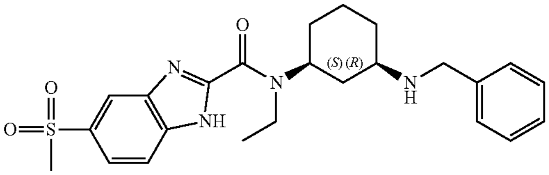
,
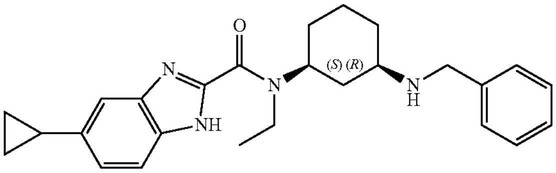
,
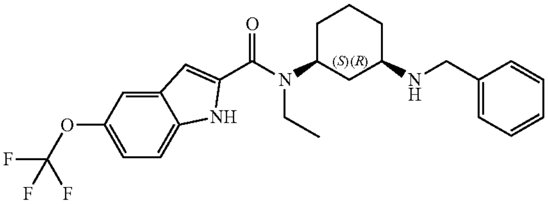
,
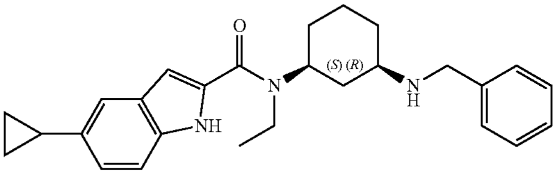
,
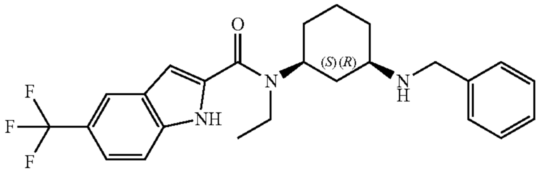
,
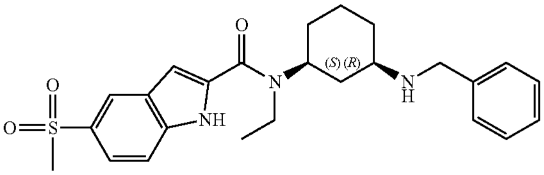
,
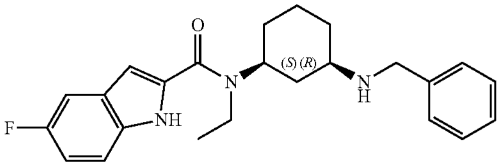
,
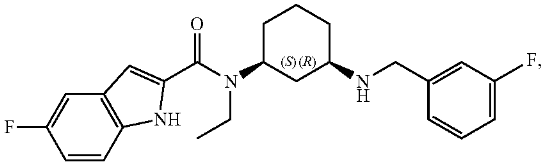
,
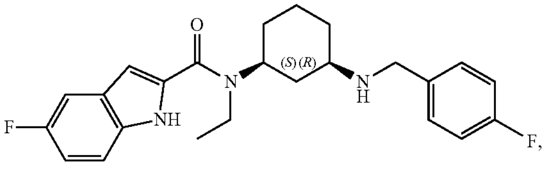
, -continued
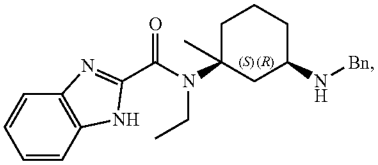
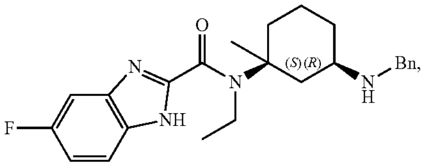
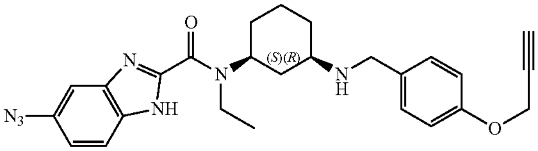
,
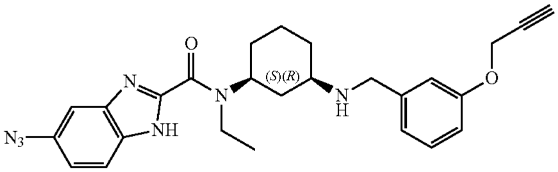
,
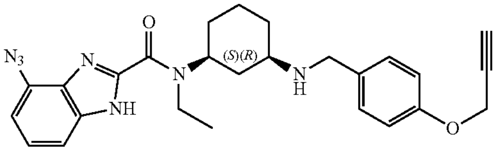
,
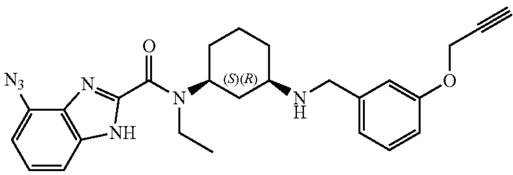
,
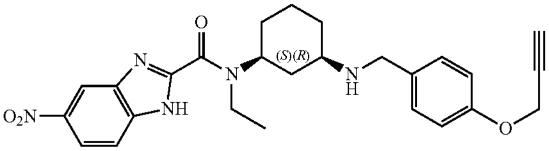
,
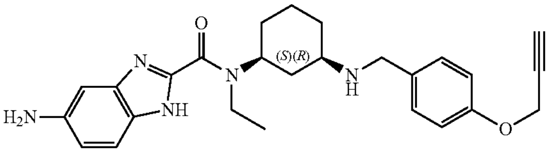
,
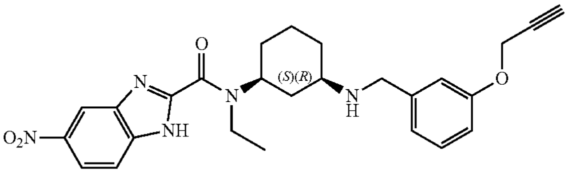
,
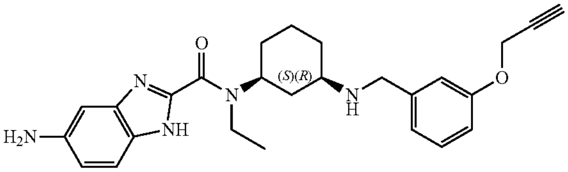
,
-continued
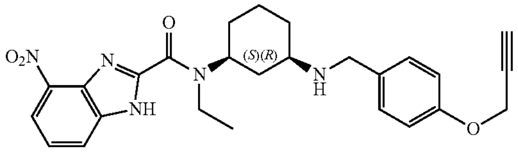
,
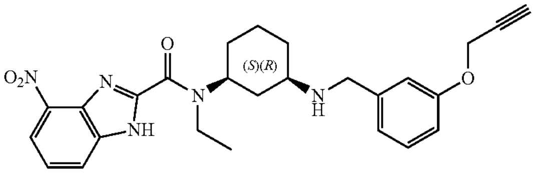
,
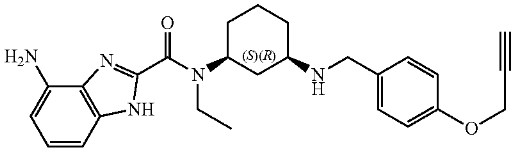
, and
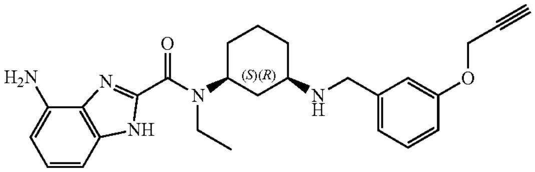
.
18. The compound of claim 1, wherein the compound of Formula (I) is selected from the group consisting of:
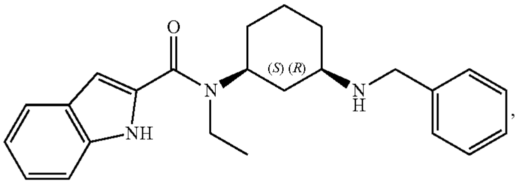
,
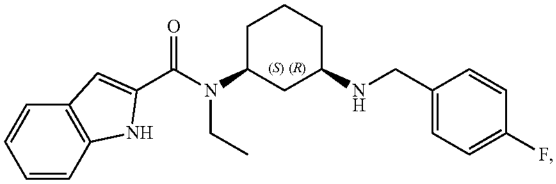
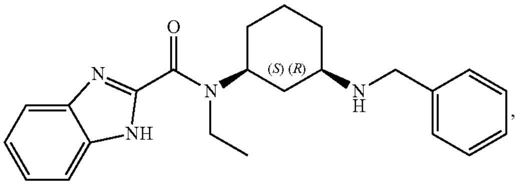
,
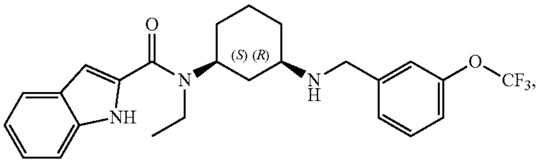
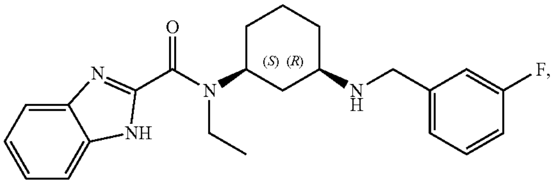

-continued
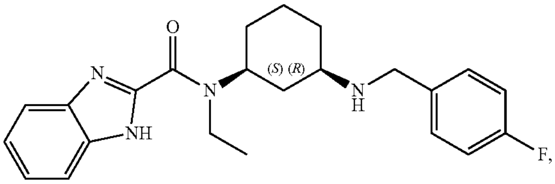
,
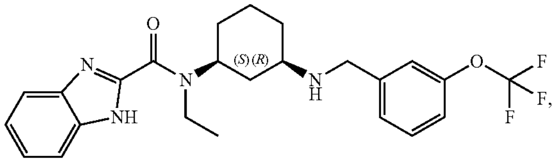
,
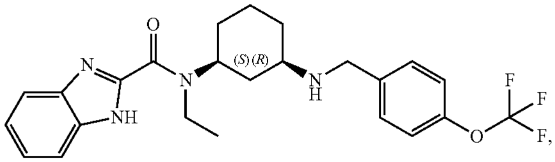
,
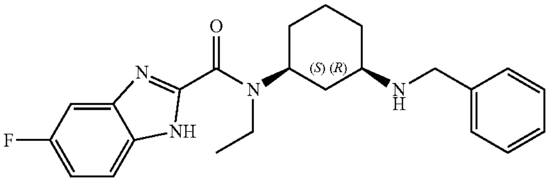
,
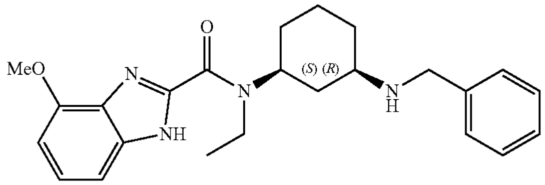
,
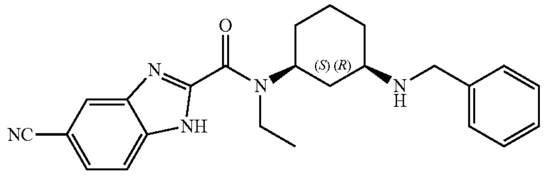
,
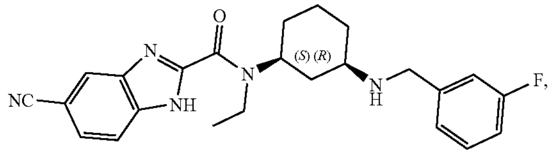
,
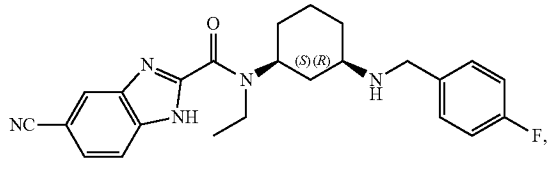
,
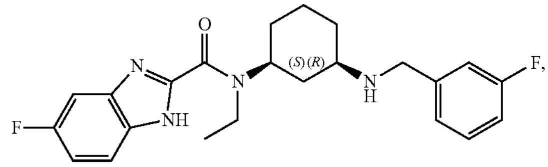
,
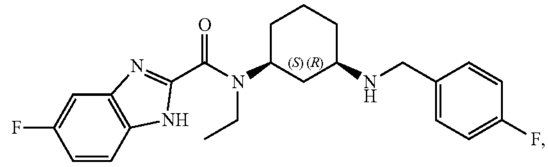
,
-continued
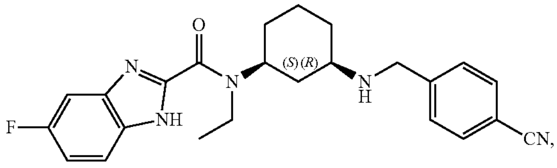
,
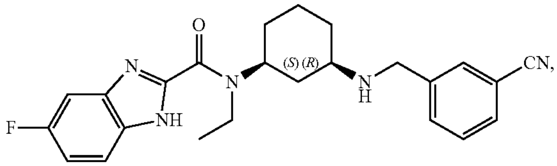
,
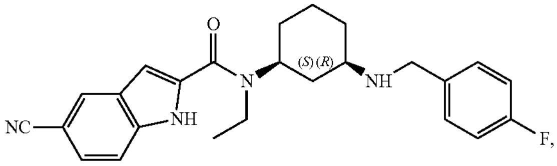
,
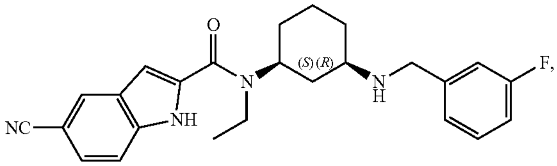
,
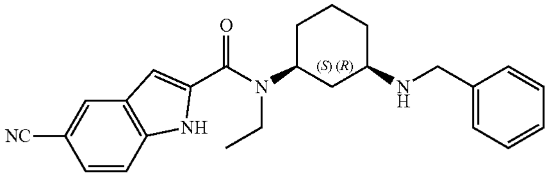
,
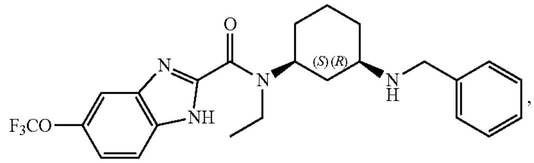
,
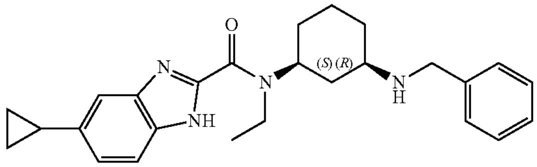
,
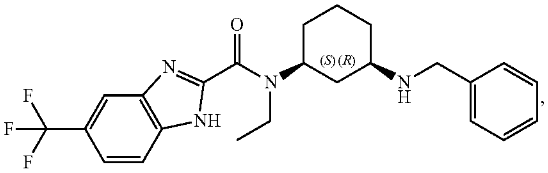
,
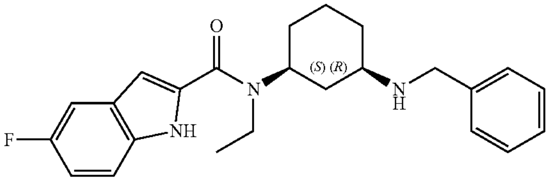
,
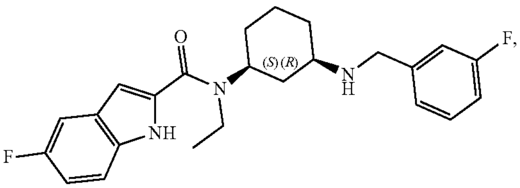
, and -continued

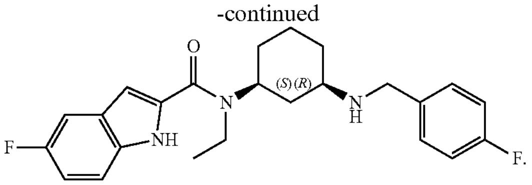

19. A pharmaceutical composition comprising at least one compound according to claim 1 or a pharmaceutically acceptable salt thereof in a mixture with a pharmaceutically acceptable excipient, diluent or carrier.

20. A method for modulating stress granules, wherein the method comprises administering to a subject in need thereof a compound of Formula (I) or a pharmaceutically acceptable salt thereof according to claim 1.

21. A method for modulating TDP-43 inclusion formation, wherein the method comprises administering to a subject in need thereof a compound of Formula (I) or a pharmaceutically acceptable salt thereof according to claim 1.

22. The method of claim 20, wherein the subject has a neurodegenerative disease or disorder, a musculoskeletal disease or disorder, a cancer, an ophthalmological disease or disorder, and/or a viral infection.

23. The method of claim 22, wherein the neurodegenerative disease is selected from the group consisting of Alzheimer's disease, frontotemporal dementia (FTD), FTLD-U, FTD caused by mutations in the progranulin protein or tau protein, frontotemporal dementia with inclusion body myopathy (IBMPFD), frontotemporal dementia with motor neuron disease, amyotrophic lateral sclerosis (ALS), Huntington's disease (HD), Huntington's chorea, Creutzfeld-Jacob disease, bovine spongiform encephalopathy, Kuru, scrapie, Lewy Body disease, diffuse Lewy body disease (DLBD), polyglutamine (polyQ)-repeat diseases, trinucleotide repeat diseases, cerebral degenerative diseases, presenile dementia, senile dementia, Parkinsonism linked to chromosome 17 (FTDP-17), progressive supranuclear palsy (PSP), progressive bulbar palsy (PBP), psuedobulbar palsy, spinal and bulbar muscular atrophy (SBMA), primary lateral sclerosis, Pick's disease, primary progressive aphasia, corticobasal dementia, HIV-associated dementia, Parkinson's disease, Parkinson's disease with dementia, dementia with Lewy bodies, Down's syndrome, multiple system atrophy, spinal muscular atrophy, post-polio syndrome (PPS), spinocerebellar ataxia, pantothenate kinase-associated neurodegeneration (PANK), spinal degenerative disease/motor neuron degenerative diseases, upper motor neuron disorder, lower motor neuron disorder, age-related disorders and dementias, Hallervorden-Spatz syndrome, cerebral infarction, cerebral trauma, chronic traumatic encephalopathy, transient ischemic attack, Lytigo-bodig (amyotrophic lateral sclerosis-parkinsonism dementia), Guam-Parkinsonism dementia, hippocampal sclerosis, corticobasal degeneration, Alexander disease, Apler's disease, Krabbe's disease, neuroborreliosis, neurosyphilis, Sandhoff disease, Tay-Sachs disease, Schilder's disease, Batten disease, Cockayne syndrome, Kearns-Sayre syndrome, Gerstmann-Straussler-Scheinker syndrome and other transmissible spongiform encephalopathies, hereditary spastic paraparesis, Leigh's syndrome, demyelinating diseases, neuronal ceroid lipofuscinoses, epilepsy, tremors, depression, mania, anxiety and anxiety disorders, sleep disorders, acute brain injuries, autism, or any combination thereof.

24. The method of claim 22, wherein the musculoskeletal disease is selected from the group consisting of muscular dystrophy, facioscapulohumeral muscular dystrophy, Freidrich's ataxia, progressive muscular atrophy (PMA), mitochondrial encephalomyopathy (MELAS), multiple sclerosis, inclusion body myopathy, inclusion body myositis, post-polio muscular atrophy (PPMA), motor neuron disease, myotonia, myotonic dystrophy, sacropenia, multifocal motor neuropathy, inflammatory myopathies, and paralysis.

25. The method of claim 22, wherein the cancer is selected from the group consisting of breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, ophthalmological cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, vulval cancer, or any combination thereof.

26. The method of claim 22, wherein the ophthalmological disease is selected from the group consisting of macular degeneration, age-related macular degeneration, diabetes retinopathy, histoplasmosis, macular hole, macular pucker, Bietti's crystalline dystrophy, retinal detachment, retinal thinning, retinoblastoma, retinopathy of prematurity, Usher's syndrome, vitreous detachment, Refsum disease, retinitis pigmentosa, onchocerciasis, choroideremia, Leber congenital amaurosis, retinoschisis, juvenile retinoschisis, Stargardt disease, ophthalmoplegia, or any combination thereof.

27. The method of claim 22, wherein the viral infection is caused by a virus selected from the group consisting of West Nile virus, respiratory syncytial virus (RSV), herpes simplex virus 1, herpes simplex virus 2, Epstein-Barr virus (EBV), hepatitis virus A, hepatitis virus B, hepatitis virus C, influenza viruses, chicken pox, avian flu viruses, smallpox, polio viruses, HIV-1, HIV-2, Ebola virus, and any combination thereof.

* * * * *